(12) United States Patent
Aulakh et al.

(10) Patent No.: US 9,174,978 B2
(45) Date of Patent: Nov. 3, 2015

(54) MONOBACTAM ORGANIC COMPOUNDS FOR THE TREATMENT OF BACTERIAL INFECTIONS

(71) Applicants: Virender Singh Aulakh, Whitehorse (CA); Anthony Casarez, San Francisco, CA (US); Xiaodong Lin, Orinda, CA (US); Mika Lindvall, Oakland, CA (US); Glenn McEnroe, San Mateo, CA (US); Heinz Ernst Moser, San Mateo, CA (US); Folkert Reck, San Mateo, CA (US); Meiliana Tjandra, Walnut Creek, CA (US); Robert Lowell Simmons, San Francisco, CA (US); Aregahegn Yifru, Pleasant Hill, CA (US); Qingming Zhu, Walnut Creek, CA (US)

(72) Inventors: Virender Singh Aulakh, Whitehorse (CA); Anthony Casarez, San Francisco, CA (US); Xiaodong Lin, Orinda, CA (US); Mika Lindvall, Oakland, CA (US); Glenn McEnroe, San Mateo, CA (US); Heinz Ernst Moser, San Mateo, CA (US); Folkert Reck, San Mateo, CA (US); Meiliana Tjandra, Walnut Creek, CA (US); Robert Lowell Simmons, San Francisco, CA (US); Aregahegn Yifru, Pleasant Hill, CA (US); Qingming Zhu, Walnut Creek, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/665,245

(22) Filed: Mar. 23, 2015

(65) Prior Publication Data
US 2015/0266867 A1     Sep. 24, 2015

Related U.S. Application Data

(60) Provisional application No. 61/969,735, filed on Mar. 24, 2014, provisional application No. 62/088,304, filed on Dec. 5, 2014.

(51) Int. Cl.
| | | |
|---|---|---|
| A61K 31/40 | (2006.01) | |
| C07D 417/14 | (2006.01) | |
| A61K 31/427 | (2006.01) | |
| A61K 31/454 | (2006.01) | |
| A61K 31/4439 | (2006.01) | |
| A61K 31/433 | (2006.01) | |
| A61K 31/496 | (2006.01) | |
| A61K 31/4545 | (2006.01) | |
| C07D 487/04 | (2006.01) | |
| A61K 45/06 | (2006.01) | |

(52) U.S. Cl.
CPC .......... *C07D 417/14* (2013.01); *A61K 31/427* (2013.01); *A61K 31/433* (2013.01); *A61K 31/4439* (2013.01); *A61K 31/454* (2013.01); *A61K 31/4545* (2013.01); *A61K 31/496* (2013.01); *A61K 45/06* (2013.01); *C07D 487/04* (2013.01)

(58) Field of Classification Search
USPC .......................................... 514/422; 548/202
See application file for complete search history.

(56) References Cited

U.S. PATENT DOCUMENTS

| | | | |
|---|---|---|---|
| 4,775,670 A | 10/1988 | Sykes | |
| 4,782,147 A | 11/1988 | Ochiai | |
| 5,112,968 A | 5/1992 | Treuner | |
| 2012/0302542 A1* | 11/2012 | Brown et al. | ............ 514/210.15 |

FOREIGN PATENT DOCUMENTS

| | | |
|---|---|---|
| CN | 103044416 | 4/2013 |
| EP | 48953 A2 | 4/1982 |
| EP | 53816 A1 | 6/1982 |
| EP | 73061 A2 | 3/1983 |
| EP | 83039 A1 | 7/1983 |
| EP | 93376 A2 | 11/1983 |
| EP | 95778 A1 | 12/1983 |
| EP | 96297 A2 | 12/1983 |
| EP | 177940 A2 | 10/1985 |
| JP | 61053282 | 3/1986 |
| JP | 61053283 | 3/1986 |
| NL | 8100571 | 9/1981 |
| WO | 2012/073138 A1 | 6/2012 |
| WO | 2013/110643 A1 | 8/2013 |
| WO | 2015/103583 A1 | 7/2015 |

OTHER PUBLICATIONS

Brown et al., "Pyridone-Conjugated Monobactam Antibiotics with Gram-Negative Activity" J. Med. chem 56:5541-5552, 2013.
Uri, High Degree of Specificity of the Color Reaction for the Aminothiazolyl Oxyimino Beta-Lactam Antibiotics: Aet Chimica Hungarica 128(1):89-91 1991.

(Continued)

*Primary Examiner* — Rei-Tsang Shiao
(74) *Attorney, Agent, or Firm* — Michael G. Smith

(57) ABSTRACT

This invention pertains generally to antibacterial compounds of Formula I,

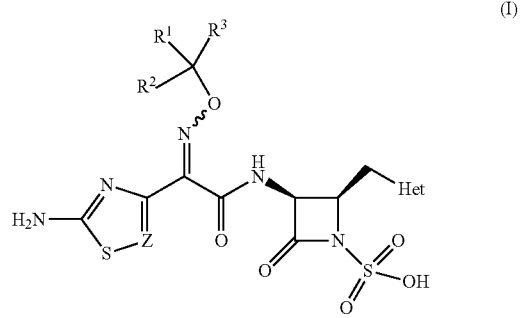

as further described herein, and pharmaceutically acceptable salts and formulations thereof. In certain aspects, the invention pertains to methods of using such compounds to treat infections such as those caused by Gram-negative bacteria.

24 Claims, No Drawings

(56) References Cited

OTHER PUBLICATIONS

Matsuda et al., Preferential Hydrolysis of cis Configuration Compounds at the 3,4 Position of Monobactams by Beta-Lactamase from *Morganella morganii* Antimicrobial Agents and Chemotherapy 35(3):458-461, Mar. 1991.

Matsuda et al., "Structure-Activity Relations of 4-Fluoromethyl Monobactams" Journal of Antimicrobial Chemotherapy 19:753-760, 1987.

Neu and Chen, "In vitro Activity and Beta-Lactamase Stability of a new Monobactam, B0-1165" Antimicrobia; Agents Chemotherapy 31(4):505-511, 987.

Sendai et al., "Chemical Modification of Sulfazecin Synthesis of 4-(Substituted Methyl)-2-Azetidinone-1-Sulfonic Acid Derivatives" The Journal of Antibiotics 38(3):346-371, Mar. 1985.

Page, "Siderophore Conjugates" Ann NY Acad. Sci. 1277:115-126, 2013.

Tomaras et al., "Adaptation-Based Resistance to Siderophore-Conjugated Antibacterial Agents by *Pseudomonas aeruginosa*" Antimicrobial Agents and Chemotherapy 57(9):4197-4207, Sep. 2013.

\* cited by examiner

MONOBACTAM ORGANIC COMPOUNDS FOR THE TREATMENT OF BACTERIAL INFECTIONS

CROSS-REFERENCE TO RELATED APPLICATIONS

This application claims benefit of priority to U.S. Provisional Application No. 61/969,735, filed 24 Mar. 2014, and U.S. Provisional Application No. 62/088,304, filed 5 Dec. 2014; the contents of these applications are incorporated herein by reference.

FIELD OF THE INVENTION

This invention relates to novel β-lactam compounds, and their preparation and use. In particular, the invention relates to novel β-lactam compounds where the lactam ring is monocyclic, and their uses to treat bacterial infections, especially those caused by Gram-negative bacteria.

BACKGROUND

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial infections occuring each year in the United States, 50 to 60% are caused by antimicrobial-resistant strains of bacteria. The high rate of resistance to commonly used antibacterial agents increases the morbidity, mortality, and costs associated with nosocomial infections. In the United States, nosocomial infections are thought to contribute to or cause more than 77,000 deaths per year and cost approximately $5 to $10 billion annually.

Important causes of Gram-negative resistance include extended-spectrum β-lactamases (ESBLs), serine carbapenemases (KPCs) and metallo-β-lactamases (for example NDM-1) in *Klebsiella pneumoniae, Escherichia coli*, and *Proteus mirabilis*, high-level third-generation cephalosporin (AmpC) β-lactamase resistance among *Enterobacter* species and *Citrobacter freundii*, and multidrug-resistance genes observed in *Pseudomonas, Acinetobacter*, and *Stenotrophomonas*. The problem of antibacterial resistance is compounded by the existence of bacterial strains resistant to multiple antibacterials. For example, *Klebsiella pneumonia* harboring NDM-1 metallo-β-lactamase carries frequently additional serine-β-lactamases on the same plasmid that carries the NDM-1.

Thus there is a need for new antibacterials, particularly antibacterial compounds that are effective against existing drug-resistant microbes, or are less susceptible to development of new bacterial resistance. The current invention provides such compounds.

SUMMARY

The invention includes novel compounds, pharmaceutical formulations including the compounds, and methods of using such compounds and compositions for treatment of patients with bacterial infections. The compounds are monobactams, which comprise a monocyclic beta-lactam ring, and which typically act by inhibition of penicillin-binding proteins (PBPs), which are involved in biosynthesis of peptidoglycans required for normal bacterial cell walls. Some known members of this class include aztreonam and carumonam. Other monobactam compounds are disclosed in WO2013/110643 and WO2012/073138. The compounds are primarily effective against Gram-negative bacteria.

The compounds of the invention can be used to treat infection caused by Enterobacteriaceae, including *Salmonella, E. coli, Klebsiella pneumoniae, Proteus, Enterobacter, Serratia,* and *Citrobacter*, including pathogens such as KPC producing *Klebsiella pneumoniae* that are less susceptible to previous monobactams like aztreonam, as well as non-fermenting bacteria, including *Pseudomonas aeruginosa, Acinetobacter, Burkholderia, Moraxella* and *Stenotrophomonas*.

The compounds of the invention can be used alone or in combination with other antibiotics, and can be used in combination with compounds such as beta-lactamase inhibitors that potentiate the activity of the compounds of the invention against certain pathogens or reduce the frequency or extent of bacterial resistance to the compounds of the invention against certain pathogens. Suitable beta-lactamase inhibitors for use in combination with the compounds of the invention include avibactam, tazobactam, sulbactam and clavulanic acid.

In one aspect, the invention provides compounds of Formula (I):

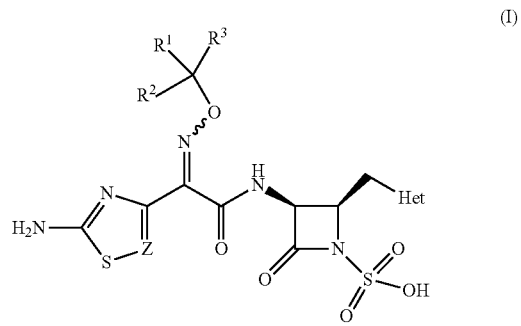

or a pharmaceutically acceptable salt thereof, wherein:

Z is $CR^4$ or N;

$R^1$ is H or $C_1$-$C_4$ alkyl;

$R^2$ is selected from the group consisting of H, $C_1$-$C_4$ alkyl, and —COOH or $R^1$ and $R^2$ taken together with the carbon to which they are attached form a ring selected from a $C_3$-$C_6$ cycloalkyl ring and a 4-6 membered heterocyclic ring containing up to two heteroatoms selected from N, O and S as ring members;

$R^3$ is selected from H, —COOH, and -$L^1$-W—$(CH_2)_{0-2}$-X—$R^5$;

$R^4$ is H or halo;

each $L^1$ is independently a straight chain or branched $C_{1-4}$ alkylene;

W is a bond, O, NH or S;

X is phenyl, or a 5-6 membered heteroaryl ring containing 1-3 heteroatoms selected from N, O and S as ring members; where the phenyl and 5-6 membered heteroaryl are optionally substituted with one or two groups selected from $C_{1-4}$ alkyl, hydroxy, —CN, F, $C_{1-4}$ alkoxy, —$NH_2$, —NH($C_{1-4}$ alkyl) and —N($C_{1-4}$ alkyl)$_2$;

$R^5$ is selected from

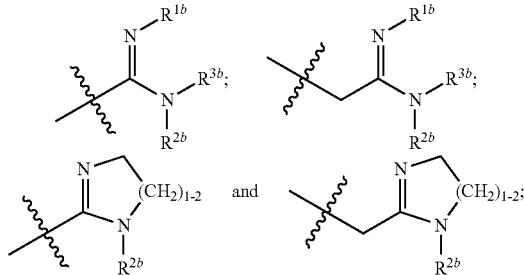

and

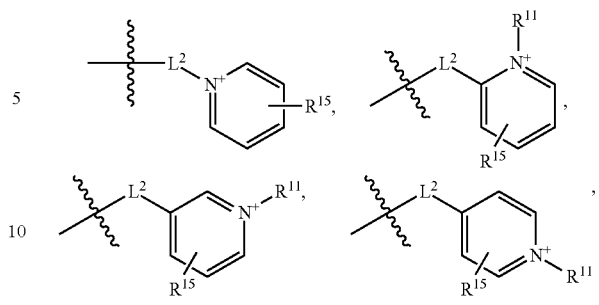

wherein $R^{1b}$, $R^{2b}$, and $R^{3b}$ are independently hydrogen, hydroxy, CN, ($C_1$-$C_4$)alkyl, ($C_1$-$C_4$)alkoxy, ($C_3$-$C_6$) cycloalkyl, or 4-, 5-, 6- or 7-membered heterocyclyl containing N, O or S as a ring member, wherein each ($C_1$-$C_4$)alkyl, ($C_1$-$C_4$)alkoxy, ($C_3$-$C_6$)cycloalkyl, or 4-, 5-, 6- or 7-membered heterocyclyl containing N, O or S as a ring member may be substituted with one, two or three substituents selected independently from Y, and wherein $R^{2b}$ and $R^{3b}$ together with the nitrogen atom to which they are bonded can optionally form a 5- to 7-membered heterocyclyl including 0 or 1 further heteroatoms selected from N, O and S, said heterocyclyl optionally substituted by Y;

Y is selected from F, CN, —$NH_2$, Q, -$L^2$-C(O)$NR^{10}$-$L^2$-Q, -$L^2$-$NR^{10}$—C(O)-$L^2$-Q, -$L^2$-$OR^{10}$, -$L^2$-N($R^1$)$_2$, -$L^2$-$N^+$($R^{11}$)$_3$, -$L^2$-$NR^{10}$—C(O)$R^{10}$, -$L^2$-$NR^{10}$-$L^2$-N($R^1$)$_2$, -$L^2$-O—C(O)$OR^{10}$, -$L^2$-O—C(O)—N($R^1$)$_2$, -$L^2$-$NR^{10}$—C(O)—N($R^1$)$_2$, -$L^2$-$NR^{10}$—C(O)—$OR^{11}$, -$L^2$-C(=$NR^1$)—N($R^1$)$_2$, —CON($R^1$)$_2$, -$L^2$-$NR^{10}$—C(=$NR^1$)—N($R^1$)$_2$, -$L^2$-$NR^{10}$—C(=$NR^1$)—$R^{10}$, -$L^2$-C(O)N($R^1$)$_2$, -$L^2$-O—$SO_3R^{10}$;

$L^2$ is independently at each occurrence a bond or a straight chain or branched $C_{1-4}$ alkylene, optionally substituted with $NH_2$, OH, or F;

Het is a 4-6 membered heteroaryl or heterocyclic ring, where the heteroaryl ring contains 1 to 4 heteroatoms selected from N, O and S as ring members and is optionally substituted with one or two groups selected from Y, OH, $NH_2$, —C(O)$NR^{10}_2$, and $C_{1-4}$ alkyl optionally substituted with one or two Y; and the heterocyclic ring contains 1 or 2 heteroatoms selected from N, O and S as ring members and is optionally substituted with up to three groups selected from halo, Y, $C_{1-4}$ alkyl optionally substituted with one or two groups selected from Y, =$NR^{10}$, =N—$OR^{10}$, =N—CN, and oxo;

and Het is optionally fused to a 5 or 6 membered heterocyclic or heteroaryl ring containing up to two heteroatoms selected from N—$R^{10}$, O and S as ring members, and optionally substituted with one or two $R^{16}$;

$R^{10}$ and $R^{12}$ are independently H or $C_{1-4}$ alkyl optionally substituted by one or two groups selected from OH, $NH_2$ or Q;

Q is selected from -$L^2$-N($R^{13}$)$_2$, -$L^2$-$N^+$($R^{14}$)$_3$, -$L^2$-$NR^{13}$—C(=$NR^{13}$)—N($R^{13}$)$_2$, -$L^2$-$NR^{13}$—CR$^{13}$(=$NR^{13}$), -$L^2$-$NR^{13}$-$L^2$-Cy, -$L^2$-$NR^{13}$—C(=$NR^{13}$)—$NR^{13}$-$L^2$-Cy, -$L^2$-$NR^{13}$—C(=$NR^{13}$)-$L^2$-Cy, -$L^2$-Cy-$L^2$-$R^{13}$, -$L^2$-Cy-$L^2$-N($R^{13}$)$_2$, -$L^2$-$NR^{13}$—$SO_2$N—($R^{13}$)$_2$, -$L^2$-$SO_2$—N($R^{13}$)$_2$, -$L^2$-$NR^{13}$—$SO_2$—$R^{13}$, -$L^2$-$NR^{13}$-$L^2$-Ar, -$L^2$-S-$L^2$-Cy, -$L^2$-$NR^{13}$—(=O)—O—$R^{13}$, each Cy is independently a 3-6 membered cycloalkyl or 3-6 membered heterocyclyl containing one or two heteroatoms selected from N, O and S as a ring member and optionally fused to a 5-6 membered aryl or heteroaryl ring, wherein each Cy is optionally substituted with one or two groups selected from halo, $C_{1-3}$ haloalkyl, $R^{14}$, hydroxy, $C_{1-4}$ alkoxy, —$NH_2$, —NH($C_{1-4}$ alkyl) or —N($C_{1-4}$ alkyl)$_2$;

Ar is phenyl, optionally substituted with one or two groups selected from halo, $C_{1-3}$ haloalkyl, $R^{14}$, hydroxy, $C_{1-4}$ alkoxy, —$NH_2$, —NH($C_{1-4}$ alkyl) or —N($C_{1-4}$ alkyl)$_2$;

$R^{11}$ is independently at each occurrence $C_{1-4}$ alkyl;

and two $R^{10}$, or two $R^{11}$, or two $R^{12}$ on the same N can cyclize to form a 4-6 membered heterocyclic ring optionally substituted with $C_{1-4}$ alkyl, $C_{1-4}$ alkoxy, hydroxy, or oxo;

$R^{13}$ is independently at each occurrence H or $C_{1-4}$ alkyl optionally substituted with hydroxy, $C_{1-4}$ alkoxy, —$NH_2$, —NH($C_{1-4}$ alkyl) or —N($C_{1-4}$ alkyl)$_2$;

$R^{14}$ is independently at each occurrence $C_{1-4}$ alkyl optionally substituted with hydroxy, $C_{1-4}$ alkoxy, —$NH_2$, —NH($C_{1-4}$ alkyl) or —N($C_{1-4}$ alkyl)$_2$;

wherein two $R^{13}$ or two $R^{14}$ on the same N can cyclize to form a 4-6 membered heterocyclic ring optionally substituted with $C_{1-4}$ alkyl, $C_{1-4}$ alkoxy, hydroxy, amino or oxo;

$R^{15}$ is H, halo, $C_{1-4}$ alkyl, CN, or —O($C_{1-4}$ alkyl);

each $R^{16}$ is independently halo, $C_{1-4}$ alkyl, —$NH_2$, CN, or —O($C_{1-4}$ alkyl);

or a pharmaceutically acceptable salt thereof;

including variants of such compounds disclosed herein.

In another aspect, the invention provides a method of inhibiting bacterial growth or modulating the virulence of a bacterial infection, wherein the method comprises administering to a patient in need of such inhibition a compound of formula (I).

In another aspect, the invention provides a method for treating a subject having a Gram-negative bacterial infection, which comprises administering to the subject in need thereof an antibacterially effective amount of a compound of formula (I), optionally in combination with a pharmaceutically acceptable carrier. In certain embodiments, the subject is a mammal and in some embodiments, the subject is a human.

The Gram-negative bacteria may be of a genus selected from *Citrobacter, Enterobacter, Escherichia, Klebsiella, Morganella, Proteus, Salmonella, Serratia, Pseudomonas, Acinetobacter, Bacteroides, Burkholderia, Campylobacter, Neisseria,* and *Stenotrophomonas*. In particular, a bacterial infection caused by a species of *Citrobacter, Enterobacter, Escherichia, Klebsiella, Morganella, Proteus, Salmonella, Serratia, Pseudomonas,* or *Acinetobacter* is treatable. Particular bacterial species for such treatment include *Citrobacter freundii, Citrobacter koseri, Enterobacter cloacae,*

*Enterobacter faecalis, Enterobacter faecium, Escherichia coli, Klebsiella pneumoniae, Klebsiella oxytoca, Morganella morganii, Proteus mirabilis, Salmonella* species, *Serratia marcescens, Pseudomonas aeruginosa,* and *Acinetobacter baumanii,* as well as *Bacteroides bivius, Bacteroides fragilis, Burkholderia cepacia, Campylobacter jejuni, Neisseria gonorrhoeae,* and *Stenotrophomonas maltophilia.*

In another aspect, the invention provides a method of administering an inhibitory amount of a compound of formula (I) to fermenting or non-fermenting Gram-negative bacteria. In certain embodiment of the method of administering an inhibitory amount of a compound of formula (I) to fermenting or non-fermenting Gram-negative bacteria, the Gram-negative bacteria are species of *Burkholderia, Citrobacter, Enterobacter, Escherichia, Klebsiella, Morganella, Neisseria, Proteus, Salmonella, Serratia, Pseudomonas,* and *Acinetobacter.* Particular bacterial species for such methods include *Citrobacter freundii, Citrobacter koseri, Enterobacter cloacae, Enterobacter faecalis, Enterobacter faecium, Escherichia coli, Klebsiella pneumonia, Klebsiella oxytoca, Neisseria meningiditis* and *Burkholderia cepacia, Morganella morganii, Proteus mirabilis, Salmonella* species, *Serratia marcescens, Pseudomonas aeruginosa,* and *Acinetobacter baumanii,* as well as *Bacteroides bivius, Bacteroides fragilis, Burkholderia cepacia, Campylobacter jejuni, Neisseria gonorrhoeae,* and *Stenotrophomonas maltophilia.*

In another embodiment, the invention provides a method of administering an inhibitory amount of a compound of formula (I) to Gram-negative bacteria, such as an Enterobacteriaceae; in some embodiments the Gram-negative bacteria is selected from the group consisting of species of *Citrobacter, Enterobacter, Escherichia, Klebsiella, Morganella, Proteus, Salmonella, Serratia, Pseudomonas,* and *Acinetobacter.*

Another embodiment of the invention provides a pharmaceutical composition comprising an effective amount of a compound of Formula (I) combined with a pharmaceutically acceptable carrier or excipient. An 'effective amount' as used here refers to an amount sufficient to reduce the severity or symptoms of an infection, or an amount effective to reduce bacteria load in the patient.

Pharmaceutical compositions according to the present invention are provided which include any of the compounds described herein and a pharmaceutically acceptable carrier. In some embodiments the composition includes an additional therapeutic agent or a beta lactamase inhibitor.

In another aspect, the invention provides a pharmaceutical combination comprising a compound of the invention and an additional therapeutic agent or a beta lactamase inhibitor or optionally both.

The present invention provides novel compounds, methods for inhibiting survival and population growth of Gram-negative bacteria, and novel methods and compositions for treating bacterial infections in mammals, particularly in human subjects. The compounds provided herein can be formulated into pharmaceutical formulations and medicaments that are useful in methods to inhibit bacterial growth or severity or duration of a bacterial infection, or to treat a subject having a bacterial infection that is susceptible to inhibition by the compounds of Formula (I). The invention also provides for the use of the compounds in preparing medicaments and pharmaceutical formulations, for use of the compounds in inhibiting bacterial growth, and for use of the compounds in treating bacterial infections in a subject in need of such treatment, e.g., a subject infected with a Gram-negative bacteria or at especially high risk for such infection.

Other aspects of the invention are discussed herein.

DETAILED DESCRIPTION

For purposes of interpreting this specification, the following definitions apply unless specified otherwise or clearly contradicted by context. Whenever appropriate, terms used in the singular will also include the plural and vice versa.

DEFINITIONS

Terms used in the specification have the following meanings:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human.

As used herein, the term "inhibition" or "inhibiting" refers to the reduction or suppression of a given condition, symptom, or disorder, or disease, or a significant decrease in the baseline activity of a biological activity or process, or decrease in the viability, number or growth rate of a bacterial population.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of *P. aeruginosa* and/or other Gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated.

"Optionally substituted" means the group referred to can be substituted at one or more positions by any one or any combination of the radicals listed thereafter. Such substitution involves the replacement of a hydrogen atom of the unsubstituted group with another moiety; thus the number of substituents that can be added to any unsubstituted group is equal to the number of hydrogen atoms on the unsubstituted group. If not otherwise specified, 'optionally substituted' means that up to three non-hydrogen substituent groups can be added.

"Halo" or "halogen", as used herein, may be fluorine, chlorine, bromine or iodine.

"$C_1$-$C_6$ alkyl", or "$C_{1-6}$alkyl" as used herein, denotes straight chain or branched alkyl having 1-6 carbon atoms. If a different number of carbon atoms is specified, such as $C_8$ or $C_3$, then the definition is to be interpreted accordingly, such as "$C_1$-$C_4$ alkyl" will include methyl, ethyl, propyl, isopropyl, butyl, isobutyl, sec-butyl and tert-butyl.

"$C_1$-$C_6$ alkoxy", or "$C_{1-6}$alkoxy" as used herein, denotes straight chain or branched alkoxy having 1-6 carbon atoms. If a different number of carbon atoms is specified, such as $C_8$ or $C_3$, then the definition is to be interpreted accordingly, e.g., "$C_1$-$C_4$ alkoxy" will represent methoxy, ethoxy, propoxy, isopropoxy, butoxy, isobutoxy, sec-butoxy and tert-butoxy.

"$C_1$-$C_4$-Haloalkyl" or "$C_{1-4}$ haloalkyl" as used herein, denotes straight chain or branched alkyl having 1-4 carbon atoms, wherein at least one hydrogen has been replaced by a halogen. If a different number of carbon atoms is specified, such as $C_6$ or $C_3$, then the definition is to be interpreted accordingly, thus "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2-$, $(CF_3)_2CH-$, $CH_3-CF_2-$, $CF_3CF_2-$, $CF_3$, $CF_2H-$, $CF_3CF_2CHCF_3$ or $CF_3CF_2CF_2CF_2-$.

"$C_3$-$C_8$-cycloalkyl" or "$C_{3-8}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be interpreted accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refer, respectively, to 4- to 8-membered, 5- to 6-membered, 3- to 10-membered, 3- to 14-membered, 4- to 14-membered and 5- to 14-membered heterocyclic rings containing 1 to 7, 1 to 5 or 1 to 4 heteroatoms selected from the group consisting of nitrogen, oxygen and sulphur, which may be saturated, or partially saturated. "Heterocyclic" may be used interchangeably with "heterocyclyl". The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, oxazolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo [2.2.1]heptane, 2,5-Diaza-bicyclo[2.2.1]heptane, azetidine, ethylenedioxo, oxtane and thiazolidine. Preferably, a heterocyclic or heterocyclyl group is a saturated or partially saturated monocyclic group unless otherwise specified, and contains 5-7 ring atoms with up to two heteroatoms selected from N, O and S as ring members. In some embodiments, a heterocyclic group further includes bicyclic ring systems containing 1 or 2 heteroatoms such as N, O or S as ring members and comprising two fused 3-, 4-, 5-, or 6-membered rings, such as 3-azabicyclo[3.1.0]hexane, 8-aza-bicyclo[3.2.1]octane, 3,8-diazabicyclo[3.2.1]octane, 3-Oxa-8-aza-bicyclo [3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O and S. Typically, the heteroaryl is a 5-10 membered ring system (e.g., 5-6 membered monocycle or an 8-10 membered bicycle) or a 5-6 membered ring system. Unless otherwise specified, a heteroaryl is preferably an isolated 5-6 membered ring containing up to 4 heteroatoms selected from N, O and S as ring members. Typical heteroaryl groups include furan, isothiazole, thiadiazole, oxadiazole, indazole, indole, quinoline, 2- or 3-thienyl; 2- or 3-furyl; 2- or 3-pyrrolyl; 1-, 2-, 4-, or 5-imidazolyl; 1, 3-, 4-, or 5-pyrazolyl; 2-, 4-, or 5-thiazolyl, 3-, 4-, or 5-isothiazolyl, 2-, 4-, or 5-oxazolyl, 3-, 4-, or 5-isoxazolyl, 3- or 5-(1, 2,4-triazolyl), 4- or 5-(1,2,3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" refers to the group —OH, or when used as part of a group name such as hydroxyalkyl, it refers to the named group substituted with an —OH. Various embodiments of the invention are described herein. It will be recognized that features specified in each embodiment may be combined with other specified features to provide further embodiments. The following numbered embodiments are representative of some aspects of the invention.

1. A compound of Formula (I):

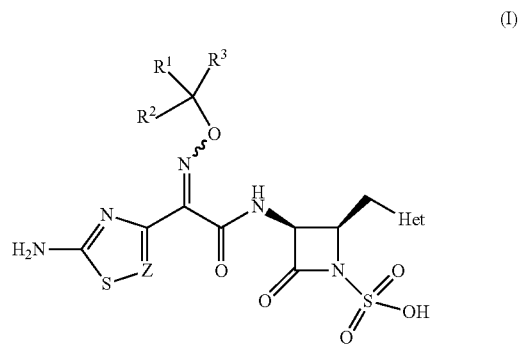

(I)

or a pharmaceutically acceptable salt thereof,
wherein:
Z is $CR^4$ or N;
$R^1$ is H or $C_1$-$C_4$ alkyl;
$R^2$ is selected from the group consisting of H, $C_1$-$C_4$ alkyl, and —COOH
or $R^1$ and $R^2$ taken together with the carbon to which they are attached form a ring selected from a $C_3$-$C_6$ cycloalkyl ring and a 4-6 membered heterocyclic ring containing up to two heteroatoms selected from N, O and S as ring members;
$R^3$ is selected from H, —COOH, and -$L^1$-W—$(CH_2)_{0-2}$-X—$R^5$;
$R^4$ is H or halo;
each $L^1$ is independently a straight chain or branched $C_{1-4}$ alkylene;
W is a bond, O, NH or S;
X is phenyl, or a 5-6 membered heteroaryl ring containing 1-3 heteroatoms selected from N, O and S as ring members; where the phenyl and 5-6 membered heteroaryl are optionally substituted with one or two groups selected from $C_{1-4}$ alkyl, hydroxy, —CN, F, $C_{1-4}$ alkoxy, —$NH_2$, —$NH(C_{1-4}$ alkyl) and —$N(C_{1-4}$ alkyl$)_2$;

$R^5$ is selected from

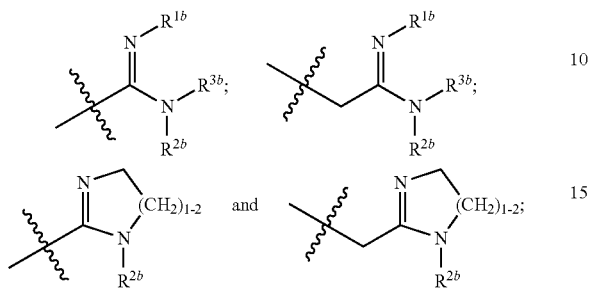

wherein $R^{1b}$, $R^{2b}$, and $R^{3b}$ are independently hydrogen, hydroxy, CN, $(C_1-C_4)$alkyl, $(C_1-C_4)$alkoxy, $(C_3-C_6)$cycloalkyl, or 4-, 5-, 6- or 7-membered heterocyclyl containing N, O or S as a ring member, wherein each $(C_1-C_4)$alkyl, $(C_1-C_4)$alkoxy, $(C_3-C_6)$cycloalkyl, or 4-, 5-, 6- or 7-membered heterocyclyl containing N, O or S as a ring member may be substituted with one, two or three substituents selected independently from Y, and wherein $R^{2b}$ and $R^{ab}$ together with the nitrogen atom to which they are bonded can optionally form a 5- to 7-membered heterocyclyl including 0 or 1 further heteroatoms selected from N, O and S, said heterocyclyl optionally substituted by Y;

Y is selected from F, CN, —$NH_2$, Q, -$L^2$-C(O)$NR^{10}$-$L^2$-Q, -$L^2$-$NR^{10}$—C(O)-$L^2$-Q, -$L^2$-$OR^{10}$, -$L^2$-$N(R^{10})_2$, -$L^2$-$N^+(R^{11})_3$, -$L^2$-$NR^{10}$—C(O)$R^{10}$, -$L^2$-$NR^{10}$-$L^2$-$N(R^{10})_2$, -$L^2$-O—C(O)$OR^{10}$, -$L^2$-O—C(O)—$N(R^{10})_2$, -$L^2$-$NR^{10}$—C(O)—$N(R^{10})_2$, -$L^2$-$NR^{10}$—C(O)—$OR^{11}$, -$L^2$-C(=$NR^{10}$)—$N(R^{10})_2$, —$CON(R^{10})_2$, -$L^2$-$NR^{10}$—C(=$NR^{10}$)—$N(R^{10})_2$, -$L^2$-$NR^{10}$—C(=$NR^{10}$)—$R^{10}$, -$L^2$-C(O)$N(R^{10})_2$, -$L^2$-O—$SO_3R^{10}$;

$L^2$ is independently at each occurrence a bond or a straight chain or branched $C_{1-4}$ alkylene, optionally substituted with $NH_2$, OH, or F;

Het is a 4-6 membered heteroaryl or heterocyclic ring, where the heteroaryl ring contains 1 to 4 heteroatoms selected from N, O and S as ring members and is optionally substituted with one or two groups selected from Y, OH, $NH_2$, —C(O)$NR^{10}_2$, and $C_{1-4}$ alkyl optionally substituted with one or two Y; and the heterocyclic ring contains 1 or 2 heteroatoms selected from N, O and S as ring members and is optionally substituted with up to three groups selected from halo, Y, $C_{1-4}$ alkyl optionally substituted with one or two groups selected from Y, =$NR^{10}$, =N—$OR^{10}$, =N—CN, and oxo;

and Het is optionally fused to a 5 or 6 membered heterocyclic or heteroaryl ring containing up to two heteroatoms selected from N—$R^{10}$, O and S as ring members, and optionally substituted with one or two $R^{16}$;

$R^{10}$ and $R^{12}$ are independently H or $C_{1-4}$ alkyl optionally substituted by one or two groups selected from OH, $NH_2$ or Q;

Q is selected from -$L^2$-$N(R^{13})_2$, -$L^2$-$N^+R^{14})_3$, -$L^2$-$NR^{13}$—C(=$NR^{13}$)—$N(R^{13})_2$, -$L^2$-$NR^{13}$—$CR^{13}$(=$NR^{13}$), -$L^2$-$NR^{13}$-$L^2$-Cy, -$L^2$-$NR^{13}$—C(=$NR^{13}$)—$NR^{13}$-$L^2$-Cy, -$L^2$-$NR^{13}$—C(=$NR^{13}$)-$L^2$-Cy, -$L^2$-Cy-$L^2$-$R^{13}$, -$L^2$-Cy-$L^2$-$N(R^{13})_2$, -$L^2$-$NR^{13}$—$SO_2$—$N(R^{13})_2$, -$L^2$-$SO_2$—$N(R^{13})_2$, -$L^2$-$NR^{13}$—$SO_2$—$R^{13}$, -$L^2$-$NR^{13}$-$L^2$-Ar, -$L^2$-S-$L^2$-Cy, -$L^2$-$NR^{13}$—(C=O)—O—$R^{13}$,

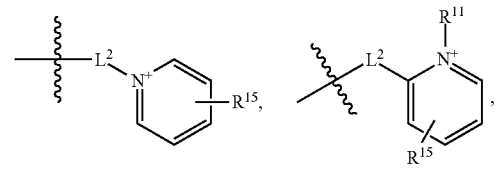

each Cy is independently a 3-6 membered cycloalkyl or 3-6 membered heterocyclyl containing one or two heteroatoms selected from N, O and S as a ring member and optionally fused to a 5-6 membered aryl or heteroaryl ring, wherein each Cy is optionally substituted with one or two groups selected from halo, $C_{1-3}$ haloalkyl, $R^{14}$, hydroxy, $C_{1-4}$ alkoxy, —$NH_2$, —$NH(C_{1-4}$ alkyl) or —$N(C_{1-4}$ alkyl$)_2$;

Ar is phenyl, optionally substituted with one or two groups selected from halo, $C_{1-3}$ haloalkyl, $R^{14}$, hydroxy, $C_{1-4}$ alkoxy, —$NH_2$, —$NH(C_{1-4}$ alkyl) or —$N(C_{1-4}$alkyl$)_2$;

$R^{11}$ is independently at each occurrence $C_{1-4}$ alkyl;

and two $R^{10}$, or two $R^{11}$, or two $R^{12}$ on the same N can cyclize to form a 4-6 membered heterocyclic ring optionally substituted with $C_{1-4}$ alkyl, $C_{1-4}$ alkoxy, hydroxy, or oxo;

$R^{13}$ is independently at each occurrence H or $C_{1-4}$ alkyl optionally substituted with hydroxy, $C_{1-4}$ alkoxy, —$NH_2$, —$NH(C_{1-4}$ alkyl) or —$N(C_{1-4}$ alkyl$)_2$; optionally, when $R^{13}$ is $C_{1-4}$ alkyl it can be substituted with —$OR^{14}$, —$NHR^{14}$, hydroxy, $C_{1-4}$ alkoxy, —$NH_2$, —$NH(C_{1-4}$ alkyl) or —$N(C_{1-4}$ alkyl$)_2$;

$R^{14}$ is independently at each occurrence $C_{1-4}$ alkyl optionally substituted with hydroxy, $C_{1-4}$ alkoxy, —$NH_2$, —$NH(C_{1-4}$ alkyl) or —$N(C_{1-4}$ alkyl$)_2$;

wherein two $R^{13}$ or two $R^{14}$ on the same N can cyclize to form a 4-6 membered heterocyclic ring optionally substituted with $C_{1-4}$ alkyl, $C_{1-4}$ alkoxy, hydroxy, amino or oxo;

$R^{15}$ is H, halo, $C_{1-4}$ alkyl, CN, or —O($C_{1-4}$ alkyl);

each $R^{16}$ is independently halo, $C_{1-4}$ alkyl, —$NH_2$, CN, or —O($C_{1-4}$ alkyl); or a pharmaceutically acceptable salt thereof.

It is understood that each of the compounds in Table B, including compounds of Examples 1-152, is an embodiment of the invention and is intended to fall within the scope of embodiment 1.

2. A compound of Formula (IA):

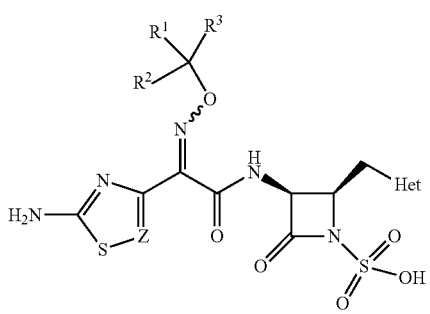

or a pharmaceutically acceptable salt thereof,
wherein:
Z is CR$^4$ or N;
R$^1$ is H or C$_1$-C$_4$ alkyl;
R$^2$ is selected from the group consisting of H, C$_1$-C$_4$ alkyl, and —COOH
  or R$^1$ and R$^2$ taken together with the carbon to which they are attached form a ring selected from a C$_3$-C$_6$ cycloalkyl ring and a 4-6 membered heterocyclic ring containing up to two heteroatoms selected from N, O and S as ring members;
R$^3$ is selected from H, —COOH, and -L$^1$-W—(CH$_2$)$_{0-2}$-X—R$^5$;
R$^4$ is H or halo;
each L$^1$ is independently a straight chain or branched C$_{1-4}$ alkylene;
W is a bond, O, NH or S;
X is phenyl, or a 5-6 membered heteroaryl ring containing 1-3 heteroatoms selected from N, O and S as ring members; where the phenyl and 5-6 membered heteroaryl are optionally substituted with one or two groups selected from C$_{1-4}$ alkyl, hydroxy, —CN, F, C$_{1-4}$ alkoxy, —NH$_2$, —NH(C$_{1-4}$ alkyl) and —N(C$_{1-4}$ alkyl)$_2$;
R$^5$ is selected from

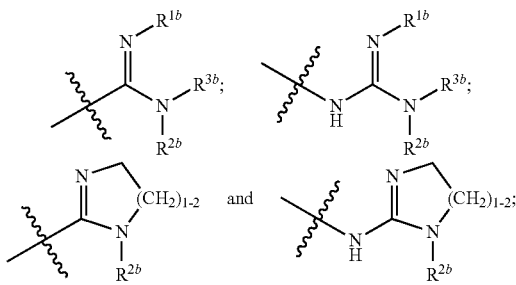

wherein R$^{1b}$, R$^{2b}$, and R$^{3b}$ are independently hydrogen, hydroxy, CN, (C$_1$-C$_4$)alkyl, (C$_1$-C$_4$)alkoxy, (C$_3$-C$_6$) cycloalkyl, or 4-, 5-, 6- or 7-membered heterocyclyl, wherein each (C$_1$-C$_4$)alkyl, (C$_1$-C$_4$)alkoxy, (C$_3$-C$_6$) cycloalkyl, or 4-, 5-, 6- or 7-membered heterocyclyl may be substituted with one, two or three substituents selected independently from Y,
and wherein R$^{2b}$ and R$^{3b}$ together with the nitrogen atom to which they are bonded can optionally form a 5- to 7-membered heterocyclyl including 0 or 1 further heteroatoms selected from N, O and S, said heterocyclyl optionally substituted by Y;

Y is selected from F, CN, —NH$_2$, Q, -L$^2$-C(O)NR$^{10}$-L$^2$-Q, -L$^2$-NR$^{10}$—C(O)-L$^2$-Q, -L$^2$-OR$^{10}$, -L$^2$-N(R$^{10}$)$_2$, -L$^2$-N$^+$(R$^{11}$)$_3$, -L$^2$-NR$^{10}$—C(O)R$^{10}$, -L$^2$-NR$^{10}$-L$^2$-N(R$^{10}$)$_2$, -L$^2$-O—C(O)OR$^{10}$, -L$^2$-O—C(O)—N(R$^{10}$)$_2$, -L$^2$-NR$^{10}$—C(O)—N(R$^{10}$)$_2$, -L$^2$-NR$^{10}$—C(O)—OR$^{11}$, -L$^2$-C(=NR$^{10}$)—N(R$^{10}$)$_2$, —CON(R$^{10}$)$_2$, -L$^2$-NR$^{10}$)—C(=NR$^{10}$)—N(R$^{10}$)$_2$, -L$^2$-NR$^{10}$—C(=NR$^{10}$)—R$^{10}$, -L$^2$-C(O)N(R$^{10}$)$_2$, -L$^2$-O—SO$_3$R$^{10}$;
L$^2$ is independently at each occurrence a bond or a straight chain or branched C$_{1-4}$ alkylene;
Het is a 5-6 membered heteroaryl or heterocyclic ring, where the heteroaryl ring contains 1 to 4 heteroatoms selected from N, O and S as ring members and is optionally substituted with one or two groups selected from Y, C$_{1-4}$ alkyl optionally substituted with one or two Y, NH$_2$, and —C(O)NR$^{10}$$_2$, and the heterocyclic ring contains 1 or 2 heteroatoms selected from N, O and S as ring members and is optionally substituted with up to three groups selected from halo, Y, C$_{1-4}$ alkyl optionally substituted with one or two groups selected from Y, =NR$^{10}$, =N—OR$^{10}$, =N—CN, and oxo;
and Het is optionally fused to a 5 or 6 membered heterocyclic or heteroaryl ring containing up to two heteroatoms selected from N, O and S as ring members, and optionally substituted with one or two R$^{16}$;
R$^{10}$ and R$^{12}$ are independently H or C$_{1-4}$ alkyl optionally substituted by Q;
Q is selected from -L$^2$-N(R$^{13}$)$_2$, -L$^2$-N$^+$(R$^{14}$)$_3$, -L$^2$-NH—C(=NH)—NH$_2$, -L$^2$-C(=NH)—NH$_2$,

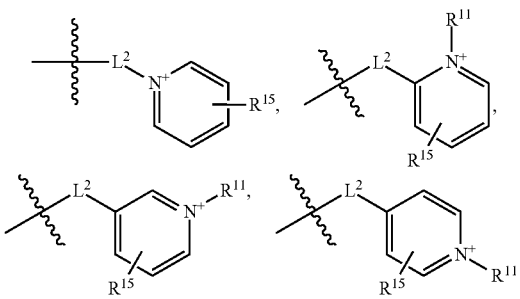

R$^{11}$ is independently at each occurrence C$_{1-4}$ alkyl;
and two R$^{10}$, or two R$^{11}$, or two R$^{12}$ on the same N can cyclize to form a 4-6 membered heterocyclic ring optionally substituted with C$_{1-4}$ alkyl, C$_{1-4}$ alkoxy, hydroxy, or oxo;
R$^{13}$ is independently at each occurrence H or C$_{1-4}$ alkyl optionally substituted with hydroxy, C$_{1-4}$ alkoxy, —NH$_2$, —NH(C$_{1-4}$ alkyl) or —N(C$_{1-4}$ alkyl)$_2$;
R$^{14}$ is independently at each occurrence C$_{1-4}$ alkyl optionally substituted with hydroxy, C$_{1-4}$ alkoxy, —NH$_2$, —NH(C$_{1-4}$ alkyl) or —N(C$_{1-4}$ alkyl)$_2$;
wherein two R$^{13}$ or two R$^{14}$ on the same N can cyclize to form a 4-6 membered heterocyclic ring optionally substituted with C$_{1-4}$ alkyl, C$_{1-4}$ alkoxy, hydroxy, amino or oxo;
R$^{15}$ is H, halo, C$_{1-4}$ alkyl, CN, or —O(C$_{1-4}$ alkyl);
each R$^{16}$ is independently halo, C$_{1-4}$ alkyl, —NH$_2$, CN, or —O(C$_{1-4}$ alkyl);
or a pharmaceutically acceptable salt thereof.
In certain embodiments of the compounds of Formula (I) or (IA), the group represented by —O—CR$^1$R$^2$R$^3$ is selected from

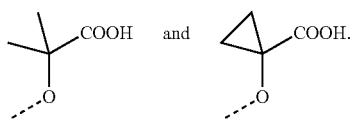

3. The compound of embodiment 1 or embodiment 2, wherein $R^1$ and $R^2$ are each methyl and $R^3$ is —COOH.
4. The compound of embodiment 1 or embodiment 2, wherein $R^1$ and $R^2$ together with the carbon to which they are both attached form a cyclopropane ring and $R^3$ is —COOH.
5. The compound of embodiment 1 or embodiment 2, wherein $R^1$ and $R^2$ are both H and $R^3$ is —COOH.
6. The compound of any of the preceding embodiments, wherein Z is CH.
7. The compound of any of embodiments 1-6, wherein Z is N.
8. The compound of any of the preceding embodiments, wherein Het is a 5-membered heteroaryl ring containing 1-4 nitrogen atoms as ring members and is optionally substituted with Y. In some such embodiments, Het is triazole optionally substituted with Y.
9. The compound of embodiment 8, wherein Het is selected from pyrrole, pyrazole, 1,2,3-triazole, 1,2,4-triazole, 1,3,4-triazole, and 1,2,3,4-tetrazole and is optionally substituted as provided in embodiment 8.
10. The compound of embodiment 8, wherein Het is a 1,2,3-triazol-2-yl group that is optionally substituted with -$L^2$-N($R^{10}$)$_2$ or $L^2$-$NR^{10}$—C(=$NR^{10}$)—N($R^1$)$_2$.
11. The compound of embodiment 8, which is of the formula:

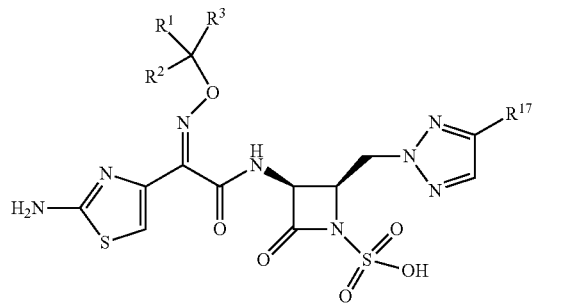

wherein $R^{17}$ is selected from —$CH_2$-$G^1$-($CH_2$)$_{1-4}$-$G^2$ and —$CH_2$-$G^1$-$R^x$—($CH_2$)$_{0-2}$-$G^2$,
$G^1$ is selected from —NH—, —NMe-, —NH—C(=NH)—, and —NH—C(=NH)—NH—,
$G^2$ is selected from —$NH_2$, —NHMe, —NH—C(=NH)—$NH_2$, azetidine, and pyrrolidine; and RX is a ring selected from cyclobutyl, azetidine, and pyrrolidine.
12. The compound of embodiment 8, wherein Het is a 1,2,3-triazol-1-yl group that is optionally substituted with -$L^2$-N($R^{10}$)$_2$ or $L^2$-$NR^{10}$—C(=$NR^{10}$)—N($R^{10}$)$_2$.
13. The compound of embodiment 8, wherein Het is a 1,2,4-triazol-1-yl group that is optionally substituted with -$L^2$-N($R^{10}$)$_2$ or $L^2$-$NR^{10}$—C(=$NR^{10}$)—N($R^{10}$)$_2$.
14. The compound of any of embodiments 1-7, wherein Het is a saturated ring substituted with oxo and optionally further substituted with Y.
15. The compound of embodiment 14, wherein Het is selected from pyrrolidine-2-one, oxazolidin-2-one, and imidazolidin-2-one, and is optionally substituted with Y. In particular embodiments of these compounds, Het is selected from:

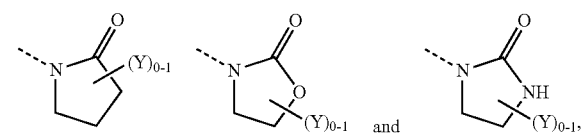

where the dashed bond indicates the point of attachment of Het to the remainder of Formula (I) or (IA), and (Y)$_{0-1}$ represents an optional substituent Y that can be attached at any available position on the ring.
16. The compound of embodiment 14, wherein Het is oxazolidin-2-one and is optionally substituted with -$L^2$-N($R^{10}$)$_2$ or $L^2$-$NR^{10}$—C(=$NR^{10}$)—N($R^1$)$_2$
17. The compound of embodiment 14, wherein Het is oxazolidin-2-one that is substituted on the 5-position with -$L^2$-N($R^{10}$)$_2$ or $L^2$-$NR^{10}$—C(=$NR^{10}$)—N($R^{10}$)$_2$ in the R-configuration
18. The compound of any of the preceding embodiments, having the structure of Formula (II):

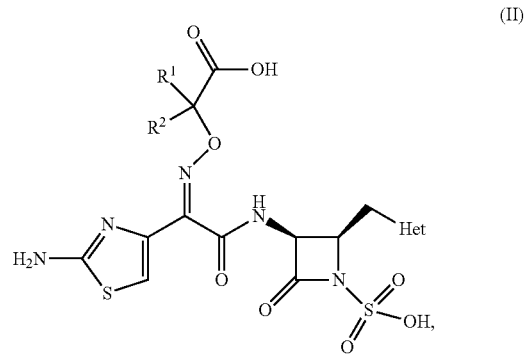

or a pharmaceutically acceptable salt thereof.
19. The compound of embodiment 1 or embodiment 2, which is of the formula (IIIa) or (IIIb):

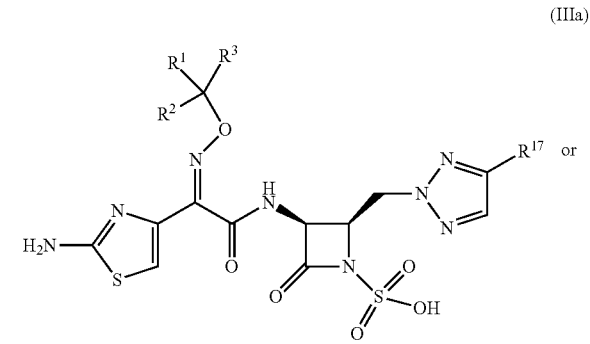

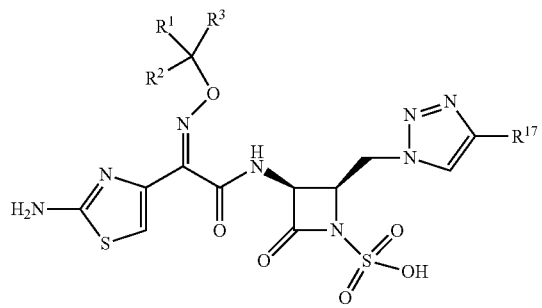
wherein $R^{17}$ is Y or $C_{1-4}$ alkyl optionally substituted with one or two Y.
20. The compound of embodiment 1 or embodiment 2, wherein —O—$CR^1R^2R^3$ is selected from
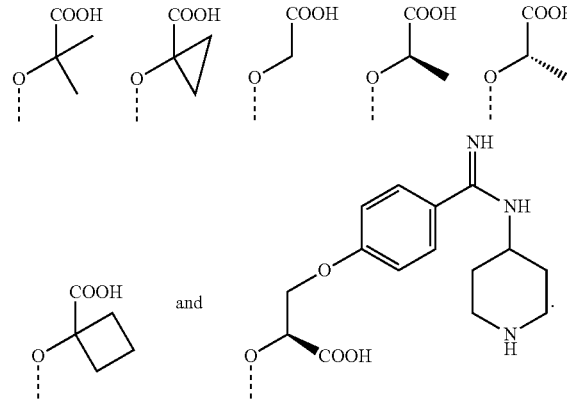
21. The compound of embodiment 1 or embodiment 20, wherein Het is selected from
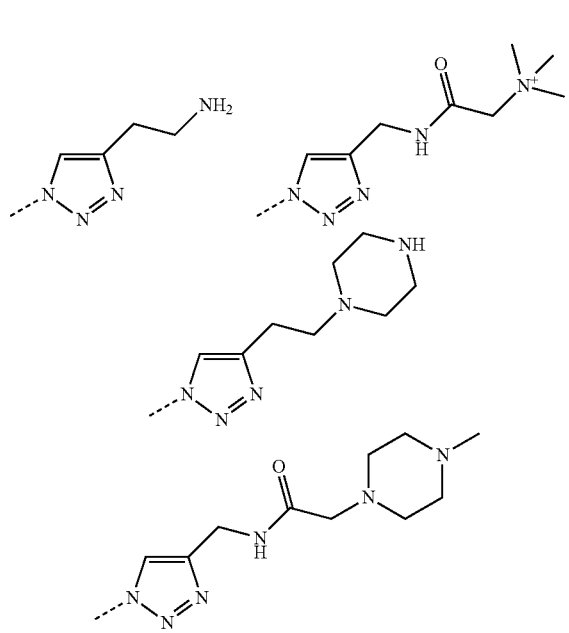
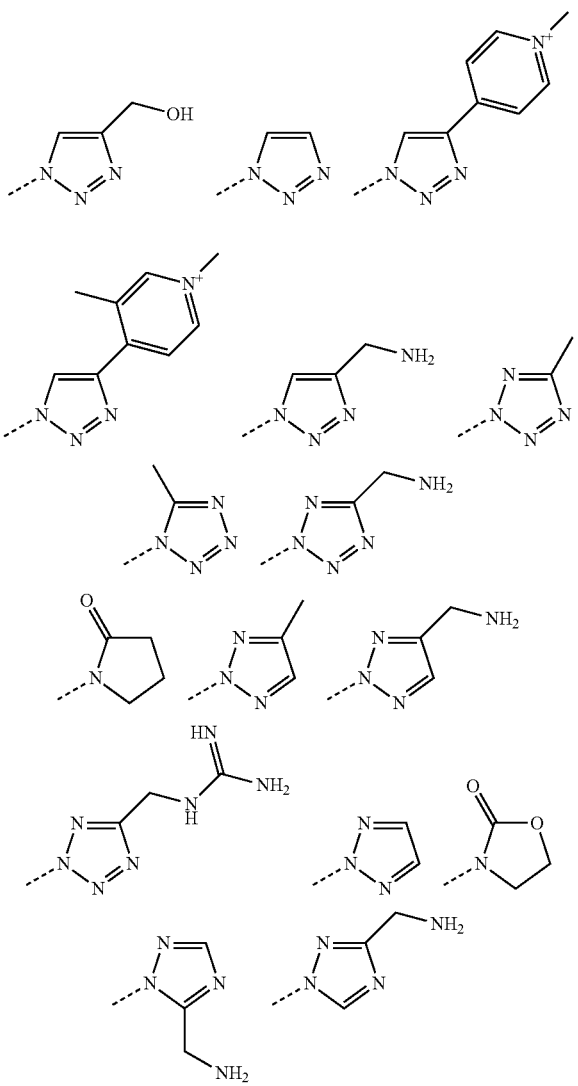

-continued

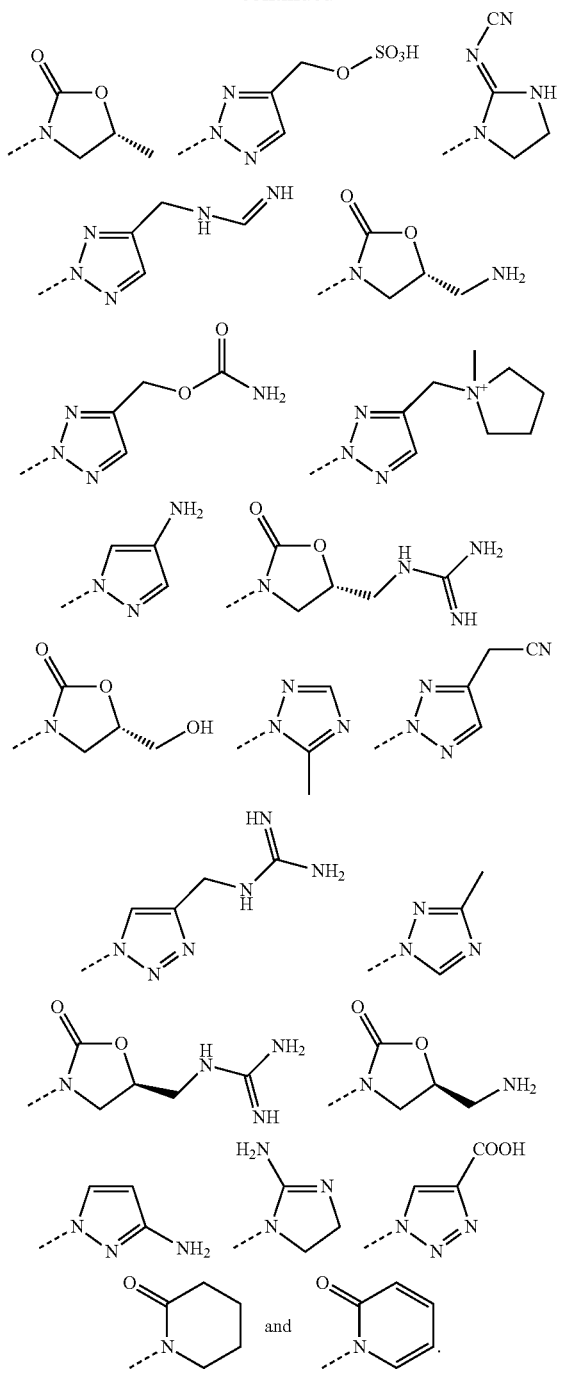

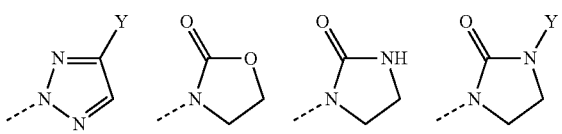

22. The compound of any of embodiments 1-16, wherein $L^2$ is —$(CH_2)_{1-3}$—.

23. The compound of embodiment 18 wherein Het is selected from:

-continued

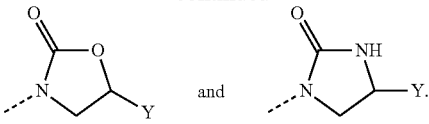

24. The compound of embodiment 18, wherein Het is selected from

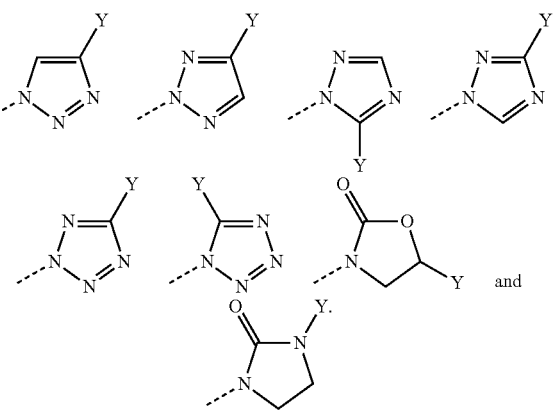

25. The compound of embodiment 19, 23, or 25, wherein Y is selected from Q, -$L^2$-$OR^{10}$, -$L^2$-$N(R^{10})_2$, -$L^2$-$N^+(R^{11})_3$, -$L^2$-$NR^{10}$—$C(O)R^{10}$, -$L^2$-O—$C(O)OR^{10}$, -$L^2$-O—C(O)—) $N(R^{10})_2$, -$L_2$-$NR^{10}$—C(O)—$N(R^{10})_2$, -$L^2$-C(=$NR^{10}$)—$N(R^{10})_2$, —$CON(R^{10})^2$, -$L^2$-$NR_{10}$—C(=$NR^{10}$)—$N(R^{10})_2$, and -$L^2$-$NR_{10}$—C(=$NR^{10}$)—$R^{10}$.

Alternatively, the compound of embodiment 19, 23 or 24 wherein Y is of the formula -$L^2$-$NR^{10}$-$L^2$-$N(R^{10})_2$, e.g. Y can be a group such as —$CH_2$—$NR^{10}$—$(CH_2)_{2-3}$-$N(R^{10})_2$; in particular embodiments of these compounds, $R^{10}$ is H.

26. The compound of any of embodiments 6-25, wherein $R^3$ is of the formula

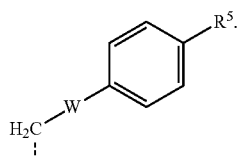

27. The compound of embodiment 26, wherein $R^3$ is

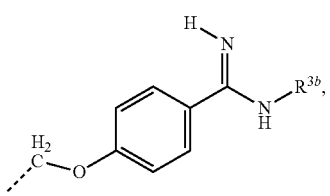

where $R^{3b}$ is selected from H, azetidine, pyrrolidine and piperidine.

28. The compound of any of the preceding embodiments, which is a pharmaceutically acceptable salt.

29. A pharmaceutical composition comprising a compound of any of the preceding embodiments and at least one pharmaceutically acceptable excipient.

30. A method to treat a Gram-negative bacterial infection, which comprises administering to a subject in need of such treatment a compound of any of embodiments 1-27, or a pharmaceutical composition of embodiment 29.

31. The method of embodiment 30, wherein the bacterial infection is caused by a species of *Burkholderia, Citrobacter, Enterobacter, Escherichia, Klebsiella, Meningitidis, Morganella, Pseudomonas, Proteus, Salmonella, Serratia, Acinetobacter, Bacteroides, Campylobacter, Neisseria*, or *Stenotrophomonas* bacteria.

32. The method of embodiment 30, wherein the bacterial infection is nosocomial pneumonia, an intraabdominal infection, or a urinary tract infection caused by a species of Enterobacteriaceae.

33. A compound according to any of embodiments 1-27 for use as a medicament.

34. The compound of embodiment 33, wherein the medicament is an antibacterial agent.

35. The compound of embodiment 33, wherein the antibacterial agent is for treatment of a Gram-negative bacterial infection caused by a species of *Citrobacter, Enterobacter, Escherichia, Klebsiella, Morganella, Pseudomonas, Proteus, Salmonella, Serratia, Acinetobacter, Bacteroides, Burkholderia, Campylobacter, Neisseria*, or *Stenotrophomonas*.

36. A pharmaceutical combination, comprising a compound according to any of embodiments 1-27 and a second therapeutic agent.

In compounds of Formula (I) and various embodiments described above, the oxime is preferably of the configuration shown here:

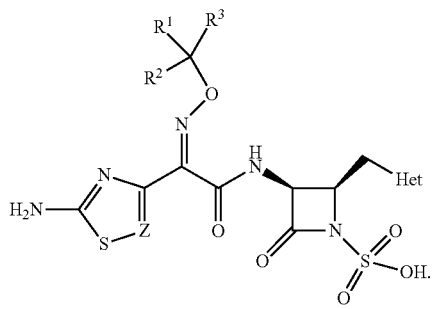

In some instances of any of the embodiments described above, unless otherwise specified, one but not both of $R^2$ and $R^3$ represent —COOH.

In many embodiments of the compounds described above, Het is not pyridine. In preferred embodiments, Het is a 5-membered heteroaryl or heterocyclic ring.

Where $R^3$ in any of the above embodiments is of the formula -$L^1$-W—$(CH_2)_{0-2}$-X—$R^5$, X can be phenyl. In some of these embodiments, $L^1$ is $CH_2$. In some such embodiments, W is O. In some of these embodiments, $R^5$ is a group of the formula

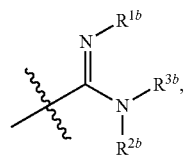

where $R^{1b}$, $R^{2b}$ and $R^{3b}$ are as described for embodiment 1 above. In certain of these embodiments, $R^5$ is of the formula

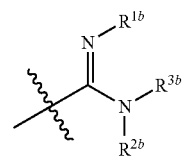

wherein $R^{1b}$ and $R^{2b}$ each represent H, and $R^{3b}$ can be H, or a heterocyclic group such as 4-piperidinyl. Suitably, in these embodiments $R^1$ is H and $R^2$ is H or COOH.

In a further aspect, the invention provides:
A pharmaceutical combination comprising (a) a first therapeutic agent which is a compound of the invention, e.g. a compound of formula (I) or any subformula thereof described herein, and (b) a second therapeutic agent as described above.

A method as defined above comprising co-administration, e.g. concomitantly or in sequence, of a therapeutically effective amount of a compound of the invention, e.g. a compound of formula (I) or any subformulae thereof that is described herein, and a second therapeutic agent as described above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

The compounds of the invention may be synthesized by the general synthetic routes below, specific examples of which are described in more detail in the Examples.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can generally be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All process steps for making compounds of the invention can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

The term "optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$, respectively. The invention includes various isotopically labeled compounds of the present invention, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The present invention provides novel compounds, pharmaceutical formulations including the compounds, and methods of treating Gram-negative bacterial infections. Particularly, the compounds are suitable for use to treat infections caused by *Burkholderia, Citrobacter, Enterobacter, Escherichia, Klebsiella, Meningitidis, Morganella, Pseudomonas, Proteus, Salmonella, Serratia, Acinetobacter, Bacteroides, Campylobacter, Neisseria,* or *Stenotrophomonas* bacteria, including species named herein.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. For example, deuterium substitution at non-exchangeable hydrocarbon bonds (e.g., C—H) may retard epimerization and/or metabolic oxidation in vivo.

Isotopically-labeled compounds of the invention, i.e. compounds of formula (I), can generally be prepared by conventional techniques known to those skilled in the art or by processes analogous to those described in the accompanying Examples and Preparations Sections using an appropriate isotopically-labeled reagent in place of the non-labeled reagent previously.

In still another aspect, the invention provides a method for treating a subject with a Gram-negative bacterial infection, the method comprising the step of administering to the subject in need thereof an antibacterially effective amount of a compound of the invention, e.g., a compound of Formula I or salt thereof with a pharmaceutically acceptable carrier.

The compounds of the invention also are useful in the treatment of patients suffering from or susceptible to pneumonia, sepsis, cystic fibrosis, wound, complicated diabetic foot or complicated urinary tract infections and sexually transmitted diseases caused by Gram-negative pathogens. The compounds of the invention also are useful in the conditions that are caused by a species of *Citrobacter, Enterobacter, Escherichia, Klebsiella, Morganella, Proteus, Salmonella, Serratia, Pseudomonas, Acinetobacter, Bacteroides, Burkholderia, Campylobacter, Neisseria,* or *Stenotrophomonas*. In particular, a bacterial infection caused by a species of *Citrobacter, Enterobacter, Escherichia, Klebsiella, Morganella, Proteus, Salmonella, Serratia, Pseudomonas,* or *Acinetobacter* is treatable by methods herein. Particular bacterial species for such treatment include *Citrobacter freundii, Citrobacter koseri, Enterobacter cloacae, Enterobacter faecalis, Enterobacter faecium, Escherichia coli, Klebsiella pneumonia, Klebsiella oxytoca, Morganella morganii, Proteus mirabilis, Salmonella* species, *Serratia marcescens, Pseudomonas aeruginosa,* and *Acinetobacter baumanii,* as well as *Bacteroides bivius, Bacteroides fragilis, Burkholderia cepacia, Campylobacter jejuni, Neisseria gonorrhoeae,* and *Stenotrophomonas maltophilia.*

A compound of the present invention may also be used in combination with other agents, e.g., an additional antibiotic agent that is or is not of the formula I, for treatment of a bacterial infection in a subject, or a compound that enhances the antibacterial activity of the compounds of the invention, including potentiators such as beta-lactamase inhibitors (BLIs). Suitable BLIs for use in combination with the compounds of the invention, including compounds of Formula (I) and subgenera therof, include avibactam, clavulanic acid, sulbactam, tazobactam, and other compounds of the formula

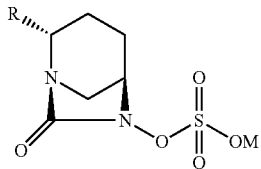

wherein M is H or a pharmaceutically acceptable cation, and R represents CN, —C(O)NR$^1$R$^2$, or an optionally substituted 5-6 membered heterocyclic or heteroaryl group. Suitable amides include those where R$^1$ is H or C$_{1-4}$ alkyl, and R$^2$ is optionally substituted C$_{1-4}$ alkyl, optionally substituted C$_{1-4}$ alkoxy, optionally substituted C$_{1-4}$ alkylamino, an optionally substituted C$_{5-6}$ heterocyclic group, or —NH—C(O)—R$^3$, where R$^3$ is optionally substituted C$_{1-4}$ alkyl, optionally substituted C$_{1-4}$ alkoxy, optionally substituted C$_{1-4}$ alkylamino, an optionally substituted C$_{5-6}$ heterocyclic group. Each heterocyclic or heteroaryl group in these compounds contains 1-2 heteroatoms selected from N, O and S as ring members, and each optionally substituted group can be substituted by 1-2 groups selected from CN, halo, —OH, C$_{1-4}$ alkyl, C$_{1-4}$ alkoxy, amino, C$_{1-4}$ alkylamino, di(C$_{1-4}$alkyl) amino, —COO(C$_{1-4}$ alkyl), and 5-6 membered heterocyclic groups. Suitable compounds of this formula are described in WO2008/039420, WO2009/091856, WO2013/122888, WO2010/126820, WO2009/091856, WO2013/038330, US2013/0225554, WO2013149121, WO2013149136, WO2014141132 and WO2014/033560.

By the term "combination", is meant either a fixed combination in one dosage unit form, or a kit or instructions for the combined administration where a compound of the present invention and a combination partner may be administered independently at the same time or separately within time intervals that especially allow that the combination partners show a cooperative, e.g., synergistic, effect, or any combination thereof.

An embodiment of the present invention provides compounds of the present invention in a pharmaceutical combination with a second therapeutic agent. In some embodiments, the second therapeutic agent is an antibacterial agent. Non-limiting examples of antibacterial agents for use in pharmaceutical combinations of the invention may be selected from the following groups:

(1) Macrolides or ketolides such as erythromycin, azithromycin, clarithromycin, and telithromycin;

(2) Beta-lactams including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, and carbapenems such as doripenem, imipenem, meropenem and PZ-601;

(3) Glycopeptides such as vancomycin and teicoplanin;

(4) Quinolones such asnalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;

(5) Antibacterial sulfonamides and antibacterial sulphanilamides, including para-aminobenzoic acid, sulfadiazine, sulfisoxazole, sulfamethoxazole and sulfathalidine;

(6) Aminoglycosides such as streptomycin, neomycin, kanamycin, paromycin, gentamicin, tobramycin, amikacin, netilmicin, spectinomycin, sisomicin, dibekalin and isepamicin;

(7) Tetracyclines such as tetracycline, chlortetracycline, demeclocycline, minocycline, oxytetracycline, methacycline, doxycycline, tigecycline;

(8) Rifamycins such as rifampicin (also called rifampin), rifapentine, rifabutin, bezoxazinorifamycin and rifaximin;

(9) Lincosamides such as lincomycin and clindamycin;

(10) Streptogramins such as quinupristin and daflopristin;

(11) Oxazolidinones such as linezolid or tedizolid;

(12) Polymyxin, colistin and colymycin;

(13) Trimethoprim and bacitracin;

(14) Efflux pump inhibitors;

(15) Beta-lactamase inhibitors, including avibactam and analogs thereof, and those described above.

The second antibacterial agent may be administered in combination with the compounds of the present inventions wherein the second antibacterial agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is an intravenous administration. An alternative example is an intramuscular administration of a solution comprising a compound of the invention and a second agent.

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) Curr Opin Immunol 14: 391779-82; Bennett et al. (2003) J. Immunol. 170:711-8). PD-1 is expressed on activated B cells, T cells, and monocytes. PD-1 is an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immunoinhibitory checkpoint molecule. When used in combination with antibacterial compounds, these immunomodulators can enhance the antimicrobial response, and thus enhance efficacy relative to treatment with the antibacterial compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells.

Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antibacterial compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; CureTech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906. Other anti-PD-L1 binding agents useful as immunomodulators for methods of the invention include YW243.55.570 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antibacterial compounds of the invention in combination with an immunomodulator include these:

i. A method to treat a bacterial infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.570, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016, xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg, e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

The language "effective amount" of the compound is that amount necessary or sufficient to treat or prevent a bacterial infection and/or a disease or condition described herein. In an example, an effective amount of the compound is an amount sufficient to treat bacterial infection in a subject. In another example, an effective amount of the compound is an amount sufficient to treat a bacterial infection, such as, but not limited to *Pseudomonas aeruginosa* and the like in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Typically, the compound is administered to a subject diagnosed as having a bacterial infection and in need of treatment therefor. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation. Typically, the compound of the invention would be administered over a course of at least 5 days, more commonly at least 7 days or at least 10 days or at least 14 days.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In some embodiments, a pharmaceutically acceptable carrier is sterilized before combination with the compound of the invention.

In some embodiments, the pharmaceutical composition of the invention comprises a compound of any of the numbered embodiments and at least one pharmaceutically acceptable carrier or excipient. In certain embodiments, the pharmaceutical composition of the invention comprises a compound of any of the numbered embodiments and at least two pharmaceutically acceptable carriers or excipients.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, $\alpha$-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. Typically, compounds of the invention would be administered intravenously, in the form of a solution that is often isotonic, such as a saline or glucose solution. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-inwater or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Intravenous administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound of the invention will be that amount of the compound that is the dose effective to produce a therapeutic effect. Such an effective dose will generally depend upon the factors described above. Generally, intravenous and subcutaneous doses of the compounds of this invention for a patient, when used for the indicated antibacterial effects, will range from about 5 to about 150 mg per kilogram of body weight per day, more preferably from about 15 to about 115 mg per kg per day, and still more preferably from about 20 to about 85 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms, or as continuous infusion.

While it is possible for a compound of the present invention to be administered alone, it is preferable to administer the compound as a pharmaceutical composition.

The compounds as defined in embodiments may be synthesized by the general synthetic routes below, specific examples of which are described in more detail in the Examples.

General Synthetic Schemes

One method for synthesizing compounds with formula (I) is described in Scheme A. An alcohol A-1 can be converted into A-2 following the "Mitsunobu" protocol, provided the heterocycle is sufficiently acidic to engage in a Misunobu reaction. Sulfonylation of A-2 provides A-3, which can be deprotected with TFA or formic acid to yield A-4.

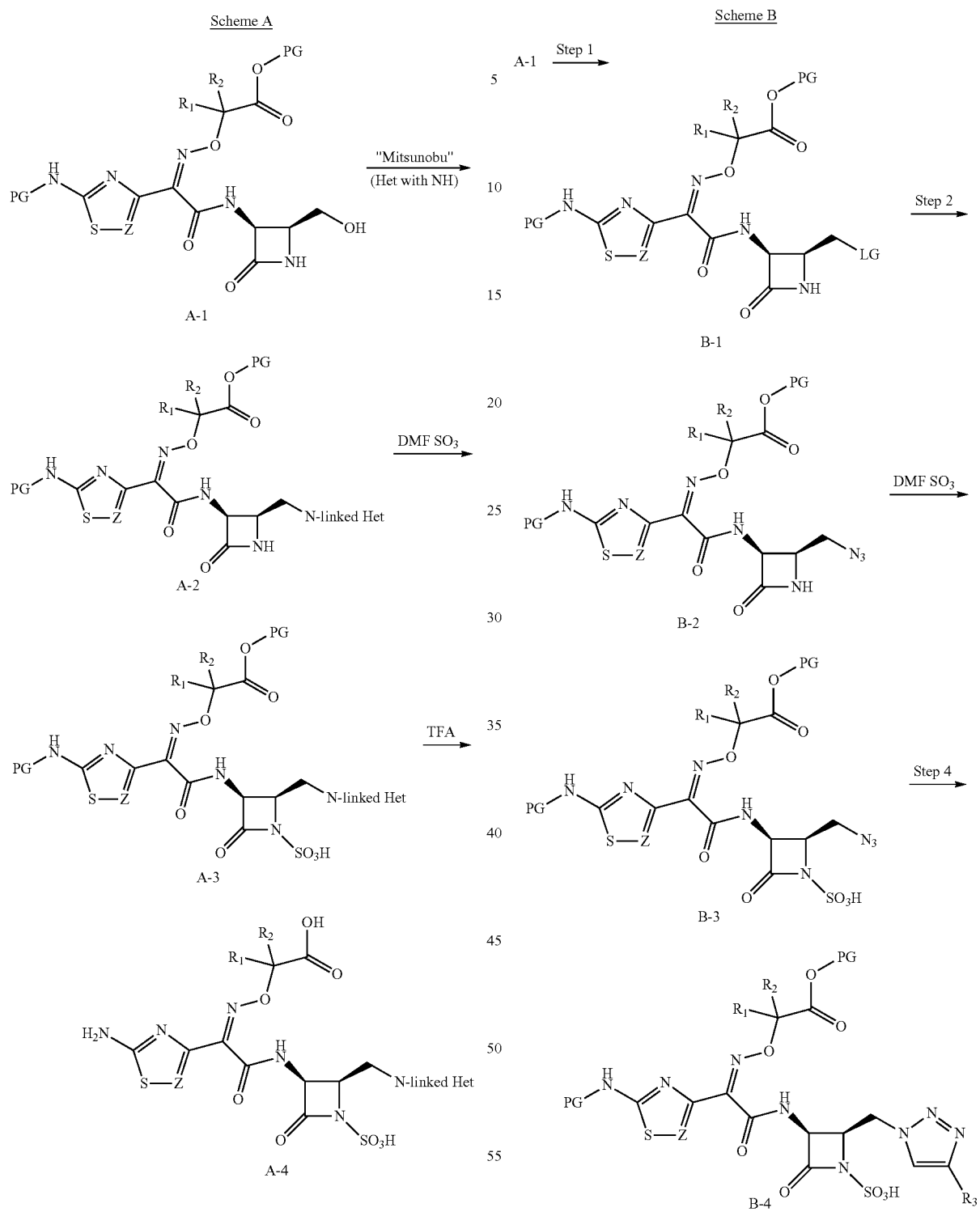

1-Linked 1,2,3 triazole analogs of the intermediate A-3 can accessed as outlined in Scheme B. The alcohol in A-1 is converted into a leaving group and the leaving group is replaced with azide to give B-2, which can be sulfonylated and reacted with an alkyne under "click chemistry" conditions according to the method by Sharpless, to give B-4. Alternatively, "click chemistry" can be performed with B-2, prior to sulfonylation.

Heterocyclic intermediates A-2 could also be obtained as outlined in Scheme C, by alkylation of an amine such as C-1. Suitable alkylation reagents include alkyl halides or epoxides. Alkylation of C-1 could also be effected by reductive amination with an appropriately functionalized and protected aldehyde. Cyclization of C-2 could be effected using a carbonylating agent like Ca Examples of the group Y in these compounds include oxygen or $NR^5$, e.g., NH.

Scheme C

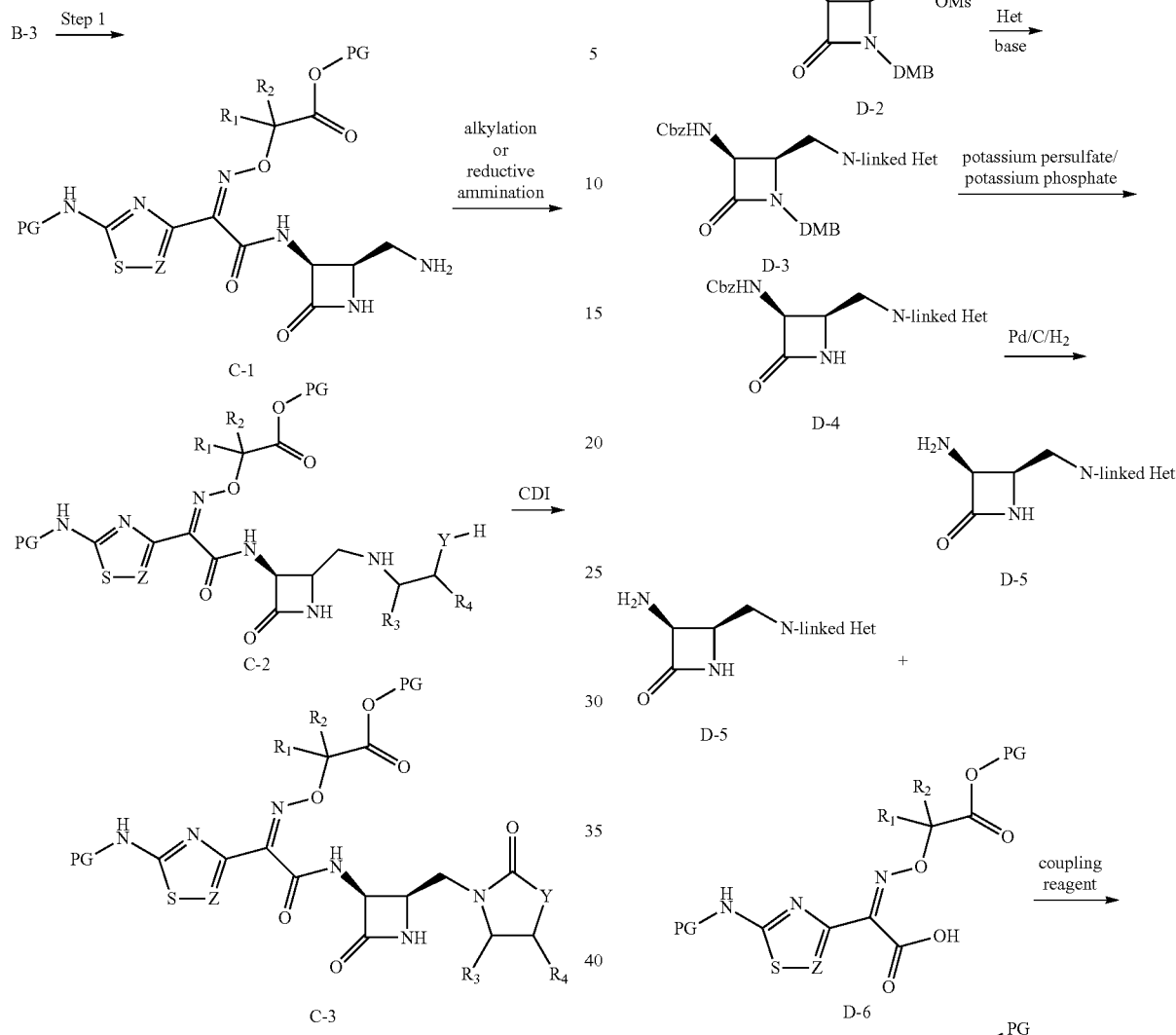

The functionalized amines C-2 were alternatively obtained from B-1 by alkylation with a functionalized amine. A lactam heterocycle may analogously be obtained by alkylation of C-1 with brominated carboxylic esters, followed by base catalyzed cyclization.

A heterocycle may be introduced to yield Intermediate A-2, by substitution of a leaving group in an appropriately protected azetidinone intermediate. Suitable protection groups include Cbz for the amine and DMB for the azetidinone. Deprotection of the Cbz group followed by acylation with appropriately functionalized and protected acids D-6 gave A-2, as outlined in Scheme D.

Scheme D

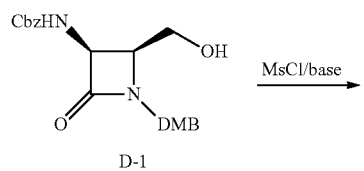

Protected intermediates such as D-1 were also used for introduction of the heterocycle under Mitsunobu conditions, as outlined in Scheme A. D-1 was also converted to the corresponding azide, which was used for "click chemistry" to introduce 1-linked 1,2,3 triazoles following a similar sequence as outlined in Scheme B. D-1 can also be used to yield functionalized amine derivatives that can be converted to heterocycles, as described in Scheme C.

Intermediates of the type A-3 may also be assembled by the sequence outlined in Scheme E, whereby the oxime moiety is introduced after the coupling step.

Scheme-E

[Chemical structures: E-1, D-5, E-2, A-3 showing synthesis scheme with PG-protected aminothiadiazole coupling with azetidinone-containing N-linked Het compound, followed by sulfonation with DMF SO₃ and reaction with H₂N-O-substituted reagent]

Compounds of the Formula (I) are prepared from commonly available compounds using these general schemes and procedures known to those skilled in the art along with the methods and examples provided herein.

EXAMPLES

The invention is further illustrated by the following examples, which should not be construed as further limiting. The assays used throughout the Examples are accepted. Demonstration of efficacy in these assays is predictive of efficacy in subjects.

General Conditions

Mass spectra were acquired on LC-MS, SFC-MS, or GC-MS systems using electrospray, chemical and electron impact ionization methods from a range of instruments of the following configurations: Waters ACQUITY UPLC system and equipped with a ZQ 2000 or SQD MS system where (M+1) refers to the protonated molecular ion of the chemical species, (M+) refers to the unprotonated quaternary ammonium cation, (M+Na) refers to the sodium-incorporated ion and (M−1) refers to the deprotonated molecular ion of the chemical species.

NMR spectra were run on Bruker AVANCE 500 MHz or Varian 400 MHz NMR spectrometers using ICON-NMR, under TopSpin program control. Spectra were measured at 298K, unless indicated otherwise, and were referenced relative to the solvent resonance.

| Instrumentation |
|---|
| MS Methods: Using Agilent 1100 HPLC systems with an Agilent 6110 Mass Spectrometer |
| Method 2m_acidic: |

| | |
|---|---|
| Column | Kinetex C18 50 × 2.1 mm, 2.6 μm |
| Column Temperature | 50° C. |
| Eluents | A: H₂O, B: acetonitrile, both containing 0.1% TFA |
| Flow Rate | 1.2 mL/min |
| Gradient | 2% to 88% B in 1.30 min, 0.15 min 95% B |
| | Method 2m_acidic_polar: |
| Column | Kinetex C18 50 × 2.1 mm, 2.6 μm |
| Column Temperature | 50° C. |
| Eluents | A: H₂O, B: acetonitrile, both containing 0.1% TFA |
| Flow Rate | 1.2 mL/min |
| Gradient | 1% to 30% B in 1.30 min, 0.15 min 98% B |

Abbreviations:
ACN acetonitrile
aq aqueous
app apparent
ATP adenosine 5'-triphosphate
BINAP racemic 2,2'-bis(diphenylphosphino)-1,1'-binaphthyl
Boc tertiary butyl carboxy
br broad
brs broad singlet
BSA bovine serum albumin
CDI 1,1'-carbonyldiimidazole
d doublet
dd doublet of doublets
DCM dichloromethane
DCE 1,2-dichloroethane
DIAD diisopropylazodicarboxylate
DIPEA diisopropylethylamine
DME 1,4-dimethoxyethane
DMF N,N-dimethylformamide
DMSO dimethylsulfoxide
EDTA ethylenediamine tetraacetic acid
ESI electrospray ionization
EtOAc ethyl acetate
g gram
h hour(s)
HATU 1-[Bis(dimethylamino)methylene]-1H-1,2,3-triazolo[4,5-b]pyridinium 3-oxid hexafluorophosphate
HBTU 1-[bis(dimethylamino)methylene]-1H-benzotriazoliumhexafluorophosphate(1-) 3-oxide
HCl hydrochloric acid
HOBt 1-hydroxybenzotriazole
HPLC high performance liquid chromatography
LCMS liquid chromatography and mass spectrometry
m multiplet
m-CPBA 3-chloroperbenzoic acid
MeOH methanol
MS mass spectrometry
mg milligram
min minutes
mL milliliter
mmol millimol
m/z mass to charge ratio NMR nuclear magnetic resonance
p pentet
PdCl$_2$(dppf)-CH$_2$Cl$_2$   1,1'-Bis(diphenylphosphino)ferrocene-palladium(II)dichloride dichloromethane complex
PPh$_3$ triphenylphosphine
ppm parts per million
PyBOP benzotriazol-1-yloxytripyrrolidinophosphonium hexafluorophosphate
q quartet
rac racemic
rt room temperature
R$_t$ retention time
s singlet
satd saturated
t triplet
TBAF tetrabutylammonium fluoride
TBME methyl tert-butyl ether
TFA trifluoroacetic acid
THF tetrahydrofuran
Tris•HCl aminotris(hydroxymethyl)methane hydrochloride Preparation of Intermediates Intermediate A: ((2S,3S)-3-(((benzyloxy)carbonyl)amino)-1-(2,4-dimethoxybenzyl)-4-oxoazetidin-2-yl)methyl methanesulfonate

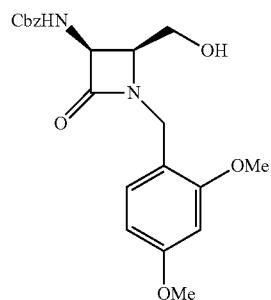

To a solution of benzyl ((2S,3S)-1-(2,4-dimethoxybenzyl)-2-(hydroxymethyl)-4-oxoazetidin-3-yl)carbamate (5.37 g, 13.41 mmol) and TEA (3.72 mL, 26.8 mmol) in DCM at 0° C. was added MsCl (1.15 mL, 14.75 mmol). After stirring at 0° C. for 1 h, it was diluted with water/DCM and the layers were separated. The aqueous layer was extracted with DCM (2×) and the combined organic layers were washed with brine, dried over Na$_2$SO$_4$ and concentrated in vacuo. The crude residue was taken up in toluene and concentrated (2×), affording the title compound as an off white solid. It was used as such in subsequent reactions. LCMS: R$_t$=0.86 min, m/z=479.2 (M+1) Method 2m_acidic.

Intermediate B: tert-Butyl ((2H-tetrazol-5-yl)methyl)carbamate

To a flask charged with (2H-tetrazol-5-yl)methylamine (1.67 g, 16.85 mmol), Boc anhydride (3.86, 17.70 mmol) and water (16.85 mL) was added NaOH (4 N, 4.42 mL, 17.70 mmol). The resulting suspension was stirred at rt for 12 h then cooled to 0° C., whereupon HCl (1 N) was added until pH=4-5. The precipitate was collected by filtration and the mother liquor was cooled to 0° C. and reacidified with HCl (1 N) until pH=4-5. More of the precipitate was collected and combined with the first batch, washing the lot with heptane to afford the title compound (2.74 g, 82%) as a white solid. LCMS: R$_t$=0.38 min, m/z=200.2 (M+1) Method 2m_acidic.

Intermediate C: tert-Butyl ((1H-1,2,4-triazol-3-yl)methyl)carbamate

To a solution of 2H-[1,2,4]triazole-3-yl-methylamine hydrochloride (583 mg, 4.33 mmol) and Boc-anhydride (993 mg, 4.55 mmol) in water (5.78 mL) was added NaOH (4N, 1.137 mL, 4.55 mmol). After stirring for 48 h the white precipitate was collected by filtration. The solid was suspended in heptane, sonicated then filtered, washing the filter cake with heptane. LCMS: R$_t$=0.41 min, m/z=199.2 (M+1) Method 2m_acidic.

Intermediate D: 3-(((2R,3S)-3-amino-4-oxoazetidin-2-yl)methyl)oxazolidin-2-one

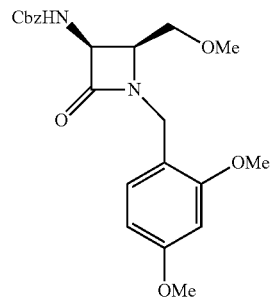

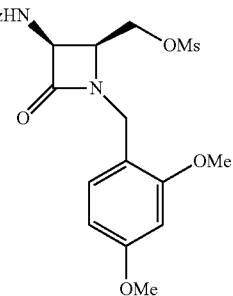

Step 1

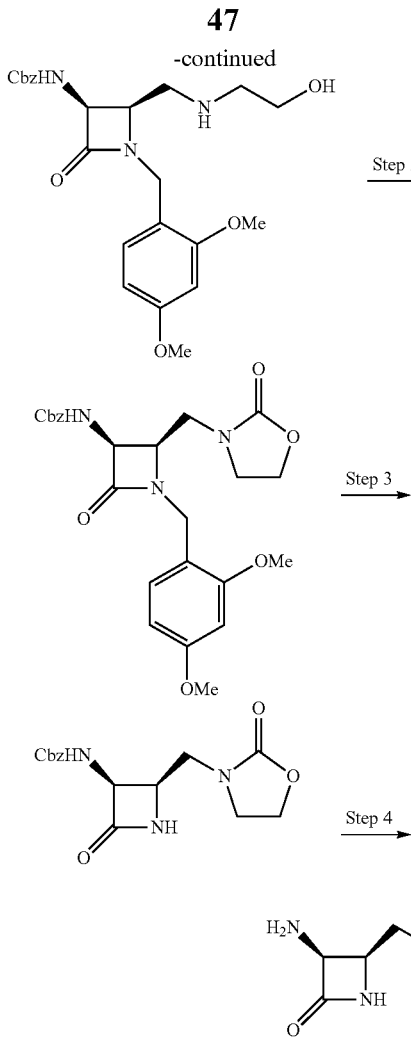

Step 1: Benzyl ((2R,3S)-1-(2,4-dimethoxybenzyl)-2-(((2-hydroxyethyl)amino)methyl)-4-oxoazetidin-3-yl)carbamate To a solution of ((2S,3S)-3-(((benzyloxy)carbonyl)amino)-1-(2,4-dimethoxybenzyl)-4-oxoazetidin-2-yl)methyl methanesulfonate (6.43 g, 13.4 mmol) in Acetonitrile (44.8 ml) was added ethanolamine (8.13 ml, 134 mmol) followed by DIPEA (7.0 ml, 40 mmol). The solution was heated to 80° C. for 20 h, whereupon it was cooled to rt, diluted with EtOAc, washed with water, dried over Na$_2$SO$_4$ and concentrated in vacuo, afford the title compound (4.47 g, 75%) as a white solid. LCMS: R$_t$=0.60 min, m/z=444.2 (M+1).

Step 2: Benzyl ((3S,4R)-1-(2,4-dimethoxybenzyl)-2-oxo-4-((2-oxooxazolidin-3-yl)methyl)azetidin-3-yl)carbamate To a solution of benzyl ((2R,3S)-1-(2,4-dimethoxybenzyl)-2-(((2-hydroxyethyl)amino)methyl)-4-oxoazetidin-3-yl)carbamate (4.47 g, 10.08 mmol) in chloroform (50 ml) was added CDI (4.90 g, 30.2 mmol). After stirring at rt for 30 min it was concentrated in vacuo. The crude residue was purified via silica gel chromatography (MeOH-DCM, 0-5%), affording the title compound (3.84 g, 81%) as a white foam. LCMS: R$_t$=0.76 min, m/z=470.1 (M+1).

Step 3: Benzyl ((3S,4R)-2-oxo-4-((2-oxooxazolidin-3-yl)methyl)azetidin-3-yl)carbamate Prepared in an analogous manner to example 4, step 2 using benzyl ((3S,4R)-1-(2,4-dimethoxybenzyl)-2-oxo-4-((2-oxooxazolidin-3-yl)methyl)azetidin-3-yl)carbamate (3.84 g, 8.18 mmol), K$_2$S$_2$O$_8$ (3.10 g, 11.5 mmol) and K$_2$HPO$_4$ (1.852 g, 10.6 mmol) in ACN:water (2:1, 136 mL) while heating for 40 min at 90° C. More K$_2$S$_2$O$_8$ (663 g, 2.45 mmol) and K$_2$HPO$_4$ (370 mg, 2.13 mmol) were added and it was heated for another 3 h. More K$_2$S$_2$O$_8$ (332 mg, 1.23 mmol) and K$_2$HPO$_4$ (185 mg, 1.06 mmol) were added, and it was heated for an additional 2 h, whereupon it was concentrated in vacuo, removing most of the ACN. The mixture was diluted with brine/EtOAc and the layers were separated. The aqueous layer was extracted with EtOAc (3×) and the combined organic layers were dried over Na$_2$SO$_4$. The crude residue was purified via silica gel chromatography (EtOAc-Heptane, 0-100% then MeOH-DCM, 10%) to afford the title compound (1.61 g, 62%) as a beige foam. LCMS: R$_t$=0.51 min, m/z=320.0 (M+1) Method 2m_acidic.

Step 4: 3-(((2R,3S)-3-amino-4-oxoazetidin-2-yl)methyl)oxazolidin-2-one

Prepared in an analogous manner to example 4, step 3 using benzyl ((3S,4R)-2-oxo-4-((2-oxooxazolidin-3-yl)methyl)azetidin-3-yl)carbamate (96 mg, 0.30 mmol) and Pd/C 10% Degussa type 101 (10%, 64 mg) in EtOH:MeOH (4:1, 1.5 mL) for 1 h. The crude residue was used as such in following step. LCMS: R$_t$=0.11 min, m/z=186.0 (M+1) Method 2m_acidic.

Intermediate E: tert-Butyl (4-(2-(((2R,3S)-2-((1H-1,2,4-triazol-1-yl)methyl)-4-oxoazetidin-3-yl)amino)-2-oxoacetyl)thiazol-2-yl)carbamate

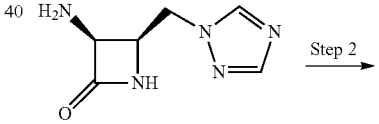

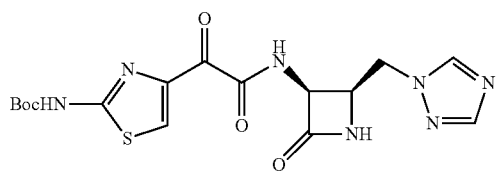

To a slurry of 2-(2-((tert-butoxycarbonyl)amino)thiazol-4-yl)-2-oxoacetic acid (2.72 g, 9.99 mmol) and HATU (3.80, 10.0 mmol) in DCM:DMF (3:1, 33.3 mL) at 0° C. was added DIPEA (2.91 mL, 16.7 mmol). A soln of (3S,4R)-4-((1H-1,2,4-triazol-1-yl)methyl)-3-aminoazetidin-2-one (1.39 g, 8.33 mmol) in DCM:DMF (1:1, 32 mL) was added followed by a DMF (3 mL) wash. After stirring for 48 h the dark solution was diluted with EtOAc (150 mL)/brine (140 mL) and the layers were separated. The aqueous was extracted with EtOAc (3×) and the combined organic layers were washed with brine (70 mL). The brine layer wash was re-extracted with EtOAc. The combined organic layers were dried over Na₂SO₄ and concd in vacuo. The crude residue was purified via silica gel chromatography (MeOH-DCM, 0-10%), affording the title compound (2.38 g, 68%) as a red solid. LCMS: R_t=0.59 min, m/z=422.0 (M+1) Method 2m_acidic; ¹H NMR (400 MHz, DMSO-d₆) δ 11.85 (s, 1H), 9.70 (d, J=9.3 Hz, 1H), 8.52 (d, J=1.6 Hz, 1H), 8.48 (s, 1H), 8.44 (s, 1H), 7.96 (s, 1H), 5.28 (ddd, J=9.3, 5.2, 1.5 Hz, 1H), 4.45 (dd, J=14.2, 5.3 Hz, 1H), 4.36 (dd, J=14.1, 7.6 Hz, 1H), 4.18 (dt, J=7.6, 5.3 Hz, 1H), 1.47 (s, 9H).

Intermediate F: (2R,3S)-2-((1H-1,2,4-triazol-1-yl)methyl)-3-(2-(2-((tert-butoxycarbonyl)amino)thiazol-4-yl)-2-oxoacetamido)-4-oxoazetidine-1-sulfonic acid

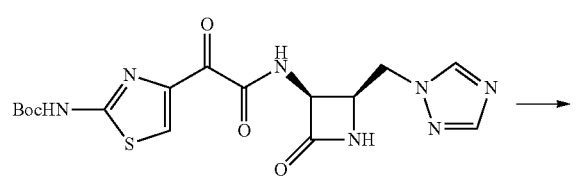

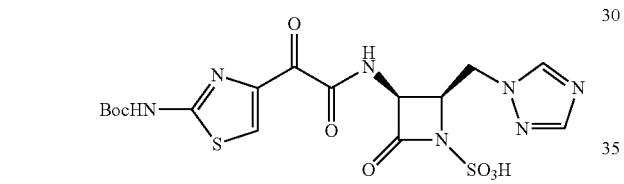

To a soln of tert-Butyl (4-(2-(((2R,3S)-2-((1H-1,2,4-triazol-1-yl)methyl)-4-oxoazetidin-3-yl)amino)-2-oxoacetyl)thiazol-2-yl)carbamate (200 mg, 0.475 mmol) in DMF (4.75 mL) at 0° C. was added SO₃.DMF (367 mg, 2.40 mmol). After 16 h of stirring it was concentrated in vacuo and purified with HP21 resin (ACN-water, 0-50%), affording the title compound (110 mg, 46%) as a pale yellow solid. LCMS: R_t=0.54 min, m/z=501.9 (M+1) Method 2m_acidic; ¹H NMR (400 MHz, DMSO-d₆) δ 11.87 (s, 1H), 9.75 (d, J=9.2 Hz, 1H), 8.94 (s, 1H), 8.44 (s, 1H), 8.34 (s, 1H), 5.25 (dd, J=9.1, 5.4 Hz, 1H), 4.75 (dd, J=14.3, 4.9 Hz, 1H), 4.61 (dd, J=14.4, 7.6 Hz, 1H), 4.43 (dt, J=7.6, 5.2 Hz, 1H), 1.49 (s, 9H).

Intermediate G: Benzyl ((2S,3S)-1-(2,4-dimethoxybenzyl)-2-(hydroxymethyl)-4-oxoazetidin-3-yl)carbamate

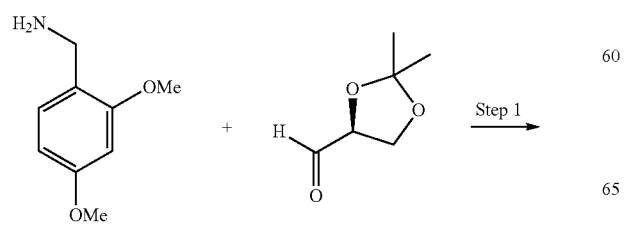

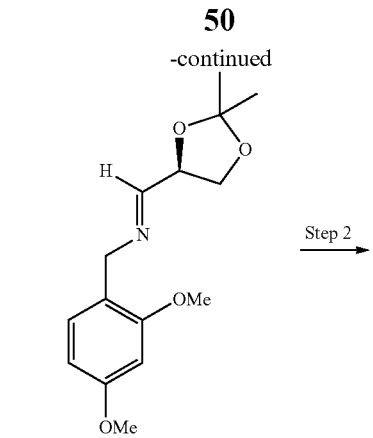

Step 2

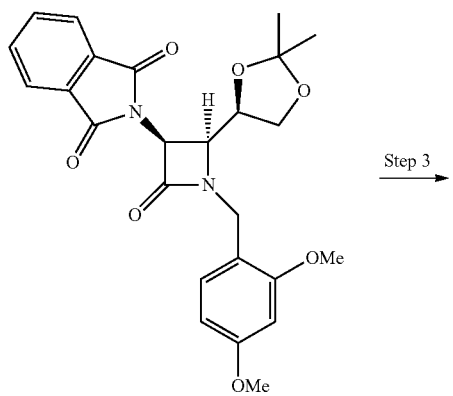

Step 3

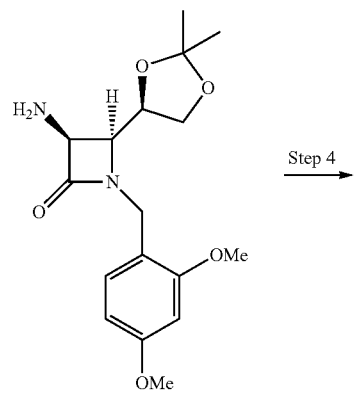

Step 4

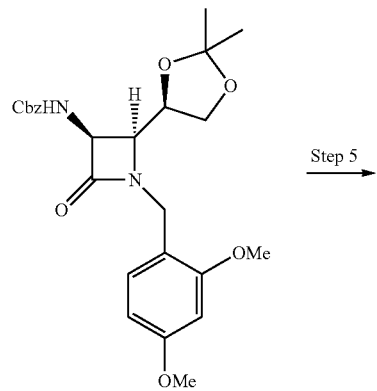

Step 5

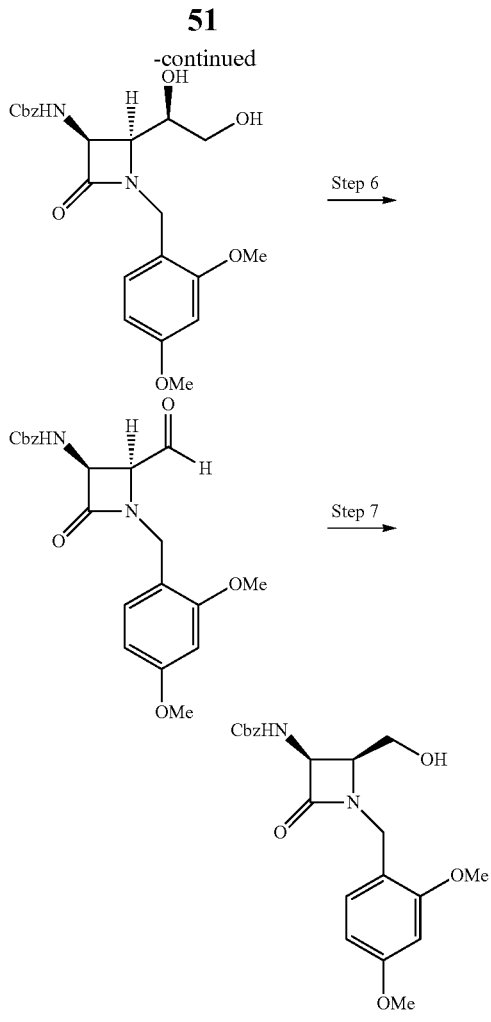

Step 1: (R,E)-1-(2,4-dimethoxyphenyl)-N-((2,2-dimethyl-1,3-dioxolan-4-yl)methylene)methanamine Prepared according to the procedure described by Hubschwerlen, C. and Schmid, G. *Helv. Chim. Acta* 1983, 66, 2206-2209 with the addition of MgSO$_4$. To a suspension of (S)-2,2-dimethyl-1,3-dioxolane-4-carbaldehyde (Carbosynth LLC, 346 g, 43% in DCM, 1.143 mol) and MgSO$_4$ (278 g) in DCM (1.5 L) at 0° C. was added 2,4-dimethoxybenzylamine (193 g, 1.154 mol) over 20 min. After stirring at rt for 2 h it was filtered, washing the filter cake with DCM (2×250 mL). The mother liquor was used directly in step 2.

Step 2: 2-((2S,3S)-1-(2,4-dimethoxybenzyl)-2-((R)-2,2-dimethyl-1,3-dioxolan-4-yl)-4-oxoazetidin-3-yl)isoindoline-1,3-dione Prepared according to the procedure described by Hubschwerlen, C. and Schmid, G. *Helv. Chim. Acta* 1983, 66, 2206-2209. After addition of TEA (322 mL, 2.31 mol) to the crude mother liquor from step 1, it was cooled to 0° C. followed by addition of a solution of 2-(1,3-dioxoisoindolin-2-yl)acetyl chloride (284.3 g, 1.272 mol) in DCM (1 L) over a period of 30 min. The mixture was allowed to warm to rt and stirred for an additional 16 h, whereupon it was washed with water (2×1 L), saturated NaHCO$_3$ (aq, 1 L), brine (1 L), dried over Na$_2$SO$_4$ and concentrated in vacuo, affording the crude title compound (631 g, assumed quantitative) as a pale yellow solid. The $^1$H NMR of a purified sample (EtOAc-Heptane, 40-60%) was an identical match to literature reported data.

Step 3: (3S,4S)-3-amino-1-(2,4-dimethoxybenzyl)-4-((R)-2,2-dimethyl-1,3-dioxolan-4-yl)azetidin-2-one To a solution of crude 2-((2S,3S)-1-(2,4-dimethoxybenzyl)-2-((R)-2,2-dimethyl-1,3-dioxolan-4-yl)-4-oxoazetidin-3-yl)isoindoline-1,3-dione (631 g, 1.143 mol, assumed quantitative conversion from step 2) in EtOH (8.2 L) was added hydrazine hydrate (235 mL, 50-60%, ~4 mol) over 20 min. The resulting mixture was heated to reflux for 3 h, cooled to rt, filtered, washed with EtOH and concentrated in vacuo. The residue was slurried in EtOAc (4 L), filtered and washed with water (2×1 L).

Step 4: Benzyl ((2S,3S)-1-(2,4-dimethoxybenzyl)-2-((R)-2,2-dimethyl-1,3-dioxolan-4-yl)-4-oxoazetidin-3-yl)carbamate To the crude organic solution from step 3 (EtOAc, 4 L) cooled to 0° C. was added saturated NaHCO$_3$ (aq, 2.05 L) followed by benzyl chloroformate (205 mL, 1.43 mol), dropwise over 1 h. After stirring at rt for 2 h the layers were separated and the aqueous layer was extracted with EtOAc (2×50 mL). The combined organic layers were washed with water, brine, dried over Na$_2$SO$_4$ and concentrated in vacuo. The crude residue was treated with MeOH (2 L), filtered and washed with MeOH (2×200 mL) to afford pure title compound (155 g) as a white solid. The mother liquor was cooled to −20° C. for 12 h and the resulting precipitate was collected by filtration, affording additional title compound (90 g) for a combined 45% yield over 4 steps. LCMS: m/z=471.1 (M+1).

Step 5: Benzyl ((2S,3S)-2-((R)-1,2-dihydroxyethyl)-1-(2,4-dimethoxybenzyl)-4-oxoazetidin-3-yl)carbamate To a solution of benzyl ((2S,3S)-1-(2,4-dimethoxybenzyl)-2-((R)-2,2-dimethyl-1,3-dioxolan-4-yl)-4-oxoazetidin-3-yl)carbamate (267 g, 0.567 mol) in THF (3 L) was added a solution of TsOH.H$_2$O (43.6 g, 0.229 mol) in water (0.75 L). The bilayer was heated to 70° C. for 16 h then cooled to rt, neutralized to pH=7 with saturated NaHCO$_3$ (aq) and concentrated in vacuo. The resulting mixture was filtered, washed with water and dried to afford the title compound (240 g, 98%) as a pale yellow solid. LCMS: m/z=431.1 (M+1).

Step 6: Benzyl ((2S,3S)-1-(2,4-dimethoxybenzyl)-2-formyl-4-oxoazetidin-3-yl)carbamate To a solution of benzyl ((2S,3S)-2-((R)-1,2-dihydroxyethyl)-1-(2,4-dimethoxybenzyl)-4-oxoazetidin-3-yl)carbamate (240 g, 0.557 mol) in EtOAc (4.5 L) was added a solution of sodium periodate (132 g, 0.617 mol) in water (1.125 L) and the bilayer was heated to 50° C. for 2 h, whereupon it was cooled to rt and the layers were separated. The aqueous layer was extracted with EtOAc (500 mL) and the combined organic layers were washed with water, brine, dried over Na$_2$SO$_4$ and concentrated in vacuo to afford the title compound (218 g, 98%) as a pale yellow solid. LCMS: m/z=399.0 (M+1). $^1$H NMR (400 MHz, DMSO-d$_6$) δ 9.32 (d, J=3.2 Hz, 1H), 8.19 (d, J=8.5 Hz, 1H), 7.39-7.23 (m, 5H), 7.16 (d, J=8.3 Hz, 1H), 6.53 (d, J=2.4 Hz, 1H), 6.47 (dd, J=8.3, 2.4 Hz, 1H), 5.00-4.96 (m, 2H), 4.90 (dd, J=8.5, 5.8

Hz, 1H), 4.38 (d, J=14.5 Hz, 1H), 4.29 (d, J=14.5 Hz, 1H), 4.05 (dd, J=5.9, 3.3 Hz, 1H), 3.73 (s, 3H), 3.70 (s, 3H).

Step 7: Benzyl ((2S,3S)-1-(2,4-dimethoxybenzyl)-2-(hydroxymethyl)-4-oxoazetidin-3-yl)carbamate To a solution of benzyl ((2S,3S)-1-(2,4-dimethoxybenzyl)-2-formyl-4-oxoazetidin-3-yl)carbamate (218 g, 0.546 mol) in a mixture of DCM:MeOH (4:1, 2.25 L) at 0° C. was added sodium borohydride (41.3 g, 1.09 mol), portion-wise. The resulting mixture was stirred at 0° C. for 2 h, whereupon it was quenched with cold water (1 L) for 30 min and the layers were separated. The aqueous layer was extracted with DCM (3×200 mL) and the combined organic layers were washed with water, brine, dried over $Na_2SO_4$ and concentrated in vacuo to afford the title compound (208 g, 95%) as an off white solid. LCMS: m/z=401.2 (M+1); $^1$H NMR (300 MHz, $CDCl_3$) δ 7.37-7.29 (m, 5H), 7.21-7.18 (m, 1H), 6.46-6.49 (m, 2H), 5.82 (bd, J=9.6 Hz, 1H), 5.18-5.08 (m, 3H), 4.45 (d, J=14.4 Hz, 1H), 4.28 (d, J=14.4 Hz, 1H), 3.83 (s, 3H), 3.79 (s, 3H), 3.76-3.72 (m, 1H), 3.63-3.52 (m, 2H), 1.87 (dd, J=9.6, 4.0 Hz, 1H).

Intermediate H: tert-Butyl 2-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)-2-methylpropanoate

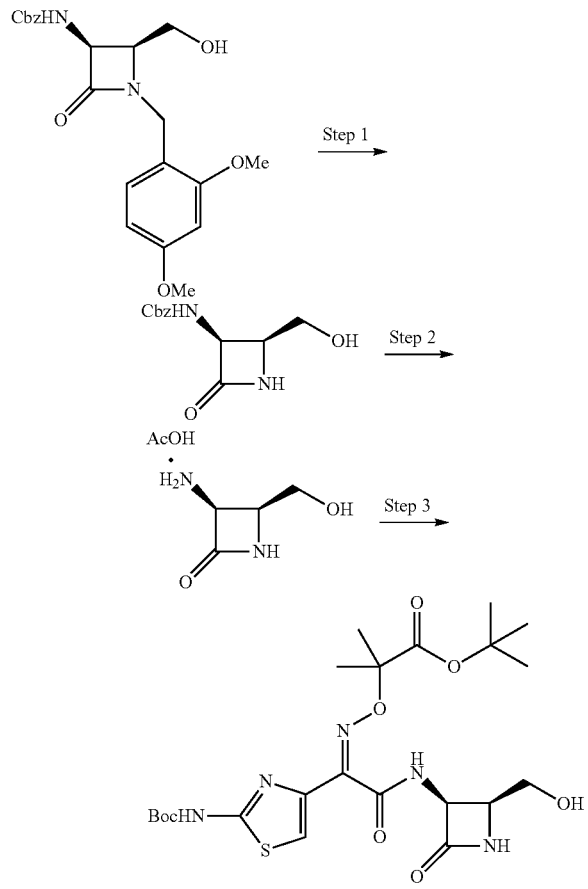

Step 1

Benzyl ((2S,3S)-2-(hydroxymethyl)-4-oxoazetidin-3-yl)carbamate. Prepared according to Mastalerz et al. *J. Med. Chem.* 1988, 31, 1190. To a solution of intermediate G (208 g, 0.529 mol) in ACN (4 L) was added potassium persulfate (243 g, 0.899 mol) followed by a solution of dipotassium phosphate (147.4 g, 0.846 mol) in water (2 L). The resulting mixture was heated to 90° C. for 4 h then cooled to rt and concentrated in vacuo, removing most of the ACN. The mixture was extracted with EtOAc (1 L, 2×200 mL) and the combined organic layers were washed with water, brine, dried over $Na_2SO_4$ and concentrated in vacuo. The crude residue was purified via silica gel chromatography (EtOAc-Hexanes, 50-100%), affording the title compound (86 g, 65%) as a white solid. Analytical data was an identical match to that reported in the literature.

Step 2: (2S,3S)-2-(hydroxymethyl)-4-oxoazetidin-3-amonium acetate

To a solution of benzyl ((2S,3S)-2-(hydroxymethyl)-4-oxoazetidin-3-yl)carbamate (25 g, 100 mmol) in MeOH (350 mL) was added Pd on C (10% wet, 2.5 g) followed by AcOH (11.4 mL, 200 mmol). The mixture was evacuated and recharged with $H_2$ (3×), bringing the final pressure to 50 psi. It was stirred at rt for 2 h, then discharged, filtered over celite and concentrated in vacuo, affording the crude title compound (22 g) as a light brown oil, which was used directly in step 3.

Step 3: tert-Butyl 2-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)-2-methylpropanoate To a solution of (Z)-tert-butyl 2-(((2-(benzo[d]thiazol-2-ylthio)-1-(2-((tert-butoxycarbonyl)amino)-thiazol-4-yl)-2-oxoethylidene)amino)oxy)-2-methylpropanoate (85 g, 116.4 mmol) in DMF (200 mL) at 0° C. was added a solution of (2S,3S)-2-(hydroxymethyl)-4-oxoazetidin-3-amonium acetate (22 g, 100 mmol, assumed quantitative from step 2) in DMF (100 mL) followed by DIPEA (52.2 mL, 300 mmol). The mixture was allowed to warm to rt and stirred for an additional 16 h, whereupon it was concentrated in vacuo and purified via silica gel chromatography (EtOAc-Hexanes, 25-100%), affording the crude title compound (44 g, 83%) as a pale yellow solid. LCMS: m/z=526.1 (M−1); $^1$H NMR (400 MHz, $CDCl_3$): δ 8.94 (s, 1H), 8.02 (d, J=7.8 Hz, 1H), 7.30 (s, 1H), 6.48 (s, 1H), 5.43 (dd, J=7.4, 4.7 Hz, 1H), 4.25 (m, 1H), 4.02 (dd, J=8.6, 4.3 Hz, 1H), 3.86 (m, 2H), 1.56 (s, 3H), 1.55 (s, 3H), 1.52 (s, 9H), 1.44 (9H, s).

Intermediate I: (Z)-tert-Butyl 2-(((2-(benzo[d]thiazol-2-ylthio)-1-(2-((tert-butoxycarbonyl)amino)thiazol-4-yl)-2-oxoethylidene)amino)oxy)-2-methylpropanoate To a suspension of (Z)-2-(((1-(tert-butoxy)-2-methyl-1-oxopropan-2-yl)oxy)imino)-2-(2-((tert-butoxycarbonyl)amino)thiazol-4-yl)acetic acid (50 g, 116.4 mmol) and 2,2'-dibenzothiazolyldisulfide (54.2 g, 163 mmol) in DCM (1 L) was added triphenylphosphine (44.3 g, 168.8 mmol) followed by drop-wise addition of TEA (22.7 mL, 163 mmol). After stirring for 16 h, the mixture was concentrated and used directly in the preparation of intermediate H. LCMS: m/z=579.0 (M+1).

Intermediate J: tert-Butyl 2-(((Z)-(2-(((2R,3S)-2-(azidomethyl)-4-oxoazetidin-3-yl)amino)-1-(2-((tert-butoxycarbonyl)amino)thiazol-4-yl)-2-oxoethylidene)amino)oxy)-2-methylpropanoate

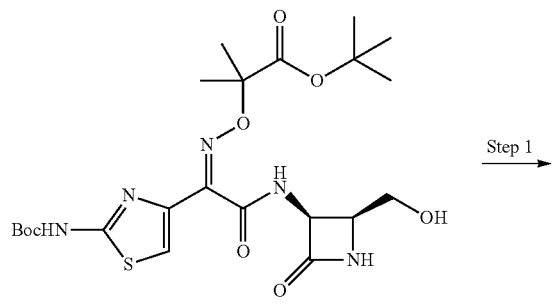

Step 1

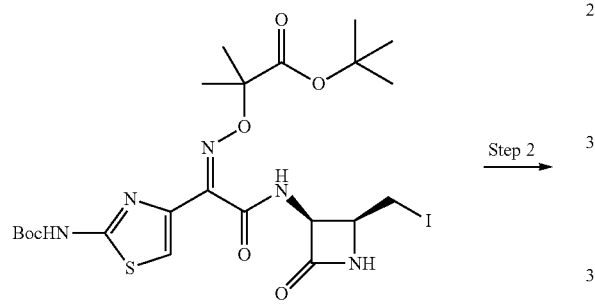

Step 2

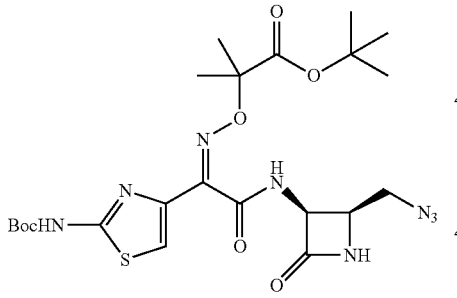

Step 1: tert-Butyl 2-(((Z)-(1-(2-((tert-butoxycarbonyl)amino)thiazol-4-yl)-2-(((2S,3S)-2-(iodomethyl)-4-oxoazetidin-3-yl)amino)-2-oxoethylidene)amino)oxy)-2-methylpropanoate To a solution of intermediate H (44.0 g, 83.4 mmol), triphenylphosphine (43.7 g, 166.8 mmol) and imidazole (11.4 g, 166.8 mmol) in DCM was added iodine (42.3 g, 166.8 mmol) portion-wise over 5 min. After stirring at rt for 16 h it was diluted with DCM (300 mL), washed with saturated $Na_2S_2O_3$ (aq, 200 mL), water, brine, dried over $Na_2SO_4$ and concentrated in vacuo. The crude residue was purified via column chromatography (EtOAc-Hexanes, 25-75%), affording the title compound (33 g, 62%) as a yellow solid. LCMS: m/z=638.0 (M−1). $^1$H NMR data was an identical match to that described in WO2012073138(A1).

Step 2: tert-Butyl 2-(((Z)-(2-(((2R,3S)-2-(azidomethyl)-4-oxoazetidin-3-yl)amino)-1-(2-((tert-butoxycarbonyl)amino)thiazol-4-yl)-2-oxoethylidene)amino)oxy)-2-methylpropanoate To a solution of tert-butyl 2-(((Z)-(1-(2-((tert-butoxycarbonyl)amino)thiazol-4-yl)-2-(((2S,3S)-2-(iodomethyl)-4-oxoazetidin-3-yl)amino)-2-oxoethylidene)amino)oxy)-2-methylpropanoate (24.0 g, 37.6 mmol) in THF (200 mL) at 0° C. was added TEA (10.5 mL, 75.2 mmol) followed by tetrabutylammonium azide (13.9 g, 48.9 mmol). The mixture was allowed to warm to rt and stirred for an additional 16 h, whereupon it was poured into ice-water (200 mL) and extracted with EtOAc (3×100 mL). The combined organic layers were washed with brine, dried over $Na_2SO_4$ and concentrated in vacuo. The crude residue was purified via silica gel chromatography, affording the title compound (17.0 g, 82%) as a pale yellow solid. LCMS: m/z=551.0 (M−1). $^1$H NMR data was an identical match to that described in WO2012073138(A1).

Intermediate K: (2R,3S)-2-(azidomethyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid

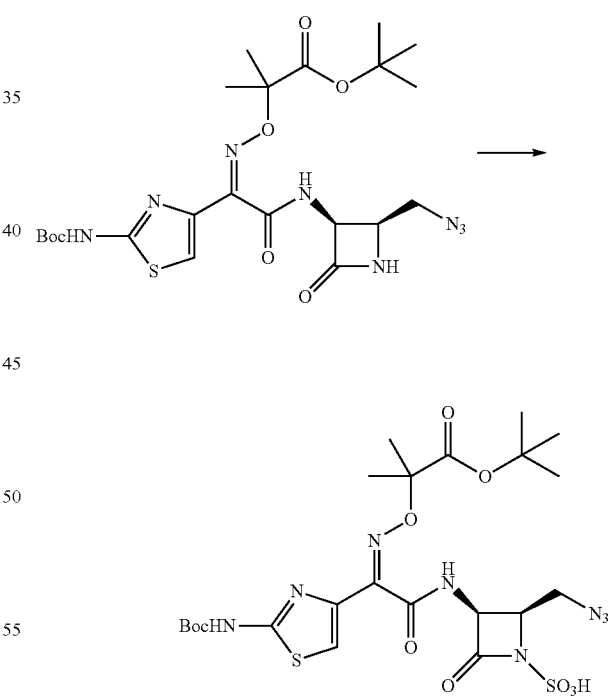

To a solution of intermediate J (500 mg, 0.905 mmol) in DMF (8 mL) was added $SO_3 \cdot DMF$ (1.38 g, 9.05 mmol). After stirring at rt for 4 h, it was diluted with EtOAc (50 mL) and washed with water, followed by brine until pH=7. The organic layer was dried over $Na_2SO_4$ and concentrated in vacuo, affording the title compound (500 mg, 87%) as a light yellow solid. LCMS: m/z=629.85 (M−1); $^1$H NMR (400 MHz, DMSO-$d_6$) δ 11.85 (s, 1H), 9.10 (d, J=8.9 Hz, 1H), 8.63

(s, 1H), 7.27 (d, J=11.1 Hz, 1H), 6.55 (s, 1H), 5.37-5.13 (m, 1H), 3.83-3.54 (m, 2H), 1.46-1.41 (m, 4H), 1.43-1.35 (m, 7H).

Intermediate L: tert-Butyl 2-(((Z)-(2-(((2R,3S)-2-(aminomethyl)-4-oxoazetidin-3-yl)amino)-1-(2-((tert-butoxycarbonyl)amino)thiazol-4-yl)-2-oxoethylidene)amino)oxy)-2-methylpropanoate

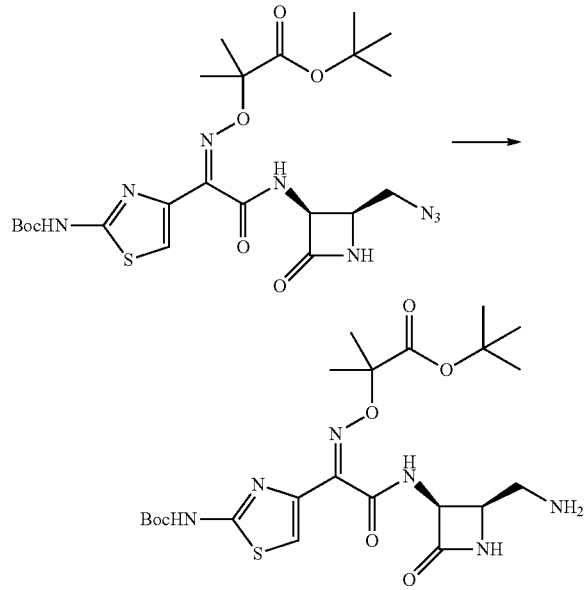

To a solution of intermediate J (17.0 g, 30.8 mmol) in EtOH (300 mL) was added Pd on C (10%, wet, 2.0 g) under nitrogen. The mixture was evacuated and recharged with H$_2$ (3×), bringing the final pressure to 50 psi. It was stirred at rt for 2 h, then discharged, filtered over celite and concentrated in vacuo, affording the crude title compound (15.5 g, 96%) as a pale yellow solid. LCMS: m/z=527.1 (M−1). $^1$H NMR data was an identical match to that described in WO2012073138 (A1).

Intermediate M: tert-Butyl 4-(but-3-yn-1-yl)piperazine-1-carboxylate

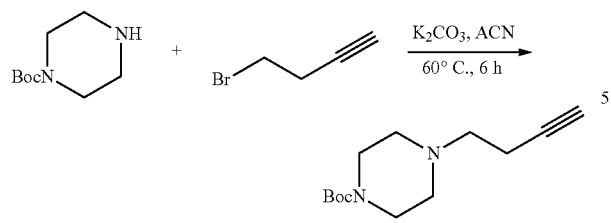

To a solution of 1-Boc-piperazine (0.5 g, 2.68 mmol) in acetonitrile (2.5 mL) was added K$_2$CO$_3$ (0.55 g, 4.02 mmol) followed by 4-bromo-1-butyne (0.39 g, 2.95 mmol). The mixture was heated at 60° C. for 6 h, allowed to come to room temperature, diluted with water and extracted with EtOAc (2×15 mL). The combined organic layers washed with water, brine, dried over Na$_2$SO$_4$ and concentrated under vacuo to afford the title compound (0.55 g, 86%); LCMS: m/z=239.10 (M+1). Method 2minLowp.

Intermediate N: N,N,N-Trimethyl-2-oxo-2-(prop-2-yn-1-ylamino)ethanaminium bromide

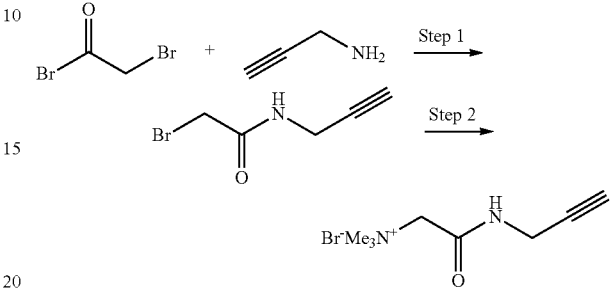

Step 1: 2-Bromo-N-(prop-2-yn-1-yl)acetamide

To a solution of bromoacetyl bromide (2.1 g, 10.34 mmol) and triethylamine (1.5 mL, 10.34 mmol) in DCM (20 mL) cooled to 0° C., was added a solution of propargylamine (0.57 g, 10.34 mmol) in DCM (10 mL) drop-wise over a period of 5 min, maintaining stirring throughout. The mixture was stirred at 0° C. for 2 h, whereupon the solids were filtered and the filtrate was concentrated in vacuo. The crude residue was purified via column chromatography (60-120 mesh silica, 50% EtOAc: Hexane), affording the title compound (1.3 g, 72%) as an off white solid; LCMS: m/z=176.2 (M+1); $^1$H NMR (300 MHz, CDCl$_3$) δ 6.68 (brs, 1H), 4.09 (dd, J=5.4, 2.6 Hz, 2H), 3.90 (s, 2H), 2.28 (t, J=2.6 Hz, 1H).

Step 2: N,N,N-Trimethyl-2-oxo-2-(prop-2-yn-1-ylamino)ethanaminium bromide

To a solution of 2-bromo-N-(prop-2-yn-1-yl)acetamide (0.6 g, 3.4 mmol) in acetonitrile (5 mL) was added trimethylamine (30% in MeOH, 5 mL). The mixture was stirred at room temperature for 16 h and concentrated in vacuo. The resulting residue was triturated with ether, resulting in the title compound (780 mg, 97%); LCMS: m/z=155.1 (M+1); $^1$H NMR (300 MHz, DMSO-d$_6$) δ 9.03 (t, J=5.3 Hz, 1H), 4.17 (s, 2H), 3.95 (dd, J=5.4, 2.6 Hz, 2H), 3.23 (s, 9H), 2.09 (s, 1H).

Intermediate O: 2-(4-methylpiperazin-1-yl)-N-(prop-2-yn-1-yl)acetamide

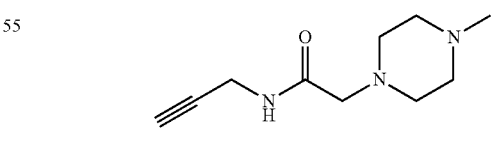

To a solution of 2-bromo-N-(prop-2-yn-1-yl)acetamide (0.7 g, 3.98 mmol) in DCM (10 mL) added N-methyl piperazine (0.66 mL, 5.96 mmol) drop wise. Reaction mixture stirred at rt for 16 h, diluted with DCM and washed with water and brine. The organic layer was dried over Na$_2$SO$_4$ and concentrated in vacuo. The crude residue was triturated with ether-pentane, affording the title compound (0.38 g, 49%);

LCMS: m/z=196.15 (M+1); $^1$H NMR (300 MHz, DMSO-$d_6$) δ 8.06 (d, J=6.1 Hz, 1H), 3.86 (dd, J=5.9, 2.5 Hz, 2H), 3.07 (t, J=2.5 Hz, 1H), 2.91 (s, 2H), 2.47-2.25 (m, 8H), 2.15 (s, 3H).

Intermediate P: 4-Ethynyl-1-methylpyridin-1-ium trifluoromethanesulfonate

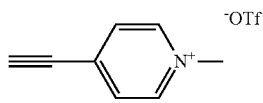

Prepared according to Rubinsztajn et al. *Tetrahedron Lett.* 1992, 33, 14, 1821-1824. To a suspension of 4-ethynylpyridine hydrochloride (500 mg, 3.58 mmol) in DCM (50 mL) at 0° C. was slowly added NaHCO$_3$ solution (aq, satd, 10 mL). After stirring for 5 min, the layers were separated and the aqueous was extracted with DCM (2×10 mL). The combined organic layers were dried over Na$_2$SO$_4$, concentrated in vacuo and subjected to high vacuum for 10 min. The crude residue was dissolved in DCM (10 mL), cooled to 0° C. and methyl triflate (450 µL, 3.94 mmol) was added drop-wise. After stirring for 30 min at 0° C., ether was added and the precipitate was collected and dried, affording the title compound (870 mg, 91%) as a light brown solid. Analytical data was identical to literature reported values.

Intermediate Q:
4-Ethynyl-1,3-dimethylpyridin-1-ium trifluoromethanesulfonate

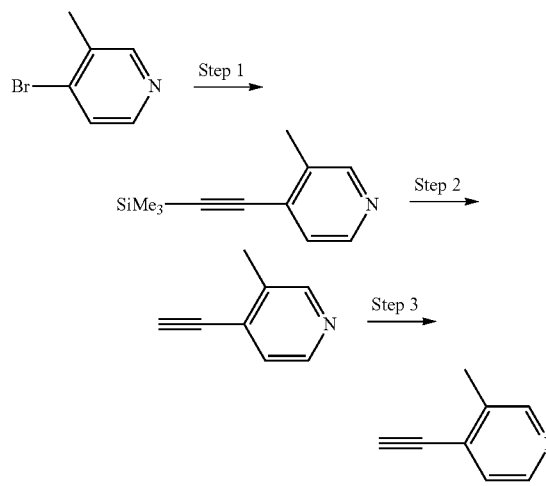

Step 1: 3-Methyl-4-((trimethylsilyl)ethynyl)pyridine

To a solution of 4-bromo-3-methyl pyridine hydrochloride (5.0 g, 24.0 mmol) in THF (degassed, 80 mL) was added copper iodide (450 mg, 2.40 mmol) and triethylamine (20.0 mL, 143.9 mmol). After degassing for 15 min, palladium tetrakis triphenylphosphine (830 mg, 0.72 mmol) and trimethylsilylacetylene (6.10 mL, 43.16 mmol) were added. The mixture was heated at 50° C. for 16 h then cooled to rt and filtered. The crude residue was purified via silica gel chromatography (EtOAc-Hexanes, 10%) to afford the title compound (3.95 g, 87%) as clear but dark oil.

Step 2: 4-Ethynyl-3-methylpyridine

Prepared according to the method described in WO2013/028590. To a solution of 4-ethynyl-3-methylpyridine (3.79 g, 20 mmol) in THF (50 mL) was added TBAF (1 M in THF, 40 mL, 40 mmol). After stirring at rt for 1 h, the solution was concentrated in vacuo. The crude residue was purified via silica gel chromatography (EtOAc-Hexanes, 20-40%) affording the title compound (1.70 g, 72%) as an off white solid.

Step 3: 4-Ethynyl-1,3-dimethylpyridin-1-ium trifluoromethanesulfonate

Prepared according to Rubinsztajn et al. *Tetrahedron Lett.* 1992, 33, 14, 1821-1824. To a solution of 4-ethynyl-3-methylpyridine (420 mg, 3.58 mmol) in DCM (10 mL) at 0° C. was added methyl triflate (450 µL, 3.94 mmol), drop-wise. After stirring for 30 min at 0° C., ether was added and the precipitate was collected and dried, affording the title compound (863 mg, 86%) as a light brown solid.

Intermediate R: tert-Butyl ((2H-1,2,3-triazol-4-yl)methyl)carbamate

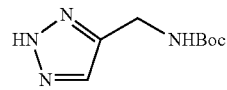

To a solution of N-Boc-propargyl amine (1.60 g, 10.3 mmol) in a mixture of DMF:MeOH (4:1, 10 mL) was added trimethylsilylazide (2.0 mL, 15.2 mmol) and CuI (95 mg, 0.50 mmol). The resulting mixture was heated to 100° C. for 16 h, whereupon it was concentrated in vacuo and purified via silica gel chromatography, affording the title compound (2.0 g, 99%) as a light yellow oil; LCMS: m/z=196.9 (M−1).

Intermediate S

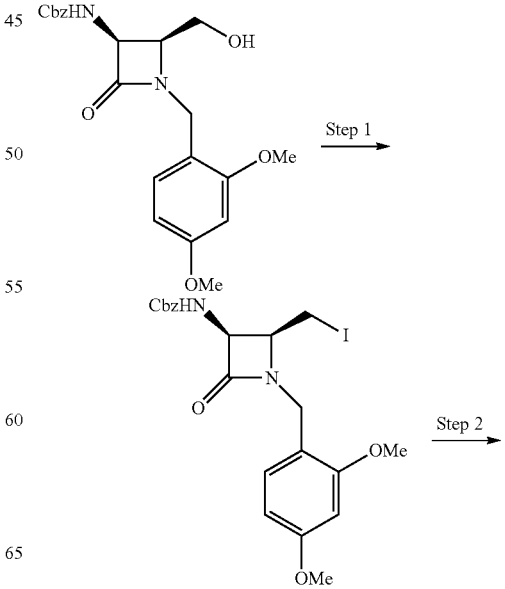

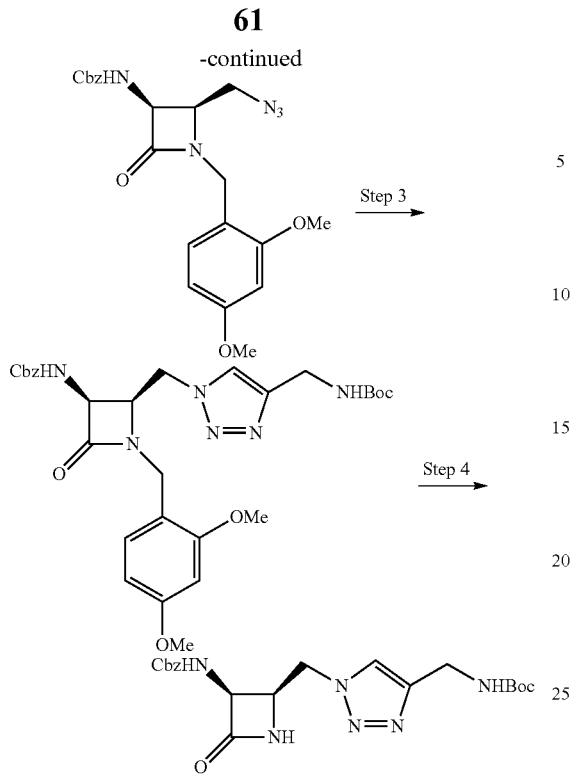

Step 1: Benzyl ((2S,3S)-1-(2,4-dimethoxybenzyl)-2-(iodomethyl)-4-oxoazetidin-3-yl)carbamate To a solution of intermediate G (10 g, 25 mmol), triphenylphosphine (19.6 g, 75 mmol) and imidazole (5.1 g, 75 mmol) in DCM (150 mL) at 0° C. was added iodine (19 g, 75 mmol) portion-wise over 10 min. After stirring at rt for 4 h, it was washed with saturated $Na_2S_2O_3$ (aq) solution, water, brine, dried over $Na_2SO_4$ anc concentrated in vacuo. The crude residue was suspended in EtOAc (150 mL) and stirred for 16 h whereupon it was filtered then washed with acetone and MeOH, affording the title compound (9.8 g, 77%) as a white solid. LCMS: m/z=510.8 (M+1).

Step 2: Benzyl ((2R,3S)-2-(azidomethyl)-1-(2,4-dimethoxybenzyl)-4-oxoazetidin-3-yl)carbamate To a solution of benzyl ((2S,3S)-1-(2,4-dimethoxybenzyl)-2-(iodomethyl)-4-oxoazetidin-3-yl)carbamate (5.00 g, 9.80 mmol) in THF (100 mL) at 0° C. was added TEA (2.73 g, 19.6 mmol) followed by a solution of tetrabutylammonium azide (3.62 g, 12.7 mmol) in THF. After stirring at rt for 16 h, it was filtered and concentrated in vacuo. The crude residue was purified via silica gel chromatography (MeOH-DCM, 2%), affording the title compound (3.4 g, 81%) as a white solid.

Step 3

To a solution of benzyl ((2R,3S)-2-(azidomethyl)-1-(2,4-dimethoxybenzyl)-4-oxoazetidin-3-yl)carbamate (3.00 g, 7.06 mmol) in DCM (6 mL) was added DMSO: water: tert-butanol (1:1:1, 6 mL) tert-butyl but-3-yn-1-ylcarbamate (2.19 g, 14.1 mmol), $CuSO_4$ (56 mg, 0.35 mmol) and sodium L-ascorbate (2.01 mg, 10.6 mmol). After stirring at rt for 3 h the mixture was partially concentrated and water was added, whereupon the solids were collected by filteration. The filter cake was suspended in DCM, filtered and the filtrate concentrated, affording the title compound (assumed quantitative) as a light yellow solid.

Step 4

To a solution of the product from step 3 (7.06 mmol) in ACN (50 mL) was added potassium persulfate (3.82 g, 14.1 mmol) followed by a solution of dipotassium phosphate (3.08 g, 17.7 mmol) in water (25 mL). The resulting mixture was heated to 90° C. for 4 h then cooled to rt, filtered and concentrated in vacuo, removing most of the ACN. The filtrate was extracted with EtOAc and concentrated in vacuo. The crude residue washed with hexanes and acetone, affording the title compound (1.72 g, 57% over 2-steps) as a white solid. LCMS: m/z=431.1 (M+1).

Intermediate T

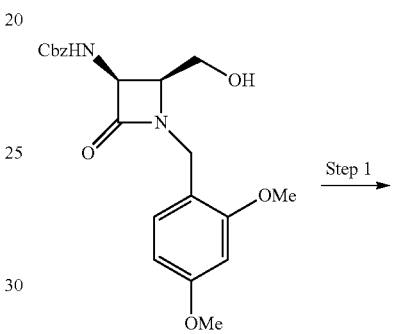

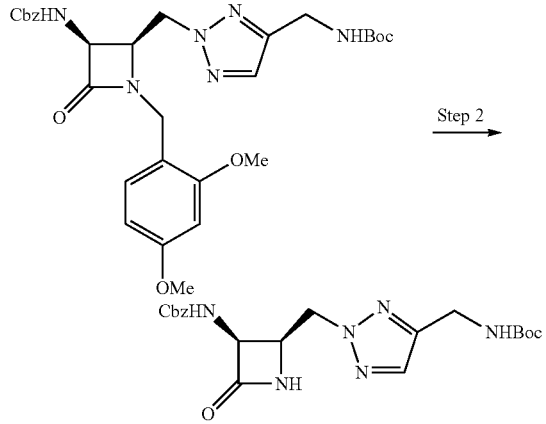

Step 1

The general procedure for the Mitsunobu reaction was followed. To a solution of intermediate G (5.00 g, 12.5 mmol), tert-butyl ((2H-1,2,3-triazol-4-yl)methyl)carbamate (2.97 mg, 15.0 mmol), triphenylphosphine (3.93 mg, 15.0 mmol) and DIAD (3.0 mL, 15 mmol) in THF (100 mL). Purified via silica gel chromatography (MeOH-DCM, 2-5%), affording the title compound (12.6 g, contaminated with triphenylphosphine oxide) as a white foam.

Step 2

To a solution of the product from step 1 (12.5 mmol) in ACN (150 mL) was added a solution of potassium persulfate (6.76 g, 25.0 mmol) and dipotassium phosphate (5.44 g, 31.2 mmol) in water (75 mL). The resulting mixture was heated to 90° C. for 4 h then cooled to rt, diluted with water and extracted with EtOAc. The organic layer was concentrated in vacuo and the crude residue was purified via silica gel chromatography, affording the title compound (2.23 g, 41% over 2-steps) as a white solid. LCMS: m/z=428.9 (M−1).

Intermediate U

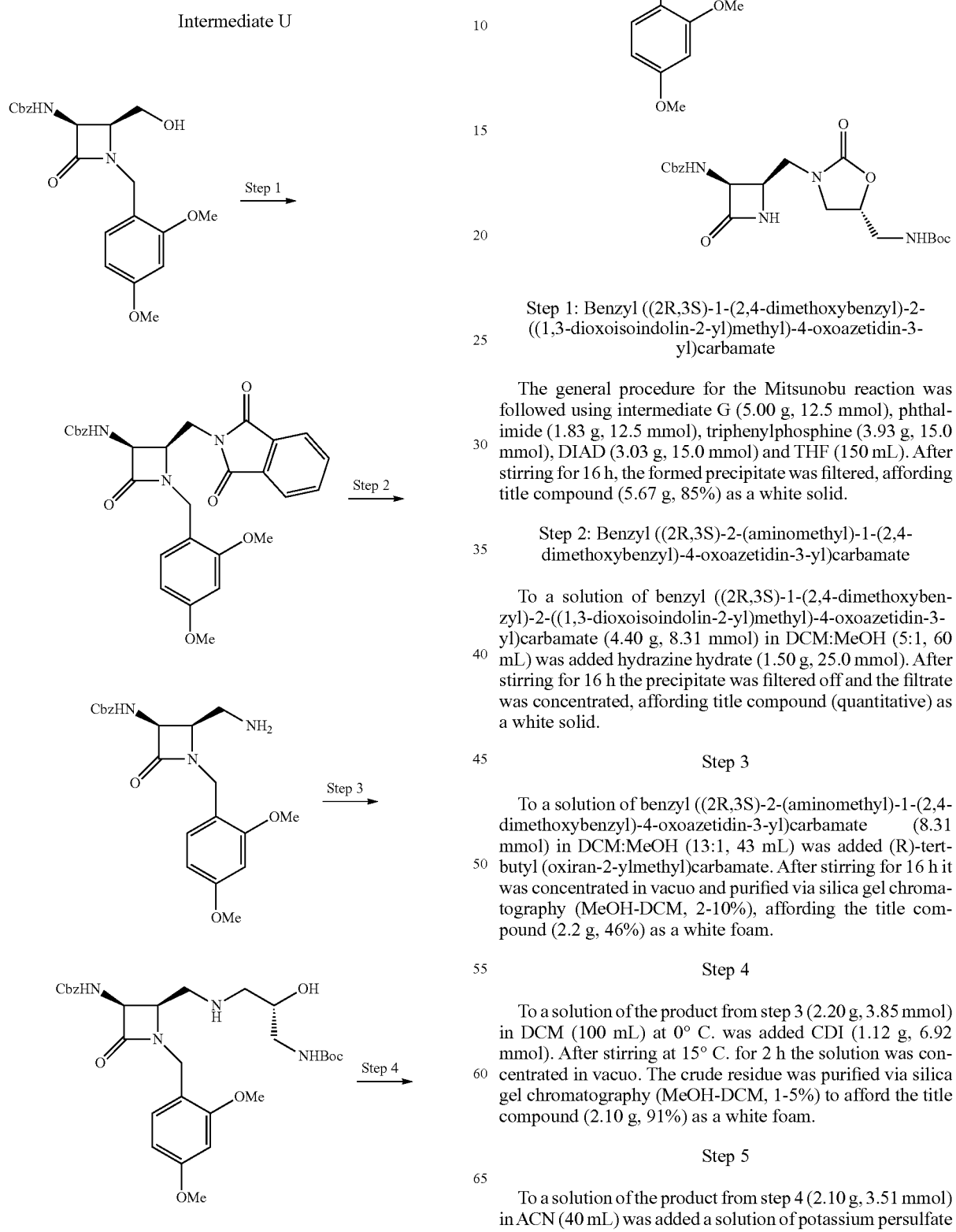

Step 1: Benzyl ((2R,3S)-1-(2,4-dimethoxybenzyl)-2-((1,3-dioxoisoindolin-2-yl)methyl)-4-oxoazetidin-3-yl)carbamate The general procedure for the Mitsunobu reaction was followed using intermediate G (5.00 g, 12.5 mmol), phthalimide (1.83 g, 12.5 mmol), triphenylphosphine (3.93 g, 15.0 mmol), DIAD (3.03 g, 15.0 mmol) and THF (150 mL). After stirring for 16 h, the formed precipitate was filtered, affording title compound (5.67 g, 85%) as a white solid.

Step 2: Benzyl ((2R,3S)-2-(aminomethyl)-1-(2,4-dimethoxybenzyl)-4-oxoazetidin-3-yl)carbamate To a solution of benzyl ((2R,3S)-1-(2,4-dimethoxybenzyl)-2-((1,3-dioxoisoindolin-2-yl)methyl)-4-oxoazetidin-3-yl)carbamate (4.40 g, 8.31 mmol) in DCM:MeOH (5:1, 60 mL) was added hydrazine hydrate (1.50 g, 25.0 mmol). After stirring for 16 h the precipitate was filtered off and the filtrate was concentrated, affording title compound (quantitative) as a white solid.

Step 3

To a solution of benzyl ((2R,3S)-2-(aminomethyl)-1-(2,4-dimethoxybenzyl)-4-oxoazetidin-3-yl)carbamate (8.31 mmol) in DCM:MeOH (13:1, 43 mL) was added (R)-tert-butyl (oxiran-2-ylmethyl)carbamate. After stirring for 16 h it was concentrated in vacuo and purified via silica gel chromatography (MeOH-DCM, 2-10%), affording the title compound (2.2 g, 46%) as a white foam.

Step 4

To a solution of the product from step 3 (2.20 g, 3.85 mmol) in DCM (100 mL) at 0° C. was added CDI (1.12 g, 6.92 mmol). After stirring at 15° C. for 2 h the solution was concentrated in vacuo. The crude residue was purified via silica gel chromatography (MeOH-DCM, 1-5%) to afford the title compound (2.10 g, 91%) as a white foam.

Step 5

To a solution of the product from step 4 (2.10 g, 3.51 mmol) in ACN (40 mL) was added a solution of potassium persulfate (1.89 g, 7.02 mmol) and dipotassium phosphate (1.52 g, 8.75 mmol) in water (20 mL). The resulting mixture was heated to 90° C. for 4 h then cooled to rt and filtered. The filtrate was concentrated, extracted with EtOAc and the organic layer was concentrated. The crude residue was purified via silica gel chromatography (MeOH-DCM, 2-5%), affording the title compound (660 mg, 42%) as a pale yellow solid. LCMS: m/z=449.09 (M+1).

Intermediate V

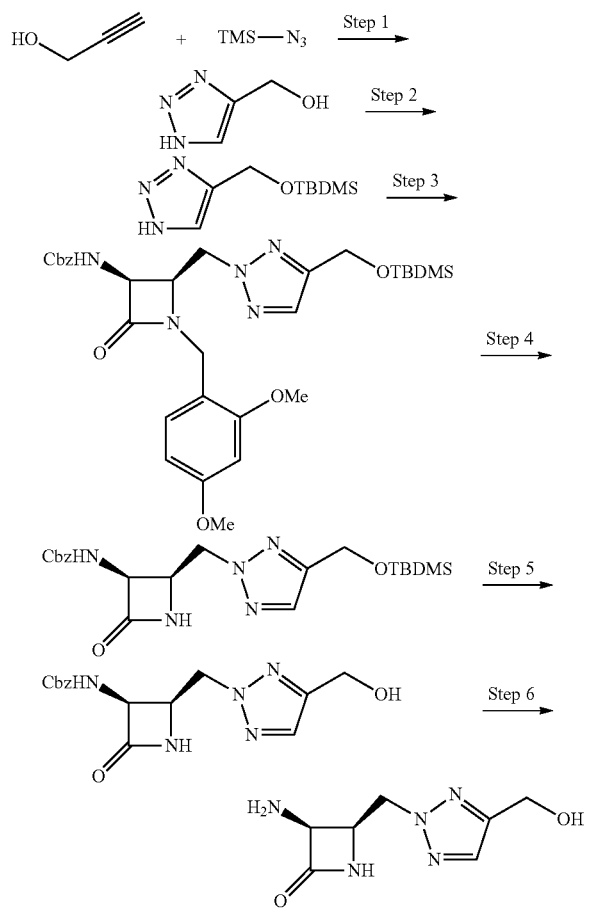

Step 1: (1H-1,2,3-triazol-4-yl)methanol

To a solution of propargyl alcohol (11.2 g, 200 mmol) in DMF (160 mL) and MeOH (40 mL) was added CuI (1.9 g, 10 mmol) and trimethylsilyl azide (34.6 g, 300 mmol). After heating to 100° C. for 16 h, the reaction mixture was cooled to rt and filtered through celite. The filtrate was concentrated in vacuo to afford the title compound (assume quantitative). The crude compound was used as such in the following step.

Step 2: 4-(((tert-butyldimethylsilyl)oxy)methyl)-1H-1,2,3-triazole

To a solution of (1H-1,2,3-triazol-4-yl)methanol (30 g, 200 mmol) in DCM (160 mL) was added imidazole (20.4 g, 300 mmol) followed by TBDMS-Cl (33.3 g, 220 mmol) as a solid in portions. After stirring at rt for 16 h, the reaction mixture was filtered through celite, and the filtrate was concentrated in vacuo. The residue was dissolved in EtOAc (500 mL) and washed with water, brine, dried over $Na_2SO_4$, and concentrated in vacuo. The crude residue was purified via silica gel chromatography (EtOAc-hexanes, 5-30%) to afford the title compound (30.2 g, 71%) as a pale yellow solid.

Step 3: Benzyl ((2R,3S)-2-((4-(((tert-butyldimethylsilyl)oxy)methyl)-2H-1,2,3-triazol-2-yl)methyl)-1-(2,4-dimethoxybenzyl)-4-oxoazetidin-3-yl)carbamate To a solution of benzyl ((2S,3S)-1-(2,4-dimethoxybenzyl)-2-(hydroxymethyl)-4-oxoazetidin-3-yl)carbamate (0.94 g, 2.34 mmol), 4-(((tert-butyldimethylsilyl)oxy)methyl)-1H-1,2,3-triazole (0.5 g, 2.34 mmol), and $PPh_3$ (0.74 g, 2.81 mmol) in THF (20 mL) at 0° C. was added DIAD (0.57 g, 2.81 mmol) slowly. After stirring at rt for 16 h, the reaction mixture was concentrated in vacuo. The crude residue was purified via silica gel chromatography (EtOAc-hexanes, 20-30%) to afford the title compound (1.25 g, 89%) as a pale yellow solid. LCMS: m/z=594.3 (M−1).

Step 4: Benzyl ((2R,3S)-2-((4-(((tert-butyldimethylsilyl)oxy)methyl)-2H-1,2,3-triazol-2-yl)methyl)-4-oxoazetidin-3-yl)carbamate To a solution of benzyl ((2R,3S)-2-((4-(((tert-butyldimethylsilyl)oxy)methyl)-2H-1,2,3-triazol-2-yl)methyl)-1-(2,4-dimethoxybenzyl)-4-oxoazetidin-3-yl)carbamate (1.25 g, 2.1 mmol) in $CH_3CN$ (20 mL) was added $K_2S_2O_8$ (0.73 g, 2.7 mmol) followed by a solution of $K_2HPO_4$ (0.84 g, 4.8 mmol) in water (10 mL). After stirring at 90° C. for 1 h, more $K_2S_2O_8$ (0.23 g, 0.84 mmol) was added. After heating at 90° C. for additional 2 h, the reaction mixture was concentrated in vacuo. The residue was extracted with EtOAc (2×30 mL). Combined organic layers were washed with water, brine, dried with $Na_2SO_4$, filtered and concentrated in vacuo. The crude residue was purified via silica gel chromatography (MeOH-DCM, 1-3%) to afford the title compound (0.44 g, 47%) as a pale yellow solid. LCMS: m/z=446.2 (M+1).

Step 5: Benzyl ((2R,3S)-2-((4-(hydroxymethyl)-2H-1,2,3-triazol-2-yl)methyl)-4-oxoazetidin-3-yl)carbamate To a solution of benzyl ((2R,3S)-2-((4-(((tert-butyldimethylsilyl)oxy)methyl)-2H-1,2,3-triazol-2-yl)methyl)-4-oxoazetidin-3-yl)carbamate (10.8 g, 24.4 mmol) in THF (100 mL) was added TBAF (1 M in THF, 26.6 mL, 26.6 mmol) slowly over a period of 15 min. After stirring at rt for 1.5 h, the reaction mixture was concentrated in vacuo. The crude residue was purified via silica gel chromatography (MeOH-DCM, 1-5%) to afford the title compound (6.8 g, 85%) as a pale yellow solid. LCMS: m/z=330.0 (M+1).

Step 6: (3S,4R)-3-amino-4-((4-(hydroxymethyl)-2H-1,2,3-triazol-2-yl)methyl)azetidin-2-one To a solution of benzyl ((2R,3S)-2-((4-(hydroxymethyl)-2H-1,2,3-triazol-2-yl)methyl)-4-oxoazetidin-3-yl)carbamate (1.54 g, 4.65 mmol) in EtOH (50 mL) and EtOH (25 mL) was added Pd/C (10%, 0.51 g, 4.65 mmol). After stirring at rt for 4 h, the reaction mixture was filtered through a celite pad, and the filtrate was concentrated in vacuo to afford the title compound (assume quantitive). The crude was used as such in the following step. LCMS: $R_t$=0.12 min, m/z=198.0 (M+1) Method 2m_acidic.

Intermediate W:
3-(ammoniomethyl)-1-methylpyridin-1-ium chloride

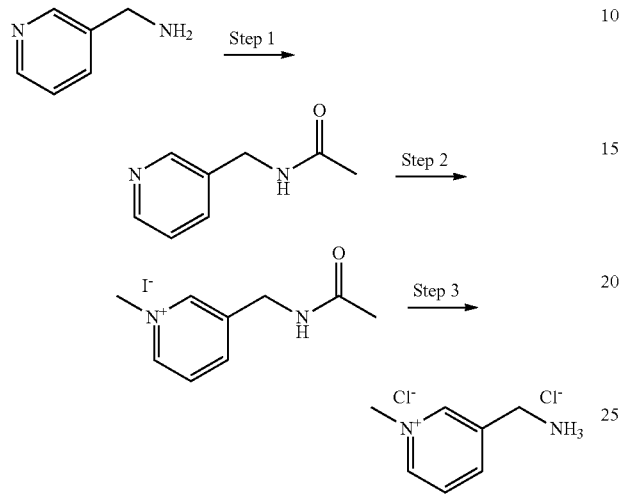

Step 1: N-(pyridin-3-yl methyl)acetamide

Prepared according to Plater et al. *Org. Biomol. Chem.* 2009, 7, 1633. To a solution of pyridin-3-ylmethanamine (9.42 ml, 92 mmol) in water (103 ml) at 10° C. was added acetic anhydride (10.47 ml, 111 mmol), stirred at a rate where the internal temperature did not rise above 25° C. After an additional 18 h of stirring, the solution was concentrated in vacuo then co-evaporated with toluene (3×) to afford the title compound (14.22 g, quantitative) as a clear oil. LCMS: $R_t$=0.12 min, m/z=151.1 (M+1) Method 2m_acidic. $^1$H NMR (400 MHz, CDCl$_3$) δ 8.49 (d, J=2.4 Hz, 2H) 7.65 (dd, J=7.8, 1.6 Hz, 1H) 7.30-7.24-(m, 1H) 6.59-6.49 (m, 1H) 4.43 (d, J=6.0 Hz, 2H) 2.02 (s, 3H).

Step 2: 3-(acetamidomethyl)-1-methylpyridin-1-ium iodide

To a solution of N-(pyridin-3-ylmethyl)acetamide (13.89 g, 92 mmol) in DCM at 0° C. was added methyl iodide (8.10 mL, 129 mmol). The cooling bath was removed after 10 min and the solution was stirred at rt for 19 h, whereupon it was concentrated in vacuo and used as crude in step 3. LCMS: $R_t$=0.18 min, m/z=164.9 (M+) Method 2m_acidic. $^1$H NMR (400 MHz, DMSO-d$_6$) δ 8.91-8.87 (m, 2H) 8.58 (brs, 1H) 8.42 (d, J=8.0 Hz, 1H) 8.09 (t, J=7.0 Hz, 1H) 4.43 (d, J=5.9 Hz, 2H) 4.35 (s, 3H) 1.92 (s, 3H).

Step 3: 3-(ammoniomethyl)-1-methylpyridin-1-ium chloride

A suspension of 3-(acetamidomethyl)-1-methylpyridin-1-ium iodide (26.9 g, 92 mmol) in HCl (6N, 307 mL, 1.84 mol) was heated to 100° C. for 3 h. The solution was concentrated under reduced pressure (bath temp 80° C.). The resulting red oil solidified overnight and was triturated with MeOH and filtered to afford the title compound (8.76 g, 49%) as an off white solid. The filtrate was concentrated to a red oil, which after standing for 4 days, the formed solid was collected and washed with cold MeOH, affording a second crop (6.5 g, 36%). LCMS: $R_t$=0.11 min, m/z=123.0 (M+) Method 2m_acidic. $^1$H NMR (400 MHz, DMSO-d$_6$) δ ppm 9.18 (s, 1H) 9.03 (d, J=6.0 Hz, 1H) 8.66 (d, J=8.1 Hz, 1H) 8.45 (brs, 3H) 8.24 (t, J=7.0 Hz, 1H) 4.38 (s, 3H) 4.30 (s, 2H).

The Intermediates described above, and similar compounds made by the same methods, can be used to prepare compounds of Formula (I) by the synthesis schemes provided herein. The following Examples illustrate synthesis of selected compounds of Formula (I) and provide methods that can be adapted to synthesis of other compounds of Formula (I).

Example 1

2-(((Z)-(1-(2-aminothiazol-4-yl)-2-oxo-2-(((3S,4R)-2-oxo-4-((2-oxopyrrolidin-1-yl)methyl)-1-sulfoazetidin-3-yl)amino)ethylidene)amino)oxy)-2-methylpropanoic acid

Step 1: tert-Butyl 2-(((Z)-(1-(2-((tert-butoxycarbonyl)amino)thiazol-4-yl)-2-oxo-2-(((3S,4R)-2-oxo-4-((2-oxopyrrolidin-1-yl)methyl)azetidin-3-yl)amino)ethylidene)amino)oxy)-2-methylpropanoate A solution of Intermediate L (100 mg, 0.190 mmol), methyl-4-bromobutyrate (25 μL, 0.194 mmol) and TEA (27 μL, 0.194 mmol) in DMF (1.3 mL) was heated to 70° C. for 16 h while stirring, whereupon the heat was then raised to 90° C. After 6 h of additional heating it was diluted with HCl (1 N) and EtOAc. The aqueous layer was extracted with EtOAc (2×) and the combined organic layers were washed with LiCl soln (5% aq), brine, dried over Na$_2$SO$_4$ and concentrated in vacuo. The crude residue was purified via silica gel chromatography (EtOAc-Heptane, 50-100% then MeOH-EtOAc, 0-7%), affording the title compound (21 mg, 18%) as a foam. LCMS: R=0.88 min, m/z=595.4 (M+1) Method 2m_acidic.

Step 2: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopyrrolidin-1-yl)methyl)azetidine-1-sulfonic acid tert-Butyl 2-(((Z)-(1-(2-((tert-butoxycarbonyl)amino)thiazol-4-yl)-2-oxo-2-(((3S,4R)-2-oxo-4-((2-oxopyrrolidin-1-yl)methyl)azetidin-3-yl)amino)ethylidene)amino)oxy)-2-methylpropanoate (43 mg, 0.072 mmol) in DMF (725 μL) was treated with SO$_3$.DMF (111 mg, 0.725 mmol). The solution was stirred at rt for 30 min then diluted with EtOAc and poured into LiCl solution (5% aq). The aqueous was extracted with EtOAc (2×) and the combined organic layers were washed with brine, dried over Na$_2$SO$_4$ and concentrated in vacuo, affording the crude title compound (55 mg) as a white solid. LCMS: Rt=0.77 min, m/z=675.3 (M+1) Method 2m_acidic. It was used in step 3 without further purification.

Step 3: 2-(((Z)-(1-(2-aminothiazol-4-yl)-2-oxo-2-(((3S,4R)-2-oxo-4-((2-oxopyrrolidin-1-yl)methyl)-1-sulfoazetidin-3-yl)amino)ethylidene)amino)oxy)-2-methylpropanoic acid

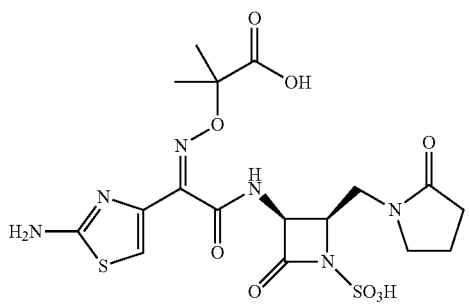 [SMILES: CC(C)(O/N=C(\C(=O)N[C@@H]1C(=O)N(S(=O)(=O)O)[C@@H]1CN1CCCC1=O)c1csc(N)n1)C(=O)O]

Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopyrrolidin-1-yl)methyl)azetidine-1-sulfonic acid (55 mg, 0.072 mmol), DCM (720 µL) and TFA (333 µL, 4.32 mmol). The crude residue was purified by reverse phase preperative HPLC (XSelect CSH, 19×100 mm, 5 µm, C18 column; ACN-water with 0.1% formic acid modifier, 24 mL/min), affording the title compound (6 mg, 16%) as a white solid. LCMS: $R_t$=0.35 min, m/z=519.0 (M+1) Method 2m_acidic; $^1$H NMR (400 MHz, D$_2$O): δ 7.17 (s, 1H), 5.46 (d, J=5.8 Hz, 1H), 4.71-4.64 (m, 1H), 3.92 (dd, J=14.7, 8.7 Hz, 1H), 3.71-3.55 (m, 2H), 3.49 (dd, J=14.7, 4.1 Hz, 1H), 2.42 (td, J=8.0, 4.8 Hz, 2H), 2.08 (p, J=7.6 Hz, 2H), 1.55 (s, 3H), 1.54 (s, 3H).

Example 2

2-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)-2-methylpropanoic acid Step 1: tert-Butyl 2-(((Z)-(1-(2-((tert-butoxycarbonyl)amino)thiazol-4-yl)-2-(((2R,3S)-2-(((2-((tert-butyldimethylsilyl)oxy)ethyl)amino)methyl)-4-oxoazetidin-3-yl)amino)-2-oxoethylidene)amino)oxy)-2-methylpropanoate.

A solution of Intermediate L (500 mg, 0.949 mmol) and (2-bromoethoxy)(tert-butyl)dimethylsilane (204 µl, 0.949 mmol) in ACN (3.2 mL) was heated at 80° C. in a microwave for 30 min then kept at rt for 12 h. It was reheated to 100° C. for 45 min in the microwave then kept at rt for 12 h, whereupon it was diluted with EtOAc and washed with sodium carbonate (2 M, aq), dried over sodium sulfate and concentrated in vacuo. The crude residue was purified via silica gel chromatography (EtOAc-Heptane, 0-100% then MeOH-DCM, 10%) to afford the title compound (111 mg, 17%). LCMS: $R_t$=1.03 min, m/z=685.4 (M+1) Method 2m_acidic; $^1$H NMR (400 MHz, CDCl$_3$) δ 8.17 (d, J=8.4 Hz, 1H), 7.30 (s, 1H), 6.30 (br s, 1H) 5.57-5.50 (m, 1H) 4.09-4.01 (m, 1H) 3.77-3.61 (m, 3H) 3.09 (dd, J=12.6, 3.7 Hz, 1H) 2.87-2.71 (m, 3H) 1.56 (s, 6H) 1.53 (s, 9H) 1.44 (s, 9H) 0.86 (s, 9H) 0.03 (s, 3H), 0.03 (s, 3H).

Step 2: tert-Butyl 2-(((Z)-(1-(2-((tert-butoxycarbonyl)amino)thiazol-4-yl)-2-(((2R,3S)-2-(((2-hydroxyethyl)amino)methyl)-4-oxoazetidin-3-yl)amino)-2-oxoethylidene)amino)oxy)-2-methylpropanoate Prepared according to Seki et al. *Synlett* 1995, 609-611. To a solution of tert-butyl 2-(((Z)-(1-(2-((tert-butoxycarbonyl)amino)thiazol-4-yl)-2-(((2R,3S)-2-(((2-((tert-butyldimethylsilyl)oxy)ethyl)amino)methyl)-4-oxoazetidin-3-yl)amino)-2-oxoethylidene)amino)oxy)-2-methylpropanoate (111 mg, 0.162 mmol) in DMF:NMP (2.7:1, 1.62 mL) was added ammonium fluoride hydrofluoride (37.0 mg, 0.648 mmol). After stirring for 65 h, the solution was diluted with water and extracted with EtOAc. The organic layer was dried over sodium sulfate and concentrated in vacuo to afford crude title compound (92 mg, 99%). The crude material was used directly in step 3. LCMS: R=0.76 min, m/z 571.3 (M+1) Method 2m_acidic.

Step 3: tert-Butyl 2-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino)ethylidene)amino)oxy)-2-methylpropanoate Prepared according to PCT Int. Appl. 2011061760. A solution of tert-butyl 2-(((Z)-(1-(2-((tert-butoxycarbonyl)amino)thiazol-4-yl)-2-(((2R,3S)-2-(((2-hydroxyethyl)amino)methyl)-4-oxoazetidin-3-yl)amino)-2-oxoethylidene)amino)oxy)-2-methylpropanoate (92 mg, 0.161 mmol) in Chloroform (806 µl) was treated with CDI (131 mg, 0.806 mmol) After stirring at rt for 3 h it was diluted with EtOAc, washed with water, brine, dried over Na$_2$SO$_4$ and concentrated in vacuo. The crude residue was purified by silica gel chromatography (MeOH-DCM, 0-10%), affording the title compound (91 mg, 95%) as an orange oil. LCMS: $R_t$=0.86 min, m/z=597.2 (M+1) Method 2m_acidic.

Step 4: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxooxazolidin-3-yl)methyl)azetidine-1-sulfonic acid A solution of tert-butyl 2-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino)ethylidene)amino)oxy)-2-methylpropanoate (91 mg, 0.153 mmol) in DMF (Volume: 763 µl) was treated with SO$_3$.DMF (234 mg, 1.525 mmol). After stirring at rt for 1 h it was diluted with EtOAc, washed with brine (3×), dried over Na$_2$SO$_4$ and concentrated in vacuo, affording the title compound (100 mg, 97%) as an orange solid. LCMS: $R_t$=0.78 min, m/z=677.3 (M+1) Method 2m_acidic.

Step 5: 2-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)-2-methylpropanoic acid

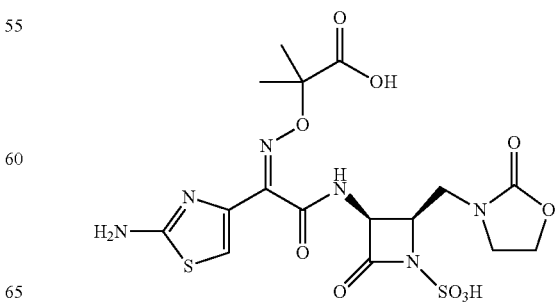

Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxooxazolidin-3-yl)methyl)azetidine-1-sulfonic acid (100 mg, 0.148 mmol), DCM (1.5 mL) and TFA (569 µl, 7.39 mmol). The crude residue was purified by reverse phase prep HPLC (XSelect CSH, 19×100 mm, 5 µm, C18 column; ACN-water with 0.1% formic acid modifier, 24 mL/min), affording the title compound (10 mg, 12%) as a white solid. LCMS: $R_t$=0.32 min, m/z=521.0 (M+1) Method 2m_acidic; $^1$H NMR (400 MHz, DMSO-$d_6$) δ 9.33 (d, J=8.8 Hz, 1H), 6.89 (s, 1H), 5.22 (dd, J=8.8, 5.7 Hz, 1H), 4.23-4.11 (m, 3H), 3.75-3.62 (m, 2H assumed; obscured by water), 3.60-3.51 (m, 1H assumed; obscured by water), 3.34 (dd, J=14.6, 5.5 Hz, 1H), 1.44 (s, 3H), 1.40 (s, 3H).

Example 3

2-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)-2-methylpropanoic acid Step 1: tert-Butyl 2-(((Z)-(2-(((2R,3S)-2-(((2-((((9H-fluoren-9-yl)methoxy)carbonyl)amino)ethyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate A solution of Intermediate L (650 mg, 1.234 mmol) and (9H-fluoren-9-yl)methyl (2-oxoethyl)carbamate (365 mg, 1.234 mmol) in DCE (12.3 ml) was treated with sodium triacetoxyborohydride (1.377 g, 6.17 mmol). After stirring at rt for 18 h it was quenched with saturated NaHCO$_3$ (aq) and extracted with EtOAc. The organic layer was washed with brine, dried over Na$_2$SO$_4$ and concentrated in vacuo. The crude residue was purified via silica gel chromatography (MeOH-DCM, 0-10%), affording the title compound (435 mg, 45%) as a white solid. LCMS: $R_t$=1.00 min, m/z=792.3 (M+1) Method 2m_acidic; $^1$H NMR (400 MHz, DMSO-$d_6$) δ 9.11 (d, J=9.0 Hz, 1H), 8.35 (s, 1H), 7.89 (d, J=7.7 Hz, 2H), 7.67 (d, J=7.5 Hz, 2H), 7.41 (t, J=7.2 Hz, 2H), 7.32 (td, J=7.4, 1.2 Hz, 2H), 7.27 (s, 1H), 7.19 (t, J=5.7 Hz, 1H), 5.20 (dd, J=9.1, 5.0 Hz, 1H), 4.30 (d, J=6.8 Hz, 2H), 4.24-4.17 (m, 1H), 3.76 (ddd, J=8.8, 5.3, 3.7 Hz, 1H), 3.11-2.97 (m, 2H), 2.76 (dd, J=12.5, 3.7 Hz, 1H), 2.63-2.52 (m, 3H), 1.45 (s, 9H), 1.42 (s, 3H), 1.39 (s, 3H), 1.38 (s, 9H).

Step 2: tert-Butyl 2-(((Z)-(2-(((2R,3S)-2-(((2-aminoethyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate A solution of tert-butyl 2-(((Z)-(2-(((2R,3S)-2-(((2-(((((9H-fluoren-9-yl)methoxy)carbonyl)amino)ethyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate (435 mg, 0.549 mmol) in DMF (2.75 mL) was treated with piperidine (1.1 mL, 11 mmol). After stirring at rt for 1 h it was diluted with toluene and concentrated (3×). The crude residue was purified by reverse phase prep HPLC (XSelect CSH, 19×100 mm, 5 µm, C18 column; ACN-water with 0.1% formic acid modifier, 24 mL/min), affording the title compound (238 mg, 64%) as a white powder. LCMS: $R_t$=0.68 min, m/z=570.3 (M+1) Method 2m_acidic; $^1$H NMR (400 MHz, DMSO-$d_6$) δ 9.12 (d, J=8.9 Hz, 1H), 8.38 (s, 1H), 8.31 (s, 1H), 7.21 (s, 1H), 5.17 (dd, J=8.3, 4.9 Hz, 1H), 3.76 (dt, J=8.7, 4.7 Hz, 1H), 2.81-2.51 (m, 6H), 1.44 (s, 9H), 1.41 (s, 3H), 1.39 (s, 3H), 1.38 (s, 9H).

Step 3: tert-Butyl 2-(((Z)-(1-(2-((tert-butoxycarbonyl)amino)thiazol-4-yl)-2-oxo-2-(((3S,4R)-2-oxo-4-((2-oxoimidazolidin-1-yl)methyl)azetidin-3-yl)amino)ethylidene)amino)oxy)-2-methylpropanoate To a solution of tert-Butyl 2-(((Z)-(2-(((2R,3S)-2-(((2-aminoethyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate (100 mg, 0.151 mmol) in chloroform (756 µl) was added CDI (98 mg, 0.604 mmol) followed by TEA (105 µl, 0.756 mmol). After stirring at rt for 1 h it was diluted with EtOAc, washed with water, brine, dried over Na$_2$SO$_4$ and concentrated in vacuo to afford the title compound (73 mg, 81%) as a white solid. It was used as crude in step 4. LCMS: $R_t$=0.70 min, m/z=596.2 (M+1) Method 2m_acidic.

Step 4: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxoimidazolidin-1-yl)methyl)azetidine-1-sulfonic acid A solution of tert-butyl 2-(((Z)-(1-(2-((tert-butoxycarbonyl)amino)thiazol-4-yl)-2-oxo-2-(((3S,4R)-2-oxo-4-((2-oxoimidazolidin-1-yl)methyl)azetidin-3-yl)amino)ethylidene)amino)oxy)-2-methylpropanoate (73 mg, 0.123 mmol) in DMF (613 µl) was treated with SO$_3$.DMF (94 mg, 0.613 mmol). After stirring at rt for 2 h it was diluted with EtOAc, washed with brine (3×), dried over Na$_2$SO$_4$ and concentrated in vacuo to afford the title compound (99 mg) as a white solid. LCMS: $R_t$=0.74 min, m/z=676.3 (M+1) Method 2m_acidic.

Step 5: 2-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)-2-methylpropanoic acid

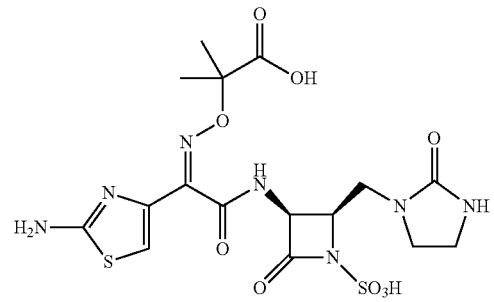

Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxoimidazolidin-1-yl)methyl)azetidine-1-sulfonic acid (99 mg, 0.147 mmol), DCM (1.47 mL) and TFA (566 µl, 7.35 mmol). The crude residue purified by reverse phase prep HPLC (XSelect CSH, 19×100 mm, 5 µm, C18 column; ACN-water with 0.1% formic acid modifier, 24 mL/min); affording the title compound (4.8 mg) as a white powder. LCMS: $R_t$=0.31 min, m/z=520.0 (M+1) Method 2m_acidic; ¹H NMR (500 MHz, DMSO-d₆) δ 9.25 (dd, J=9.0, 5.0 Hz, 1H), 6.83 (s, 1H), 5.21 (dd, J=9.0, 5.8 Hz, 1H), 4.06-4.00 (m, 1H), 3.65 (dd, J=14.5, 4.7 Hz, 1H), 3.33-3.30 (m, 1H assumed; obscured by water), 3.25 (dd, J=14.5, 6.9 Hz, 2H assumed; obscured by water), 3.17 (ddd, J=16.7, 8.6, 6.7 Hz, 2H), 1.43 (s, 3H), 1.42 (s, 3H).

Example 4

2-(((Z)-(2-(((2R,3S)-2-((5-(aminomethyl)-2H-tetrazol-2-yl)methyl)-4-oxo-1-sulfoazetidin-3-yl)amino)-1-(2-aminothiazol-4-yl)-2-oxoethylidene)amino)oxy)-2-methylpropanoic acid Step 1

A 75 mL pressure vessel was charged with Intermediate A (1.50 g, 3.13 mmol), intermediate B (1.108 g, 4.70 mmol), K₂CO₃ (1.733 g, 12.54 mmol), NaI (564 mg, 3.76 mmol) and DMF (10 mL) then heated to 70° C. with stirring. After 3 h, more intermediate B (1.108 g, 4.70 mmol), K₂CO₃ (1.733 g, 12.54 mmol) and NaI (394 mg, 2.63 mmol) were added and heating was continued. After 8 h of total heating it was cooled to rt, diluted with EtOAc/brine and the layers were separated. The aqueous layer was extracted with EtOAc (2×) and the combined organic layers were washed with brine (3×), dried over Na₂SO₄ and concentrated in vacuo. The crude residue was combined with another sample of identical scale and procedure and purified via silica gel chromatography (Acetone-DCM, 0-30%), affording the 2H-tetrazole isomer (2.15 g, 60%) and 1H-tetrazole isomer (443 mg, 12%) as white solids. A-LCMS: R$_t$=0.97 min, m/z=582.3 (M+1) Method 2m_acidic; B-LCMS: R=0.93 min, m/z=582.3 (M+1) Method 2m_acidic.

Step 2

Prepared according to Mastalerz et al. *J. Med. Chem.* 1988, 31, 1190. To a solution of 2H-tetrazole isomer (2.15 g, 3.70 mmol) from step 1 in ACN:water (2:1, 61.5 mL) was added K₂S₂O₈ (1.40 g, 5.18 mmol) followed by K₂HPO₄ (837 mg, 4.81 mmol). The resulting mixture was heated to 90° C. for 1.5 h, whereupon more K₂S₂O₈ (300 mg, 1.11 mmol) and K₂HPO₄ (167 mg, 0.961 mmol) were added. After 3.5 h of additional heating at 90° C., it was diluted with ACN and concentrated in vacuo, removing most of the ACN. The mixture was diluted with water/EtOAc and the layers separated. The aqueous layer was extracted with EtOAc (5×) and the combined organic layers were dried over Na₂SO₄ and concentrated in vacuo. The crude residue was purified via silica gel chromatography (Acetone-DCM, 50%), to afford the title compound (785 mg, 49%). LCMS: R$_t$=0.77 min, m/z=432.3 (M+1) Method 2m_acidic; ¹H NMR (500 MHz, ACN-d₃) δ 7.49-7.30 (m, 5H), 6.76 (br s, 1H), 6.55-6.41 (m, 1H), 5.85 (br s, 1H), 5.03-5.21 (m, 3H), 4.88-4.71 (m, 2H), 4.52-4.43 (m, 3H), 4.39-4.24 (m, 1H), 1.50-1.35 (m, 9H).

Step 3: tert-Butyl ((2-(((2R,3S)-3-amino-4-oxoazetidin-2-yl)methyl)-2H-tetrazol-5-yl)methyl)carbamate Prepared according to the procedure described in Malmström et al. *Bioorg. Med. Chem. Lett.* 2012, 22, 5293. A solution of compound from step 2 (785 mg, 1.819 mmol) in EtOAc:MeOH (5:1, 65 mL) was evacuated and backfilled with argon (2×) followed by addition of Pd on C (10%, 581 mg). The system was evacuated and backfilled with H₂ (3×). After 21 h of stirring, the mixture was filtered over celite, washing with MeOH, concentrated in vacuo, taken up on toluene and reconcentrated (3×). The crude residue was used as such in following step. LCMS: R$_t$=0.37 min, m/z=298.3 (M+1) Method 2m_acidic.

Step 4: tert-Butyl 2-(((Z)-(2-(((2R,3S)-2-((5-(((tert-butoxycarbonyl)amino)methyl)-2H-tetrazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a solution of (Z)-2-(((1-(tert-butoxy)-2-methyl-1-oxopropan-2-yl)oxy)imino)-2-(2-((tert-butoxycarbonyl)amino)thiazol-4-yl)acetic acid (938 mg, 2.18 mmol) in DCM:DMF (5:1, 8.5 mL) at 0° C. was added DIPEA (953 µL, 5.46 mmol) followed by HATU (830 mg, 2.18 mmol). To the resulting solution was added a solution of tert-butyl ((2-(((2R,3S)-3-amino-4-oxoazetidin-2-yl)methyl)-2H-tetrazol-5-yl)methyl)carbamate (541 mg, 1.82 mmol) in DCM:DMF (5:1, 8.5 mL). The solution was stirred at rt for 1 h then concentrated in vacuo, dissolved in EtOAc and washed with brine. The aqueous layer was extracted with EtOAc and the combined organic layers were washed with brine (3×), dried over Na₂SO₄ and concentrated in vacuo. The crude residue was purified via silica gel chromatography (Acetone-DCM, 30-50%), affording the title compound (897 mg, 70%) as a purple solid. LCMS: R$_t$=1.01 min, m/z=709.3 (M+1) Method 2m_acidic.

Step 5: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-2H-tetrazol-2-yl)methyl)-4-oxoazetidine-1-sulfonic acid tert-Butyl 2-(((Z)-(2-(((2R,3S)-2-((5-(((tert-butoxycarbonyl)amino)methyl)-2H-tetrazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate (200 mg, 0.282 mmol) in DMF (2 mL) was treated with SO₃.DMF (432 mg, 2.82 mmol). The purple solution immediately became green. After 20 min of stirring, more SO₃.DMF (432 mg, 2.82 mmol) was added. After an additional 20 min, more SO₃.DMF (432 mg, 2.82 mmol) was added. After 20 min the solution was diluted with EtOAc/brine and the layers were separated. The aqueous layer was extracted with EtOAc (3×) and the combined organic layers were dried over Na₂SO₄ and concentrated in vacuo to afford the title compound (185 mg, 83%). LCMS: $R_t$=0.91 min, m/z=789.1 (M+1) Method 2m_acidic.

Step 6: 2-(((Z)-(2-(((2R,3S)-2-((5-(aminomethyl)-2H-tetrazol-2-yl)methyl)-4-oxo-1-sulfoazetidin-3-yl)amino)-1-(2-aminothiazol-4-yl)-2-oxoethylidene)amino)oxy)-2-methylpropanoic acid

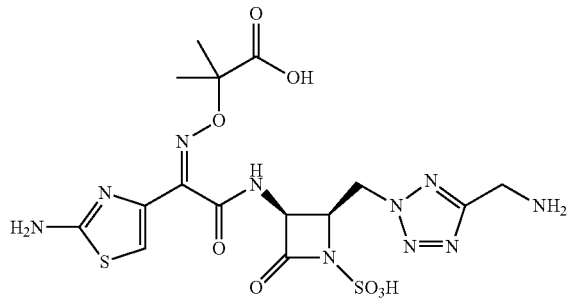 [SMILES: CC(C)(O/N=C(\C(=O)N[C@@H]1C(=O)N(S(=O)(=O)O)[C@@H]1Cn1nnc(CN)n1)c1csc(N)n1)C(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-2H-tetrazol-2-yl)methyl)-4-oxoazetidine-1-sulfonic acid (185 mg, 0.234 mmol), DCM (2.34 mL) and TFA (1.08 mL, 14.06 mmol) for 1.5 h. The crude residue purified by reverse phase prep HPLC (XSelect CSH, 19×100 mm, 5 µm, C18 column; ACN-water with 0.1% formic acid modifier, 24 mL/min), affording the title compound (55.5 mg, 45%) as a white powder. LCMS: $R_t$=0.30 min, m/z=533.0 (M+1) Method 2m_acidic; $^1$H NMR (500 MHz, DMSO-$d_6$) δ 9.34 (d, J=8.8 Hz, 1H), 8.55 (br s, 3H), 7.34 (br s, 2H), 6.73 (s, 1H), 5.37 (dd, J=8.7, 5.5 Hz, 1H), 5.19-5.13 (m, 1H), 5.01-4.94 (m, 1H), 4.62-4.57 (m, 1H), 4.43-4.37 (m, 2H), 1.38 (s, 3H) 1.34 (s, 3H).

Example 5

2-(((Z)-(1-(2-aminothiazol-4-yl)-2-(((2R,3S)-2-((5-(guanidinomethyl)-2H-tetrazol-2-yl)methyl)-4-oxo-1-sulfoazetidin-3-yl)amino)-2-oxoethylidene)amino)oxy)-2-methylpropanoic acid

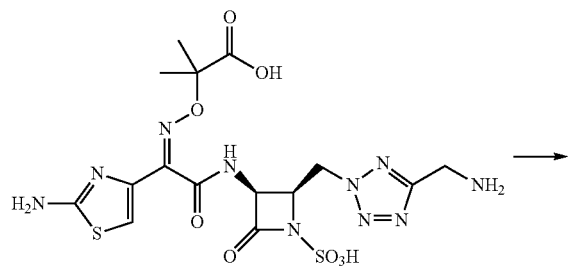

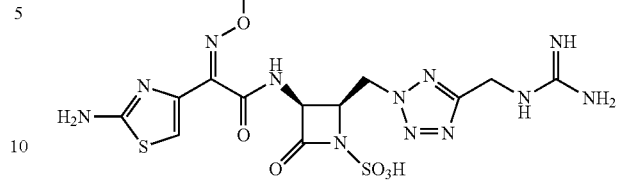

To a solution of 2-(((Z)-(2-(((2R,3S)-2-((5-(aminomethyl)-2H-tetrazol-2-yl)methyl)-4-oxo-1-sulfoazetidin-3-yl)amino)-1-(2-aminothiazol-4-yl)-2-oxoethylidene)amino)oxy)-2-methylpropanoic acid (20 mg, 0.038 mmol) and pyrazole-1-carboxamidine hydrochloride (11.6 mg, 0.079 mmol). in DMF (376 µL) was added DIPEA (26.2 µL, 0.150 mmol). After stirring at rt for 12 h the solution was concentrated in vacuo. Toluene was added and it was reconcentrated (3×). The crude residue was purified by reverse phase prep HPLC (XSelect CSH, 19×100 mm, 5 µm, C18 column; ACN-water with 0.1% formic acid modifier, 24 mL/min), affording the title compound (11 mg, 45%) as a white powder. LCMS: $R_t$=0.31 min, m/z=575.2 (M+1) Method 2m_acidic; $^1$H NMR (500 MHz, DMSO-$d_6$) δ 7.49-7.04 (m, 5H), 6.74 (br s, 1H), 5.26 (br s, 1H), 5.14-5.07 (m, 1H), 4.98-4.90 (m, 1H), 4.65 (br s, 2H), 4.59-4.52 (m, 1H), 1.36 (s, 3H), 1.34 (s, 3H).

Example 6

2-(((Z)-(2-(((2R,3S)-2-((5-(aminomethyl)-1H-tetrazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1

Prepared in an analogous manner to Example 4, step 2 using the appropriate 1H-tetrazole isomer obtained in Step 1 in Example 4 (442 mg, 0.760 mmol), $K_2S_2O_8$ (288 mg, 1.064 mmol) and $K_2HPO_4$ (172 mg, 0.988 mmol) in ACN:water (2:1, 12.6 mL) at 90° C. for 1.5 h. More $K_2S_2O_8$ (62 mg, 0.228 mmol) and $K_2HPO_4$ (42 mg, 0.198 mmol) were added and it was heated for an additional 3.5 h then cooled to rt, diluted with ACN and concentrated in vacuo, removing most of the ACN. The mixture was diluted with water/EtOAc and the layers separated. The aqueous layer was extracted with EtOAc (5×) and the combined organic layers were dried over $Na_2SO_4$. The crude residue was purified via silica gel chromatography (Acetone-DCM, 50%), to afford the title compound (179 mg, 54%). LCMS: $R_t$=0.72 min, m/z=432.3 (M+1) Method 2m_acidic.

Step 2: tert-Butyl ((1-(((2R,3S)-3-amino-4-oxoazetidin-2-yl)methyl)-1H-tetrazol-5-yl)methyl)carbamate Prepared in an analogous manner to example 4, step 3, using the product of Step 1 (179 mg, 0.415 mmol) and Pd on C (10%, 132 mg) in EtOAc:MeOH (10:1, 13.8 mL) for 21 h. The crude residue was used as such in following step. LCMS: $R_t$=0.37 min, m/z=298.3 (M+1) Method 2m_acidic.

Step 3: tert-Butyl 2-(((Z)-(2-(((2R,3S)-2-((5-(((tert-butoxycarbonyl)amino)methyl)-1H-tetrazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate Prepared in an analogous manner to example 4, step 3 using (Z)-2-(((1-(tert-butoxy)-2-methyl-1-oxopropan-2-yl)

oxy)imino)-2-(2-((tert-butoxycarbonyl)amino)thiazol-4-yl) acetic acid (214 mg, 0.498 mmol), DIPEA (953 µL, 5.46 mmol) and HATU (830 mg, 2.18 mmol) in DCM:DMF (5:1, 3.6 mL) at 0° C. followed by a solution of tert-butyl ((1-(((2R, 3S)-3-amino-4-oxoazetidin-2-yl)methyl)-1H-tetrazol-5-yl) methyl)carbamate (123 mg, 0.415 mmol) in DCM:DMF (4.3: 1, 3.7 mL). After stirring at rt for 1 h it was subjected to an identical workup then purified via silica gel chromatography (Acetone-DCM), affording the title compound (174 mg, 59%) as a light purple solid. LCMS: $R_f$=1.03 min, m/z=709.2 (M+1) Method 2m_acidic.

Step 4: (2R,3S)-3-(((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-1H-tetrazol-1-yl) methyl)-4-oxoazetidine-1-sulfonic acid Prepared in an analogous manner to example 4, step 4 using tert-Butyl 2-(((Z)-(2-(((2R,3S)-2-((5-(((tert-butoxycarbonyl)amino)methyl)-1H-tetrazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate (100 mg, 0.141 mmol) and SO$_3$.DMF (216 mg, 1.41 mmol) in DMF (1.4 mL) for 20 min at rt. Subjected to identical workup to afford the title compound (100 mg, 89%). LCMS: $R_f$=0.91 min, m/z=789.1 (M+1) Method 2m_acidic.

Step 5: 2-(((Z)-(2-(((2R,3S)-2-((5-(aminomethyl)-1H-tetrazol-1-yl)methyl)-4-oxo-1-sulfoazetidin-3-yl) amino)-1-(2-aminothiazol-4-yl)-2-oxoethylidene) amino)oxy)-2-methylpropanoic acid

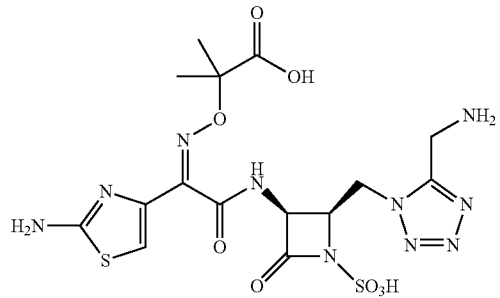 [SMILES: CC(C)(O/N=C(\C(=O)N[C@@H]1C(=O)N(S(=O)(=O)O)[C@@H]1Cn1nnnc1CN)c1csc(N)n1)C(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-1H-tetrazol-1-yl)methyl)-4-oxoazetidine-1-sulfonic acid (100 mg, 0.126 mmol), DCM (1.26 mL) and TFA (584 µL, 7.58 mmol) for 1.5 h. The crude residue purified by reverse phase prep HPLC (XSelect CSH, 19×100 mm, 5 µm, C18 column; ACN-water with 0.1% formic acid modifier, 24 mL/min), affording the title compound (18.7 mg, 28%) as a white powder. LCMS: $R_f$=0.31 min, m/z=533.2 (M+1) Method 2m_acidic; $^1$H NMR (400 MHz, DMSO-d$_6$) δ 9.21 (d, J=8.8 Hz, 1H), 7.28 (s, 2H), 6.79 (s, 1H), 5.35 (dd, J=8.8, 5.8 Hz, 1H), 4.79-4.61 (m, 2H), 4.59-4.53 (m, 1H), 4.47-4.35 (m, 2H), 1.36 (br s, 6H).

Example 7

2-(((Z)-(1-(2-aminothiazol-4-yl)-2-(((2R,3S)-2-((5-methyl-2H-tetrazol-2-yl)methyl)-4-oxo-1-sulfoazetidin-3-yl)amino)-2-oxoethylidene)amino)oxy)-2-methylpropanoic acid Step 1, Compound 1: Benzyl ((2R,3S)-1-(2,4-dimethoxybenzyl)-2-((5-methyl-2H-tetrazol-2-yl) methyl)-4-oxoazetidin-3-yl)carbamate Step 1, Compound 2: Benzyl ((2R,3S)-1-(2,4-dimethoxybenzyl)-2-((5-methyl-1H-tetrazol-1-yl) methyl)-4-oxoazetidin-3-yl)carbamate Prepared in an analogous manner to example 4, step 1 using Intermediate A (1.0 g, 2.1 mmol), 5-methyl-2H-tetrazole (527 mg, 6.27 mmol), K$_2$CO$_3$ (1.44 g, 10.5 mmol), NaI (470 mg, 3.13 mmol) in DMF (10 mL) at 70° C. for 4 h. No further reagent addition was necessary. After cooling to rt it was diluted with EtOAc, washed with brine, dried over Na$_2$SO$_4$ and concentrated in vacuo. The crude residue was purified via silica gel chromatography (Acetone-DCM), affording the title compound 1 (680 mg, 70%) and title compound 2 (221 mg, 23%) as solids. 1-LCMS: $R_f$=0.87 min, m/z=467.2 (M+1) Method 2m_acidic; 2-LCMS: $R_f$=0.80 min, m/z=467.2 (M+1) Method 2m_acidic.

Step 2: Benzyl ((2R,3S)-2-((5-methyl-2H-tetrazol-2-yl)methyl)-4-oxoazetidin-3-yl)carbamate Prepared in an analogous manner to example 4, step 2 using benzyl ((2R,3S)-1-(2,4-dimethoxybenzyl)-2-((5-methyl-2H-tetrazol-1-yl)methyl)-4-oxoazetidin-3-yl)carbamate (202 mg, 0.433 mmol), K$_2$S$_2$O$_8$ (164 mg, 0.606 mmol) and K$_2$HPO$_4$ (98 mg, 0.563 mmol) in ACN:water (2:1, 7.4 mL) at 90° C. for 1.5 h. More K$_2$S$_2$O$_8$ (35 mg, 0.13 mmol) and K$_2$HPO$_4$ (20 mg, 0.11 mmol) were added and it was heated for an additional 30 min then cooled to rt then concentrated in vacuo. The mixture was diluted with EtOAc, washed with brine, dried over Na$_2$SO$_4$ and concentrated in vacuo. The crude residue was purified via silica gel chromatography (MeOH-DCM, 0-10%), to afford the title compound (111 mg, 81%). LCMS: $R_f$=0.58 min, m/z=317.2 (M+1) Method 2m_acidic; $^1$H NMR (400 MHz, CDCl$_3$) δ 7.43-7.30 (m, 5H), 6.34 (br s, 1H), 6.01 (br s, 1H), 5.28-5.21 (m, 1H), 5.20-5.12 (m, 3H), 4.92 (dd, J=14.3, 3.9 Hz, 1H), 4.68 (dd, J=14.2, 7.9 Hz, 1H), 4.48-4.27 (m, 2H), 2.53 (s, 3H).

Step 3: (3S,4R)-3-amino-4-((5-methyl-2H-tetrazol-2-yl)methyl)azetidin-2-one

Prepared in an analogous manner to example 4, step 3 using benzyl ((2R,3S)-2-((5-methyl-2H-tetrazol-2-yl)methyl)-4-oxoazetidin-3-yl)carbamate (111 mg, 0.351 mmol) and Pd on C (10%, 50 mg) in EtOAc:MeOH (5:1, 7.0 mL) for 3 h. The crude residue was used as such in following step. LCMS: $R_f$=0.14 min, m/z=183.2 (M+1) Method 2m_acidic.

Step 4: tert-Butyl 2-(((Z)-(1-(2-((tert-butoxycarbonyl)amino)thiazol-4-yl)-2-(((2R,3S)-2-((5-methyl-2H-tetrazol-2-yl)methyl)-4-oxoazetidin-3-yl)amino)-2-oxoethylidene)amino)oxy)-2-methylpropanoate Prepared in an analogous manner to example 4, step 3 using (Z)-2-(((1-(tert-butoxy)-2-methyl-1-oxopropan-2-yl) oxy)imino)-2-(2-((tert-butoxycarbonyl)amino)thiazol-4-yl)

acetic acid (130 mg, 0.302 mmol), DIPEA (158 µL, 0.906 mmol) and HATU (138 mg, 0.362 mmol) in DCM:DMF (2:1, 3.0 mL) at 0° C. followed by a solution of (3S,4R)-3-amino-4-((5-methyl-2H-tetrazol-2-yl)methyl)azetidin-2-one (55 mg, 0.30 mmol) in DCM:DMF (2:1, 3.0 mL). After stirring at rt for 1 h it was concentrated in vacuo, dissolved in EtOAc, washed with water then brine, dried over $Na_2SO_4$ and concentrated in vacuo. The crude residue was purified via silica gel chromatography (Acetone-DCM), affording the title compound (179 mg, 99%) as a solid. LCMS: $R_t$=0.93 min, m/z=594.3 (M+1) Method 2m_acidic.

Step 5: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-2H-tetrazol-2-yl)methyl)-4-oxoazetidine-1-sulfonic acid Prepared in an analogous manner to example 4, step 4 using tert-Butyl 2-(((Z)-(1-(2-((tert-butoxycarbonyl)amino)thiazol-4-yl)-2-(((2R,3S)-2-((5-methyl-2H-tetrazol-2-yl)methyl)-4-oxoazetidin-3-yl)amino)-2-oxoethylidene)amino)oxy)-2-methylpropanoate (179 mg, 0.302 mmol) and $SO_3$.DMF (462 mg, 3.02 mmol) in DMF (3.0 mL) for 1 h at rt. The solution was diluted with EtOAc, washed with brine, dried over $Na_2SO_4$ and concentrated in vacuo to afford the title compound (assumed quantitative). LCMS: $R_t$=0.80 min, m/z=674.1 (M+1) Method 2m_acidic.

Step 6: 2-(((Z)-(1-(2-aminothiazol-4-yl)-2-(((2R,3S)-2-((5-methyl-2H-tetrazol-2-yl)methyl)-4-oxo-1-sulfoazetidin-3-yl)amino)-2-oxoethylidene)amino)oxy)-2-methylpropanoic acid Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-2H-tetrazol-2-yl)methyl)-4-oxoazetidine-1-sulfonic acid (203 mg, 0.302 mmol), DCM (3.0 mL) and TFA (1.39 mL, 18.1 mmol) for 2 h. The crude residue purified by reverse phase prep HPLC (XSelect CSH, 19×100 mm, 5 µm, C18 column; ACN-water with 0.1% formic acid modifier, 24 mL/min), affording the title compound (37 mg, 24%) as a white powder. LCMS: $R_t$=0.35 min, m/z=518.1 (M+1) Method 2m_acidic; $^1$H NMR (400 MHz, $D_2O$) δ 7.03 (s, 1H), 5.37 (d, J=5.5 Hz, 1H), 5.08-4.97 (m, 1H), 4.90-4.80 (m, 2H), 2.35 (s, 3H), 1.32 (s, 3H), 1.31 (s, 3H).

Example 8

2-(((Z)-(1-(2-aminothiazol-4-yl)-2-(((2R,3S)-2-((5-methyl-1H-tetrazol-1-yl)methyl)-4-oxo-1-sulfoazetidin-3-yl)amino)-2-oxoethylidene)amino)oxy)-2-methylpropanoic acid

Step 1: Benzyl ((2R,3S)-2-((5-methyl-1H-tetrazol-1-yl)methyl)-4-oxoazetidin-3-yl)carbamate Prepared in an analogous manner to example 4, step 2 using benzyl ((2R,3S)-1-(2,4-dimethoxybenzyl)-2-((5-methyl-1H-tetrazol-1-yl)methyl)-4-oxoazetidin-3-yl)carbamate (221 mg, 0.474 mmol), $K_2S_2O_8$ (179 mg, 0.663 mmol) and $K_2HPO_4$ (107 mg, 0.616 mmol) in ACN:water (2:1, 7.9 mL) at 90° C. for 1.5 h. More $K_2S_2O_8$ (38.4 mg, 0.142 mmol) and $K_2HPO_4$ (21.5 mg, 0.123 mmol) were added and it was heated for an additional 30 min then cooled to rt then concentrated in vacuo. The mixture was diluted with EtOAc, washed with brine, dried over $Na_2SO_4$ and concentrated in vacuo. The crude residue was purified via silica gel chromatography (MeOH-DCM, 0-10%), to afford the title compound (97 mg, 65%). LCMS: $R_t$=1.00 min, m/z=317.3 (M+1) Method 2m_acidic.

Step 2: (3S,4R)-3-amino-4-((5-methyl-1H-tetrazol-1-yl)methyl)azetidin-2-one

Prepared in an analogous manner to example 4, step 3 using benzyl ((2R,3S)-2-((5-methyl-1H-tetrazol-1-yl)methyl)-4-oxoazetidin-3-yl)carbamate (97 mg, 0.31 mmol) and Pd on C (10%, 50 mg) in EtOH:MeOH (5:1, 3.0 mL) for 3 h. The crude residue was used as such in following step. LCMS: $R_t$=0.11 min, m/z=183.2 (M+1) Method 2m_acidic.

Step 3: tert-Butyl 2-(((Z)-(1-(2-((tert-butoxycarbonyl)amino)thiazol-4-yl)-2-(((2R,3S)-2-((5-methyl-1H-tetrazol-1-yl)methyl)-4-oxoazetidin-3-yl)amino)-2-oxoethylidene)amino)oxy)-2-methylpropanoate Prepared in an analogous manner to example 4, step 3 using (Z)-2-(((1-(tert-butoxy)-2-methyl-1-oxopropan-2-yl)oxy)imino)-2-(2-((tert-butoxycarbonyl)amino)thiazol-4-yl)acetic acid (130 mg, 0.302 mmol), DIPEA (158 µL, 0.906 mmol) and HATU (115 mg, 0.302 mmol) in DCM:DMF (2:1, 3.0 mL) at 0° C. followed by a solution of (3S,4R)-3-amino-4-((5-methyl-1H-tetrazol-1-yl)methyl)azetidin-2-one (55 mg, 0.30 mmol) in DCM:DMF (2:1, 3.0 mL). After stirring at rt for 1 h it was concentrated in vacuo, dissolved in EtOAc, washed with water then brine, dried over $Na_2SO_4$ and concentrated in vacuo. The crude residue was purified via silica gel chromatography (Acetone-DCM), affording the title compound (133 mg, 74%) as a solid. LCMS: $R_t$=0.92 min, m/z=594.2 (M+1) Method 2m_acidic.

Step 4: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-1H-tetrazol-1-yl)methyl)-4-oxoazetidine-1-sulfonic acid Prepared in an analogous manner to example 4, step 4 using tert-butyl 2-(((Z)-(1-(2-((tert-butoxycarbonyl)amino)thiazol-4-yl)-2-(((2R,3S)-2-((5-methyl-1H-tetrazol-1-yl)methyl)-4-oxoazetidin-3-yl)amino)-2-oxoethylidene)amino)oxy)-2-methylpropanoate (133 mg, 0.224 mmol) and $SO_3$.DMF (343 mg, 2.24 mmol) in DMF (2.24 mL) for 1 h at rt. The solution was diluted with EtOAc, washed with brine, dried over $Na_2SO_4$ and concentrated in vacuo to afford the title compound (assumed quantitative). LCMS: R=0.85 min, m/z=674.2 (M+1) Method 2m_acidic.

Step 5: 2-(((Z)-(1-(2-aminothiazol-4-yl)-2-(((2R,3S)-2-((5-methyl-1H-tetrazol-1-yl)methyl)-4-oxo-1-sulfoazetidin-3-yl)amino)-2-oxoethylidene)amino)oxy)-2-methylpropanoic acid

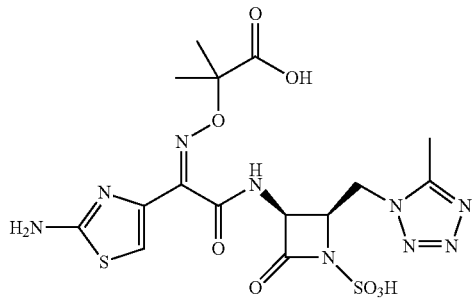 [SMILES: Cc1nnnn1C[C@@H]1[C@H](NC(=O)/C(=N\OC(C)(C)C(=O)O)c2csc(N)n2)C(=O)N1S(=O)(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-1H-tetrazol-1-yl)methyl)-4-oxoazetidine-1-sulfonic acid (151 mg, 0.224 mmol), DCM (2.24 mL) and TFA (1.04 mL, 13.45 mmol) for 2 h. The crude residue purified by reverse phase prep HPLC (XSelect CSH, 19×100 mm, 5 μm, C18 column; ACN-water with 0.1% formic acid modifier, 24 mL/min), affording the title compound (14.4 mg, 11%) as a white powder. LCMS: $R_t$=0.55 min, m/z=518.1 (M+1) Method 2m_acidic_polar; $^1$H NMR (400 MHz, D$_2$O) δ 7.04 (s, 1H), 5.37 (d, J=5.5 Hz, 1H), 4.83-4.77 (m, 1H), 4.76-4.54 (m, 2H assumed; obscured by solvent), 2.48 (s, 3H), 1.35 (s, 3H), 1.33 (s, 3H).

Example 9

2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1: benzyl ((2R,3S)-2-((1H-1,2,4-triazol-1-yl)methyl)-1-(2,4-dimethoxybenzyl)-4-oxoazetidin-3-yl)carbamate A 20 mL microwave vial was charged with Intermediate A (250 mg, 0.0522 mmol), 1,2,4-triazole (54 mg, 0.784 mmol), K$_2$CO$_3$ (215 mg, 1.56 mmol), NaI (94 mg, 0.63 mmol) and DMF (2 mL) then heated to 70° C. with stirring. After 4 h, more 1,2,4-triazole (54 mg, 0.784 mmol), K$_2$CO$_3$ (215 mg, 1.56 mmol) and NaI (94 mg, 0.63 mmol) were added and heating was continued. After 7 h of total heating it was cooled to rt, diluted with DCM/brine and the layers were separated. The aqueous layer was extracted with DCM and the combined organic layers were dried over Na$_2$SO$_4$ and concentrated in vacuo. Toluene was added and it was concentrated in vacuo (40° C. bath). The crude residue was purified via silica gel chromatography (Acetone-Heptane, 50%) to afford the title compound (156 mg, 66%). LCMS: Rt=0.77 min, m/z=452.3 (M+1) Method 2m_acidic.

Step 2: Benzyl ((2R,3S)-2-((1H-1,2,4-triazol-1-yl)methyl)-4-oxoazetidin-3-yl)carbamate Prepared in an analogous manner to example 4, step 2 using benzyl ((2R,3S)-2-((1H-1,2,4-triazol-1-yl)methyl)-1-(2,4-dimethoxybenzyl)-4-oxoazetidin-3-yl)carbamate (101 mg, 0.224 mmol), K$_2$S$_2$O$_8$ (85 mg, 0.313 mmol) and K$_2$HPO$_4$ (50.7 mg, 0.291 mmol) in ACN:water (2:1, 61.5 mL) while heating for 2 h at 90° C. More K$_2$S$_2$O$_8$ (18.1 mg, 0.067 mmol) and K$_2$HPO$_4$ (10.1 mg, 0.058 mmol) were added and heated for another 1.5 h. More K$_2$S$_2$O$_8$ (18.1 mg, 0.067 mmol) and K$_2$HPO$_4$ (10.1 mg, 0.058 mmol) were added and heated for another hour. It was diluted with ACN and concentrated in vacuo, removing most of the ACN. The mixture was diluted with water/DCM then added EtOAc and the layers separated. The aqueous layer was extracted with EtOAc (5×) and the combined organic layers were dried over Na$_2$SO$_4$. The crude residue was purified via silica gel chromatography (MeOH-DCM, 10%) to afford the title compound (38 mg, 56%). LCMS: $R_t$=0.50 min, m/z=302.2 (M+1) Method 2m_acidic; $^1$H NMR (500 MHz, ACN-d$_3$) δ 8.17 (s, 1H), 7.92 (s, 1H), 7.49-7.31 (m, 4H), 6.82-6.74 (m, 1H), 6.67 (br s, 1H), 5.18-5.01 (m, 3H), 4.49-4.42 (m, 1H), 4.37-4.30 (m, 1H), 4.21 (q, J=5.4 Hz, 1H).

Step 3: (3S,4R)-4-((1H-1,2,4-triazol-1-yl)methyl)-3-aminoazetidin-2-one

To a solution of benzyl ((2R,3S)-2-((1H-1,2,4-triazol-1-yl)methyl)-4-oxoazetidin-3-yl)carbamate (38 mg, 0.126 mmol) in MeOH (5 mL) was added Pd black (6.7 mg, 0.063 mmol) followed by formic acid (339 μL, 8.83 mmol). After 1 h of stirring, the mixture was filtered over celite, washing with MeOH, and the filtrate was concentrated in vacuo. The solution was lyophilized and the crude material was used directly in the subsequent step. LCMS: $R_t$=0.14 min, m/z=168.1 (M+1) Method 2m_acidic.

Step 4: tert-butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a slurry of (Z)-2-(((1-(tert-butoxy)-2-methyl-1-oxopropan-2-yl)oxy)imino)-2-(2-((tert-butoxycarbonyl)amino)thiazol-4-yl)acetic acid (81 mg, 0.19 mmol) in DCM (800 μL) at 0° C. was added DIPEA (88 μL, 0.504 mmol) followed by HATU (72 mg, 0.190 mmol). A few drops of DMF were added to homogenize the mixture. To the resulting solution was added a solution of (3S,4R)-4-((1H-1,2,4-triazol-1-yl)methyl)-3-aminoazetidin-2-one (21 mg, 0.126 mmol) in DCM (1 mL). After 1.5 h of stirring it was diluted with water/DCM and the layers separated. The aqueous layer was extracted with DCM and the combined organic layers were dried over Na$_2$SO$_4$ and concentrated in vacuo. The crude residue was purified via silica gel chromatography (Acetone-DCM) to afford the title compound (47 mg, 65%). LCMS: $R_t$=0.88 min, m/z=579.3 (M+1) Method 2m_acidic.

Step 5: (2R,3S)-2-((1H-1,2,4-triazol-1-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid tert-Butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate (44 mg, 0.076 mmol) in DMF (760 μL) was treated with SO3.DMF (116 mg, 0.760 mmol). After 1 h of stirring, the solution was diluted with EtOAc/brine and the layers were separated. The aqueous layer was extracted with EtOAc (3×) and the combined organic layers were dried over $Na_2SO_4$ and concentrated in vacuo to afford the title compound (assumed quantitative) as a white solid. LCMS: $R_t$=0.81 min, m/z=659.3 (M+1) Method 2m_acidic.

Step 6: 2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid

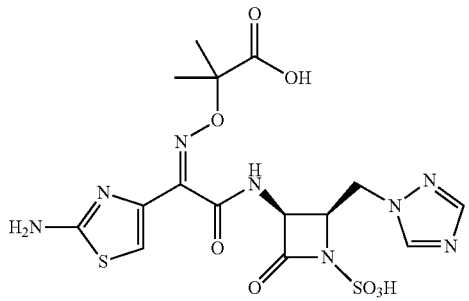 [SMILES: CC(C)(O/N=C(\C(=O)N[C@@H]1C(=O)N(S(=O)(=O)O)[C@@H]1Cn1cncn1)c1csc(N)n1)C(=O)O]

Followed the general procedure for the acid mediated deprotection using (2R,3S)-2-((1H-1,2,4-triazol-1-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid (50.1 mg, 0.076 mmol), DCM (760 μL) and TFA (351 μl, 4.56 mmol). The crude residue purified by reverse phase prep HPLC (XSelect CSH, 19×100 mm, 5 μm, C18 column; ACN-water with 0.1% formic acid modifier, 24 mL/min), affording the title compound (14.8 mg, 34%) as a white powder. LCMS: $R_t$=0.31 min, m/z=503.1 (M+1) Method 2m_acidic; $^1H$ NMR (500 MHz, DMSO-$d_6$) δ 9.39 (d, J=8.83 Hz, 1H), 8.52 (s, 1H), 8.02 (s, 1H), 6.74 (s, 1H), 5.28 (dd, J=8.8, 5.4 Hz, 1H), 4.74-4.64 (m, 1H), 4.58 (d, J=6.9 Hz, 1H), 4.32 (d, J=5.7 Hz, 1H), 1.37 (s, 3H) 1.41 (s, 3H).

Example 10

2-(((Z)-(2-(((2R,3S)-2-((3-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1

((2S,3S)-3-(((benzyloxy)carbonyl)amino)-1-(2,4-dimethoxybenzyl)-4-oxoazetidin-2-yl)methyl methanesulfonate (3.10 g, 6.48 mmol), tert-butyl ((1H-1,2,4-triazol-3-yl)methyl)carbamate (1.926 g, 9.72 mmol), $K_2CO_3$ (1.35 g, 9.72 mmol) and NaI (1.165 g, 7.78 mmol) were slurried in DMF (20 mL) and heated to 70° C. with stirring. After 3 h, more tert-butyl ((1H-1,2,4-triazol-3-yl)methyl)carbamate (1.926 g, 9.72 mmol), $K_2CO_3$ (1.35 g, 9.72 mmol) and NaI (777 mg, 8.10 mmol) were added and it was heated an additional 4 h, whereupon it was diluted with EtOAc/water and the layers were separated. The aqueous layer was extracted with EtOAc (2×) and the combined organic layers were washed with brine (3×), dried over $Na_2SO_4$ and concentrated in vacuo. The crude residue was purified via silica gel chromatography (Acetone-Heptane, 0-70%) to afford the 3-substituted isomer (1.16 g, 31%) along with the 5-substituted isomer (375 mg, 10%). A-LCMS: $R_t$=0.87 min, m/z=581.2 (M+1) Method 2m_acidic; B-LCMS: $R_t$=0.94 min, m/z=581.2 (M+1) Method 2m_acidic; B-$^1H$ NMR (500 MHz, CDCl$_3$) δ 7.86 (s, 1H), 7.44-7.31 (m, 4H), 7.29 (s, 3H), 6.90 (d, J=8.2 Hz, 1H), 6.49-6.37 (m, 2H), 5.25-5.04 (m, 3H), 4.54-4.43 (m, 2H), 4.43-4.22 (m, 3H), 4.13 (d, J=5.4 Hz, 1H), 3.90-3.71 (m, 7H), 1.36-1.51 (m, 9H).

Step 2

Prepared in an analogous manner to Example 4, step 2 using the 3-substituted isomer from Step 1 (1.16 g, 2.00 mmol), $K_2S_2O_8$ (756 mg, 2.80 mmol) and $K_2HPO_4$ (452 mg, 2.60 mmol) in ACN:water (2:1, 33.3 mL) while heating for 1.5 h at 90° C. More $K_2S_2O_8$ (162 mg, 0.599 mmol) and $K_2HPO_4$ (90 mg, 0.52 mmol) were added and heated for another 3.5 h, whereupon it was concentrated in vacuo, removing most of the ACN. The mixture was diluted with water/EtOAc and the layers were separated. The aqueous layer was extracted with EtOAc (5×) and the combined organic layers were dried over $Na_2SO_4$. The crude residue was purified via silica gel chromatography (Acetone-DCM, 0-100%) to afford the title compound (416 mg, 48%). LCMS: $R_t$=0.71 min, m/z=431.3 (M+1) Method 2m_acidic; $^1H$ NMR (500 MHz, ACN-$d_3$) δ 8.08 (s, 1H), 7.49-7.25 (m, 5H), 6.82-6.60 (m, 2H), 5.81-5.62 (m, 1H), 5.21-5.03 (m, 3H), 4.48-4.07 (m, 6H), 1.46-1.33 (m, 9H).

Step 3: tert-butyl ((1-(((2R,3S)-3-amino-4-oxoazetidin-2-yl)methyl)-1H-1,2,4-triazol-3-yl)methyl)carbamate Prepared according to the procedure described in Malmström et al. *Bioorg. Med. Chem. Lett.* 2012, 22, 5293. A solution of the product of Step 2 (416 mg, 0.966 mmol) in EtOAc:MeOH (5:1, 32.2 mL) was evacuated and backfilled with argon (2×) followed by addition of Pd on C (10%, 103 mg). The system was evacuated and backfilled with $H_2$ (3×). After 21 h of stirring MeOH (282 μL) was added. After an additional 4 h of stirring the mixture was filtered over celite, washing with MeOH, concentrated in vacuo, taken up on toluene and reconcentrated (3×). The crude residue was used as such in following step. LCMS: $R_t$=0.33 min, m/z=297.2 (M+1) Method 2m_acidic.

Step 4: tert-Butyl 2-(((Z)-(2-(((2R,3S)-2-((3-(((tert-butoxycarbonyl)amino)methyl)-1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a slurry of (Z)-2-(((1-(tert-butoxy)-2-methyl-1-oxopropan-2-yl)oxy)imino)-2-(2-((tert-butoxycarbonyl)amino)thiazol-4-yl)acetic acid (47 mg, 0.109 mmol) in DCM:DMF (12:1, 6.5 mL) at 0° C. was added DIPEA (505 μL, 2.89 mmol) followed by HATU (440 mg, 1.16 mmol). To the resulting solution was added a solution of tert-butyl ((1-(((2R, 3S)-3-amino-4-oxoazetidin-2-yl)methyl)-1H-1,2,4-triazol-3-yl)methyl)carbamate (286 mg, 0.964 mmol) in DCM:DMF (14:1, 7.5 mL). After 1 h of stirring it was diluted with water/EtOAc and the layers separated. The aqueous layer was extracted with EtOAc and the combined organic layers were washed with brine (3×), dried over $Na_2SO_4$ and concentrated in vacuo. The crude residue was purified via silica gel chromatography (Acetone-DCM, 70%) to afford the title compound (428 mg, 63%). LCMS: $R_t$=0.99 min, m/z=708.2 (M+1) Method 2m_acidic.

Step 5: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-(((tert-butoxycarbonyl)amino)methyl)-1H-1,2,4-triazol-1-yl)methyl)-4-oxoazetidine-1-sulfonic acid tert-Butyl 2-(((Z)-(2-(((2R,3S)-2-((3-(((tert-butoxycarbonyl)amino)methyl)-1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate (200 mg, 0.283 mmol) in DMF (2.0 mL) was treated with SO3.DMF (433 mg, 2.83 mmol). After 20 min of stirring, the solution was diluted with EtOAc/brine and the layers were separated. The aqueous layer was extracted with EtOAc (3×) and the combined organic layers were dried over $Na_2SO_4$ and concentrated in vacuo to afford the title compound (assumed quantitatie) as a white solid. LCMS: $R_t$=0.91 min, m/z=788.4 (M+1) Method 2m_acidic.

Step 6: 2-(((Z)-(2-(((2R,3S)-2-((3-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid

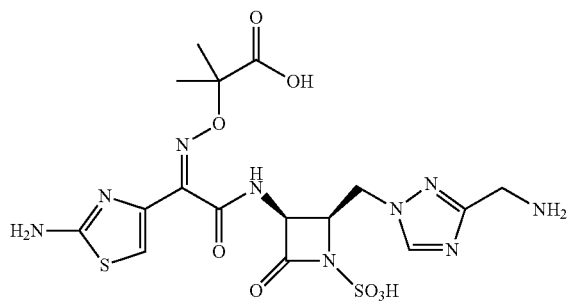 [SMILES: CC(C)(O/N=C(\C(=O)N[C@@H]1C(=O)N(S(=O)(=O)O)[C@@H]1Cn1cnc(CN)n1)c1csc(N)n1)C(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-(((tert-butoxycarbonyl)amino)methyl)-1H-1,2,4-triazol-1-yl)methyl)-4-oxoazetidine-1-sulfonic acid (223 mg, 0.283 mmol), DCM (2.89 mL) and TFA (1.31 ml, 16.98 mmol). The crude residue purified by reverse phase prep HPLC (XSelect CSH, 19×100 mm, 5 μm, C18 column; ACN-water with 0.1% formic acid modifier, 24 mL/min), affording the title compound (99 mg, 65%) as a white powder. LCMS: $R_t$=0.31 min, m/z=532.2 (M+1) Method 2m_acidic; $^1$H NMR (500 MHz, DMSO-$d_6$) δ 9.45 (d, J=8.5 Hz, 1H), 8.53 (s, 1H), 8.39 (br s, 3H), 7.32 (s, 2H), 6.74 (s, 1H), 5.23 (dd, J=8.5, 5.7 Hz, 1H), 4.76-4.65 (m, 1H), 4.62-4.55 (m, 1H), 4.32-4.27 (m, 1H), 4.16-4.08 (m, 2H), 1.36 (s, 3H) 1.43 (s, 3H).

Example 11

2-(((Z)-(1-(2-aminothiazol-4-yl)-2-(((2R,3S)-2-((3-(guanidinomethyl)-1H-1,2,4-triazol-1-yl)methyl)-4-oxo-1-sulfoazetidin-3-yl)amino)-2-oxoethylidene)amino)oxy)-2-methylpropanoic acid

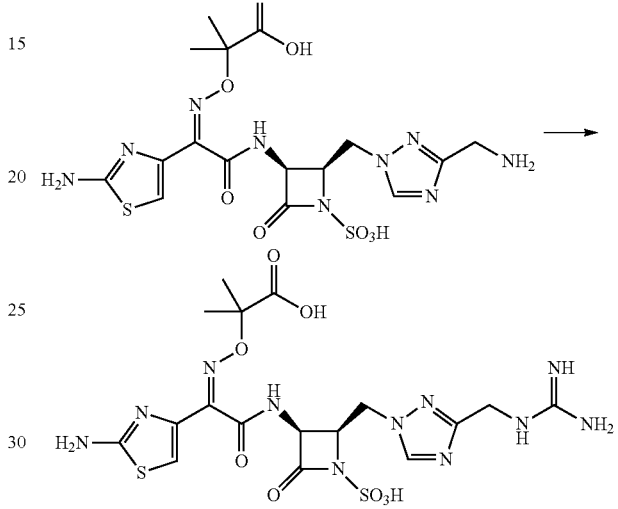

To a solution 2-(((Z)-(2-(((2R,3S)-2-((3-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid (25 mg, 0.047 mmol) and pyrazole-1-carboxamidine hydrochloride (10.9 mg, 0.099 mmol) in DMF (470 μL) was added DIPEA (33 μL, 0.188 mmol). After stirring at rt for 12 h the solution was concentrated in vacuo. Toluene was added and it was reconcentrated (3×). The crude residue was purified by reverse phase prep HPLC (XSelect CSH, 19×100 mm, 5 μm, C18 column; ACN-water with 0.1% formic acid modifier, 24 mL/min), affording the title compound (16 mg, 52%) as a white powder. LCMS: $R_t$=0.31 min, m/z=574.3 (M+1) Method 2m_acidic; $^1$H NMR (500 MHz, DMSO-$d_6$) δ 9.45 (br s, 1H), 8.47 (s, 1H), 7.86 (br s, 1H), 7.31 (br s, 3H), 6.74 (br s, 1H), 6.55 (s, 1H), 5.22 (br s, 1H), 4.69-4.59 (m, 1H), 4.60-4.50 (m, 1H), 4.45-4.36 (m, 2H), 4.34-4.26 (m, 1H), 1.35 (s, 3H) 1.41 (s, 3H).

Example 12

2-(((Z)-(2-(((2R,3S)-2-((5-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1

Prepared in an analogous manner to Example 4, step 2 using the 5-substituted isomer from Step 1 in Example 10 (361 mg, 0.622 mmol), $K_2S_2O_8$ (235 mg, 0.870 mmol) and $K_2HPO_4$ (115 mg, 0.808 mmol) in ACN:water (2:1, 10.4 mL) while heating for 1.5 h at 90° C. More $K_2S_2O_8$ (50 mg, 0.187 mmol) and $K_2HPO_4$ (23 mg, 0.162 mmol) were added and heated for another 3.5 h, whereupon it was concentrated in vacuo, removing most of the ACN. The mixture was diluted with water/EtOAc and the layers were separated. The aqueous layer was extracted with EtOAc (5×) and the combined organic layers were dried over $Na_2SO_4$. The crude residue was purified via silica gel chromatography (Acetone-DCM, 0-100%) to afford the title compound (155 mg, 58%). LCMS: $R_t$=0.71 min, m/z=431.2 (M+1) Method 2m_acidic.

Step 2: tert-Butyl (1-(((2R,3S)-3-amino-4-oxoazetidin-2-yl)methyl)-1H-1,2,4-triazol-5-yl)methyl)carbamate Prepared according to Example 7, step 3. A solution of the product of Step 1 (134 mg, 0.311 mmol) in EtOAc:MeOH (5:1, 10.4 mL) was evacuated and backfilled with argon (2×) followed by addition of Pd on C (10%, 33 mg). The system was evacuated and backfilled with $H_2$ (3×). After 21 h of stirring MeOH (282 µL) was added. After an additional 4 h of stirring the mixture was filtered over celite, washing with MeOH, concentrated in vacuo, taken up on toluene and reconcentrated (3×). The crude residue was used as such in following step. LCMS: $R_t$=0.38 min, m/z=297.2 (M+1) Method 2m_acidic.

Step 3: tert-Butyl 2-(((Z)-(2-(((2R,3S)-2-((5-(((tert-butoxycarbonyl)amino)methyl)-1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a slurry of (Z)-2-(((1-(tert-butoxy)-2-methyl-1-oxopropan-2-yl)oxy)imino)-2-(2-((tert-butoxycarbonyl)amino) thiazol-4-yl)acetic acid (160 mg, 0.373 mmol) in DCM:DMF (30:1, 3.1 mL) at 0° C. was added DIPEA (163 µL, 0.933 mmol) followed by HATU (142 mg, 0.373 mmol). To the resulting solution was added a solution of tert-butyl ((1-(((2R, 3S)-3-amino-4-oxoazetidin-2-yl)methyl)-1H-1,2,4-triazol-5-yl)methyl)carbamate (92 mg, 0.311 mmol) in DCM:DMF (30:1, 3.1 mL). After 1 h of stirring it was concentrated in vacuo and taken up in EtOAc/brine. The layers separated and the aqueous layer was extracted with EtOAc. The combined organic layers were washed with brine (3×), dried over $Na_2SO_4$ and concentrated in vacuo. The crude residue was purified via silica gel chromatography (Acetone-DCM, 70%) to afford the title compound (128 mg, 58%). LCMS: $R_t$=0.97 min, m/z=708.2 (M+1) Method 2m_acidic.

Step 4: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-1H-1,2,4-triazol-1-yl)methyl)-4-oxoazetidine-1-sulfonic acid tert-Butyl 2-(((Z)-(2-(((2R,3S)-2-((5-(((tert-butoxycarbonyl)amino)methyl)-1H-1,2,4-triazol-1-yl)methyl)-4-oxoazetidin-3-yl)amino)-1-(2-((tert-butoxycarbonyl)amino) thiazol-4-yl)-2-oxoethylidene)amino)oxy)-2-methylpropanoate (128 mg, 0.181 mmol) in DMF (1.3 mL) was treated with SO3.DMF (277 mg, 1.81 mmol). After 20 min of stirring, the solution was diluted with EtOAc/brine and the layers were separated. The aqueous layer was extracted with EtOAc (3×) and the combined organic layers were dried over $Na_2SO_4$ and concentrated in vacuo to afford the title compound (assumed quantitatie) as a white solid. LCMS: Rt=0.90 min, m/z=788.3 (M+1) Method 2m_acidic.

Step 5: 2-(((Z)-(2-(((2R,3S)-2-((5-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid

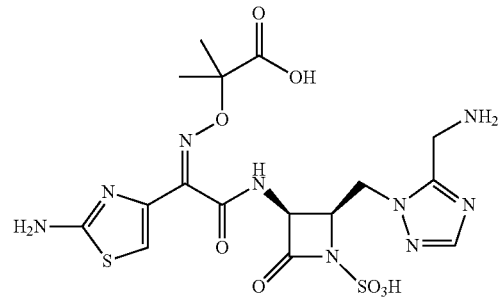 [SMILES: CC(C)(O/N=C(\C(=O)N[C@@H]1C(=O)N(S(=O)(=O)O)[C@@H]1Cn1ncnc1CN)c1csc(N)n1)C(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)-1H-1,2,4-triazol-1-yl)methyl)-4-oxoazetidine-1-sulfonic acid (143 mg, 0.181 mmol), DCM (1.81 mL) and TFA (837 µl, 10.9 mmol). The crude residue purified by reverse phase prep HPLC (XSelect CSH, 19×100 mm, 5 µm, C18 column; ACN-water with 0.1% formic acid modifier, 24 mL/min), affording the title compound (60 mg, 62%) as a white powder. LCMS: $R_t$=0.28 min, m/z=532.2 (M+1) Method 2m_acidic; $^1$H NMR (500 MHz, DMSO-$d_6$) δ 9.23 (d, J=9.1 Hz, 1H), 8.40 (br s, 3H), 8.06 (s, 1H), 7.59-7.27 (m, 2H), 6.84 (s, 1H), 5.37 (dd, J=9.0, 5.5 Hz, 1H), 4.61-4.51 (m, 1H), 4.49-4.34 (m, 3H), 4.25 (dd, J=15.3, 5.8 Hz, 1H), 1.37 (s, 6H).

Example 13

2-(((Z)-(1-(2-aminothiazol-4-yl)-2-(((2R,3S)-2-((5-(guanidinomethyl)-1H-1,2,4-triazol-1-yl)methyl)-4-oxo-1-sulfoazetidin-3-yl)amino)-2-oxoethylidene) amino)oxy)-2-methylpropanoic acid

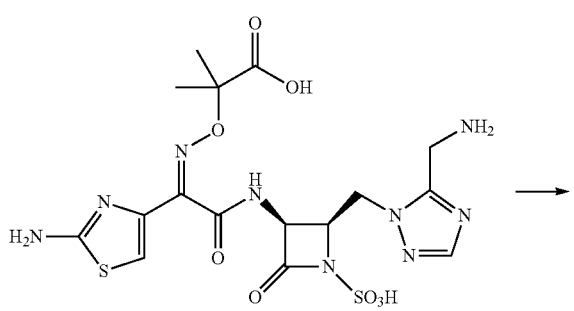

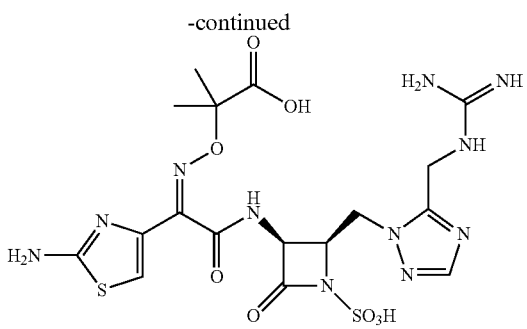

To a solution 2-(((Z)-(2-(((2R,3S)-2-((5-(aminomethyl)-1H-1,2,4-triazol-1-yl)methyl)-4-oxo-1-sulfoazetidin-3-yl)amino)-1-(2-aminothiazol-4-yl)-2-oxoethylidene)amino)oxy)-2-methylpropanoic acid (25 mg, 0.047 mmol) and pyrazole-1-carboxamidine hydrochloride (10.9 mg, 0.099 mmol) in DMF (470 µL) was added DIPEA (33 µL, 0.188 mmol). After stirring at rt for 12 h the solution was concentrated in vacuo. Toluene was added and it was reconcentrated (3×). The crude residue was purified by reverse phase prep HPLC (XSelect CSH, 19×100 mm, 5 µm, C18 column; ACN-water with 0.1% formic acid modifier, 24 mL/min), affording the title compound (13 mg, 42%) as a white powder. LCMS: $R_t$=0.29 min, m/z=574.2 (M+1) Method 2m_acidic; $^1$H NMR (500 MHz, DMSO-$d_6$) δ 7.96-7.78 (m, 1H), 7.41-6.96 (m, 5H), 6.80-6.71 (m, 1H), 6.55 (s, 1H), 5.42-5.32 (m, 1H), 4.75-4.63 (m, 1H), 4.62-4.42 (m, 1H), 4.39-4.28 (m, 1H), 1.38 (s, 3H) 1.34 (s, 3H).

Example 14

2-(((Z)-(1-(2-aminothiazol-4-yl)-2-oxo-2-(((3S,4R)-2-oxo-4-((2-oxopiperidin-1-yl)methyl)-1-sulfoazetidin-3-yl)amino)ethylidene)amino)oxy)-2-methylpropanoic acid Step 1: Benzyl ((3S,4R)-1-(2,4-dimethoxybenzyl)-2-oxo-4-((2-oxopyridin-1(2H)-yl)methyl)azetidin-3-yl)carbamate ((2S,3S)-3-(((benzyloxy)carbonyl)amino)-1-(2,4-dimethoxybenzyl)-4-oxoazetidin-2-yl)methyl methanesulfonate (860 mg, 1.80 mmol), pyridin-2(1H)-one (855 mg, 8.99 mmol), $K_2CO_3$ (1.74 g, 12.6 mmol) and NaI (746 mg, 4.49 mmol) were slurried in DMF (6.9 mL) and heated to 80° C. with stirring. After 4 h, it was cooled to rt, diluted with EtOAc and washed with brine. The organic layer was dried over $Na_2SO_4$ and concentrated in vacuo. The crude residue was purified via silica gel chromatography (Acetone-DCM) to afford title compound (304 mg, 35%). LCMS: $R_t$=0.79 min, m/z=478.2 (M+1) Method 2m_acidic; $^1$H NMR (500 MHz, CDCl$_3$) δ 7.39-7.28 (m, 6H), 7.07 (d, J=5.9 Hz, 1H), 6.93-6.85 (m, 1H), 6.55 (d, J=9.0 Hz, 1H), 6.40 (d, J=2.4 Hz, 1H), 6.35 (dd, J=8.2, 2.4 Hz, 1H), 6.10-6.02 (m, 1H), 5.87 (d, J=7.8 Hz, 1H), 5.10 (s, 2H), 4.93 (br s, 1H), 4.63 (d, J=14.5 Hz, 1H), 4.27-4.10 (m, 1H), 3.97 (d, J=9.0 Hz, 2H), 3.88 (d, J=14.5 Hz, 1H), 3.78 (s, 3H), 3.76 (s, 3H).

Step 2: Benzyl ((3S,4R)-2-oxo-4-((2-oxopyridin-1(2H)-yl)methyl)azetidin-3-yl)carbamate Prepared in an analogous manner to example 4, step 2 using Benzyl ((3S,4R)-1-(2,4-dimethoxybenzyl)-2-oxo-4-((2-oxopyridin-1(2H)-yl)methyl)azetidin-3-yl)carbamate (361 mg, 0.622 mmol), $K_2S_2O_8$ (225 mg, 0.833 mmol) and $K_2HPO_4$ (135 mg, 0.773 mmol) in ACN:water (2:1, 9.9 mL) while heating for 1.5 h at 90° C. More $K_2S_2O_8$ (45 mg, 0.17 mmol) and $K_2HPO_4$ (26.9 mg, 0.155 mmol) were added and heated for another 30 min, whereupon it was concentrated, redissolved in EtOAc, washed with brine, dried over $Na_2SO_4$, and concentrated in vacuo. The crude residue was purified via silica gel chromatography (MeOH-DCM, 0-10%) to afford the title compound (157 mg, 81%). LCMS: $R_t$=0.56 min, m/z=328.2 (M+1) Method 2m_acidic.

Step 3, Compound 1: 1-(((2R,3S)-3-amino-4-oxoazetidin-2-yl)methyl)pyridin-2(1H)-one Step 3, Compound 2: 1-(((2R,3S)-3-amino-4-oxoazetidin-2-yl)methyl)piperidin-2-one Prepared according to example 7, step 3. A solution of benzyl ((3S,4R)-2-oxo-4-((2-oxopyridin-1(2H)-yl)methyl)azetidin-3-yl)carbamate (157 mg, 0.480 mmol) in EtOH:MeOH (5:1, 4.8 mL) was evacuated and backfilled with argon (2×) followed by addition of Pd on C (10%, 33 mg). The system was evacuated and backfilled with $H_2$ (3×). After 3 h of stirring the mixture was filtered over celite, washing with MeOH and concentrated in vacuo. The crude residue was used as such in following step.

Step 4, Compound 1: tert-Butyl 2-(((Z)-(1-(2-((tert-butoxycarbonyl)amino)thiazol-4-yl)-2-oxo-2-(((3S,4R)-2-oxo-4-((2-oxopyridin-1(2H)-yl)methyl)azetidin-3-yl)amino)ethylidene)amino)oxy)-2-methylpropanoate Step 4, Compound 2: tert-Butyl 2-(((Z)-(1-(2-((tert-butoxycarbonyl)amino)thiazol-4-yl)-2-oxo-2-(((3S,4R)-2-oxo-4-((2-oxopiperidin-1-yl)methyl)azetidin-3-yl)amino)ethylidene)amino)oxy)-2-methylpropanoate To a slurry of (Z)-2-(((1-(tert-butoxy)-2-methyl-1-oxopropan-2-yl)oxy)imino)-2-(2-((tert-butoxycarbonyl)amino)thiazol-4-yl)acetic acid (60 mg, 0.14 mmol) in DCM:DMF (1:1, 1.4 mL) at 0° C. was added DIPEA (73 µL, 0.42 mmol) followed by HATU (63.7 mg, 0.168 mmol). To the resulting solution, after 20 min, was added a mixture solution of 1-(((2R,3S)-3-amino-4-oxoazetidin-2-yl)methyl)pyridin-2(1H)-one and 1-(((2R,3S)-3-amino-4-oxoazetidin-2-yl)methyl)piperidin-2-one (90 mg, ~0.46 mmol) in DCM (200 µL). After 1 h of stirring it was concentrated in vacuo and taken up in EtOAc, washed with water, brine, dried over $Na_2SO_4$ and concentrated in vacuo. The crude residue was purified via silica gel chromatography (Acetone-DCM) to afford title compound 1 (54 mg) and title compound 2 (30 mg). 1-LCMS: $R_t$=0.88 min, m/z=605.2 (M+1) Method 2m_acidic; 2-LCMS: $R_t$=0.90 min, m/z=609.2 (M+1) Method 2m_acidic.

Step 5: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopiperidin-1-yl)methyl)azetidine-1-sulfonic acid tert-butyl 2-(((Z)-(1-(2-((tert-butoxycarbonyl)amino)thiazol-4-yl)-2-oxo-2-(((3S,4R)-2-oxo-4-((2-oxopiperidin-1-yl)methyl)azetidin-3-yl)amino)ethylidene)amino)oxy)-2-methylpropanoate (30 mg, 0.049 mmol) in DMF (493 µL) was treated with $SO_3$.DMF (151 mg, 0.986 mmol). After 1 h of Step 6: 2-(((Z)-(1-(2-aminothiazol-4-yl)-2-oxo-2-(((3S,4R)-2-oxo-4-((2-oxopiperidin-1-yl)methyl)-1-sulfoazetidin-3-yl)amino)ethylidene)amino)oxy)-2-methylpropanoic acid

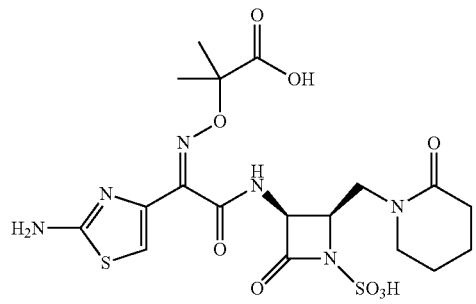 [SMILES: CC(C)(O/N=C(\C(=O)N[C@@H]1C(=O)N(S(=O)(=O)O)[C@@H]1CN1CCCCC1=O)c1csc(N)n1)C(=O)O]

Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopiperidin-1-yl)methyl)azetidine-1-sulfonic acid (34 mg, 0.049 mmol), DCM (494 µL) and TFA (228 µl, 2.96 mmol). The crude residue purified by reverse phase prep HPLC (XSelect CSH, 30×100 mm, 5 µm, C18 column; ACN-water with 0.1% formic acid modifier, 60 mL/min), affording the title compound (5.2 mg, 17%) as a white powder. LCMS: $R_t$=0.63 min, m/z=533.1 (M+1) Method 2m_acidic_polar; $^1$H NMR (400 MHz, $D_2O$) δ 7.02 (s, 1H), 5.27 (d, J=5.5 Hz, 1H), 4.59-4.48 (m, 1H), 3.61 (d, J=4.7 Hz, 2H), 3.48-3.37 (m, 1H), 3.32 (d, J=5.9 Hz, 1H), 2.34-2.13 (m, 2H), 1.78-1.57 (m, 4H), 1.39 (br s, 6H).

Example 15

2-(((Z)-(1-(2-aminothiazol-4-yl)-2-oxo-2-(((3S,4R)-2-oxo-4-((2-oxopyridin-1(2H)-yl)methyl)-1-sulfoazetidin-3-yl)amino)ethylidene)amino)oxy)-2-methylpropanoic acid

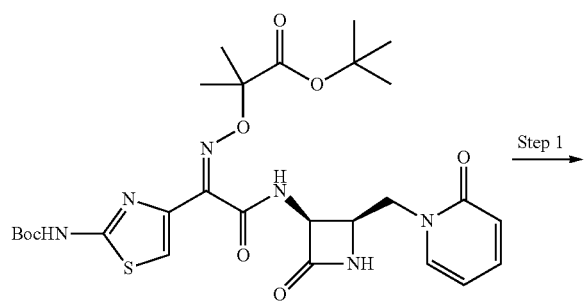

Step 1: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopyridin-1(2H)-yl)methyl)azetidine-1-sulfonic acid

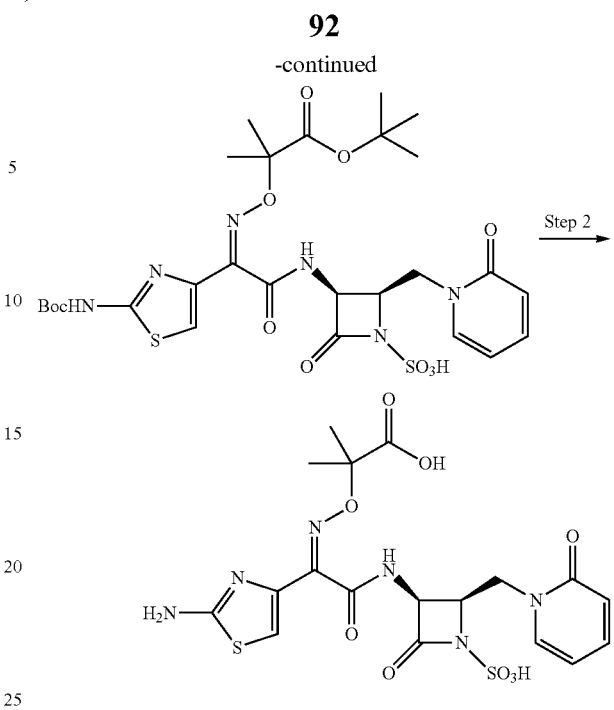

tert-Butyl 2-(((Z)-(1-(2-((tert-butoxycarbonyl)amino)thiazol-4-yl)-2-oxo-2-(((3S,4R)-2-oxo-4-((2-oxopyridin-1(2H)-yl)methyl)azetidin-3-yl)amino)ethylidene)amino)oxy)-2-methylpropanoate (54 mg, 0.089 mmol) in DMF (893 µL) was treated with $SO_3$.DMF (205 mg, 1.34 mmol). After 1 h of stirring, the solution was diluted with EtOAc, washed with brine, dried over $Na_2SO_4$ and concentrated in vacuo to afford the title compound (assumed quantitative) as a white solid. LCMS: Rt=0.76 min, m/z=685.1 (M+1) Method 2m_acidic.

Step 2: 2-(((Z)-(1-(2-aminothiazol-4-yl)-2-oxo-2-(((3S,4R)-2-oxo-4-((2-oxopyridin-1(2H)-yl)methyl)-1-sulfoazetidin-3-yl)amino)ethylidene)amino)oxy)-2-methylpropanoic acid Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-((2-oxopyridin-1(2H)-yl)methyl)azetidine-1-sulfonic acid (61 mg, 0.089 mmol), DCM (891 µL) and TFA (412 µl, 5.35 mmol). The crude residue purified by reverse phase prep HPLC (XSelect CSH, 30×100 mm, 5 µm, C18 column; ACN-water with 0.1% formic acid modifier, 60 mL/min), affording the title compound (9.6 mg, 19%) as a white powder. LCMS: $R_t$=0.57 min, m/z=529.1 (M+1) Method 2m_acidic_polar; $^1$H NMR (400 MHz, $D_2O$) δ 7.59 (d, J=6.7 Hz, 1H), 7.56-7.48 (m, 1H), 7.05 (s, 1H), 6.50 (d, J=9.0 Hz, 1H), 6.39 (t, J=6.7 Hz, 1H), 5.30 (d, J=5.9 Hz, 1H), 4.47 (dd, J=14.5, 2.7 Hz, 1H), 4.07 (dd, J=14.5, 8.6 Hz, 1H), 1.37 (s, 3H), 1.36 (s, 3H).

Example 16

2-(((Z)-(2-(((2R,3S)-2-((1H-1,2,4-triazol-1-yl)methyl)-4-oxo-1-sulfoazetidin-3-yl)amino)-1-(5-amino-1,2,4-thiadiazol-3-yl)-2-oxoethylidene)amino)oxy)-2-methylpropanoic acid

Step 1: (3S,4R)-4-((1H-1,2,4-triazol-1-yl)methyl)-3-aminoazetidin-2-one

Prepared in an analogous manner to example 4, step 3 using benzyl ((2R,3S)-2-((1H-1,2,4-triazol-1-yl)methyl)-4-oxoazetidin-3-yl)carbamate (250 mg, 0.830 mmol) and Pd on C (10%, 125 mg) in EtOH:MeOH (4:1, 8.3 mL) for 3 h. The crude residue was used as such in following step. LCMS: $R_t$=0.13 min, m/z=168.1 (M+1) Method 2m_acidic.

Step 2: tert-butyl 2-(((Z)-(2-(((2R,3S)-2-((1H-1,2,4-triazol-1-yl)methyl)-4-oxoazetidin-3-yl)amino)-1-(5-((tert-butoxycarbonyl)amino)-1,2,4-thiadiazol-3-yl)-2-oxoethylidene)amino)oxy)-2-methylpropanoate To a slurry of (Z)-2-(((1-(tert-butoxy)-2-methyl-1-oxopropan-2-yl)oxy)imino)-2-(5-((tert-butoxycarbonyl)amino)-1,2,4-thiadiazol-3-yl)acetic acid (129 mg, 0.299 mmol) in DCM:DMF (1:1, 3 mL) at 0° C. was added DIPEA (157 μL, 0.897 mmol) followed by HATU (136 mg, 0.359 mmol). To the resulting solution, after 20 min, was added a solution of (3S,4R)-4-((1H-1,2,4-triazol-1-yl)methyl)-3-aminoazetidin-2-one (50 mg, 0.299 mmol) in DCM. After 2 h of stirring it was concentrated in vacuo and taken up in EtOAc, washed with water, brine, dried over Na₂SO₄ and concentrated in vacuo. The crude residue was purified via silica gel chromatography (Acetone-DCM) to afford the title compound (100 mg, 58%). LCMS: $R_t$=0.82 min, m/z=580.2 (M+1) Method 2m_acidic.

Step 3: (2R,3S)-2-((1H-1,2,4-triazol-1-yl)methyl)-3-((Z)-2-(((1-(tert-butoxy)-2-methyl-1-oxopropan-2-yl)oxy)imino)-2-(5-((tert-butoxycarbonyl)amino)-1,2,4-thiadiazol-3-yl)acetamido)-4-oxoazetidine-1-sulfonic acid tert-butyl 2-(((Z)-(2-(((2R,3S)-2-((1H-1,2,4-triazol-1-yl)methyl)-4-oxoazetidin-3-yl)amino)-1-(5-((tert-butoxycarbonyl)amino)-1,2,4-thiadiazol-3-yl)-2-oxoethylidene)amino)oxy)-2-methylpropanoate (100 mg, 0.173 mmol) in DMF (1.7 mL) was treated with SO₃.DMF (396 mg, 2.59 mmol). After 1 h of stirring, the solution was diluted with EtOAc, washed with brine, dried over Na₂SO₄ and concentrated in vacuo to afford the title compound (assumed quantitative) as a white solid. LCMS: Rt=0.74 min, m/z=660.2 (M+1) Method 2m_acidic.

Step 4: 2-(((Z)-(2-(((2R,3S)-2-((1H-1,2,4-triazol-1-yl)methyl)-4-oxo-1-sulfoazetidin-3-yl)amino)-1-(5-amino-1,2,4-thiadiazol-3-yl)-2-oxoethylidene)amino)oxy)-2-methylpropanoic acid

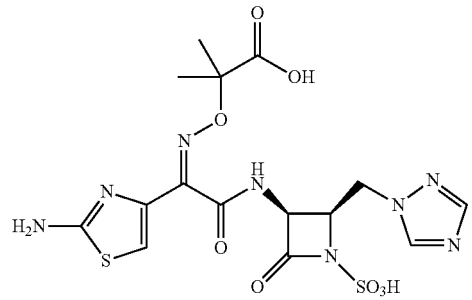

Followed the general procedure for the acid mediated deprotection using (2R,3S)-2-((1H-1,2,4-triazol-1-yl)methyl)-3-((Z)-2-(((1-(tert-butoxy)-2-methyl-1-oxopropan-2-yl)oxy)imino)-2-(5-((tert-butoxycarbonyl)amino)-1,2,4-thiadiazol-3-yl)acetamido)-4-oxoazetidine-1-sulfonic acid (114 mg, 0.173 mmol), DCM (1.7 mL) and TFA (800 μl, 10.4 mmol). The crude residue purified by reverse phase prep HPLC (XSelect CSH, 30×100 mm, 5 μm, C18 column; ACN-water with 0.1% formic acid modifier, 60 mL/min), affording the title compound (46 mg, 46%) as a white powder. LCMS: $R_t$=0.42 min, m/z=504.0 (M+1) Method 2m_acidic_polar; ¹H NMR (400 MHz, DMSO-d₆) δ 9.42 (d, J=8.6 Hz, 1H), 8.65 (s, 1H), 8.21 (br s, 2H), 8.10 (s, 1H), 5.22 (dd, J=8.6, 5.5 Hz, 1H), 4.67-4.58 (m, 1H), 4.56-4.47 (m, 1H), 4.28 (q, J=5.5 Hz, 1H), 1.39 (s, 3H), 1.34 (s, 3H).

Example 17

2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)acetic acid

Step 1: tert-Butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)acetate To a solution of (Z)-2-((2-(tert-butoxy)-2-oxoethoxy)imino)-2-(2-((tert-butoxycarbonyl)amino)thiazol-4-yl)acetic acid (108 mg, 0.269 mmol) in DCM (2.7 mL) at 0° C. was added DIPEA (141 μL, 0.808 mmol) followed by HATU (113 mg, 0.296 mmol). To the resulting solution, after 20 min, was added a solution of (3S,4R)-4-((1H-1,2,4-triazol-1-yl)methyl)-3-aminoazetidin-2-one (50 mg, 0.299 mmol) in DCM. After 1 h of stirring it was diluted with EtOAc, washed with water, brine, dried over Na₂SO₄ and concentrated in vacuo. The crude residue was purified via silica gel chromatography (Acetone-DCM) to afford the title compound (106 mg, 72%). LCMS: R=0.78 min, m/z=551.2 (M+1) Method 2m_acidic.

Step 2: (2R,3S)-2-((1H-1,2,4-triazol-1-yl)methyl)-3-((Z)-2-((2-(tert-butoxy)-2-oxoethoxy)imino)-2-(2-((tert-butoxycarbonyl)amino)thiazol-4-yl)acetamido)-4-oxoazetidine-1-sulfonic acid tert-Butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)acetate (100 mg, 0.182 mmol) in DMF (1.8 mL) was treated with $SO_3$.DMF (278 mg, 1.82 mmol). After 1 h of stirring, the solution was diluted with EtOAc, washed with ice-cold water, brine, dried over $Na_2SO_4$ and concd in vacuo, affording the title compound (assumed quantitative) as a white solid. LCMS: Rt=0.71 min, m/z=631.1 (M+1) Method 2m_acidic.

Step 3: 2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)acetic acid

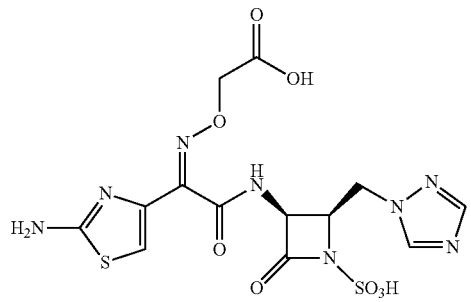 [SMILES: Nc1nc(/C(=N/OCC(=O)O)C(=O)N[C@@H]2C(=O)N(S(=O)(=O)O)[C@@H]2Cn2cncn2)cs1]

Followed the general procedure for the acid mediated deprotection using (2R,3S)-2-((1H-1,2,4-triazol-1-yl)methyl)-3-((Z)-2-((2-(tert-butoxy)-2-oxoethoxy)imino)-2-(2-((tert-butoxycarbonyl)amino)thiazol-4-yl)acetamido)-4-oxoazetidine-1-sulfonic acid (97 mg, 0.154 mmol), DCM (1.54 mL) and TFA (711 µl, 9.23 mmol). The crude residue purified by reverse phase prep HPLC (XSelect CSH, 30×100 mm, 5 µm, C18 column; ACN-water with 0.1% formic acid modifier, 60 mL/min), affording the title compound (22.7 mg, 22%) as a white powder. LCMS: $R_t$=0.28 min, m/z=475.0 (M+1) Method 2m_acidic; $^1$H NMR (400 MHz, DMSO-$d_6$) δ 9.50 (d, J=9.0 Hz, 1H), 8.56 (s, 1H), 8.07 (s, 1H), 6.80 (s, 1H), 5.25 (dd, J=9.0, 5.9 Hz, 1H), 4.69-4.49 (m, 4H), 4.36 (dt, J=7.4, 4.9 Hz, 1H).

Example 18

1-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid

Step 1: Benzhydryl 1-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of (Z)-2-(((1-((benzhydryloxy)carbonyl)cyclopropoxy)imino)-2-(2-((tert-butoxycarbonyl)amino)thiazol-4-yl)acetic acid (prepared according to Yamawaki et al. *Bioorg. Med. Chem. Lett.* 2007, 15, 6716-6732) (150 mg, 0.279 mmol) in DCM:DMF (1:1, 2.8 mL) at 0° C. was added DIPEA (146 µL, 0.837 mmol) followed by HATU (127 mg, 0.335 mmol). To the resulting solution, after 20 min, was added a solution of (3S,4R)-4-((1H-1,2,4-triazol-1-yl)methyl)-3-aminoazetidin-2-one (51 mg, 0.31 mmol) in DCM. After 1 h of stirring it was diluted with EtOAc, washed with water, brine, dried over $Na_2SO_4$ and concentrated in vacuo. The crude residue was purified via silica gel chromatography (Acetone-DCM) to afford the title compound (147 mg, 77%). LCMS: $R_t$=0.98 min, m/z=687.1 (M+1) Method 2m_acidic.

Step 2: (2R,3S)-2-((1H-1,2,4-triazol-1-yl)methyl)-3-((Z)-2-(((1-((benzhydryloxy)carbonyl)cyclopropoxy)imino)-2-(2-((tert-butoxycarbonyl)amino)thiazol-4-yl)acetamido)-4-oxoazetidine-1-sulfonic acid Benzhydryl 1-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (147 mg, 0.214 mmol) in DMF (2.14 mL) was treated with $SO_3$.DMF (328 mg, 2.14 mmol). After 1 h of stirring, the solution was diluted with EtOAc, washed with ice cold water, brine, dried over $Na_2SO_4$ and concd in vacuo, affording the title compound (assumed quantitative) as a white solid. LCMS: Rt=0.89 min, m/z=767.0 (M+1) Method 2m_acidic.

Step 3: 1-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid

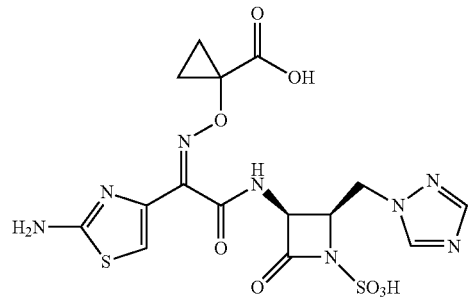 [SMILES: Nc1nc(/C(=N/OC2(C(=O)O)CC2)C(=O)N[C@@H]2C(=O)N(S(=O)(=O)O)[C@@H]2Cn2cncn2)cs1]

Followed the general procedure for the acid mediated deprotection using (2R,3S)-2-((1H-1,2,4-triazol-1-yl)methyl)-3-((Z)-2-(((1-((benzhydryloxy)carbonyl)cyclopropoxy)imino)-2-(2-((tert-butoxycarbonyl)amino)thiazol-4-yl)acetamido)-4-oxoazetidine-1-sulfonic acid (164 mg, 0.214 mmol), DCM (2.14 mL) and TFA (989 µl, 12.8 mmol). The crude residue purified by reverse phase prep HPLC (XSelect CSH, 30×100 mm, 5 µm, C18 column; ACN-water with 0.1% formic acid modifier, 60 mL/min), affording the title compound (50 mg, 41%) as a white powder. LCMS: $R_t$=0.29 min, m/z=501.1 (M+1) Method 2m_acidic; $^1$H NMR (400 MHz, DMSO-$d_6$) δ 9.31 (d, J=9.0 Hz, 1H), 8.59 (s, 1H), 8.09 (s, 1H), 6.83 (s, 1H), 5.26 (dd, J=9.0, 5.5 Hz, 1H), 4.67 (dd, J=14.5, 4.3 Hz, 1H), 4.49-4.39 (m, 1H), 4.33 (ddd, J=7.4, 5.5, 4.3 Hz, 1H), 1.34-1.27 (m, 4H).

Example 19

1-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

Step 1: tert-Butyl ((2-(((2R,3S)-3-amino-4-oxoazetidin-2-yl)methyl)-2H-1,2,3-triazol-4-yl)methyl)carbamate Prepared in an analogous manner to example 4, step 3 using Intermediate T (1.20 g, 2.79 mmol) and Pd on C (10%, 830 mg) in EtOAc:MeOH (5:1, 24 mL) for 19 h. The crude residue was used as such in following step. LCMS: $R_t$=0.41 min, m/z=297.0 (M+1) Method 2m_acidic.

Step 2: Benzhydryl 1-(((Z)-(2-(((2R,3S)-2-((4-(((tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of (Z)-2-(((1-((benzhydryloxy)carbonyl)cyclopropoxy)imino)-2-(2-((tert-butoxycarbonyl)amino)thiazol-4-yl)acetic acid (prepared according to Yamawaki et al. *Bioorg. Med. Chem. Lett.* 2007, 15, 6716-6732) (1.50 g, 2.79 mmol) in DCM (15 mL) at 0° C. was added DIPEA (1.22 mL, 6.98 mmol) and HATU (1.11 g, 2.93 mmol). After warming to rt, a solution of tert-butyl ((2-(((2R,3S)-3-amino-4-oxoazetidin-2-yl)methyl)-2H-1,2,3-triazol-4-yl)methyl)carbamate (827 mg, 2.79 mmol) in DCM:DMF (1.7:1, 12.7 mL). After 1 h of stirring it was diluted with DCM and washed with water, brine, dried over Na$_2$SO$_4$ and concentrated in vacuo. The crude residue was purified via silica gel chromatography (EtOAc-Heptane, 0-90%), to afford the title compound (1.92 g, 84%) as a purple oil. LCMS: $R_t$=1.08 min, m/z=816.5 (M+1) Method 2m_acidic.

Step 3: (2R,3S)-3-(((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)amino)methyl)-2H-1,2,3-triazol-2-yl)methyl)-4-oxoazetidine-1-sulfonic acid Benzhydryl 1-(((Z)-(2-(((2R,3S)-2-((4-(((tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (1.92 g, 2.35 mmol) in DMF (20 mL) was treated with SO$_3$.DMF (3.60 g, 23.5 mmol). After 30 min of stirring, the solution was diluted with EtOAc/water and the layers were separated. The aqueous was extracted with EtOAc and the combined organic layers were washed with brine, dried over Na$_2$SO$_4$ and concd in vacuo, affording the title compound (1.98 g, 94%) as a purple foam. LCMS: $R_t$=0.99 min, m/z=896.4 (M+1) Method 2m_acidic.

Step 4: 1-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-cyclopropanecarboxylic acid

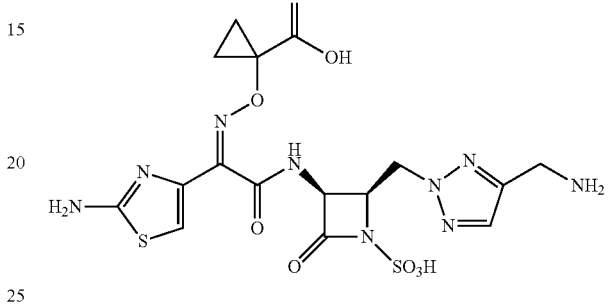

Followed the general procedure for the acid mediated deprotection using (2R,3S)-3-(((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)amino)methyl)-2H-1,2,3-triazol-2-yl)methyl)-4-oxoazetidine-1-sulfonic acid (1.98 g, 2.21 mmol), DCM (18.4 mL) and TFA (10.2 mL, 133 mmol). Half of the crude residue purified by reverse phase prep HPLC (XSelect CSH, 30×100 mm, 5 μm, C18 column; ACN-water with 0.1% formic acid modifier, 60 mL/min), affording the title compound (300 mg, ca 50%) as an off-white powder. LCMS: $R_t$=0.29 min, m/z=530.1 (M+1) Method 2m_acidic; $^1$H NMR (400 MHz, D$_2$O) δ 7.69 (s, 1H), 7.04 (br s, 1H), 5.43 (d, J=5.5 Hz, 1H), 4.93-4.78 (m, 2H), 4.74-4.67 (m, 1H), 4.22-4.12 (m, 2H), 1.36-1.20 (m, 2H), 1.20-1.00 (m, 2H).

Example 20

1-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene)amino)oxy)-cyclopropanecarboxylic acid

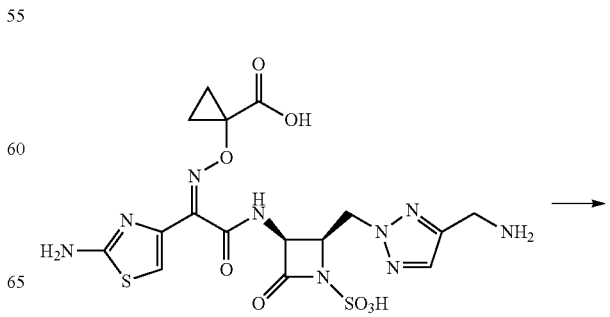

To a solution of 1-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene) amino)oxy)-cyclopropanecarboxylic acid (582 mg, 1.10 mmol) in DMF (12 mL) at 0° C. was added pyrazole-1-carboxamidine hydrochloride (322 mg, 2.20 mmol) and DIPEA (1.54 mL, 8.80 mmol). After 16 h of stirring at rt, the solution was diluted with toluene (60 mL), causing a dense oil to separate out. The top layer was decanted and the remaining oil was purified by reverse phase prep HPLC (XSelect CSH, 30×100 mm, 5 µm, C18 column; ACN-water with 0.1% formic acid modifier, 60 mL/min), affording the title compound (240 mg, 37%) as an off-white powder. LCMS: R$_t$=0.31 min, m/z=572.2 (M+H) Method 2m_acidic; $^1$H NMR (400 MHz, D$_2$O) δ 7.59 (s, 1H), 6.99 (br s, 1H), 5.43 (d, J=5.5 Hz, 1H), 4.91-4.75 (m, 2H assumed; obscured by solvent residual peak), 4.70 (dd, J=8.2, 6.3 Hz, 1H), 4.41-4.34 (m, 2H), 1.20 (br s, 2H), 1.05 (br s, 2H). E-isomer was also obtained. LCMS: R$_t$=0.33 min, m/z=572.2 (M+H) Method 2m_acidic; $^1$H NMR (400 MHz, D$_2$O) δ 7.58 (s, 1H), 7.46 (br. s., 1H), 5.45 (br. s., 1H), 4.84 (s, 3H), 4.37 (s, 2H), 1.33-1.08 (m, 4H).

Example 21

2-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)acetic acid Step 1: tert-Butyl 2-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino) ethylidene)amino)oxy)acetate To a solution of (Z)-2-((2-(tert-butoxy)-2-oxoethoxy)imino)-2-(2-((tert-butoxycarbonyl)amino)thiazol-4-yl)acetic acid (100 mg, 0.249 mmol), Intermediate D (51 mg, 0.27 mmol) and HATU (123 mg, 0.324 mmol) in DMF (1.25 mL) was added DIPEA (131 µL, 0.747 mmol). After 4 h of stirring it was diluted with EtOAc, washed with water, brine, dried over Na$_2$SO$_4$ and concentrated in vacuo. The crude residue was purified via silica gel chromatography (0-10% MeOH-DCM) to afford the title compound (118 mg, 83%). LCMS: R$_t$=0.81 min, m/z=569.1 (M+1) Method 2m_acidic.

Step 2: (3S,4R)-3-((Z)-2-((2-(tert-butoxy)-2-oxoethoxy)imino)-2-(2-((tert-butoxycarbonyl)amino)thiazol-4-yl)acetamido)-2-oxo-4-((2-oxooxazolidin-3-yl) methyl)azetidine-1-sulfonic acid tert-Butyl 2-(((Z)-(1-(2-((tert-butoxycarbonyl)amino) thiazol-4-yl)-2-oxo-2-(((3S,4R)-2-oxo-4-((2-oxooxazolidin-3-yl)methyl)azetidin-3-yl)amino)ethylidene)amino) oxy)acetate (118 mg, 0.208 mmol) in DMF (2.14 mL) was treated with SO$_3$.DMF (159 mg, 1.04 mmol). After 30 min of stirring, the solution was diluted with EtOAc, washed with ice-cold brine, dried over Na$_2$SO$_4$ and concd in vacuo, affording the title compound (assumed quantitative) as a white solid. LCMS: Rt=0.72 min, m/z=649.1 (M+1) Method 2m_acidic.

Step 3: 2-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) acetic acid

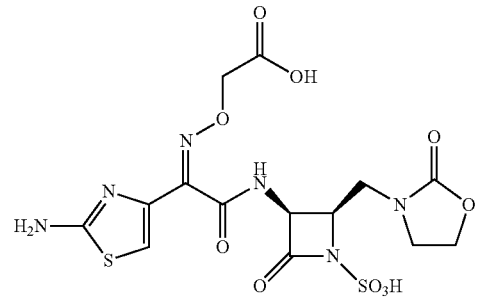 [SMILES: Nc1nc(/C(=N/OCC(=O)O)C(=O)N[C@@H]2C(=O)N(S(=O)(=O)O)[C@@H]2CN2CCOC2=O)cs1]

Followed the general procedure for the acid mediated deprotection using (3S,4R)-3-((Z)-2-((2-(tert-butoxy)-2-oxoethoxy)imino)-2-(2-((tert-butoxycarbonyl)amino)thiazol-4-yl)acetamido)-2-oxo-4-((2-oxooxazolidin-3-yl)methyl)azetidine-1-sulfonic acid (135 mg, 0.208 mmol), DCM (1.04 mL) and TFA (801 µl, 10.4 mmol). The crude residue purified by reverse phase prep HPLC (XSelect CSH, 19×100 mm, 5 µm, C18 column; ACN-water with 0.1% formic acid modifier, 24 mL/min), affording the title compound (25 mg, 23%) as a white powder. LCMS: R$_t$=0.25 min, m/z=493.0 (M+1) Method 2m_acidic; $^1$H NMR (500 MHz, DMSO-d$_6$) δ 9.41 (d, J=9.1 Hz, 1H) 6.86 (s, 1H) 5.24 (dd, J=9.0, 5.8 Hz, 1H) 4.62 (s, 2H) 4.20-4.11 (m, 3H) 3.72-3.63 (m, 2H) 3.40-3.31 (m, 2H assumed; obscured by water).

Example 22

1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid Step 1: Benzhydryl 1-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino) ethylidene)amino)oxy)cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (854 mg, 1.59 mmol), Intermediate D (324 mg, 1.75 mmol) and HATU (785 mg, 2.07 mmol) in DMF (7.9 mL) was added DIPEA (832 µL, 4.77 mmol). After 1 h of stirring, it was poured into water and extracted with EtOAc. Brine was added to the aqueous layer, and it was further extracted with EtOAc (3×). The combined organic layers were dried over $Na_2SO_4$ and concentrated in vacuo. The crude residue was purified via silica gel chromatography (0-10% MeOH-DCM) to afford the title compound (1.09 g, 97%) as a beige foam. LCMS: $R_t$=0.97 min, m/z=705.3 (M+1) Method 2m_acidic.

Step 2: (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((2-oxooxazolidin-3-yl)methyl)azetidine-1-sulfonic acid Benzhydryl 1-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino)ethylidene)amino)oxy)cyclopropanecarboxylate (1.00 g, 1.42 mmol) in DMF (7.0 mL) at 0° C. was treated with $SO_3$.DMF (448 mg, 2.84 mmol). After 2 h of stirring at rt, the solution was poured into ice-cold brine and extracted with EtOAc (3×). The combined organic layers were dried over $Na_2SO_4$ and concd in vacuo, affording the title compound (assumed quantitative) as a white solid. LCMS: Rt=0.90 min, m/z=785.2 (M+1) Method 2m_acidic.

Step 3: 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid

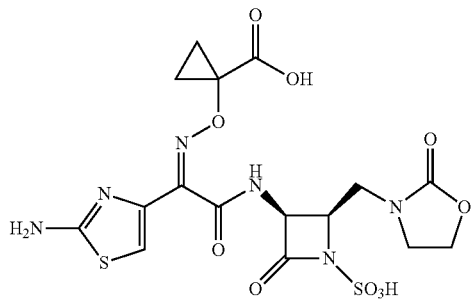

Followed the general procedure for the acid mediated deprotection using (3S,4R)-3-((Z)-2-(((1-((benzhydryloxy)carbonyl)cyclopropoxy)imino)-2-(2-((tert-butoxycarbonyl)amino)thiazol-4-yl)acetamido)-2-oxo-4-((2-oxooxazolidin-3-yl)methyl)azetidine-1-sulfonic acid (1.10 g, 1.40 mmol), DCM (7.0 mL) and TFA (5.39 mL, 70.0 mmol). Additional TFA (3.24 mL, 42.0 mmol) was added after 1 h at rt and the solution was diluted with DCM and concentrated in vacuo after an additional 30 min. The crude residue purified by reverse phase prep HPLC (XSelect CSH, 30×100 mm, 5 µm, C18 column; ACN-water with 0.1% formic acid modifier, 60 mL/min), affording the title compound (178 mg, 23%) as a white powder. LCMS: $R_t$=0.30 min, m/z=518.9 (M+1) Method 2m_acidic; $^1$H NMR (400 MHz, DMSO-$d_6$) δ 9.27 (d, J=9.0 Hz, 1H) 6.92 (s, 1H) 5.23 (dd, J=9.1, 5.7 Hz, 1H) 4.12-4.23 (m, 3H) 3.72-3.62 (m, 2H assumed; obscured by water) 3.61-3.52 (m, 1H assumed; obscured by water) 3.26 (dd, J=14.5, 5.9 Hz, 1H) 1.36 (s, 4H). $^1$H NMR (400 MHz, $D_2O$) δ 7.23 (s, 1H), 5.48 (d, J=5.8 Hz, 1H), 4.71-4.65 (m, 1H), 4.44 (t, J=8.2 Hz, 2H), 3.89-3.73 (m, 3H), 3.54 (dd, J=14.9, 4.9 Hz, 1H), 1.65-1.56 (m, 2H), 1.56-1.46 (m, 2H).

Example 23

2-(((Z)-(1-(2-aminothiazol-4-yl)-2-(((2R,3S)-2-(((R)-5-methyl-2-oxooxazolidin-3-yl)methyl)-4-oxo-1-sulfoazetidin-3-yl)amino)-2-oxoethylidene)amino)oxy)-2-methylpropanoic acid Step 1: tert-Butyl 2-(((Z)-(1-(2-((tert-butoxycarbonyl)amino)thiazol-4-yl)-2-(((2R,3S)-2-((((R)-2-hydroxypropyl)amino)methyl)-4-oxoazetidin-3-yl)amino)-2-oxoethylidene)amino)oxy)-2-methylpropanoate A solution of Intermediate L (500 mg, 0.949 mmol) and (R)-propylene oxide (996 µl, 14.2 mmol) in DCM (1.9 ml) was stirred at rt for 16 h whereupon precipitation was observed. More (R)-propylene oxide (332 µl, 4.75 mmol) was added. After an additional 3 h, more (R)-propylene oxide (500 µl, 7.14 mmol) was added. After another 24 h of stirring it was concentrated in vacuo and the crude residue purified by reverse phase prep HPLC (XSelect CSH, 30×100 mm, 5 µm, C18 column; ACN-water with 0.1% formic acid modifier, 60 mL/min), affording the title compound (185 mg, 33%) as a white powder. LCMS: $R_t$=0.82 min, m/z=585.2 (M+1) Method 2m_acidic.

Step 2: tert-Butyl 2-(((Z)-(1-(2-((tert-butoxycarbonyl)amino)thiazol-4-yl)-2-(((2R,3S)-2-(((R)-5-methyl-2-oxooxazolidin-3-yl)methyl)-4-oxoazetidin-3-yl)amino)-2-oxoethylidene)amino)oxy)-2-methylpropanoate To a solution of tert-butyl 2-(((Z)-(1-(2-((tert-butoxycarbonyl)amino)thiazol-4-yl)-2-(((2R,3S)-2-((((R)-2-hydroxypropyl)amino)methyl)-4-oxoazetidin-3-yl)amino)-2-oxoethylidene)amino)oxy)-2-methylpropanoate (185 mg, 0.316 mmol) in chloroform (3.16 mL) was added CDI (257 mg, 1.58 mmol). After stirring at rt for 20 min the solution was diluted with EtOAc/water and the layers separated. The aqueous layer was extracted with EtOAc and the combined organic layers were dried over $Na_2SO_4$ and concentrated in vacuo. The crude residue was purified via silica gel chromatography (Acetone-DCM, 0-100%) to afford the title compound (81 mg, 42%). LCMS: $R_t$=0.92 min, m/z=611.2 (M+1) Method 2m_acidic.

Step 3: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((R)-5-methyl-2-oxooxazolidin-3-yl)methyl)-4-oxoazetidine-1-sulfonic acid tert-Butyl 2-(((Z)-(1-(2-((tert-butoxycarbonyl)amino)thiazol-4-yl)-2-(((2R,3S)-2-(((R)-5-methyl-2-oxooxazolidin-3-yl)methyl)-4-oxoazetidin-3-yl)amino)-2-oxoethylidene)amino)oxy)-2-methylpropanoate (81 mg, 0.133 mmol) in DMF (1.33 mL) was treated with $SO_3$.DMF (203 mg, 1.33 mmol). After 20 min of stirring at rt, the solution was diluted with EtOAc/brine and the layers separated. The aqueous layer was extracted with EtOAc (3×) and the combined organic layers were dried over $Na_2SO_4$ and concentrated in vacuo, affording the title compound (assumed quantitative) as a solid. LCMS: Rt=0.84 min, m/z=691.0 (M+1) Method 2m_acidic.

Step 4: 2-(((Z)-(1-(2-aminothiazol-4-yl)-2-(((2R,3S)-2-(((R)-5-methyl-2-oxooxazolidin-3-yl)methyl)-4-oxo-1-sulfoazetidin-3-yl)amino)-2-oxoethylidene)amino)oxy)-2-methylpropanoic acid

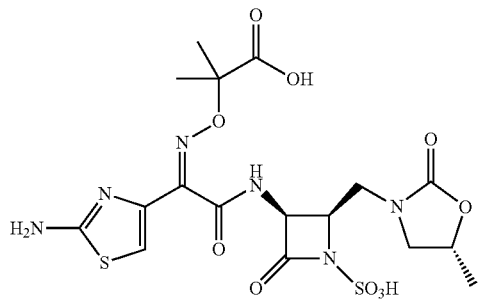 [SMILES: C[C@@H]1CN(C[C@@H]2[C@H](NC(=O)/C(=N\OC(C)(C)C(=O)O)c3csc(N)n3)C(=O)N2S(=O)(=O)O)C(=O)O1]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((R)-5-methyl-2-oxooxazolidin-3-yl)methyl)-4-oxoazetidine-1-sulfonic acid (92 mg, 0.133 mmol), DCM (1.33 mL) and TFA (615 µL, 7.98 mmol). The crude residue purified by reverse phase prep HPLC (XSelect CSH, 30×100 mm, 5 µm, C18 column; ACN-water with 0.1% formic acid modifier, 60 mL/min), affording the title compound (18.6 mg, 23%) as a white powder. LCMS: R$_t$=0.39 min, m/z=535.1 (M+1) Method 2m_acidic; $^1$H NMR (500 MHz, DMSO-d$_6$) δ 9.29 (d, J=8.8 Hz, 1H), 6.85 (s, 1H), 5.22 (dd, J=8.8, 5.7 Hz, 1H), 4.55 (dt, J=13.5, 6.5 Hz, 1H), 4.15 (q, J=6.0 Hz, 1H), 3.72-3.63 (m, 2H), 3.34-3.27 (m, 2H), 1.46 (s, 3H), 1.42 (s, 3H), 1.28 (d, J=6.3 Hz, 3H).

Example 24

2-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene)amino)oxy)-2-methylpropanoic acid

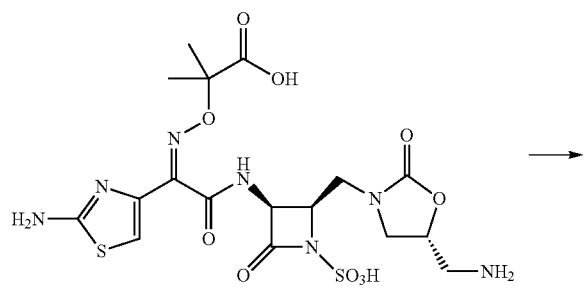

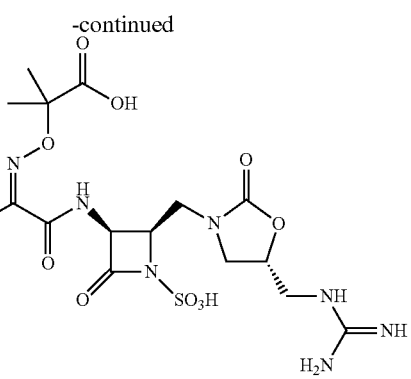

To a solution of 2-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-2-methylpropanoic acid (30.1 mg, 0.055 mmol) and Pyrazole-1-carboxamidine hydrochloride (16.1 mg, 0.110 mmol) in DMF (548 µl) was added DIPEA (38.3 µl, 0.219 mmol). After 5 h of stirring at rt, the solution was concentrated in vacuo and purified by reverse phase prep HPLC (XSelect CSH, 30×100 mm, 5 µm, C18 column; ACN-water with 0.1% formic acid modifier, 60 mL/min), affording the title compound (17.5 mg, 49%) as a white powder. LCMS: R$_t$=0.30 min, m/z=592.2 (M+1) Method 2m_acidic; $^1$H NMR (400 MHz, D$_2$O) δ 6.97 (s, 1H), 5.31 (d, J=5.9 Hz, 1H), 4.74 (dtd, J=9.3, 5.9, 3.2 Hz, 1H), 4.55 (ddd, J=9.2, 5.9, 3.1 Hz, 1H), 3.86 (t, J=9.3 Hz, 1H), 3.66 (dd, J=15.0, 9.5 Hz, 1H), 3.53 (dd, J=15.5, 3.2 Hz, 1H), 3.47-3.34 (m, 3H), 1.39 (s, 3H), 1.37 (s, 3H).

Example 25

1-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-cyclopropanecarboxylic acid Step 1: tert-Butyl (((R)-3-(((2R,3S)-3-amino-4-oxoazetidin-2-yl)methyl)-2-oxooxazolidin-5-yl)methyl)carbamate Prepared in an analogous manner to example 4, step 3 using Intermediate U (1.16 g, 2.28 mmol) and Pd on C (10%, 246 mg) in EtOH:MeOH (5:1, 3 mL) for 19 h. The crude residue was used as such in following step.

Step 2: Benzhydryl 1-(((Z)-(2-(((2R,3S)-2-(((R)-5-(((tert-butoxycarbonyl)amino)methyl)-2-oxooxazolidin-3-yl)methyl)-4-oxoazetidin-3-yl)amino)-1-(2-((tert-butoxycarbonyl)amino)-thiazol-4-yl)-2-oxoethylidene)amino)oxy)cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (1.29 g, 2.28 mmol) and HATU (909 mg, 2.39 mmol) in DMF:DCM (3:1, 9.0 mL) at 0° C. was added DIPEA (1.0 mL, 5.72 mmol). After 15 min of stirring at 0° C. tert-butyl (((R)-3-(((2R,3S)-3-amino-4-oxoazetidin-2-yl)methyl)-2-oxooxazolidin-5-yl)methyl)carbamate (715 mg, 2.28 mmol) was added as a solution in DMF:DCM (1:1, 9 mL) followed by a DMF (1.5 mL) wash. After 1.2 h at rt it was diluted with EtOAc and washed with LiCl (5% aq). The aqueous layer was extracted with EtOAc (3×) and the combined organic layers were washed with LiCl (5% aq), NaHCO$_3$ (aq satd), brine, dried over Na$_2$SO$_4$ and concentrated in vacuo. The crude residue was purified via silica gel chromatography (EtOAc-Heptane, 5-90%) to afford the title compound (1.357 g, 72%) as a white solid. LCMS: R$_t$=1.04 min, m/z=834.4 (M+1) Method 2m_acidic.

Step 3: (2R,3S)-3-(((Z)-2-((1-((benzhydryloxy)carbonyl)cyclopropoxy)imino)-2-(2-((tert-butoxycarbonyl)amino)thiazol-4-yl)acetamido)-2-(((R)-5-(((tert-butoxycarbonyl)amino)-methyl)-2-oxooxazolidin-3-yl)methyl)-4-oxoazetidine-1-sulfonic acid Benzhydryl 1-(((Z)-(2-(((2R,3S)-2-(((R)-5-(((tert-butoxycarbonyl)amino)methyl)-2-oxooxazolidin-3-yl)methyl)-4-oxoazetidin-3-yl)amino)-1-(2-((tert-butoxycarbonyl)amino)-thiazol-4-yl)-2-oxoethylidene)amino)oxy)cyclopropanecarboxylate (1.357 g, 1.627 mmol) in DMF (8.1 mL) at 0° C. was treated with SO$_3$.DMF (748 mg, 4.88 mmol). After 2 h of stirring at rt, the solution was diluted with EtOAc/LiCl (5% aq) and the layers separated. The aqueous layer was extracted with EtOAc (3×) and the combined organic layers were washed with LiCl (5% aq), brine, dried over Na$_2$SO$_4$ and concentrated in vacuo, affording the title compound (assumed quantitative) as a solid. LCMS: Rt=0.96 min, m/z=914.4 (M+1) Method 2m_acidic.

Step 4: 1-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-cyclopropanecarboxylic acid

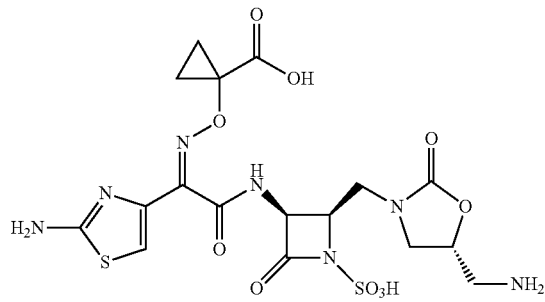 [SMILES: NC[C@@H]1CN(C[C@@H]2[C@H](NC(=O)/C(=N\OC3(C(=O)O)CC3)c3csc(N)n3)C(=O)N2S(=O)(=O)O)C(=O)O1]

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-(((R)-5-(((tert-butoxycarbonyl)amino)-methyl)-2-oxooxazolidin-3-yl)methyl)-4-oxoazetidine-1-sulfonic acid (725 mg, 0.794 mmol), DCM (8.0 mL) and TFA (3.7 mL, 48.0 mmol). The crude residue purified by reverse phase prep HPLC (XSelect CSH, 30×100 mm, 5 µm, C18 column; ACN-water with 0.1% formic acid modifier, 60 mL/min), affording the title compound (231 mg, 52%) as a white powder. LCMS: R$_t$=0.41 min, m/z=548.1 (M+1) Method 2m_acidic_polar; $^1$H NMR (400 MHz, DMSO-d$_6$) δ 9.18 (d, J=8.8 Hz, 1H), 8.00 (t, J=5.8 Hz, 3H), 6.83 (s, 1H), 5.22 (dd, J=8.8, 5.9 Hz, 1H), 4.68 (tdd, J=9.0, 5.8, 3.4 Hz, 1H), 4.24 (ddd, J=9.3, 5.9, 3.6 Hz, 1H), 3.75 (t, J=8.8 Hz, 1H assumed; obscured by water), 3.61 (dd, J=8.7, 5.8 Hz, 1H assumed; obscured by water), 3.41 (dd, J=14.7, 9.0 Hz, 1H), 3.30 (dd, J=14.7, 3.7 Hz, 1H), 3.25-3.05 (m, 2H), 1.40-1.27 (m, 4H). 1H NMR (400 MHz, D$_2$O) δ 7.18 (d, J=2.4 Hz, 1H), 5.45 (d, J=5.8 Hz, 1H), 5.02-4.93 (m, 1H), 4.70 (ddd, J=9.2, 5.8, 3.7 Hz, 1H), 4.04 (t, J=9.2 Hz, 1H), 3.78 (dd, J=15.0, 9.0 Hz, 1H), 3.60-3.56 (m, 1H), 3.54 (dd, J=11.3, 3.6 Hz, 1H), 3.40 (s, 1H), 3.38 (d, J=2.0 Hz, 1H), 1.57-1.49 (m, 2H), 1.49-1.40 (m, 2H).

Example 26

1-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene)amino)oxy)-cyclopropanecarboxylic acid

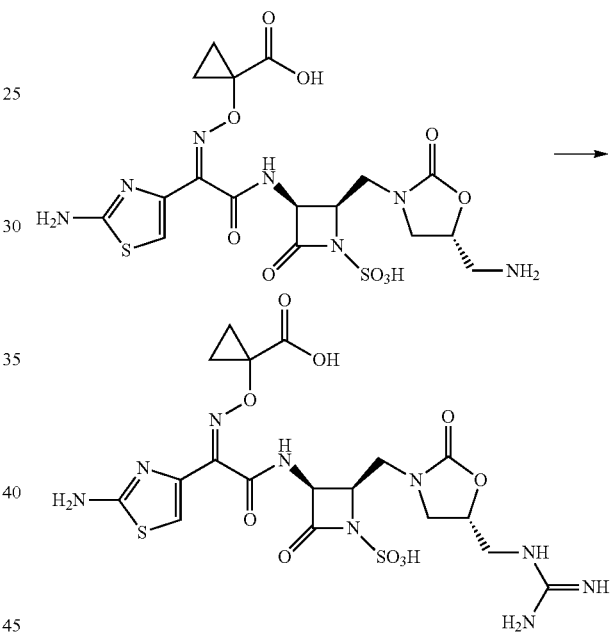

To a solution of 1-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropane-carboxylic acid (0.795 mmol) and Pyrazole-1-carboxamidine hydrochloride (234.8 mg, 1.602 mmol) in DMF (7.0 mL) was added DIPEA (1.20 mL, 8.06 mmol). After 19 h of stirring at rt, the solution was concd in vacuo and purified by reverse phase prep HPLC (XSelect CSH, 30×100 mm, 5 µm, C18 column; ACN-water with 0.1% formic acid modifier, 60 mL/min), affording the title compound (177 mg, 37%) as a white powder. LCMS: R$_t$=0.47 min, m/z=590.1 (M+H) Method 2m_acidic_polar; $^1$H NMR (400 MHz, DMSO-d$_6$) δ 9.15 (d, J=8.9 Hz, 1H), 7.62 (br s, 1H), 7.24 (s, 3H), 6.81 (s, 1H), 5.23 (dd, J=8.9, 5.9 Hz, 1H), 4.60-4.51 (m, 1H), 4.23 (ddd, J=9.0, 5.8, 3.7 Hz, 1H), 3.70 (t, J=8.8 Hz, 1H), 3.52 (dd, J=8.8, 5.4 Hz, 1H), 3.49-3.44 (m, 1H), 3.43-3.34 (m, 3H), 1.38-1.24 (m, 4H).

Example 27

1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid

Step 1: tert-Butyl ((1-(((2R,3S)-3-amino-4-oxoazetidin-2-yl)methyl)-1H-1,2,3-triazol-4-yl)methyl)carbamate To a suspension of palladium on carbon (823 mg, 0.774 mmol) in EtOAc/MeOH (5:1, 16.8 mL) was added Intermediate S (1.11 g, 2.58 mmol) in one portion. The system was evacuated and backfilled with H₂ (3×). After stirring for 19 h the mixture was diluted with EtOAc, filtered through celite, washing with MeOH-EtOAc (20%, 100 mL×3) and concentrated in vacuo, affording crude title compound (730 mg) as an off-white powder. LCMS: $R_f$=0.37 min, m/z=297.0 (M+1) Method 2m_acidic.

Step 2: Benzhydryl 1-(((Z)-(2-(((2R,3S)-2-((4-(((tert-butoxycarbonyl)amino)methyl)-1H-1,2,3-triazol-1-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a slurry of (Z)-2-((1-((benzhydryloxy)carbonyl)cyclopropoxy)imino)-2-(2-((tert-butoxycarbonyl)amino)thiazol-4-yl)acetic acid (1.32 g, 2.46 mmol) in DCM (12 mL) at 0° C. was added DIPEA (1.08 mL, 6.16 mmol) followed by HATU (0.984 g, 2.59 mmol). The reaction mixture was warmed to room temperature and tert-butyl ((1-(((2R,3S)-3-amino-4-oxoazetidin-2-yl)methyl)-1H-1,2,3-triazol-4-yl)methyl)carbamate (0.73 g, 2.5 mmol) was added as a solution in DCM:DMF (1.7:1, 9.6 mL). After stirring for 1.3 h, a color change from yellow to dark purple was observed, whereupon it was diluted with DCM, washed with water, brine, dried over sodium sulfate and concentrated in vacuo. The crude residue was purified by silica gel chromatography (EtOAc-Heptane, 0-90%), affording the title compound (1.62 g, 81%) as a purple foam. LCMS: R=1.05 min, m/z=816.5 (M+1) Method 2m_acidic.

Step 3: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)amino)methyl)-1H-1,2,3-triazol-1-yl)methyl)-4-oxoazetidine-1-sulfonic acid To a solution of benzhydryl 1-(((z)-(2-(((2R,3S)-2-((4-(((tert-butoxycarbonyl)amino)methyl)-1H-1,2,3-triazol-1-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (1.58 g, 1.94 mmol) in DMF (15 mL) was added SO₃.DMF complex (2.97 g, 19.4 mmol). After 45 min of stirring it was diluted with EtOAc (120 mL), brine (80 mL), water (40 mL) and the layers were separated. The aqueous layer was extracted with EtOAc (2×20 mL) and the combined organic layers were dried over Na₂SO₄ and concentrated in vacuo to afford the title compound (assumed quantitative) as a purple foam. LCMS: $R_f$=0.96 min, m/z=896.4 (M+1) Method 2m_acidic.

Step 4: 1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-cyclopropanecarboxylic acid

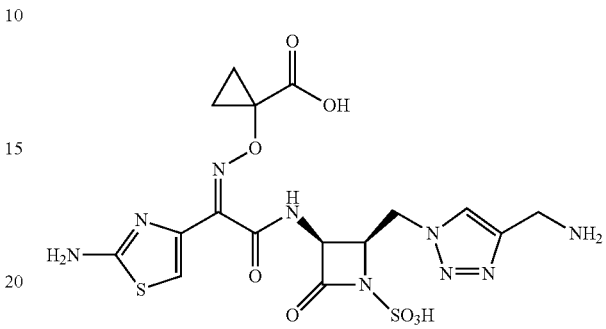

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)amino)methyl)-1H-1,2,3-triazol-1-yl)methyl)-4-oxoazetidine-1-sulfonic acid (1.74 g, 1.94 mmol), DCM (19.4 mL) and TFA (8.95 mL, 116 mmol). After 3 h at rt, it was cooled to 0° C. and more TFA (200 μL, 2.6 mmol) was added whereupon it was allowed to warm to rt. After another 1 h at rt, it was cooled to 0° C. and more TFA (200 μL, 2.6 mmol) was added, again allowing to warm to rt. After an additional 1 h at rt it was diluted with DCM and concentrated in vacuo. Half of the crude residue was purified by reverse phase prep HPLC (XSelect CSH, 30×100 mm, 5 μm, C18 column; ACN-water with 0.1% formic acid modifier, 60 mL/min), affording the title compound (140 mg, ca 23%) as a white powder. LCMS: $R_f$=0.27 min, m/z=530.1 (M+1) Method 2m_acidic; ¹H NMR (400 MHz, D₂O) δ 8.07 (s, 1H), 7.08-6.99 (m, 1H) 5.42-5.31 (m, 1H), 4.88-4.74 (m, 2H assumed; partially obscured by solvent residual peak), 4.74-4.68 (m, 1H), 4.20 (s, 2H), 1.36-1.23 (m, 2H), 1.23-1.07 (m, 2H).

Example 28

1-(((Z)-(1-(2-aminothiazol-4-yl)-2-(((2R,3S)-2-((4-(guanidinomethyl)-1H-1,2,3-triazol-1-yl)methyl)-4-oxo-1-sulfoazetidin-3-yl)amino)-2-oxoethylidene)amino)oxy)-cyclopropanecarboxylic acid

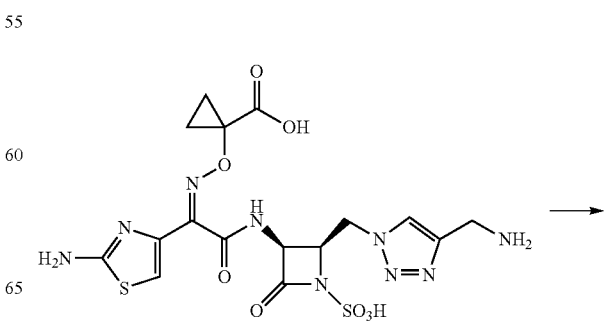

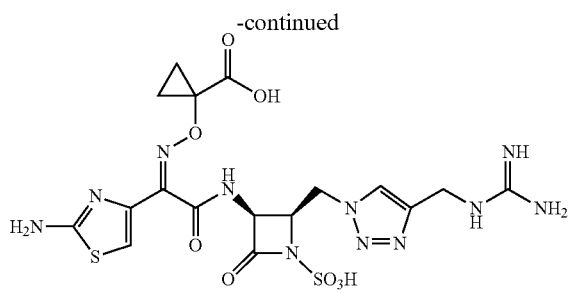

+

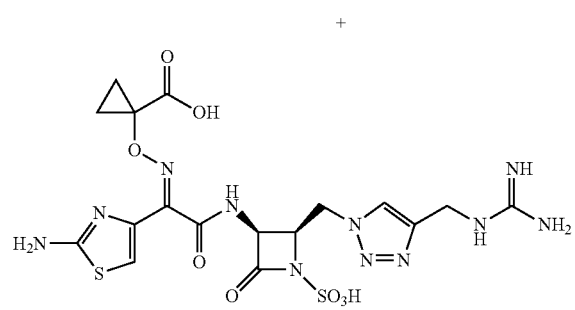

To a solution of 1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2oxoethylidene)amino)oxy)cyclopropane-carboxylic acid (559 mg, 1.06 mmol) and Pyrazole-1-carboxamidine hydrochloride (310 mg, 2.12 mmol) in DMF (12 mL) was added DIPEA (1.48 mL, 8.45 mmol). After 16 h of stirring at rt, the solution was diluted with toluene (20 mL), causing a dense oil to separate out. The top layer was decanted and the remaining oil was purified by reverse phase prep HPLC (XSelect CSH, 30×100 mm, 5 μm, C18 column; ACN-water with 0.1% formic acid modifier, 60 mL/min), affording the title compound (240 mg, 39%) as a white powder. LCMS: $R_t$=0.28 min, m/z=572.0 (M+H) Method 2m_acidic; $^1$H NMR (400 MHz, D$_2$O) δ 8.09 (s, 1H), 7.18 (s, 1H), 5.52 (d, J=5.4 Hz, 1H), 4.97 (dd, J=14.1, 5.5 Hz, 1H), 4.91 (q, J=5.5 Hz, 1H), 4.84-4.76 (m, 1H assumed; partially obscured by solvent residual peak), 4.55 (s, 2H), 1.49-1.36 (m, 2H), 1.34-1.23 (m, 2H). E-isomer was also obtained. LCMS: $R_t$=0.32 min, m/z=572.0 (M+H) Method 2m_acidic. $^1$H NMR (400 MHz, DMSO-d$_6$) δ 9.37 (d, J=9.6 Hz, 1H), 8.11 (s, 1H), 7.41 (s, 1H), 7.13 (s, 2H), 6.50 (s, 1H), 5.18 (dd, J=9.6, 5.3 Hz, 1H), 4.97 (d, J=13.5 Hz, 1H), 4.76-4.58 (m, 1H), 4.52 (dd, J=16.11, 7.70 Hz, 1H), 4.26-4.05 (m, 2H), 1.86-2.08 (m, 1H), 1.34-1.07 (m, 6H).

Example 29

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)propanoic acid Step 1: (R)-tert-Butyl 2-chloropropanoate Prepared according to Wright et al. Tetrahedron Lett. 1997, 38, 7345. A 500 mL glass bomb was charged with magnesium sulfate (4.21 g, 35.0 mmol) and DCM (43.8 mL). To this suspension was added sulfuric acid (486 μL, 8.75 mmol), drop-wise with vigorous stirring. After 15 min of stirring, (R)-2-chloropropanoic acid (950 mg, 8.75 mmol) was added followed by tert-butanol (4.20 ml, 43.8 mmol). The bomb was sealed and stirred at rt for 19 h, whereupon sodium bicarbonate (aq satd, 100 mL) was carefully added, at which point all solids had dissolved. The layers were separated and the aqueous layer was extracted with DCM (2×). The combined organics layers were washed with brine, dried over Na$_2$SO$_4$ and concentrated in vacuo (20° C. bath, 50 mBar) to afford the title compound (1.36 g, 94%) as a light pink oil. $^1$H NMR (500 MHz, CDCl$_3$) δ 4.29 (q, J=6.9 Hz, 1H) 1.65 (d, J=6.9 Hz, 3H) 1.49 (s, 9H).

Step 2: (S)-tert-butyl 2-((1,3-dioxoisoindolin-2-yl)oxy)propanoate

Prepared according to Yamawaki et al. Bioorg. Med. Chem. 2007, 15, 6716. To a slurry of N-hydroxyphthalimide (517 mg, 3.17 mmol) and potassium carbonate (657 mg, 4.76 mmol) in DMF (4.5 mL) was added (R)-tert-butyl 2-chloropropanoate (522 mg, 3.17 mmol). Additional DMF (4.5 mL) was added after the slurry became viscous. After stirring for 5 d it was diluted with EtOAc and poured into LiCl soln (5% aq, 90 mL). The aqueous layer was extracted with EtOAc (3×) and the combined organic layers were washed with LiCl (5% aq), brine, dried over Na$_2$SO$_4$ and concd in vacuo. The crude residue was purified by silica gel chromatography (EtOAc-Heptane, 0-50%), affording the title compound (348 mg, 38%) as a white solid. LCMS: $R_t$=0.89 min, m/z=314.0 (M+23) Method 2m_acidic; $^1$H NMR (400 MHz, CDCl$_3$) δ 7.87-7.81 (m, 2H), 7.75 (dd, J=5.5, 3.1 Hz, 2H), 4.79 (q, J=6.8 Hz, 1H), 1.61 (s, 3H), 1.46 (s, 9H).

Step 3: (S)-tert-butyl 2-(aminooxy)propanoate

To a solution of (S)-tert-butyl 2-((1,3-dioxoisoindolin-2-yl)oxy)propanoate (73.3 mg, 0.252 mmol) in DCM (Volume: 500 μL) at 0° C. was added methyl hydrazine (13.5 μL, 0.252 mmol). After stirring for 3 h at 0° C., the solids were filtered off and the filtrate was concentrated in vacuo, affording the title compound (assumed quantitative) as a clear oil.

Step 4: (S)-tert-butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-propanoate To a soln of Intermediate E (62.2 mg, 0.148 mmol) in MeOH (1 mL) at 0° C. was added a soln of (S)-tert-butyl 2-(aminooxy)propanoate (24 mg, 0.15 mmol) in DCM (300 μL). After stirring for 6 d acetic acid (8.5 μl, 0.15 mmol) was added. After 4 d more acetic acid (8.5 μl, 0.15 mmol) was added. After an additional 24 h, it was partially concentrated in vacuo then diluted with EtOAc/water. The layers were separated and the organic layer was washed with brine, dried over Na$_2$SO$_4$ and concd in vacuo. The crude residue was purified by silica gel chromatography (MeOH-DCM, 0-10%), affording the title compound (20.2 mg, 24%) as a white solid. LCMS: $R_t$=0.81 min, m/z=565.1 (M+1) Method 2m_acidic.

Step 5: (2R,3S)-2-((1H-1,2,4-triazol-1-yl)methyl)-3-((Z)-2-((((S)-1-(tert-butoxy)-1-oxopropan-2-yl)oxy)imino)-2-(2-((tert-butoxycarbonyl)amino)thiazol-4-yl)acetamido)-4-oxoazetidine-1-sulfonic acid To a soln of (S)-tert-butyl 2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)propanoate (20.2 mg, 0.036 mmol) in DMF (400 μl) was added SO$_3$.DMF (54.8 mg, 0.358 mmol). After 2.5 h of stirring it was diluted with EtOAc/LiCl (5% aq) and the layers were separated. The aqueous layer was extracted with EtOAc (3×) and the combined organic layers were washed with LiCl (5% aq), brine, dried over $Na_2SO_4$ and concd in vacuo, affording the title compound (assumed quantitative) as a white solid. LCMS: $R_t$=0.74 min, m/z=645.3 (M+1) Method 2m_acidic.

Step 6: (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)propanoic acid

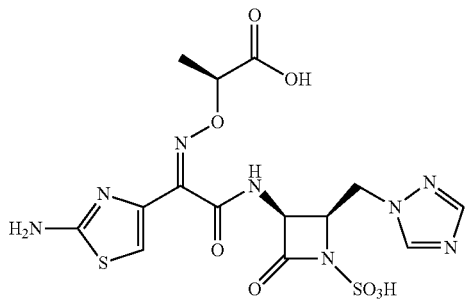 [SMILES: C[C@H](O/N=C(\C(=O)N[C@@H]1C(=O)N(S(=O)(=O)O)[C@@H]1Cn1cncn1)c1csc(N)n1)C(=O)O]

Followed the general procedure for the acid mediated deprotection using (2R,3S)-2-((1H-1,2,4-triazol-1-yl)methyl)-3-((Z)-2-((((S)-1-(tert-butoxy)-1-oxopropan-2-yl)oxy)imino)-2-(2-((tert-butoxycarbonyl)amino)thiazol-4-yl)acetamido)-4-oxoazetidine-1-sulfonic acid (23 mg, 0.036 mmol), DCM (357 µL) and TFA (165 µL, 2.14 mmol). The crude residue was purified by reverse phase prep HPLC (XSelect CSH, 19×100 mm, 5 µm, C18 column; ACN-water with 0.1% formic acid modifier, 24 mL/min), affording the title compound (7.9 mg, 36%) as a white powder. LCMS: $R_t$=0.40 min, m/z=489.0 (M+1) Method 2m_acidic_polar; $^1$H NMR (400 MHz, $D_2O$) δ 8.69 (s, 1H), 8.18 (s, 1H), 7.20 (s, 1H), 5.54 (d, J=5.7 Hz, 1H), 4.96-4.67 (m, 4H assumed; partially obscured by solvent residual peak), 1.44 (d, J=7.0 Hz, 3H).

Example 30

(R)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)propanoic acid Step 1: (S)-tert-Butyl 2-chloropropanoate Prepared according to Wright et al. *Tetrahedron Lett.* 1997, 38, 7345. A 500 mL glass bomb was charged with magnesium sulfate (21.7 g, 181 mmol) and DCM (182 mL). To this suspension was added sulfuric acid (2.5 mL, 45 mmol), dropwise with vigorous stirring. After 15 min of stirring, (S)-2-chloropropanoic acid (5.0 g, 45 mmol) was added followed by tert-butanol (21.6 ml, 226 mmol). The bomb was sealed and stirred at rt for 19 h, whereupon it was cooled to 0° C. and sodium bicarbonate (aq satd, 350 mL) was carefully added, at which point all solids had dissolved. The layers were separated and the aqueous layer was extracted with DCM (2×). The combined organics layers were washed with brine, dried over $Na_2SO_4$ and concentrated in vacuo (20° C. bath, 50 mBar) to afford the title compound (7.64 g, 96%) as a light yellow oil (93% purity). $^1$H NMR data was an identical match to the previously prepared enantiomer.

Step 2: (R)-tert-butyl 2-((1,3-dioxoisoindolin-2-yl)oxy)propanoate

To a slurry of N-hydroxyphthalimide (3.71 g, 22.1 mmol) and potassium carbonate (4.58 g, 33.1 mmol) in DMF (55 mL) was added (S)-tert-butyl 2-chloropropanoate (4.30 g, 24.3 mmol). After 72 h of stirring, the slurry was heated to 40° C. for an additional 16 h, at which point it was diluted with EtOAc/LiCl (5% aq) and the layers were separated. The aqueous layer was extracted with EtOAc (2×) and the combined organic layers were washed with LiCl (5% aq), brine, dried over $Na_2SO_4$ and concentrated in vacuo, affording the title compound (5.45 g, 85%) as an off-white solid. LCMS: $R_t$=0.88 min, m/z=313.9 (M+23) Method 2m_acidic.

Step 3: (R)-tert-butyl 2-(aminooxy)propanoate

To a solution of (R)-tert-butyl 2-((1,3-dioxoisoindolin-2-yl)oxy)propanoate (69.6 mg, 0.239 mmol) in DCM (478 µL) at 0° C. was added methyl hydrazine (12.8 µL, 0.239 mmol). After stirring for 3 h at 0° C., the solids were filtered off and the filtrate was concentrated in vacuo, affording the title compound (assumed quantitative) as a clear oil.

Step 4: (2R,3S)-2-((1H-1,2,4-triazol-1-yl)methyl)-3-((Z)-2-((((R)-1-(tert-butoxy)-1-oxopropan-2-yl)oxy)imino)-2-(2-((tert-butoxycarbonyl)amino)thiazol-4-yl)acetamido)-4-oxoazetidine-1-sulfonic acid To a soln of Intermediate F (110 mg, 0.219 mmol) in MeOH (2 mL) at 0° C. was added a soln of (R)-tert-butyl 2-(aminooxy)propanoate (38.5 mg, 0.239 mmol) in DCM:MeOH (2:1, 600 µL) followed by a DCM (400 µL) wash. After stirring for 16 h it was partially concentrated in vacuo then diluted with EtOAc/water and the layers were separated. The aqueous layer was extracted with EtOAc (2×) and the combined organic layers were dried over $Na_2SO_4$ and concd in vacuo, affording the title compound (assumed quantitative) as a white solid. LCMS: $R_t$=0.74 min, m/z=645.3 (M+1) Method 2m_acidic.

Step 5: (R)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)propanoic acid

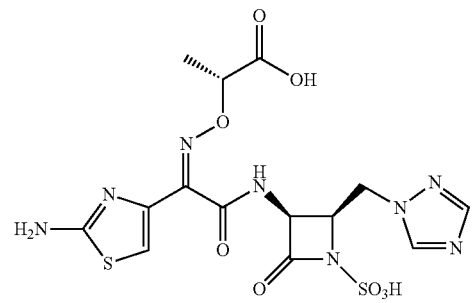 [SMILES: C[C@@H](O/N=C(\C(=O)N[C@@H]1C(=O)N(S(=O)(=O)O)[C@@H]1Cn1cncn1)c1csc(N)n1)C(=O)O]

Followed the general procedure for the acid mediated deprotection using (2R,3S)-2-((1H-1,2,4-triazol-1-yl)methyl)-3-((Z)-2-((((R)-1-(tert-butoxy)-1-oxopropan-2-yl)oxy)imino)-2-(2-((tert-butoxycarbonyl)amino)thiazol-4-yl)acetamido)-4-oxoazetidine-1-sulfonic acid (141 mg, 0.219 mmol), DCM (2.19 mL) and TFA (1.0 mL, 13 mmol). The crude residue was purified by reverse phase prep HPLC (XSelect CSH, 30×100 mm, 5 μm, C18 column; ACN-water with 0.1% formic acid modifier, 60 mL/min), affording the title compound (35.5 mg, 29%) as a white powder. LCMS: $R_t$=0.42 min, m/z=489.0 (M+1) Method 2m_acidic_polar; $^1$H NMR (400 MHz, D$_2$O) δ 8.58 (s, 1H), 8.06 (s, 1H), 7.06 (s, 1H), 5.41 (d, J=5.6 Hz, 1H), 4.81-4.52 (m, 4H assumed; partly obscured by solvent peak), 1.29 (d, J=7.0 Hz, 3H).

Example 31

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(piperidin-4-yl)carbamimidoyl)-phenoxy)propanoic acid Step 1: tert-Butyl 4-(4-((S)-2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene)amino)oxy)-3-(benzhydryloxy)-3-oxopropoxy)benzimidamido)piperidine-1-carboxylate To a solution of (S,Z)-2-(((1-(benzhydryloxy)-3-(4-(N-(1-(tert-butoxycarbonyl)piperidin-4-yl)carbamimidoyl)phenoxy)-1-oxopropan-2-yl)oxy)imino)-2-(2-((tert-butoxycarbonyl)amino)thiazol-4-yl)acetic acid (Prepared according to WO2013110643, 72 mg, 0.085 mmol), (3S,4R)-4-((1H-1,2,4-triazol-1-yl)methyl)-3-aminoazetidin-2-one (15.7 mg, 0.094 mmol) and HATU (42.2 mg, 0.111 mmol) in DMF (854 μL) was added DIPEA (44.8 μL, 0.256 mmol). After stirring at for 3 h it was diluted with EtOAc, washed with water, NaHCO$_3$ (aq satd), brine, dried over Na$_2$SO$_4$ and concentrated in vacuo, affording the title compound (82 mg, 87%) as an olive film. LCMS: $R_t$=0.97 min, m/z=992.5 (M+1) Method 2m_acidic.

Step 2: (2R,3S)-2-((1H-1,2,4-triazol-1-yl)methyl)-3-((Z)-2-((((S)-1-(benzhydryloxy)-3-(4-(N-(1-(tert-butoxycarbonyl)piperidin-4-yl)carbamimidoyl)phenoxy)-1-oxopropan-2-yl)oxy)imino)-2-(2-((tert-butoxycarbonyl)amino)thiazol-4-yl)acetamido)-4-oxoazetidine-1-sulfonic acid tert-Butyl 4-(4-((S)-2-(((Z)-(2-(((2R,3S)-2-((1H-1,2,4-triazol-1-yl)methyl)-4-oxoazetidin-3-yl)amino)-1-(2-((tert-butoxycarbonyl)amino)thiazol-4-yl)-2-oxoethylidene) amino)oxy)-3-(benzhydryloxy)-3-oxopropoxy)benzimidamido)piperidine-1-carboxylate (99 mg, 0.10 mmol) in DMF (500 μL) was treated with SO$_3$.DMF (45.9 mg, 0.299 mmol). After stirring for 40 min more SO$_3$.DMF (45.9 mg, 0.299 mmol) was added. After 1.3 h more SO$_3$.DMF (45.9 mg, 0.299 mmol) was added. After stirring for an additional 30 min the solution was poured into ice-cold brine and extracted with EtOAc. The layers were separated and the organic layer was dried over Na$_2$SO$_4$ and concentrated in vacuo, affording the title compound (assumed quantitative) as an off white solid. LCMS: $R_t$=0.97 min, m/z=1073.1 (M+1) Method 2m_acidic.

Step 3: (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(piperidin-4-yl)carbamimidoyl)-phenoxy)propanoic acid

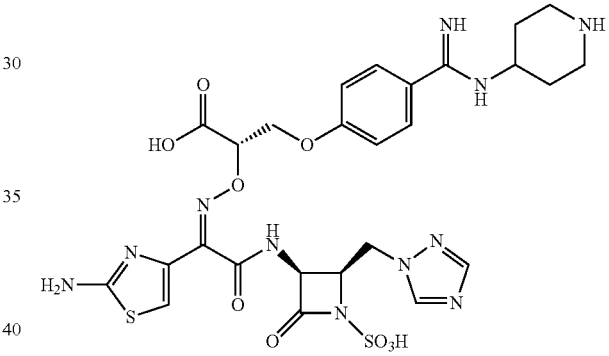

Followed the general procedure for the acid mediated deprotection using (2R,3S)-2-((1H-1,2,4-triazol-1-yl)methyl)-3-((Z)-2-(((((S)-1-(benzhydryloxy)-3-(4-(N-(1-(tert-butoxycarbonyl)piperidin-4-yl)carbamimidoyl)phenoxy)-1-oxopropan-2-yl)oxy)imino)-2-(2-((tert-butoxycarbonyl)amino)thiazol-4-yl)acetamido)-4-oxoazetidine-1-sulfonic acid (0.085 mmol), DCM (850 μL) and TFA (327 μL, 4.25 mmol). The crude residue was purified by reverse phase prep HPLC (XSelect CSH, 19×100 mm, 5 μm, C18 column; ACN-water with 0.1% formic acid modifier, 24 mL/min), affording the title compound (12 mg, 17%) as a white powder. LCMS: $R_t$=0.41 min, m/z=706.2 (M+1) Method 2m_acidic_polar; $^1$H NMR (400 MHz, DMSO-d$_6$) δ 9.55 (d, J=7.4 Hz, 1H) 9.40 (br s, 1H) 9.01 (br s, 1H) 8.53-8.71 (m, 1H) 8.41 (s, 1H) 7.92 (s, 1H) 7.67 (d, J=9.0 Hz, 2H) 7.21 (br s, 2H) 7.03 (d, J=7.8 Hz, 1H) 6.76 (s, 1H) 5.17-5.24 (m, 1H) 4.94 (d, J=3.9 Hz, 1H) 4.46-4.53 (m, 2H) 4.37-4.45 (m, 1H) 4.25-4.32 (m, 1H) 3.88 (br s, 1H) 3.39 (br s, 4H) 2.92 (t, J=11.5 Hz, 2H) 2.05-2.14 (m, 2H) 1.79 (d, J=11.0 Hz, 2H).

Example 32

1-(((Z)-(2-((((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)cyclobutanecarboxylic acid

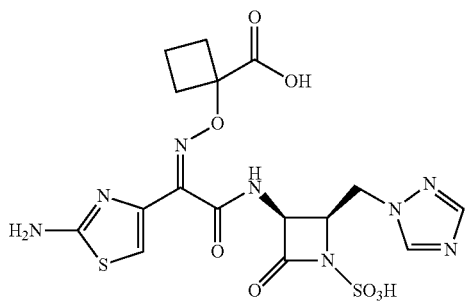 [SMILES: Nc1nc(/C(=N/OC2(C(=O)O)CCC2)C(=O)N[C@@H]2C(=O)N(S(=O)(=O)O)[C@@H]2Cn2cncn2)cs1]

LCMS: $R_t$=0.58 min, m/z=515.0 (M+1) Method 2m_acidic_polar; $^1$H NMR (400 MHz, D$_2$O) δ 8.75 (s, 1H), 8.22 (s, 1H), 7.23 (s, 1H), 5.56 (d, J=5.6 Hz, 1H), 4.95-4.85 (m, 2H), 4.86-4.82 (m, 1H assumed; partially obscured by solvent residual peak), 4.78-4.70 (m, 1H assumed; partially obscured by solvent residual peak), 2.61-2.46 (m, 2H), 2.38-2.27 (m, 2H), 2.00-1.89 (m, 2H).

Example 33

2-(((Z)-(1-(2-aminothiazol-4-yl)-2-(((2R,3S)-2-((4-(cyanomethyl)-2H-1,2,3-triazol-2-yl)methyl)-4-oxo-1-sulfoazetidin-3-yl)amino)-2-oxoethylidene)amino)oxy)-2-methylpropanoic acid

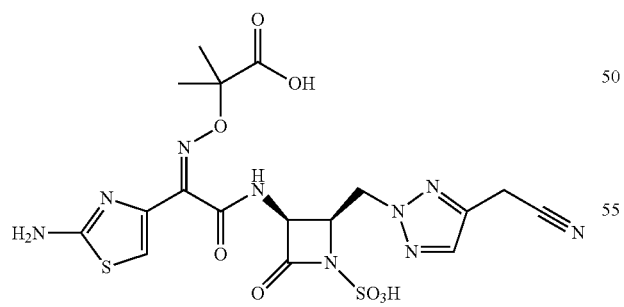

LCMS: $R_t$=0.57 min, m/z=542.1 (M+1) Method 2m_acidic_polar; $^1$H NMR (400 MHz, DMSO-d$_6$) δ 9.19 (d, J=9.0 Hz, 1H), 7.71 (s, 1H), 6.65 (s, 1H), 5.43-5.23 (m, 1H), 4.93-4.84 (m, 1H), 4.76-4.67 (m, 1H), 4.47 (ddd, J=8.71, 5.4, 3.5 Hz, 1H), 4.07 (d, J=1.6 Hz, 2H), 1.35 (s, 6H).

Example 34

2-(((Z)-(2-((((2R,3S)-2-((3-amino-1H-pyrazol-1-yl)methyl)-4-oxo-1-sulfoazetidin-3-yl)amino)-1-(2-aminothiazol-4-yl)-2-oxoethylidene)amino)oxy)-2-methylpropanoic acid

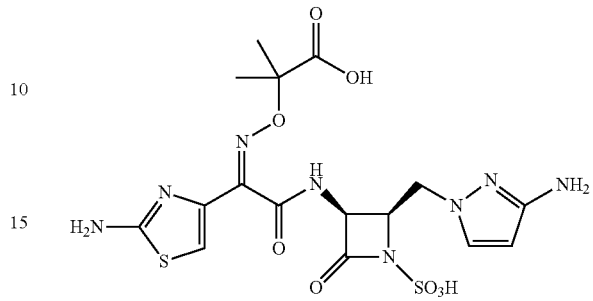

LCMS: $R_t$=0.50 min, m/z=517.3 (M+1) Method 2m_acidic_polar; $^1$H NMR (400 MHz, D$_2$O) δ 7.54 (d, J=2.5 Hz, 1H), 6.97 (s, 1H), 6.00 (d, J=2.4 Hz, 1H), 5.40 (d, J=5.8 Hz, 1H), 4.69 (q, J=5.5 Hz, 1H), 4.43 (d, J=5.4 Hz, 2H), 1.31 (d, J=1.8 Hz, 6H).

Example 35

2-(((Z)-(2-((((2R,3S)-2-((4-amino-1H-pyrazol-1-yl)methyl)-4-oxo-1-sulfoazetidin-3-yl)amino)-1-(2-aminothiazol-4-yl)-2-oxoethylidene)amino)oxy)-2-methylpropanoic acid

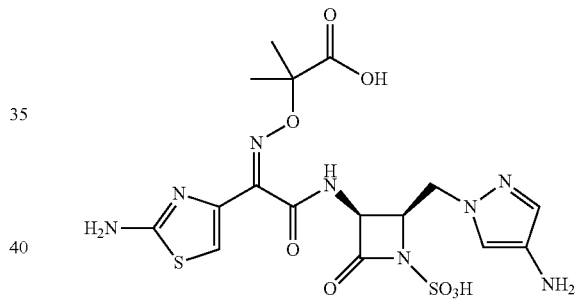

LCMS: $R_t$=0.39 min, m/z=517.1 (M+1) Method 2m_acidic_polar; $^1$H NMR (400 MHz, D$_2$O) δ 7.86 (s, 1H), 7.56 (s, 1H), 6.90 (s, 1H), 5.35 (d, J=5.9 Hz, 1H), 4.72-4.67 (m, 1H), 4.54-4.49 (m, 2H), 1.28 (s, 3H), 1.27 (s, 3H).

Example 36

(2R,3S)-3-((Z)-2-(2-aminothiazol-4-yl)-2-(((2-carboxypropan-2-yl)oxy)imino)acetamido)-2-((4-((1-methylpyrrolidin-1-ium-1-yl)methyl)-2H-1,2,3-triazol-2-yl)methyl)-4-oxoazetidine-1-sulfonate

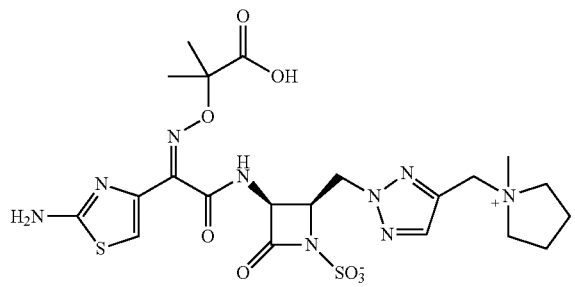

LCMS: $R_t$=0.55 min, m/z=600.3 (M+) Method 2m_acidic_polar; ¹H NMR (400 MHz, DMSO-$d_6$) δ 12.50 (s, 1H), 9.34 (s, 1H), 7.94 (s, 1H), 7.27 (s, 2H), 6.72 (s, 1H), 5.33 (dd, J=8.6, 5.6 Hz, 1H), 4.82 (dd, J=15.1, 9.2 Hz, 1H), 4.69-4.53 (m, 4H), 3.60-3.50 (m, 2H), 3.46-3.33 (m, 2H), 2.95 (s, 3H), 2.14-2.00 (m, 4H), 1.35 (s, 3H), 1.29 (s, 3H).

Example 37

2-(((Z)-(1-(2-aminothiazol-4-yl)-2-(((2R,3S)-2-((4-((carbamoyloxy)methyl)-2H-1,2,3-triazol-2-yl)methyl)-4-oxo-1-sulfoazetidin-3-yl)amino)-2-oxoethylidene)amino)oxy)-2-methylpropanoic acid

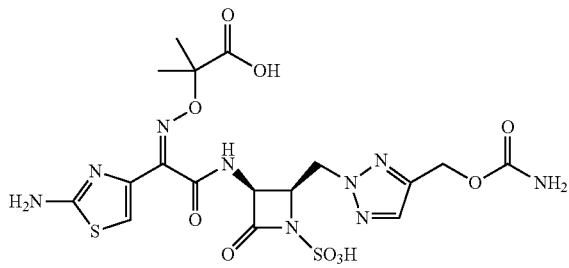 [SMILES: CC(C)(O/N=C(\C(=O)N[C@@H]1C(=O)N(S(=O)(=O)O)[C@@H]1Cn1ncc(COC(N)=O)n1)c1csc(N)n1)C(=O)O]

LCMS: $R_t$=0.53 min, m/z=576.0 (M+1) Method 2m_acidic_polar; ¹H NMR (400 MHz, DMSO-$d_6$) δ 9.23 (d, J=9.3 Hz, 1H), 7.70 (s, 1H), 6.74 (s, 1H), 6.59 (br s, 2H), 5.31 (dd, J=9.2, 5.4 Hz, 1H), 4.94 (s, 2H), 4.91 (dd, J=14.3, 3.2 Hz, 1H), 4.72 (dd, J=14.2, 9.0 Hz, 1H), 4.42 (ddd, J=8.8, 5.5, 3.1 Hz, 1H), 1.38 (s, 3H), 1.37 (s, 3H).

Example 38

2-(((Z)-(1-(2-aminothiazol-4-yl)-2-oxo-2-(((3S,4R)-2-oxo-1-sulfo-4-((4-((sulfooxy)methyl)-2H-1,2,3-triazol-2-yl)methyl)azetidin-3-yl)amino)ethylidene)amino)oxy)-2-methylpropanoic acid

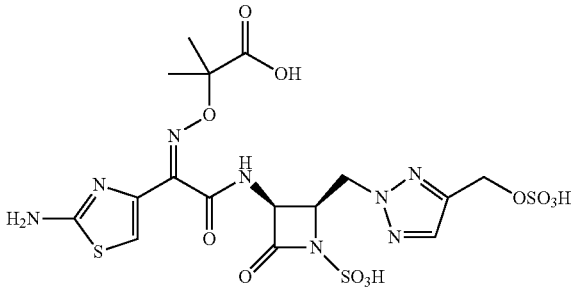

LCMS: $R_t$=0.43 min, m/z=612.9 (M+1) Method 2m_acidic_polar; ¹H NMR (400 MHz, $D_2O$) δ 7.71 (s, 1H), 6.96-7.11 (m, 1H), 5.40 (d, J=5.5 Hz, 1H), 4.98 (s, 2H), 4.93-4.65 (m 3H assumed; partially obscured by solvent residual peak), 1.34 (s, 6H).

Example 39

2-(((Z)-(2-(((2R,3S)-2-((2-amino-4,5-dihydro-1H-imidazol-1-yl)methyl)-4-oxo-1-sulfoazetidin-3-yl)amino)-1-(2-aminothiazol-4-yl)-2-oxoethylidene)amino)oxy)-2-methylpropanoic acid

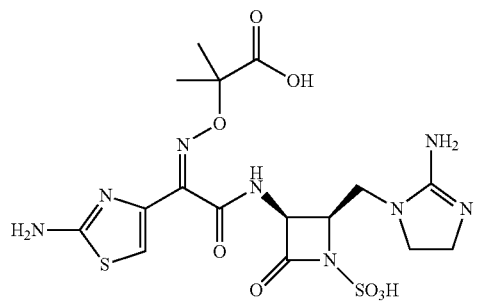 [SMILES: CC(C)(O/N=C(\C(=O)N[C@@H]1C(=O)N(S(=O)(=O)O)[C@@H]1CN1CCN=C1N)c1csc(N)n1)C(=O)O]

LCMS: $R_t$=0.30 min, m/z=520.1 (M+1) Method 2m_acidic; ¹H NMR (400 MHz, DMSO-$d_6$) δ 12.63 (br s, 1H) 9.12 (d, J=8.6 Hz, 1H) 7.74 (d, J=15.3 Hz, 3H) 7.31-7.49 (m, 2H) 6.77 (s, 1H) 5.22 (dd, J=8.5, 5.8 Hz, 1H) 4.24 (dt, J=7.1, 5.3 Hz, 1H) 3.76-3.85 (m, 1H) 3.59-3.73 (m, 2H) 3.43-3.55 (m, 3H) 1.43 (s, 3H) 1.41, (s, 3H).

Example 40

2-(((Z)-(1-(2-aminothiazol-4-yl)-2-(((2R,3S)-2-ME)-2-(cyanoimino)imidazolidin-1-yl)methyl)-4-oxo-1-sulfoazetidin-3-yl)amino)-2-oxoethylidene)amino)oxy)-2-methylpropanoic acid

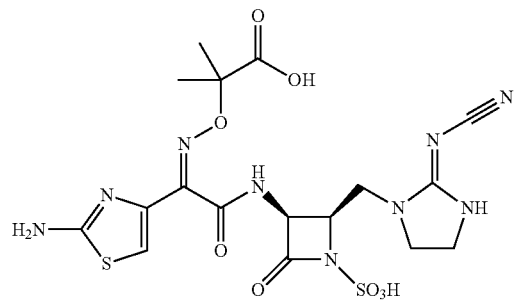 [SMILES: CC(C)(O/N=C(\C(=O)N[C@@H]1C(=O)N(S(=O)(=O)O)[C@@H]1CN1CCN/C1=N\C#N)c1csc(N)n1)C(=O)O]

LCMS: $R_t$=0.33 min, m/z=544.0 (M+1) Method 2m_acidic; ¹H NMR (500 MHz, DMSO-$d_6$) δ 9.29 (d, J=9.1 Hz, 1H) 7.74 (br s, 1H) 6.85 (s, 1H) 5.20 (dd, J=8.8, 5.7 Hz, 1H) 4.10-4.17 (m, 1H) 3.72-3.81 (m, 1H) 3.62 (dd, J=14.7, 6.8 Hz, 1H) 3.48-3.56 (m, 1H) 3.31-3.42 (m, 3H) 1.43 (s, 3H) 1.41, (s, 3H).

Example 41

2-(((Z)-(2-(((2R,3S)-2-((4-(2-aminoethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid

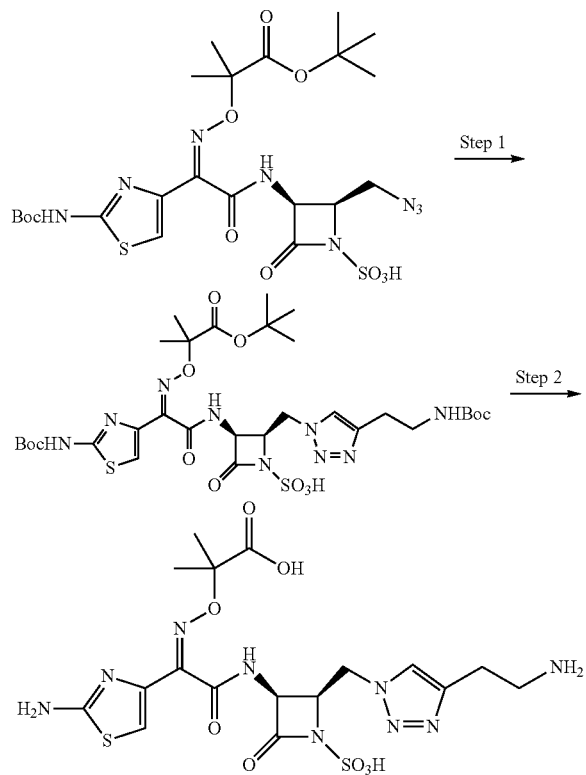

Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(2-((tert-butoxycarbonyl)amino)ethyl)-1H-1,2,3-triazol-1-yl)methyl)-4-oxoazetidine-1-sulfonic acid To a mixture of Intermediate K (100 mg, 0.158 mmol) and tert-butyl but-3-yn-1-ylcarbamate (54 mg, 0.32 mmol) in DMSO:water:tert-butanol (1:1:1, 3 mL) was added CuSO₄ (13 mg, 0.079 mmol) and sodium L-ascorbate (32 mg, 0.16 mmol). After overnight stirring the mixture was diluted with EtOAc and water. The layers were separated and aqueous layer was extracted with EtOAc (3×). The combined organic layers were washed with water, brine, dried over Na₂SO₄ and concentrated in vacuo. The crude residue was washed with diethyl ether/pentane, affording the title compound (80 mg, 63%) as a white solid. LCMS: m/z=799.8 (M−1).

Step 2: 2-(((Z)-(2-(((2R,3S)-2-((4-(2-aminoethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid To a solution of (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(2-((tert-butoxycarbonyl)amino)ethyl)-1H-1,2,3-triazol-1-yl)methyl)-4-oxoazetidine-1-sulfonic acid (110 mg, 0.137 mmol) in DCM (1.4 mL) at 0° C. added TFA: DCM (1:1, 4.2 mL) followed by triethylsilane (65 μL, 0.411 mmol). The reaction mixture was stirred at 0° C. for 30 min and slowly warmed to room temperature. After 2 h at rt it was concentrated in vacuo and triturated with MTBE:Heptane (1:2) whereupon a solid was observed. The crude solid was purified by reverse phase prep HPLC (C18 column, acetonitrile: water solvent system with 0.1% formic acid modifier) to afford the title compound (5 mg, 7%); LCMS: m/z=543.9 (M−1); ¹H NMR (400 MHz, MeOH-d₄) δ 8.06 (s, 1H), 6.95 (s, 1H), 5.44 (d, J=5.8 Hz, 1H), 4.66 (q, J=6.0 Hz, 1H), 4.95-4.83 (m, 2H assumed; obscured by water), 3.29-3.24 (m, 2H), 3.07 (t, J=6.5 Hz, 2H), 1.54 (s, 3H), 1.52 (s, 3H).

Example 42

2-(((Z)-(1-(2-aminothiazol-4-yl)-2-oxo-2-(((3S,4R)-2-oxo-4-((4-(2-(piperazin-1-yl)ethyl)-1H-1,2,3-triazol-1-yl)methyl)-1-sulfoazetidin-3-yl)amino)ethylidene)amino)oxy)-2-methylpropanoic acid Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(2-(4-(tert-butoxycarbonyl)piperazin-1-yl)ethyl)-1H-1,2,3-triazol-1-yl)methyl)-4-oxoazetidine-1-sulfonic acid To a solution of Intermediate K (90 mg, 0.142 mmol) and tert-butyl 4-(but-3-yn-1-yl)piperazine-1-carboxylate (34 mg, 0.14 mmol) in a mixture of DMSO:water:tert-butanol (1:1:1, 2.16 mL) was added CuSO₄ (2.5 mg, 0.016 mmol) and sodium L-ascorbate (5 mg, 0.15 mmol). After overnight stirring the mixture was diluted with EtOAc and water. The layers were separated and aqueous layer was extracted with EtOAc (3×). The combined organic layers were washed with water, brine, dried over Na₂SO₄ and concentrated in vacuo. The crude residue was washed with diethyl ether/pentane, affording the title compound (120 mg, crude); LCMS: m/z=871.4 (M+1).

Step 2: 2-(((Z)-(1-(2-aminothiazol-4-yl)-2-oxo-2-(((3S,4R)-2-oxo-4-((4-(2-(piperazin-1-yl)ethyl)-1H-1,2,3-triazol-1-yl)methyl)-1-sulfoazetidin-3-yl)amino)ethylidene)amino)oxy)-2-methylpropanoic acid

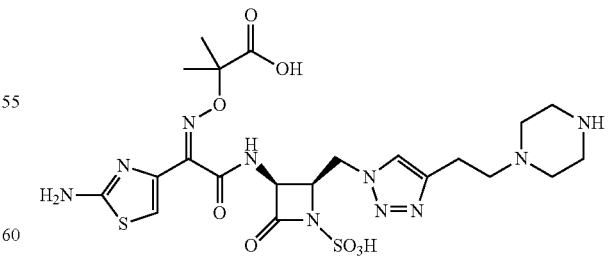

To a solution of (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(2-(4-(tert-butoxycarbonyl)piperazin-1-yl)ethyl)-1H-1,2,3-triazol-1-yl)methyl)-4-oxoazetidine-1-sulfonic acid (120 mg, 0.138 mmol) in DCM (1.4 mL) at 0° C. added TFA: DCM (1:1, 4.2 mL) followed by triethylsilane (65 μL, 0.411 mmol). The reaction mixture was stirred at 0° C. for 30 min and slowly warmed to room temperature. After 2 h at rt it was concentrated in vacuo and triturated with MTBE: Heptane (1:2) whereupon a solid was observed. The crude solid was purified by reverse phase prep HPLC (C18 column, acetonitrile: water solvent system with 0.1% formic acid modifier) to afford the title compound (9.3 mg, 11%); LCMS: m/z=612.8 (M−1); $^1$H NMR (400 MHz, DMSO-d$_6$) δ 9.67 (s, 1H), 7.99 (s, 1H), 7.30 (s, 2H), 6.66 (s, 1H), 5.27 (dd, J=8.8, 5.5 Hz, 1H), 4.82 (dd, J=14.7, 4.0 Hz, 1H), 4.68 (dd, J=14.7, 6.6 Hz, 1H), 4.24 (td, J=5.9, 4.2 Hz, 1H), 3.10 (t, J=5.2 Hz, 4H), 2.76 (t, J=7.0 Hz, 2H), 2.64-2.54 (m, 6H), 1.37 (s, 3H), 1.30 (s, 3H).

Example 43

(3S,4R)-3-((Z)-2-(2-aminothiazol-4-yl)-2-(((2-carboxypropan-2-yl)oxy)imino)acetamido)-2-oxo-4-((4-((2-(trimethylammonio)acetamido)methyl)-1H-1,2,3-triazol-1-yl)methyl)azetidine-1-sulfonate Step 1: 2-(((1-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxo-1-sulfoazetidin-2-yl)methyl)-1H-1,2,3-triazol-4-yl)methyl)amino)-N,N,N-trimethyl-2-oxoethanamonium bromide To a solution of Intermediate K (100 mg, 0.158 mmol) and N,N,N-trimethyl-2-oxo-2-(prop-2-yn-1-ylamino)ethanamonium bromide (50 mg, 0.212 mmol) in a mixture of DMSO: water:tert-butanol (1:1:1, 3 mL) was added CuSO$_4$ (2.5 mg, 0.016 mmol) and sodium L-ascorbate (5 mg, 0.15 mmol). The mixture was stirred overnight and quenched with ice-cold water, whereupon the resulting solids were filtered and dried in vacuo to afford crude title compound (50 mg, 40%); LCMS: m/z=784.85 (M−1).

Step 2: (3S,4R)-3-((Z)-2-(2-aminothiazol-4-yl)-2-(((2-carboxypropan-2-yl)oxy)imino)acetamido)-2-oxo-4-((4-((2-(trimethylammonio)acetamido)methyl)-1H-1,2,3-triazol-1-yl)methyl)azetidine-1-sulfonate

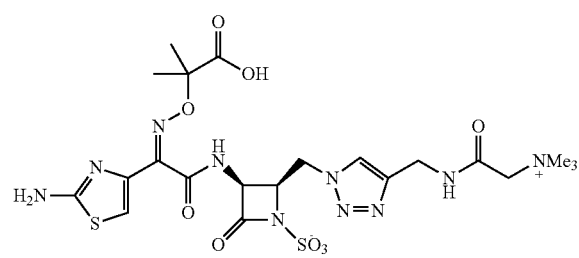

To a slurry of 2-(((1-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxo-1-sulfoazetidin-2-yl)methyl)-1H-1,2,3-triazol-4-yl)methyl)amino)-N,N,N-trimethyl-2-oxoethanaminium bromide (50 mg, 0.0635 mmol) In DCM (640 μL) at 0° C. was added TFA: DCM (1:1, 1.92 mL) followed by triethylsilane (31 μL, 0.19 mmol). The reaction mixture was stirred at 0° C. for 30 min and slowly warmed to room temperature. After 2 h at rt, it was concentrated in vacuo and triturated with MTBE:Heptane (1:2) whereupon a solid was observed. The crude solid was purified by reverse phase prep HPLC (C18 column, acetonitrile: water solvent system with 0.1% formic acid modifier) to afford the title compound (11 mg, 27%). LCMS: m/z=630.9 (M−1); $^1$H NMR (400 MHz, DMSO-d$_6$) δ 9.40 (d, J=8.6 Hz, 1H), 9.06 (t, J=5.6 Hz, 1H), 8.06 (s, 1H), 7.32 (s, 2H), 6.71 (s, 1H), 5.28 (dd, J=8.6, 5.5 Hz, 1H), 4.89-4.64 (m, 2H), 4.38 (t, J=5.1 Hz, 2H), 4.22 (q, J=5.3 Hz, 1H), 4.08 (s, 2H), 3.22 (s, 9H), 1.33 (s, 3H), 1.26 (s, 3H).

Example 44

2-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(((tert-butoxycarbonyl)amino)methyl)-1H-1,2,3-triazol-1-yl)methyl)-4-oxoazetidine-1-sulfonic acid To a solution of Intermediate K (100 mg, 0.158 mmol) in a mixture of DMSO:water:tert-butanol (1:1:1, 1.5 mL) at 0° C. was added N-Boc-propargyl amine (50 mg, 0.321 mmol), CuSO$_4$ (13 mg, 0.079 mmol) and sodium L-ascorbate (48 mg, 0.237 mmol). The resulting mixture was gradually brought to rt and stirred for 3 h. It was then diluted with EtOAc and brine and the layers were separated. The aqueous layer was extracted with EtOAc (3×) and the combined organic layers were washed with brine, dried over Na$_2$SO$_4$ then concentrated in vacuo to afford crude title compound (120 mg, 96%); LCMS: m/z=787.95 (M+1).

Step 2: 2-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid

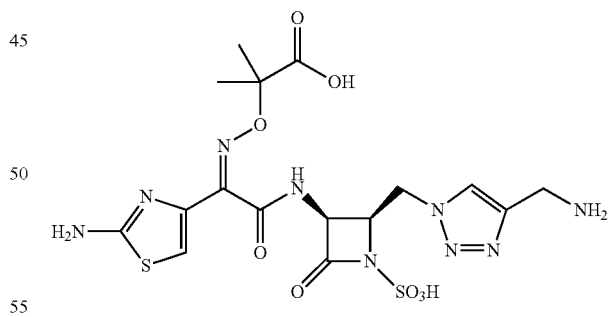

To a slurry of (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(((tert-butoxycarbonyl)amino)methyl)-1H-1,2,3-triazol-1-yl)methyl)-4-oxoazetidine-1-sulfonic acid (120 mg, 0.15 mmol) In DCM (1.5 mL) at 0° C. was added TFA: DCM (1:1, 4.5 mL) followed by triethylsilane (72 μL, 0.45 mmol). The reaction mixture was stirred at 0° C. for 30 min and slowly warmed to room temperature. After 2 h at rt it was concentrated in vacuo and triturated with MTBE: Heptane (1:2) whereupon a solid was observed. The crude solid was purified by reverse phase prep HPLC (C18 column, acetonitrile: water solvent system with 0.1% formic acid modifier) to afford the title compound (11.3 mg, 14%). LCMS: m/z=528.9 (M−1); $^1$H NMR (400 MHz, DMSO-$d_6$) δ 9.47 (d, J=8.5 Hz, 1H), 8.25 (s, 1H), 7.30 (s, 2H), 6.75 (s, 1H), 5.27 (dd, J=8.6, 5.6 Hz, 1H), 4.82 (qd, J=14.9, 5.0 Hz, 2H), 4.23 (q, J=5.1 Hz, 1H), 4.09 (s, 2H), 1.37 (s, 3H), 1.32 (s, 3H).

Example 45

2-(((Z)-(1-(2-aminothiazol-4-yl)-2-(((2R,3S)-2-((4-(guanidinomethyl)-1H-1,2,3-triazol-1-yl)methyl)-4-oxo-1-sulfoazetidin-3-yl)amino)-2-oxoethylidene)amino)oxy)-2-methylpropanoic acid

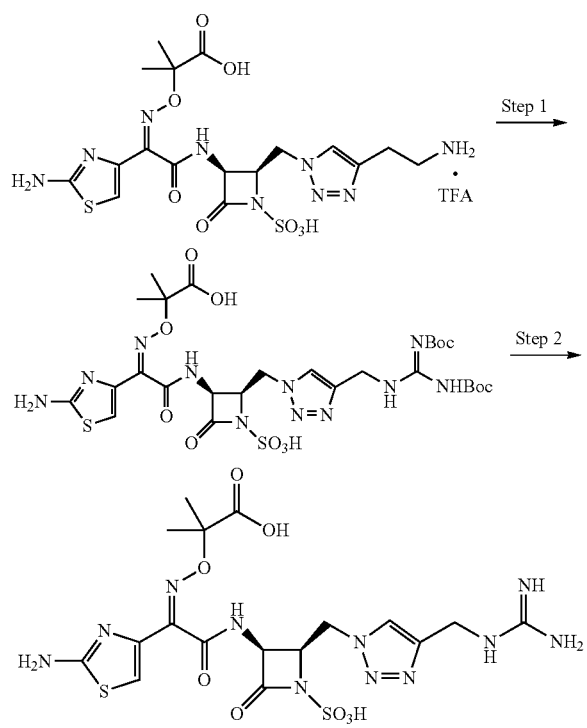

Step 1: 2-(((Z)-(1-(2-aminothiazol-4-yl)-2-(((2R,3S)-2-((4-((2,3-bis(tert-butoxycarbonyl)guanidino)methyl)-1H-1,2,3-triazol-1-yl)methyl)-4-oxo-1-sulfoazetidin-3-yl)amino)-2-oxoethylidene)amino)oxy)-2-methylpropanoic acid To a solution of 2-(((Z)-(2-(((2R,3S)-2-((4-(ammoniomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid trifluoroacetate (150 mg, 0.122 mmol) In DCM (10 mL) was added DIPEA (100 µL, 0.610 mmol) followed N,N-di-Boc-1H-pyrazole-1-carboxamidine (42 mg, 0.134 mmol). The solution was stirred at RT overnight whereupon it was concentrated in vacuo, water was added and it was lyophilized for 72 h to afford crude title compound (210 mg, assumed quantitative conversion). LCMS: m/z=772.1 (M−1).

Step 2: 2-(((Z)-(1-(2-aminothiazol-4-yl)-2-(((2R,3S)-2-((4-(guanidinomethyl)-1H-1,2,3-triazol-1-yl)methyl)-4-oxo-1-sulfoazetidin-3-yl)amino)-2-oxoethylidene)amino)oxy)-2-methylpropanoic acid General Procedure for Acid Mediated Deprotection.

To a solution of 2-(((Z)-(1-(2-aminothiazol-4-yl)-2-(((2R,3S)-2-((4-((2,3-bis(tert-butoxycarbonyl)guanidino)methyl)-1H-1,2,3-triazol-1-yl)methyl)-4-oxo-1-sulfoazetidin-3-yl)amino)-2-oxoethylidene)amino)oxy)-2-methylpropanoic acid (0.15 mmol, assumed quantitative conversion) In DCM (1.5 mL) at 0° C. was added TFA (689 µL, 9 mmol). The cold bath was removed after 10 min. After 4 h at rt it was diluted with DCM (1.5 mL) and concentrated in vacuo. The crude residue was purified by reverse phase prep HPLC (X-Bridge, 30×100 mm, 5 µm, C18 column; acetonitrile-water with 0.1% formic acid modifier, 1 mL/min) to afford the title compound (2.7 mg, 3%). LCMS: m/z=572.0 (M−1); $^1$H NMR (400 MHz, $D_2O$): δ $^1$H NMR (400 MHz, $D_2O$): δ 7.91 (s, 1H), 6.80 (s, 1H), 5.31 (d, J=5.2 Hz, 1H), 4.54 (s, 1H), 4.35 (s, 2H), 3.50-3.35 (m, 2H), 1.19 (s, 3H), 1.18 (s, 3H).

Example 46

2-(((Z)-(1-(2-aminothiazol-4-yl)-2-(((2R,3S)-2-((4-((2-(4-methylpiperazin-1-yl)acetamido)methyl)-1H-1,2,3-triazol-1-yl)methyl)-4-oxo-1-sulfoazetidin-3-yl)amino)-2-oxoethylidene)amino)oxy)-2-methylpropanoic acid Step 1: (2R,3S)-3-(((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-((2-(4-methylpiperazin-1-yl)acetamido)methyl)-1H-1,2,3-triazol-1-yl)methyl)-4-oxoazetidine-1-sulfonic acid To a solution of Intermediate K (100 mg, 0.158 mmol) in a mixture of DMSO:water:tert-butanol (1:1:1, 1 mL) at 0° C. was added 2-(4-methylpiperazin-1-yl)-N-(prop-2-yn-1-yl)acetamide (47 mg, 0.24 mmol), CuSO$_4$ (13 mg, 0.079 mmol) and sodium L-ascorbate (48 mg, 0.237 mmol). The resulting mixture was gradually brought to room temperature and stirred for 3 h. It was then diluted with EtOAc and brine and the layers were separated. The aqueous layer was extracted with EtOAc (3×) and the combined organic layers were washed with brine, dried over $Na_2SO_4$ then concentrated in vacuo to afford crude title compound (110 mg, 84%); LCMS: m/z=829.1 (M+1).

Step 2: 2-(((Z)-(1-(2-aminothiazol-4-yl)-2-(((2R,3S)-2-((4-((2-(4-methylpiperazin-1-yl)acetamido)methyl)-1H-1,2,3-triazol-1-yl)methyl)-4-oxo-1-sulfoazetidin-3-yl)amino)-2-oxoethylidene)amino)oxy)-2-methylpropanoic acid

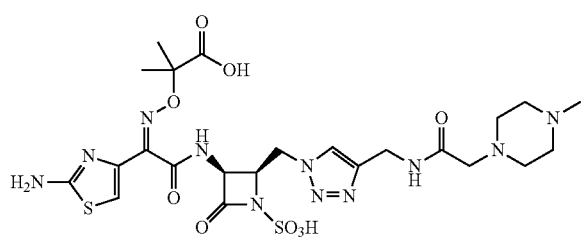 [SMILES: CN1CCN(CC(=O)NCc2cn(C[C@@H]3[C@H](NC(=O)/C(=N\OC(C)(C)C(=O)O)c4csc(N)n4)C(=O)N3S(=O)(=O)O)nn2)CC1]

To a slurry of (2R,3S)-3-(((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-((2-(4-methylpiperazin-1-yl)acetamido)methyl)-1H-1,2,3-triazol-1-yl)methyl)-4-oxoazetidine-1-sulfonic acid (120 mg, 0.13 mmol) In DCM (1.3 mL) at 0° C. was added TFA: DCM (1:1, 3.9 mL) followed by triethylsilane (62 µL, 0.39 mmol). The reaction mixture was stirred at 0° C. for 30 min and slowly warmed to room temperature. After 2 h at rt it was concentrated in vacuo and triturated with MTBE: Heptane (1:2) whereupon a solid was observed. The crude solid was purified by reverse phase prep HPLC (C18 column, ACN-water solvent system with 0.1% formic acid modifier) to afford the title compound (9 mg). LCMS: m/z=669.75 (M−1); $^1$H NMR (400 MHz, DMSO-d$_6$) δ 9.40 (d, J=8.7 Hz, 1H), 8.25 (s, 1H), 8.00 (s, 1H), 7.33 (s, 2H), 6.71 (s, 1H), 5.29 (dd, J=8.7, 5.6 Hz, 1H), 4.88-4.60 (m, 2H), 4.34 (d, J=5.7 Hz, 2H), 4.24 (q, J=5.3 Hz, 1H), 3.20-2.87 (m, 8H), 2.77 (s, 3H), 1.34 (s, 3H), 1.30 (s, 3H).

Example 47

2-(((Z)-(1-(2-aminothiazol-4-yl)-2-(((2R,3S)-2-((4-(hydroxymethyl)-1H-1,2,3-triazol-1-yl)methyl)-4-oxo-1-sulfoazetidin-3-yl)amino)-2-oxoethylidene)amino)oxy)-2-methylpropanoic acid Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(hydroxymethyl)-1H-1,2,3-triazol-1-yl)methyl)-4-oxoazetidine-1-sulfonic acid To a solution of Intermediate K (126 mg, 0.20 mmol) in a mixture of DMSO:water:tert-butanol (1:1:1, 1.5 mL) at 0° C. was added propargyl alcohol (24 µL, 0.40 mmol), CuSO$_4$ (16 mg, 0.10 mmol) and sodium L-ascorbate (59 mg, 0.30 mmol). Th resulting mixture was gradually brought to rt and stirred for 3 h. It was then frozen and lyophilized. The crude residue was purified with HP21 resin (ACN-water, 10-100%) to afford the title compound as a light brown solid (100 mg, 73%); LCMS: m/z=687.1 (M−1).

Step 2: 2-(((Z)-(1-(2-aminothiazol-4-yl)-2-(((2R,3S)-2-((4-(hydroxymethyl)-1H-1,2,3-triazol-1-yl)methyl)-4-oxo-1-sulfoazetidin-3-yl)amino)-2-oxoethylidene)amino)oxy)-2-methylpropanoic acid

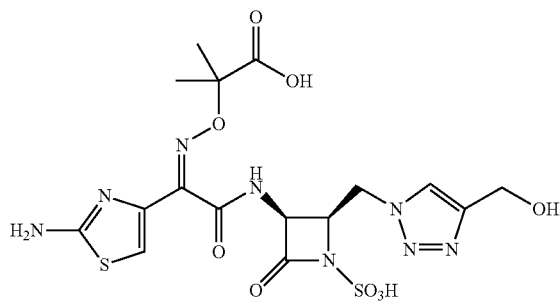 [SMILES: CC(C)(O/N=C(\C(=O)N[C@@H]1C(=O)N(S(=O)(=O)O)[C@@H]1Cn1cc(CO)nn1)c1csc(N)n1)C(=O)O]

Followed the general procedure for the acid mediated deprotection using (2R,3S)-3-(((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(hydroxymethyl)-1H-1,2,3-triazol-1-yl)methyl)-4-oxoazetidine-1-sulfonic acid (100 mg, 0.145 mmol), DCM (4 mL) and TFA (1 mL, 13 mmol). The crude residue was purified by reverse phase prep HPLC (T3, 30×100 mm, 5 µm, C18 column; acetonitrile-water with 0.1% formic acid modifier, 1 mL/min), affording the title compound (22 mg, 29%) as a white solid. LCMS: m/z=530.9 (M−1); $^1$H NMR (400 MHz, DMSO-d$_6$): δ 12.50 (br s, 1H), 9.36 (d, J=9.2 Hz, 1H), 7.97 (s, 1H), 7.50 (br s, 2H), 6.70 (s, 1H), 5.28 (dd, J=8.8, 5.2, Hz, 1H), 4.86 (dd, J=14.4, 4.0 Hz, 1H), 4.69 (dd, J=14.8, 7.2 Hz, 1H), 4.48 (s, 2H), 4.27-4.21 (m, 1H), 1.35 (s, 3H), 1.34 (s, 3H).

Example 48

(2R,3S)-3-((Z)-2-(2-aminothiazol-4-yl)-2-(((2-carboxypropan-2-yl)oxy)imino)acetamido)-2-((4-(1-methylpyridin-1-ium-4-yl)-1H-1,2,3-triazol-1-yl)methyl)-4-oxoazetidine-1-sulfonate Step 1: 4-(1-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidin-2-yl)methyl)-1H-1,2,3-triazol-4-yl)-1-methylpyridin-1-ium trifluoromethanesulfonate To a solution of Intermediate K (85 mg, 0.134 mmol) in a mixture of DMSO:water:tert-butanol (1:1:1, 1.0 mL) at 0° C. was added 4-ethynyl-1-methylpyridin-1-ium trifluoromethanesulfonate (72 µL, 0.27 mmol), CuSO$_4$ (11 mg, 0.067 mmol) and sodium L-ascorbate (40 mg, 0.201 mmol). The resulting mixture was gradually brought to rt and stirred for 3 h whereupon it was diluted with water (5 mL). The resulting precipitate was washed with water (2 mL) and dried via N$_2$ stream, affording the title compound (80 mg) as a mixture with its N-sulfonylated azetidinone analog as a light brown solid; LCMS: m/z=748.1 (M−1).

Step 2: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(1-methylpyridin-1-ium-4-yl)-1H-1,2,3-triazol-1-yl)methyl)-4-oxoazetidine-1-sulfonate 4-(1-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidin-2-yl)methyl)-1H-1,2,3-triazol-4-yl)-1-methylpyridin-1-ium trifluoromethanesulfonate (70 mg, 0.10 mmol) in DMF (1 mL) was treated with SO$_3$.DMF (80 mg, 0.52 mmol). The reaction mixture was stirred at rt for 16 h then concentrated in vacuo and purified by HP21 resin (ACN-water, 10-100%), affording the title compound (24 mg, 31%) as a beige solid. LCMS: m/z=748.1 (M−1).

Step 3: (2R,3S)-3-((Z)-2-(2-aminothiazol-4-yl)-2-(((2-carboxypropan-2-yl)oxy)imino)acetamido)-2-((4-(1-methylpyridin-1-ium-4-yl)-1H-1,2,3-triazol-1-yl)methyl)-4-oxoazetidine-1-sulfonate

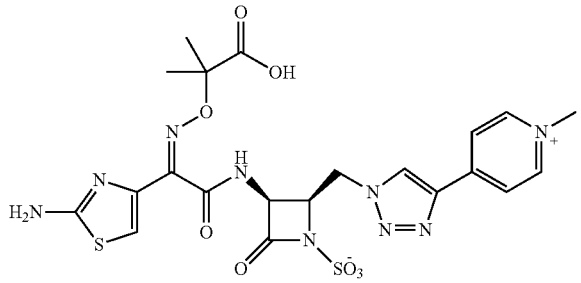

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(1-methylpyridin-1-ium-4-yl)-1H-1,2,3-triazol-1-yl)methyl)-4-oxoazetidine-1-sulfonate (24 mg, 0.032 mmol), DCM (1.2 mL) and TFA (0.3 mL, 3.9 mmol). The crude residue was purified by reverse phase prep HPLC (XBridge, 30×100 mm, 5 μm, C18 column; ACN-water with 0.1% formic acid modifier, 1 mL/min), affording the title compound (7.9 mg, 41%) as a white solid. LCMS: m/z=592.0 (M−1); $^1$H NMR (400 MHz, D$_2$O): δ 8.76 (s, 1H), 8.62 (d, J=6.8 Hz, 2H), 8.19 (d, J=6.4 Hz, 2H), 6.76 (s, 1H), 5.42 (d, J=5.2 Hz, 1H), 4.98-4.81 (m, 2H; partially obscured by residual solvent peak), 4.66-4.54 (m, 1H assumed: obscured by residual solvent peak), 4.22 (s, 3H), 1.30 (s, 3H), 1.27 (s, 3H).

Example 49

(2R,3S)-3-((Z)-2-(2-aminothiazol-4-yl)-2-(((2-carboxypropan-2-yl)oxy)imino)acetamido)-2-((4-(1,3-dimethylpyridin-1-ium-4-yl)-1H-1,2,3-triazol-1-yl)methyl)-4-oxoazetidine-1-sulfonate Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(1,3-dimethylpyridin-1-ium-4-yl)-1H-1,2,3-triazol-1-yl)methyl)-4-oxoazetidine-1-sulfonate To a solution of intermediate K (120 mg, 0.19 mmol) in a mixture of DMSO:water:tert-butanol (1:1:1, 1.5 mL) at 0° C. was added 4-ethynyl-1,3-dimethylpyridin-1-ium trifluoromethanesulfonate (107 mg, 0.38 mmol), CuSO$_4$ (15 mg, 0.095 mmol) and sodium L-ascorbate (56 mg, 0.285 mmol). The resulting mixture was gradually brought to rt and stirred for 3 h whereupon it was diluted with water (10 mL). The resulting precipitate was washed with water (5 mL) and dried. The crude residue was purified with HP21 resin (ACN-water, 10-100%), affording the title compound (80 mg, 55%) as a light brown solid; LCMS: m/z=762.2 (M−1).

Step 2: (2R,3S)-3-((Z)-2-(2-aminothiazol-4-yl)-2-(((2-carboxypropan-2-yl)oxy)imino)acetamido)-2-((4-(1,3-dimethylpyridin-1-ium-4-yl)-1H-1,2,3-triazol-1-yl)methyl)-4-oxoazetidine-1-sulfonate

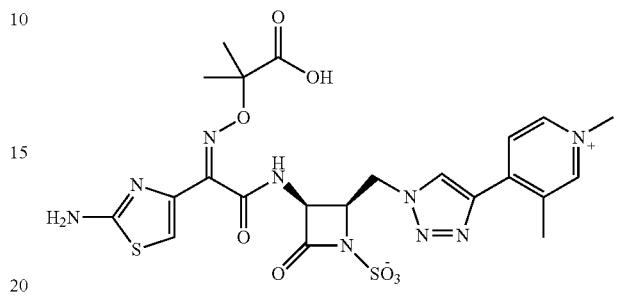

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(1,3-dimethylpyridin-1-ium-4-yl)-1H-1,2,3-triazol-1-yl)methyl)-4-oxoazetidine-1-sulfonate (24 mg, 0.032 mmol), DCM (1.2 mL) and TFA (0.3 mL, 3.9 mmol). The crude residue was purified by reverse phase prep HPLC (T3, 30×150 mm, 5 μm, C18 column; ACN-water with 0.1% formic acid modifier, 1 mL/min), affording the title compound (12 mg, 62%) as a white solid. LCMS: m/z=606.1 (M−1); $^1$H NMR (400 MHz, D$_2$O): δ 8.65 (s, 1H), 8.57 (s, 1H), 8.49 (d, J=5.6 Hz, 1H), 8.27 (d, J=6.8 Hz, 1H), 6.74 (br s, 1H), 5.47 (d, J=5.2 Hz, 1H), 4.97-4.88 (m, 3H), 4.21 (s, 3H), 2.46 (s, 3H), 1.30 (s, 3H), 1.28 (s, 3H).

Example 50

2-(((Z)-(2-(((2R,3S)-2-((1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid Step 1: tert-Butyl 2-(((Z)-(1-(2-((tert-butoxycarbonyl)amino)thiazol-4-yl)-2-oxo-2-(((3S,4R)-2-oxo-4-((4-(trimethylsilyl)-1H-1,2,3-triazol-1-yl)methyl)azetidin-3-yl)amino)ethylidene)amino)oxy)-2-methylpropanoate To a solution of Intermediate J (120 mg, 0.19 mmol) in a mixture of DMSO:water:tert-butanol (1:1:1, 2.0 mL) at 0° C. was added trimethylsilylacetylene (100 μL, 0.724 mmol), CuSO$_4$ (29 mg, 0.181 mmol) and sodium L-ascorbate (108 mg, 0.543 mmol). The resulting mixture was gradually brought to rt and stirred for 4 h, whereupon it was diluted with brine (5 mL) and extracted with EtOAc (3×10 mL). The combined organic layers were dried over Na$_2$SO$_4$ and concentrated in vacuo. The crude residue was purified via silica gel chromatography (MeOH-DCM, 7%), affording the title compound (170 mg, 72%) as a light brown solid; LCMS: m/z=651.2 (M+1).

Step 2: tert-Butyl 2-(((Z)-(2-(((2R,3S)-2-((1H-1,2,3-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate Prepared according to the method described in WO2013/028590. To a solution of tert-butyl 2-(((Z)-(1-(2-((tert-butoxycarbonyl)amino)thiazol-4-yl)-2-oxo-2-(((3S,4R)-2-oxo-4-((4-(trimethylsilyl)-1H-1,2,3-triazol-1-yl)methyl)azetidin-3-yl)amino)ethylidene)amino)oxy)-2-methylpropanoate (140 mg, 0.261 mmol) in THF (4 mL) was added TBAF (1 M in THF, 860 µL, 0.86 mmol). After stirring at rt for 16 h, additional TBAF (1M in THF, 1.0 mL, 1.0 mmol) was added. After stirring for an another 48 h, the solution was concentrated in vacuo. The crude residue was purified via silica gel chromatography (MeOH-DCM, 7%) affording the title compound (84 mg, 68%) as an off white solid. LCMS: m/z=579.2 (M+1).

Step 3: (2R,3S)-2-((1H-1,2,3-triazol-1-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid tert-Butyl 2-(((Z)-(2-(((2R,3S)-2-((1H-1,2,3-triazol-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate (84 mg, 0.145 mmol) in DMF (2 mL) was treated with SO$_3$.DMF (222 mg, 1.45 mmol). The reaction mixture was stirred at rt for 16 h then diluted with EtOAc (50 mL) and water. The layers were separated and the organic layer was washed with brine, dried over Na$_2$SO$_4$ and concentrated in vacuo, affording the crude title compound as a light yellow solid (84 mg, 88%). LCMS: m/z=657.1 (M−1).

Step 4: 2-(((Z)-(2-(((2R,3S)-2-((1H-1,2,3-triazol-1-yl)methyl)-4-oxo-1-sulfoazetidin-3-yl)amino)-1-(2-aminothiazol-4-yl)-2-oxoethylidene)amino)oxy)-2-methylpropanoic acid

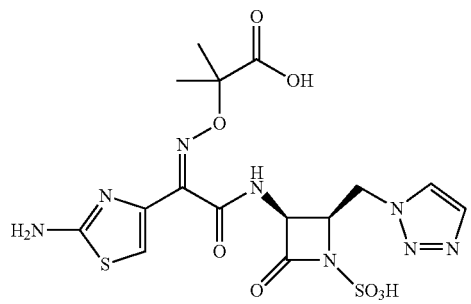 [SMILES: CC(C)(O/N=C(\C(=O)N[C@@H]1C(=O)N(S(=O)(=O)O)[C@@H]1Cn1ccnn1)c1csc(N)n1)C(=O)O]

Followed the general procedure for the acid mediated deprotection using (2R,3S)-2-((1H-1,2,3-triazol-1-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid (80 mg, 0.121 mmol), DCM (4 mL) and TFA (1 mL, 13 mmol). The crude residue was purified by reverse phase prep HPLC (T3, 30×150 mm, 5 µm, C18 column; ACN-water with 0.1% formic acid modifier, 1 mL/min), affording the title compound (12 mg, 20%) as a white solid. LCMS: m/z=500.9 (M−1); $^1$H NMR (400 MHz, D$_2$O): δ 7.95 (s, 1H), 7.67 (s, 1H), 7.04 (s, 1H), 5.38 (d, J=5.6 Hz, 1H), 4.88-4.80 (m, 1H), 4.78-4.70 (m, 2H assumed; obscured by solvent residual peak), 1.34 (s, 6H).

Example 51

1-(((2R,3S)-3-((Z)-2-(2-aminothiazol-4-yl)-2-(((2-carboxypropan-2-yl)oxy)imino)acetamido)-4-oxo-1-sulfoazetidin-2-yl)methyl)-1H-1,2,3-triazole-4-carboxylic acid Step 1: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(tert-butoxycarbonyl)-1H-1,2,3-triazol-1-yl)methyl)-4-oxoazetidine-1-sulfonic acid To a solution of Intermediate K (157 mg, 0.248 mmol) in a mixture of DMSO:water:tert-butanol (1:1:1, 2.0 mL) at 0° C. was added tert-butyl propiolate (68 µL, 0.496 mmol), CuSO$_4$ (20 mg, 0.124 mmol) and sodium L-ascorbate (198 mg, 0.372 mmol). The resulting mixture was gradually brought to room temperature and stirred for 3 h, whereupon it was diluted with water (20 mL) and extracted with EtOAc (3×50 mL). The combined organic layers were dried over Na$_2$SO$_4$, concentrated in vacuo dissolved in water and lyophilized, affording the title compound (180 mg, 96%) as a light yellow solid; LCMS: m/z=759.3 (M+1).

Step 2: 1-(((2R,3S)-3-((Z)-2-(2-aminothiazol-4-yl)-2-(((2-carboxypropan-2-yl)oxy)imino)acetamido)-4-oxo-1-sulfoazetidin-2-yl)methyl)-1H-1,2,3-triazole-4-carboxylic acid

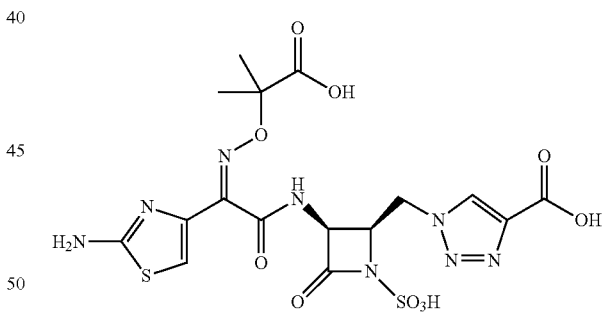

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(tert-butoxycarbonyl)-1H-1,2,3-triazol-1-yl)methyl)-4-oxoazetidine-1-sulfonic acid (180 mg, 0.237 mmol), DCM (8 mL) and TFA (2 mL, 26 mmol). The crude residue was purified by reverse phase prep HPLC (T3, 30×150 mm, 5 µm, C18 column; ACN-water with 0.1% formic acid modifier, 1 mL/min), affording the title compound (35 mg, 27%) as a white solid. LCMS: m/z=544.9 (M−1); $^1$H NMR (400 MHz, D$_2$O): δ 8.43 (s, 1H), 6.99 (s, 1H), 5.38 (d, J=5.2 Hz, 1H), 4.92-4.71 (m, 3H; partially obscured by solvent residual peak), 1.33 (s, 6H).

Example 52

2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid

Step 1: tert-butyl 2-(((Z)-(2-(((2R,3S)-2-((4-(((tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate General Procedure for the Mitsunobu Reaction.

To a solution of Intermediate H (300 mg, 0.569 mmol), tert-butyl ((2H-1,2,3-triazol-4-yl)methyl)carbamate (135 mg, 0.682 mmol) and triphenylphosphine (178 mg, 0.682 mmol) in THF (10 mL) at 0° C. was added DIAD (145 mg, 0.682 mmol), drop-wise. After stirring at rt for 16 h, the solution was concentrated and purified silica gel chromatography (MeOH-DCM, 2-5%), affording the title compound (300 mg, 75%) as a yellow foam. LCMS: m/z=706.2 (M+1).

Step 2: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(((tert-butoxycarbonyl)amino)methyl)-2H-1,2,3-triazol-2-yl)methyl)-4-oxoazetidine-1-sulfonic acid tert-Butyl 2-(((Z)-(2-(((2R,3S)-2-((4-(((tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate (220 mg, 0.311 mmol) in DMF (5 mL) was treated with SO$_3$.DMF (476 mg, 3.11 mmol). The solution was stirred at rt for 48 h then concentrated in vacuo and purified with HP21 resin (ACN-water, 10-50%), affording the title compound (82 mg, 33%). LCMS: m/z=786.2 (M−1).

Step 3: 2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid

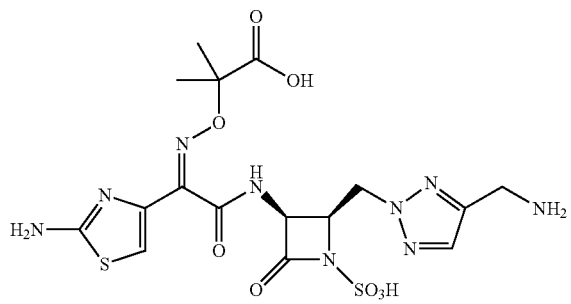 [SMILES: CC(C)(O/N=C(\C(=O)N[C@@H]1C(=O)N(S(=O)(=O)O)[C@@H]1Cn1ncc(CN)n1)c1csc(N)n1)C(=O)O]

(2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-(((tert-butoxycarbonyl)amino)methyl)-2H-1,2,3-triazol-2-yl)methyl)-4-oxoazetidine-1-sulfonic acid (82 mg, 0.104 mmol) was stirred with formic acid (2.0 mL) at rt for 5 h, which removed both Boc groups. After concentration in vacuo, the material was dissolved in DCM (1.5 mL), cooled to 0° C. and treated with TFA (0.5 mL, 6.5 mmol) for 1 h, whereupon it was concentrated in vacuo. The crude residue was purified by reverse phase prep HPLC (T3, 30×150 mm, 5 μm, C18 column; ACN-water with 0.1% formic acid modifier, 1 mL/min), affording the title compound (17.2 mg, 31%) as a white solid. LCMS: m/z=529.9 (M−1); $^1$H NMR (400 MHz, D$_2$O): δ 7.67 (s, 1H), 6.92 (s, 1H), 5.39 (d, J=5.6 Hz, 1H), 4.86-4.74 (m, 3H assumed; obscured by solvent residual peak), 4.16 (s, 2H), 1.25 (s, 3H), 1.23 (3H, s).

Example 53

2-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene)amino)oxy)-2-methylpropanoic acid

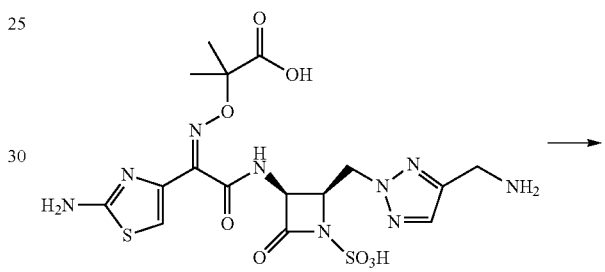

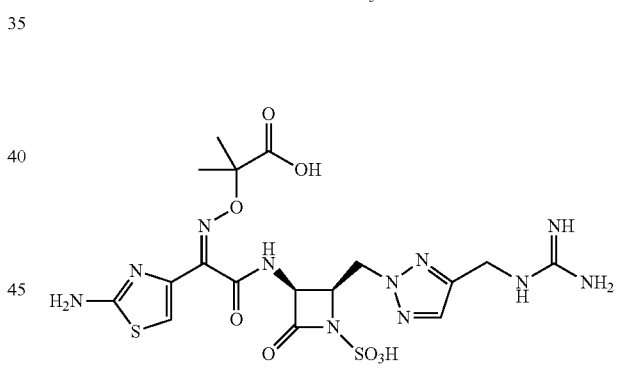

To a solution of 2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid (60 mg, 0.089 mmol) and pyrazole-1-carboxamide hydrochloride (16 mg, 0.11 mmol) in DMF (3 mL) was added DIPEA (45 μL, 0.27 mmol). After stirring for 16 h, the solution was concentrated and washed with ether. The crude residue was purified by reverse phase prep HPLC (XBridge, 30×150 mm, 5 μm, C18 column; ACN-water with 0.1% formic acid modifier, 1 mL/min), affording the title compound (7.5 mg, 15%) as a white solid. LCMS: m/z=571.9 (M−1); $^1$H NMR (400 MHz, D$_2$O): δ 7.55 (s, 1H), 6.78 (s, 1H), 5.38 (d, J=5.2 Hz, 1H), 4.82-4.76 (m, 1H assumed; obscured by solvent residual peak), 4.76-4.72 (m, 2H assumed; obscured by solvent residual peak), 4.32 (s, 2H), 1.15 (s, 3H), 1.14 (s, 3H).

Example 54

2-(((Z)-(2-(((2R,3S)-2-((2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid

Step 1: tert-Butyl 2-(((Z)-(2-(((2R,3S)-2-((2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate The general procedure for the Mitsunobu reaction was followed using Intermediate H (300 mg, 0.569 mmol), 1,2,3-triazole (47 mg, 0.682 mmol), triphenylphosphine (178 mg, 0.682 mmol), DIAD (145 mg, 0.682 mmol) and THF (10 mL). Purified via silica gel chromatography (MeOH-DCM, 2-5%), affording the title compound (320 mg, 97%) as a yellow foam. LCMS: m/z=579.2 (M+1).

Step 2: (2R,3S)-2-((2H-1,2,3-triazol-2-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid tert-Butyl 2-(((Z)-(2-(((2R,3S)-2-((2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)-2-methylpropanoate (320 mg, 0.553 mmol) in DMF (5 mL) was treated with $SO_3 \cdot DMF$ (846 mg, 5.53 mmol). The solution was stirred at rt for 24 h then concentrated in vacuo and purified with HP21 resin (ACN-water, 10-50%), affording the title compound (70 mg, 19%). LCMS: m/z=657.1 (M−1).

Step 3: 2-(((Z)-(2-(((2R,3S)-2-((2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid

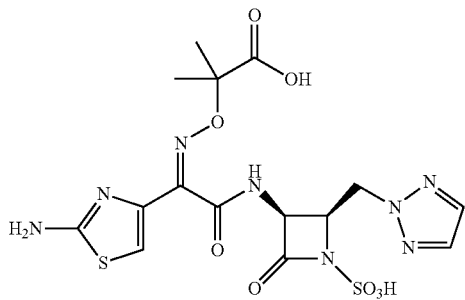 [SMILES: CC(C)(O/N=C(\C(=O)N[C@@H]1C(=O)N(S(=O)(=O)O)[C@@H]1Cn1nccn1)c1csc(N)n1)C(=O)O]

(2R,3S)-2-((2H-1,2,3-triazol-2-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid (70 mg, 0.11 mmol) was stirred with formic acid (2.0 mL) at rt for 4 h then concentrated in vacuo. The crude residue was purified by reverse phase prep HPLC (XBridge, 30×100 mm, 5 μm, C18 column; ACN-water with 0.1% formic acid modifier, 1 mL/min), affording the title compound (8.1 mg, 15%) as a white solid. LCMS: m/z=500.9 (M−1); $^1H$ NMR (400 MHz, $D_2O$): δ 7.60 (s, 2H), 6.94 (s, 1H), 5.39 (d, J=5.2 Hz, 1H),), 4.83-4.78 (m, 2H), 4.78-4.68 (m, 1H assumed; obscured by solvent residual peak), 1.26 (s, 3H), 1.25 (s, 3H).

Example 55

2-(((Z)-(1-(2-aminothiazol-4-yl)-2-(((2R,3S)-2-((4-methyl-2H-1,2,3-triazol-2-yl)methyl)-4-oxo-1-sulfoazetidin-3-yl)amino)-2-oxoethylidene)amino)oxy)-2-methylpropanoic acid

Step 1: tert-Butyl 2-(((Z)-(1-(2-((tert-butoxycarbonyl)amino)thiazol-4-yl)-2-(((2R,3S)-2-((4-methyl-2H-1,2,3-triazol-2-yl)methyl)-4-oxoazetidin-3-yl)amino)-2-oxoethylidene)amino)oxy)-2-methylpropanoate The general procedure for the Mitsunobu reaction was followed using Intermediate H (300 mg, 0.569 mmol), 4-methyl-1,2,3-triazole (83 mg, 0.683 mmol), triphenylphosphine (179 mg, 0.683 mmol), DIAD (138 mg, 0.648 mmol) and THF (8 mL). Purified via silica gel chromatography (MeOH-DCM, 2-4%), affording the title compound (160 mg, 47%) as a yellow foam. LCMS: m/z=591 (M−1).

Step 2: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-methyl-2H-1,2,3-triazol-2-yl)methyl)-4-oxoazetidine-1-sulfonic acid tert-Butyl 2-(((Z)-(1-(2-((tert-butoxycarbonyl)amino)thiazol-4-yl)-2-(((2R,3S)-2-((4-methyl-2H-1,2,3-triazol-2-yl)methyl)-4-oxoazetidin-3-yl)amino)-2-oxoethylidene)amino)oxy)-2-methylpropanoate (160 mg, 0.270 mmol) in DMF (5 mL) was treated with $SO_3 \cdot DMF$ (413 mg, 2.70 mmol). The solution was stirred at rt for 16 h then concentrated in vacuo and purified with HP21 resin (ACN-water, 10-50%), affording the title compound (77 mg, 43%). LCMS: m/z=671.1 (M−1).

Step 3: 2-(((Z)-(1-(2-aminothiazol-4-yl)-2-(((2R,3S)-2-((4-methyl-2H-1,2,3-triazol-2-yl)methyl)-4-oxo-1-sulfoazetidin-3-yl)amino)-2-oxoethylidene)amino)oxy)-2-methylpropanoic acid

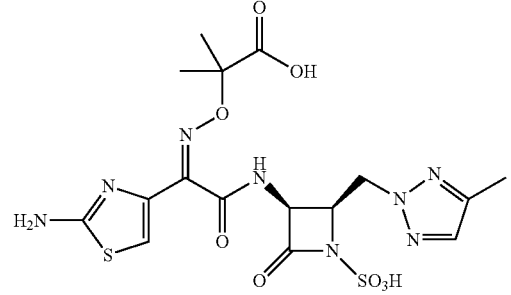 [SMILES: Cc1cnn(C[C@@H]2[C@H](NC(=O)/C(=N\OC(C)(C)C(=O)O)c3csc(N)n3)C(=O)N2S(=O)(=O)O)n1]

(2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((4-methyl-2H-1,2,3-triazol-2-yl)methyl)-4-oxoazetidine-1-sulfonic acid (67 mg, 0.10 mmol) was stirred with formic acid (1.5 mL) at rt for 3.5 h then concentrated in vacuo. The crude residue was purified by reverse phase prep HPLC (XBridge, 30×100 mm, 5 μm, C18 column; ACN-water with 0.1% formic acid modifier, 1 mL/min), affording the title compound (13.7 mg, 27%) as a white solid. LCMS: m/z=514.9 (M−1); $^1H$ NMR (400 MHz, D₂O): δ 7.39 (s, 1H), 6.94 (s, 1H), 5.38 (d, J=5.6 Hz, 1H), 4.80-4.60 (m, 3H assumed; obscured by solvent residual peak), 2.10 (s, 3H), 1.26 (s, 3H), 1.25 (s, 3H).

Example 56

2-(((Z)-(2-(((2R,3S)-2-((4H-1,2,4-triazol-4-yl)methyl)-4-oxo-1-sulfoazetidin-3-yl)amino)-1-(2-aminothiazol-4-yl)-2-oxoethylidene)amino)oxy)-2-methylpropanoic acid Step 1: tert-Butyl 2-(((Z)-(2-(((2R,3S)-2-((4H-1,2,4-triazol-4-yl)methyl)-4-oxoazetidin-3-yl)amino)-1-(2-((tert-butoxycarbonyl)amino)thiazol-4-yl)-2-oxoethylidene)amino)oxy)-2-methylpropanoate A solution of formic acid hydrazide (27.4 mg, 0.456 mmol) and triethyl orthoformate (67.6 mg, 0.456 mmol) in MeOH (5 mL) was heated to reflux for 4 h. After cooling to 40° C., Intermediate L (120 mg, 0.228 mmol) was added and the mixture was heated to reflux for an additional 20 h. Upon cooling to rt the solvent was evaporated in vacuo and the resulting residue was dissolved in EtOAc, washed with water, brine, dried over Na₂SO₄ and concentrated in vacuo. The crude residue was purified via silica gel chromatography (0-10% MeOH-EtOAc), affording the title compound (95 mg, 72%) as a foam. LCMS: m/z=529.1 (M+1).

Step 2: (2R,3S)-2-((4H-1,2,4-triazol-4-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid tert-Butyl 2-(((Z)-(2-(((2R,3S)-2-((4H-1,2,4-triazol-4-yl)methyl)-4-oxoazetidin-3-yl)amino)-1-(2-((tert-butoxycarbonyl)amino)thiazol-4-yl)-2-oxoethylidene)amino)oxy)-2-methylpropanoate (95 mg, 0.16 mmol) in DMF (2 mL) was treated with SO₃.DMF (251 mg, 1.64 mmol). The solution was stirred at rt for 24 h whereupon more SO₃.DMF (502 mg, 3.28 mmol) was added and the solution stirred for an additional 72 h. It was diluted with water and extracted with EtOAc (2×). The combined organic layers were washed with brine (2×), dried over Na₂SO₄ and concentrated in vacuo, affording the title compound (77 mg) as a solid. LCMS: m/z=657.1 (M−1).

Step 3: 2-(((Z)-(2-(((2R,3S)-2-((4H-1,2,4-triazol-4-yl)methyl)-4-oxo-1-sulfoazetidin-3-yl)amino)-1-(2-aminothiazol-4-yl)-2-oxoethylidene)amino)oxy)-2-methylpropanoic acid

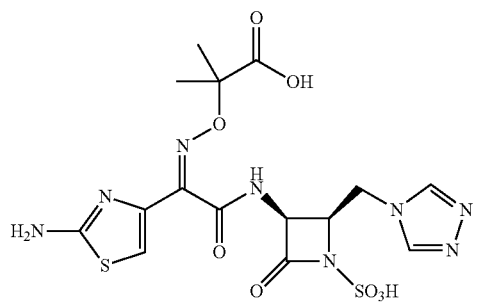

Followed the general procedure for the acid mediated deprotection using (2R,3S)-2-((4H-1,2,4-triazol-4-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonic acid (77 mg, 0.117 mmol), DCM (3 mL) and TFA (1 mL, 13.0 mmol) for 2 h. The crude residue purified by reverse phase prep HPLC (XBridge, 30×100 mm, 5 μm, C18 column; ACN-water with 0.1% formic acid modifier, 1 ml/min), affording the title compound (5.6 mg, 10%) as a white powder. LCMS: m/z=500.8 (M−1); ¹H NMR (400 MHz, D₂O): δ 8.52 (s, 2H), 6.90 (s, 1H), 5.30 (d, J=5.6 Hz, 1H), 4.56 (m, 2H), 4.42 (q, 1H), 1.30 (s, 6H).

Example 57

2-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-2-methylpropanoic acid Step 1: tert-Butyl 2-(((Z)-(2-(((2R,3S)-2-(MS)-3-((tert-butoxycarbonyl)amino)-2-hydroxypropyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate A solution of Intermediate L (250 mg, 0.475 mmol) and (R)-tert-butyl (oxiran-2-ylmethyl)carbamate (410 mg, 2.38 mmol) in DCM (3 ml) was stirred at rt for 16 h then concentrated in vacuo. The crude residue was purified by silica gel chromatography (MeOH-DCM, 4-10%), affording the title compound (250 mg, 75%) as a white solid. LCMS: m/z=698.1 (M−1).

Step 2: tert-Butyl 2-(((Z)-(2-(((2R,3S)-2-(((R)-5-(((tert-butoxycarbonyl)amino)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a solution of tert-butyl 2-(((Z)-(1-(2-((tert-butoxycarbonyl)amino)thiazol-4-yl)-2-(((2R,3S)-2-((((R)-2-hydroxypropyl)amino)methyl)-4-oxoazetidin-3-yl)amino)-2-oxoethylidene)amino)oxy)-2-methylpropanoate (250 mg, 0.357 mmol) in DCM (10 mL) at 0° C. was added CDI (104 mg, 0.643 mmol). After stirring at 15° C. for 2 h the solution was concentrated in vacuo. The crude residue was purified via silica gel chromatography (MeOH-DCM, 3-5%) to afford the title compound (155 mg, 60%). LCMS: m/z=724.0 (M−1).

Step 3: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((R)-5-(((tert-butoxycarbonyl)amino)methyl)-2-oxooxazolidin-3-yl)methyl)-4-oxoazetidine-1-sulfonic acid tert-Butyl 2-(((Z)-(2-(((2R,3S)-2-(((R)-5-(((tert-butoxycarbonyl)amino)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate (155 mg, 0.213 mmol) in DMF (1 mL) was treated with SO₃.DMF (130 mg, 0.854 mmol). The solution was stirred at rt for 2 h whereupon it was concentrated in vacuo and purified with HP21 resin (ACN-water, 10-50%), affording the title affording the title compound (160 mg, 93%) as a white solid. LCMS: m/z=804.0 (M−1).

Step 4: 2-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-2-methylpropanoic acid

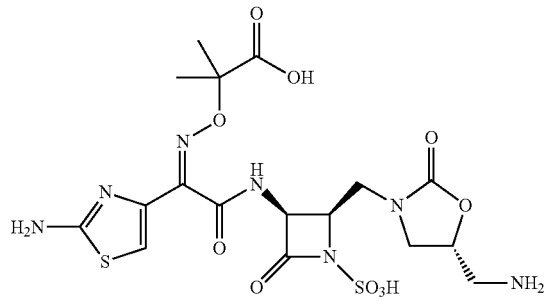 [SMILES: CC(C)(O/N=C(\C(=O)N[C@@H]1C(=O)N(S(=O)(=O)O)[C@@H]1CN1C[C@@H](CN)OC1=O)c1csc(N)n1)C(=O)O]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((R)-5-(((tert-butoxycarbonyl)amino)methyl)-2-oxooxazolidin-3-yl) methyl)-4-oxoazetidine-1-sulfonic acid (160 mg, 0.199 mmol), DCM (1.5 mL) and TFA (500 µL, 6.49 mmol). The crude residue purified by reverse phase prep HPLC (XSelect CSH, 30×100 mm, 5 µm, C18 column; ACN-water with 0.1% formic acid modifier, 60 mL/min), affording the title compound (85.8 mg, 78%) as a white powder. LCMS: m/z=548.0 (M+1); $^1$H NMR (400 MHz, D$_2$O) δ ppm 6.93 (s, 1H), 5.23 (d, J=5.6 Hz, 1H), 4.76-4.69 (m, 1H), 4.54-4.49 (m, 1H), 3.84 (t, J=9.6 Hz, 1H), 3.56 (dd, J=14.8, 9.6 Hz, 1H), 3.41-3.34 (m, 2H), 3.21-3.11 (m, 2H), 1.34 (s, 3H), 1.32 (s, 3H).

Example 58

2-(((Z)-(2-(((2R,3S)-2-MS)-5-(aminomethyl)-2-oxooxazolidin-3-yl)methyl)-4-oxo-1-sulfoazetidin-3-yl)amino)-1-(2-aminothiazol-4-yl)-2-oxoethylidene) amino)oxy)-2-methylpropanoic acid Step 1: tert-Butyl 2-(((Z)-(2-(((2R,3S)-2-((((R)-3-((tert-butoxycarbonyl)amino)-2-hydroxypropyl) amino)methyl)-4-oxoazetidin-3-yl)amino)-1-(2-((tert-butoxycarbonyl)amino)thiazol-4-yl)-2-oxoethylidene)amino)oxy)-2-methylpropanoate A solution of Intermediate L (400 mg, 0.760 mmol) and (S)-tert-butyl (oxiran-2-ylmethyl)carbamate (658 mg, 3.80 mmol) in DCM (4 ml) was stirred at rt for 16 h then concentrated in vacuo. The crude residue was purified by silica gel chromatography (MeOH-DCM, 4-10%), affording the title compound (390 mg, 73%) as a white solid. LCMS: m/z=700.1 (M+1).

Step 2: tert-Butyl 2-(((Z)-(2-(((2R,3S)-2-MS)-5-(((tert-butoxycarbonyl)amino)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a solution of tert-Butyl 2-(((Z)-(2-(((2R,3S)-2-((((R)-3-((tert-butoxycarbonyl)amino)-2-hydroxypropyl)amino) methyl)-4-oxoazetidin-3-yl)amino)-1-(2-((tert-butoxycarbonyl)amino)thiazol-4-yl)-2-oxoethylidene)amino)oxy)-2-methylpropanoate (390 mg, 0.557 mmol) in DCM (20 mL) at 0° C. was added CDI (162 mg, 1.00 mmol). After stirring at 15° C. for 2 h the solution was concentrated in vacuo. The crude residue was purified via silica gel chromatography (MeOH-DCM, 3-5%) to afford the title compound (168 mg, 41%). LCMS: m/z=726.1 (M+1).

Step 3: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-MS)-5-(((tert-butoxycarbonyl)amino)methyl)-2-oxooxazolidin-3-yl)methyl)-4-oxoazetidine-1-sulfonic acid tert-Butyl 2-(((Z)-(2-(((2R,3S)-2-(((S)-5-(((tert-butoxycarbonyl)amino)methyl)-2-oxooxazolidin-3-yl)methyl)-4-oxoazetidin-3-yl)amino)-1-(2-((tert-butoxycarbonyl)amino) thiazol-4-yl)-2-oxoethylidene)amino)oxy)-2-methylpropanoate (168 mg, 0.231 mmol) in DMF (1 mL) was treated with SO$_3$.DMF (142 mg, 0.926 mmol). The solution was stirred at rt for 2 h whereupon it was concentrated in vacuo and purified with HP21 resin (ACN-water, 10-50%), affording the title compound (155 mg, 83%) as a white solid. LCMS: m/z=804.0 (M−1).

Step 4: 2-(((Z)-(2-(((2R,3S)-2-MS)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-2-methylpropanoic acid

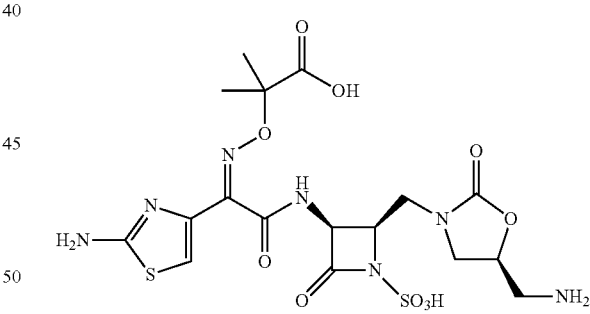

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(((S)-5-(((tert-butoxycarbonyl)amino)methyl)-2-oxooxazolidin-3-yl) methyl)-4-oxoazetidine-1-sulfonic acid (155 mg, 0.192 mmol), DCM (1.5 mL) and TFA (500 µL, 6.49 mmol). Half of the crude residue was purified by reverse phase prep HPLC (XSelect CSH, 30×100 mm, 5 µm, C18 column; ACN-water with 0.1% formic acid modifier, 60 mL/min), affording the title compound (21.8 mg, ca 82%) as a white powder. LCMS: m/z=547.8 (M−1); $^1$H NMR (400 MHz, D$_2$O) 6 ppm 6.96 (s, 1H), 5.27 (d, J=6.0 Hz, 1H), 4.80-4.78 (m, 1H), 4.52-4.47 (m, 1H), 3.75-3.66 (m, 2H), 3.49-3.45 (m, 1H), 3.32-3.16 (m, 3H), 1.37 (s, 3H), 1.35 (s, 3H).

Example 59

2-(((Z)-(1-(2-aminothiazol-4-yl)-2-(((2R,3S)-2-MS)-5-(guanidinomethyl)-2-oxooxazolidin-3-yl)methyl)-4-oxo-1-sulfoazetidin-3-yl)amino)-2-oxoethylidene)amino)oxy)-2-methylpropanoic acid

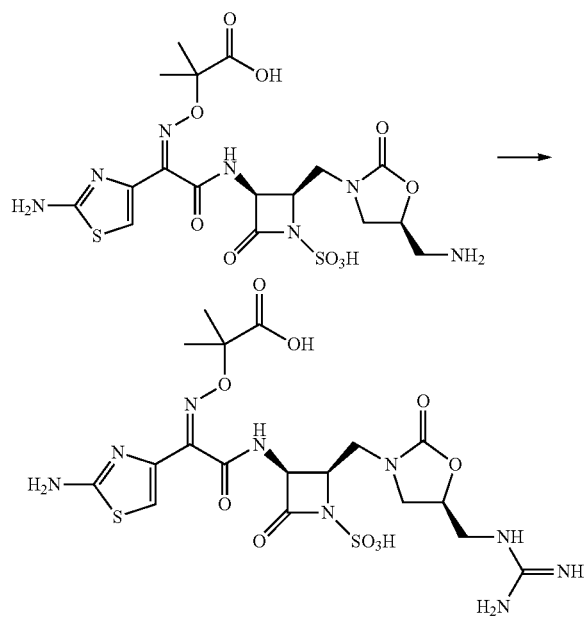

To a solution of 2-(((Z)-(2-(((2R,3S)-2-WS)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-2-methylpropanoic acid (0.096 mmol) and Pyrazole-1-carboxamidine hydrochloride (21 mg, 0.144 mmol) in DMF (3 mL) was added DIPEA (100 µL, 0.576 mmol). After 16 h of stirring at rt, the solution was concentrated in vacuo and washed with ether. The crude residue was purified by reverse phase prep HPLC (XSelect CSH, 30×100 mm, 5 µm, C18 column; ACN-water with 0.1% formic acid modifier, 60 mL/min), affording the title compound (29 mg, 51%) as a white solid. LCMS m/z=589.8 (M−1); $^1$H NMR (400 MHz, D$_2$O) δ ppm 6.93 (s, 1H), 5.26 (d, J=6.0 Hz, 1H), 4.65-4.55 (m, 1H), 4.52-4.45 (m, 1H), 3.69-3.61 (m, 2H), 3.44-3.30 (m, 4H), 1.34 (s, 3H), 1.32 (s, 3H).

Example 60

2-(((Z)-(1-(2-aminothiazol-4-yl)-2-(((2R,3S)-2-((3-methyl-1H-1,2,4-triazol-1-yl)methyl)-4-oxo-1-sulfoazetidin-3-yl)amino)-2-oxoethylidene)amino)oxy)-2-methylpropanoic acid Step 1, Compound A: Benzyl ((2R,3S)-1-(2,4-dimethoxybenzyl)-2-((3-methyl-1H-1,2,4-triazol-1-yl)methyl)-4-oxoazetidin-3-yl)carbamate Step 1, Compound B: Benzyl ((2R,3S)-1-(2,4-dimethoxybenzyl)-2-((5-methyl-1H-1,2,4-triazol-1-yl)methyl)-4-oxoazetidin-3-yl)carbamate ((2S,3S)-3-(((benzyloxy)carbonyl)amino)-1-(2,4-dimethoxybenzyl)-4-oxoazetidin-2-yl)methyl methanesulfonate (3.74 g, 8.0 mmol), 3-methyl-1H-1,2,4-triazole (2.00 g, 24.0 mmol), K$_2$CO$_3$ (6.64 g, 48.0 mmol) and NaI (2.88 g, 17.2 mmol) were slurried in DMF (16 mL) and heated to 70° C. with stirring. After 24 h the mixture was concentrated in vacuo. The crude residue was purified via silica gel chromatography (MeOH-DCM, 2%) to afford title compounds (1.64 g, 44% combined) as an off-white solid (inseparable mixture). LCMS: m/z=466.2 (M+1).

Step 2, Compound A: Benzyl ((2R,3S)-2-((3-methyl-1H-1,2,4-triazol-1-yl)methyl)-4-oxoazetidin-3-yl)carbamate Step 2, Compound B: Benzyl ((2R,3S)-2-((5-methyl-1H-1,2,4-triazol-1-yl)methyl)-4-oxoazetidin-3-yl)carbamate Prepared according to Mastalerz et al. *J. Med. Chem.* 1988, 31, 1190. To a solution of compounds NB, step 1 (1.60 g, 3.44 mmol) in ACN:water (2:1, 45 mL) was added K$_2$S$_2$O$_8$ (1.86 g, 6.88 mmol) followed by K$_2$HPO$_4$ (1.50 g, 8.60 mmol). The resulting mixture was heated to 90° C. for 4 h, whereupon it was cooled to rt then diluted with EtOAc and the layers separated. The aqueous layer was extracted with EtOAc (3×) and the combined organic layers were dried over Na$_2$SO$_4$ and concentrated in vacuo. The crude residue was purified via silica gel chromatography (MeOH-DCM, 10%), to afford the title compounds (mixture, 670 mg, 62%) as a white solid. The mixture was further purified via chiral HPLC (Chiralcel-OJ, 2×25 cm, EtOH-Hexanes, 18%), affording compound A (250 mg) and compound B (240 mg).

Step 3: (3S,4R)-3-amino-4-((3-methyl-1H-1,2,4-triazol-1-yl)methyl)azetidin-2-one A slurry of benzyl ((2R,3S)-2-((3-methyl-1H-1,2,4-triazol-1-yl)methyl)-4-oxoazetidin-3-yl)carbamate (250 mg, 0.79 mmol) and Pd on C (10%, 100 mg) in MeOH (20 mL) was evacuated and backfilled with H$_2$ (3×), bringing the final pressure to 35 psi. After 2 h of stirring the mixture was filtered over celite, washing with MeOH and the filtrate was concentrated in vacuo. The crude residue was used as such in the following step.

Step 4: tert-Butyl 2-(((Z)-(1-(2-((tert-butoxycarbonyl)amino)thiazol-4-yl)-2-(((2R,3S)-2-((3-methyl-1H-1,2,4-triazol-1-yl)methyl)-4-oxoazetidin-3-yl)amino)-2-oxoethylidene)amino)oxy)-2-methylpropanoate To a solution of (Z)-2-(((1-(tert-butoxy)-2-methyl-1-oxopropan-2-yl)oxy)imino)-2-(2-((tert-butoxycarbonyl)amino)thiazol-4-yl)acetic acid (310 mg, 0.72 mmol), (3S,4R)-3-amino-4-((3-methyl-1H-1,2,4-triazol-1-yl)methyl)azetidin-2-one (130 mg, 0.72 mmol) and EDCI (150 mg, 0.79 mmol) in DMF (5 mL) at 0° C. was added pyridine (64 µL, 0.79 mmol). After stirring at rt for 24 h, more (Z)-2-(((1-(tert-butoxy)-2-methyl-1-oxopropan-2-yl)oxy)imino)-2-(2-((tert-butoxycarbonyl)amino)thiazol-4-yl)acetic acid (310 mg, 0.72 mmol) and EDCI (150 mg, 0.79 mmol) were added, along with HOBt (110 mg, 0.79 mmol) and DIPEA (250 µL, 1.44 mmol). After an additional 16 h of stirring it was concentrated in vacuo. The crude residue was purified via silica gel chromatography (MeOH-DCM, 5%), affording the title compound (230 mg, 54%) as a white solid. LCMS: m/z=593.0 (M+1).

Step 5: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-methyl-1H-1,2,4-triazol-1-yl)methyl)-4-oxoazetidine-1-sulfonic acid tert-Butyl 2-(((Z)-(1-(2-((tert-butoxycarbonyl)amino)thiazol-4-yl)-2-(((2R,3S)-2-((3-methyl-1H-1,2,4-triazol-1-yl)methyl)-4-oxoazetidin-3-yl)amino)-2-oxoethylidene)amino)oxy)-2-methylpropanoate (230 mg, 0.388 mmol) in DMF (4 mL) was treated with SO₃.DMF (594 mg, 3.88 mmol). After 24 h of stirring the solution was concentrated in vacuo. The crude residue was purified with HP21 resin (ACN-water, 5-50%), affording the title compound (100 mg, 38%) as a pale yellow solid. LCMS: m/z=673.1 (M+1).

Step 6: 2-(((Z)-(1-(2-aminothiazol-4-yl)-2-(((2R,3S)-2-((3-methyl-1H-1,2,4-triazol-1-yl)methyl)-4-oxo-1-sulfoazetidin-3-yl)amino)-2-oxoethylidene)amino)oxy)-2-methylpropanoic acid

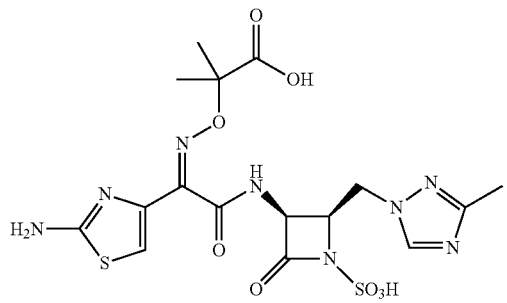 [SMILES: Cc1ncn(C[C@@H]2[C@H](NC(=O)/C(=N\OC(C)(C)C(=O)O)c3csc(N)n3)C(=O)N2S(=O)(=O)O)n1]

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-methyl-1H-1,2,4-triazol-1-yl)methyl)-4-oxoazetidine-1-sulfonic acid (100 mg, 0.149 mmol), DCM (4.0 mL) and TFA (1.0 mL, 13.0 mmol) for 3 h. The crude residue purified by reverse phase prep HPLC (XSelect CSH, 30×100 mm, 5 μm, C18 column; ACN-water with 0.1% formic acid modifier, 60 mL/min), affording the title compound (50 mg, 65%) as a white powder. LCMS: m/z=514.7 (M−1); $^1$H NMR (400 MHz, DMSO-d$_6$) δ 9.40 (d, J=8.4 Hz, 1H), 8.72 (br s, 1H), 6.78 (s, 1H), 5.25 (dd, J=8.8, 5.6 Hz, 1H), 4.61 (dd, J=14.4, 5.2 Hz, 1H), 4.47 (dd, J=14.4, 6.0 Hz, 1H), 4.33 (dd, J=6.0, 5.2 Hz, 1H), 2.30 (s, 3H), 1.42 (s, 3H), 1.38 (s, 3H).

Example 61

2-(((Z)-(1-(2-aminothiazol-4-yl)-2-(((2R,3S)-2-((5-methyl-1H-1,2,4-triazol-1-yl)methyl)-4-oxo-1-sulfoazetidin-3-yl)amino)-2-oxoethylidene)amino)oxy)-2-methylpropanoic acid Step 1: (3S,4R)-3-amino-4-((5-methyl-1H-1,2,4-triazol-1-yl)methyl)azetidin-2-one A slurry of benzyl ((2R,3S)-2-((5-methyl-1H-1,2,4-triazol-1-yl)methyl)-4-oxoazetidin-3-yl)carbamate (240 mg, 0.76 mmol) and Pd on C (10%, 100 mg) in MeOH (20 mL) was evacuated and backfilled with H₂ (3×), bringing the final pressure to 35 psi. After 2 h of stirring the mixture was filtered over celite, washing with MeOH and the filtrate was concentrated in vacuo. The crude residue was used as such in the following step.

Step 2: tert-Butyl 2-(((Z)-(1-(2-((tert-butoxycarbonyl)amino)thiazol-4-yl)-2-(((2R,3S)-2-((5-methyl-1H-1,2,4-triazol-1-yl)methyl)-4-oxoazetidin-3-yl)amino)-2-oxoethylidene)amino)oxy)-2-methylpropanoate To a solution of (Z)-2-(((1-(tert-butoxy)-2-methyl-1-oxopropan-2-yl)oxy)imino)-2-(2-((tert-butoxycarbonyl)amino)thiazol-4-yl)acetic acid (310 mg, 0.72 mmol), (3S,4R)-3-amino-4-((5-methyl-1H-1,2,4-triazol-1-yl)methyl)azetidin-2-one (130 mg, 0.72 mmol) and EDCI (150 mg, 0.79 mmol) in DMF (5 mL) at 0° C. was added pyridine (64 μL, 0.79 mmol). After stirring at rt for 24 h it was concentrated in vacuo. The crude residue was purified via silica gel chromatography (MeOH-DCM, 10%), affording the title compound (190 mg, 45%) as a white solid. LCMS: m/z=593.0 (M+1).

Step 3: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-1H-1,2,4-triazol-1-yl)methyl)-4-oxoazetidine-1-sulfonic acid tert-Butyl 2-(((Z)-(1-(2-((tert-butoxycarbonyl)amino)thiazol-4-yl)-2-(((2R,3S)-2-((5-methyl-1H-1,2,4-triazol-1-yl)methyl)-4-oxoazetidin-3-yl)amino)-2-oxoethylidene)amino)oxy)-2-methylpropanoate (180 mg, 0.304 mmol) in DMF (4 mL) was treated with SO₃.DMF (466 mg, 3.04 mmol). After 24 h of stirring the solution was concentrated in vacuo. The crude residue was purified with HP21 resin (ACN-water, 0-50%), affording the title compound (80 mg, 39%) as a white solid. LCMS: m/z=671.0 (M+1).

Step 4: 2-(((Z)-(1-(2-aminothiazol-4-yl)-2-(((2R,3S)-2-((5-methyl-1H-1,2,4-triazol-1-yl)methyl)-4-oxo-1-sulfoazetidin-3-yl)amino)-2-oxoethylidene)amino)oxy)-2-methylpropanoic acid

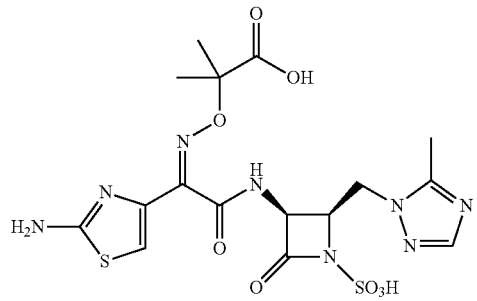

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-methyl-1H-1,2,4-triazol-1-yl)methyl)-4-oxoazetidine-1-sulfonic acid (80 mg, 0.119 mmol), DCM (4.0 mL) and TFA (1.0 mL, 13.0 mmol) for 3 h. The crude residue purified by reverse phase prep HPLC (XSelect CSH, 30×100 mm, 5 μm, C18 column; ACN-water with 0.1% formic acid modifier, 60 mL/min), affording the title compound (15 mg, 24%) as a white powder.

LCMS: m/z=514.8 (M−1); $^1$H NMR (400 MHz, D$_2$O) δ 7.86 (s, 1H), 6.89 (s, 1H), 5.36-5.28 (m, 1H), 4.78-4.66 (m, 1H assumed; obscured by solvent residual peak), 4.54-4.44 (m, 1H), 4.42-4.30 (m, 1H), 2.35 (s, 3H), 1.25 (s, 6H).

Example 62

2-(((Z)-(1-(2-aminothiazol-4-yl)-2-(((2R,3S)-2-((4-(formimidamidomethyl)-2H-1,2,3-triazol-2-yl)methyl)-4-oxo-1-sulfoazetidin-3-yl)amino)-2-oxoethylidene)amino)oxy)-2-methylpropanoic acid

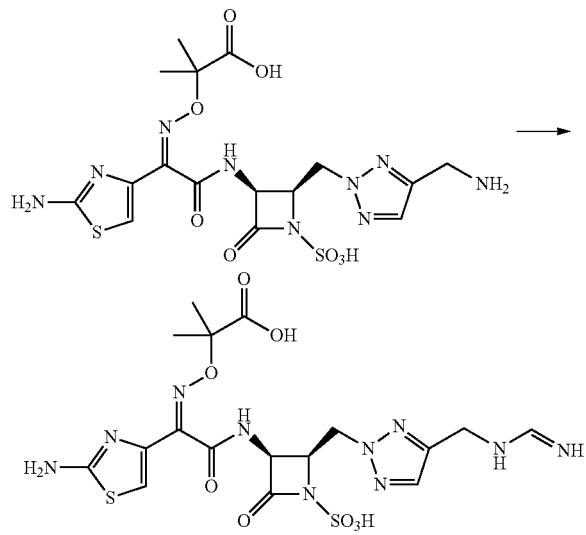

To a solution of 2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid (100 mg, 0.159 mmol) and ethylformamidate hydrochloride (17.4 mg, 0.159 mmol) in DMF (1 mL) was added DIPEA (41 mg, 0.32 mmol). After 2 h of stirring, more ethylformamidate hydrochloride (9.0 mg, 0.082 mmol) and DIPEA (20 mg, 0.16 mmol) was added. After an additional 4 h the solution was concentrated and washed with ether. The crude residue was purified by reverse phase prep HPLC (XSelect CSH, 30×100 mm, 5 μm, C18 column; ACN-water with 0.1% formic acid modifier, 60 mL/min), affording the title compound (15.5 mg, 18%) as mixture of amidine tautomers. LCMS: m/z=556.8 (M−1); $^1$H NMR (400 MHz, D$_2$O): δ 7.73 (s, 0.4H), 7.65 (s, 0.6H), 7.57 (m, 1H), 6.83 (s, 1H), 5.37 (d, J=5.6 Hz, 1H), 4.80-4.61 (m, 3H assumed; obscured by solvent residual peak) 4.48 (s, 0.4H), 4.45 (s, 0.6H), 1.17 (s, 3H), 1.15 (s, 3H).

Example 63

2-(((Z)-(1-(2-aminothiazol-4-yl)-2-(((2R,3S)-2-MS)-5-(hydroxymethyl)-2-oxooxazolidin-3-yl)methyl)-4-oxo-1-sulfoazetidin-3-yl)amino)-2-oxoethylidene)amino)oxy)-2-methylpropanoic acid Step 1: Tert-butyl 2-(((Z)-(1-(2-((tert-butoxycarbonyl)amino)thiazol-4-yl)-2-(((2R,3S)-2-((S)-9-hydroxy-2,2-dimethyl-5,7-dioxa-11-aza-2-siladodecan-12-yl)-4-oxoazetidin-3-yl)amino)-2-oxoethylidene)amino)oxy)-2-methylpropanoate To a solution of tert-butyl 2-(((Z)-(2-(((2R,3S)-2-(aminomethyl)-4-oxoazetidin-3-yl)amino)-1-(2-((tert-butoxycarbonyl)amino)thiazol-4-yl)-2-oxoethylidene)amino)oxy)-2-methylpropanoate (500 mg, 0.95 mmol) in DCM (5 mL) was added (S)-trimethyl(2-((oxiran-2-ylmethoxy)methoxy)ethyl)silane (485 mg, 2.38 mmol). After stirring at rt for 12 h, another 2.5 equiv of (S)-trimethyl(2-((oxiran-2-ylmethoxy)methoxy)ethyl)silane was added. After stirring at rt for additional 12 h, the reaction mixture was concentrated in vacuo. The crude residue was purified via silica gel chromatography (MeOH-DCM, 2-10%) to afford the title compound (155 mg, 22%). LCMS: m/z=731.4 (M+1).

Step 2: Tert-butyl 2-(((Z)-(1-(2-((tert-butoxycarbonyl)amino)thiazol-4-yl)-2-oxo-2-(((3S,4R)-2-oxo-4-(((S)-2-oxo-5-(((2-(trimethylsilyl)ethoxy)methoxy)methyl)oxazolidin-3-yl)methyl)azetidin-3-yl)amino)ethylidene)amino)oxy)-2-methylpropanoate To a solution of tert-butyl 2-(((Z)-(1-(2-((tert-butoxycarbonyl)amino)thiazol-4-yl)-2-(((2R,3S)-2-((S)-9-hydroxy-2,2-dimethyl-5,7-dioxa-11-aza-2-siladodecan-12-yl)-4-oxoazetidin-3-yl)amino)-2-oxoethylidene)amino)oxy)-2-methylpropanoate (155 mg, 0.21 mmol) in DCM (10 mL) at 0° C. was added CDI (62 mg, 0.38 mmol). After stirring at <15° C. for 2 h, the reaction mixture was concentrated in vacuo. The crude residue was purified via silica gel chromatography (MeOH-DCM, 3-5%) to afford the title compound (130 mg, 81%). LCMS: m/z=755.3 (M−1).

Step 3: (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-(((S)-2-oxo-5-(((2-(trimethylsilyl)ethoxy)methoxy)methyl)oxazolidin-3-yl)methyl)azetidine-1-sulfonic acid To a solution of tert-butyl 2-(((Z)-(1-(2-((tert-butoxycarbonyl)amino)thiazol-4-yl)-2-oxo-2-(((3S,4R)-2-oxo-4-(((S)-2-oxo-5-(((2-(trimethylsilyl)ethoxy)methoxy)methyl)oxazolidin-3-yl)methyl)azetidin-3-yl)amino)ethylidene)amino)oxy)-2-methylpropanoate (130 mg, 0.17 mmol) in DMF (1 mL) was added SO$_3$.DMF (105 mg, 0.69 mmol). After stirring at rt for 2 h, the reaction mixture was concentrated in vacuo. The crude mixture was purified via HP21 resin (ACN-water, 10-50%) to afford the title compound (140 mg, 97%). LCMS: m/z=705.42 (M-SEM).

Step 4: 2-(((Z)-(1-(2-aminothiazol-4-yl)-2-(((2R,3S)-2-(((S)-5-(hydroxymethyl)-2-oxooxazolidin-3-yl)methyl)-4-oxo-1-sulfoazetidin-3-yl)amino)-2-oxoethylidene)amino)oxy)-2-methylpropanoic acid

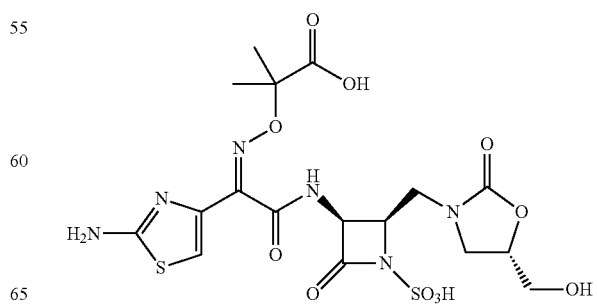

Followed the general procedure for the acid mediated deprotection using (3S,4R)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-oxo-4-WS)-2-oxo-5-(((2-(trimethylsilyl)ethoxy)methoxy)methyl)oxazolidin-3-yl)methyl)azetidine-1-sulfonic acid (140 mg, 0.17 mmol), DCM (2 mL) and TFA (1 mL) for 3 h. The crude residue was purified by reverse phase prep HPLC (XSelect CSH, 30×100 mm, 5 μm, C18 column; ACN-water with 0.1% formic acid modifier, 60 mL/min), affording the title compound (28 mg, 30%) LCMS: m/z=549.0 (M−1); $^1$H NMR (400 MHz, D$_2$O): δ 7.00 (s, 1H), 5.23 (d, J=5.2 Hz, 1H), 4.80-4.70 (m, 1H), 4.45-4.40 (m, 1H), 4.10-3.95 (m, 2H), 3.77 (t, J=9.2 Hz, 1H), 3.49 (t, J=7.6 Hz, 2H), 3.39 (m, 1H), 1.39 (s, 3H), 1.38 (s, 3H).

Example 64

(S)-2-(((Z)-(1-(2-aminothiazol-4-yl)-2-oxo-2-(((3S,4R)-2-oxo-4-((2-oxooxazolidin-3-yl)methyl)azetidin-3-yl)amino)ethylidene)amino)oxy)-3-(4-(N-(piperidin-4-yl)carbamimidoyl)phenoxy)propanoic acid Step 1: tert-Butyl (4-(2-oxo-2-(((3S,4R)-2-oxo-4-((2-oxooxazolidin-3-yl)methyl)azetidin-3-yl)amino)acetyl)thiazol-2-yl)carbamate Prepared in an analogous manner to intermediate E, using intermediate D (0.776 g, 4.19 mmol), 2-(2-((tert-butoxycarbonyl)amino)thiazol-4-yl)-2-oxoacetic acid (1.141 g, 4.19 mmol), HATU (3.071 g, 8.08 mmol) in DMF (20 mL) followed by DIPEA (3.66 mL, 20.95 mmol). LCMS: R$_t$=0.60 min, m/z=440.1 (M+1) Method 2m_acidic.

Step 2: (3S,4R)-3-(2-(2-((tert-butoxycarbonyl)amino)thiazol-4-yl)-2-oxoacetamido)-2-oxo-4-((2-oxooxazolidin-3-yl)methyl)azetidine-1-sulfonic acid Prepared in an analogous manner to intermediate F, using tert-butyl (4-(2-oxo-2-(((3S,4R)-2-oxo-4-((2-oxooxazolidin-3-yl)methyl)azetidin-3-yl)amino)acetyl)thiazol-2-yl)carbamate (500 mg, 1.138 mmol), SO$_3$.DMF (523 mg, 3.41 mmol) in DMF (5.7 mL). LC/MS: Rt=0.54 min; m/z=520.0 (M+1) Method 2m_acidic.

Step 3: (3S,4R)-3-((Z)-2-((((S)-1-(benzhydryloxy)-3-(4-(N-(1-(tert-butoxycarbonyl)piperidin-4-yl)carbamimidoyl)phenoxy)-1-oxopropan-2-yl)oxy)imino)-2-(2-((tert-butoxycarbonyl)amino)thiazol-4-yl)acetamido)-2-oxo-4-((2-oxooxazolidin-3-yl)methyl)azetidine-1-sulfonic acid To a soln of (3S,4R)-3-(2-(2-((tert-butoxycarbonyl)amino)thiazol-4-yl)-2-oxoacetamido)-2-oxo-4-((2-oxooxazolidin-3-yl)methyl)azetidine-1-sulfonic acid (170 mg, 0.328 mmol) in CHCl$_3$ (2 mL, ratio: 1) and EtOH (6 mL, ratio: 3) was added (S)-tert-butyl 4-(4-(2-(aminooxy)-3-(benzhydryloxy)-3-oxopropoxy)benzimidamido)piperidine-1-carboxylate (prepared according to WO2013110643, 193 mg, 0.328 mmol). After stirring for 2 h, AcOH (19 μL, 0.328 mmol) was added. After 12 h, more solution of (3S,4R)-3-(2-(2-((tert-butoxycarbonyl)amino)thiazol-4-yl)-2-oxoacetamido)-2-oxo-4-((2-oxooxazolidin-3-yl)methyl)azetidine-1-sulfonic acid (170 mg, 0.328 mmol) in 3:1 CHCl$_3$:EtOH was added. After stirring for 45 h, it was concentrated in vacuo, and the crude residue was purified with HP21 resin (10-100% ACN-water),
affording the title compound (117 mg, 33%) as an off white solid. LCMS: Rt=0.96 min, m/z=1091.1 (M+1) Method 2m_acidic.

Step 4: (S)-2-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)-3-(4-(N-(piperidin-4-yl)carbamimidoyl)phenoxy)propanoic acid

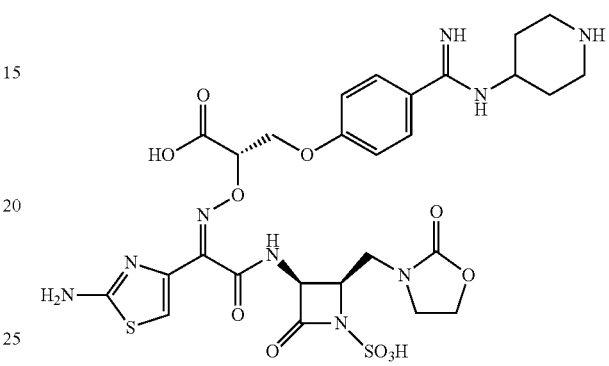

Followed the general procedure for the acid mediated deprotection using (3S,4R)-3-((Z)-2-((((S)-1-(benzhydryloxy)-3-(4-(N-(1-(tert-butoxycarbonyl)piperidin-4-yl)carbamimidoyl)phenoxy)-1-oxopropan-2-yl)oxy)imino)-2-(2-((tert-butoxycarbonyl)amino)thiazol-4-yl)acetamido)-2-oxo-4-((2-oxooxazolidin-3-yl)methyl)azetidine-1-sulfonic acid (117 mg, 0.107 mmol), DCM (5.3 mL) and TFA (0.413 mL, 5.37 mmol). The crude residue was purified by reverse phase prep HPLC (Xselect CSH, 30×100 mm, 5 μM, C18 column; ACN-water with 0.1% formic acid modifier, 60 mL/min), affording the title compound (23 mg, 28%) as a white powder. LC/MS: R$_t$=0.42 min, m/z=724.5 (M+1) Method 2m_acidic_polar; $^1$H NMR (500 MHz, DMSO-d$_6$) δ 9.53 (d, J=7.57 Hz, 1H), 9.43-9.36 (m, 2H), 9.01 (br s, 1H), 8.53-8.36 (m, 2H), 7.72 (d, J=8.5 Hz, 3H), 7.26 (br s, 2H), 7.15 (d, J=8.8 Hz, 2H), 6.82 (s, 1H), 5.19 (dd, J=8.7, 5.8 Hz, 1H), 5.02 (t, J=3.8 Hz, 1H), 4.51-4.42 (m, 2H), 4.12-3.96 (m, 3H), 3.90-3.81 (m, 1H), 3.73 (d, J=7.3 Hz, 1H), 3.69-3.62 (m, 1H), 3.58-3.53 (m, 1H), 3.20-3.16 (m, 1H), 2.98-2.85 (m, 1H) 2.13-2.04 (m, 1H), 1.85-1.72 (m, 1H).

Example 65

2-(((Z)-(1-(2-aminothiazol-4-yl)-2-oxo-2-(((3S,4R)-2-oxo-4-((4-((sulfamoylamino)methyl)-2H-1,2,3-triazol-2-yl)methyl)-1-sulfoazetidin-3-yl)amino)ethylidene)amino)oxy)-2-methylpropanoic acid

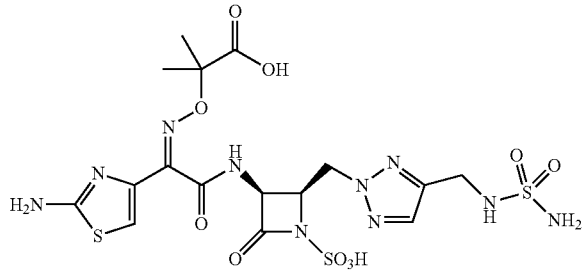 [SMILES: CC(C)(O/N=C(\C(=O)N[C@@H]1C(=O)N(S(=O)(=O)O)[C@@H]1Cn1ncc(CNS(N)(=O)=O)n1)c1csc(N)n1)C(=O)O]

Prepared in an analogous manner to example 53, using 2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-2-methylpropanoic acid TFA salt, crude compound (200 mg, 0.318 mmol), tert-butyl chlorosulfonylcarbamate (68 mg, 0.318 mmol), DIPEA (113 mL, 0.636 mmol) and DMF (1 mL). LCMS: m/z=609.1 (M−1). $^1$H NMR (400 MHz, D$_2$O): δ 7.65 (s, 1H), 6.98 (s, 1H), 5.40 (d, J=6.0 Hz, 1H), 4.85-4.83 (m, 1H), 4.76-4.74 (m, 2H), 4.13 (s, 2H), 1.26 (s, 3H), 1.25 (s, 3H).

Preparation of tert-butyl chlorosulfonylcarbamate: To a solution of tert-butanol (3.2 g, 36.9 mmol) in benzene (13 mL) was added sulfurisocyanatidoyl chloride (3.5 mL, 36.6 mmol). After stirring at rt for 2 h, the reaction mixture was quenched with hexane. The mixture was cooled in an ice-bath, resulted in white solid precipitation. The solid was filtered, washed with hexane, dried and used in the next step immediately (3.2 g, 41%).

Example 66

(S)-3-(4-(N-(2-aminoethyl)carbamimidoyl)phenoxy)-2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)propanoic acid

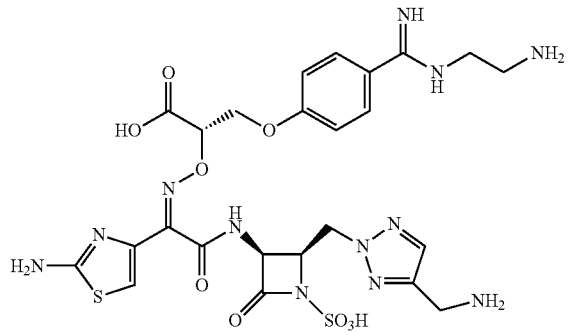 [SMILES: N=C(NCCN)c1ccc(OC[C@H](O/N=C(\C(=O)N[C@@H]2C(=O)N(S(=O)(=O)O)[C@@H]2Cn2ncc(CN)n2)c2csc(N)n2)C(=O)O)cc1]

Prepared in analogous manner to example 31, using tert-butyl ((2-(((2R,3S)-3-amino-4-oxoazetidin-2-yl)methyl)-2H-1,2,3-triazol-4-yl)methyl)carbamate and (S,Z)-2-(((1-(benzhydryloxy)-3-(4-(N-(2-((tert-butoxycarbonyl)amino)ethyl)carbamimidoyl)phenoxy)-1-oxopropan-2-yl)oxy)imino)-2-(2-((tert-butoxycarbonyl)amino)thiazol-4-yl)acetic acid (prepared according to WO2013110643). The crude residue was purified by reverse phase prep HPLC (Xselect CSH, 30×100 mm, 5 μM, C18 column; ACN-water with 0.1% formic acid modifier, 60 mL/min). LCMS: R$_t$=0.25 min, m/z=695.2 (M+1) Method 2m_acidic; $^1$H NMR (400 MHz, DMSO-d$_6$) δ 9.48 (s, 3H), 8.99 (s, 1H), 8.21 (s, 4H), 7.89 (s, 4H), 7.82-7.77 (m, 2H), 7.71 (s, 1H), 7.22 (dd, J=10.5, 8.2 Hz, 4H), 6.72 (s, 1H), 5.33 (dd, J=9.3, 5.5 Hz, 1H), 4.99 (dd, J=5.7, 3.3 Hz, 1H), 4.90 (ddd, J=12.8, 8.0, 3.9 Hz, 1H), 4.78-4.68 (m, 2H), 4.51-4.36 (m, 3H), 4.08 (s, 3H), 3.13 (s, 2H).

Example 67

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(2-aminoethyl)carbamimidoyl)phenoxy)propanoic acid

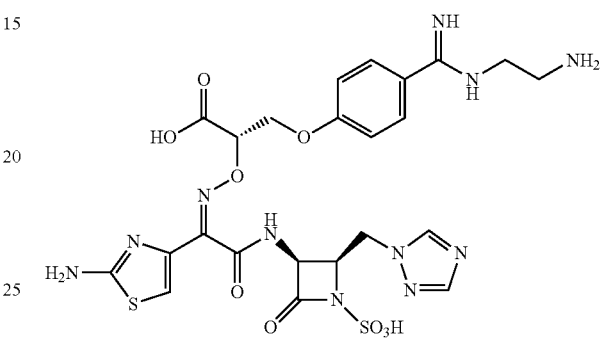

Prepared in analogous manner to example 66, using (3S,4R)-4-((1H-1,2,4-triazol-1-yl)methyl)-3-aminoazetidin-2-one. The crude residue was purified by reverse phase prep HPLC (Xselect CSH, 30×100 mm, 5 μM, C18 column; ACN-water with 0.1% formic acid modifier, 60 mL/min). LCMS: R$_t$=0.25 min, m/z=666.1 (M+1) Method 2m_acidic.

Example 68

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(azetidin-3-yl)carbamimidoyl)phenoxy)propanoic acid

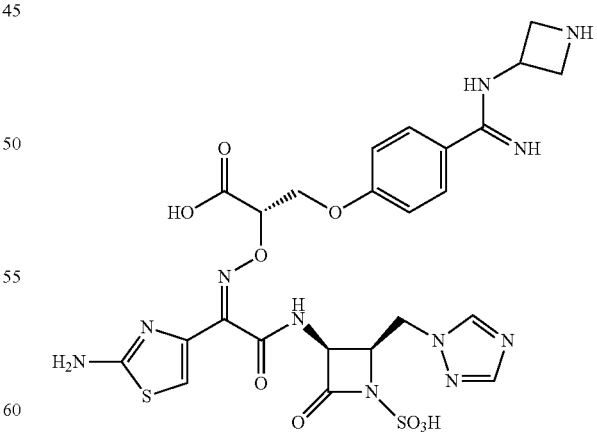

Prepared in analogous manner to example 64, using intermediate F and (S)-tert-butyl 3-(4-(2-(aminooxy)-3-(benzhydryloxy)-3-oxopropoxy)benzimidamido)azetidine-1-carboxylate (prepared according to WO2013110643). The crude residue was purified by reverse phase prep HPLC (Xselect CSH, 30×100 mm, 5 μM, C18 column; ACN-water with 0.1% formic acid modifier, 60 mL/min). LCMS: $R_t$=0.35 min, m/z=678.2 (M+1) Method 2m_acidic_polar; $^1$H NMR (500 MHz, DMSO-$d_6$): δ 13.68-13.03 (m, 1H), 10.02 (d, J=5.9 Hz, 1H), 9.57-9.51 (m, 2H), 9.05 (br s, 1H), 8.91-8.76 (m, 2H), 8.39 (s, 1H), 7.91 (s, 1H), 7.69 (d, J=8.5 Hz, 2H), 7.30 (br s, 2H), 6.92 (d, J=8.8 Hz, 2H), 6.80 (s, 1H), 5.12-5.04 (m, 2H), 4.74-4.66 (m, 1H), 4.54 (d, J=8.8 Hz, 1H), 4.49-4.35 (m, 3H), 4.31-4.16 (m, 5H).

Example 69

1-(((Z)-(2-(((2R,3S)-2-((4-(((3-aminopropyl)amino) methyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid compound with formic acid (1:1)

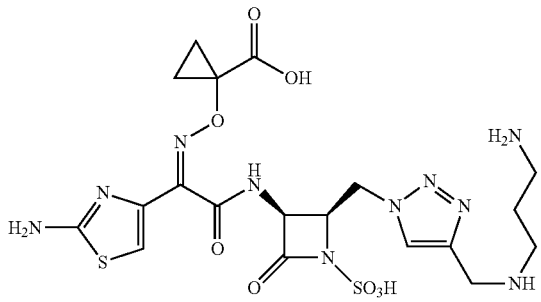 [SMILES: NCCCNCc1cn(C[C@@H]2[C@H](NC(=O)/C(=N\OC3(C(=O)O)CC3)c3csc(N)n3)C(=O)N2S(=O)(=O)O)nn1]

Prepared in analogous manner to example 28, using 1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid (20 mg, 0.038 mmol), tert-butyl (3-bromopropyl)carbamate (60 mg, 0.252 mmol), DIPEA (0.1 mL, 0.572 mmol), and DMF (0.5 mL). The crude residue was purified by reverse phase prep HPLC (Xselect CSH, 19×100 mm, 5 μM, C18 column; ACN-water with 0.1% formic acid modifier, 24 mL/min). LCMS: $R_t$=0.29 min, m/z=587.1 (M+1) Method 2m_acidic. $^1$H NMR (500 MHz, D$_2$O) δ 8.31 (s, 1H), 8.14 (s, 1H), 6.93 (s, 1H), 5.32 (d, J=5.1 Hz, 1H), 4.86-4.78 (m, 2H), 4.73-4.66 (m, 1H assumed; obscured by solvent residual peak), 4.29 (s, 2H), 3.04-3.01 (m, 2H), 2.97-2.92 (m, 2H), 1.96 (p, J=7.9 Hz, 2H), 1.22-1.11 (m, 2H), 1.10-0.96 (m, 2H).

Example 70

2-(((Z)-(2-(((2R,3S)-2-((3-(2-aminoethyl)-2-oxoimidazolidin-1-yl)methyl)-4-oxo-1-sulfoazetidin-3-yl) amino)-1-(2-aminothiazol-4-yl)-2-oxoethylidene) amino)oxy)-2-methylpropanoic acid Step 1: Tert-butyl 2-(((Z)-(1-(2-((tert-butoxycarbonyl)amino)thiazol-4-yl)-2-(((2R,3S)-2-(11,11-dimethyl-9-oxo-10-oxa-2,5,8-triazadodecyl)-4-oxoazetidin-3-yl)amino)-2-oxoethylidene)amino)oxy)-2-methylpropanoate To a solution of tert-butyl 2-(((Z)-(2-(((2R,3S)-2-(((2-aminoethyl)amino)methyl)-4-oxoazetidin-3-yl)amino)-1-(2-((tert-butoxycarbonyl)amino)thiazol-4-yl)-2-oxoethylidene) amino)oxy)-2-methylpropanoate (100 mg, 0.176 mmol) in DCE (1.8 mL) was added tert-butyl(2-oxoethyl)carbamate (27.9 mg, 0.176 mmol). After stirring for 2 h, sodium triacetoxyborohydride (112 mg, 0.527 mmol) was added. After 12 h, the reaction mixture was quenched with saturated NaHCO$_3$ (aq) and extracted with EtOAc. The organic layer was washed with brine, dried over Na$_2$SO$_4$ and concentrated in vacuo. It was used as crude in step 2.

Step 2: Tert-butyl 2-(((Z)-(2-(((2R,3S)-2-((3-(2-((tert-butoxycarbonyl)amino)ethyl)-2-oxoimidazolidin-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate Prepared in analogous manner to example 3 step 3, using tert-butyl 2-(((Z)-(1-(2-((tert-butoxycarbonyl)amino)thiazol-4-yl)-2-(((2R,3S)-2-(11,11-dimethyl-9-oxo-10-oxa-2,5,8-triazadodecyl)-4-oxoazetidin-3-yl)amino)-2-oxoethylidene)amino)oxy)-2-methylpropanoate (135 mg, 0.189 mmol), CDI (46.1 mg, 0.284 mmol), TEA (132 μl, 0.947 mmol) and chloroform (1.9 mL). The crude residue was used as such in the following step. LC/MS: R=1.02 min, m/z=739.4 (M+1) Method 2m_acidic.

Step 3: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-(2-((tert-butoxycarbonyl)amino)ethyl)-2-oxoimidazolidin-1-yl)methyl)-4-oxoazetidine-1-sulfonic acid Prepared in analogous manner to example 3, step 4, using tert-butyl 2-(((Z)-(2-(((2R,3S)-2-((3-(2-((tert-butoxycarbonyl)amino)ethyl)-2-oxoimidazolidin-1-yl)methyl)-4-oxoazetidin-3-yl)amino)-1-(2-((tert-butoxycarbonyl)amino)thiazol-4-yl)-2-oxoethylidene)amino)oxy)-2-methylpropanoate (60 mg, 0.081 mmol), SO$_3$.DMF (124 mg, 0.812 mmol), DMF (812 μl). The crude residue was used as such in the following step. LC/MS: $R_t$=0.94 min, m/z=819.2 (M+1) Method 2m_acidic.

Step 4: 2-(((Z)-(2-(((2R,3S)-2-((3-(2-aminoethyl)-2-oxoimidazolidin-1-yl)methyl)-4-oxo-1-sulfoazetidin-3-yl)amino)-1-(2-aminothiazol-4-yl)-2-oxoethylidene)amino)oxy)-2-methylpropanoic acid

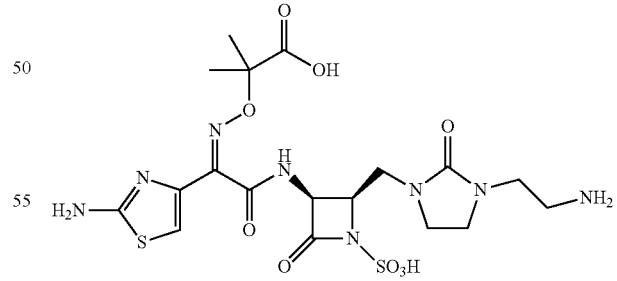

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((3-(2-((tert-butoxycarbonyl)amino)ethyl)-2-oxoimidazolidin-1-yl) methyl)-4-oxoazetidine-1-sulfonic acid (42 mg, 0.051 mmol), TFA (237 μl, 3.08 mmol) in DCM (500 μL). The crude residue was purified by reverse phase prep HPLC (Xselect CSH, 30×100 mm, 5 μM, C18 column; ACN-water with 0.1% formic acid modifier, 60 mL/min) to afford the title compound (1.2 mg, 4%). LC/MS: R$_f$=0.35 min, m/z=563.2 (M+1) Method 2m_acidic; $^1$H NMR (400 MHz, D$_2$O): δ $^1$H NMR 6.99 (s, 1H), 5.32 (d, J=5.9 Hz, 1H), 4.56-4.50 (m, 1H), 3.70 (dd, J=15.1, 9.6 Hz, 1H), 3.59-3.49 (m, 1H), 3.46 3.30 (m, 4H), 3.29-3.20 (m, 2H), 3.08-3.02 (m, 2H), 1.40 (s, 3H), 1.38 (s, 3H).

Example 71

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((S)-pyrrolidin-3-yl)carbamimidoyl)phenoxy)propanoic acid

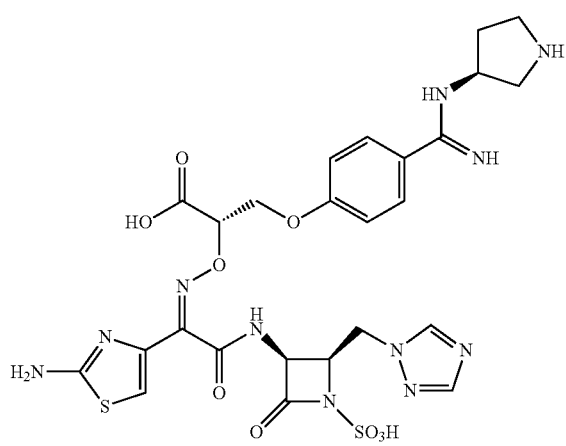 [SMILES: N=C(N[C@H]1CCNC1)c1ccc(OC[C@H](O/N=C(\C(=O)N[C@@H]2C(=O)N(S(=O)(=O)O)[C@@H]2Cn2cncn2)c2csc(N)n2)C(=O)O)cc1]

Prepared in analogous manner to example 64, using intermediate F and (R)-tert-butyl 3-(4-((S)-2-(aminooxy)-3-(benzhydryloxy)-3-oxopropoxy)benzimidamido)pyrrolidine-1-carboxylate (prepared according to WO2013110643). The crude residue was purified by reverse phase prep HPLC (Xselect CSH, 30×100 mm, 5 μM, C18 column; ACN-water with 0.1% formic acid modifier, 60 mL/min). LCMS: R$_f$=0.39 min, m/z=692.3 (M+1) Method 2m_acidic_polar; $^1$H NMR (500 MHz, DMSO-d$_6$): δ 9.52 (d, J=7.6 Hz, 3H), 9.11 (br s, 1H), 8.92-8.78 (m, 2H), 8.40 (s, 1H), 7.92 (s, 1H), 7.67 (d, J=8.8 Hz, 2H), 7.30 (br s, 2H), 6.90 (d, J=9.1 Hz, 2H), 6.80 (s, 1H), 5.11-5.04 (m, 2H), 4.58-4.51 (m, 1H), 4.48-4.35 (m, 4H), 4.25-4.20 (m, 2H), 3.53-3.44 (m, 1H), 2.35-2.25 (m, 1H), 2.20-2.11 (m, 1H).

Example 72

2-(((Z)-(1-(2-aminothiazol-4-yl)-2-(((2R,3S)-2-(((R)-5-(hydroxymethyl)-2-oxooxazolidin-3-yl)methyl)-4-oxo-1-sulfoazetidin-3-yl)amino)-2-oxoethylidene)amino)oxy)-2-methylpropanoic acid Step 1: Tert-butyl 2-(((Z)-(2-(((2R,3S)-2-((((R)-3-(benzyloxy)-2-hydroxypropyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate Prepared in analogous manner to example 63 step 1, using tert-butyl 2-(((Z)-(2-(((2R,3S)-2-(aminomethyl)-4-oxoazetidin-3-yl)amino)-1-(2-((tert-butoxycarbonyl)amino)thiazol-4-yl)-2-oxoethylidene)amino)oxy)-2-methylpropanoate (200 mg, 0.38 mmol), (R)-2-((benzyloxy)methyl)oxirane (623 mg, 3.8 mmol), DCM (2 mL). The crude residue was purified via silica gel chromatography (MeOH-DCM, 4-10%) to afford the title compound (126 mg, 48%). LCMS: m/z=691.3 (M+1).

Step 2: Tert-butyl 2-(((Z)-(2-(((2R,3S)-2-(((R)-5-((benzyloxy)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate Prepared in analogous manner to example 63 step 2, using tert-butyl 2-(((Z)-(2-(((2R,3S)-2-((((R)-3-(benzyloxy)-2-hydroxypropyl)amino)methyl)-4-oxoazetidin-3-yl)amino)-1-(2-((tert-butoxycarbonyl)amino)thiazol-4-yl)-2-oxoethylidene)amino)oxy)-2-methylpropanoate (126 mg, 0.182 mmol), CDI (53 mg, 0.33 mmol), DCM (5 mL). The crude residue was purified via silica gel chromatography (MeOH-DCM, 3-5%) to afford the title compound (76 mg, 58%). LCMS: m/z=715.3 (M−1).

Step 3: Tert-butyl 2-(((Z)-(2-(((2R,3S)-2-(((R)-5-((benzyloxy)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate (2R,3S)-2-(((R)-5-((benzyloxy)methyl)-2-oxooxazolidin-3-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonate Prepared in analogous manner to example 63 step 3, using tert-butyl 2-(((Z)-(2-(((2R,3S)-2-(((R)-5-((benzyloxy)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate (76 mg, 0.11 mmol), SO$_3$.DMF (65 mg, 0.42 mmol), DMF (1 mL). The crude residue was purified via HP21 resin (CH$_3$CN-water, 10-50%) to afford the title compound (80 mg, 95%). LCMS: m/z=797.3 (M+1).

Step 4: 2-(((Z)-(1-(2-aminothiazol-4-yl)-2-(((2R,3S)-2-(((R)-5-(hydroxymethyl)-2-oxooxazolidin-3-yl)methyl)-4-oxo-1-sulfoazetidin-3-yl)amino)-2-oxoethylidene)amino)oxy)-2-methylpropanoic acid

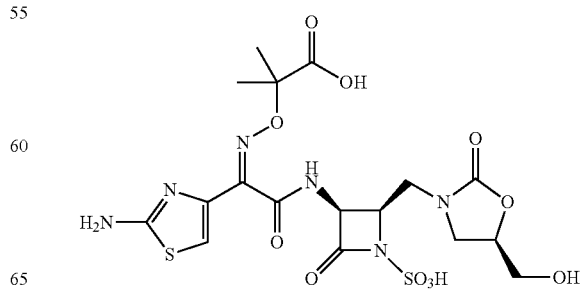

To a solution of tert-butyl 2-(((Z)-(2-(((2R,3S)-2-(((R)-5-((benzyloxy)methyl)-2-oxooxazolidin-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate (2R,3S)-2-(((R)-5-((benzyloxy)methyl)-2-oxooxazolidin-3-yl)methyl)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidine-1-sulfonate (80 mg, 0.1 mmol) in DCM (10 mL) was added BCl₃ (1 M in DCM, 0.6 mL). After stirring at rt for 15 min, the reaction mixture was quenched with EtOH and concentrated in vacuo. The crude residue was purified by reverse phase prep HPLC (XSelect CSH, 30×100 mm, 5 μm, C18 column; ACN-water with 0.1% formic acid modifier, 60 mL/min), affording the title compound (1.1 mg, 2%). LCMS: m/z=549.0 (M−1); ¹H NMR (400 MHz, D₂O): δ 6.96 (s, 1H), 5.29 (d, J=5.2 Hz, 1H), 4.48 (m, 2H), 3.73-3.35 (m, 6H), 1.36 (s, 3H), 1.35 (s, 3H).

Example 73

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((R)-pyrrolidin-3-yl)carbamimidoyl)phenoxy) propanoic acid

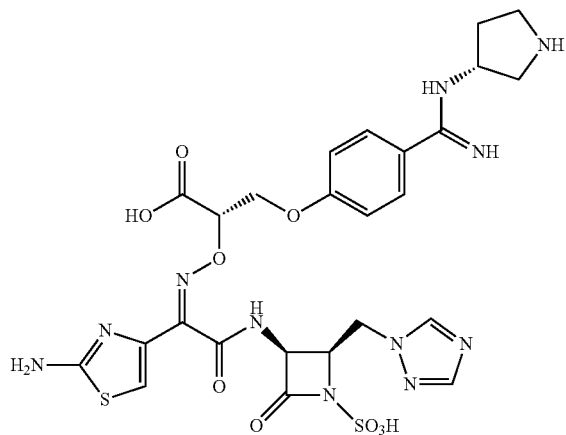 [SMILES: N=C(N[C@@H]1CCNC1)c1ccc(OC[C@H](O/N=C(\C(=O)N[C@@H]2C(=O)N(S(=O)(=O)O)[C@@H]2Cn2cncn2)c2csc(N)n2)C(=O)O)cc1]

Prepared in analogous manner to example 64, using intermediate F and (S)-tert-butyl 3-(4-((S)-2-(aminooxy)-3-(benzhydryloxy)-3-oxopropoxy)benzimidamido)pyrrolidine-1-carboxylate (prepared according to WO2013110643). The crude residue was purified by reverse phase prep HPLC (Xselect CSH, 30×100 mm, 5 μM, C18 column; ACN-water with 0.1% formic acid modifier, 60 mL/min). LCMS: R$_t$=0.39 min, m/z=692.3 (M+1) Method 2m_acidic_polar; ¹H NMR (500 MHz, DMSO-d₆): δ 9.52 (d, J=7.6 Hz, 3H), 9.11 (br s, 1H), 8.92-8.78 (m, 2H), 8.40 (s, 1H), 7.92 (s, 1H) 7.67 (d, J=8.8 Hz, 2H), 7.30 (br s, 2H), 6.90 (d, J=9.1 Hz, 2H), 6.80 (s, 1H), 5.11-5.04 (m, 2H), 4.51-4.58 (m, 1H), 4.48-4.35 (m, 4H), 4.25-4.19 (m, 1H), 3.53-3.44 (m, 1H), 2.35-2.26 (m, 1H), 2.29-2.11 (m, 1H).

Example 74

2-(((Z)-(1-(2-aminothiazol-4-yl)-2-(((2R,3S)-2-((3-carbamoyl-1H-1,2,4-triazol-1-yl)methyl)-4-oxo-1-sulfoazetidin-3-yl)amino)-2-oxoethylidene)amino)oxy)-2-methylpropanoic acid

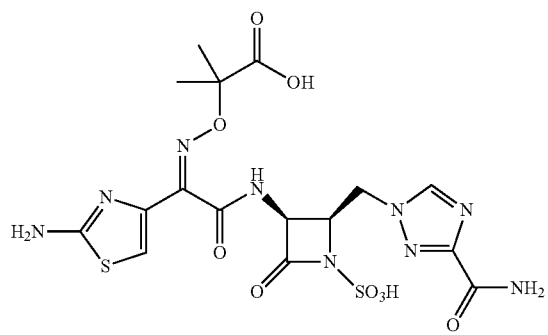 [SMILES: CC(C)(O/N=C(\C(=O)N[C@@H]1C(=O)N(S(=O)(=O)O)[C@@H]1Cn1cnc(C(N)=O)n1)c1csc(N)n1)C(=O)O]

Prepared in analogous manner to example 4, using tert-butyl (1-(((2R,3S)-3-amino-4-oxoazetidin-2-yl)methyl)-1H-1,2,4-triazole-3-carbonyl)carbamate. LCMS: m/z=544.0 (M−1); ¹H NMR (400 MHz, D₂O): δ 8.41 (s, 1H), 6.94 (s, 1H), 5.36-5.32 (m, 1H), 4.75-4.50 (m, 3H, partially obscured by solvent residual peak), 1.23 (s, 6H).

Example 75

(S)-2-(((Z)-(2-(((2R,3S)-2-((1H-1,2,4-triazol-1-yl)methyl)-4-oxo-1-sulfoazetidin-3-yl)amino)-1-(5-amino-1,2,4-thiadiazol-3-yl)-2-oxoethylidene)amino)oxy)-3-(4-(N-(piperidin-4-yl)carbamimidoyl) phenoxy)propanoic acid Prepared in analogous manner to example 31, using 2-(5-((tert-butoxycarbonyl)amino)-1,2,4-thiadiazol-3-yl)-2-oxoacetic acid. LCMS: R$_t$=0.305 min, m/z=707.4 (M+1) Method 2m_acidic; ¹H NMR (500 MHz, D₂O): δ 8.02 (s, 1H), 7.66 (s, 1H), 7.43 (d, J=8.8 Hz, 2H), 6.77 (d, J=9.1 Hz, 2H), 5.24 (d, J=5.9 Hz, 1H), 5.10-5.06 (m, 1H), 4.44-4.29 (m, 4H), 4.01-3.88 (m, 1H), 3.49 (d, J=13.6 Hz, 2H), 3.21-2.99 (m, 2H), 2.33-2.23 (m, 2H), 1.92-1.80 (m, 2H).

Example 76

2-(((Z)-(2-(((2R,3S)-2-MS)-3-amino-2-oxopyrrolidin-1-yl)methyl)-4-oxo-1-sulfoazetidin-3-yl)amino)-1-(2-aminothiazol-4-yl)-2-oxoethylidene)amino)oxy)-2-methylpropanoic acid

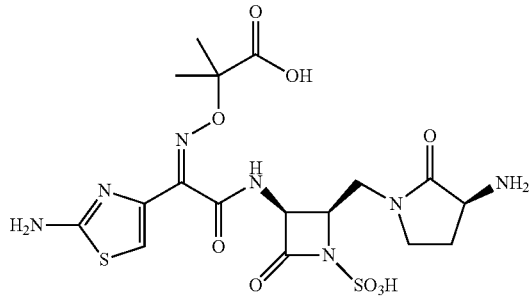 [SMILES: CC(C)(O/N=C(\C(=O)N[C@@H]1C(=O)N(S(=O)(=O)O)[C@@H]1CN1CC[C@H](N)C1=O)c1csc(N)n1)C(=O)O]

Prepared in analogous manner to example 1, using (S)-methyl 4-bromo-2-((tert-butoxycarbonyl)amino)butanoate. LCMS: m/z=532.0 (M−1); $^1$H NMR (400 MHz, D$_2$O): δ 6.99 (s, 1H), 5.31 (d, J=6.0 Hz, 1H), 4.70-4.58 (m, 1H), 4.02 (t, J=9.6, 9.2 Hz, 1H), 3.85 (dd, J=9.6, 9.2 Hz, 1H), 3.59 (m, 1H), 3.47 (m, 1H), 3.34 (dd, J=14.8, 2.4 Hz, 1H), 2.48 (m, 1H), 2.01 (m, 1H), 1.39 (s, 3H), 1.37 (s, 3H).

Example 77

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1r,3S)-3-aminocyclobutyl)carbamimidoyl)phenoxy)propanoic acid

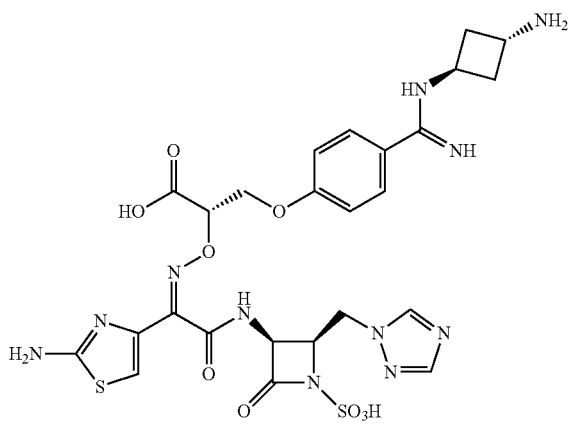 [SMILES: N=C(N[C@H]1C[C@H](N)C1)c1ccc(OC[C@H](O/N=C(\C(=O)N[C@@H]2C(=O)N(S(=O)(=O)O)[C@@H]2Cn2cncn2)c2csc(N)n2)C(=O)O)cc1]

Prepared in analogous manner to example 31, using (S)-benzhydryl 2-(aminooxy)-3-(4-(N-((1r,3S)-3-((tert-butoxycarbonyl)amino)cyclobutyl)carbamimidoyl)phenoxy)propanoate LCMS: R$_t$=0.39 min, m/z=692.1 (M+1) Method 2m_acidic_polar; $^1$H NMR (400 MHz, DMSO-d$_6$) δ 9.83-9.76 (m, 1H), 9.51 (d, J=8.1 Hz, 1H), 9.33 (br s, 1H), 8.71 (br s, 1H), 8.39 (s, 1H), 8.05-7.97 (m, 3H), 7.91 (s, 1H), 7.66 (d, J=8.5 Hz, 2H), 7.30 (br s, 2H), 6.89 (d, J=9.2 Hz, 2H), 6.80 (s, 1H), 5.13-5.04 (m, 2H), 4.55-4.49 (m, 1H), 4.47-4.33 (m, 3H), 4.24-4.16 (m, 2H), 3.97-3.86 (m, 1H), 2.69-2.52 (m, 4H).

Example 78

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(3-aminopropyl)carbamimidoyl)phenoxy)propanoic acid

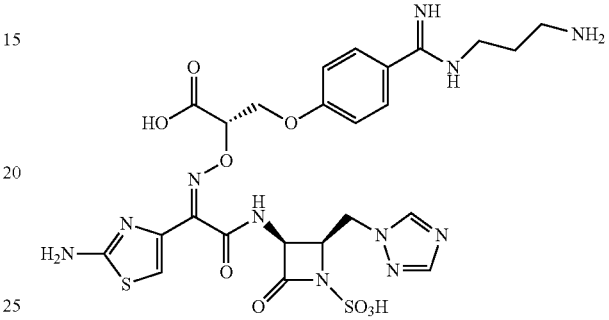

Prepared in analogous manner to example 67, using (S)-benzhydryl 2-(aminooxy)-3-(4-(N-(3-((tert-butoxycarbonyl)amino)propyl)carbamimidoyl)phenoxy)propanoate (prepared according to WO2013110643). LCMS: R$_t$=0.38 min, m/z=680.2 (M+1) Method 2m_acidic_polar; $^1$H NMR (400 MHz, DMSO-d$_6$) δ $^1$H NMR (400 MHz, DMSO-d$_6$) δ 9.59-9.47 (m, 2H), 9.34 (s, 1H), 8.88 (s, 1H), 8.37 (s, 1H), 7.90 (s, 1H), 7.79-7.67 (m, 3H), 7.66-7.62 (m, 2H), 7.29 (s, 2H), 6.94-6.88 (m, 2H), 6.80 (s, 1H), 5.10 (dd, J=8.1, 5.5 Hz, 1H), 5.06 (dd, J=5.0, 2.7 Hz, 1H), 4.56-4.48 (m, 1H), 4.48-4.35 (m, 3H), 4.26-4.19 (m, 1H), 2.90 (dd, J=8.9, 5.5 Hz, 3H), 1.96-1.83 (m, 2H).

Example 79

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-((6-(N-(piperidin-4-yl)carbamimidoyl)pyridin-3-yl)oxy)propanoic acid

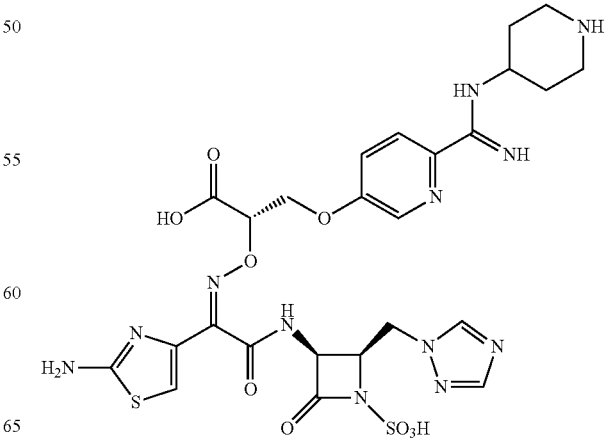

Prepared in analogous manner to example 68, using intermediate F and (R)-tert-butyl 4-(5-(2-(aminooxy)-3-(benzhydryloxy)-3-oxopropoxy)picolinimidamido)piperidine-1-carboxylate (prepared according to WO2013110643). LCMS: $R_t$=0.29 min, m/z=707.0 (M+1) Method 2m_acidic; $^1$H NMR (400 MHz, DMSO-$d_6$): δ 9.71 (d, J=7.8 Hz, 1H), 9.58 (br s, 1H), 9.24 (br s, 1H), 8.45-8.40 (m, 1H), 8.36 (s, 1H), 8.27-8.21 (m, 1H), 8.12 (d, J=8.6 Hz, 1H), 7.84 (s, 1H), 7.65-7.59 (m, 1H), 7.24 (br s, 2H), 6.77 (s, 1H), 6.50 (s, 1H), 5.18-5.11 (m, 1H), 5.09-5.03 (m, 1H), 4.64-4.58 (m, 1H), 4.55-4.49 (m, 1H), 4.48-4.42 (m, 1H), 4.23 (q, J=5.5 Hz, 1H), 3.96-3.85 (m, 1H), 3.45-3.40 (m, 2H), 2.94-2.83 (m, 2H), 2.10-2.02 (m, 2H), 1.92-1.81 (m, 2H).

Example 80

2-(((Z)-(1-(2-aminothiazol-4-yl)-2-(((2R,3S)-2-(((S)-3-guanidino-2-oxopyrrolidin-1-yl)methyl)-4-oxo-1-sulfoazetidin-3-yl)amino)-2-oxoethylidene)amino)oxy)-2-methylpropanoic acid

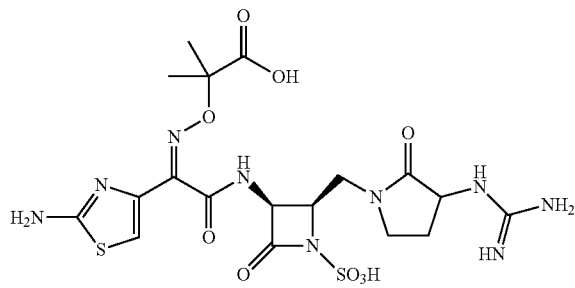 [SMILES: CC(C)(O/N=C(\C(=O)N[C@@H]1C(=O)N(S(=O)(=O)O)[C@@H]1CN1CCC(NC(=N)N)C1=O)c1csc(N)n1)C(=O)O]

Prepared in analogous manner to example 20 using 2-(((Z)-(2-(((2R,3S)-2-(((S)-3-amino-2-oxopyrrolidin-1-yl)methyl)-4-oxo-1-sulfoazetidin-3-yl)amino)-1-(2-aminothiazol-4-yl)-2-oxoethylidene)amino)oxy)-2-methylpropanoic acid and 1H-pyrazole-1-carboximidamide HCl. LCMS: m/z=576.2 (M+1); $^1$H NMR (400 MHz, $D_2O$): δ 6.95 (s, 1H), 5.31 (d, J=6.0 Hz, 1H), 4.72-4.57 (m, 1H), 4.27 (t, J=9.6 & 9.2 Hz, 1H), 3.85 (dd, J=9.6 Hz, 1H), 3.59 (t, J=9.2, 8.8 Hz, 1H), 3.49 (q, 1H), 3.34 (dd, 1H), 2.46 (m, 1H), 1.88 (m, 1H), 1.35 (s, 3H), 1.33 (s, 3H).

Example 81

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1R,5S,6s)-3-azabicyclo[3.1.0]hexan-6-yl)carbamimidoyl)phenoxy)propanoic acid

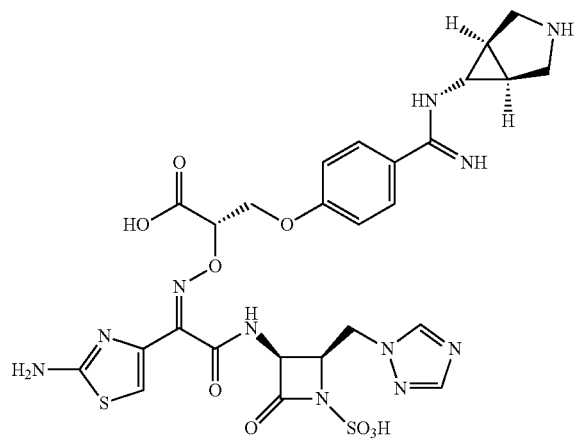

Prepared in analogous manner to example 31, using (1R,5S,6s)-tert-butyl 6-(4-(((R)-2-(aminooxy)-3-(benzhydryloxy)-3-oxopropoxy)benzimidamido)-3-azabicyclo[3.1.0]hexane-3-carboxylate hydrate. LCMS: $R_t$=0.42 min, m/z=704.2 (M+1) Method 2m_acidic; $^1$H NMR (400 MHz, DMSO-$d_6$) δ 9.70 (br s, 1H), 9.56-9.45 (m, 2H), 9.14-8.96 (m, 2H), 8.54 (br s, 1H), 8.36 (s, 1H), 7.88 (s, 1H), 7.63 (d, J=7.9 Hz, 2H), 7.28 (br s, 2H), 6.88 (d, J=9.6 Hz, 2H), 6.78 (s, 1H), 5.10-5.02 (m, 2H), 4.54-4.48 (m, 1H), 4.45-4.35 (m, 3H), 4.23-4.17 (m, 1H), 3.61-3.54 (m, 4H), 2.73-2.68 (m, 1H), 2.25 (br s, 2H).

Example 82

2-(((Z)-(2-(((2R,3S)-2-((5-(aminomethyl)isoxazol-3-yl)methyl)-4-oxo-1-sulfoazetidin-3-yl)amino)-1-(2-aminothiazol-4-yl)-2-oxoethylidene)amino)oxy)-2-methylpropanoic acid Step 1: Benzyl ((2R,3S)-1-(2,4-dimethoxybenzyl)-2-((E)-2-methoxyvinyl)-4-oxoazetidin-3-yl)carbamate To a suspension of (methoxymethyl)triphenylphosphonium chloride (10.34 g, 30.2 mmol) in THF (100 mL) at −78° C. was added KHMDS (in toluene) (66.3 ml, 33.1 mmol) slowly. After stirring for 30 min, the above prepared ylide soln was added to a soln of benzyl ((2S,3S)-1-(2,4-dimethoxybenzyl)-2-formyl-4-oxoazetidin-3-yl)carbamate (3 g, 7.53 mmol) in THF (38 ml) at −78° C. After 3 h, the reaction mixture was quenched with saturated NaHCO$_3$ (aq, 60 mL), and it was stirred overnight. The mixture was diluted with EtOAc, and the layers were separated. The aqueous layer was extracted with EtOAc (2×), and the combined organic layers were washed with brine, dried with Na$_2$SO$_4$ and concentrated in vacuo. The crude residue was purified via silica gel chromatography (EtOAc-Heptane, 0-60%) to afford the title compound (1.6 g, 49%) along with the trans-isomer (0.8 g, 25%). LCMS: $R_t$=0.91 min, m/z=427.0 (M+1). Method 2m_acidic.

Step 2: Benzyl ((3S,4R)-1-(2,4-dimethoxybenzyl)-2-oxo-4-(2-oxoethyl)azetidin-3-yl)carbamate To a solution of benzyl ((2R,3S)-1-(2,4-dimethoxybenzyl)-2-((E)-2-methoxyvinyl)-4-oxoazetidin-3-yl)carbamate (1.58 g, 3.70 mmol) in dioxane (37 ml) was added HCl (7.4 ml, 7.4 mmol) and heated to 50° C. for 4 h. After cooling to rt, the reaction mixture was quenched with saturated NaHCO$_3$ (aq) and extracted with EtOAc (3×). The combined organic layers were washed with brine, dried with Na$_2$SO$_4$ and concentrated in vacuo. The crude residue was purified by silica gel chromatography (EtOAc-Heptane, 0-80%) to afford the title compound (0.89 g, 58%). LCMS: $R_t$=0.86 min, m/z=413.0 (M+1). Method 2m_acidic.

Step 3: Benzyl ((2R,3S)-1-(2,4-dimethoxybenzyl)-2-((E)-2-(hydroxyimino)ethyl)-4-oxoazetidin-3-yl)carbamate To a solution of hydroxylamine hydrochloride (160 mg, 2.25 mmol) and sodium bicarbonate (2.4 mL, 2.23 mmol) in water (6 mL) was added a solution of benzyl ((3S,4R)-1-(2,4-dimethoxybenzyl)-2-oxo-4-(2-oxoethyl)azetidin-3-yl)carbamate (886 mg, 2.15 mmol) in EtOH (200 μL) followed by an EtOH (200 μL) wash. After stirring for 20 h, the reaction mixture was partially concentrated in vacuo and partitioned between DCM and brine. The aqueous layer was extracted with DCM (2×). The combined organic layers were washed with brine, dried over Na₂SO₄, filtered and concentrated in vacuo. The crude residue was used as such in the following step. LCMS: $R_t$=0.76 min, m/z=428.1 (M+1). Method 2m_acidic.

Step 4

To a solution of benzyl ((2R,3S)-1-(2,4-dimethoxybenzyl)-2-((E)-2-(hydroxyimino)ethyl)-4-oxoazetidin-3-yl)carbamate (403 mg, 0.94 mmol) and N-Boc-propargylamine (156 mg, 0.97 mmol) in DCM (12 mL) at 0° C. was added sodium hypochlorite (5%, 2.6 mL, 1.89 mmol) dropwise. After stirring for 18 h, the reaction mixture was diluted with DCM and water. The aqueous layer was extracted with DCM (2×). The combined organic layers were washed with brine, dried over Na₂SO₄ and concentrated in vacuo. The crude residue was purified by silica gel chromatography (EtOAc-Heptane, 0-80%), affording the title compound (127 mg, 23%). LCMS: $R_t$=0.96 min, m/z=581.2 (M+1). Method 2m_acidic.

Step 5

To a solution of intermediate from step 4 (279 mg, 0.48 mmol) in acetonitrile (4.6 mL, ratio: 2) and water (2.3 mL, ratio: 1) was added potassium peroxydisulfate (169 mg, 0.62 mmol), and potassium phosphate, dibasic (192 mg, 1.1 mmol) and heated to 90° C. After 3 h, more potassium peroxydisulfate (81 mg, 0.3 mmol) was added and heated to 90° C. After 2 h of additional heating, the reaction mixture was quenched with NaHCO₃ and extracted with EtOAc (3×). The combined organic layers were washed with brine, dried over Na₂SO₄ and concentrated in vacuo. The crude residue was purified by silica gel chromatography (EtOAc-Heptane, 0-80%), affording the title compound (71 mg, 34%). LCMS: $R_t$=0.77 min, m/z=431.0 (M+1). Method 2m_acidic.

Step 6: Tert-butyl ((Z)-4-amino-5-((2R,3S)-3-amino-4-oxoazetidin-2-yl)-2-oxopent-3-en-1-yl)carbamate To a solution of intermediate from step 5 (84 mg, 0.20 mmol) in EtOH (1.9 mL, ratio: 2) and MeOH (0.93 mL, ratio: 1) was added Pd—C (22 mg, 20 µmol) and purged with N₂. The flask was fitted with a H₂ balloon, evacuated and backfilled with H₂ (3×). After 1.5 h, the reaction mixture was filtered through celite with MeOH wash (3×). The filtrate was concentrated in vacuo and azeotropped with toluene. The crude residue was used as such in the following step. LCMS: $R_t$=0.39 min, m/z=229.1 (M+1). Method 2m_acidic.

Step 7: Tert-butyl 2-(((Z)-(2-(((2R,3S)-2-((Z)-2-amino-5-((tert-butoxycarbonyl)amino)-4-oxopent-2-en-1-yl)-4-oxoazetidin-3-yl)amino)-1-(2-((tert-butoxycarbonyl)amino)thiazol-4-yl)-2-oxoethylidene)amino)oxy)-2-methylpropanoate Prepared in analogous manner to example 4 step 4, using (Z)-2-(((1-(tert-butoxy)-2-methyl-1-oxopropan-2-yl)oxy)imino)-2-(2-((tert-butoxycarbonyl)amino)thiazol-4-yl)acetic acid (100 mg, 0.23 mmol), HATU (89 mg, 0.23 mmol), DIPEA (68 µl, 0.39 mmol), tert-butyl ((Z)-4-amino-5-((2R,3S)-3-amino-4-oxoazetidin-2-yl)-2-oxopent-3-en-1-yl)carbamate (58 mg, 0.19 mmol) and DCM:DMF (3:1, 2 mL). 79 mg. LCMS: $R_t$=0.98 min, m/z=710.4 (M+1). Method 2m_acidic.

Step 8: Tert-butyl 2-(((Z)-(2-(((2R,3S)-2-((5-(((tert-butoxycarbonyl)amino)methyl)isoxazol-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate To a solution of tert-butyl 2-(((Z)-(2-(((2R,3S)-2-((Z)-2-amino-5-((tert-butoxycarbonyl)amino)-4-oxopent-2-en-1-yl)-4-oxoazetidin-3-yl)amino)-1-(2-((tert-butoxycarbonyl)amino)thiazol-4-yl)-2-oxoethylidene)amino)oxy)-2-methylpropanoate (77 mg, 0.108 mmol)) in ethanol (0.4 mL) was added hydroxylamine hydrochloride (19 mg, 0.27 mmol) and potassium carbonate (18 mg, 0.13 mmol) and heated to 60° C. After 6 h, the reaction mixture was partially concentrated in vacuo and partitioned between EtOAc and water. The aqueous layer was extracted with EtOAc (3×). Combined organic layers were washed with brine, dried over Na₂SO₄, filtered and concentrated in vacuo. The crude residue was purified by column chromatography (EtOAc-Heptane, 5-90%) to afford the title compound (13 mg, 17%). LCMS: $R_t$=1.04 min, m/z=708.3 (M+1). Method 2m_acidic.

Step 9: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert-butoxycarbonyl)amino)methyl)isoxazol-3-yl)methyl)-4-oxoazetidine-1-sulfonic acid Prepared in analogous manner to example 4 step 5, using tert-butyl 2-(((Z)-(2-(((2R,3S)-2-((5-(((tert-butoxycarbonyl)amino)methyl)isoxazol-3-yl)methyl)-4-oxoazetidin-3-yl)amino)-1-(2-((tert-butoxycarbonyl)amino)thiazol-4-yl)-2-oxoethylidene)amino)oxy)-2-methylpropanoate (13 mg, 18 µmol), SO₃.DMF (16.8 mg, 0.11 mmol), DMF (200 µl). The crude residue was used as such in the following step. LCMS: $R_t$=0.94 min, m/z=788.4 (M+1). Method 2m_acidic.

Step 10: 2-(((Z)-(2-(((2R,3S)-2-((5-(aminomethyl)isoxazol-3-yl)methyl)-4-oxo-1-sulfoazetidin-3-yl)amino)-1-(2-aminothiazol-4-yl)-2-oxoethylidene)amino)oxy)-2-methylpropanoic acid

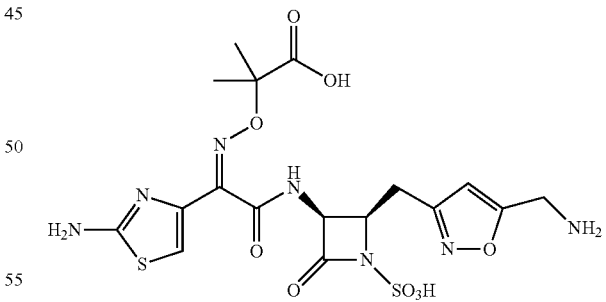

Followed the general procedure for the acid mediated deprotection using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((5-(((tert butoxycarbonyl)amino)methyl)isoxazol-3-yl)methyl)-4-oxoazetidine-1-sulfonic acid (10.9 mg, 14 µmol), TFA (70 µl, 0.91 mmol), and DCM (0.2 mL). The crude residue was purified by reverse phase prep HPLC (Xselect CSH, 19×100 mm, 5 µM, C18 column; ACN-water with 0.1% formic acid modifier, 24 mL/min) to afford the title compound (1.7 mg, 17%). LCMS: $R_t$=0.48 min, m/z=532.1 (M+1). Method 2m_acidic_polar. $^1$H NMR (400 MHz, D$_2$O) δ 6.85 (s, 1H), 6.52 (s, 1H), 5.38 (d, J=5.6 Hz, 1H), 4.26 (s, 2H), 3.22 (dd, J=16.2, 7.1 Hz, 2H), 3.10 (dd, J=16.2, 6.0 Hz, 1H), 1.33 (s, 3H), 1.29 (s, 3H).

Example 83

2-(((Z)-(1-(2-aminothiazol-4-yl)-2-(((2R,3S)-2-((4-((benzyl(methyl)amino)methyl)-2H-1,2,3-triazol-2-yl)methyl)-4-oxo-1-sulfoazetidin-3-yl)amino)-2-oxoethylidene)amino)oxy)-2-methylpropanoic acid

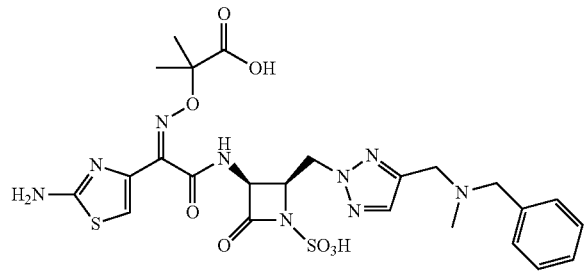 [SMILES: CN(Cc1ccccc1)Cc1cnn(C[C@@H]2[C@H](NC(=O)/C(=N\OC(C)(C)C(=O)O)c3csc(N)n3)C(=O)N2S(=O)(=O)O)n1]

Prepared in analogous manner to example 52, using N-((2H-1,2,3-triazol-4-yl)methyl)-N-methyl-1-phenylmethanamine. LCMS: m/z=634.1 (M−1). $^1$H NMR (400 MHz, D$_2$O) δ 7.79 (s, 1H), 7.40-7.31 (m, 5H), 6.89 (s, 1H), 5.43 (d, J=5.2 Hz, 1H), 4.96-4.89 (m, 1H), 4.87-4.83 (m, 2H), 4.70-4.60 (m, 2H, partially overlapped with D$_2$O signal), 4.36 (s, 2H), 2.64 (s, 3H), 1.28 (s, 3H), 1.27 (s, 3H).

Example 84

(S)-2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-3-(4-(N-(piperidin-4-yl)carbamimidoyl)phenoxy)propanoic acid

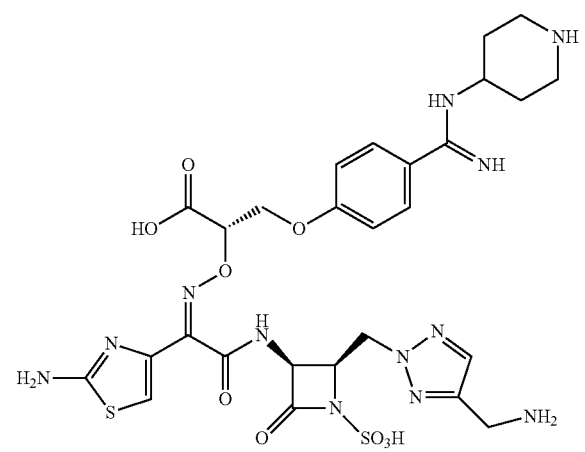 [SMILES: N=C(NC1CCNCC1)c1ccc(OC[C@H](O/N=C(\C(=O)N[C@@H]2C(=O)N(S(=O)(=O)O)[C@@H]2Cn2ncc(CN)n2)c2csc(N)n2)C(=O)O)cc1]

Prepared in analogous manner to example 31, using tert-butyl ((2-(((2R,3S)-3-amino-4-oxoazetidin-2-yl)methyl)-2H-1,2,3-triazol-4-yl)methyl)carbamate. LCMS: $R_t$=0.44 min, m/z=735.3 (M+1). Method 2m_acidic. $^1$H NMR (400 MHz, DMSO-d$_6$) δ 9.63-9.48 (m, 1H), 9.45-9.33 (m, 2H), 9.02 (s, 1H), 8.56 (br s, 1H), 8.44 (br s, 1H), 8.22 (s, 3H), 7.74-7.67 (m, 3H), 7.26 (br s, 2H), 7.19 (d, J=8.6 Hz, 2H), 6.72 (s, 1H), 5.38-5.30 (m, 1H), 5.01-4.96 (m, 1H), 4.93-4.86 (m, 1H), 4.77-4.68 (m, 1H), 4.49-4.35 (m, 3H), 4.08 (br s, 2H), 3.85 (br s, 2H), 2.96-2.84 (m, 2H), 2.13-2.03 (m, 2H), 1.83-1.70 (m, 2H).

Example 85

1-(((Z)-(1-(2-aminothiazol-4-yl)-2-(((2R,3S)-2-((4-(((azetidin-3-ylmethyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid Step 1: Benzhydryl 1-(((Z)-(1-(2-((tert-butoxycarbonyl)amino)thiazol-4-yl)-2-(((2R,3S)-2-((4-(hydroxymethyl)-2H-1,2,3-triazol-2-yl)methyl)-4-oxoazetidin-3-yl)amino)-2-oxoethylidene)amino)oxy)cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (218 mg, 0.39 mmol) in DCM (5 mL) and DMF (1 ml) at 0° C. was added DIPEA (0.11 mL, 0.61 mmol), HATU (170 mg, 0.446 mmol), and (3S,4R)-3-amino-4-((4-(hydroxymethyl)-2H-1,2,3-triazol-2-yl)methyl)azetidin-2-one (80 mg, 0.41 mmol). After stirring at 0° C. for 1 h, the reaction mixture was diluted with DCM, washed with water, brine, dried over Na$_2$SO$_4$ and concentrated in vacuo. The crude residue was purified via silica gel chromatography (MeOH-DCM, 0-5%), affording the title compound (250 mg, 86%). LCMS: Rt=0.98 min, m/z=717.3 (M+1). Method 2m_acidic.

Step 2: Benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate To a solution of benzhydryl 1-(((Z)-(1-(2-((tert-butoxycarbonyl)amino)thiazol-4-yl)-2-(((2R,3S)-2-((4-(hydroxymethyl)-2H-1,2,3-triazol-2-yl)methyl)-4-oxoazetidin-3-yl)amino)-2-oxoethylidene)amino)oxy)cyclopropanecarboxylate (440 mg, 0.614 mmol) in THF (4 mL) was added MnO$_2$ (1.2 g, 13.51 mmol). After stirring at rt for 20 h, the reaction mixture was filtered through a pad of celite with THF wash (20 mL). The filtrate was concentrated, and the residue was purified via silica gel chromatography (MeOH-DCM, 0-5%) to afford the title compound (300 mg, 68%). LCMS: $R_t$=1.04 min, m/z=715.3 (M+H). Method 2m_acidic.

Step 3: Tert-butyl 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)amino)methyl)azetidine-1-carboxylate To a solution of benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate (150 mg, 0.21 mmol) in DCE (4 ml) at 0° C. was added tert-butyl 3-(aminomethyl)azetidine-1-carboxylate (78 mg, 0.420 mmol), sodium triacetoxyborohydride (66.7 mg, 0.315 mmol), and DMF (0.4 mL). After stirring at rt for 3 h, the reaction mixture was quenched with saturated NaHCO$_3$ (aq) and diluted with 10% EtOH/DCM (40 mL). The organic layer was separated, dried with Na$_2$SO$_4$, filtered and concentrated in vacuo. The crude residue was used as such in the following step. LCMS: R$_t$=0.55 min, m/z=885.5 (M+1). Method 2m_acidic.

Step 4: Tert-butyl 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)(tert-butoxycarbonyl)amino)methyl)azetidine-1-carboxylate To a solution of tert-butyl 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)amino)methyl)azetidine-1-carboxylate (186 mg, 0.21 mmol) and saturated NaHCO$_3$ (aq, 4 ml, 0.210 mmol) in DCM (4 mL) was added Boc$_2$O (137 mg, 0.630 mmol). After stirring at rt for 12 h, the reaction mixture layers were separated. The aqueous layer was extracted with DCM, and the combined organic layers were washed with brine, dried over Na$_2$SO$_4$, filtered and concentrated in vacuo. The crude residue was purified by silica gel chromatography (EtOAc-Hept, 50-80%) to afford the title compound (120 mg, 58%). LCMS: R$_t$=1.24 min, m/z=985.7 (M+1). Method 2m_acidic.

Step 5: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)((1-(tert-butoxycarbonyl)azetidin-3-yl)methyl)amino)methyl)-2H-1,2,3-triazol-2-yl)methyl)-4-oxoazetidine-1-sulfonic acid Prepared in analogous manner to example 19 step 3, using tert-butyl 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)(tert-butoxycarbonyl)amino)methyl)azetidine-1-carboxylate (120 mg, 0.122 mmol), SO$_3$.DMF (192 mg, 1.22 mmol), and DMF (1.2 mL). The crude residue was used as such in the following step. LCMS: R$_t$=1.12 min, m/z=1065.7 (M+1). Method 2m_acidic.

Step 6: 1-(((Z)-(1-(2-aminothiazol-4-yl)-2-(((2R,3S)-2-((4-(((azetidin-3-ylmethyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid

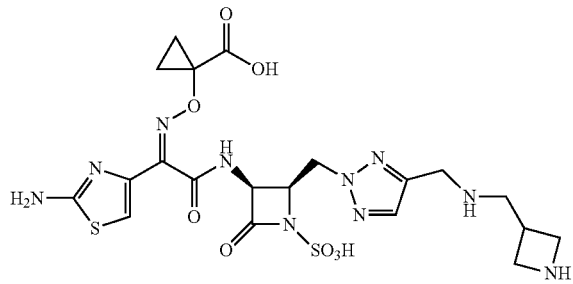 [SMILES: Nc1nc(/C(=N/OC2(C(=O)O)CC2)C(=O)N[C@@H]2C(=O)N(S(=O)(=O)O)[C@@H]2Cn2ncc(CNCC3CNC3)n2)cs1]

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)((1-(tert-butoxycarbonyl)azetidin-3-yl)methyl)amino)methyl)-2H-1,2,3-triazol-2-yl)methyl)-4-oxoazetidine-1-sulfonic acid (130 mg, 0.122 mmol), TFA (0.56 mL, 7.32 mmol), and DCM (1.5 mL). 6.3 mg. LCMS: R$_t$=0.47 min, m/z=599.3 (M+1). Method 2m_acidic_polar. $^1$H NMR (400 MHz, D$_2$O) δ 7.82 (s, 1H), 7.10 (s, 1H), 5.61 (d, J=5.9 Hz, 1H), 5.01 (q, J=5.6 Hz, 1H), 4.95-4.85 (m, 2H), 4.36 (s, 2H), 4.26-4.15 (m, 2H) 4.11-3.97 (m, 2H), 3.46-3.30 (m, 3H), 1.26 (s, 2H), 1.20-1.05 (m, 2H).

Example 86

2-(((Z)-(2-(((2R,3S)-2-(((R)-3-amino-2-oxopyrrolidin-1-yl)methyl)-4-oxo-1-sulfoazetidin-3-yl)amino)-1-(2-aminothiazol-4-yl)-2-oxoethylidene)amino)oxy)-2-methylpropanoic acid

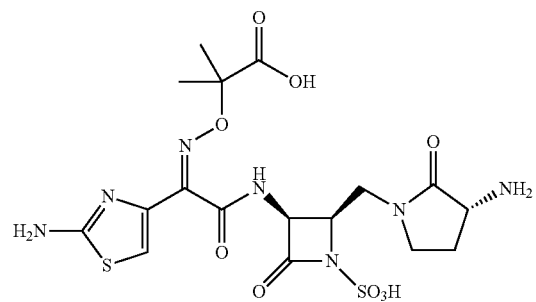 [SMILES: CC(C)(O/N=C(\C(=O)N[C@@H]1C(=O)N(S(=O)(=O)O)[C@@H]1CN1CC[C@@H](N)C1=O)c1csc(N)n1)C(=O)O]

Prepared in analogous manner to example 76, using (R)-methyl 4-bromo-2-((tert-butoxycarbonyl)amino)butanoate. LCMS: m/z=532.0 (M−1); $^1$H NMR (400 MHz, D$_2$O): δ 6.96 (s, 1H), 5.28 (d, J=6.0 Hz, 1H), 4.53 (m, 1H), 3.96 (t, J=10.0 & 9.2 Hz, 1H), 3.85 (dd, J=10.4 & 10.0 Hz, 1H), 3.58 (m, 1H), 3.44 (m, 1H), 3.31 (dd, 1H), 2.47 (m, 1H), 1.96 (m, 1H), 1.34 (s, 3H), 1.34 (s, 3H).

Example 87

2-(((Z)-(1-(2-aminothiazol-4-yl)-2-oxo-2-(((3S,4R)-2-oxo-4-((2-oxo-2,3-dihydro-1H-imidazol-1-yl)methyl)-1-sulfoazetidin-3-yl)amino)ethylidene)amino)oxy)-2-methylpropanoic acid Step 1: Benzyl ((2R,3S)-1-(2,4-dimethoxybenzyl)-2-((2,5-dioxoimidazolidin-1-yl)methyl)-4-oxoazetidin-3-yl)carbamate The general procedure for the Mitsunobu reaction was followed using intermediate G (10.0 g, 25 mmol), imidazolidine-2,4-dione (2.5 g, 25 mmol), triphenylphosphine (7.9 g, 30 mmol), DIAD (6.1 g, 30 mmol) and THF (200 mL). The resulting precipitate (8.3 g, 69%) which was slightly contaminated with triphenylphosphine oxide, was collected by filtration. LCMS: m/z=481.0 (M−1).

Step 2: tert-Butyl 3-(((2R,3S)-3-(((benzyloxy)carbonyl)amino)-1-(2,4-dimethoxybenzyl)-4-oxoazetidin-2-yl)methyl)-2,4-dioxoimidazolidine-1-carboxylate To a solution of benzyl ((2R,3S)-1-(2,4-dimethoxybenzyl)-2-((2,5-dioxoimidazolidin-1-yl)methyl)-4-oxoazetidin- 3-yl)carbamate (4.60 g, 9.54 mmol) and di-tert-butyldicarbonate (2.30 g, 10.5 mmol) in DCM (55 mL) was added DMAP (0.150 g, 1.33 mmol). After 3 h at rt, water was added, whereupon the layers were separated. The organic layer was dried over $Na_2SO_4$ and concentrated in vacuo. The crude residue was purified via silica gel chromatography, affording the title compound (4.20 g, 75%).

Step 3: tert-Butyl 3-(((2R,3S)-3-(((benzyloxy)carbonyl)amino)-4-oxoazetidin-2-yl)methyl)-2,4-dioxoimidazolidine-1-carboxylate Prepared in an analogous manner to example 4, step 2 using tert-butyl 3-(((2R,3S)-3-(((benzyloxy)carbonyl)amino)-1-(2,4-dimethoxybenzyl)-4-oxoazetidin-2-yl)methyl)-2,4-dioxoimidazolidine-1-carboxylate (900 mg, 1.70 mmol) $K_2S_2O_8$ (280 mg, 2.89 mmol), and $K_2HPO_4$ (680 mg, 2.91 mmol) in ACN:water (2:1, 30 mL) while heating at 90° C. for 4 h. After cooling to rt, the mixture was filtered and the filtrate was concentrated in vacuo, removing most of the ACN. The mixture was diluted with water/EtOAc and the layers were separated. The aqueous layer was extracted with EtOAc and the combined organic layers were dried over $Na_2SO_4$ and concentrated in vacuo. The crude residue was purified via silica gel chromatography (MeOH-DCM, 2-6%) to afford the title compound (170 mg, 23%). LCMS: m/z=431.0 (M−1).

Step 4: tert-Butyl 3-(((2R,3S)-3-(((benzyloxy)carbonyl)amino)-4-oxoazetidin-2-yl)methyl)-4-hydroxy-2-oxoimidazolidine-1-carboxylate To a solution of tert-butyl 3-(((2R,3S)-3-(((benzyloxy)carbonyl)amino)-4-oxoazetidin-2-yl)methyl)-2,4-dioxoimidazolidine-1-carboxylate (170 mg, 0.390 mmol) in EtOH (10 mL) at 0° C. was added sodium borohydride (30 mg, 0.78 mmol). After 3 h at 0° C., the mixture was quenched with saturated $NH_4Cl$ (aq) and partially concentrated in vacuo. The bilayer was extracted with DCM and the organic layer was dried over $Na_2SO_4$ and concentrated in vacuo. The resulting residue was used as such in step 5. LCMS: m/z=457.1 (M+Na).

Step 5: tert-Butyl 3-(((2R,3S)-3-(((benzyloxy)carbonyl)amino)-4-oxoazetidin-2-yl)methyl)-2-oxo-2,3-dihydro-1H-imidazole-1-carboxylate To a solution of tert-butyl 3-(((2R,3S)-3-(((benzyloxy)carbonyl)amino)-4-oxoazetidin-2-yl)methyl)-4-hydroxy-2-oxoimidazolidine-1-carboxylate (160 mg, 0.368 mmol) in DCM (5 mL) at 0° C. was added methanesulfonyl chloride (31 µL, 0.41 mmol) followed by TEA (0.15 mL, 1.1 mmol). After stirring for 1 h at 0° C., the solution was concentrated in vacuo and purified via silica gel chromatography (MeOH-DCM, 2-5%), affording the title compound (100 mg, 65%). LCMS: m/z=415.1 (M−1); $^1$H NMR (400 MHz, $CDCl_3$): δ 8.02 (s, 1H), 7.41-7.27 (m, 5H), 7.06 (d, J=8.4 Hz, 1H), 6.61 (d, J=3.2 Hz, 1H), 6.15 (d, J=3.2 Hz, 1H), 5.21-5.09 (m, 3H), 4.30 (dd, J=14.4, 9.6 Hz, 1H), 4.01-3.94 (m, 1H), 3.49 (dd, J=14.8, 3.2 Hz, 1H), 1.46 (s, 9H).

Step 6: tert-Butyl 3-(((2R,3S)-3-amino-4-oxoazetidin-2-yl)methyl)-2-oxo-2,3-dihydro-1H-imidazole-1-carboxylate A mixture of tert-Butyl 3-(((2R,3S)-3-(((benzyloxy)carbonyl)amino)-4-oxoazetidin-2-yl)methyl)-2-oxo-2,3-dihydro-1H-imidazole-1-carboxylate (490 mg, 1.18 mmol) and Palladium on carbon (10% wt, 140 mg) in MeOH (60 mL) was evacuated and backfilled with $H_2$ (3×), bringing the final pressure up to 30 psi. After 2 h of stirring, the mixture was filtered through celite and concentrated in vacuo. The crude residue was purified via silica gel chromatography (MeOH-DCM, 6%), affording the title compound (50 mg, 25%).

Step 7: tert-Butyl 3-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidin-2-yl)methyl)-2-oxo-2,3-dihydro-1H-imidazole-1-carboxylate Prepared in analogous manner to example 4 step 4, using (Z)-2-(((1-(tert-butoxy)-2-methyl-1-oxopropan-2-yl)oxy)imino)-2-(2-((tert-butoxycarbonyl)amino)thiazol-4-yl)acetic acid (117 mg, 0.276 mmol), HATU (105 mg, 0.276 mmol), DIPEA (36 mg, 0.28 mmol), tert-butyl 3-(((2R,3S)-3-amino-4-oxoazetidin-2-yl)methyl)-2-oxo-2,3-dihydro-1H-imidazole-1-carboxylate (65 mg, 0.23 mmol) and DMF (5 mL). The crude residue was purified via silica gel chromatography (MeOH-DCM, 3%), affording the title compound (140 mg, 88%). LCMS: m/z=694.0 (M+1).

Step 8: (2R,3S)-3-((Z)-2-(((1-(tert-Butoxy)-2-methyl-1-oxopropan-2-yl)oxy)imino)-2-(2-((tert-butoxycarbonyl)amino)thiazol-4-yl)acetamido)-2-((3-(tert-butoxycarbonyl)-2-oxo-2,3-dihydro-1H-imidazol-1-yl)methyl)-4-oxoazetidine-1-sulfonic acid To a solution of tert-butyl 3-(((2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-4-oxoazetidin-2-yl)methyl)-2-oxo-2,3-dihydro-1H-imidazole-1-carboxylate (140 mg, 0.202 mmol) in DMF (1.0 mL) was added $SO_3$.DMF (185 mg, 1.21 mmol). After 4 h at rt, the solution was concentrated in vacuo and purified over HP21 resin (ACN-water, 10-50%), affording the title compound (90 mg, 58%). LCMS: m/z=772.3 (M−1).

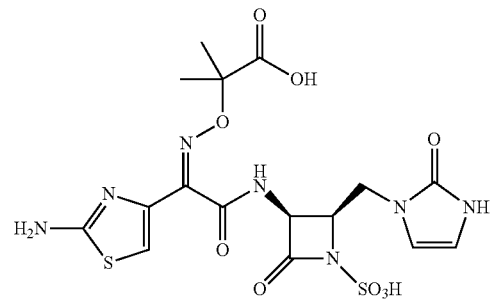 [SMILES: CC(C)(O/N=C(\C(=O)N[C@@H]1C(=O)N(S(=O)(=O)O)[C@@H]1Cn1cc[nH]c1=O)c1csc(N)n1)C(=O)O]

Step 9: 2-(((Z)-(1-(2-aminothiazol-4-yl)-2-oxo-2-(((3S,4R)-2-oxo-4-((2-oxo-2,3-dihydro-1H-imidazol-1-yl)methyl)-1-sulfoazetidin-3-yl)amino)ethylidene)amino)oxy)-2-methylpropanoic acid Followed the general procedure for the acid mediated deprotection using tert-butyl 3-(((2R,3S)-3-amino-4-oxoazetidin-2-yl)methyl)-2-oxo-2,3-dihydro-1H-imidazole-1-carboxylate (prepared from tert-butyl 3-(((2R,3S)-3-(((benzyloxy)carbonyl)amino)-4-oxoazetidin-2-yl)methyl)-2,4- dioxoimidazolidine-1-carboxylate) (90 mg, 1.16 mmol), TFA (0.5 mL, 6.4 mmol) and DCM (1.5 mL). The crude residue was purified via reverse phase prep HPLC (XSelect CSH, 30×100 mm, 5 μm, C18 column; ACN-water with 0.1% formic acid modifier, 60 mL/min) to afford the title compound (15.6 mg, 60%) as an off-white solid. LCMS: m/z=516.0 (M−1); $^1$H NMR (400 MHz, D$_2$O): δ 6.98 (s, 1H), 6.41 (d, J=2.8 Hz, 1H), 6.30 (d, J=2.8 Hz, 1H), 5.30 (d, J=6.0 Hz, 1H), 4.54-4.52 (m, 1H), 4.00-3.95 (m, 1H), 3.84-3.79 (m, 1H), 1.35 (s, 3H), 1.34 (s, 3H).

Example 88

2-(((Z)-(1-(2-aminothiazol-4-yl)-2-(((2R,3S)-2-(((R)-3-guanidino-2-oxopyrrolidin-1-yl)methyl)-4-oxo-1-sulfoazetidin-3-yl)amino)-2-oxoethylidene)amino)oxy)-2-methylpropanoic acid

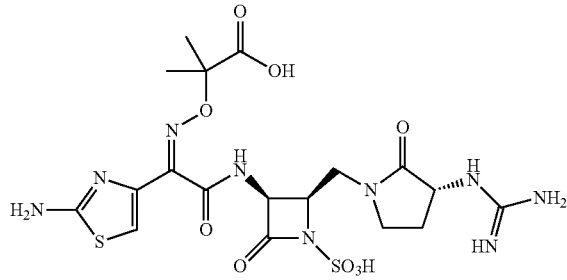

Prepared in analogous manner to example 20, using 2-(((Z)-(2-(((2R,3S)-2-(((R)-3-amino-2-oxopyrrolidin-1-yl)methyl)-4-oxo-1-sulfoazetidin-3-yl)amino)-1-(2-aminothiazol-4-yl)-2-oxoethylidene)amino)oxy)-2-methylpropanoic acid and 1H-pyrazole-1-carboximidamide HCl. LCMS: m/z=574.1 (M−1); $^1$H NMR (400 MHz, D$_2$O): δ 6.93 (s, 1H), 5.28 (d, J=5.6 Hz, 1H), 4.53 (m, 1H), 4.24 (t, J=9.6 & 9.2 Hz, 1H), 3.85 (dd, J=9.2 & 9.2 Hz, 1H), 3.51 (m, 1H), 3.40 (t, J=9.2 & 8.8 Hz, 1H), 3.32 (dd, 1H), 3.34 (dd, 1H), 2.43 (m, 1H), 1.87 (m, 1H), 1.36 (s, 3H), 1.32 (s, 3H).

Example 89

1-(((Z)-(1-(2-aminothiazol-4-yl)-2-oxo-2-(((3S,4R)-2-oxo-4-((4-(((R)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid

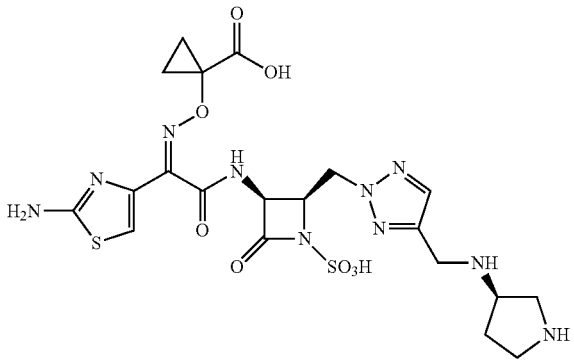

Prepared in analogous manner to example 85, using (R)-tert-butyl 3-aminopyrrolidine-1-carboxylate. LCMS: R$_t$=0.46 min, m/z=599.3 (M+1) Method 2m_acidic_polar; $^1$H NMR (400 MHz, D$_2$O): δ 7.86 (s, 1H), 7.16 (s, 1H), 5.60 (d, J=5.5 Hz, 1H), 4.99 (s, 1H), 4.90 (d, J=3.9 Hz, 2H), 4.46 (d, J=5.1 Hz, 2H), 4.20-4.14 (m, 1H), 3.82 (dd, J=13.1, 8.0 Hz, 1H), 3.65-3.38 (m, 2H), 2.67-2.57 (m, 1H), 2.31-2.20 (m, 1H), 1.34 (t, J=4.3 Hz, 3H), 1.25-1.19 (m, 2H).

Example 90

1-(((Z)-(2-(((2R,3S)-2-((4-(((3-aminopropyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: Benzhydryl 1-(((Z)-(1-(2-((tert-butoxycarbonyl)amino)thiazol-4-yl)-2-(((2R,3S)-2-((4-(hydroxymethyl)-2H-1,2,3-triazol-2-yl)methyl)-4-oxoazetidin-3-yl)amino)-2-oxoethylidene)amino)oxy)cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (2.5 g, 4.43 mmol) in DCM (78 mL) and DMF (15 ml) at 0° C. was added DIPEA (1.2 ml, 7.00 mmol), HATU (1.9 g, 5.13 mmol), and (3S,4R)-3-amino-4-((4-(hydroxymethyl)-2H-1,2,3-triazol-2-yl)methyl)azetidin-2-one (0.92 g, 4.67 mmol). After stirring at 0° C. for 1 h, the reaction mixture was diluted with DCM, washed with water, brine, dried over Na$_2$SO$_4$ and concentrated in vacuo. The crude residue was purified via silica gel chromatography (MeOH-DCM, 0-5%), affording the title compound (2.5 g, 75%). LCMS: R=0.98 min, m/z=717.3 (M+1) Method 2m_acidic.

Step 2: Benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate To a solution of benzhydryl 1-(((Z)-(1-(2-((tert-butoxycarbonyl)amino)thiazol-4-yl)-2-(((2R,3S)-2-((4-(hydroxymethyl)-2H-1,2,3-triazol-2-yl)methyl)-4-oxoazetidin-3-yl)amino)-2-oxoethylidene)amino)oxy)cyclopropanecarboxylate (1.8 g, 2.57 mmol) in THF (21 ml) was added MnO$_2$ (4.9 g, 56.5 mmol). After stirring at rt for 20 h, the reaction mixture was filtered through a pad of celite with THF wash (250 mL). The filtrate was concentrated, and the residue was purified via silica gel chromatography (MeOH-DCM, 0-5%) to afford the title compound (1.4 g, 76%). LCMS: R$_t$=1.04 min, m/z=715.3 (M+H). Method 2m_acidic.

Step 3: Benzhydryl 1-(((Z)-2-(((2R,3S)-2-((4-(((3-((tert-butoxycarbonyl)amino)propyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate (370 mg, 0.52 mmol) in DCE (4 mL) at 0° C. was added tert-butyl(3-aminopropyl)carbamate (180 mg, 1.04 mmol) and sodium triacetoxyhydroborate (165 mg, 0.78 mmol) sequentially. After stirring at rt for 16 h, the reaction mixture was diluted with DCM, washed with saturated NaHCO$_3$ (aq), brine, dried over Na$_2$SO$_4$, filtered and concentrated in vacuo to give the title compound (assumed quantitative). The crude residue was used as such in the following step. LCMS: R$_t$=0.99 min, m/z=873.2 (M+1). Method 2m_acidic.

Step 4: Benzhydryl 1-(((Z)-2-(((2R,3S)-2-((4-(((tert-butoxycarbonyl)(3-((tert-butoxycarbonyl)amino)propyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-2-(((2R,3S)-2-((4-(((3-((tert-butoxycarbonyl)amino)propyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (0.45 g, 0.52 mmol) in DMF (6 mL) at 0° C. was added Boc-anhydride (0.24 mL, 1.04 mmol). After stirring at rt for 18 h, DIPEA (0.18 mL, 1.04 mmol) was added. After stirring for 36 h, the reaction mixture was poured into water and extracted with DCM. Combined organic layers were washed with 5% LiCl, brine, dried over Na$_2$SO$_4$, filtered and concentrated in vacuo. The crude residue was purified via silica gel chromatography (EtOAc-Heptane, 0-60%) to afford the title compound (0.40 g, 80%). LCMS: R$_t$=1.26 min, m/z=973.3 (M+H). Method 2m_acidic.

Step 5: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)(3-((tert-butoxycarbonyl)amino)propyl)amino)methyl)-2H-1,2,3-triazol-2-yl)methyl)-4-oxoazetidine-1-sulfonic acid To a solution of benzhydryl 1-(((Z)-2-(((2R,3S)-2-((4-(((tert-butoxycarbonyl)(3-((tert-butoxycarbonyl)amino)propyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (0.40 g, 0.41 mmol) in DMF (5 mL) at 0° C. was added SO$_3$.DMF (0.63 g, 4.12 mmol). After stirring at rt for 1 h, the reaction mixture was diluted with EtOAc, washed with 5% LiC (aq), brine, dried over Na$_2$SO$_4$, filtered and concentrated in vacuo to give the title compound (0.42 g, 97%). LCMS: R$_t$=1.10 min, m/z=1053.6 (M+H). Method 2m_acidic.

Step 6: 1-(((Z)-(2-(((2R,3S)-2-((4-(((3-aminopropyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

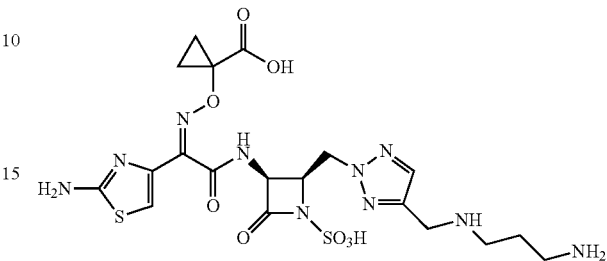

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)(3-((tert-butoxycarbonyl)amino)propyl)amino)methyl)-2H-1,2,3-triazol-2-yl)methyl)-4-oxoazetidine-1-sulfonic acid (0.5 g, 0.48 mmol), DCM (2.5 mL), and TFA (1 mL, 13 mmol) for 1.5 h. The crude residue was purified by reverse phase prep HPLC (XSelect CSH, 30×100 mm, C18 column; ACN-water with 0.1% formic acid modifier, 60 mL/min) affording the title compound (123 mg, 42%). LCMS: R$_t$=0.31 min, m/z=587.2 (M+1) Method 2m_acidic; $^1$H NMR (400 MHz, DMSO-d$_6$): δ 9.39 (br s, 1H), 7.76 (s, 1H), 7.22 (s, 2H), 6.73 (s, 1H), 5.33 (dd, J=9.0, 5.5 Hz, 1H), 4.84 (dd, J=14.3, 4.5 Hz, 1H), 4.73-4.61 (m, 1H), 4.61-4.48 (m, 1H), 4.27-4.14 (m, 2H), 3.02-2.89 (m, 3H), 2.85 (t, J=7.4 Hz, 3H), 1.85 (p, J=7.5 Hz, 3H) 1.32-1.04 (m, 6H); $^1$H NMR (400 MHz, D$_2$O) δ 7.90 (s, 1H), 7.15 (s, 1H), 5.67 (d, J=5.5 Hz, 1H), 5.12-5.04 (m, 1H), 5.04-4.88 (m, 2H), 4.45 (s, 2H), 3.30-3.22 (m, 2H), 3.16 (t, J=7.6 Hz, 2H), 2.24-2.08 (m, 2H), 1.37-1.26 (m, 2H), 1.26-1.08 (m, 2H).

Example 91

1-(((Z)-(1-(2-aminothiazol-4-yl)-2-oxo-2-(((3S,4R)-2-oxo-4-((4-(((S)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid

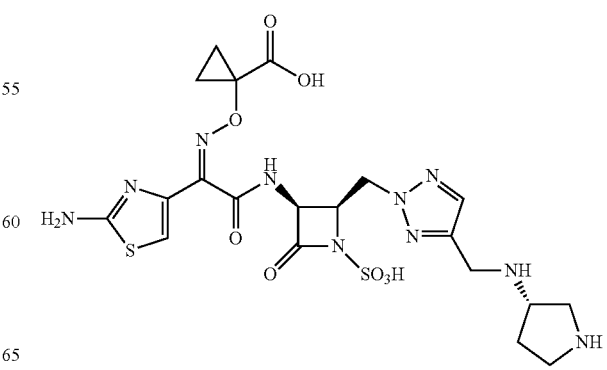

Prepared in analogous manner to example 90, using (S)-tert-butyl 3-aminopyrrolidine-1-carboxylate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_t$=0.3 min, m/z=599.0 (M+1) Method 2m_acidic; $^1$H NMR (400 MHz, DMSO-$d_6$): δ 9.18 (d, J=9.0 Hz, 1H), 9.04-8.59 (m, 2H), 7.79 (s, 1H), 7.24 (br s, 2H), 6.72 (s, 1H), 5.35 (dd, J=9.0, 5.5 Hz, 1H), 4.93-4.81 (m, 1H), 4.68-4.60 (m, 1H), 4.55 (s, 1H), 4.24 (br s, 2H), 3.95-3.79 (m, 1H), 2.27-2.11 (m, 1H), 2.04-1.90 (m, 1H), 1.38-1.06 (m, 4H).

Example 92

1-(((Z)-(2-(((2R,3S)-2-((4-((3-(aminomethyl)azetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

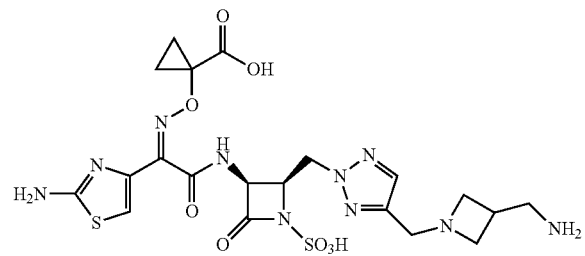 [SMILES: NCC1CN(Cc2cnn(C[C@@H]3[C@H](NC(=O)/C(=N\OC4(C(=O)O)CC4)c4csc(N)n4)C(=O)N3S(=O)(=O)O)n2)C1]

Prepared in analogous manner to example 90, using tert-butyl (azetidin-3-ylmethyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_t$=0.46 min, m/z=599.4 (M+1) Method 2m_acidic; $^1$H NMR (400 MHz, $D_2O$): δ 7.84 (s, 1H) 7.11 (s, 1H) 5.56 (d, J=5.5 Hz, 1H) 5.00 (m, 1H) 4.89 (m, 2H) 4.52 (s, 2H) 4.35 (m, 2H) 4.23-4.03 (m, 2H) 3.38-3.21 (m, 3H) 1.31 (m, 2H) 1.18 (m, 2H).

Example 93

1-(((Z)-(2-(((2R,3S)-2-((4-((((1r,3R)-3-aminocyclobutyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

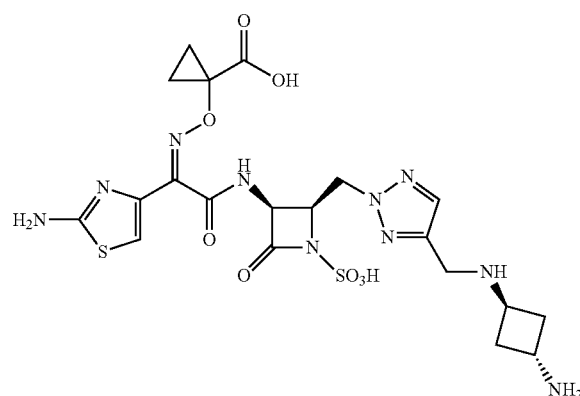

Prepared in analogous manner to example 90, using tert-butyl ((1r,3r)-3-aminocyclobutyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_t$=0.46 min, m/z=599.3 (M+1) Method 2m_acidic; $^1$H NMR (400 MHz, $D_2O$): δ 7.82 (s, 1H), 7.09 (s, 1H), 5.58 (d, J=5.9 Hz, 1H), 5.04-4.84 (m, 3H), 4.31 (s, 2H), 4.14-4.00 (m, 2H), 2.81-2.60 (m, 4H) 1.26 (s, 2H), 1.19-1.06 (m, 2H).

Example 94

(((Z)-(1-(5-amino-1,2,4-thiadiazol-3-yl)-2-(((2R,3S)-2-((4-(((3-aminopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid

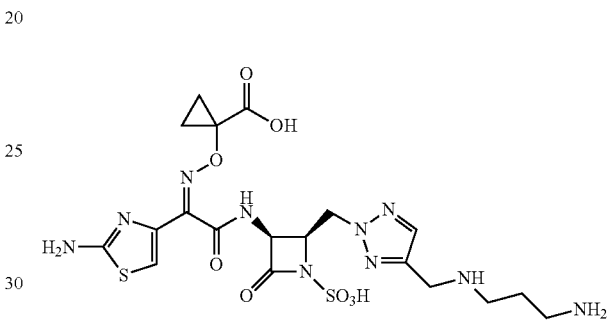

Prepared in analogous manner to example 90, using (Z)-2-((1-((benzhydryloxy)carbonyl)cyclopropoxy)imino)-2-(5-((tert-butoxycarbonyl)amino)-1,2,4-thiadiazol-3-yl)acetic acid. LCMS: $R_t$=0.29 min, m/z=588.0 (M+1) Method 2m_acidic; $^1$H NMR (400 MHz, DMSO-$d_6$): δ 9.53-9.29 (m, 1H), 8.15 (s, 2H), 7.75 (s, 1H) 5.40-5.28 (m, 1H), 4.82-4.69 (m, 1H), 4.63 (s, 2H), 4.21 (d, J=5.1 Hz, 2H), 3.00-2.91 (m, 2H), 2.85 (s, 2H), 1.91-1.74 (m, 2H), 1.37-1.04 (m, 4H).

Example 95

1-(((Z)-(1-(2-aminothiazol-4-yl)-2-(((2R,3S)-2-((2,4-dioxooxazolidin-3-yl)methyl)-4-oxo-1-sulfoazetidin-3-yl)amino)-2-oxoethylidene)amino)oxy)cyclopropanecarboxylic acid

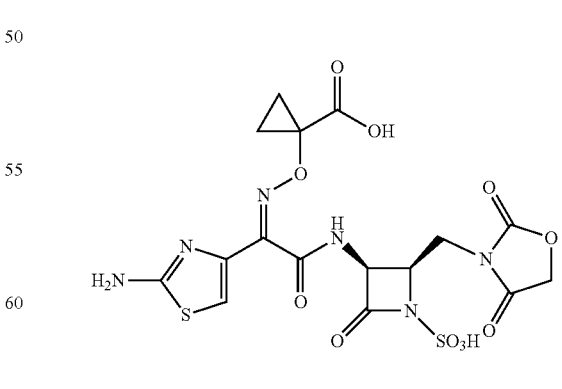

Prepared in analogous manner to example 54, using benzhydryl 1-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)

cyclopropanecarboxylate and oxazolidine-2,4-dione. LCMS: R=0.31 min, m/z=533.0 (M+1) Method 2m_acidic; $^1$H NMR (400 MHz, D$_2$O) δ 7.23 (s, 1H), 5.42 (d, J=5.9 Hz, 1H), 4.86-4.83 (m, 3H), 4.07 (dd, J=14.5, 9.8 Hz, 1H), 3.72 (dd, J=14.5, 3.9 Hz, 1H), 1.58-1.52 (m, 2H), 1.51-1.45 (m, 2H).

Example 96

1-(((Z)-(2-(((2R,3S)-2-((5-(((3-aminopropyl)amino)methyl)-2H-tetrazol-2-yl)methyl)-4-oxo-1-sulfoazetidin-3-yl)amino)-1-(2-aminothiazol-4-yl)-2-oxoethylidene)amino)oxy)cyclopropanecarboxylic acid

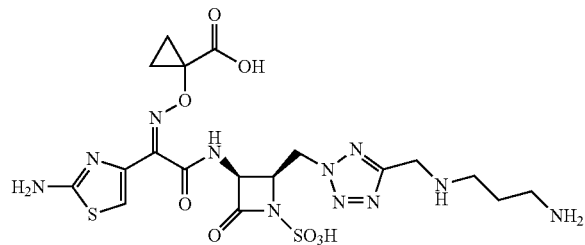 [SMILES: NCCCNCc1nnn(C[C@@H]2[C@H](NC(=O)/C(=N\OC3(C(=O)O)CC3)c3csc(N)n3)C(=O)N2S(=O)(=O)O)n1]

Prepared in analogous manner to procedures described in examples 54 and 90, using benzhydryl 1-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)cyclopropanecarboxylate and 5-(((tert-butyldimethylsilyl)oxy)methyl)-2H-tetrazole. LCMS: R$_t$=0.31 min, m/z=588.4 (M+1) Method 2m_acidic; $^1$H NMR (400 MHz, DMSO-d$_6$) δ 9.41 (br s, 1H), 7.78 (s, 1H), 7.24 (s, 1H), 6.75 (s, 1H), 5.38-5.32 (m, 1H), 4.86 (dd, J=14.3, 4.5 Hz, 1H), 4.72-4.63 (m, 1H), 4.61-4.55 (m, 1H), 4.28-4.16 (m, 1H), 3.01-2.94 (m, 1H), 2.87 (t, J=7.4 Hz, 1H), 1.92-1.82 (m, 1H), 1.33-1.18 (m, 2H), 1.18-1.08 (m, 1H).

Example 97

1-(((Z)-(2-(((2R,3S)-2-(((R)-5-(((2-aminoethyl)amino)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid

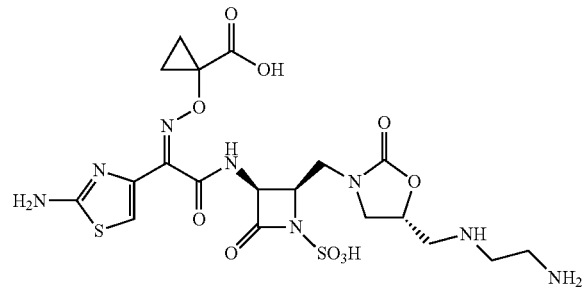 [SMILES: NCCNC[C@@H]1CN(C[C@@H]2[C@H](NC(=O)/C(=N\OC3(C(=O)O)CC3)c3csc(N)n3)C(=O)N2S(=O)(=O)O)C(=O)O1]

Prepared in an analogous manner to example 26, using tert-butyl(2-bromoethyl)carbamate. LCMS: R$_t$=0.380 min, m/z=591.1 (M+1) Method 2m_acidic; $^1$H NMR (400 MHz, D$_2$O) δ 6.93 (s, 1H), 5.28 (d, J=5.8 Hz, 1H), 3.85 (t, J=9.3 Hz, 1H), 3.68 (dd, J=15.0, 8.1 Hz, 1H), 3.46-3.36 (m, 2H), 3.25-3.01 (m, 5H), 2.60 (s, 1H), 1.30-1.21 (m, 2H), 1.18-1.09 (m, 2H).

Example 98

2-(((Z)-(1-(2-aminothiazol-4-yl)-2-(((2R,3S)-2-((4-methyl-5-oxo-4,5-dihydro-1H-1,2,4-triazol-1-yl)methyl)-4-oxo-1-sulfoazetidin-3-yl)amino)-2-oxoethylidene)amino)oxy)-2-methylpropanoic acid

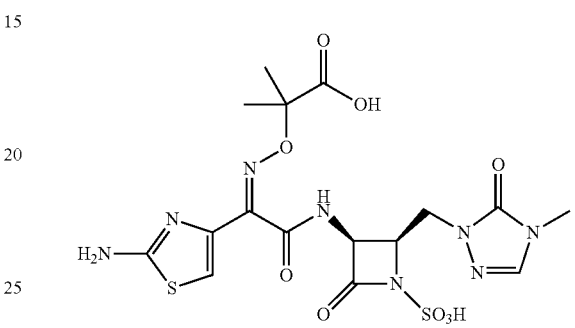

Prepared in analogous manner to example 31, using 1-(((2R,3S)-3-amino-4-oxoazetidin-2-yl)methyl)-4-methyl-1H-1,2,4-triazol-5(4H)-one and (Z)-2-(((1-(tert-butoxy)-2-methyl-1-oxopropan-2-yl)oxy)imino)-2-(2-((tert-butoxycarbonyl)amino)thiazol-4-yl)acetic acid. LCMS: m/z=531.0 (M−1); $^1$H NMR (400 MHz, D$_2$O): δ 7.67 (s, 1H), 7.02 (s, 1H), 5.36 (d, J=5.6 Hz, 1H), 4.70-4.60 (m, 1H, partially obscured by solvent residual peak), 4.14 (dd, J=15.2 and 7.6 Hz, 1H), 3.96 (dd, J=15.2 and 4.8 Hz, 1H), 3.14 (s, 3H), 1.37 (s, 3H), 1.35 (s, 3H).

Example 99

2-(((Z)-(1-(2-aminothiazol-4-yl)-2-(((2R,3S)-2-((4-((dimethylamino)methyl)-2H-1,2,3-triazol-2-yl)methyl)-4-oxo-1-sulfoazetidin-3-yl)amino)-2-oxoethylidene)amino)oxy)-2-methylpropanoic acid

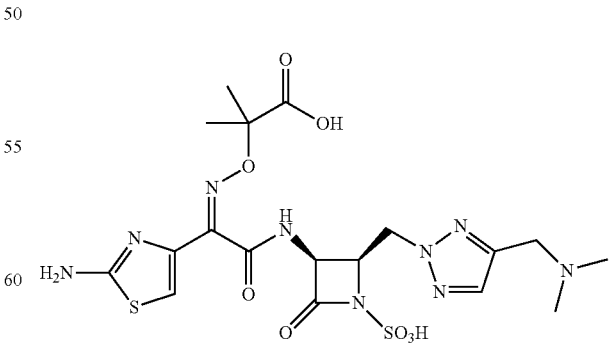

Prepared in analogous manner to example 54, using N,N-dimethyl-1-(2H-1,2,3-triazol-4-yl)methanamine. LCMS: m/z=560.2 (M+1); $^1$H NMR (400 MHz, D$_2$O) δ 7.80 (s, 1H), 6.98 (s, 1H), 5.43 (d, J=4.8 Hz, 1H), 4.94-4.88 (m, 1H), 4.85-4.80 (m, 2H), 4.32 (s, 2H), 2.75 (s, 6H), 1.28 (s, 6H).

Example 100

2-(((Z)-(1-(2-aminothiazol-4-yl)-2-(((2R,3S)-2-((4-((methylamino)methyl)-2H-1,2,3-triazol-2-yl)methyl)-4-oxo-1-sulfoazetidin-3-yl)amino)-2-oxoethylidene)amino)oxy)-2-methylpropanoic acid

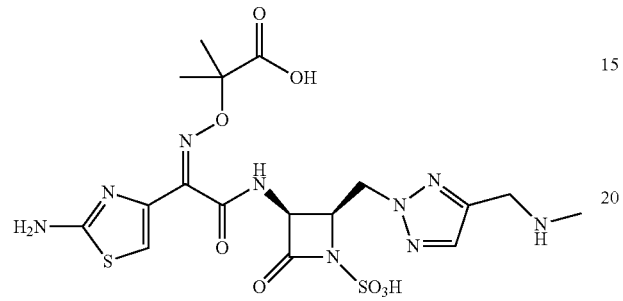

Prepared in analogous manner to example 54, using tert-butyl ((2H-1,2,3-triazol-4-yl)methyl)(methyl)carbamate. LCMS: m/z=544.1 [M−H]−; 1H NMR (400 MHz, D2O) δ 7.73 (s, 1H), 7.02 (s, 1H), 5.42 (d, J=5.6 Hz, 1H), 4.92-4.86 (m, 1H), 4.82-4.78 (m, 2H), 4.22 (s, 2H), 2.60 (s, 3H), 1.30 (s, 6H).

Example 101

2-(((Z)-(2-(((2R,3S)-2-((1-(2-aminoethyl)-1H-1,2,3-triazol-4-yl)methyl)-4-oxo-1-sulfoazetidin-3-yl)amino)-1-(2-aminothiazol-4-yl)-2-oxoethylidene)amino)oxy)-2-methylpropanoic acid

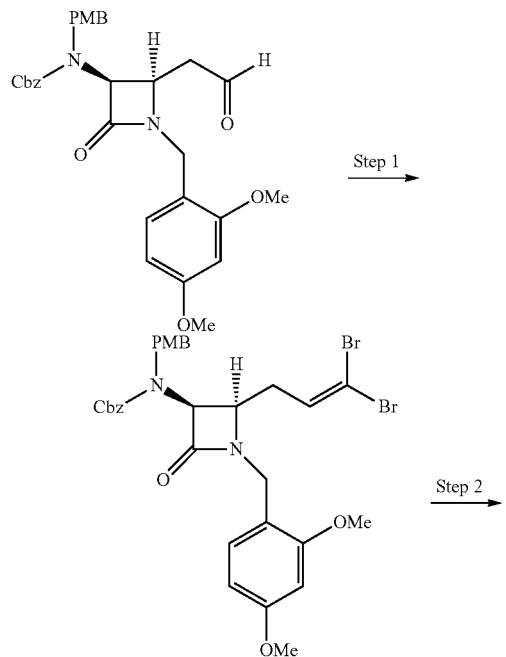

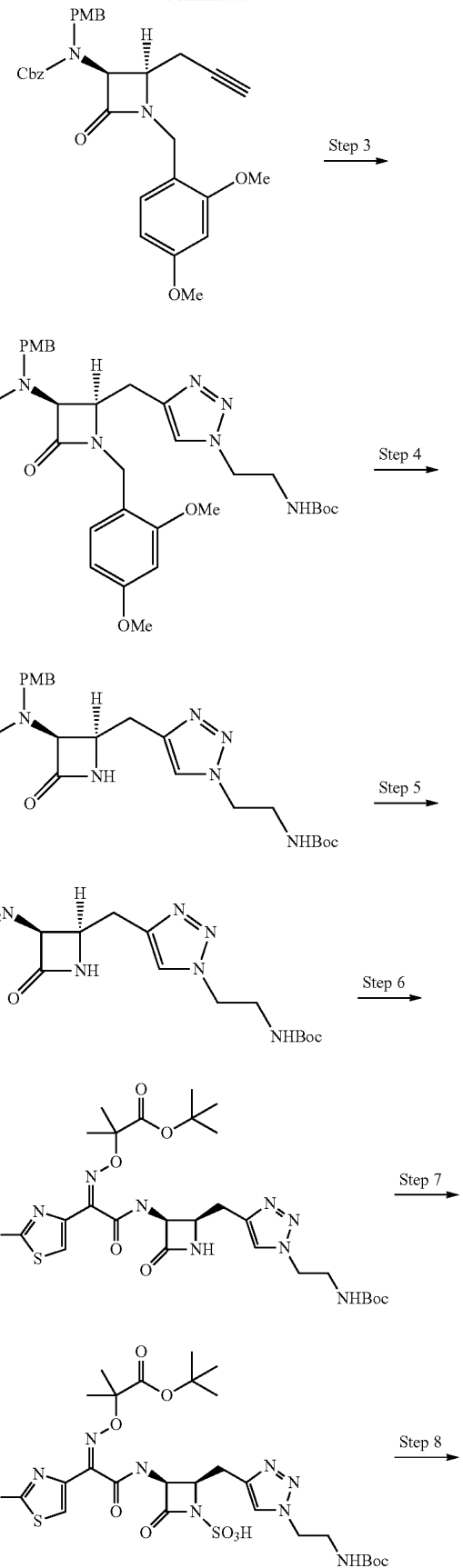

-continued

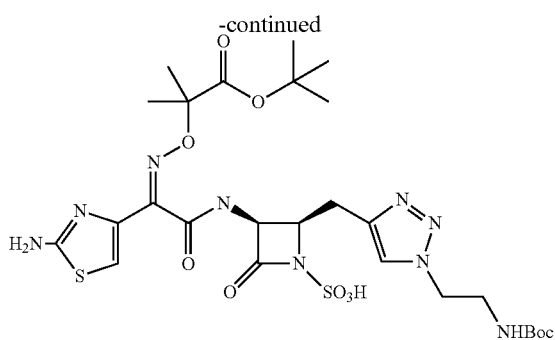

Step 1: Benzyl ((2R,3S)-2-(3,3-dibromoallyl)-1-(2,4-dimethoxybenzyl)-4-oxoazetidin-3-yl)(4-methoxybenzyl)carbamate To a solution of PPh$_3$ (302.4 mg, 1.15 mmol) in DCM (1 mL) at 0° C. was added CBr$_4$ (192 mg, 0.58 mmol). After 10 min, a solution of benzyl ((3S,4R)-1-(2,4-dimethoxybenzyl)-2-oxo-4-(2-oxoethyl)azetidin-3-yl)(4-methoxybenzyl)carbamate (152.7 mg, 0.29 mmol) in DCM (800 μL) was added dropwise followed by DCM (800 μL) wash. After 20 min, the reaction mixture was diluted with DCM and water, and the layers were separated. The aqueous layer was extracted with DCM (2×). Combined organic layers were washed with brine, dried over Na$_2$SO$_4$, filtered and concentrated in vacuo. The residue was purified via silica gel chromatography (0-40% EtOAc-Hept) to afford the title compound (162 mg, 82%). LCMS: R$_t$=1.2 min, m/z=689.1 (M+1) Method 2m_acidic.

Preparation of benzyl ((3S,4R)-1-(2,4-dimethoxybenzyl)-2-oxo-4-(2-oxoethyl)azetidin-3-yl)(4-methoxybenzyl)carbamate: To a solution of benzyl ((2R,3S)-1-(2,4-dimethoxybenzyl)-2-((E)-2-methoxyvinyl)-4-oxoazetidin-3-yl)carbamate (example 82, step 1, 1.44 g, 3.38 mmol) in DMF (33.8 ml) at −10° C. (salt-ice bath) was addeds sodium hydride (60%, 162 mg, 4.05 mmol). After stirring for 30 min, p-methoxybenzylchloride (506, μL, 3.71 mmol) was added. After warming to 0° C. and stirring for an additional 30 min, it was quenched with NH$_4$Cl (aq, satd) then diluted with EtOAc and LiCl (5% aq). The layers were separated and aqueous layer was extracted with EtOAc (2×). The combined organic layers washed with LiCl (5% aq), brine, dried over Na$_2$SO$_4$ and concd in vacuo. The crude material was subjected to conditions described in example 82, step 2 then purified via silica gel chromatography (EtOAc-Hept, 0-70%) to afford the title compound (684 mg, 38%). LCMS: R$_t$=0.97 min, m/z=533.2 (M+1) Method 2m_acidic.

Step 2: Benzyl ((3S,4R)-1-(2,4-dimethoxybenzyl)-2-oxo-4-(prop-2-yn-1-yl)azetidin-3-yl)(4-methoxybenzyl)carbamate tert-Butyllithium (0.291 mL, 0.494 mmol) was added to the solution of benzyl ((2R,3S)-2-(3,3-dibromoallyl)-1-(2,4-dimethoxybenzyl)-4-oxoazetidin-3-yl)(4-methoxybenzyl)carbamate (162 mg, 0.235 mmol) in THF (Volume: 3.4 mL) at −78° C. After 15 min, the reaction mixture was quenched with NH$_4$Cl, and diluted with water and EtOAc. The layers were separated, and the organic layer was extracted with EtOAc (2×). Combined organic layers were washed with brine, dried over Na$_2$SO$_4$, filtered and concentrated in vacuo. The residue was purified via silica gel chromatography (EtOAc-Hept, 0-40%) to afford the title compound (98 mg, 79%). LCMS: R$_t$=1.08 min, m/z=529.3 (M+1) Method 2m_acidic.

Step 3: Benzyl ((2R,3S)-2-((1-(2-((tert-butoxycarbonyl)amino)ethyl)-1H-1,2,3-triazol-4-yl)methyl)-1-(2,4-dimethoxybenzyl)-4-oxoazetidin-3-yl)(4-methoxybenzyl)carbamate To a solution of benzyl ((3S,4R)-1-(2,4-dimethoxybenzyl)-2-oxo-4-(prop-2-yn-1-yl)azetidin-3-yl)(4-methoxybenzyl)carbamate (95.6 mg, 0.18 mmol) in a mixture of DMSO (1.2 mL), tert-butanol (1.2 mL) and water (1.2 mL), was added copper(II) sulfate pentahydrate (4.5 mg, 0.018 mmol), sodium L-ascorbate (35.8 mg, 0.18 mmol) and N-Boc-2-azidoethylamine (76 mg, 0.39 mmol). After stirring for 12 h, more copper(II) sulfate pentahydrate (10.6 mg, 0.23 equiv), sodium L-ascorbate (37.4 mg, 1.04 equiv) and N-Boc-2-azidoethylamine (82.1 mg, 2.44 equiv) were added. After stirring for 4 days total, the reaction mixture was diluted with EtOAc and water. The layers were separated, and the aqueous layer was extracted with EtOAc (2×). Combined organic layers were washed with LiCl (5% aq), brine, dried over Na$_2$SO$_4$, filtered and concentrated in vacuo. The residue was purified via silica gel chromatography (EtOAc-Hep, 0-40%) to afford the title compound (57.2 mg, 44%). LCMS: R$_t$=1.06 min, m/z=715.5 (M+1) Method 2m_acidic.

Step 4: Benzyl ((2R,3S)-2-((1-(2-((tert-butoxycarbonyl)amino)ethyl)-1H-1,2,3-triazol-4-yl)methyl)-4-oxoazetidin-3-yl)(4-methoxybenzyl)carbamate Prepared in analogous manner to example 82 step 5, using benzyl ((2R,3S)-2-((1-(2-((tert-butoxycarbonyl)amino)ethyl)-1H-1,2,3-triazol-4-yl)methyl)-1-(2,4-dimethoxybenzyl)-4-oxoazetidin-3-yl)(4-methoxybenzyl)carbamate (57.2 mg, 0.080 mmol), CH$_3$CN (762 μl), water (381 μl), potassium peroxydisulfate (31 mg, 0.12 mmol), and potassium phosphate, dibasic (19 mg, 0.109 mmol). 20.2 mg. LCMS: R$_t$=0.89 min, m/z=565.3 (M+1). Method 2m_acidic.

Step 5: Tert-butyl (2-(4-(((2R,3S)-3-amino-4-oxoazetidin-2-yl)methyl)-1H-1,2,3-triazol-1-yl)ethyl)carbamate To a slurry of benzyl ((2R,3S)-2-((1-(2-((tert-butoxycarbonyl)amino)ethyl)-1H-1,2,3-triazol-4-yl)methyl)-4-oxoazetidin-3-yl)(4-methoxybenzyl)carbamate (20.2 mg, 0.036 mmol) in MeOH (0.68 mL) was added Pd black (19 mg, 0.018 mmol) and formic acid (31 μl, 0.711 mmol). After stirring at rt for 3 h, more Pd black (9.7 mg) was added. After stirring at rt for additional 5.5 h, the reaction mixture was filtered through cellulose with MeOH eluent, and the filtrate was concentrated in vacuo. It was used in step 6 without further purification. LCMS: R$_t$=0.396 min, m/z=311.1 (M+1). Method 2m_acidic.

Step 6: Tert-butyl 2-(((Z)-(2-(((2R,3S)-2-((1-(2-((tert-butoxycarbonyl)amino)ethyl)-1H-1,2,3-triazol-4-yl)methyl)-4-oxoazetidin-3-yl)amino)-1-(2-((tert-butoxycarbonyl)amino)thiazol-4-yl)-2-oxoethylidene)amino)oxy)-2-methylpropanoate Prepared in analogous manner to example 82 step 7, using (Z)-2-(((1-(tert-butoxy)-2-methyl-1-oxopropan-2-yl)oxy)imino)-2-(2-((tert-butoxycarbonyl)amino)thiazol-4-yl)acetic acid (18.55 mg, 0.043 mmol), HATU (17.7 mg, 0.047 mmol), DCM:DMF (1:3, 800 μl), DIPEA (18.86 μl, 0.108 mmol), tert-butyl (2-(4-(((2R,3S)-3-amino-4-oxoazetidin-2-yl)methyl)-1H-1,2,3-triazol-1-yl)ethyl)carbamate (11.17 mg, 0.036 mmol). 6.5 mg. LCMS: $R_f$=0.971 min, m/z=722.4 (M+1). Method 2m_acidic. $^1$H NMR (400 MHz, Methanol-$d_4$) δ 7.82 (s, 1H), 7.32 (s, 1H), 5.34 (d, J=4.9 Hz, 1H), 4.43 (t, J=5.9 Hz, 3H), 4.19 (dt, J=9.3, 4.5 Hz, 1H), 4.09 (q, J=7.1 Hz, 1H), 3.54-3.45 (m, 3H), 3.13 (ddd, J=15.0, 11.8, 6.0 Hz, 2H), 2.93 (dd, J=15.2, 9.6 Hz, 1H), 2.01 (s, 2H), 1.53 (d, J=1.4 Hz, 14H), 1.49 (s, 7H), 1.46 (d, J=1.7 Hz, 15H), 1.38 (s, 14H), 1.23 (t, J=7.1 Hz, 3H).

Step 7: (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-(1-(2-((tert-butoxycarbonyl)amino)ethyl)-1H-1,2,3-triazol-4-yl)methyl)-4-oxoazetidine-1-sulfonic acid Prepared in analogous manner to example 82 step 9, using tert-butyl 2-(((Z)-(2-(((2R,3S)-2-((1-(2-((tert-butoxycarbonyl)amino)ethyl)-1H-1,2,3-triazol-4-yl)methyl)-4-oxoazetidin-3-yl)amino)-1-(2-((tert-butoxycarbonyl)amino)thiazol-4-yl)-2-oxoethylidene)amino)oxy)-2-methylpropanoate (6.5 mg, 9.00 μmol), DMF (200 μl), SO$_3$.DMF (5.8 mg, 0.037 mmol). It was used in step 8 without further purification. LCMS: $R_f$=0.911 min, m/z=802.1 (M+1). Method 2m_acidic.

Step 8: 2-(((Z)-(2-(((2R,3S)-2-((1-(2-aminoethyl)-1H-1,2,3-triazol-4-yl)methyl)-4-oxo-1-sulfoazetidin-3-yl)amino)-1-(2-aminothiazol-4-yl)-2-oxoethylidene)amino)oxy)-2-methylpropanoic acid Followed the general procedure for the acid mediated deprotection, using (2R,3S)-3-((Z)-2-(((1-(tert-butoxy)-2-methyl-1-oxopropan-2-yl)oxy)imino)-2-(2-((tert-butoxycarbonyl)amino)thiazol-4-yl)acetamido)-2-((1-(2-((tert-butoxycarbonyl)amino)ethyl)-1H-1,2,3-triazol-4-yl)methyl)-4-oxoazetidine-1-sulfonic acid (7.22 mg, 9.00 μmol), DCM (200 μl) and TFA (50 μl, 649 μmol). The crude residue was purified by reverse phase prep HPLC (XSelect CSH, 19×100 mm, 5 μm, C18 column; AcN-water with 0.1% formic acid modifier, 24 mL/min) affording the title compound (1.2 mg, 24%). LCMS: $R_f$=0.487 min, m/z=546.2 (M+1). Method 2m_acidic.

Example 102

1-(((Z)-(2-(((2R,3S)-2-((4-(((2-aminoethyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

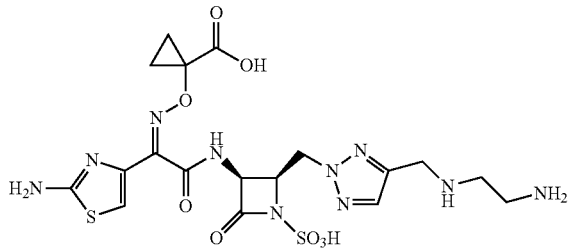 [SMILES: NCCNCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 90, using tert-butyl(2-aminoethyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy) cyclopropanecarboxylate in step 3. LCMS: $R_f$=0.31 min, m/z=573.2 (M+1) Method 2m_acidic; $^1$H NMR (400 MHz, DMSO-$d_6$) δ 9.24 (d, J=9.0 Hz, 1.0H), 7.75 (s, 1H), 7.22 (s, 2H), 6.71 (s, 1H), 5.42-5.28 (m, 1H), 4.86 (dd, J=14.3, 4.1 Hz, 1H), 4.72-4.59 (m, 1H), 4.53 (ddd, J=7.4, 5.5, 4.3 Hz, 1H), 4.24-4.09 (m, 2H), 3.10-2.97 (m, 5H), 1.34-1.19 (m, 3H), 1.19-1.06 (m, 1H).

Example 103

1-(((Z)-(1-(2-aminothiazol-4-yl)-2-(((2R,3S)-2-((4-((azetidin-3-ylamino)methyl)-2H-1,2,3-triazol-2-yl)methyl)-4-oxo-1-sulfoazetidin-3-yl)amino)-2-oxoethylidene)amino)oxy)cyclopropanecarboxylic acid

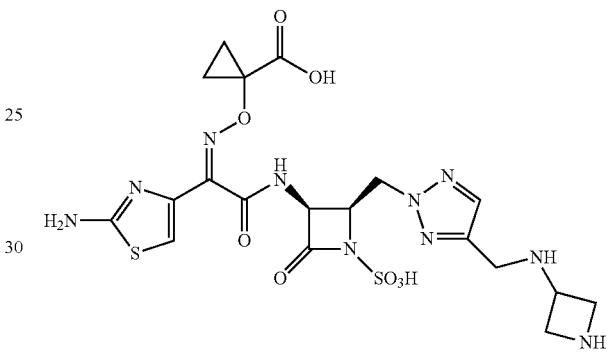

Prepared in analogous manner to example 90, using tert-butyl 3-aminoazetidine-1-carboxylate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_f$=0.31 min, m/z=585.2 (M+1) Method 2m_acidic; $^1$H NMR (500 MHz, D$_2$O) δ 7.84 (s, 1H), 7.14 (s, 1H), 5.60 (d, J=5.6 Hz, 1H), 5.04-4.87 (m, 3H), 4.52-4.36 (m, 5H), 4.35 (s, 1H), 1.35-1.29 (m, 2H), 1.24-1.14 (m, 2H).

Example 104

1-(((Z)-(1-(2-aminothiazol-4-yl)-2-(((2R,3S)-2-(((R)-5-(formimidamidomethyl)-2-oxooxazolidin-3-yl)methyl)-4-oxo-1-sulfoazetidin-3-yl)amino)-2-oxoethylidene)amino)oxy)cyclopropanecarboxylic acid

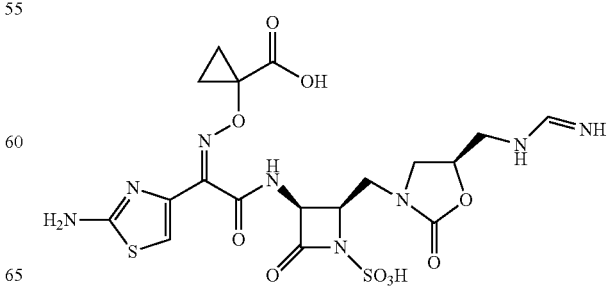

Prepared in analogous manner to example 26, using ethyl formamidate-HCl. LCMS: $R_t$=0.29 min, m/z=575.0 (M+1) Method 2m_acidic.

Example 105

2-(((Z)-(1-(2-aminothiazol-4-yl)-2-(((2R,3S)-2-((3-cyano-1H-1,2,4-triazol-1-yl)methyl)-4-oxo-1-sulfoazetidin-3-yl)amino)-2-oxoethylidene)amino)oxy)-2-methylpropanoic acid

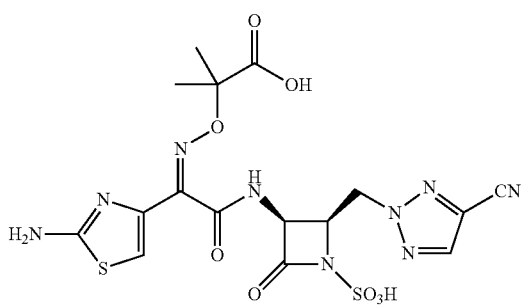 [SMILES: CC(C)(O/N=C(\C(=O)N[C@@H]1C(=O)N(S(=O)(=O)O)[C@@H]1Cn1ncc(C#N)n1)c1csc(N)n1)C(=O)O]

Prepared in analogous manner to example 54, using 1H-1,2,4-triazole-3-carbonitrile. LCMS: m/z=526.0 [M–H]; $^1$H NMR (400 MHz, D$_2$O) δ 8.57 (s, 1H), 6.90 (s, 1H), 5.34 (br s, 1H), 5.20-4.77 (m, 3H), 1.31 (s, 6H).

Example 106

1-(((Z)-(2-(((2R,3S)-2-((4-((3-aminoazetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

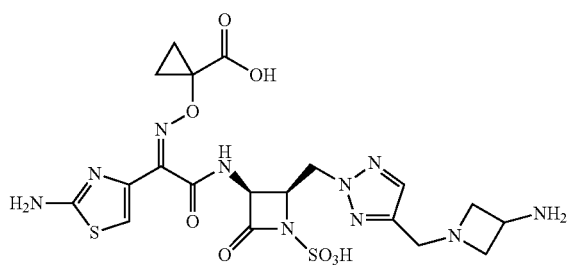 [SMILES: Nc1nc(/C(=N/OC2(C(=O)O)CC2)C(=O)N[C@@H]2C(=O)N(S(=O)(=O)O)[C@@H]2Cn2ncc(CN3CC(N)C3)n2)cs1]

Prepared in analogous manner to example 90, using tert-butyl(2-oxoethyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3, except there was an additional workup in the sulfonylation step. The crude sulfonylation product was treated with pyridine in MeOH at 40° C. for 1 h to remove over-sulfonylation product on azetidine. LCMS: $R_t$=0.30 min, m/z=585.2 (M+1) Method 2m_acidic; $^1$H NMR (500 MHz, D$_2$O) δ 7.76 (s, 1H), 7.03 (s, 1H), 5.50 (d, J=5.5 Hz, 1H), 4.97-4.89 (m, 1H), 4.89-4.77 (m, 2H), 4.56-4.48 (m, 3H), 4.46-4.35 (m, 3H), 1.29-1.18 (m, 2H), 1.15-1.08 (m, 2H).

Example 107

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-carbamimidoylphenoxy)propanoic acid

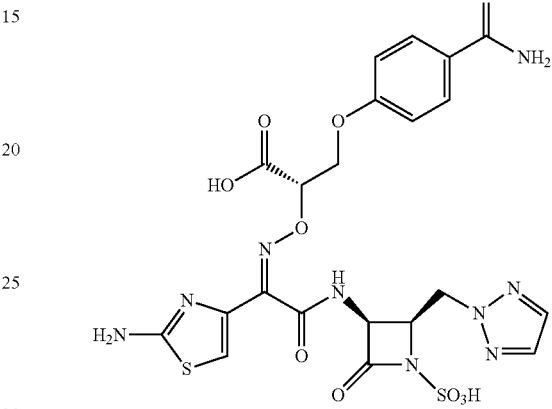

Prepared in analogous manner to example 68, using (R)-benzhydryl 2-(aminooxy)-3-(4-(N-(tert-butoxycarbonyl)carbamimidoyl)phenoxy)propanoate (prepared according to WO2013110643). LCMS: $R_t$=0.30 min, m/z=623.4 (M+1) Method 2m_acidic; $^1$H NMR (400 MHz, DMSO-d$_6$): δ 9.14 (s, 2H), 8.68 (br s, 2H), 8.37 (s, 1H), 7.90 (s, 1H), 7.77-7.70 (m, 2H), 7.28 (br s, 2H), 6.95 (br s, 1H), 6.79 (s, 1H), 6.55 (br s, 1H), 5.19-5.11 (m, 1H), 5.07-4.98 (m, 1H), 4.54-4.39 (m, 3H), 4.28-4.22 (m, 1H).

Example 108

1-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)cyclopropanecarboxylic acid Step 1: Benzhydryl 1-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)cyclopropanecarboxylate To a solution of (Z)-2-(((1-((benzhydryloxy)carbonyl)cyclopropoxy)imino)-2-(2-((tert-butoxycarbonyl)amino)thiazol-4-yl)acetic acid (6.66 g, 12.38 mmol) at 0° C. in DCM (61.9 ml, ratio: 1) and DMF (61.9 ml, ratio: 1) were added DIPEA (6.49 ml, 37.2 mmol) and HATU (5.65 g, 14.86 mmol). After 20 min, (3S,4S)-3-amino-4-(hydroxymethyl) azetidin-2-one (1.44 g, 12.38 mmol) was added. After stirring for 2 h at rt, the reaction mixture was concentrated in vacuo and diluted with EtOAc. The organic layer was washed with water, brine, dried over Na$_2$SO$_4$, filtered and concentrated in vacuo. The crude residue was purified via silica gel chromatography (Acetone-DCM) to afford the title compound (4.4 g, 56%). LCMS: $R_t$=0.97 min, m/z=636.1 (M+1), Method 2m_acidic. $^1$H NMR (400 MHz, DMSO-d$_6$): 11.80 (br s, 1H), 9.08 (d, J=9.0 Hz, 1H), 8.41 (s, 1H), 7.48-7.32 (m, 5H), 7.32-7.15 (m, 6H), 6.84 (s, 1H), 5.20 (ddd, J=9.2, 5.1, 0.9 Hz, 1H), 4.77 (t, J=5.3 Hz, 1H), 3.76-3.70 (m, 1H), 3.62-3.48 (m, 1H), 3.47-3.33 (m, 1H), 1.56-1.33 (m, 13H).

Step 2: Benzhydryl 1-(((Z)-(1-(2-((tert-butoxycarbonyl)amino)thiazol-4-yl)-2-(((2S,3S)-2-(((methylsulfonyl)oxy)methyl)-4-oxoazetidin-3-yl)amino)-2-oxoethylidene)amino)oxy)cyclopropanecarboxylate To a solution of benzhydryl 1-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)cyclopropanecarboxylate (1 g, 1.57 mmol) at 0° C. in THF (15.7 ml) was added TEA (0.66 ml, 4.7 mmol) and MsCl (25 µl, 0.32 mmol). After 2 h, the reaction mixture was diluted with EtOAc, washed with brine, dried over Na$_2$SO$_4$, filtered and concentrated in vacuo, affording the title compound (assumed quantitative). LCMS: R=0.99 min, m/z=714.1 (M+1), Method 2m_acidic.

Step 3: Benzhydryl 1-(((Z)-(2-(((2R,3S)-2-(azidomethyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-(1-(2-((tert-butoxycarbonyl)amino)thiazol-4-yl)-2-(((2S,3S)-2-(((methylsulfonyl)oxy)methyl)-4-oxoazetidin-3-yl)amino)-2-oxoethylidene)amino)oxy)cyclopropanecarboxylate (1.3 g, 1.82 mmol) in DMF (20 ml) was added NaI (0.82 g, 5.5 mmol) and sodium azide (0.83 g, 12.8 mmol). After stirring at 60° C. for 6 h, the reaction mixture was quenched with ice cold water and extracted with EtOAc. Combined organic layers were washed with water, brine, dried over anhydrous Na$_2$SO$_4$, concentrated in vacuo. The crude residue was purified via silica gel chromatography (EtOAc-heptane) to afford the title compound (689 mg, 57%). LCMS: R=1.02 min, m/z=661.1 (M+1), Method 2m_acidic.

Step 4: Benzhydryl 1-(((Z)-(2-(((2R,3S)-2-(aminomethyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-(2-(((2R,3S)-2-(azidomethyl)-4-oxoazetidin-3-yl)amino)-1-(2-((tert-butoxycarbonyl)amino)thiazol-4-yl)-2-oxoethylidene)amino)oxy)cyclopropanecarboxylate (689 mg, 1.04 mmol) in THF (10 mL) and MeOH (1.3 mL) was added Ph$_3$P (301 mg, 1.15 mmol). After 12 h, the reaction mixture was concentrated in vacuo. The crude residue was purified via silica gel chromatography (MeOH-DCM, 0-100%) to afford the title compound (369 mg, 56%). LCMS: R$_t$=0.88 min, m/z=635.1 (M+1), Method 2m_acidic.

Step 5: Benzhydryl 1-(((Z)-(2-(((2R,3S)-2-(((2-((((9H-fluoren-9-yl)methoxy)carbonyl)amino)ethyl)amino)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-(2-(((2R,3S)-2-(aminomethyl)-4-oxoazetidin-3-yl)amino)-1-(2-((tert-butoxycarbonyl)amino)thiazol-4-yl)-2-oxoethylidene)amino)oxy)cyclopropanecarboxylate (199 mg, 0.29 mmol) in DCE (2.9 mL) was added (9H-fluoren-9-yl)methyl (2-oxoethyl)carbamate (84 mg, 0.30 mmol) and sodium triacetoxyborohydride (181 mg, 0.86 mmol). After 12 h, the reaction mixture was quenched with saturated NaHCO$_3$ (aq), diluted with EtOAc, and the layers were separated. The aqueous layer was extracted with EtOAc, and the combined organic layers were washed with brine, dried over Na$_2$SO$_4$, filtered and concentrated in vacuo. The crude residue was purified via silica gel chromatography (MeOH-DCM, 0-100%) to afford the title compound (150 mg, 58%). LCMS: R$_t$=1.10 min, m/z=900.0 (M+1), Method 2m_acidic. $^1$H NMR (400 MHz, DMSO-d$_6$): 9.16 (d, J=9.0 Hz, 1H), 8.35 (s, 1H), 7.87 (d, J=7.4 Hz, 2H), 7.66 (d, J=7.4 Hz, 2H), 7.45-7.18 (m, 16H), 6.83 (s, 1H), 5.24-5.17 (m, 1H), 4.28 (d, J=6.7 Hz, 2H), 4.19 (d, J=6.3 Hz, 1H), 3.79-3.67 (m, 1H), 3.03-2.95 (m, 2H), 2.73-2.63 (m, 1H), 1.54-1.37 (m, 13H).

Step 6: Benzhydryl 1-(((Z)-(2-(((2R,3S)-2-(((2-aminoethyl)amino)methyl)-4-oxoazetidin-3-yl)amino)-1-(2-((tert-butoxycarbonyl)amino)thiazol-4-yl)-2-oxoethylidene)amino)oxy)cyclopropanecarboxylate To a solution of benzhydryl 1-(((Z)-(2-(((2R,3S)-2-(((2-((((9H-fluoren-9-yl)methoxy)carbonyl)amino)ethyl)amino)methyl)-4-oxoazetidin-3-yl)amino)-1-(2-((tert-butoxycarbonyl)amino)thiazol-4-yl)-2-oxoethylidene)amino)oxy)cyclopropanecarboxylate (150 mg, 0.167 mmol) in DCM (1.7 mL) was added piperidine (16.50 µl, 0.167 mmol). After 2 h, the reaction mixture was concentrated in vacuo and lyophilized in CH$_3$CN/water mixture to afford the title compound (assumed quantitative). LCMS: R$_t$=0.93 min, m/z=678.5 (M+1), Method 2m_acidic.

Step 7: Benzhydryl 1-(((Z)-(1-(2-((tert-butoxycarbonyl)amino)thiazol-4-yl)-2-oxo-2-(((3S,4R)-2-oxo-4-((2-oxoimidazolidin-1-yl)methyl)azetidin-3-yl)amino)ethylidene)amino)oxy)cyclopropanecarboxylate To a solution of benzhydryl 1-(((Z)-(2-(((2R,3S)-2-(((2-aminoethyl)amino)methyl)-4-oxoazetidin-3-yl)amino)-1-(2-((tert-butoxycarbonyl)amino)thiazol-4-yl)-2-oxoethylidene)amino)oxy)cyclopropanecarboxylate (90 mg, 0.133 mmol) in chloroform (2.7 mL) was added CDI (43.1 mg, 0.266 mmol) and TEA (111 µl, 0.797 mmol). After 12 h, the reaction mixture was concentrated in vacuo. The crude residue was purified via silica gel chromatography (MeOH-DCM, 0-100%) to afford the title compound (46 mg, 49%). LCMS: R$_t$=0.95 min, m/z=704.0 (M+1), Method 2m_acidic.

Step 8: (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((2-oxoimidazolidin-1-yl)methyl)azetidine-1-sulfonic acid, (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((3-oxo-1,2,4-triazinan-1-yl)methyl)azetidine-1-sulfonic acid To a solution of benzhydryl 1-(((Z)-(1-(2-((tert-butoxycarbonyl)amino)thiazol-4-yl)-2-oxo-2-(((3S,4R)-2-oxo-4-((2-oxoimidazolidin-1-yl)methyl)azetidin-3-yl)amino)ethylidene)amino)oxy)cyclopropanecarboxylate (46 mg, 65 µmol) in DMF (654 µl) was added SO$_3$.DMF (100 mg, 0.654 mmol). After stirring at rt for 2 h, the reaction mixture was diluted with EtOAc, washed with brine, dried over Na$_2$SO$_4$, filtered and concentrated in vacuo to afford the title compound (50 mg, 98%). LCMS: R=0.84 min, m/z=784.0 (M+1), Method 2m_acidic. The crude residue was used as such in the following step.

Step 9: 1-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)cyclopropanecarboxylic acid

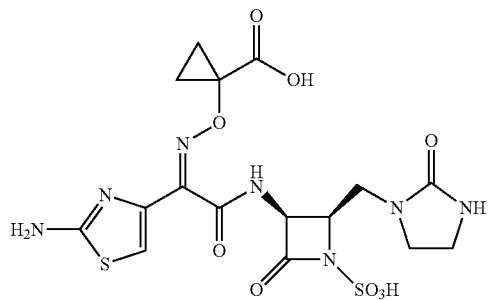 [SMILES: Nc1nc(/C(=N/OC2(C(=O)O)CC2)C(=O)N[C@@H]2C(=O)N(S(=O)(=O)O)[C@@H]2CN2CCNC2=O)cs1]

Followed the general procedure for the acid mediated deprotection using (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((2-oxoimidazolidin-1-yl)methyl)azetidine-1-sulfonic acid, (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((3-oxo-1,2,4-triazinan-1-yl)methyl)azetidine-1-sulfonic acid (48 mg, 61 µmol), DCM (0.61 mL), and TFA (0.28 mL, 3.7 mmol) for 4 h. The crude residue was purified by reverse phase prep HPLC (XSelect CSH, 30×100 mm, 5 µm, C18 column; AcN-water with 0.1% formic acid modifier, 60 mL/min) affording the title compound (3.6 mg, 10%). LCMS: $R_f$=0.45 min, m/z=518.1 (M+1), Method 2m_acidic; $^1$H NMR (500 MHz, D$_2$O): δ 7.01 (s, 1H), 5.32 (d, J=5.5 Hz, 1H), 4.53-4.39 (m, 1H), 3.61 (dd, J=14.8, 6.9 Hz, 1H), 3.56-3.41 (m, 2H), 3.35-3.21 (m, 3H), 1.46-1.19 (m, 4H).

Example 109

1-(((Z)-(1-(2-aminothiazol-4-yl)-2-(((2R,3S)-2-((4,5-bis(aminomethyl)-2H-1,2,3-triazol-2-yl)methyl)-4-oxo-1-sulfoazetidin-3-yl)amino)-2-oxoethylidene)amino)oxy)cyclopropanecarboxylic acid Step 1

To a solution of di-tert-butyliminodicarbonate (1.02 g, 4.60 mmol) in DMF (14 mL) at 0° C. was added sodium hydride (0.19 g, 4.83 mmol). The cold bath was removed, and more DMF (20 mL) was added. After stirring for 15 min, 1,4-dichlorobut-2-yne (0.91 ml, 9.20 mmol) was quickly added. After stirring at rt for 12 h, the reaction mixture was poured into a cold solution of LiCl (5% aq.). The aqueous layer was extracted with EtOAc (3×), and the combined organic layers were washed with LiCl (5% aq.), brine, dried over Na$_2$SO$_4$, filtered and concentrated in vacuo. The crude residue was purified via silica gel chromatography (EtOAc-Heptane, 0-10%) to afford the title compound (467 mg, 33%). LCMS: $R_f$=1.07 min, m/z=326.0 (M+Na), Method 2m_acidic; $^1$H NMR (400 MHz, CDCl$_3$) δ 4.13 (t, J=1.9 Hz, 2H) 4.40 (t, J=1.9 Hz, 2H), 1.57-1.51 (m, 18H).

Step 2

Prepared according to the procedure described in Sharpless, K. B. *Synthesis*. 2005, 9, 1514. To a solution of intermediate from step 1 (466 mg, 1.53 mmol) in 1,4-dioxane (5.8 mL) and water (1.9 mL) was added sodium azide (401 mg, 6.17 mmol) followed by ammonium chloride (167.8 mg, 3.14 mmol). After heating to 75° C. for 11 h, the reaction mixture was poured into separatory funnel, and the layers were separated. The aqueous was extracted with EtOAc (3×). The combined organic layers were washed with brine, dried over Na$_2$SO$_4$, filtered and concentrated in vacuo. The crude residue was purified via silica gel chromatography (EtOAc-Hep, 0-40%) to afford the title compound (224 mg, 41%). LCMS: $R_f$=0.90 min, m/z=354.1 (M+1), Method 2m_acidic; $^1$H NMR (400 MHz, CDCl$_3$) δ 4.87 (s, 2H), 4.56 (s, 2H), 1.50 (s, 18H)

Step 3: Benzhydryl 1-(((Z)-(2-(((2R,3S)-2-((4-(azidomethyl)-5-((bis(tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a slurry of benzhydryl 1-(((Z)-(1-(2-((tert-butoxycarbonyl)amino)thiazol-4-yl)-2-(((2S,3S)-2-(hydroxymethyl)-4-oxoazetidin-3-yl)amino)-2-oxoethylidene)amino)oxy)cyclopropanecarboxylate (202 mg, 0.32 mmol), intermediate from step 2 (136 mg, 0.38 mmol) and triphenylphosphine (100 mg, 0.38 mmol) in THF (4 mL) at 0° C. was added DIAD (0.079 mL, 0.38 mmol) dropwise. After stirring at rt for 12 h, the reaction mixture was diluted with DCM and concentrated in vacuo. The crude residue was purified via silica gel chromatography (EtOAc-Hep, 0-70%) to afford the title compound. LCMS: $R_f$=1.27 min, m/z=971.5 (M+1), Method 2m_acidic; $^1$H NMR (400 MHz, DMSO-d$_6$) δ 9.38 (d, J=9.1 Hz, 1H), 8.56 (d, J=1.7 Hz, 1H), 7.45-7.38 (m, 5H), 7.32-7.20 (m, 7H), 6.84 (s, 1H), 5.41 (dd, J=9.0, 5.2 Hz, 1H), 4.78 (d, J=1.5 Hz, 2H), 4.51 (d, J=1.2 Hz, 2H), 4.48-4.42 (m, 2H), 4.37-4.30 (m, 1H), 1.42 (d, J=39.1 Hz, 31H).

Step 4: (2R,3S)-2-((4-(azidomethyl)-5-((bis(tert-butoxycarbonyl)amino)methyl)-2H-1,2,3-triazol-2-yl)methyl)-3-((Z)-2-((1-((benzhydryloxy)carbonyl)cyclopropoxy)imino)-2-(2-((tert-butoxycarbonyl)amino)thiazol-4-yl)acetamido)-4-oxoazetidine-1-sulfonic acid To a solution of benzhydryl 1-(((Z)-(2-(((2R,3S)-2-((4-(azidomethyl)-5-((bis(tert-butoxycarbonyl)amino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (103 mg, 0.11 mol) in DMF (530 µl) at 0° C. was added SO$_3$.DMF (33.5 mg, 0.21 mmol). After stirring at rt for 3 h, the reaction mixture was diluted with EtOAc, washed with LiCl (5% aq.), brine, dried over Na$_2$SO$_4$, filtered and concentrated in vacuo to afford the title compound (assumed quantitative). LCMS: $R_f$=1.16 min, m/z=1051.6 (M+1), Method 2m_acidic. The crude residue was used as such in the following step.

Step 5: (2R,3S)-2-((4-(aminomethyl)-5-((bis(tert-butoxycarbonyl)amino)methyl)-2H-1,2,3-triazol-2-yl)methyl)-3-((Z)-2-((1-((benzhydryloxy)carbonyl)cyclopropoxy)imino)-2-(2-((tert-butoxycarbonyl)amino)thiazol-4-yl)acetamido)-4-oxoazetidine-1-sulfonic acid To a solution of (2R,3S)-2-((4-(azidomethyl)-5-((bis(tert-butoxycarbonyl)amino)methyl)-2H-1,2,3-triazol-2-yl)methyl)-3-(((Z)-2-((1-((benzhydryloxy)carbonyl)cyclopropoxy)imino)-2-(2-((tert-butoxycarbonyl)amino)thiazol-4-yl)acetamido)-4-oxoazetidine-1-sulfonic acid (111 mg, 0.11 mmol) in EtOAc (1.1 mL) and EtOH (0.22 mL) under N₂ was added Pd—C (22 mg, 0.021 mmol). The system was evacuated and backfilled with H₂ (3×). After stirring at rt for 4 h, the reaction mixture was filtered through celite with EtOAc and EtOH wash. The filtrate was concentrated in vacuo to afford the title compound (assumed quantitative). The crude residue was used as such in the following step. LCMS: R$_t$=1.06 min, m/z=1025.7 (M+1), Method 2m_acidic.

Step 6: 1-(((Z)-(1-(2-aminothiazol-4-yl)-2-(((2R,3S)-2-((4,5-bis(aminomethyl)-2H-1,2,3-triazol-2-yl)methyl)-4-oxo-1-sulfoazetidin-3-yl)amino)-2-oxoethylidene)amino)oxy)cyclopropanecarboxylic acid

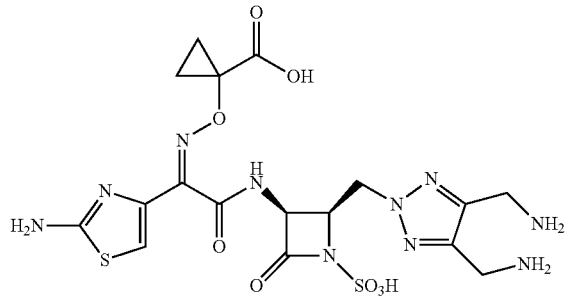 [SMILES: NCc1nn(C[C@@H]2[C@H](NC(=O)/C(=N\OC3(C(=O)O)CC3)c3csc(N)n3)C(=O)N2S(=O)(=O)O)nc1CN]

Followed the general procedure for the acid mediated deprotection using (2R,3S)-2-((4-(aminomethyl)-5-((bis(tert-butoxycarbonyl)amino)methyl)-2H-1,2,3-triazol-2-yl)methyl)-3-((Z)-2-((1-((benzhydryloxy)carbonyl)cyclopropoxy)imino)-2-(2-((tert-butoxycarbonyl)amino)thiazol-4-yl)acetamido)-4-oxoazetidine-1-sulfonic acid (109 mg, 0.11 DCM (1.1 mL), and TFA (0.49 mL, 6.36 mmol) for 2 h. The crude residue was purified by reverse phase prep HPLC (XSelect CSH, 30×100 mm, 5 μm, C18 column; ACN-water with 0.1% formic acid modifier, 60 mL/min) affording the title compound (12 mg, 19%). LCMS: R$_t$=0.46 min, m/z=559.2 (M+1), Method 2m_acidic; ¹H NMR (400 MHz, D₂O): δ 7.16 (s, 1H), 5.61 (d, J=5.6 Hz, 1H), 5.07-4.88 (m, 3H), 4.34 (s, 4H), 1.39-1.13 (m, 4H).

Example 110

2-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)-3-(4-carbamimidoylphenoxy)propanoic acid

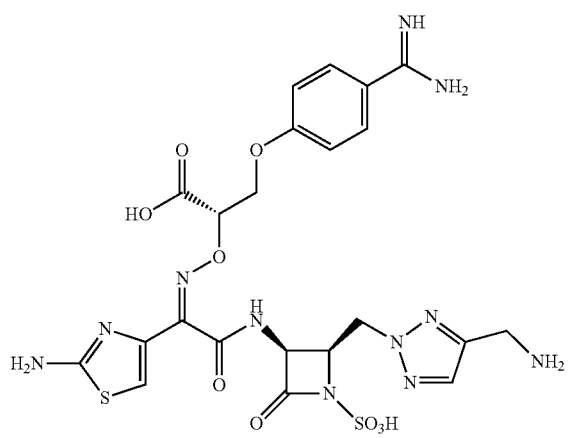 [SMILES: N=C(N)c1ccc(OC[C@H](O/N=C(\C(=O)N[C@@H]2C(=O)N(S(=O)(=O)O)[C@@H]2Cn2ncc(CN)n2)c2csc(N)n2)C(=O)O)cc1]

Prepared in analogous manner to example 107, using tert-butyl ((2-(((2R,3S)-3-amino-4-oxoazetidin-2-yl)methyl)-2H-1,2,3-triazol-4-yl)methyl)carbamate. LCMS: R$_t$=0.29 min, m/z=652.1 (M+1), Method 2m_acidic; ¹H NMR (400 MHz, D₂O): δ 7.53 (d, J=8.9 Hz, 2H), 7.43 (s, 1H), 7.03 (s, 1H), 6.82 (d, J=8.9 Hz, 2H), 5.35-5.28 (m, 1H), 4.97-4.91 (m, 1H), 4.77-4.70 (m, 1H), 4.61-4.55 (m, 2H), 4.38-4.29 (m, 1H), 4.27-4.19 (m, 1H), 4.00 (s, 2H).

Example 111

1-(((Z)-(2-(((2R,3S)-2-(((R)-5-((3-(2-aminoethyl)ureido)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid

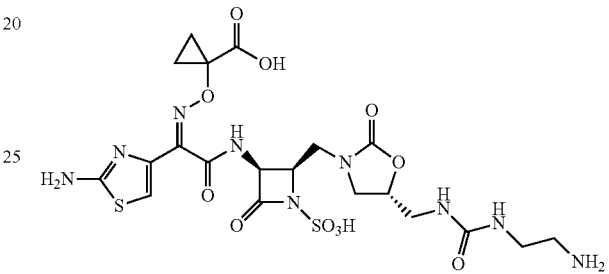

Prepared in analogous manner to example 26, using tert-butyl (2-(1H-imidazole-1-carboxamido)ethyl)carbamate. LCMS: R$_t$=0.31 min, m/z=634.3 (M+1), Method 2m_acidic; ¹H NMR (500 MHz, DMSO-d₆): δ 9.18 (d, J=8.8 Hz, 1H), 7.68 (br s, 2H), 7.28 (br s, 2H), 6.82 (s, 1H), 6.41 (t, J=5.9 Hz, 1H), 6.31-6.20 (m, 1H), 5.23 (dd, J=8.9, 5.83 Hz, 1H), 4.52-4.44 (m, 1H), 4.24-4.12 (m, 1H), 3.69-3.58 (m, 1H), 2.90-2.75 (m, 2H), 1.38-1.27 (m, 4H).

Example 112

1-(((Z)-(1-(2-aminothiazol-4-yl)-2-oxo-2-(((3S,4R)-2-oxo-4-((4-((piperidin-4-ylamino)methyl)-2H-1,2,3-triazol-2-yl)methyl)-1-sulfoazetidin-3-yl)amino)ethylidene)amino)oxy)cyclopropanecarboxylic acid

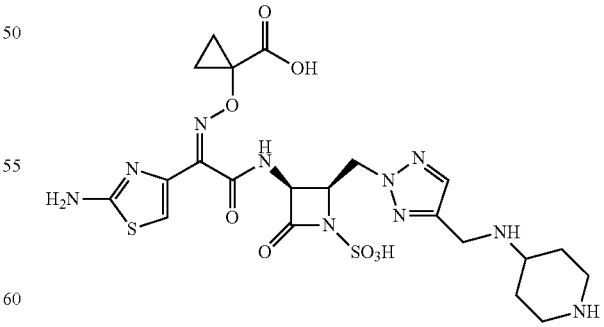

Prepared in analogous manner to 90, using tert-butyl 4-aminopiperidine-1-carboxylate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)

cyclopropanecarboxylate in step 3. LCMS: $R_t$=0.31 min, m/z=613.5 (M+1) Method 2m_acidic; $^1$H NMR (400 MHz, D$_2$O): δ 7.73 (s, 1H), 7.00 (s, 1H), 5.49 (d, J=5.6 Hz, 1H), 4.90 (q, J=5.5 Hz, 1H), 4.85-4.74 (m, 2H), 4.33 (s, 2H), 3.53-3.37 (m, 2H), 3.09-2.88 (m, 2H), 2.29 (t, J=12.5 Hz, 2H), 1.87-1.66 (m, 2H), 1.25-1.12 (m, 2H), 1.11-0.95 (m, 2H).

Example 113

2-(((Z)-(1-(2-aminothiazol-4-yl)-2-oxo-2-(((3S,4R)-2-oxo-4-((2-oxoazetidin-1-yl)methyl)-1-sulfoazetidin-3-yl)amino)ethylidene)amino)oxy)-2-methylpropanoic acid

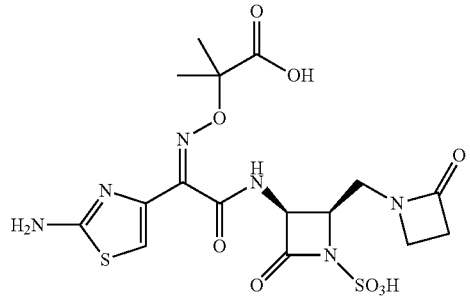 [SMILES: CC(C)(O/N=C(\C(=O)N[C@@H]1C(=O)N(S(=O)(=O)O)[C@@H]1CN1CCC1=O)c1csc(N)n1)C(=O)O]

Prepared in analogous manner to example 1, using 3-bromopropanoic acid. LCMS: m/z=503.0 [M–H]; $^1$H NMR (400 MHz, D$_2$O) δ 6.95 (s, 1H), 5.27 (d, J=5.2 Hz, 1H), 4.52-4.43 (m, 1H), 3.66-3.60 (m, 1H), 3.36-3.31 (m, 2H), 3.28 (m, 1H), 2.76 (t, J=3.6 Hz, 2H), 1.36 (s, 3H), 1.35 (s, 3H).

Example 114

1-(((Z)-(1-(2-aminothiazol-4-yl)-2-(((2R,3S)-2-((4-(((3-guanidinopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid

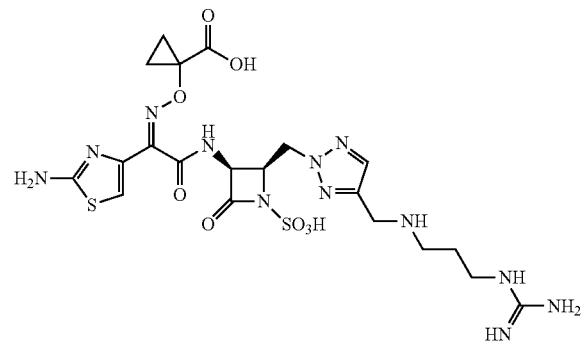 [SMILES: N=C(N)NCCCNCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 90, using N-(3-aminopropyl)-N'-tert-butoxycarbonyl guanidine and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_t$=0.55 min, m/z=629.4 (M+1) Method 2m_acidic_polar; $^1$H NMR (400 MHz, D$_2$O): δ 7.80 (s, 1H), 7.05 (s, 1H), 5.68-5.57 (m, 1H), 5.05-4.90 (m, 2H), 4.84-4.79 (m, 1H), 4.34 (s, 2H), 3.29-3.21 (m, 2H), 3.19-3.08 (m, 2H), 2.02-1.91 (m, 2H), 1.29-0.94 (m, 4H).

Example 115

1-(((Z)-(2-(((2R,3S)-2-((4-(((3-aminopropyl)(methyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

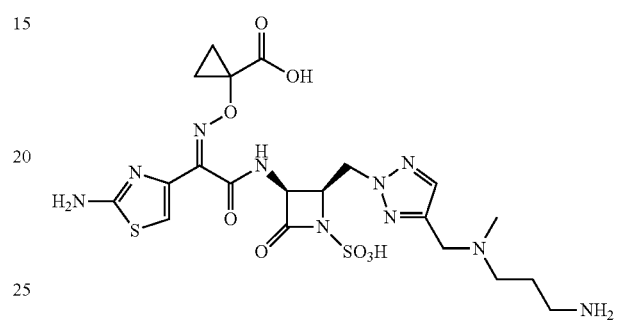

Prepared in analogous manner to example 90, using tert-butyl (3-(methylamino)propyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_t$=0.53 min, m/z=601.4 (M+1) Method 2m_acidic_polar; $^1$H NMR (400 MHz, D$_2$O): δ 7.91 (s, 1H), 7.06 (s, 1H), 5.55 (d, 1H, J=6.1 Hz), 5.06-4.88 (m, 3H), 4.49 (s, 2H), 3.26-3.15 (m, 2H), 3.06 (t, 2H, J=7.5 Hz), 2.89 (s, 3H), 2.20-2.07 (m, 2H), 1.30-1.07 (m, 4H).

Example 116

1-(((Z)-(1-(2-aminothiazol-4-yl)-2-(((2R,3S)-2-((4-(((3-(methylamino)propyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid

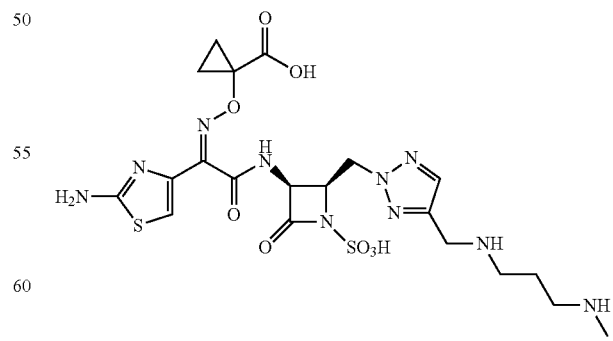

Prepared in analogous manner to example 90, using tert-butyl(3-aminopropyl)(methyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4- oxoazetidin-3-yl)amino)-2-oxoethylidene)amino)oxy)cyclopropanecarboxylate in step 3. LCMS: $R_f$=0.48 min, m/z=601.4 (M+1) Method 2m_acidic_polar; $^1$H NMR (400 MHz, $D_2O$): δ 7.82 (s, 1H), 7.09 (s, 1H), 5.66-5.53 (m, 1H), 5.03-4.87 (m, 3H), 4.37 (s, 2H), 3.21-3.05 (m, 4H), 2.68 (s, 3H), 2.17-2.02 (m, 2H), 1.30-1.04 (m, 4H).

Example 117

1-(((Z)-(1-(2-aminothiazol-4-yl)-2-(((2R,3S)-2-((4-(((2-(methylamino)ethyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid

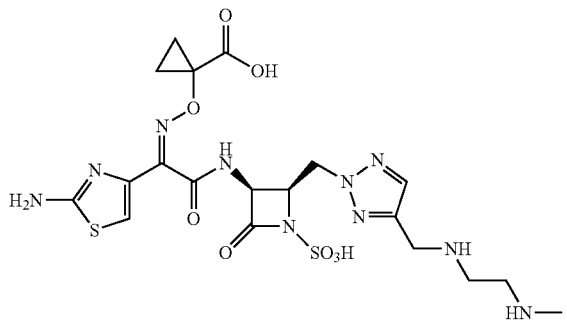 [SMILES: CNCCNCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 90, using tert-butyl(2-aminoethyl)(methyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_f$=0.44 min, m/z=587.2 (M+1) Method 2m_acidic_polar; $^1$H NMR (400 MHz, $D_2O$): δ 7.82 (s, 1H), 7.09 (s, 1H), 5.58 (d, J=5.5 Hz, 1H), 5.02-4.82 (m, 3H), 4.42 (s, 2H), 3.55-3.40 (m, 4H), 2.75 (s, 3H), 1.30-1.04 (m, 4H).

Example 118

1-(((Z)-(2-(((2R,3S)-2-((4-(((4-aminobutyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

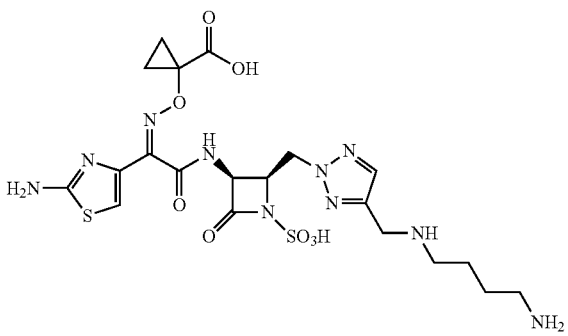 [SMILES: NCCCCNCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 90, using tert-butyl(4-aminobutyl)carbamate and benzhydryl 1-(((Z)-(1-(2-((tert-butoxycarbonyl)amino)thiazol-4-yl)-2-(((2R,3S)-2-((4-formyl-2H-1,2,3-triazol-2-yl)methyl)-4-oxoazetidin-3-yl)amino)-2-oxoethylidene)amino)oxy)cyclopropanecarboxylate in step 3. LCMS: $R_f$=0.32 min, m/z=601.3 (M+1) Method 2m_acidic_polar; $^1$H NMR (400 MHz, $D_2O$): δ 7.71 (s, 1H), 6.99 (s, 1H), 5.48 (d, J=5.6 Hz, 1H), 4.95-4.69 (m, 3H), 4.24 (s, 2H), 3.00 (t, J=7.3 Hz, 2H), 2.87 (t, J=7.1 Hz, 2H), 1.77-1.51 (m, 4H), 1.23-1.12 (m, 2H), 1.12-0.90 (m, 2H).

Example 119

1-(((Z)-(2-(((2R,3S)-2-((4-((3-(3-aminopropyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1 ert-Butyl (3-(3-benzoylthioureido)propyl)carbamate

Prepared according to the procedure described by Jubian at al. Angew. Chem, 1995, 107, 1343 and Rasmussen et al. *Synthesis*, 1988, 456. To a solution of benzoyl isothiocyanate (0.93 g, 5.70 mmol) in acetone (10 mL) was added tert-butyl (3-aminopropyl)carbamate (0.95 g, 5.45 mmol). After heating at 60° C. for 2.5 h, the reaction mixture was concentrated in vacuo. The crude residue was purified via silica gel chromatography (EtOAc-heptane, 0-40%), affording the title compound (0.83 g, 43%). LCMS: $R_f$=0.93 min, m/z=338.0 (M+1) Method 2m_acidic.

Step 2: Tert-butyl(3-thioureidopropyl)carbamate

To a solution of tert-butyl (3-(3-benzoylthioureido)propyl)carbamate (0.83 g, 2.45 mmol) in MeOH (15 mL) was added sodium hydroxide aqueous solution (1.96 mL, 2.45 mmol). After stirring at rt for 2 h, the reaction mixture was concentrated in vacuo and azeotropped with toluene. The crude residue was purified via silica gel chromatography (MeOH-DCM, 9% with 1% $NH_4OH$), affording the title compound (0.83 g, 43%). LCMS: $R_f$=0.47 min, m/z=234.2 (M+1) Method 2m_acidic.

Step 3: Tert-butyl (3-((imino(methylthio)methyl)amino)propyl)carbamate

To a solution of tert-butyl(3-thioureidopropyl)carbamate (0.29 g, 1.28 mmol) in MeOH (8 mL) was added iodomethane (80 μL, 1.29 mmol). After stirring at rt for 18 h, bicarbonate on polymer support (0.5 g, 3.5 mmol $NaCO_3$/g resin) was added to the reaction mixture. After 30 min, the reaction mixture was filtered, and the filtrate was concentrated in vacuo to give the desired product along with the N-methylated product, tert-butyl (3-(3-methylthioureido)propyl)carbamate (0.28 g, 87%, 2:1 ratio). The crude residue was used as such in the following step. LCMS: $R_f$=0.44 min and 0.49 min, m/z=248.1 (M+1) Method 2m_acidic.

Step 4: 1-(((Z)-(1-(2-aminothiazol-4-yl)-2-(((2R,3S)-2-((4-(3-imino-11,11-dimethyl-9-oxo-10-oxa-2,4,8-triazadodecyl)-2H-1,2,3-triazol-2-yl)methyl)-4-oxo-1-sulfoazetidin-3-yl)amino)-2-oxoethylidene)amino)oxy)cyclopropanecarboxylic acid To a solution of tert-butyl (3-((imino(methylthio)methyl)amino)propyl)carbamate (32.1 mg, 87 μmol) in dioxane (1 mL, ratio: 2) at rt was added triethylamine (30 μL, 0.22 mmol), 1-(((Z)-(2-(((2R,3S)-2-((4-(aminomethyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid (example 19, 23 mg, 43 μmol), and DMF (0.5 mL, ratio: 1). After heated to 60° C. for 17 h, the reaction mixture was diluted with EtOAc and water. The aqueous layer was separated, concentrated in vacuo, azeotroped with toluene, and dried on high vac to give the title compound (assumed quantitative). LCMS: $R_t$=0.51 min, m/z=729.6 (M+1), Method 2m_acidic.

Step 5: 1-(((Z)-(2-(((2R,3S)-2-((4-((3-(3-aminopropyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

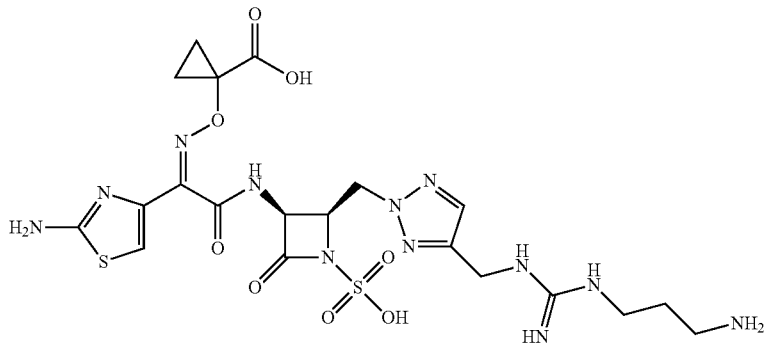

Followed the general procedure for the acid mediated deprotection using 1-(((Z)-(1-(2-aminothiazol-4-yl)-2-(((2R,3S)-2-((4-(3-imino-11,11-dimethyl-9-oxo-10-oxa-2,4,8-triazadodecyl)-2H-1,2,3-triazol-2-yl)methyl)-4-oxo-1-sulfoazetidin-3-yl)amino)-2-oxoethylidene)amino)oxy)cyclopropanecarboxylic acid (37 mg, 15 μmol), DCM (0.8 mL), and TFA (0.2 mL, 2.60 mmol) for 1.5 h. The crude residue was purified by reverse phase prep HPLC (XSelect CSH, 19×100 mm, 5 μm, C18 column; ACN-water with 0.1% formic acid modifier, 24 mL/min) affording the title compound (5.2 mg, 20%). LCMS: $R_t$=0.39 min, m/z=629.2 (M+1), Method 2m_acidic; $^1$H NMR (400 MHz, D$_2$O) δ 7.77 (s, 1H), 7.15 (s, 1H), 5.63 (d, J=5.7 Hz, 1H), 5.06-4.99 (m, 1H), 4.98-4.89 (m, 2H), 4.57 (s, 2H), 3.39-3.34 (m, 2H), 3.14-3.06 (m, 2H), 2.01 (p, J=7.2 Hz, 2H), 1.39-1.29 (m, 2H), 1.26-1.15 (m, 2H).

Example 120

1-(((Z)-(2-(((2R,3S)-2-((4-((3-(3-aminopropyl)guanidino)methyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid

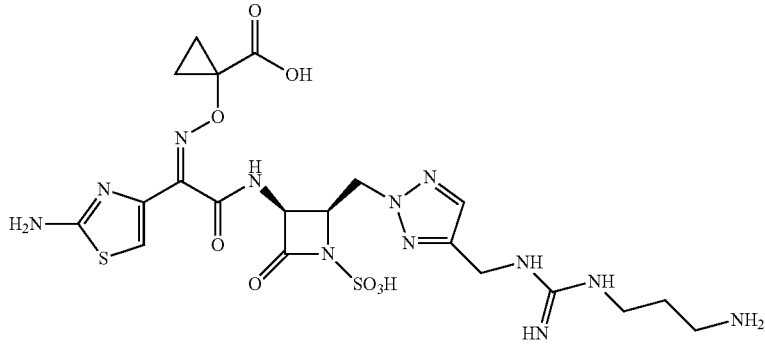

Prepared in analogous manner to example 119, using tert-butyl (3-((imino(methylthio)methyl)amino)propyl)carbamate. LCMS: $R_t$=0.30 min, m/z=629.1 (M+1) Method 2m_acidic_polar; ¹H NMR (500 MHz, D₂O) δ 7.97 (s, 1H), 7.05 (s, 1H), 5.42 (d, J=5.4 Hz, 1H), 4.87-4.78 (m, 1H), 4.45 (s, 1H), 3.24 (t, J=6.9 Hz, 1H), 2.98-2.93 (m, 1H), 2.64 (s, 1H), 1.87 (dt, J=14.9, 7.18 Hz, 3H), 1.33-1.25 (m, 3H), 1.21-1.10 (m, 4H).

Example 121

2-(((Z)-(1-(2-aminothiazol-4-yl)-2-(((2R,3S)-2-((2,5-dioxopyrrolidin-1-yl)methyl)-4-oxo-1-sulfoazetidin-3-yl)amino)-2-oxoethylidene)amino)oxy)-2-methylpropanoic acid

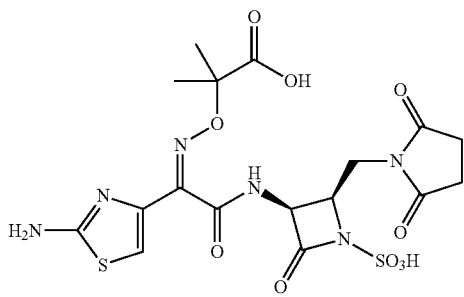 [SMILES: CC(C)(O/N=C(\C(=O)N[C@@H]1C(=O)N(S(=O)(=O)O)[C@@H]1CN1C(=O)CCC1=O)c1csc(N)n1)C(=O)O]

Prepared in analogous manner to example 54, using pyrrolidine-2,5-dione. LCMS: $R_t$=0.55 min, m/z=533.3 (M+1) Method 2m_acidic_polar; ¹H NMR (400 MHz, DMSO-d₆:D₂O (1:1)): δ 6.94 (s, 1H), 5.18 (d, J=5.9 Hz, 1H), 4.53-4.43 (m, 1H), 3.96-3.86 (m, 1H), 3.36-3.25 (m, 1H) 2.53 (s, 4H), 1.40 (s, 3H) 1.37 (s, 3H).

Example 122

1-(((Z)-(2-(((2R,3S)-2-((4-(aminomethyl)-2-oxoimidazolidin-1-yl)methyl)-4-oxo-1-sulfoazetidin-3-yl)amino)-1-(2-aminothiazol-4-yl)-2-oxoethylidene)amino)oxy)cyclopropanecarboxylic acid

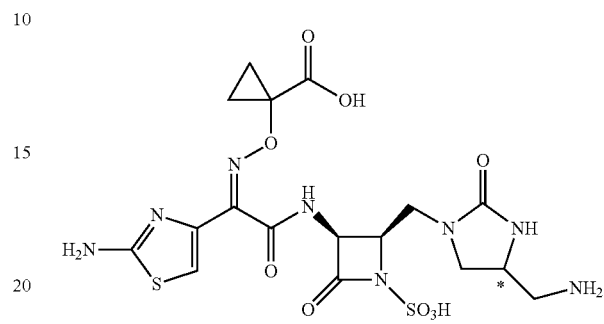

Prepared in analogous manner to example 108, using benzhydryl 1-(((Z)-(2-(((2R,3S)-2-((((S)-2-((((9H-fluoren-9-yl)methoxy)carbonyl)amino)-3-((tert butoxycarbonyl)amino)propyl)amino)methyl)-4-oxoazetidin-3-yl)amino)-1-(2-((tert-butoxycarbonyl)amino)thiazol-4-yl)-2-oxoethylidene)amino)oxy)cyclopropanecarboxylate.

Diastereomer A: 3.1 mg. LCMS: $R_t$=0.65 min, m/z=547.1 (M+1) Method 2m_acidic; ¹H NMR (400 MHz, D₂O): δ 7.12 (s, 1H), 5.39 (d, J=6.8 Hz, 1H), 4.60-4.56 (m, 1H), 3.84 (t, J=9.9 Hz, 1H), 3.59-3.53 (m, 1H), 3.48-3.41 (m, 2H), 3.21-3.09 (m, 3H), 1.46 (br s, 3H), 1.36 (br s, 3H).

Diastereomer B: 2.9 mg, LCMS: $R_t$=0.65 min, m/z=547.1 (M+1) Method 2m_acidic; ¹H NMR (400 MHz, D₂O): δ 7.12 (s, 1H), 5.42 (d, J=5.6 Hz, 1H), 4.61-4.54 (m, 1H), 4.16-4.08 (m, 1H), 3.82-3.72 (m, 2H), 3.55-3.49 (m, 1H), 3.27-3.15 (m, 3H), 1.47 (br s, 3H), 1.37 (br s, 3H).

Example 123

3-(((2-(((2R,3S)-3-((Z)-2-(2-aminothiazol-4-yl)-2-((1-carboxycyclopropoxy)imino)acetamido)-4-oxo-1-sulfoazetidin-2-yl)methyl)-2H-1,2,3-triazol-4-yl)methyl)amino)-N,N,N-trimethylpropan-1-aminium

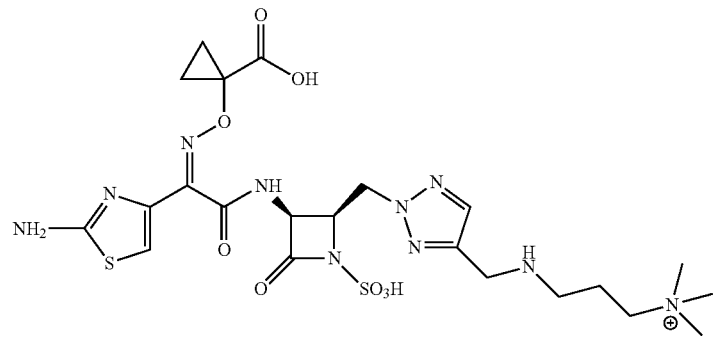

Prepared in analogous manner to example 90, using $N^1,N^1,N^1$-trimethylpropane-1,3-diaminium 2,2,2-trifluoroacetate. LCMS: $R_t$=0.51 min, m/z=629.5 (M+1) Method 2m_acidic_polar; $^1$H NMR (400 MHz, $D_2O$): δ 7.81 (s, 1H), 7.09 (s, 1H), 5.70-5.63 (m, 1H), 5.03-4.93 (m, 3H), 4.83-4.82 (m, 1H), 4.37 (s, 2H), 3.44-3.37 (m, 2H), 3.22-3.16 (m, 2H), 3.07 (s, 9H), 2.26-2.17 (m, 2H), 1.29-1.10 (m, 4H).

Example 124

1-(((Z)-(2-(((2R,3S)-2-((4-((4-aminobutanamido) methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: Benzhydryl 1-(((Z)-(1-(2-((tert-butoxycarbonyl)amino)thiazol-4-yl)-2-(((2R,3S)-2-((4-(((methylsulfonyl)oxy)methyl)-2H-1,2,3-triazol-2-yl)methyl)-4-oxoazetidin-3-yl)amino)-2-oxoethylidene)amino) oxy)cyclopropanecarboxylate To a solution of benzhydryl 1-(((Z)-(1-(2-((tert-butoxycarbonyl)amino)thiazol-4-yl)-2-(((2R,3S)-2-((4-(hydroxymethyl)-2H-1,2,3-triazol-2-yl)methyl)-4-oxoazetidin-3-yl)amino)-2-oxoethylidene)amino)oxy) cyclopropanecarboxylate (178 mg, 0.25 mmol) and DIPEA (65 µL, 0.37 mmol) in DCM (2.5 mL) at 0° C. was added MsCl (25 µL, 0.32 mmol). After 1 h at 0° C., the reaction mixture was diluted with DCM (10 mL), washed with 0.2 N HCl and saturated NaHCO$_3$ (aq). The organic layer was dried over Na$_2$SO$_4$, concentrated in vacuo to afford the title compound (190 mg, 96%). The crude residue was used as such in the following step. LCMS: $R_t$=1.05 min, m/z=795.4 (M+1) Method 2m_acidic.

Step 2: Benzhydryl 1-(((Z)-(2-(((2R,3S)-2-((4-(aminomethyl)-2H-1,2,3-triazol-2-yl)methyl)-4-oxoazetidin-3-yl)amino)-1-(2-((tert-butoxycarbonyl)amino) thiazol-4-yl)-2-oxoethylidene)amino)oxy) cyclopropanecarboxylate To a solution of aq. NH$_4$OH (2 mL, 28-30% wt) in EtOH (2 mL, ratio:1) and THF (2 mL, ratio:1) was added a solution of benzhydryl 1-(((Z)-(1-(2-((tert-butoxycarbonyl) amino)thiazol-4-yl)-2-(((2R,3S)-2-((4-(((methylsulfonyl) oxy)methyl)-2H-1,2,3-triazol-2-yl)methyl)-4-oxoazetidin-3-yl)amino)-2-oxoethylidene)amino)oxy) cyclopropanecarboxylate (190 mg, 0.24 mmol) in THF (1 mL) at −5° C. dropwise. After stirring at −5° C. for 1 h and rt for 12 h, the reaction mixture was diluted with 40 mL of DCM and washed with 10 mL of aq. saturated NaHCO$_3$ (aq), dried over Na$_2$SO$_4$, filtered and concentrated in vacuo. The residue was purified via silica gel chromatography (MeOH-DCM, 5-10%) to afford the title compound (120 mg, 49%). LCMS: $R_t$=0.87 min, m/z=716.4 (M+1) Method 2m_acidic.

Step 3: Benzhydryl 1-(((Z)-(2-(((2R,3S)-2-((4-((4-((tert-butoxycarbonyl)amino)butanamido)methyl)-2H-1,2,3-triazol-2-yl)methyl)-4-oxoazetidin-3-yl) amino)-1-(2-((tert-butoxycarbonyl)amino)thiazol-4-yl)-2-oxoethylidene)amino)oxy) cyclopropanecarboxylate To a solution of 4-((tert-butoxycarbonyl)amino)butanoic acid (30.7 mg, 0.15 mmol) in DCM (2 mL) at 0° C. was added DIPEA (35 µL, 0.20 mmol) and HATU (65 mg, 0.17 mmol). After 10 min, benzhydryl 1-(((Z)-(2-(((2R,3S)-2-((4-(aminomethyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy) cyclopropanecarboxylate (90 mg, 0.10 mmol) was added. After stirring at 0° C. for 1 h, the reaction mixture was diluted with DCM (40 mL), washed with 2M aq. Na$_2$CO$_3$ (20 mL), brine, dried over Na$_2$SO$_4$, filtered and concentrated in vacuo. The residue was purified via silica gel chromatography (MeOH-DCM, 5-10%) to afford the title compound (42 mg, 46%). LCMS: $R_t$=1.07 min, m/z=901.5 (M+1) Method 2m_acidic.

Step 4: (2R,3S)-3-((Z)-2-((1-((benzhydryloxy)carbonyl)cyclopropoxy)imino)-2-(2-((tert-butoxycarbonyl) amino)thiazol-4-yl)acetamido)-2-((4-((4-((tert-butoxycarbonyl)amino)butanamido)methyl)-2H-1,2,3-triazol-2-yl)methyl)-4-oxoazetidine-1-sulfonic acid To a solution of benzhydryl 1-(((Z)-(2-(((2R,3S)-2-((4-((4-((tert-butoxycarbonyl)amino)butanamido)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene) amino)oxy)cyclopropanecarboxylate (42 mg, 47 µmol) in DMF (0.47 mL) was added SO$_3$.DMF (74 mg, 0.47 mmol). After stirring at rt for 5 h, another 10 eq of SO$_3$.DMF was added and stirred at rt for 2 h. The reaction mixture was diluted with EtOAc (60 mL) and brine (40 mL), and the layers were separated. Aqueous layer was extracted with EtOAc (40 mL). Combined organic layers were dried with Na$_2$SO$_4$, filtered and concentrated in vacuo to afford the title compound (45.3 mg, 99%). The crude residue was used as such in the following step. LCMS: $R_t$=0.96 min, m/z=981.6 (M+1) Method 2m_acidic.

Step 5: 1-(((Z)-(2-(((2R,3S)-2-((4-((4-aminobutanamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

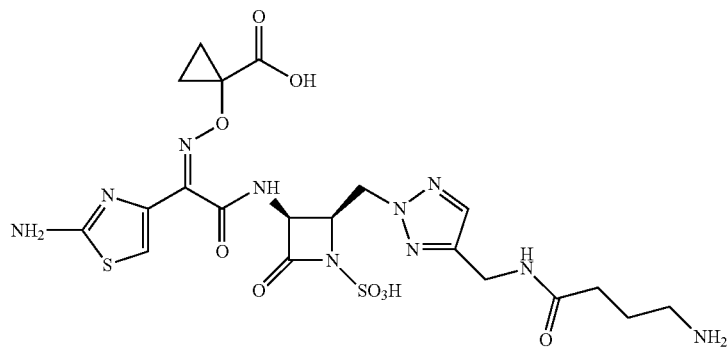

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((4-((tert-butoxycarbonyl)amino)butanamido)methyl)-2H-1,2,3-triazol-2-yl)methyl)-4-oxoazetidine-1-sulfonic acid (47 mg, 48 µmol), DCM (0.5 mL), and TFA (0.2 mL, 2.87 mmol) for 2 h. The reaction mixture was concentrated in vacuo, and the residued was partitioned between DCM and ice water. The water layer was purified by reverse phase prep HPLC (XSelect CSH, 30×100 mm, 5 µm, C18 column; AcN-water with 0.1% formic acid modifier, 60 mL/min) affording the title compound LCMS: $R_t$=0.53 min, m/z=615.3 (M+1) Method 2m_acidic_polar; $^1$H NMR (400 MHz, D$_2$O): δ 7.63 (s, 1H), 7.05 (s, 1H), 5.58-5.49 (m, 1H), 4.96-4.83 (m, 3H), 4.41 (br s, 2H), 3.06-2.90 (m, 2H), 2.44-2.28 (m, 2H), 1.98-1.83 (m, 2H), 1.38-1.04 (m, 4H).

Example 125

1-(((Z)-(2-(((2R,3S)-2-((4-((3-(((1r,3R)-3-aminocyclobutyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

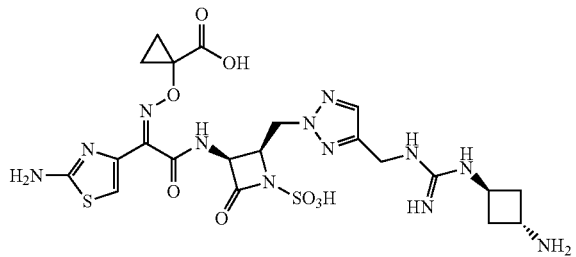 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N[C@H]1C[C@H](N)C1]

Prepared in analogous manner to example 119, using tert-butyl ((1r,3r)-3-((imino(methylthio)methyl)amino)cyclobutyl)carbamate. LCMS: $R_t$=0.33 min, m/z=641.0 (M+1) Method 2m_acidic; $^1$H NMR (400 MHz, D$_2$O) δ 7.72 (s, 1H), 7.10 (s, 1H), 5.58 (d, J=5.5 Hz, 1H), 5.01-4.95 (m, 1H), 4.89-4.85 (m, 2H), 4.53 (s, 2H), 4.25-4.17 (m, 1H), 4.05-3.95 (m, 1H), 2.69-2.59 (m, 2H), 2.58-2.48 (m, 2H), 1.34-1.27 (m, 2H), 1.19-1.12 (m, 2H).

Example 126

1-(((Z)-(1-(2-aminothiazol-4-yl)-2-(((2R,3S)-2-((4-((3-(azetidin-3-ylmethyl)guanidino)methyl)-2H-1,2,3-triazol-2-yl)methyl)-4-oxo-1-sulfoazetidin-3-yl)amino)-2-oxoethylidene)amino)oxy)cyclopropanecarboxylic acid Step 1: Tert-butyl 3-((3-((2-(((2R,3S)-3-(((benzyloxy)carbonyl)amino)-4-oxoazetidin-2-yl)methyl)-2H-1,2,3-triazol-4-yl)methyl)-1,2-bis(tert-butoxycarbonyl)guanidino)methyl)azetidine-1-carboxylate Preparation of benzyl ((2R,3S)-2-((4-(aminomethyl)-2H-1,2,3-triazol-2-yl)methyl)-4-oxoazetidin-3-yl)carbamate 2,2,2-trifluoroacetate. To a solution of NH-Boc[benzyl ((2R,3S)-2-((4-(aminomethyl)-2H-1,2,3-triazol-2-yl)methyl)-4-oxoazetidin-3-yl)carbamate] (368 mg, 0.86 mmol) in DCM (4 mL) was added TFA (1.05 mL, 13.68 mmol). After stirring at rt for 1 h, the reaction mixture was concentrated in vacuo to give the title compound as TFA salt (assume quantitative). The crude residue was used as such in the following step. LCMS: $R_t$=0.43 min, m/z=331.0 (M+1) Method 2m_acidic.

Preparation of tert-butyl 3-((N,N'-bis(tert-butoxycarbonyl)-1H-pyrazole-1-carboximidamido)methyl)azetidine-1-carboxylate. To a solution of Bis-Boc-pyrazolecarboxamidine (2.49 g, 8.01 mmol), N-Boc-3-hydroxymethylazetidine (1.50 g, 8.01 mmol) and triphenylphosphine (2.10 g, 8.01 mmol) in THF (80 mL) at 0° C. was added DIAD (1.62 g, 8.01 mmol) dropwise. After stirring at rt for 12 h, the reaction mixture was concentrated in vacuo, and the residue was dissolved in 10% EtOAc/heptane to triturate triphenylphosphine oxide. The filtrate was concentrated in vacuo and chromatographed via silica gel column chromatography (EtOAc-heptane, 0-35%) to afford the title compound (1.6 g, 41%). LCMS: $R_t$=1.12 min, m/z=480.0 (M+1) Method 2m_acidic.

Preparation of tert-butyl 3-((3-((2-(((2R,3S)-3-(((benzyloxy)carbonyl)amino)-4-oxoazetidin-2-yl)methyl)-2H-1,2,3-triazol-4-yl)methyl)-1,2-bis(tert-butoxycarbonyl)guanidino)methyl)azetidine-1-carboxylate. To a solution of benzyl ((2R,3S)-2-((4-(aminomethyl)-2H-1,2,3-triazol-2-yl)methyl)-4-oxoazetidin-3-yl)carbamate 2,2,2-trifluoroacetate (340 mg, 0.77 mmol) in dioxane (6 mL) was added DIPEA (0.147 mL, 0.842 mmol) and a solution of tert-butyl 3-((N,N'-bis(tert-butoxycarbonyl)-1H-pyrazole-1-carboximidamido)methyl)azetidine-1-carboxylate (367 mg, 0.765 mmol) in dioxane (1 mL). After heating to 60° C. for 12 h, the reaction mixture was concentrated in vacuo and purified via silica gel chromatography (EtOAc-heptane, 0-95%) to afford the title compound (390 mg, 69%). LCMS: $R_t$=0.94 min, m/z=742.5 (M+1) Method 2m_acidic.

Step 2: Tert-butyl 3-((3-((2-(((2R,3S)-3-amino-4-oxoazetidin-2-yl)methyl)-2H-1,2,3-triazol-4-yl)methyl)-1,2-bis(tert-butoxycarbonyl)guanidino)methyl)azetidine-1-carboxylate To a solution of tert-butyl 3-((3-((2-(((2R,3S)-3-(((benzyloxy)carbonyl)amino)-4-oxoazetidin-2-yl)methyl)-2H-1,2,3-triazol-4-yl)methyl)-1,2-bis(tert-butoxycarbonyl)guanidino)methyl)azetidine-1-carboxylate (390 mg, 0.526 mmol) in EtOH (10 mL) and MeOH (10.00 mL) was added Pd/C (5%, 112 mg, 53 µmol) and hydrogen baloon after evacuation and backfilled with H$_2$. After 1 h, the reaction mixture was filtered over celite pad, and the filtrate was concentrated in vacuo to afford title compound (302 mg, 95%). The crude residue was used as such in the following step. LCMS: $R_t$=0.74 min, m/z=608.4 (M+1) Method 2m_acidic.

Step 3: Tert-butyl 3-((3-((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)-1,2-bis(tert-butoxycarbonyl)guanidino)methyl)azetidine-1-carboxylate To a solution of tert-butyl 3-((3-((2-(((2R,3S)-3-amino-4-oxoazetidin-2-yl)methyl)-2H-1,2,3-triazol-4-yl)methyl)-1,2-bis(tert-butoxycarbonyl)guanidino)methyl)azetidine-1-carboxylate (309 mg, 0.51 mmol) and (Z)-2-((1-((benzhydryloxy)carbonyl)cyclopropoxy)imino)-2-(2-((tert-butoxycarbonyl)amino)thiazol-4-yl)acetic acid (273 mg, 0.51 mmol) in DMF (6 mL, ratio: 1) and DCM (6 mL, ratio: 1) was added HATU (232 mg, 0.61 mmol) followed by DIPEA (0.22 mL, 1.27 mmol). After stirring at rt for 12 h, EtOAc was added to the reaction mixture and washed with water, brine, dried over $Na_2SO_4$, filtered and concentrated in vacuo. The crude residue was purified via silica gel chromatography (EtOAc-heptane, 0-95%) to afford the title compound (330 mg, 58%). LCMS: $R_f$=1.15 min, m/z=1127.8 (M+1) Method 2m_acidic.

Step 4: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((2,3-bis(tert-butoxycarbonyl)-3-((1-(tert-butoxycarbonyl)azetidin-3-yl)methyl)guanidino)methyl)-2H-1,2,3-triazol-2-yl)methyl)-4-oxoazetidine-1-sulfonic acid To a solution of tert-butyl 3-((3-((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)-1,2-bis(tert-butoxycarbonyl)guanidino)methyl)azetidine-1-carboxylate (330 mg, 0.29 mmol) in DMF (2 mL) at 0° C. was added a solution of $SO_3$.DMF (359 mg, 2.34 mmol) in DMF (1 mL). After stirring at rt for 5 h, the reaction mixture was diluted with EtOAc and washed with brine, dried over $Na_2SO_4$, filtered and concentrated in vacuo to afford the title compound (300 mg, 85%). The crude residue was used as such in the following step. LCMS: $R_f$=1.25 min, m/z=1208.7 (M+1) Method 2m_acidic.

Step 5: 1-(((Z)-(1-(2-aminothiazol-4-yl)-2-(((2R,3S)-2-((4-((3-(azetidin-3-ylmethyl)guanidino)methyl)-2H-1,2,3-triazol-2-yl)methyl)-4-oxo-1-sulfoazetidin-3-yl)amino)-2-oxoethylidene)amino)oxy)cyclopropanecarboxylic acid Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((2,3-bis(tert-butoxycarbonyl)-3-((1-(tert-butoxycarbonyl)azetidin-3-yl)methyl)guanidino)methyl)-2H-1,2,3-triazol-2-yl)methyl)-4-oxoazetidine-1-sulfonic acid (300 mg, 0.248 mmol), DCM (3 mL) and TFA (1.90 mL, 24.85 mmol). The crude residue was purified by reverse phase prep HPLC (XSelect CSH, 19×100 mm, 5 μm, C18 column; AcN-water with 0.1% formic acid modifier, 24 mL/min) affording the title compound (19 mg, 12%). LCMS: $R_f$=0.32 min, m/z=641.3 (M+1), Method 2m_acidic; $^1$H NMR (400 MHz, DMSO-$d_6$) δ 10.26 (br s, 1H), 8.79 (br s, 3H), 7.78-7.54 (m, 3H), 7.14 (s, 2H), 6.84 (s, 1H), 5.06 (br s, 1H), 4.88 (dd, J=14.1, 3.94 Hz, 1H), 4.70-4.59 (m, 1H), 4.54-4.46 (m, 1H), 4.35 (d, J=3.8 Hz, 2H), 4.00-3.89 (m, 2H), 3.76-3.65 (m, 2H), 3.08-2.94 (m, 1H), 1.30-1.09 (m, 4H).

Example 127

1-(((Z)-(2-(((2R,3S)-2-((4-((3-(aminomethyl)azetidine-1-carboximidamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: Benzyl ((2R,3S)-2-((4-(hydroxymethyl)-2H-1,2,3-triazol-2-yl)methyl)-4-oxoazetidin-3-yl)carbamate To a solution of benzyl ((2R,3S)-2-((4-(((tert-butyldimethylsilyl)oxy)methyl)-2H-1,2,3-triazol-2-yl)methyl)-4-oxoazetidin-3-yl)carbamate (1.8 g, 4.04 mmol) in MeOH (60 mL) was added MeOH pre-washed DOWEX-50W-X4 100-200 (3.60 g, 4.04 mmol) resin. After stirring at rt for 2 h, the reaction mixture was filtered, and the filtrate was concentrated in vacuo to give the title compound (assume quantitative). LCMS: $R_f$=0.52 min, m/z=332.1 (M+1) Method 2m_acidic.

Step 2: Tert-butyl ((2-(((2R,3S)-3-(((benzyloxy)carbonyl)amino)-4-oxoazetidin-2-yl)methyl)-2H-1,2,3-triazol-4-yl)methyl)(((tert-butoxycarbonyl)imino)(1H-pyrazol-1-yl)methyl)carbamate To a solution of benzyl ((2R,3S)-2-((4-(hydroxymethyl)-2H-1,2,3-triazol-2-yl)methyl)-4-oxoazetidin-3-yl)carbamate (1.33 g, 4.01 mmol) and bis-Boc-pyrazolecarboxamidine (1.37 g, 4.42 mmol) in THF (50 mL) was added triphenylphosphine (1.16 g, 4.42 mmol) followed by DIAD (0.89 g, 4.42 mmol). After stirring at rt for 12 h, the reaction mixture was concentrated in vacuo. The crude residue was purified via silica gel chromatography (EtOAc-heptane, 0-90%) to afford the title compound (1.73 g, 69%). LCMS: $R_f$=0.99 min, m/z=624.4 (M+1) Method 2m_acidic.

Step 3

To a solution of tert-butyl ((2-(((2R,3S)-3-(((benzyloxy)carbonyl)amino)-4-oxoazetidin-2-yl)methyl)-2H-1,2,3-tria-

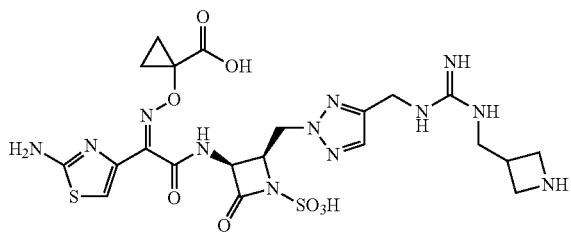 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)NCC1CNC1]

zol-4-yl)methyl)(((tert-butoxycarbonyl)imino)(1H-pyrazol-1-yl)methyl)carbamate (320 mg, 0.51 mmol) in CH$_3$CN (2 mL) was added Boc-aminomethylazetidine (105 mg, 0.56 mmol). After heating to 70° C. for 1 h, the reaction mixture was concentrated in vacuo to afford the title compound. The crude residue was used as such in the following step. LCMS: R$_t$=0.91 min, m/z=742.5 (M+1) Method 2m_acidic.

Step 4: Tert-butyl ((2-(((2R,3S)-3-amino-4-oxoazetidin-2-yl)methyl)-2H-1,2,3-triazol-4-yl)methyl)((3-(((tert-butoxycarbonyl)amino)methyl)azetidin-1-yl)((tert-butoxycarbonyl)imino)methyl)carbamate To a solution of compound from step 3 (570 mg, 0.77 mmol) in EtOH (10 mL) and MeOH (10 mL) was added Pd/C (5%, 16.35 mg, 77 µmol) and hydrogen baloon after evacuation and backfilled with H$_2$. After 4 h, the reaction mixture was filtered over celite pad, and the filtrate was concentrated in vacuo to afford title compound (302 mg, 95%). The crude residue was used as such in the following step. LCMS: R$_t$=0.68 min, m/z=608.4 (M+1) Method 2m_acidic.

Step 5: Benzhydryl 1-(((Z)-(2-(((2R,3S)-2-((4-((N,N'-bis(tert-butoxycarbonyl)-3-(((tert-butoxycarbonyl)amino)methyl)azetidine-1-carboximidamido)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate Prepared in analogous manner to example 126 step 3, using tert-butyl ((2-(((2R,3S)-3-amino-4-oxoazetidin-2-yl)methyl)-2H-1,2,3-triazol-4-yl)methyl)((3-(((tert-butoxycarbonyl)amino)methyl)azetidin-1-yl)((tert-butoxycarbonyl)imino)methyl)carbamate (460 mg, 0.76 mmol), (Z)-2-(((1-((benzhydryloxy)carbonyl)cyclopropoxy)imino)-2-(2-((tert-butoxycarbonyl)amino)thiazol-4-yl)acetic acid (407 mg, 0.76 mmol), DMF (8 mL), DCM (8 mL), HATU (345 mg, 0.91 mmol) and DIPEA (0.33 µL, 1.89 mmol). The crude residue was purified via silica gel chromatography (EtOAc-heptane, 0-100%) to afford the title compound (0.65 g, 76%). LCMS: R$_t$=1.15 min, m/z=1127.9 (M+1) Method 2m_acidic.

Step 6: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((N,N'-bis(tert-butoxycarbonyl)-3-(((tert-butoxycarbonyl)amino)methyl)azetidine-1-carboximidamido)methyl)-2H-1,2,3-triazol-2-yl)methyl)-4-oxoazetidine-1-sulfonic acid To a solution of benzhydryl 1-(((Z)-(2-(((2R,3S)-2-((4-((N,N'-bis(tert-butoxycarbonyl)-3-(((tert-butoxycarbonyl)amino)methyl)azetidine-1-carboximidamido)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (650 mg, 0.58 mmol) in DMF (3 mL) at 0° C. was added a solution of SO$_3$.DMF (883 mg, 5.77 mmol) in DMF (1 mL) at 0° C. After stirring at rt for 12 h, the reaction mixture was diluted with EtOAc and washed with brine, dried over Na$_2$SO$_4$, filtered and concentrated in vacuo to afford the title compound (assumed quantitative). The crude residue was used as such in the following step. LCMS: R$_t$=1.18 min, m/z=1208.5 (M+1) Method 2m_acidic.

Step 7: 1-(((Z)-(2-(((2R,3S)-2-((4-((3-(Aminomethyl)azetidine-1-carboximidamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

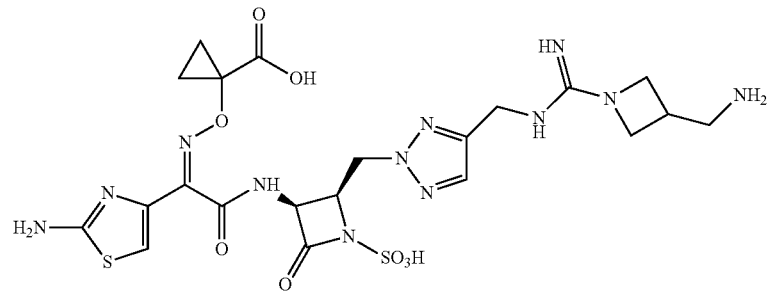

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((N,N'-bis(tert-butoxycarbonyl)-3-(((tert-butoxycarbonyl)amino)methyl)azetidine-1-carboximidamido)methyl)-2H-1,2,3-triazol-2-yl)methyl)-4-oxoazetidine-1-sulfonic acid (690 mg, 0.57 mmol), DCM (3 mL) and TFA (2.1 mL, 27.4 mmol). The crude residue was purified via reverse phase prep HPLC (XSelect CSH, 30×100 mm, 5 µm, C18 column; ACN-water with 0.1% formic acid modifier, 60 mL/min) affording the title compound (98 mg, 27%). LCMS: R$_t$=0.32 min, m/z=641.3 (M+1), Method 2m_acidic; $^1$H NMR (400 MHz, DMSO-d$_6$) δ 10.73 (s, 1H), 8.06 (s, 1H), 7.72-7.54 (m, 3H), 7.18 (s, 2H), 6.74 (s, 1H), 5.25 (dd, J=8.9, 5.5 Hz, 1H), 4.88 (dd, J=14.2, 4.3 Hz, 1H), 4.65 (dd, J=14.2, 7.7 Hz, 1H), 4.53 (ddd, J=7.6, 5.6, 4.4 Hz, 1H), 4.46-4.31 (m, 2H), 4.15 (td, J=8.7, 5.0 Hz, 2H), 3.96-3.81 (m, 2H), 3.11 (d, J=7.3 Hz, 2H assumed; partially obscured by water), 2.91 (p, J=6.8 Hz, 1H), 1.26-1.11 (m, 2H), 1.08-0.95 (m, 2H).

Example 128

1-(((Z)-(1-(2-aminothiazol-4-yl)-2-oxo-2-(((3S,4R)-2-oxo-4-((4-((3-(piperidin-4-yl)guanidino)methyl)-2H-1,2,3-triazol-2-yl)methyl)-1-sulfoazetidin-3-yl)amino)ethylidene)amino)oxy)cyclopropanecarboxylic acid

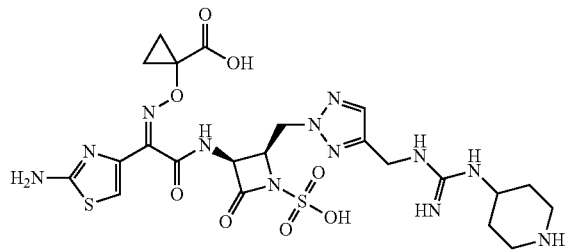 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)NC1CCNCC1]

Prepared in analogous manner to example 119, using tert-butyl 4-((imino(methylthio)methyl)amino)piperidine-1-carboxylate. LCMS: R$_t$=0.32 min, m/z=655.1 (M+1) Method 2m_acidic; $^1$H NMR (400 MHz, D$_2$O) δ 7.73 (s, 1H), 7.14 (s, 1H), 5.59 (d, J=5.6 Hz, 1H), 5.01-4.94 (m, 1H), 4.90-4.84 (m, 1H), 4.80 (s, 1H), 4.54 (s, 2H), 3.80-3.71 (m, 1H), 3.48 (d, J=13.4 Hz, 2H), 3.10 (t, J=12.5 Hz, 2H), 2.21 (d, J=12.9 Hz, 2H), 1.85-1.71 (m, 2H), 1.38-1.31 (m, 2H), 1.24-1.16 (m, 2H).

Example 129

1-(((Z)-2-(((2R,3S)-2-((4-((3-(2-aminoethyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

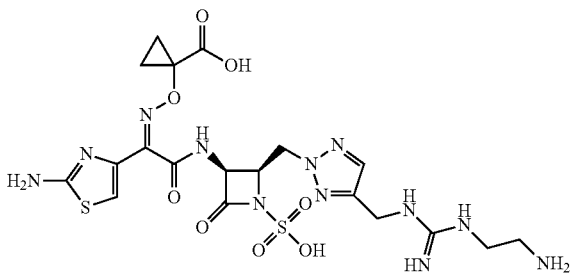 [SMILES: N=C(NCCN)NCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 119, using tert-butyl (2-((imino(methylthio)methyl)amino)ethyl)carbamate. LCMS: R$_t$=0.31 min, m/z=615.4 (M+1) Method 2m_acidic; $^1$H NMR (400 MHz, D$_2$O) δ 7.63 (s, 1H), 7.02 (s, 1H), 5.49 (d, J=5.6 Hz, 1H), 4.88 (q, J=5.6 Hz, 1H), 4.77 (d, J=5.6 Hz, 2H), 4.44 (s, 2H), 3.48 (t, J=5.9 Hz, 2H), 3.14 (t, J=5.9 Hz, 2H), 1.28-1.15 (m, 2H), 1.12-1.00 (m, 2H).

Example 130

1-(((Z)-(2-(((2R,3S)-2-((4-((1-(3-aminopropyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: Benzyl ((2R,3S)-2-((4-(hydroxymethyl)-2H-1,2,3-triazol-2-yl)methyl)-4-oxoazetidin-3-yl)carbamate To a solution of benzyl ((2R,3S)-2-((4-(((tert-butyldimethylsilyl)oxy)methyl)-2H-1,2,3-triazol-2-yl)methyl)-4-oxoazetidin-3-yl)carbamate (500 mg, 1.12 mmol) in MeOH (15 mL) was added DOWEX-50W-X4 100-200 (1 g, 1.12 mmol) resin. After stirring at rt for 3 h, the reaction mixture was filtered, and the filtrate was concentrated in vacuo to give the title compound (assume quantitative). LCMS: R$_t$=0.51 min, m/z=332.1 (M+1) Method 2m_acidic.

Step 2: Benzyl ((2R,3S)-2-((4-formyl-2H-1,2,3-triazol-2-yl)methyl)-4-oxoazetidin-3-yl)carbamate To a solution of benzyl ((2R,3S)-2-((4-(hydroxymethyl)-2H-1,2,3-triazol-2-yl)methyl)-4-oxoazetidin-3-yl)carbamate (385 mg, 1.16 mmol) in THF (10 mL) was added manganese dioxide (2.0 g, 23 mmol). After stirring at rt for 12 h, another 1 g of MnO$_2$ was added and stirred for another 1 h. The reaction mixture was filtered over celite with MeOH wash. The filtrate was concentrated in vacuo to give the title compound (340 mg, 89%). The crude residue was used as such in the following step. LCMS: R$_t$=0.61 min, m/z=330.0 (M+1) Method 2m_acidic.

Step 3

To a solution of benzyl ((2R,3S)-2-((4-formyl-2H-1,2,3-triazol-2-yl)methyl)-4-oxoazetidin-3-yl)carbamate (340 mg, 1.03 mmol) and Boc-1,3-diaminopropane (360 mg, 2.07 mmol) in DCE (16 mL) and THF (6 mL) at 0° C. was added sodium triacetoxyborohydride (328 mg, 1.55 mmol). After stirring at rt for 18 h, the reaction mixture was concentrated in vacuo, re-dissolved in DCM, washed with 5% sodium bicarbonate, brine, dried over MgSO4, filtered and concentrated in vacuo to give the title compound (470 mg, 93%). The crude residue was used as such in the following step. LCMS: R$_t$=0.64 min, m/z=488.2 (M+1) Method 2m_acidic.

Step 4

To a solution of DIPEA (0.17 mL, 0.96 mmol) and product from step 3 (470 mg, 0.96 mmol) in dioxane (15 mL) was added bis-Boc-pyrazolecarboxamidine (359 mg, 1.16 mmol). After heated to 60° C. for 3 h, the reaction mixture was concentrated in vacuo and purified via silica gel chromatography (EtOAc-Heptane, 20-100%) to afford the title compound (130 mg, 18%). LCMS: R$_t$=0.93 min, m/z=730.5 (M+1) Method 2m_acidic.

Step 5

Prepared in analogous manner to example 126 step 2, using product from step 4 (130 mg, 0.178 mmol), EtOH (5 mL) and methanol (3 mL), Pd/C (5%, 37.9 mg, 18 µmol). The crude residue was used as such in the following step (100 mg, 94%). LCMS: R=0.70 min, m/z=596.0 (M+1) Method 2m_acidic.

Step 6: Benzhydryl 1-(((Z)-(2-(((2R,3S)-2-((4-((2,3-bis(tert-butoxycarbonyl)-1-(3-((tert-butoxycarbonyl) amino)propyl)guanidino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate Prepared in analogous manner to example 126 step 3, using product from step 5 (100 mg, 0.168 mmol), tert-butyl 3-((3-((2-(((2R,3S)-3-amino-4-oxoazetidin-2-yl)methyl)-2H-1,2,3-triazol-4-yl)methyl)-1,2-bis(tert-butoxycarbonyl)guanidino)methyl)azetidine-1-carboxylate (309 mg, 0.51 mmol) and (Z)-2-((1-((benzhydryloxy)carbonyl)cyclopropoxy) imino)-2-(2-((tert-butoxycarbonyl)amino)thiazol-4-yl)acetic acid (90 mg, 0.17 mmol), DMF (3 mL), DCM (2 mL), HATU (83 mg, 0.22 mmol) and DIPEA (73 µL, 0.42 mmol). The crude residue was purified via silica gel chromatography (EtOAc-heptane, 15-90%) to afford the title compound (110 mg, 59%) along with the bis-Boc product. LCMS: R$_t$=1.13 min, m/z=1115.7 (M+1) Method 2m_acidic.

Step 7: (2R,3S)-3-((Z)-2-((1-((benzhydryloxy)carbonyl)cyclopropoxy)imino)-2-(2-((tert-butoxycarbonyl) amino)thiazol-4-yl)acetamido)-2-((4-((2,3-bis(tert-butoxycarbonyl)-1-(3-((tert-butoxycarbonyl)amino) propyl)guanidino)methyl)-2H-1,2,3-triazol-2-yl) methyl)-4-oxoazetidine-1-sulfonic acid Prepared in analogous manner to example 126 step 4, using benzhydryl 1-(((Z)-(2-(((2R,3S)-2-((4-((2,3-bis(tert-butoxycarbonyl)-1-(3-((tert-butoxycarbonyl)amino)propyl)guanidino)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (110 mg, 99 µmol), DMF (2 mL), a solution of SO$_3$.DMF (121 mg, 0.79 mmol) in DMF (1 mL) followed by another 140 mg of SO$_3$.DMF. The crude residue was used as such in the following step (assumed quantitative). LCMS: R$_t$=1.15 min, m/z=1195.9 (M+1) Method 2m_acidic.

Step 8: 1-(((Z)-(2-(((2R,3S)-2-((4-((1-(3-aminopropyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy) cyclopropanecarboxylic acid

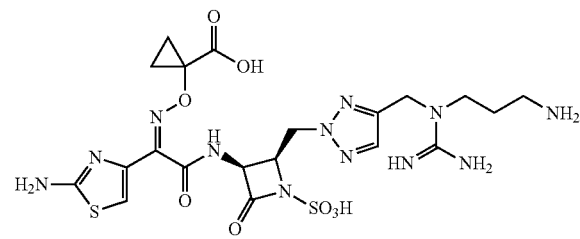 [SMILES: N=C(N)N(CCCN)Cc1cnn(C[C@@H]2[C@H](NC(=O)/C(=N\OC3(C(=O)O)CC3)c3csc(N)n3)C(=O)N2S(=O)(=O)O)n1]

Followed the general procedure for the acid mediated deprotection using (2R,3S)-3-((Z)-2-((1-((benzhydryloxy) carbonyl)cyclopropoxy)imino)-2-(2-((tert-butoxycarbonyl) amino)thiazol-4-yl)acetamido)-2-((4-((2,3-bis(tert-butoxycarbonyl)-1-(3-((tert-butoxycarbonyl)amino)propyl)

guanidino)methyl)-2H-1,2,3-triazol-2-yl)methyl)-4-oxoazetidine-1-sulfonic acid (118 mg, 99 µmol), DCM (2 mL) and TFA (2.0 mL, 26 mmol). The crude residue was purified via reverse phase prep HPLC (XSelect CSH, 30×100 mm, 5 µm, C18 column; ACN-water with 0.1% formic acid modifier, 60 mL/min) affording the title compound (5.1 mg, 8%). LCMS: R$_t$=0.28 min, m/z=629.4 (M+1). Method 2m_acidic.

Example 131

1-(((Z)-(2-(((2R,3S)-2-((4-(((3-amino-3-methylbutyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy) cyclopropanecarboxylic acid

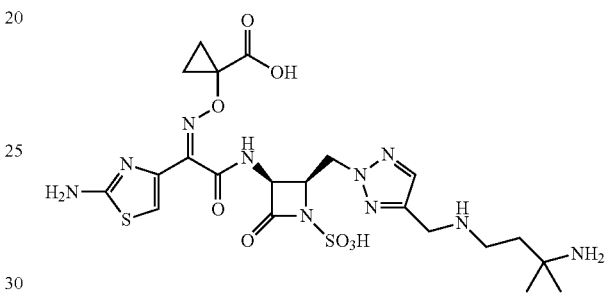

Prepared in analogous manner to example 90, using tert-butyl (4-amino-2-methylbutan-2-yl)carbamate. The crude residue was purified by reverse phase prep HPLC (XSelect CSH, 30×100 mm, 5 µm, C18 column; ACN-water with 0.1% formic acid modifier, 60 mL/min). LCMS: R$_t$=0.33 min, m/z=615.3 (M+1) Method 2m_acidic; $^1$H NMR (400 MHz, D$_2$O): δ 7.76 (s, 1H), 7.03 (s, 1H), 5.52 (d, J=5.6 Hz, 1H), 4.97-4.90 (m, 1H), 4.88-4.74 (m, 2H), 4.31 (s, 2H), 3.18-3.08 (m, 2H), 2.04-1.94 (m, 2H), 1.29 (s, 6H), 1.23-1.18 (m, 2H), 1.14-0.99 (m, 2H).

Example 132

1-(((Z)-(2-(((2R,3S)-2-((4-(((4-amino-2-methylbutan-2-yl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy) cyclopropanecarboxylic acid

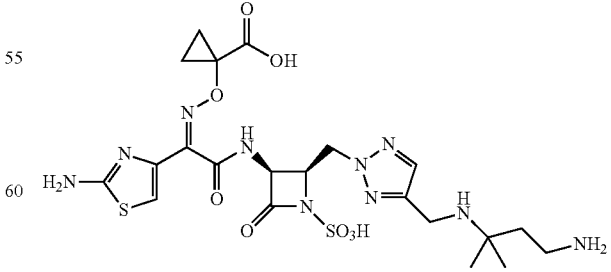

Prepared in analogous manner to example 90, using tert-butyl (3-amino-3-methylbutyl)carbamate (Boc protection was not necessary due to hindered amine). The crude residue was purified by reverse phase prep HPLC (XSelect CSH, 30×100 mm, 5 μm, C18 column; ACN-water with 0.1% formic acid modifier, 60 mL/min). LCMS: $R_t$=0.49 min, m/z=615.3 (M+1) Method 2m_acidic; $^1$H NMR (400 MHz, D$_2$O): δ 7.86 (s, 1H), 7.16 (s, 1H), 5.62 (d, J=5.4 Hz, 1H), 5.07-4.91 (m, 2H), 4.88-4.79 (m, 3H), 4.40 (s, 2H), 3.23-3.13 (m, 2H), 2.22-2.12 (m, 2H), 1.49 (s, 6H), 1.39-1.11 (m, 4H).

Example 133

1-(((Z)-(2-(((2R,3S)-2-((4-((((2-aminoethoxy)carbonyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

Step 1: 2-((tert-butoxycarbonyl)amino)ethyl 1H-imidazole-1-carboxylate

To a solution of CDI (218 mg, 1.30 mmol) in DCM (4 mL) was added a solution of tert-butyl(2-hydroxyethyl)carbamate (0.22 mL, 1.37 mmol) in DCM (1 mL). After stirring at rt for 1 h, the reaction mixture was used directly in DCM for the next step.

Step 2: Benzhydryl 1-(((Z)-(1-(2-((tert-butoxycarbonyl)amino)thiazol-4-yl)-2-(((2R,3S)-2-((4-(10,10-dimethyl-3,8-dioxo-4,9-dioxa-2,7-diazaundecyl)-2H-1,2,3-triazol-2-yl)methyl)-4-oxoazetidin-3-yl)amino)-2-oxoethylidene)amino)oxy)cyclopropanecarboxylate To a solution of benzhydryl 1-(((Z)-(2-(((2R,3S)-2-((4-(aminomethyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (90 mg, 0.13 mmol) in DCM (2 mL) at 0° C. was added a solution of 2-((tert-butoxycarbonyl)amino)ethyl 1H-imidazole-1-carboxylate (0.59 ml, 0.19 mmol) in DCM (0.6 mL). After stirring at rt for 12 h, another 3 equiv 2-((tert-butoxycarbonyl)amino)ethyl 1H-imidazole-1-carboxylate (1.18 ml, 0.38 mmol) was added. After stirring at rt for additional 60 h, the reaction mixture was partitioned between DCM (40 mL) and water (20 mL). The organic layer was dried with Na$_2$SO$_4$, filtered and concentrated in vacuo. The crude residue was purified via silica gel chromatography (MeOH-DCM, 0-5%) to afford the title compound (64 mg, 56%). LCMS: $R_t$=1.09 min, m/z=903.5 (M+1) Method 2m_acidic.

Step 3: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(10,10-dimethyl-3,8-dioxo-4,9-dioxa-2,7-diazaundecyl)-2H-1,2,3-triazol-2-yl)methyl)-4-oxoazetidine-1-sulfonic acid To a solution of benzhydryl 1-(((Z)-(1-(2-((tert-butoxycarbonyl)amino)thiazol-4-yl)-2-(((2R,3S)-2-((4-(10,10-dimethyl-3,8-dioxo-4,9-dioxa-2,7-diazaundecyl)-2H-1,2,3-triazol-2-yl)methyl)-4-oxoazetidin-3-yl)amino)-2-oxoethylidene)amino)oxy)cyclopropanecarboxylate (108 mg, 0.120 mmol) in DMF (1.2 mL) was added SO$_3$.DMF (189 mg, 1.20 mmol). After stirring at rt for 5 h, the reaction mixture was diluted with EtOAc (60 mL) and brine (20 mL). Aqueous layer was extracted with EtOAc (20 mL). Combined organic layers were dried with Na$_2$SO$_4$, filtered and concentrated in vacuo to give the title compound (68 mg, 58%). The crude residue was used as such in the following step. LCMS: $R_t$=0.96 min, m/z=983.6 (M+1) Method 2m_acidic.

Step 4: 1-(((Z)-(2-(((2R,3S)-2-((4-((((2-aminoethoxy)carbonyl)amino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

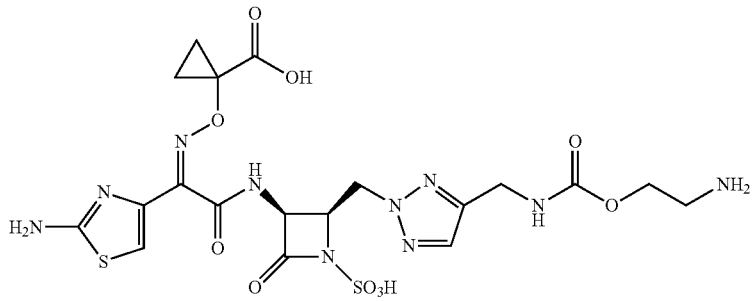

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(10,10-dimethyl-3,8-dioxo-4,9-dioxa-2,7-diazaundecyl)-2H-1,2,3-triazol-2-yl)methyl)-4-oxoazetidine-1-sulfonic acid (68 mg, 69 μmol), DCM (0.7 mL) and TFA (0.32 mL, 4.15 mmol). The crude residue was purified by reverse phase prep HPLC (XSelect CSH, 30×100 mm, 5 μm, C18 column; ACN-water with 0.1% formic acid modifier, 60 mL/min), affording the title compound (19 mg, 44%). LCMS: R=0.54 min, m/z=617.3 (M+1) Method 2m_acidic_polar; $^1$H NMR (400 MHz, D$_2$O) δ 7.67 (s, 1H), 7.10 (s, 1H), 5.60-5.52 (m, 1H), 5.01-4.84 (m, 3H), 4.43-4.37 (s, 2H), 4.35-4.27 (m, 2H), 3.33-3.25 (m, 2H), 1.36-1.13 (m, 4H).

Example 134

1-(((Z)-(2-(((2R,3S)-2-((4-((2-aminoacetamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

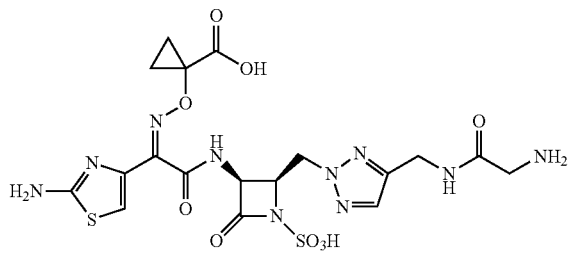 [SMILES: NCC(=O)NCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 124, using 2-((tert-butoxycarbonyl)amino)acetic acid. The crude residue was purified by reverse phase prep HPLC (XSelect CSH, 30×100 mm, 5 μm, C18 column; ACN-water with 0.1% formic acid modifier, 60 mL/min). LCMS: R$_t$=0.48 min, m/z=587.2 (M+1) Method 2m_acidic_polar; $^1$H NMR (400 MHz, D$_2$O) δ 7.68 (s, 1H), 7.12 (s, 1H), 5.57-5.53 (m, 1H), 4.96 (m, 3H), 4.51 (s, 2H), 3.84 (s, 2H), 1.35 (m, 4H).

Example 135

1-(((Z)-(2-(((2R,3S)-2-((4-((3-(2-aminoethyl)ureido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

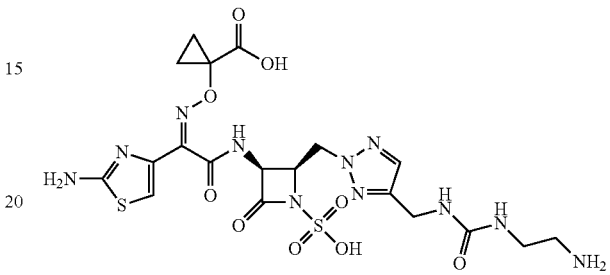

Prepared in analogous manner to example 133, using tert-butyl (2-(1H-imidazole-1-carboxamido)ethyl)carbamate (without additional base) in step 2. The crude residue was purified by reverse phase prep HPLC (Xselect CSH, 30×100 mm, 5 μm, C18 column; ACN-water with 0.1% formic acid modifier, 60 mL/min). LCMS: R$_t$=0.51 min, m/z=616.3 (M+1) Method 2m_acidic_polar; $^1$H NMR (400 MHz, D$_2$O) δ 7.62 (s, 1H), 7.07 (s, 1H), 5.55-5.49 (m, 1H), 4.97-4.86 (m, 3H), 4.34 (s, 2H), 3.44-3.35 (m, 2H), 3.12-3.03 (m, 2H), 1.36-1.10 (m, 4H).

Example 136

1-(((Z)-(2-(((2R,3S)-2-((4-((3-(3-aminopropyl)ureido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

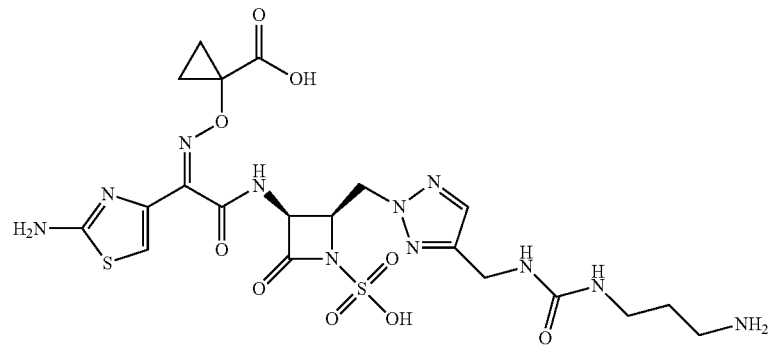

Prepared in analogous manner to example 133, tert-butyl (3-(1H-imidazole-1-carboxamido)propyl)carbamate (without additional base) in step 2. The crude residue was purified by reverse phase prep HPLC (Xselect CSH, 30×100 mm, 5 μm, C18 column; AcN-water with 0.1% formic acid modifier, 60 mL/min). LCMS: $R_t$=0.52 min, m/z=630.4 (M+1) Method 2m_acidic_polar; $^1$H NMR (400 MHz, $D_2O$) δ 7.60 (s, 1H), 7.07 (s, 1H), 5.57-5.48 (m, 1H), 4.97-4.86 (m, 3H), 4.32 (s, 2H), 3.18 (m, 2H), 2.97 (m, 2H), 1.79 (m, 2H), 1.33 (m, 4H).

Example 137

(2R,3S)-3-((Z)-2-(2-aminothiazol-4-yl)-2-((1-carboxycyclopropoxy)-imino)acetamido)-2-((4-((((1-methylpyridin-1-ium-3-yl)methyl)amino)methyl)-2H-1,2,3-triazol-2-yl)methyl)-4-oxoazetidine-1-sulfonate Step 1: 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)amino)methyl)-1-methylpyridin-1-ium chloride To a suspension of 3-(ammoniomethyl)-1-methylpyridin-1-ium (147 mg, 0.755 mmol) in THF:EtOH (1:1, 1.26 mL) was added triethylamine (175 μl, 1.26 mmol) followed by a solution of benzhydryl 1-(((Z)-(1-(2-((tert-butoxycarbonyl)amino)thiazol-4-yl)-2-(((2R,3S)-2-((4-(((methylsulfonyl)oxy)methyl)-2H-1,2,3-triazol-2-yl)methyl)-4-oxoazetidin-3-yl)amino)-2-oxoethylidene)amino)oxy)cyclopropanecarboxylate (200 mg, 0.252 mmol) in THF (500 uL), dropwise. After stirring at rt for 20 h, the mixture was concentrated in vacuo then re-dissolved in DMSO and purified by reverse phase prep HPLC (Xselect CSH, 30×100 mm, 5 μm, C18 column; ACN-water with 0.1% formic acid modifier, 60 mL/min), affording the title compound (50 mg, 23%) as a white solid. LCMS: $R_t$=0.85 min, m/z=821.3 (M+) Method 2m_acidic.

Step 2: 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)(tert-butoxycarbonyl)amino)methyl)-1-methylpyridin-1-ium chloride Prepared in an anologous manner to example 85, step 4 using 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)amino)methyl)-1-methylpyridin-1-ium chloride (50 mg, 0.058 mmol), Boc-anhydride (0.027 mL, 0.115 mmol), $NaHCO_3$ (satd aq, 1.22 mL) and DCM (1.15 mL). LCMS: $R_t$=0.99 min, m/z=921.3 (M+) Method 2m_acidic.

Step 3: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)((1-methylpyridin-1-ium-3-yl)methyl)amino)methyl)-2H-1,2,3-triazol-2-yl)methyl)-4-oxoazetidine-1-sulfonate Prepared in analogous manner to example 19, step 3 using 3-(((((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)(tert-butoxycarbonyl)-amino)methyl)-1-methylpyridin-1-ium chloride (49 mg, 0.051 mmol), $SO_3$.DMF (78 mg, 0.51 mmol) and DMF (1 mL). LCMS: $R_t$=0.99 min, m/z=1002 (M+) Method 2m_acidic.

Step 4: (2R,3S)-3-((Z)-2-(2-aminothiazol-4-yl)-2-((1-carboxycyclopropoxy)-imino)acetamido)-2-((4-((((1-methylpyridin-1-ium-3-yl)methyl)amino)methyl)-2H-1,2,3-triazol-2-yl)methyl)-4-oxoazetidine-1-sulfonate

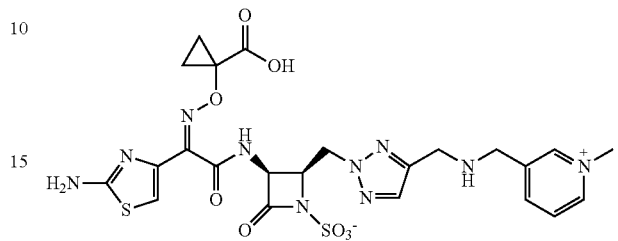

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)((1-methylpyridin-1-ium-3-yl)methyl)amino)methyl)-2H-1,2,3-triazol-2-yl)methyl)-4-oxoazetidine-1-sulfonate (53 mg, 0.053 mmol), TFA (81 μl, 1.1 mmol) and DCM (72 mL). The crude residue purified by reverse phase prep HPLC (Xselect CSH, 30×100 mm, C18 column; ACN-water with 0.1% formic acid modifier, 60 mL/min), affording the title compound (13 mg, 35%) as a white powder. LCMS: $R_t$=0.30 min, m/z=635.3 (M+1) Method 2m_acidic; $^1$H NMR (400 MHz, $D_2O$) δ 9.00 (s, 1H), 8.78-8.67 (m, 2H), 7.97 (t, J=7.1 Hz, 1H), 7.86 (s, 1H), 6.93 (s, 1H), 5.75 (d, J=5.3 Hz, 1H), 5.11 (dd, J=14.4, 3.7 Hz, 1H), 5.06-4.99 (m, 1H), 4.70-4.46 (m, 4H), 4.38 (s, 3H), 3.77-3.62 (m, 1H), 1.35-1.26 (m, 1H), 1.20-1.10 (m, 2H), 0.93-0.82 (m, 1H).

Example 138

1-(((Z)-(2-(((2R,3S)-2-((4-((4-aminopiperidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: Benzhydryl 1-(((Z)-(2-(((2R,3S)-2-((4-((4-((tert-butoxycarbonyl)amino)piperidin-1-yl)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate Benzhydryl 1-(((Z)-(1-(2-((tert-butoxycarbonyl)amino)thiazol-4-yl)-2-(((2R,3S)-2-((4-(((methylsulfonyl)oxy)methyl)-2H-1,2,3-triazol-2-yl)methyl)-4-oxoazetidin-3-yl)amino)-2-oxoethylidene)amino)oxy)cyclopropanecarboxylate (64 mg, 0.081 mmol) and sodium iodide (18.1 mg, 0.121 mmol) were stirred in DMF (700 μL) for 14 h, whereupon cesium carbonate (33.4 mg, 0.103 mmol) and tert-butyl piperidin-4-ylcarbamate (17.7 mg, 0.089 mmol) were added. After 3 h of additional stirring the mixture was diluted with EtOAc and LiCl (5% aq) solution. The aqueous layer was extracted with EtOAc (2×) and the combined organic layers were washed with LiCl (5% aq) solution, brine, dried over $Na_2SO_4$ and concentrated in vacuo. The crude residue was purified via silica gel chromatography (1-8% MeOH-DCM), affording the title compound (52.6 mg, 73%) as an off-white solid. LCMS: $R_t$=0.98 min, m/z=899.7 (M+1) Method 2m_acidic.

215

Step 2: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((4-((tert-butoxycarbonyl)amino)piperidin-1-yl)methyl)-2H-1,2,3-triazol-2-yl)methyl)-4-oxoazetidine-1-sulfonic acid To a solution of benzhydryl 1-(((Z)-(2-(((2R,3S)-2-((4-((4-((tert-butoxycarbonyl)amino)piperidin-1-yl)methyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (53 mg, 59 μmol) in DMF (293 μL) at 0° C. was added SO₃.DMF (24.3 mg, 0.159 mmol). After stirring for 2 h at rt, more SO₃.DMF (24.3 mg, 81 μmol) was added. After additional stirring for 16 h, the solution was concentrated in vacuo. The crude material was used directly in step 3. LCMS: R$_f$=0.97 min, m/z=979.9 (M+1) Method 2m_acidic.

Step 3: 1-(((Z)-(2-(((2R,3S)-2-((4-((4-aminopiperidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

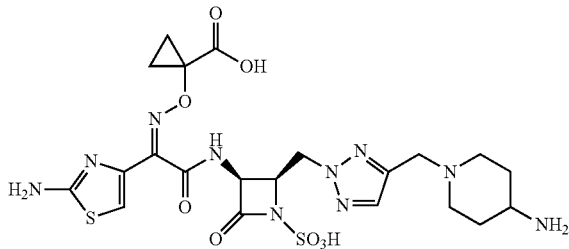 [SMILES: Nc1nc(/C(=N/OC2(C(=O)O)CC2)C(=O)N[C@@H]2C(=O)N(S(=O)(=O)O)[C@@H]2Cn2ncc(CN3CCC(N)CC3)n2)cs1]

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((4-((tert-butoxycarbonyl)amino)piperidin-1-yl)methyl)-2H-1,2,3-triazol-2-yl)methyl)-4-oxoazetidine-1-sulfonic acid (58 mg, 59 μmol), DCM (590 μL), anisole (13 μL, 0.12 mmol) and TFA (273 μL, 3.54 mmol). The crude residue was purified by reverse phase prep HPLC (Xselect CSH, 30×100 mm, 5 μm, C18 column; ACN-water with 0.1% formic acid modifier, 60 mL/min), affording the title compound (2.7 mg, 7.3%) as an off-white powder. LCMS: R$_f$=0.50 min, m/z=613.4 (M+1) Method 2m_acidic_polar; ¹H NMR (400 MHz, D₂O) δ 7.93 (s, 1H), 7.12 (s, 1H), 5.59 (d, J=5.5 Hz, 1H), 5.07-5.00 (m, 1H), 4.99-4.96 (m, 1H), 4.93-4.90 (m, 1H), 4.39 (s, 2H), 3.75-3.62 (m, 2H), 3.63-3.51 (m, 1H), 3.28-3.08 (m, 2H), 2.33 (d, J=13.7 Hz, 2H), 2.04-1.89 (m, 2H), 1.38-1.11 (m, 4H).

Example 139

(2R,3S)-3-((Z)-2-(2-aminothiazol-4-yl)-2-((1-carboxycyclopropoxy)imino)acetamido)-2-((4-(((6,7-dihydro-5H-pyrazolo[1,2-a][1,2,4]triazol-4-ium-6-yl)thio)methyl)-2H-1,2,3-triazol-2-yl)methyl)-4-oxoazetidine-1-sulfonate Step 1: 6-(((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)thio)-6,7-dihydro-5H-pyrazolo[1,2-a][1,2,4]triazol-4-ium chloride Prepared in an anlogous manner to example 138, step 1 using benzhydryl 1-(((Z)-(1-(2-((tert-butoxycarbonyl)amino)thiazol-4-yl)-2-(((2R,3S)-2-((4-(((methylsulfonyl)oxy)methyl)-2H-1,2,3-triazol-2-yl)methyl)-4-oxoazetidin-3-yl)amino)-2-oxoethylidene)amino)oxy)cyclopropanecarboxylate (54 mg, 0.068 mmol), sodium iodide (17.2 mg, 0.115 mmol), cesium carbonate (24.5 mg, 0.075 mmol), 6-mercapto-6,7-dihydro-5H-pyrazolo[1,2-a][1,2,4]triazol-4-ium chloride (13.4 mg, 0.075 mmol) and DMF (600 μL). The slurry was concentrated in vacuo, and the crude residue was purified via reverse phase prep HPLC (Xselect CSH, 30×100 mm, 5 μm, C18 column; ACN-water with 0.1% formic acid modifier, 60 mL/min), affording the title compound (19.7 mg, 34%) as white solid. LCMS: R$_f$=0.91 min, m/z=840.4 (M+) Method 2m_acidic.

Step 2: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((6,7-dihydro-5H-pyrazolo[1,2-a][1,2,4]triazol-4-ium-6-yl)thio)methyl)-2H-1,2,3-triazol-2-yl)methyl)-4-oxoazetidine-1-sulfonate Prepared in an analogous manner to example 138, step 2 using 6-(((2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-2H-1,2,3-triazol-4-yl)methyl)thio)-6,7-dihydro-5H-pyrazolo[1,2-a][1,2,4]triazol-4-ium chloride (21 mg, 0.025 mmol), DMF (250 μL), SO₃.DMF (18.9 mg, 0.123 mmol) then additional SO₃.DMF (22.3 mg, 0.146 mmol). The crude material was used directly in step 3. LCMS: R$_f$=0.92 min, m/z=921.7 (M+1) Method 2m_acidic.

Step 3: (2R,3S)-3-((Z)-2-(2-aminothiazol-4-yl)-2-((1-carboxycyclopropoxy)imino)-acetamido)-2-((4-(((6,7-dihydro-5H-pyrazolo[1,2-a][1,2,4]triazol-4-ium-6-yl)thio)methyl)-2H-1,2,3-triazol-2-yl)methyl)-4-oxoazetidine-1-sulfonate

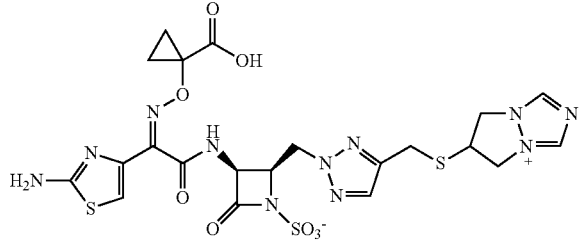

Prepared in analogous manner to example 138, step 3 using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((6,7-dihydro-5H-pyrazolo[1,2-a][1,2,4]triazol-4-ium-6-yl)thio)methyl)-2H-1,2,3-triazol-2-yl)methyl)-4-oxoazetidine-1-sulfonate (23 mg, 0.025 mmol), anisole (5.5 μL, 0.050 mmol), TFA (116 μL, 1.50 mmol) and DCM (300 μL). The crude residue purified by reverse phase prep HPLC (Xselect CSH, 30×100 mm, 5 μm, C18 column; ACN-water with 0.1% formic acid modifier, 60 mL/min), affording the title compound (1.5 mg, 8%). LCMS: R$_f$=0.60 min, m/z=654.4 (M+1) Method 2m_acidic; ¹H NMR (400 MHz, D₂O) δ 9.02 (d, J=4.8 Hz, 2H), 7.84 (s, 1H), 7.17 (s, 1H), 5.65 (d, J=5.8 Hz, 1H), 5.12-4.97 (m, 3H), 4.94-4.89 (m, 1H), 4.64-4.50 (m, 4H), 4.09 (s, 2H), 1.48-1.36 (m, 2H), 1.32-1.24 (m, 2H).

Example 140

1-((((Z)-(2-(((2R,3S)-2-((4-((3-((1s,3S)-3-aminocyclobutyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

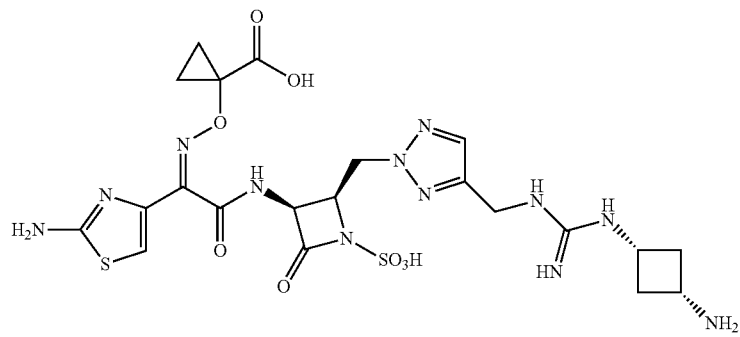

Prepared in analogous manner to example 119, using tert-butyl ((1S,3S)-3-((imino(methylthio)methyl)amino)cyclobutyl)carbamate. LCMS: R$_t$=0.49 min, m/z=641.2 (M+1) Method 2m_acidic; $^1$H NMR (400 MHz, D$_2$O) δ ppm 7.61 (s, 1H) 7.00 (s, 1H) 5.47 (d, J=5.6 Hz, 1H) 4.91-4.84 (m, 1H) 4.79-4.76 (m, 3H) 4.41 (s, 3H) 3.78 (t, J=7.6 Hz, 1H) 3.51 (t, J=8.0 Hz, 1H) 2.84-2.67 (m, 1H) 2.12 (d, J=9.7 Hz, 1H) 1.23-1.19 (m, 2H) 1.05 (d, J=4.5 Hz, 2H).

Example 141

1-((((Z)-(1-(2-aminothiazol-4-yl)-2-oxo-2-(((3S,4R)-2-oxo-4-((4-((3-((S)-pyrrolidin-3-yl)guanidino)methyl)-2H-1,2,3-triazol-2-yl)methyl)-1-sulfoazetidin-3-yl)amino)ethylidene)amino)oxy)cyclopropanecarboxylic acid

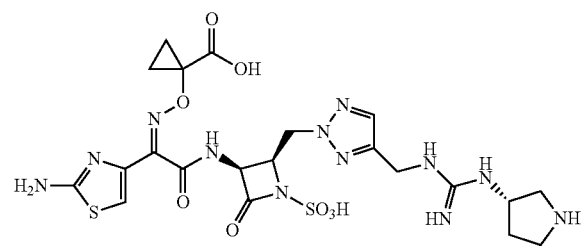 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N[C@H]1CCNC1]

Prepared in analogous manner to example 119, using (S)-tert-butyl 3-((imino(methylthio)methyl)amino)pyrrolidine-1-carboxylate. LCMS: R$_t$=0.49 min, m/z=640.8 (M+1) Method 2m_acidic; $^1$H NMR (400 MHz, D$_2$O) δ ppm 7.62 (s, 1H) 7.00 (s, 1H) 5.49 (d, J=5.6 Hz, 1H) 4.83-4.91 (m, 1H) 4.80-4.75 (m, 2H) 4.44 (s, 2H) 4.30 (t, J=4.0 Hz, 1H) 3.60-3.18 (m, 5H) 2.38-2.24 (m, 1H) 2.04 (dq, J=12.5, 6.5 Hz, 1H) 1.24-1.12 (m, 2H) 1.04 (br s, 2H).

Example 142

1-((((Z)-(1-(2-aminothiazol-4-yl)-2-oxo-2-(((3S,4R)-2-oxo-4-((4-((3-((R)-pyrrolidin-3-yl)guanidino)methyl)-2H-1,2,3-triazol-2-yl)methyl)-1-sulfoazetidin-3-yl)amino)ethylidene)amino)oxy)cyclopropanecarboxylic acid

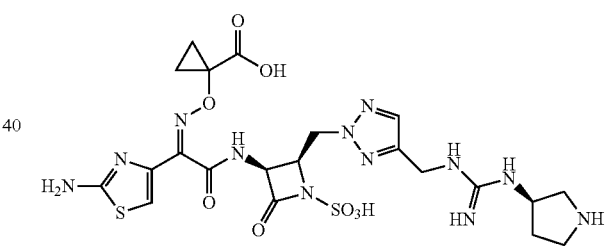

Prepared in analogous manner to example 119, Usi®(R)-tert-butyl 3-((imino(methylthio)methyl)amino)pyrrolidine-1-carboxylate. LCMS: R$_t$=0.29 min, m/z=641.1 (M+1) Method 2m; $^1$H NMR (400 MHz, D$_2$O) δ ppm 7.62 (s, 1H) 7.01 (s, 1H) 5.49 (d, J=5.6 Hz, 1H) 4.87 (q, J=5.7 Hz, 1H) 4.80-4.75 (m, 2H) 4.44 (s, 2H) 4.31 (t, J=4.0 Hz, 1H) 3.61-3.20 (m, 4H) 2.41-2.21 (m, 1H) 2.08-2.00 (m, 1H) 1.18 (m, 2H) 1.14 (m, 2H).

Example 143

1-((((Z)-(2-(((2R,3S)-2-((4-(aminomethyl)-5-methyl-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: 4-(azidomethyl)-5-methyl-2H-1,2,3-triazole To a solution of 1-bromo-2-butyne (640 μL, 7.31 mmol) in 1,4-dioxane/Water (3:1, 36 mL) was added sodium azide (1.901 g, 29.2 mmol) followed by ammonium chloride (782 mg, 14.6 mmol). The slurry was heated to 75° C. for 8 h. The layers were separated and the aqueous was extracted with EtOAc (3×). The combined organic layers were washed with brine, dried over $Na_2SO_4$ and concd in vacuo to yield a crude material (833 mg, 78%) that was used directly in step 2. LCMS: $R_t$=0.35 min, m/z=138.9 (M+1) Method 2m_acidic.

Step 2: tert-Butyl ((5-methyl-2H-1,2,3-triazol-4-yl) methyl)carbamate

A slurry of 4-(azidomethyl)-5-methyl-2H-1,2,3-triazole (803 mg, 5.81 mmol), Boc-anhydride (1.36 mL, 5.88 mmol) and Pd—C (157 mg, 0.148 mmol) in EtOH (39 mL) was evacuated and recharged with $H_2$ (3×). The reaction mixture was stirred under $H_2$ for 1 h 45 min. The resulting black suspension was filtered through celite and eluted with EtOAc. The filtrate was concentrated in vacuo. The crude residue was purified via silica gel chromatography (EtOAc-Heptane, 0-60%) to afford the title compound (878 mg, 71%). LCMS: $R_t$=0.82 min, m/z=213.0 (M+1) Method 2m_acidic.

Step 3

To a solution of benzyl ((2S,3S)-1-(2,4-dimethoxybenzyl)-2-(hydroxymethyl)-4-oxoazetidin-3-yl)carbamate (331 mg, 0.826 mmol), tert-butyl ((5-methyl-2H-1,2,3-triazol-4-yl) methyl)carbamate (235.3 mg, 1.109 mmol) and triphenylphosphine (265.6 mg, 1.013 mmol) in THF (8.3 mL) at 0° C. was added DIAD (0.210 mL, 1.016 mmol), drop-wise. After stirring at room temperature for 2 h, the reaction mixture was concentrated onto silica gel. Purification via silica gel chromatography (EtOAc-Heptane, 0-60%) afforded the desired compound (360 mg, 73%). LCMS: $R_t$=0.99 min, m/z=595.3 (M+1) Method 2m_acidic.

Step 4

A slurry of the product from the above step (step 4) (396.8 mg, 0.667 mmol), $K_2S_2O_8$ (243 mg, 0.870 mmol) and $K_2HPO_4$ (268.1 mg, 1.539 mmol) in ACN/water (2:1, 9.4 mL) was heated to 90° C. for 2 h. Additional $K_2S_2O_8$ (55.6 mg, 0.200 mmol) was added and continued heating for an additional 2 h. The reaction mixture was partially concentrated in vacuo then quenched with $NaHCO_3$ and extracted with EtOAc (3×). The combined organic layers were washed with brine, dried over $Na_2SO_4$ and concentrated in vacuo. Purification via silica gel chromatography (EtOAc-Heptane, 0-90%), then HPLC (OBD C18, 5μ, 30×100 mm, 30-70% ACN/$H_2O$ w/0.1% TFA buffer over 18 min, 60 mL/min), afforded the desired compound (157 mg, 53%) as a white solid. LCMS: $R_t$=0.80 min, m/z=445.2 (M+1) Method 2m_acidic.

Step 5: tert-Butyl ((2-(((2R,3S)-3-amino-4-oxoazetidin-2-yl)methyl)-5-methyl-2H-1,2,3-triazol-4-yl) methyl)carbamate To a $N_2$ flushed flask containing product from the above step (93.2 mg, 0.210 mmol) and Pd—C (18 mg) was added ethanol (1.6 mL) followed by methanol (0.4 mL). The slurry was evacuated and backfilled with $H_2$ (3×). The reaction mixture was stirred under $H_2$ for 2 h. The resulting black suspension was filtered through celite, eluting with methanol. The filtrate was concentrated in vacuo and the crude residue was used as such in step 6. LCMS: $R_t$=0.46 min, m/z=311.1 (M+1) Method 2m_acidic.

Step 6: Benzhydryl 1-(((Z)-(2-(((2R,3S)-2-((4-(((tert-butoxycarbonyl)amino)methyl)-5-methyl-2H-1,2,3-triazol-2-yl)methyl)-4-oxoazetidin-3-yl) amino)-1-(2-((tert-butoxycarbonyl)amino)thiazol-4-yl)-2-oxoethylidene)amino)oxy) cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (120 mg, 0.213 mmol), tert-butyl ((2-(((2R,3S)-3-amino-4-oxoazetidin-2-yl)methyl)-5-methyl-2H-1,2,3-triazol-4-yl)methyl)carbamate (65.2 mg, 0.210 mmol) and HATU (86 mg, 0.22 mmol) in DMF (2.1 mL) at 0° C., was added DIPEA (0.073 mL, 0.420 mmol). After stirring for 16 h, the reaction mixture was diluted with EtOAc and washed with LiCl solution (5% aq). The aqueous layer was extracted with EtOAc (3×) and the combined organic layers were washed with LiCl solution (5% aq), saturated $NaHCO_3$ (aq), brine, dried over $Na_2SO_4$ and concentrated in vacuo. Purification of the crude residue via silica gel chromatography (EtOAc-Heptane, 0-90%) afforded the title compound (144 mg, 82%). LCMS: $R_t$=1.12 min, m/z=830.5 (M+1) Method 2m_acidic.

Step 7: (2R,3S)-3-((Z)-2-((1-((benzhydryloxy)carbonyl)cyclopropoxy)imino)-2-(2-((tert-butoxycarbonyl) amino)thiazol-4-yl)acetamido)-2-((4-(((tert-butoxycarbonyl)amino)methyl)-5-methyl-2H-1,2,3-triazol-2-yl)methyl)-4-oxoazetidine-1-sulfonic acid To a solution of benzhydryl 1-(((Z)-(2-(((2R,3S)-2-((4-(((tert-butoxycarbonyl)amino)methyl)-5-methyl-2H-1,2,3-triazol-2-yl)methyl)-4-oxoazetidin-3-yl)amino)-1-(2-((tert-butoxycarbonyl)amino)thiazol-4-yl)-2-oxoethylidene) amino)oxy)cyclopropanecarboxylate (140 mg, 0.170 mmol) in DMF (848 μl) at 0° C. was added $SO_3$.DMF (54.4 mg, 0.355 mmol). The reaction mixture was stirred for 2.5 h, whereupon additional $SO_3$.DMF (27.4 mg, 0.170 mmol) was added. After an additional 22 h the solution was diluted with EtOAc and poured into the cold LiCl solution (5%, aq). The layers were separated and the aqueous layer was extracted with EtOAc (2×). The combined organic layers were washed with LiCl (5% aq), brine, dried over $Na_2SO_4$ and concentrated in vacuo to afford 163.1 mg of the crude material which was used in step 8 without further purification. LCMS: $R_t$=1.01 min, m/z=910.5 (M+1) Method 2m_acidic.

Step 8: 1-(((Z)-(2-(((2R,3S)-2-((4-(aminomethyl)-5-methyl-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

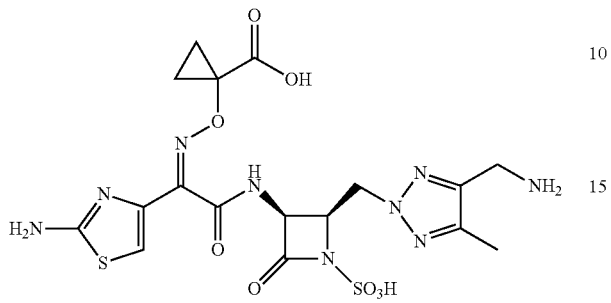

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(((tert-butoxycarbonyl)amino)methyl)-5-methyl-2H-1,2,3-triazol-2-yl)methyl)-4-oxoazetidine-1-sulfonic acid (155 mg, 0.170 mmol), DCM (1.70 mL), anisole (37 µL, 0.34 mmol) anf TFA (0.787 mL, 10.2 mmol). The crude material was purified by reverse phase preparative HPLC (XSELECT C18, 5µ, 30×100 mm, ACN—H$_2$O w/0.1% formic acid buffer, 60 mL/min), affording the title compound (55 mg, 57%) as an off-white solid. LCMS: R$_t$=0.49 min, m/z=544.1 (M+1) Method 2m_acidic_polar. $^1$H NMR (400 MHz, D$_2$O) δ 7.04 (s, 1H), 5.46 (d, J=5.6 Hz, 1H), 4.91-4.84 (m, 1H), 4.84-4.76 (m, 1H), 4.62-4.56 (m, 1H assumed; obscured by solvent residual peak), 4.13 (s, 2H), 2.16 (s, 3H), 1.32-1.18 (m, 2H), 1.18-1.00 (m, 2H).

Example 144

1-(((Z)-2-(((2R,3S)-2-((4-((3-(3-aminopropyl)guanidino)methyl)-5-methyl-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: tert-Butyl (3-((tert-butoxycarbonyl)amino)propyl)(((tert-butoxycarbonyl)imino)(1H-pyrazol-1-yl)methyl)carbamate To an ice cold solution of tert-butyl (((tert-butoxycarbonyl)amino)(1H-pyrazol-1-yl)methylene)carbamate (500 mg, 1.611 mmol), tert-butyl(3-hydroxypropyl)carbamate (282 mg, 1.611 mmol) and triphenylphosphine (634 mg, 2.417 mmol) dissolved in THF (16 mL) was added DIAD (470 µl, 2.417 mmol) and stirred for 16 h. The reaction mixture was concentrated in vacuo and the crude residue was purified via silica gel chromatography (EtOAc-Heptane) to afford the title compound (600 mg, 80%). LCMS: R$_t$=1.02 min, m/z=468.4 (M+1) Method 2m_acidic.

Step 2: 1-(((Z)-(1-(2-aminothiazol-4-yl)-2-(((2R,3S)-2-((4-((Z)-4-(tert-butoxycarbonyl)-3-((tert-butoxycarbonyl)imino)-11,11-dimethyl-9-oxo-10-oxa-2,4,8-triazadodecyl)-5-methyl-2H-1,2,3-triazol-2-yl)methyl)-4-oxo-1-sulfoazetidin-3-yl)amino)-2-oxoethylidene)amino)oxy)cyclopropanecarboxylic acid To a soln of 1-(((Z)-(2-(((2R,3S)-2-((4-(aminomethyl)-5-methyl-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid (33.9 mg, 0.062 mmol) and tert-butyl (3-((tert-butoxycarbonyl)amino)propyl)(((tert-butoxycarbonyl)imino)(1H-pyrazol-1-yl)methyl)carbamate (54.2 mg, 0.116 mmol) in DMF (624 µl) at 0° C. was added DIPEA (32.7 µl, 0.187 mmol). After stirring at rt for 16 h, the solution was concentrated in vacuo and used as such without further purification. LCMS: R$_t$=0.75 min, m/z=943.7 (M+1) Method 2m_acidic.

Step 3: 1-(((Z)-(2-(((2R,3S)-2-((4-((3-(3-aminopropyl)guanidino)methyl)-5-methyl-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

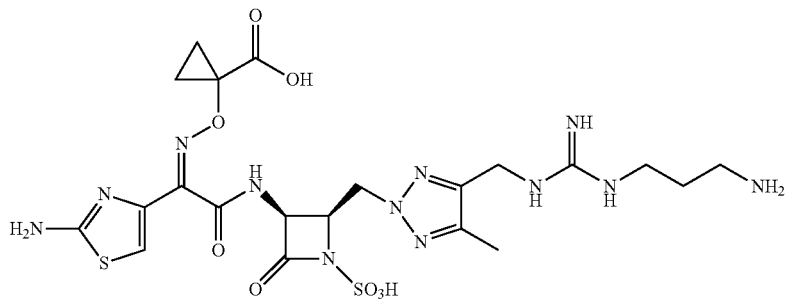 [SMILES: Cc1nn(C[C@@H]2[C@H](NC(=O)/C(=N\OC3(C(=O)O)CC3)c3csc(N)n3)C(=O)N2S(=O)(=O)O)nc1CNC(=N)NCCCN]

Followed the general procedure for the acid mediated deprotection using 1-(((Z)-(1-(2-aminothiazol-4-yl)-2-(((2R,3S)-2-((4-((Z)-4-(tert-butoxycarbonyl)-3-((tert-butoxycarbonyl)imino)-11,11-dimethyl-9-oxo-10-oxa-2,4,8-triazadodecyl)-5-methyl-2H-1,2,3-triazol-2-yl)methyl)-4-oxo-1-sulfoazetidin-3-yl)amino)-2-oxoethylidene)amino)oxy) cyclopropanecarboxylic acid (58.5 mg, 0.062 mmol), DCM (621 µL), anisole (20.4 µL, 0.186 mmol) and TFA (427 µL, 4.55 mmol). The reaction mixture was diluted with ice-cold water (1 mL) and the layers were separated. The organic layer was extracted with water (1 mL) and the combined aqueous layers were washed with DCM (1 mL) and then purified by reverse phase preparative HPLC (XSELECT C18, 5µ, 30×100 mm, 1-20% ACN/H$_2$O w/0.1% formic acid buffer over 18 min, 60 mL/min), affording the title compound (19 mg, 44%) as an off-white solid. LCMS: R$_t$=0.54 min, m/z=643.2 (M+1) Method 2m_acidic_polar. $^1$H NMR (400 MHz, D$_2$O) δ 7.11 (s, 1H), 5.62 (d, J=5.6 Hz, 1H), 5.01-4.94 (m, 1H), 4.91-4.74 (m, 2H assumed; obscured by solvent residual peak), 4.50 (br s, 2H), 3.36 (t, J=6.9 Hz, 2H), 3.11 (t, J=7.8 Hz, 2H), 2.29 (s, 3H), 2.01 (p, J=7.2 Hz, 2H), 1.35-1.25 (m, 2H), 1.21-1.05 (m, 2H).

Example 145

1-(((Z)-(2-(((2R,3S)-2-((4-(1-(3-(3-aminopropyl) guanidino)ethyl)-2H-1,2,3-triazol-2-yl)methyl)-4-oxo-1-sulfoazetidin-3-yl)amino)-1-(2-aminothiazol-4-yl)-2-oxoethylidene)amino)oxy) cyclopropanecarboxylic acid Step 1: 1-(2H-1,2,3-triazol-4-yl)ethanol To a solution of but-3-yn-2-ol (3.63 g, 50.2 mmol) in DMF (40 ml) and MeOH (10 ml) was added azidotrimethylsilane (10.22 ml, 75 mmol). The reaction mixture was heated at 100° C. for 16 h. The reaction was cooled and filtered through a celite pad. The filtrate was concentrated to ~25 ml and used directly in next step. LCMS: R$_t$=0.16 min, m/z=113.8 (M+1) Method 2m_acidic_polar.

Step 2: 4-(1-((tert-butyldiphenylsilyl)oxy)ethyl)-1H-1,2,3-triazole

To a solution of 1-(1H-1,2,3-triazol-4-yl)ethanol (50.2 mmol) and imidazole (5.13 mg, 75 mmol) in DCM (50 ml) 0° C. was added TBDPSCl (14.6 mL, 55.2 mmol). After stirring at room temperature overnight the mixture was filtered through a celite pad and then concentrated to dryness. The resulting residue was dissolved in EtOAc, washed with water, brine, dried with sodium sulfate and concentrated. Purification of the crude residue via silica gel chromatography (EtOAc-Heptane, 5-25%) afforded the title compound (8.16 g, 46%) as a yellow oil. LCMS: R$_t$=1.09 min, m/z=352.1 (M+1) Method 2m_acidic. $^1$H NMR (400 MHz, CDCl$_3$) δ ppm 7.71 (d, J=6.5 Hz, 2H) 7.64-7.54 (m, 3H) 7.49-7.28 (m, 6H) 5.14 (q, J=6.3 Hz, 1H) 1.46 (dd, J=6.3, 3.0 Hz, 3H) 1.08 (s, 9H).

Step 3: Benzyl ((2R,3S)-2-((4-(1-((tert-butyldiphenylsilyl)oxy)ethyl)-2H-1,2,3-triazol-2-yl)methyl)-1-(2,4-dimethoxybenzyl)-4-oxoazetidin-3-yl)carbamate To a solution of 4-(1-((tert-butyldiphenylsilyl)oxy)ethyl)-1H-1,2,3-triazole (2.42 g, 6.88 mmol), benzyl ((2S,3S)-1-(2,4-dimethoxybenzyl)-2-(hydroxymethyl)-4-oxoazetidin-3-yl)carbamate (2.76 g, 6.88 mmol), and PPh$_3$ (2.17 mg, 8.26 mmol) in THF (35 ml) at 0° C. was added DIAD (1.60 ml, 8.26 mmol) dropwise. The reaction was stirred at room temperature for 5 h then concentrated in vacuo. Purification of the crude residue via silica gel chromatography (EtOAc-Heptane, 30-60%) afforded the title compound (4.32 g, 85%) as a solid. LCMS: R$_t$=1.12 min, m/z=734 (M+1) Method 2m_acidic.

Step 4: Benzyl ((2R,3S)-2-((4-(1-((tert-butyldiphenylsilyl)oxy)ethyl)-2H-1,2,3-triazol-2-yl)methyl)-4-oxoazetidin-3-yl)carbamate To a solution of benzyl ((2R,3S)-2-((4-(1-((tert-butyldiphenylsilyl)oxy)ethyl)-2H-1,2,3-triazol-2-yl)methyl)-1-(2,4-dimethoxybenzyl)-4-oxoazetidin-3-yl)carbamate (2.50 g, 3.41 mmol) in ACN/water (2:1, 45 mL) at room temperature was added K$_2$S$_2$O$_8$ (1.57 mg, 5.79 mmol) and K$_2$HPO$_4$ (949 mg, 5.45 mmol). The mixture was heated to 90° C. under nitrogen with stirring for 6 h. The reaction mixture was concentrated in vacuo to remove ACN. To the resulting slurry was added EtOAc and water. The organic layer was separated and the aqueous layer was extracted with EtOAc (2×). The organic portions were combined, dried with Na$_2$SO$_4$, filtered and concentrated in vacuo. Purification of the crude residue via silica gel chromatography (EtOAc-Heptane, 30-60%) afforded the title compound (1.35 g, 68%). LCMS: R$_t$=1.18 min, m/z=584.3 (M+1) Method 2m_acidic.

Step 5: Benzyl ((2R,3S)-2-((4-(1-hydroxyethyl)-2H-1,2,3-triazol-2-yl)methyl)-4-oxoazetidin-3-yl)carbamate A mixture of ((2R,3S)-2-((4-(1-((tert-butyldiphenylsilyl)oxy)ethyl)-2H-1,2,3-triazol-2-yl)methyl)-4-oxoazetidin-3-yl)carbamate (1.35 g, 2.31 mmol) and TBAF (1 M in THF, 4.63 ml, 4.63 mmol) in THF (23 ml) was stirred at room temperature 3 h. The solvent was removed and the residue was purified via silica gel chromatography (EtOAc-Heptane) to afford the title compound (450 mg, 56%) as a light yellow solid. LCMS: R$_t$=0.53 min, m/z=346.1 (M+1) Method 2m_acidic.

Step 6: tert-Butyl (1-(2-(((2R,3S)-3-(((benzyloxy) carbonyl)amino)-4-oxoazetidin-2-yl)methyl)-2H-1,2,3-triazol-4-yl)ethyl)((Z)-((tert-butoxycarbonyl) imino)(1H-pyrazol-1-yl)methyl)carbamate To a solution of benzyl ((2R,3S)-2-((4-(1-hydroxyethyl)-2H-1,2,3-triazol-2-yl)methyl)-4-oxoazetidin-3-yl)carbamate (460 mg, 1.33 mmol), (E)-tert-butyl (((tert-butoxycarbonyl)imino)(1H-pyrazol-1-yl)methyl)carbamate (455 mg, 1.465 mmol), and triphenylphosphine (419 mg, 1.60 mmol) in THF (7 ml) at 0° C. was added DIAD (0.311 ml, 1.598 mmol) dropwise. The reaction was stirred at room temperature overnight and concentrated to dryness. Purification of the crude residue via silica gel chromatography (EtOAc-Heptane, 30-60%) afforded the title compound (190 mg, 22%) as a light yellow solid. LCMS: R$_t$=0.99 min, m/z=638.4 (M+1) Method 2m_acidic.

Step 7

A mixture of tert-butyl (1-(2-(((2R,3S)-3-(((benzyloxy) carbonyl)amino)-4-oxoazetidin-2-yl)methyl)-2H-1,2,3-triazol-4-yl)ethyl)((Z)-((tert-butoxycarbonyl)imino)(1H-pyrazol-1-yl)methyl)carbamate (190 mg, 0.298 mmol) and tert-butyl(3-aminopropyl)carbamate (57.1 mg, 0.328 mmol) in ACN (1490 µl) was stirred at room temperature for 16 h. The solvent was then removed in vacuo and the crude residue was purified via silica gel chromatography (EtOAc-Heptane, 50-80%), affording the desired compound (100 mg, 45%). LCMS: $R_t$=0.91 min, m/z=744.5 (M+1) Method 2m_acidic.

Step 8

A mixture of the product obtained from step 7 (100 mg, 0.134 mmol) and 10% Pd—C (30 mg, 0.134 mmol) in EtOH (2 ml) and MeOH (1 ml) was stirred under hydrogen for 4 h. Palladium was filtered off through a celite pad and the solvent was removed to give the crude material which was used in step 9 without further purification. LCMS: $R_t$=0.68 min, m/z=610.4 (M+1) Method 2m_acidic.

Step 9: Benzhydryl 1-(((Z)-(2-(((2R,3S)-2-((4-((E)-3-(tert-butoxycarbonyl)-4-((tert-butoxycarbonyl) imino)-12,12-dimethyl-10-oxo-11-oxa-3,5,9-triazatridecan-2-yl)-2H-1,2,3-triazol-2-yl)methyl)-4-oxoazetidin-3-yl)amino)-1-(2-((tert-butoxy carbonyl) amino)thiazol-4-yl)-2-oxoethylidene)amino)oxy) cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (76 mg, 0.13 mmol) and DIPEA (35.1 µl, 0.201 mmol) in DCM/DMF (2:1, 1.34 mL) at 0° C. was added HATU (61.1 mg, 0.161 mmol). This mixture was stirred at 0° C. for 30 min. To this was added the product obtained from step 8 (82 mg, 0.13 mmol). The reaction mixture was stirred at 0° C. for 30 min then diluted with EtOAc (60 ml), washed with saturated aqueous Na₂CO₃, brine, dried over Na₂SO₄ and concentrated in vacuo. Purification of the crude residue via silica gel chromatography (EtOAc-Heptane, 40-60%) afforded the title compound (150 mg, 99%) as a light yellow solid. LCMS: $R_t$=1.12 min, m/z=1129.8 (M+1) Method 2m_acidic.

Step 10: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((E)-3-(tert-butoxycarbonyl)-4-((tert-butoxycarbonyl)imino)-12, 12-dimethyl-10-oxo-11-oxa-3,5,9-triazatridecan-2-yl)-2H-1,2,3-triazol-2-yl)methyl)-4-oxoazetidine-1-sulfonic acid To a solution of benzhydryl 1-(((Z)-(2-(((2R,3S)-2-((4-((E)-3-(tert-butoxycarbonyl)-4-((tert-butoxycarbonyl) imino)-12,12-dimethyl-10-oxo-11-oxa-3,5,9-triazatridecan-2-yl)-2H-1,2,3-triazol-2-yl)methyl)-4-oxoazetidin-3-yl) amino)-1-(2-((tert-butoxycarbonyl)amino)thiazol-4-yl)-2-oxoethylidene)amino)oxy)cyclopropanecarboxylate (150 mg, 0.133 mmol) in DMF (1 ml) at 0° C. was added SO₃.DMF complex (203 mg, 1.33 mmol). After stirring at rt for 2.5 h the solution was diluted with EtOAc, washed cold brine, dried with Na₂SO₄, filtered and concentrated in vacuo. The crude residue was used as such in step 11. LCMS: $R_t$=1.15 min, m/z=1210.5 (M+1) Method 2m_acidic.

Step 11: 1-(((Z)-(2-(((2R,3S)-2-((4-(1-(3-(3-aminopropyl)guanidino)ethyl)-2H-1,2,3-triazol-2-yl)methyl)-4-oxo-1-sulfoazetidin-3-yl)amino)-1-(2-aminothiazol-4-yl)-2-oxoethylidene)amino)oxy) cyclopropanecarboxylic acid

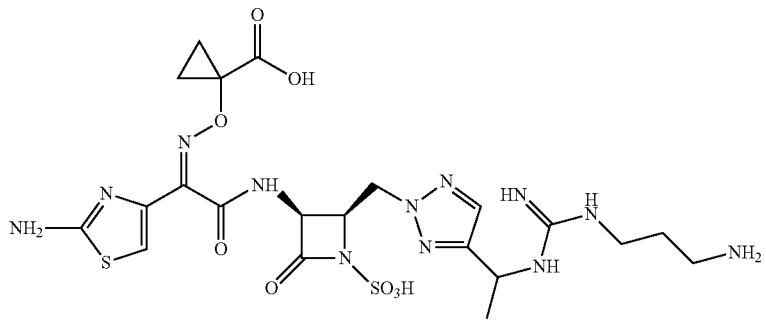

Followed the general procedure for the acid mediated deprotection using (2R,3S)-3-((Z)-2-((1-((benzhydryloxy) carbonyl)cyclopropoxy)imino)-2-(2-((tert-butoxycarbonyl)amino)thiazol-4-yl)acetamido)-2-((4-((E)-3-(tert-butoxycarbonyl)-4-((tert-butoxycarbonyl)imino)-12,12-dimethyl-10-oxo-11-oxa-3,5,9-triazatridecan-2-yl)-2H-1,2,3-triazol-2-yl)methyl)-4-oxoazetidine-1-sulfonic acid (0.133 mmol), TFA (410 µl, 5.32 mmol) anisole (29 µL, 0.27 mmol) and DCM (1.33 mL). The reaction mixture was cooled to 0° C. and diluted with DCM and ice water, Whereupon the layers were separated. The aqueous layer was purified by reverse phase preparative HPLC (XSELECT, C18 5 um 30×100 mm; ACN-water with 0.1% formic acid), affording the title compound (34 mg, 39%) as a white powder. LCMS: $R_t$=0.52 min, m/z=643.2 (M+1) Method 2m_acidic_polar. ¹H NMR (400 MHz, D₂O, reported as a 1:1 mixture of diastereomers) δ 7.79 (s, 1H) 7.77 (s, 1H), 7.12 (s, 1H), 7.12 (s, 1H), 5.64 (d, J=5.6 Hz, 1H), 5.61 (d, J=5.6 Hz, 1H), 5.05-4.73 (m, 8H assumed; partially obscured by solvent residual peak), 3.39-3.32 (m, 4H), 3.13-3.05 (m, 4H), 2.00 (p, J=7.0 Hz, 4H), 1.64 (d, J=3.6 Hz, 3H), 1.63 (d, J=3.7 Hz, 3H), 1.37-1.28 (m, 4H), 1.21-1.12 (m, 4H).

Example 146

1-(((Z)-(2-(((2R,3S)-2-((4-((S)-1-((3-aminopropyl)amino)ethyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

Step 1: (R)-But-3-yn-2-yl methanesulfonate

To a solution of R-(+)-3-butyn-2-ol (1000 mg, 14.27 mmol) and DIPEA (3.72 ml, 21.4 mmol) in DCM (50 ml) at 0° C. was added methanesulfonyl chloride (1.44 mL, 18.6 mmol). The mixture was stirred at 0° C. for 2 h then diluted with DCM, washed with HCl (0.2 N, aq) followed by saturated NaHCO$_3$ (aq). The organic layer was dried over Na$_2$SO$_4$ and concentrated in vacuo, providing the title compound (2.093 g, 99%) as a light orange oil. $^1$H NMR (400 MHz, CDCl$_3$) δ ppm 5.28 (m, J=6.7, 2.1 Hz, 1H) 3.12 (s, 3H) 2.71 (d, J=2.2 Hz, 1H) 1.66 (d, J=6.7 Hz, 3H).

Step 2: (S)-tert-Butyl (3-(but-3-yn-2-ylamino)propyl)carbamate

A solution of (R)-but-3-yn-2-yl methanesulfonate (2189 mg, 14.77 mmol) in ACN (10 ml) was added dropwise to a suspension of tert-butyl(3-aminopropyl)carbamate (2831 mg, 16.25 mmol) and potassium carbonate (2446 mg, 17.72 mmol) in ACN (50 ml). The reaction mixture was stirred at room temperature for 24 h, whereupon the slurry was filtered and the filtrate was concentrated in vacuo. The crude residue was purified via silica gel chromatography (MeOH-DCM, 0-8%) to afford the title compound (570 mg, 17%) as a light orange oil. LCMS: R=0.43 min, m/z=227.0 (M+1) Method 2m_acidic.

Step 3: (S)-tert-Butyl but-3-yn-2-yl(3-((tert-butoxycarbonyl)amino)propyl)carbamate A mixture of (S)-tert-butyl (3-(but-3-yn-2-ylamino)propyl)carbamate (570 mg, 2.52 mmol), di-tert-butyl dicarbonate (1.10 g, 5.04 mmol) and saturated NaHCO$_3$ (aq, 17 mL) in DCM (16.8 mL) was stirred at rt for 16 h, whereupon the two layers were separated and the organic layer was dried over Na$_2$SO$_4$ and concentrated in vacuo. Purification via silica gel chromatography (MeOH-DCM, 0-5%) afforded the title compound (710 mg, 86%) as a viscous oil. LCMS: R$_t$=0.99 min, m/z=327.1 (M+1) Method 2m_acidic.

Step 4: (S)-tert-butyl (1-(2H-1,2,3-triazol-4-yl)ethyl)(3-((tert-butoxycarbonyl)amino)propyl)carbamate A mixture of (S)-tert-butyl but-3-yn-2-yl(3-((tert-butoxycarbonyl)amino)propyl)carbamate (710 mg, 2.18 mmol), azidotrimethylsilane (452 µl, 3.26 mmol) and copper (I) iodide (21 mg, 0.11 mmol) in DMF/MeOH (1:1, 3.4 mL) was heated to 100° C. for 8 h. Upon cooling, the mixture was filtered through a celite pad, and the filtrate was concentrated in vacuo and purified via silica gel chromatography (EtOAc-Heptane, 30-80%) to afford the title compound (636 mg, 79%) as an oil. LCMS: R$_t$=0.78 min, m/z=370.1 (M+1) Method 2m_acidic.

Step 5

To a solution of (S)-tert-butyl (1-(1H-1,2,3-triazol-4-yl)ethyl)(3-((tert-butoxycarbonyl)amino)propyl)carbamate (636 mg, 1.72 mmol), benzyl ((2S,3S)-1-(2,4-dimethoxybenzyl)-2-(hydroxymethyl)-4-oxoazetidin-3-yl)carbamate (689 mg, 1.72 mmol) and triphenylphosphine (542 mg, 2.07 mmol) in THF (8.6 mL) at 0° C. was added DIAD (402 µl, 2.07 mmol), drop-wise. After stirring at rt for 5 h the mixture was concentrated in vacuo. Purification via silica gel chromatography (EtOAc-Heptane, 30-60%) afforded the desired compound (970 mg, 75%) as a white solid. LCMS: R$_t$=1.08 min, m/z=752.1 (M+1) Method 2m_acidic.

Step 6

A mixture of the product obtained step 5 (970 mg, 1.29 mmol), K$_2$S$_2$O$_8$ (611 mg, 2.19 mmol) and K$_2$HPO$_4$ (360 mg, 2.06 mmol) in ACN/water (2:1, 15 mL) was heated to 90° C. under nitrogen with for 4 h. The reaction mixture was concentrated in vacuo to remove ACN. The mixture was partitioned between EtOAc/water and the layers were separated. The aqueous layer was extracted with EtOAc and the combined organic portions were dried over Na$_2$SO$_4$, filtered and concentrated in vacuo. Purification via silica gel chromatography (EtOAc-Heptane, 50-100%) afforded the desired compound (443 mg, 57%). LCMS: R$_t$=0.95 min, m/z=602.4 (M+1) Method 2m_acidic.

Step 7: tert-Butyl ((S)-1-(2-(((2R,3S)-3-amino-4-oxoazetidin-2-yl)methyl)-2H-1,2,3-triazol-4-yl)ethyl)(3-((tert-butoxycarbonyl)amino)propyl)carbamate A mixture of the product obtained from step 6 (443 mg, 0.736 mmol) and 10% Pd/C (100 mg) in EtOH/MeOH (2:1, 15 mL) was stirred under hydrogen for 4 h, whereupon the mixture was filtered over celite and the solvent was removed in vacuo to give the title compound (assumed quantitative) which was used directly without further purification. LCMS: R$_t$=0.68 min, m/z=468.3 (M+1) Method 2m_acidic.

Step 8: Benzhydryl 1-(((Z)-(2-(((2R,3S)-2-((4-((S)-1-((tert-butoxycarbonyl)(3-((tert-butoxycarbonyl)amino)propyl)amino)ethyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate To a mixture of (Z)-2-((1-((benzhydryloxy)carbonyl)cyclopropoxy)imino)-2-(2-((tert-butoxycarbonyl)amino)thiazol-4-yl)acetic acid (416 mg, 0.736 mmol), tert-butyl ((S)-1-(2-(((2R,3S)-3-amino-4-oxoazetidin-2-yl)methyl)-2H-1,2,3-triazol-4-yl)ethyl)(3-((tert-butoxycarbonyl)amino)propyl)carbamate (0.736 mmol) and DIPEA (193 µl, 1.10 mmol) in DCM/DMF (5:1, 7.3 mL) at 0° C. was added HATU (308 mg, 0.810 mmol). After stirring at 0° C. for 1 h it was diluted with EtOAc, washed with water, brine, dried over sodium sulfate and concentrated in vacuo. Purification via silica gel chromatography (EtOAc-Heptane, 50-90%) afforded the desired compound (700 mg, 96%) as a red solid. LCMS: R$_t$=1.17 min, m/z=987.7 (M+1) Method 2m_acidic. Chiral SFC analysis (SFC-X5, CO$_2$/EtOH=90/10, SFC=5 ml/min, AD column, Rt=12.28 min) confirmed it was a single diastereomer.

Step 9: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((S)-1-((tert-butoxycarbonyl)(3-((tert-butoxycarbonyl)amino)propyl)amino)ethyl)-2H-1,2,3-triazol-2-yl)methyl)-4-oxoazetidine-1-sulfonic acid To benzhydryl 1-(((Z)-(2-(((2R,3S)-2-((4-((S)-1-((tert-butoxycarbonyl)(3-((tert-butoxycarbonyl)amino)propyl)

amino)ethyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (700 mg, 0.709 mmol) in DMF (3.5 ml) at 0° C. was added SO₃.DMF (760 mg, 4.96 mmol). The reaction mixture was stirred at room temperature for 2 h, whereupon additional 3 equiv of SO₃.DMF was added and stirred for another 2 h. The reaction mixture was diluted with EtOAc, washed with LiCl (5%, aq, 2×), brine, dried with Na₂SO₄, filtered and concentrated in vacuo to give the title compound (assumed quantitative) which was used as such without further purification. LCMS: R$_t$=1.07 min, m/z=1067.6 (M+1) Method 2m_acidic.

Step 10: 1-(((Z)-(2-(((2R,3S)-2-((4-((S)-1-((3-aminopropyl)amino)ethyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

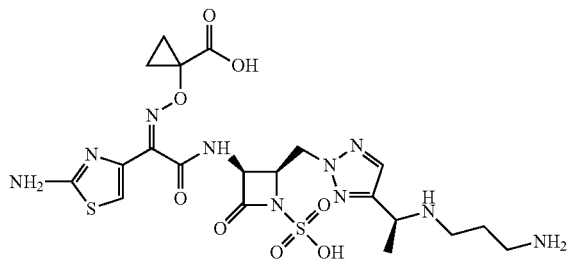 [SMILES: C[C@H](NCCCN)c1cnn(C[C@@H]2[C@H](NC(=O)/C(=N\OC3(C(=O)O)CC3)c3csc(N)n3)C(=O)N2S(=O)(=O)O)n1]

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-((S)-1-((tert-butoxycarbonyl)(3-((tert-butoxycarbonyl)amino)propyl)amino)ethyl)-2H-1,2,3-triazol-2-yl)methyl)-4-oxoazetidine-1-sulfonic acid (0.709 mmol), anisole (153 mg, 1.42 mmol), TFA (273 µl, 35.5 mmol) and DCM (7.1 mL). The reaction mixture was cooled to 0° C. and diluted with DCM and ice water. After vigorous stirring the two layers were separated and aqueous layer was purified by reverse phase prepatory HPLC (XSELECT, C18, 5 um 30×100 mm ACN-water with 0.1 formic acid), affording title compound (110 mg, 25%) as a white solid. LCMS: R$_t$=0.50 min, m/z=601.3 (M+1) Method 2m_acidic_polar; ¹H NMR (400 MHz, D₂O) δ 7.87 (s, 1H) 7.04 (s, 1H) 5.61 (d, J=5.6 Hz, 1H) 5.04-4.97 (m, 1H) 4.89 (d, J=5.4 Hz, 2H) 4.69-4.62 (m, 1H) 3.13-3.00 (m, 4H) 2.04 (t, J=4.0 Hz, 2H) 1.68 (d, J=6.9 Hz, 3H) 1.23 (t, J=3.9 Hz, 2H) 1.11-1.02 (m, 2H).

Example 147

1-(((Z)-(2-(((2R,3S)-2-((4-((3-(2-(2-aminoethoxy)ethyl)guanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

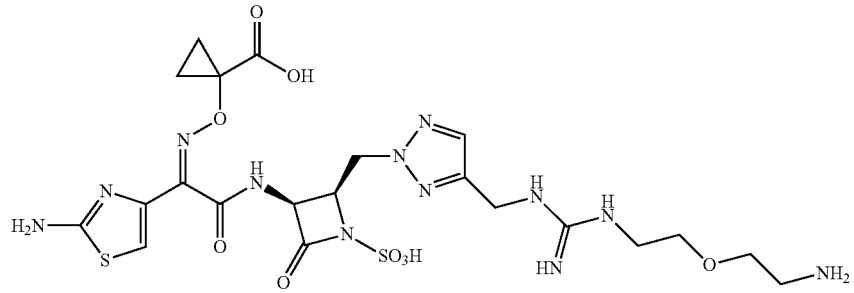 [SMILES: N=C(NCCOCCN)NCc1cnn(C[C@@H]2[C@H](NC(=O)/C(=N\OC3(C(=O)O)CC3)c3csc(N)n3)C(=O)N2S(=O)(=O)O)n1]

Prepared in analogous manner to example 119, using tert-butyl (2-(2-((imino(methylthio)methyl)amino)ethoxy)ethyl)carbamate. LCMS: R$_t$=0.31 min, m/z=659.0 (M+1) Method 2m_acidic. ¹H NMR (500 MHz, D₂O) δ ppm 7.61 (s, 1H), 6.99 (s, 1H), 5.47 (d, J=5.7 Hz, 1H), 4.87 (q, J=5.6 Hz, 1H), 4.81-4.70 (m, 2H assumed; partially obscured by solvent residual peak), 4.42 (s, 2H), 3.66-3.54 (m, 4H), 3.32 (t, J=5.0 Hz, 2H), 3.13-3.06 (m, 2H), 1.28-0.93 (m, 4H).

Example 148

1-(((Z)-(2-(((2R,3S)-2-((4-((3-(3-aminopropyl)-1-methylguanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: tert-Butyl (3-((tert-butoxycarbonyl)amino)propyl)(((tert-butoxycarbonyl)imino)(1H-pyrazol-1-yl)methyl)carbamate To an ice-cold solution of tert-butyl (((tert-butoxycarbonyl)amino)(1H-pyrazol-1-yl)methylene)carbamate (500 mg, 1.61 mmol), tert-butyl(3-hydroxypropyl)carbamate (282 mg, 1.611 mmol) and triphenylphosphine (634 mg, 2.42 mmol) in THF (16 mL) was added DIAD (470 µl, 2.42 mmol). The mixture was stirred at room temperature for 16 h, whereupon the volatiles were removed in vacuo. Purification via silica gel chromatography (EtOAc-Heptane, 0-100%) afforded the title compound (600 mg, 80%). LCMS: R$_t$=1.02 min, m/z=468.4 (M+1) Method 2m_acidic.

Step 2: Benzyl ((2R,3S)-2-((4-formyl-2H-1,2,3-triazol-2-yl)methyl)-4-oxoazetidin-3-yl)carbamate A mixture of benzyl ((2R,3S)-2-((4-(hydroxymethyl)-2H-1,2,3-triazol-2-yl)methyl)-4-oxoazetidin-3-yl)carbamate (360 mg, 1.09 mmol) and MnO₂ (2.36 g, 27.2 mmol) in THF (11 mL) was stirred at room temperature for 2 h, whereupon the mixture was filtered through celite and concentrated. The resulting material (340 mg, 95%) was used as such in step 3.

Step 3: Benzyl ((2R,3S)-2-((4-((methylamino)methyl)-2H-1,2,3-triazol-2-yl)methyl)-4-oxoazetidin-3-yl)carbamate To a solution of benzyl ((2R,3S)-2-((4-formyl-2H-1,2,3-triazol-2-yl)methyl)-4-oxoazetidin-3-yl)carbamate (340 mg, 1.03 mmol) in DCE (10 mL) was added MeNH$_2$ (1032 µl, 2.065 mmol). After stirring for 1 h at rt, sodium triacetoxyborohydride (438 mg, 2.07 mmol) was added and the mixture was stirred overnight, whereupon it was quenched with saturated NaHCO$_3$ (aq) at 0° C. and extracted with EtOAc (2×). The organic extracts were combined, washed with brine, dried over Na$_2$SO$_4$, filtered and concentrated in vacuo. The resulting crude material (assumed quantitative) was used as such in step 4.

Step 4

A solution of benzyl ((2R,3S)-2-((4-((methylamino)methyl)-2H-1,2,3-triazol-2-yl)methyl)-4-oxoazetidin-3-yl)carbamate (93 mg, 0.27 mmol), tert-butyl (3-((tert-butoxycarbonyl)amino)propyl)(((tert-butoxycarbonyl)imino)(1H-pyrazol-1-yl)methyl)carbamate (152 mg, 0.324 mmol), DIPEA (94 µl, 0.540 mmol) in ACN (1800 µl) was heated to 90° C. overnight. All volatiles were removed in vacuo and purification of the crude residue via silica gel chromatography (EtOAc-Heptane) afforded the desired product. LCMS: R$_t$=0.94 min, m/z=744.6 (M+1) Method 2m_acidic.

Step 5

A mixture of the product from step 4 (46 mg, 0.062 mmol) and Pd on C (10% wt, 23 mg) in EtOH/MeOH (4:1, 620 µL) was stirred under hydrogen for 16 h. The reaction mixture was filtered through a celite pad and concentrated and the resulting material (assumed quantitative) was used as such without further purification.

Step 6: Benzhydryl 1-(((Z)-(2-(((2R,3S)-2-((4-(4-(tert-butoxycarbonyl)-3-((tert-butoxycarbonyl)imino)-2,11,11-trimethyl-9-oxo-10-oxa-2,4,8-triazadodecyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate A solution of (Z)-2-((1-((benzhydryloxy)carbonyl)cyclopropoxy)imino)-2-(2-((tert-butoxycarbonyl)amino)thiazol-4-yl)acetic acid (30.9 mg, 0.057 mmol), DIPEA (30.1 µl, 0.172 mmol) and HATU (26.2 mg, 0.069 mmol) in DCM/DMF (1:1, 574 µl) was stirred for 20 min, whereupon the product from step 5 (35 mg, 0.057 mmol) was added. The resulting mixture was stirred for and additional 2 h, at which point the volatiles were removed in vacuo and the material was diluted with EtOAc, washed with brine, dried over Na$_2$SO$_4$, filtered and concentrated in vacuo. Purification via silica gel chromatography (EtOAc-Heptane) afforded the title compound. LCMS: R$_t$=1.11 min, m/z=1029.9 (M+1) Method 2m_acidic.

Step 7: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(4-(tert-butoxycarbonyl)-3-((tert-butoxycarbonyl)imino)-2,11,11-trimethyl-9-oxo-10-oxa-2,4,8-triazadodecyl)-2H-1,2,3-triazol-2-yl)methyl)-4-oxoazetidine-1-sulfonic acid To an ice-cold solution of benzhydryl 1-(((Z)-(2-(((2R,3S)-2-((4-(4-(tert-butoxycarbonyl)-3-((tert-butoxycarbonyl)imino)-2,11,11-trimethyl-9-oxo-10-oxa-2,4,8-triazadodecyl)-2H-1,2,3-triazol-2-yl)methyl)-4-oxoazetidin-3-yl)amino)-1-(2-((tert-butoxycarbonyl)amino)thiazol-4-yl)-2-oxoethylidene)amino)oxy)cyclopropanecarboxylate (32 mg, 0.028 mmol) in DMF (283 µl) was added SO$_3$.DMF (43.4 mg, 0.283 mmol). After stirring for 2 h, the reaction mixture was diluted with EtOAc, washed with brine, dried over Na$_2$SO$_4$ and concentrated in vacuo. This crude residue was used in the next step without further purification.

Step 8: 1-(((Z)-(2-(((2R,3S)-2-((4-((3-(3-aminopropyl)-1-methylguanidino)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

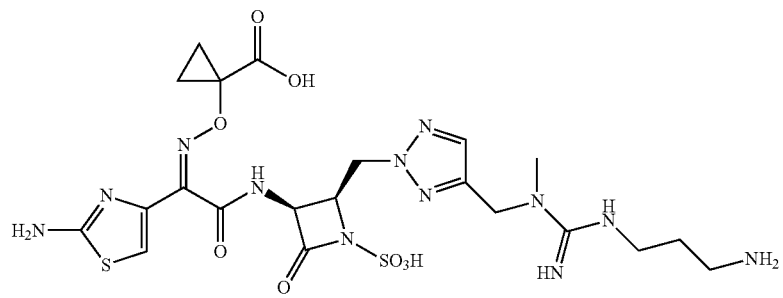

Followed the general procedure for the acid mediated deprotection using (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((4-(4-(tert-butoxycarbonyl)-3-((tert-butoxycarbonyl)imino)-2,11,11-trimethyl-9-oxo-10-oxa-2,4,8-triazadodecyl)-2H-1,2,3-triazol-2-yl)methyl)-4-oxoazetidine-1-sulfonic acid (27 mg, 0.022 mmol), TFA (103 µl, 1.34 mmol) and DCM (223 µl). The crude material was purified by reverse phase preparative HPLC (XSELECT C18, 5µ, 30×100 mm, ACN/H$_2$O w/0.1% formic acid buffer), affording the title compound (1.1 mg, 7%) as a white solid. LCMS: R$_t$=0.32 min, m/z=643.3 (M+1) Method 2m_acidic. $^1$H NMR (500 MHz, D$_2$O) δ ppm 7.65 (s, 1H) 7.00 (s, 1H) 5.48 (d, J=5.7 Hz, 1H) 4.89-4.83 (m, 1H) 4.60-4.45 (m, 2H) 3.25 (td, J=6.9, 3.6 Hz, 2H) 2.95 (t, J=7.7 Hz, 2H) 2.91 (s, 3H) 1.98-1.74 (m, 2H) 1.23-1.10 (m, 2H) 1.05-1.00 (m, 2H).

Example 149

1-(((Z)-(2-(((2R,3S)-2-((4-(((3-(aminomethyl)azetidine-1-carbonyl)oxy)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

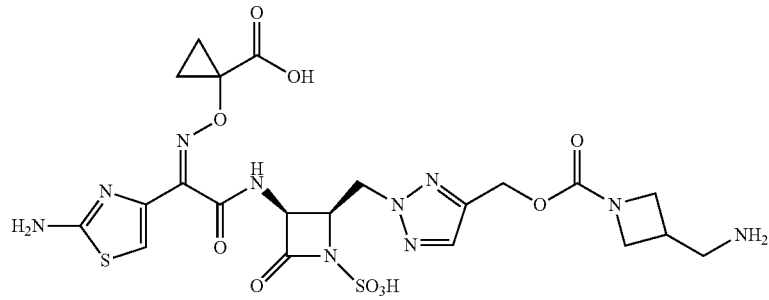

Prepared in an analogous manner to example 126 using (2-(((2R,3S)-3-(((benzyloxy)carbonyl)amino)-4-oxoazetidin-2-yl)methyl)-2H-1,2,3-triazol-4-yl)methyl 3-(((tert-butoxycarbonyl)amino)methyl)azetidine-1-carboxylate in step 2. LCMS: $R_t$=0.52 min, m/z=643.2 (M+1) Method 2m_acidic_polar. $^1$H NMR (400 MHz, D$_2$O) δ 7.83 (s, 1H), 7.11 (s, 1H), 5.61 (d, J=5.3 Hz, 1H), 5.25-5.16 (m, 2H), 5.08-4.97 (m, 2H), 4.93-4.86 (m, 1H assumed; partially obscured by the solvent residual peak), 4.22 (t, J=8.6 Hz, 2H), 3.89-3.77 (m, 2H), 3.32 (d, J=7.6 Hz, 2H), 3.07-2.95 (m, 1H), 1.49-1.37 (m, 2H), 1.34-1.19 (m, 2H).

Preparation of (2-(((2R,3S)-3-(((benzyloxy)carbonyl)amino)-4-oxoazetidin-2-yl)methyl)-2H-1,2,3-triazol-4-yl)methyl 3-(((tert-butoxycarbonyl)amino)methyl)azetidine-1-carboxylate. Prepared in an anologous manner as example 4, step 2 using (2-(((2R,3S)-3-(((benzyloxy)carbonyl)amino)-1-(2,4-dimethoxybenzyl)-4-oxoazetidin-2-yl)methyl)-2H-1,2,3-triazol-4-yl)methyl 3-(((tert-butoxycarbonyl)amino)methyl)azetidine-1-carboxylate (410 mg, 0.591 mmol), K$_2$S$_2$O$_8$ (272 mg, 1.01 mmol) and K$_2$HPO$_4$ (165 mg, 0.946 mmol) in ACN:water (2:1, 7.2 mL) while heating for 5 h at 90° C. The crude residue was purified via silica gel chromatography (EtOAc-Heptane, 30-90%), affording the title compound (80 mg, 25%) as a solid. LCMS: $R_t$=0.78 min, m/z=544.2 (M+1) Method 2m_acidic.

Preparation of (2-(((2R,3S)-3-(((benzyloxy)carbonyl)amino)-1-(2,4-dimethoxybenzyl)-4-oxoazetidin-2-yl)methyl)-2H-1,2,3-triazol-4-yl)methyl 3-(((tert-butoxycarbonyl)amino)methyl)azetidine-1-carboxylate. A 20 mL scintillation vial was charged with benzyl ((2R,3S)-1-(2,4-dimethoxybenzyl)-2-((4-(hydroxymethyl)-2H-1,2,3-triazol-2-yl)methyl)-4-oxoazetidin-3-yl)carbamate (660 mg, 1.37 mmol, obtained as a by-product during the preparation of intermediate V), CDI (252 mg, 1.51 mmol) and DCM (11.4 mL). After stirring for 2 h, tert-butyl (azetidin-3-ylmethyl)carbamate (383 mg, 2.06 mmol) was added and it was stirred for an additional 16 h. The mixture was concentrated in vacuo and purified via silica gel chromatography (EtOAc-Heptane, 40-90%), affording the title compound (410 mg, 43%) as a solid. $R_t$=0.94 min, m/z=694.3 (M+1) Method 2m_acidic.

Example 150

1-(((Z)-(2-(((2R,3S)-2-((4-MS)-3-aminopyrrolidine-1-carboximidamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

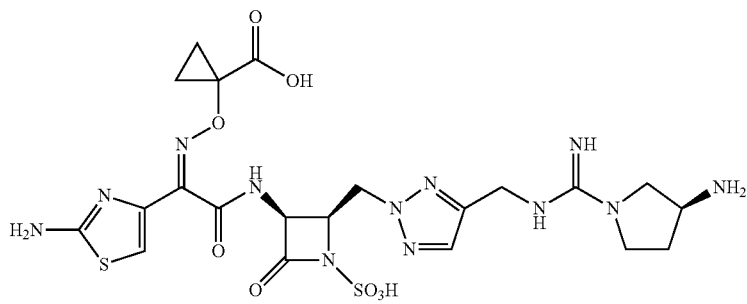

Prepared in an anologous manner to example 127 using (S)-tert-butyl pyrrolidin-3-ylcarbamate in step 3. $R_t$=0.25 min, m/z=641.4 (M+1) Method 2m_acidic. $^1$H NMR (400

MHz, DMSO-d$_6$) δ 10.55-10.15 (m, 1H), 8.06-7.78 (m, 1H), 7.66 (d, J=1.4 Hz, 1H), 7.59 (br s, 2H), 7.20 (s, 2H), 6.74 (d, J=3.9 Hz, 1H), 5.23 (ddd, J=14.6, 8.8, 5.5 Hz, 1H), 4.90 (dt, J=13.8, 3.7 Hz, 1H), 4.71-4.60 (m, 1H), 4.59-4.35 (m, 3H), 3.90 (br s, 1H), 3.70-3.38 (m, 3H assumed; overlaps with water peak), 2.30-2.15 (m, 1H), 2.09-1.98 (m, 1H), 1.30-1.13 (m, 2H), 1.13-0.98 (m, 2H).

Example 151

1-(((Z)-(2-(((2R,3S)-2-((4-(1-((3-aminopropyl)amino)ethyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

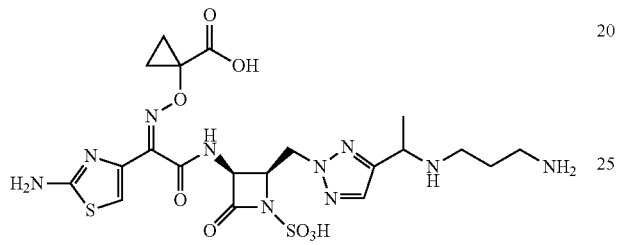

Prepared in an analogous manner to example 146 using 3-bromobut-1-yne in step 2. LCMS: R$_t$=0.50 min, m/z=601.2 (M+1) Method 2m_acidic_polar. $^1$H NMR (400 MHz, D$_2$O, reported as a 1.3:1 mixture of diastereomers) δ 7.94 (s, 0.75H), 7.90 (s, 1H), 5.69 (d, J=5.6 Hz, 0.75H), 5.64 (d, J=5.6 Hz, 1H), 5.08 (q, J=5.5 Hz, 1.8H), 4.97 (q, J=9.3, 7.7 Hz, 3.9H), 4.76-4.68 (m, 1.7H assumed; partially obscured by solvent residual peak), 3.24-3.02 (m, 7.5H), 2.21-2.02 (m, 3.8H), 1.76 (d, J=7.0 Hz, 2.35H), 1.73 (d, J=6.9 Hz, 3.1H), 1.41-1.21 (m, 4.9H), 1.20-1.08 (m, 2.5H).

Example 152

1-(((Z)-(2-(((2R,3S)-2-((4-(((2-aminoethyl)sulfonyl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid Step 1: (2-(((2R,3S)-3-(((benzyloxy)carbonyl)amino)-4-oxoazetidin-2-yl)methyl)-2H-1,2,3-triazol-4-yl)methyl methanesulfonate To a solution of benzyl ((2R,3S)-2-((4-(hydroxymethyl)-2H-1,2,3-triazol-2-yl)methyl)-4-oxoazetidin-3-yl)carbamate (100 mg, 0.302 mmol, obtained during the preparation of intermediate V) in DCM (3.0 mL) at 0° C. was added TEA (84 µL, 0.60 mmol) followed by methanesulfonyl chloride (28.2 µL, 0.362 mmol). After stirring at rt for 2 h, the solution was diluted with DCM, washed with saturated NaHCO$_3$ (aq), brine, dried over Na$_2$SO$_4$ and concentrated in vacuo. The crude residue was used with no additional purification. LCMS: R$_t$=0.66 min, m/z=410.2 (M+1) Method 2m_acidic.

Step 2

Prepared in an anologous manner to example 138, step 1 using the product from step 1 (525 mg, 1.28 mmol), tert-butyl (2-mercaptoethyl)carbamate (273 mg, 1.53 mmol), sodium iodide (192 mg, 1.28 mmol) and cesium carbonate (836 mg, 2.56 mmol) in DMF (12.8 mL). The crude residue was purified via silica gel chromatography (EtOAc-Heptane) to afford the product (190 mg, 30%). LCMS: R$_t$=0.80 min, m/z=491.2 (M+1) Method 2m_acidic.

Step 3

To a solution of the product (190 mg, 0.387 mmol) from step 2 in DCM (3.9 mL) at 0° C. was added m-CPBA (147 mg, 0.852 mmol). After stirring for 1 h, it was partioned between water/DCM. The aqueous layer was extracted with DCM and the combined organic layers were dried over Na$_2$SO$_4$ and concentrated in vacuo. The crude residue was purified via silica gel chromatography (EtOAc-Heptane), affording the product (148 mg, 73%). LCMS: R$_t$=0.72 min, m/z=523.2 (M+1) Method 2m_acidic.

Step 4: 1-(((Z)-(2-(((2R,3S)-2-((4-(((2-aminoethyl)sulfonyl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

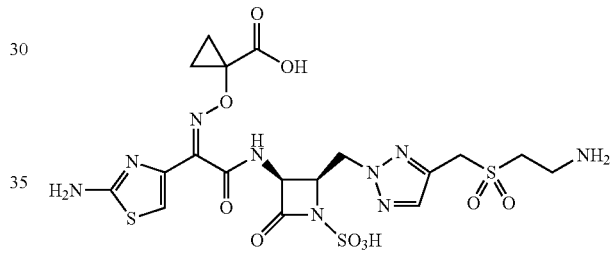

Prepared in an analogous manner to example 4, steps 3-6. LCMS: R$_t$=0.31 min, m/z=622.1 (M+1) Method 2m_acidic. $^1$H NMR (500 MHz, D$_2$O) δ 7.90 (s, 1H), 7.15 (s, 1H), 5.59 (d, J=5.7 Hz, 1H), 5.03 (q, J=5.6 Hz, 1H), 4.91 (d, J=5.6 Hz, 2H), 4.78 (s, 2H assumed; obscured by solvent residual peak), 3.63-3.58 (m, 2H), 3.54-3.50 (m, 2H), 1.41-1.33 (m, 2H), 1.24 (t, J=3.2 Hz, 2H).

Example 153

1-(((Z)-(2-(((2R,3S)-2-((4-(((R)-3-aminopyrrolidine-1-carboximidamido)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid

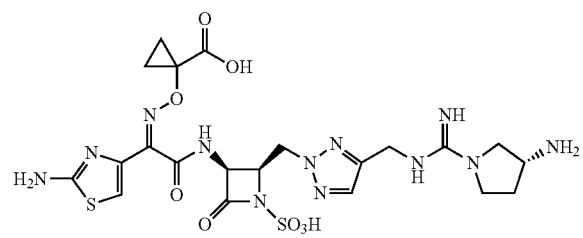 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N1CC[C@@H](N)C1]

Prepared in an analogous manner to example 127 using (R)-tert-butyl pyrrolidin-3-ylcarbamate in step 3. $R_t$=0.30 min, m/z=641.4 (M+1) Method 2m_acidic. $^1$H NMR (400 MHz, DMSO-$d_6$) δ 10.51-9.87 (m, 1H), 8.07-7.75 (m, 1H), 7.66 (s, 1H), 7.59 (br s, 2H), 7.20 (s, 2H), 6.73 (d, J=5.6 Hz, 1H), 5.22 (ddd, J=15.1, 8.8, 5.4 Hz, 1H), 4.94-4.85 (m, 1H), 4.70-4.59 (m, 1H), 4.59-4.36 (m, 3H), 3.97-3.83 (m, 1H), 3.70-3.38 (m, 3H assumed; overlaps with water peak), 2.29-2.17 (m, 1H), 2.08-1.98 (m, 1H), 1.27-1.15 (m, 2H), 1.13-1.01 (m, 2H).

Example 154

1-(((Z)-(1-(2-aminothiazol-4-yl)-2-(((2R,3S)-2-((5,6-dihydropyrrolo[3,4-d][1,2,3]triazol-2(4H)-yl)methyl)-4-oxo-1-sulfoazetidin-3-yl)amino)-2-oxoethylidene)amino)oxy)cyclopropanecarboxylic acid Step 1: tert-Butyl((4-chlorobut-2-yn-1-yl)oxy)diphenylsilane To a solution of imidazole (691 mg, 10.2 mmol) and tert-butylchlorodiphenylsilane (2.65 ml, 10.1 mmol) in DCM (15.3 mL) at 0° C. was added 4-chlorobut-2-yn-1-ol (824 μL, 9.18 mmol). After 2 h of stirring at rt it was diluted with DCM/water and the layers were separated. The aqueous layer was extracted with DCM (2×) and the combined organic layers were washed with brine, dried over $Na_2SO_4$ and concentrated in vacuo. The crude residue dissolved in dioxane and reconcentrated (2×) then used directly without further purification.

Step 2: 5-(azidomethyl)-4-(((tert-butyldiphenylsilyl)oxy)methyl)-1H-1,2,3-triazole To a solution of tert-butyl((4-chlorobut-2-yn-1-yl)oxy)diphenylsilane (3.15 g, 9.18 mmol) in dioxane/water (46 mL, 3:1) was added ammonium chloride (982 mg, 18.4 mmol) followed by sodium azide (2.39 g, 36.8 mmol). The biphasic solution was heated to 75° C. for 33 h, whereupon the layers were separated and the aqueous was extracted with EtOAc (3×20 mL). The combined organic layers were washed with water, brine, dried over $Na_2SO_4$ and concentrated in vacuo. The crude residue was purified via silica gel chromatography (EtOAc-Heptane, 0-35%) to afford the title compound (1.692 g, 47%) as a white solid. $R_t$=1.11 min, m/z=393.2 (M+1) Method 2m_acidic. $^1$H NMR (400 MHz, CDCl$_3$) δ 11.54 (s, 1H), 7.71-7.63 (m, 4H), 7.49-7.36 (m, 6H), 4.87 (s, 2H), 4.46 (s, 2H), 1.58 (s, 2H), 1.07 (s, 9H).

Step 3: tert-butyl ((4-(((tert-butyldiphenylsilyl)oxy)methyl)-1H-1,2,3-triazol-5-yl)methyl)carbamate A flask was charged with 5-(azidomethyl)-4-(((tert-butyldiphenylsilyl)oxy)methyl)-1H-1,2,3-triazole (1.044 g, 2.420 mmol), Boc-anhydride (581 mg, 2.66 mmol) and Pd—C (5%, 200 mg). After flushing the system with $N_2$, EtOH (24.2 ml) was added. The mixture was then evacuated and recharged with $H_2$ (3×). After vigorously stirring for 17 h the system was purged with $N_2$ and the slurry was filtered over celite and concentrated in vacuo. The crude residue was purified via silica gel chromatography (EtOAc-Heptane, 0-50%) to afford the title compound (777 mg, 69%) as a white solid. $R_t$=1.12 min, m/z=467.1 (M+1) Method 2m_acidic. $^1$H NMR (500 MHz, CDCl$_3$) δ 7.71-7.64 (m, 4H), 7.49-7.36 (m, 6H), 4.87 (s, 2H), 4.40 (br s, 2H), 1.43 (s, 9H), 1.08 (s, 9H).

Step 4

To a solution of benzyl ((2S,3S)-1-(2,4-dimethoxybenzyl)-2-(hydroxymethyl)-4-oxoazetidin-3-yl)carbamate (674 mg, 1.68 mmol), tert-butyl ((4-(((tert-butyldiphenylsilyl)oxy)methyl)-1H-1,2,3-triazol-5-yl)methyl)carbamate (777 mg, 1.67 mmol) and triphenylphosphine (525 mg, 2.00 mmol) in THF (16.7 mL) at 0° C. was added DIAD (414 μL, 1.10 mmol), drop-wise. After stirring at rt for 11 h, the mixture was concentrated onto silica gel and purified via silica gel chromatography (EtOAc-Heptane, 0-50%) to afford the product (1.196 g, 85%) as a white solid. $R_t$=1.31 min, m/z=849.4 (M+1) Method 2m_acidic.

Step 5: Benzyl ((2R,3S)-2-((4-(aminomethyl)-5-(((tert-butyldiphenylsilyl)oxy)methyl)-2H-1,2,3-triazol-2-yl)methyl)-1-(2,4-dimethoxybenzyl)-4-oxoazetidin-3-yl)carbamate To a solution of the product from step 4 (265 mg, 0.312 mmol) in DCM (3.1 mL) at 0° C. was added TFA (721 μL, 9.36 mmol). After stirring at 0° C. for 3 h it was diluted with DCE and concentrated in vacuo. The residue was redissolved in DCM and washed with saturated NaHCO$_3$ (aq). The aqueous layer was extracted with DCM (3×) and the combined organic layers were dried over $Na_2SO_4$ and concentrated in vacuo. The crude residue was used as such without further purication. $R_t$=1.03 min, m/z=749.4 (M+1) Method 2m_acidic.

Step 6: Benzyl ((2R,3S)-2-((4-(((tert-butyldiphenylsilyl)oxy)methyl)-5-((2-nitrophenylsulfonamido)methyl)-2H-1,2,3-triazol-2-yl)methyl)-1-(2,4-dimethoxybenzyl)-4-oxoazetidin-3-yl)carbamate To a solution of benzyl ((2R,3S)-2-((4-(aminomethyl)-5-(((tert-butyldiphenylsilyl)oxy)methyl)-2H-1,2,3-triazol-2-yl)methyl)-1-(2,4-dimethoxybenzyl)-4-oxoazetidin-3-yl)carbamate (234 mg, 0.312 mmol) in DCM (3.1 mL) at 0° C. was added 2-nitrobenzene-1-sulfonyl chloride (77.2 mg, 0.338 mmol) followed by TEA (87 μL, 0.62 mmol). After 2.2 h of stirring at rt, it was diluted with DCM and washed with KHSO$_4$ (2%, aq). The aqueous layer was extracted with DCM (3×) and the combined organic layers were washed with brine, dried over $Na_2SO_4$ and concd in vacuo. The crude residue was purified via silica gel chromatography (EtOAc-Heptane, 0-60%), affording the title compound (252 mg, 87%) as an off-white solid. $R_t$=1.24 min, m/z=934.4 (M+1) Method 2m_acidic.

Step 7: Benzyl ((2R,3S)-1-(2,4-dimethoxybenzyl)-2-((4-(hydroxymethyl)-5-((2-nitrophenylsulfonamido)methyl)-2H-1,2,3-triazol-2-yl)methyl)-4-oxoazetidin-3-yl)carbamate To a solution of benzyl ((2R,3S)-2-((4-(((tert-butyldiphenylsilyl)oxy)methyl)-5-((2-nitrophenylsulfonamido)methyl)-2H-1,2,3-triazol-2-yl)methyl)-1-(2,4-dimethoxybenzyl)-4-oxoazetidin-3-yl)carbamate (252 mg, 0.270 mmol) in THF (2.8 mL) at 0° C. was added TBAF (1.0 M in THF, 270 μL, 0.270 mmol). After stirring for 2.6 h, the solution was diluted with EtOAc and partially concentrated in vacuo. Additional EtOAc was added along with KHSO$_4$ (2%, aq) and water. The layers were separated and the aqueous layer was extracted with EtOAc (3×). The combined organic layers were washed with brine, dried over $Na_2SO_4$ and concentrated in vacuo. The crude residue was purified via silica gel chromatography (EtOAc-Heptane, 0-100%), affording the title compound (165 mg, 88%) as a white solid. $R_t$=0.83 min, m/z=696.3 (M+1) Method 2m_acidic.

Step 8: Benzyl ((2R,3S)-1-(2,4-dimethoxybenzyl)-2-((5-((2-nitrophenyl)sulfonyl)-5,6-dihydropyrrolo[3,4-d][1,2,3]triazol-2(4H)-yl)methyl)-4-oxoazetidin-3-yl)carbamate To a soln of benzyl ((2R,3S)-1-(2,4-dimethoxybenzyl)-2-((4-(hydroxymethyl)-5-((2-nitrophenylsulfonamido)methyl)-2H-1,2,3-triazol-2-yl)methyl)-4-oxoazetidin-3-yl)carbamate (165 mg, 0.237 mmol), and triphenylphosphine (91.6 mg, 0.349 mmol) in THF (11.9 mL) at 0° C. was added DIAD (72 µL, 0.35 mmol), drop-wise. After 3 h, more triphenylphosphine (46.4 mg, 0.177 mmol) was added, whereupon it was cooled to 0° C. followed by addition of DIAD (37 µL, 0.18 mmol). After stirring at rt for 2.5 h it was concentrated in vacuo and purified via silica gel chromatography (EtOAc-Heptane, 0-100%) to afford the title compound (318 mg), which was contaminated with triphenylphosphine oxide. $R_t$=0.93 min, m/z=678.3 (M+1) Method 2m_acidic.

Step 9: tert-Butyl 2-(((2R,3S)-3-(((benzyloxy)carbonyl)amino)-1-(2,4-dimethoxybenzyl)-4-oxoazetidin-2-yl)methyl)-4,6-dihydropyrrolo[3,4-d][1,2,3]triazole-5(2H)-carboxylate To a slurry of benzyl ((2R,3S)-1-(2,4-dimethoxybenzyl)-2-((5-((2-nitrophenyl)sulfonyl)-5,6-dihydropyrrolo[3,4-d][1,2,3]triazol-2(4H)-yl)methyl)-4-oxoazetidin-3-yl)carbamate (241 mg, ~50%/wt, ~0.178 mmol) and potassium carbonate (77.4 mg, 0.560 mmol) in DMF (3.0 mL) was added thiophenol (23.8 µl, 0.231 mmol). After stirring at rt for 2 h, Boc-anhydride (78 mg, 0.36 mmol) was added. After an additional 2 h, the slurry was diluted with EtOAc and washed with saturated NaHCO₃ (aq). The aqueous layer was extracted with EtOAc (2×) and the combined organic layers were washed with LiCl (5% aq), brine, dried over Na₂SO₄ and concd in vacuo. The crude residue was combined with the residues from 2 like transformations (15 mg and 20 mg scales) and purified via silica gel chromatography (EtOAc-Heptane, 0-100%) to afford the title compound (85.5 mg, 81% combined). $R_t$=0.96 min, m/z=593.2 (M+1) Method 2m_acidic. ¹H NMR (500 MHz, DMSO-d₆) δ 8.21 (d, J=9.6 Hz, 1H), 7.40-7.27 (m, 5H), 6.92 (d, J=8.3 Hz, 1H), 6.49 (d, J=2.1 Hz, 1H), 6.40 (d, J=8.3 Hz, 1H), 5.04 (s, 2H), 5.00 (dd, J=9.6, 5.1 Hz, 1H), 4.65 (dd, J=14.0, 7.1 Hz, 1H), 4.56 (dd, J=4.1, 6.2 Hz, 1H), 4.38-4.24 (m, 5H), 4.12 (q, J=6.2 Hz, 1H), 3.86 (d, J=15.1 Hz, 1H), 3.74 (s, 3H), 3.72 (s, 3H), 1.46 (s, 9H).

Step 10: tert-Butyl 2-(((2R,3S)-3-(((benzyloxy)carbonyl)amino)-4-oxoazetidin-2-yl)methyl)-4,6-dihydropyrrolo[3,4-d][1,2,3]triazole-5(2H)-carboxylate Slurried tert-butyl 2-(((2R,3S)-3-(((benzyloxy)carbonyl)amino)-1-(2,4-dimethoxybenzyl)-4-oxoazetidin-2-yl)methyl)-4,6-dihydropyrrolo[3,4-d][1,2,3]triazole-5(2H)-carboxylate (85.5 mg, 0.144 mmol), potassium peroxydisulfate (51.8 mg, 0.186 mmol) and potassium phosphate, dibasic (57 mg, 0.33 mmol) in ACN/water (2 mL, 2:1) for 5 min, then heated to 90° C. for 1.5 h. More potassium peroxydisulfate (13.9 mg, 0.050 mmol) was added and it was heated for an additional hour. More potassium peroxydisulfate (12.1 mg, 0.043 mmol) was added and it was heated an additional hour, whereupon the slurry was partially concentrated in vacuo then partitioned between saturated NaHCO₃ (aq) and EtOAc. After separating the layers, the aqueous was extracted with EtOAc (3×). The combined organic layers were washed with brine, dried over Na₂SO₄ and concentrated in vacuo. The crude residue was purified via silica gel chromatography (EtOAc-Heptane, 0-100%) to afford contaminated product (33 mg), which was repurified by reverse phase HPLC (XSELECT CSH, C18, 5µ, 30×100 mm, ACN/H₂O with 0.1% formic acid buffer, 60 mL/min). The title compound (12.1 mg, 19%) was obtained as a white solid. $R_t$=0.78 min, m/z=433.2 (M+1) Method 2m_acidic. ¹H NMR (500 MHz, DMSO-d₆) δ 8.40 (s, 1H), 8.17 (d, J=9.7 Hz, 1H), 7.42-7.26 (m, 5H), 5.05 (s, 2H), 5.04-4.99 (m, 1H), 4.58 (d, J=6.6 Hz, 2H), 4.40 (d, J=4.7 Hz, 4H), 4.22 (q, J=6.5 Hz, 1H), 1.45 (s, 9H).

Step 11: tert-Butyl 2-(((2R,3S)-3-amino-4-oxoazetidin-2-yl)methyl)-4,6-dihydropyrrolo[3,4-d][1,2,3]triazole-5(2H)-carboxylate Slurried tert-butyl 2-(((2R,3S)-3-(((benzyloxy)carbonyl)amino)-4-oxoazetidin-2-yl)methyl)-4,6-dihydropyrrolo[3,4-d][1,2,3]triazole-5(2H)-carboxylate (11.8 mg, 0.027 mmol) and Pd—C (5%, 2.3 mg) in MeOH/EtOH (740 µl, 1.7:1) under N₂, whereupon the system was evacuated and back-filled with H₂ (3×). After vigorous stirring for 1.7 h, the system was purged with N₂ and the solids were filtered through a 0.45µ syringe filter. The filtrate was concentrated in vacuo and used as such without further purification.

Step 12: tert-Butyl 2-(((2R,3S)-3-((Z)-2-((1-((benzhydryloxy)carbonyl)-cyclopropoxy)imino)-2-(2-((tert-butoxycarbonyl)amino)-thiazol-4-yl)acetamido)-4-oxoazetidin-2-yl)methyl)-4,6-dihydropyrrolo[3,4-d][1,2,3]triazole-5(2H)-carboxylate To a cooled (0° C.) slurry of (Z)-2-((1-((benzhydryloxy)carbonyl)cyclopropoxy)-imino)-2-(2-((tert-butoxycarbonyl)amino)thiazol-4-yl)acetic acid (15.3 mg, 0.028 mmol), tert-butyl 2-(((2R,3S)-3-amino-4-oxoazetidin-2-yl)methyl)-4,6-dihydropyrrolo[3,4-d][1,2,3]triazole-5(2H)-carboxylate (8.3 mg, 0.027 mmol) and HATU (11.4 mg, 0.029 mmol) in DMF (500 µL) was added DIPEA (9.5 µL, 0.054 mmol). After stirring at rt for 16 h, it was diluted with EtOAc and washed with LiCl (5%, aq). The aqueous layer was extracted with EtOAc (3×) and the combined organic layers were washed with brine, dried over Na₂SO₄ and concentrated in vacuo. The crude residue was purified via silica gel chromatography (EtOAc-Heptane) to afford the title compound (18.1 mg, 81%) as a white solid. $R_t$=1.08 min, m/z=828.5 (M+1) Method 2m_acidic.

Step 13: (2R,3S)-3-((Z)-2-((1-((benzhydryloxy)carbonyl)cyclopropoxy)imino)-2-(2-((tert-butoxycarbonyl)amino)thiazol-4-yl)acetamido)-2-((5-(tert-butoxycarbonyl)-5,6-dihydropyrrolo[3,4-d][1,2,3]triazol-2(4H)-yl)methyl)-4-oxoazetidine-1-sulfonic acid To a soln of tert-butyl 2-(((2R,3S)-3-((Z)-2-((1-((benzhydryloxy)carbonyl)cyclopropoxy)imino)-2-(2-((tert-butoxycarbonyl)amino)thiazol-4-yl)acetamido)-4-oxoazetidin-2-yl)methyl)-4,6-dihydropyrrolo[3,4-d][1,2,3]triazole-5(2H)-carboxylate (18.1 mg, 0.022 mmol) in DMF (300 µL) at 0° C. was added SO₃.DMF (12.3 mg, 0.078 mmol). After stirring at rt for 2 h, the solution was cooled to 0° C. and more SO₃.DMF (22.2 mg, 0.141 mmol) was added. After an additional 4 h at rt it was diluted with EtOAc and washed with LiCl (5% aq). The aqueous layer was extracted with EtOAc (2×) and the combined organic layers were washed with brine, dried over $Na_2SO_4$ and concd in vacuo. It was used as such (assumed quantitative) without further purification. $R_f$=0.96 min, m/z=908.4 (M+1) Method 2m_acidic.

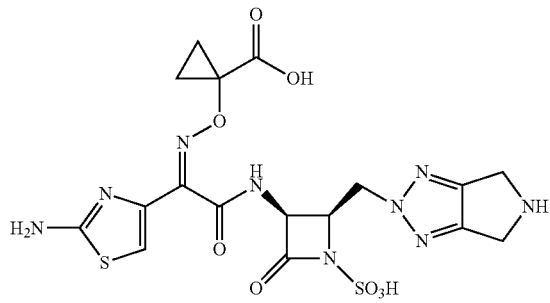 [SMILES: Nc1nc(/C(=N/OC2(C(=O)O)CC2)C(=O)N[C@@H]2C(=O)N(S(=O)(=O)O)[C@@H]2Cn2nc3c(n2)CNC3)cs1]

Step 14: 1-(((Z)-(1-(2-aminothiazol-4-yl)-2-(((2R,3S)-2-((5,6-dihydropyrrolo[3,4-d][1,2,3]triazol-2(4H)-yl)methyl)-4-oxo-1-sulfoazetidin-3-yl)amino)-2-oxoethylidene)amino)oxy)cyclopropanecarboxylic acid Followed the general procedure for the acid mediated deprotection using (2R,3S)-3-((Z)-2-((1-((benzhydryloxy)carbonyl)-cyclopropoxy)imino)-2-(2-((tert-butoxycarbonyl)amino)thiazol-4-yl)acetamido)-2-((5-(tert-butoxycarbonyl)-5,6-dihydropyrrolo[3,4-d][1,2,3]triazol-2(4H)-yl)methyl)-4-oxoazetidine-1-sulfonic acid (20 mg, 0.022 mmol), anisole (5 µl, 0.046 mmol), DCM (300 µL) and TFA (51 µL, 0.66 mmol). The crude residue was purified by reverse phase prep HPLC (XSELECT CSH, 30×100 mm, 5 µm, C18 column; ACN-water with 0.1% formic acid modifier, 60 mL/min), affording the title compound (7.3 mg, 60%) as a white powder. LCMS: $R_f$=0.37 min, m/z=542.1 (M+1) Method 2m_acidic_polar; $^1$H NMR (500 MHz, $D_2O$) δ 7.18 (s, 1H), 5.51 (d, J=5.3 Hz, 1H), 5.01-4.92 (m, 2H), 4.87 (d, J=6.0 Hz, 1H), 4.61-4.35 (m, 4H), 1.42-1.32 (m, 2H), 1.32-1.23 (m, 2H).

Example 155

1-(((Z)-(1-(2-aminothiazol-4-yl)-2-(((2R,3S)-2-((4-((S)-1,3-diaminopropyl)-2H-1,2,3-triazol-2-yl)methyl)-4-oxo-1-sulfoazetidin-3-yl)amino)-2-oxoethylidene)amino)oxy)cyclopropanecarboxylic acid Example 156

1-(((Z)-(1-(2-aminothiazol-4-yl)-2-(((2R,3S)-2-((4-((R)-1,3-diaminopropyl)-2H-1,2,3-triazol-2-yl)methyl)-4-oxo-1-sulfoazetidin-3-yl)amino)-2-oxoethylidene)amino)oxy)cyclopropanecarboxylic acid Step 1: (S)-tert-butyl (1-((tert-butyldiphenylsilyl)oxy)-4-oxobutan-2-yl)carbamate To a solution of (S)-tert-butyl (1-((tert-butyldiphenylsilyl)oxy)-4-hydroxybutan-2-yl)carbamate (prepared according to the procedure described in WO2013124826 A1 using L-aspartic acid) (15.0 g, 33.8 mmol) and DIPEA (29.5 mL, 169 mmol) in DCM (50 mL) at 0° C. was added a slurry of DMSO (7.20 mL, 101 mmol) and sulfurtrioxide pyridine complex (16.14 g, 101 mmol) in DCM (50 mL). After stirring at rt for 1.5 h, the mixture was diluted with saturated $NaHCO_3$ (aq) and the layers were separated. The aqueous layer was extracted with DCM and the combined organic portions were dried over $Na_2SO_4$ and concentrated in vacuo to afford the title compound (16.9 g, assumed quantitative) as a ight brown oil. It was used as such without further purification. LCMS: $R_f$=1.20 min, m/z=442.2 (M+1) Method 2m_acidic.

Step 2: (S)-tert-butyl (4-(benzylamino)-1-((tert-butyldiphenylsilyl)oxy)butan-2-yl)carbamate To (S)-tert-butyl (1-((tert-butyldiphenylsilyl)oxy)-4-oxobutan-2-yl)carbamate (14.93 g, 33.8 mmol) in DCE (100 mL) at 0° C. was added benzylamine (3.69 mL, 33.8 mmol) and sodium triacetoxyhydroborate (8.60 g, 40.6 mmol) sequentially. After stirring at rt 18 h, it was quenched by addition of saturated $NaHCO_3$ (aq, 300 mL) and stirred for an additional 30 min. The phases were separated and the aqueous phase was extracted with EtOAc. The combined organic layers were washed with brine, dried over $Na_2SO_4$ and concentrated in vacuo. The crude material was purified via silica gel chromatography (EtOAc-Heptane) to afford the title compound (8 g, 44%). LCMS: $R_f$=1.08 min, m/z=533.2 (M+1) Method 2m_acidic.

Step 3: (S)-tert-butyl (4-amino-1-((tert-butyldiphenylsilyl)oxy)butan-2-yl)carbamate To (S)-tert-butyl (4-(benzylamino)-1-((tert-butyldiphenylsilyl)oxy)butan-2-yl)carbamate (8.0 g, 15.0 mmol) in MeOH (100 mL) was added ammonium formate (9.47 g, 150 mmol) and $Pd(OH)_2$ (1.054 g, 1.502 mmol). The reaction mixture was stirred at 70° C. for 1.5 h then cooled to rt and filtered through a celite, eluting with MeOH/EtOAc (1:2, ~800 mL). The filtrate was concentrated in vacuo to afford the title compound (7 g) of a light brown residue which was used as such without further purification. LCMS: $R_f$=0.95 min, m/z=443.2 (M+1) Method 2m_acidic.

Step 4: (S)-di-tert-butyl (4-((tert-butyldiphenylsilyl)oxy)butane-1,3-diyl)dicarbamate To (S)-tert-butyl (4-amino-1-((tert-butyldiphenylsilyl)oxy)butan-2-yl)carbamate (6.65 g, 15.02 mmol) in DCM (75 mL) was added saturated $NaHCO_3$ (aq, 50 mL) and di-tert-butyl dicarbonate (5.24 g, 24.03 mmol), sequentially. After stirring for 16 h, the layers of were separated and the organic layer was washed with brine, dried over $Na_2SO_4$ and concentrated in vacuo. The crude residue was purified via silica gel chromatography (EtOAc-Heptane) to afford the title compound (6.25 g, 77%). LCMS: R=1.31 min, m/z=543.2 (M+1) Method 2m_acidic. $^1$H NMR (400 MHz, $CDCl_3$) δ ppm 7.70-7.58 (m, 4H) 7.49-7.34 (m, 6H) 5.29-5.12 (m, 1H) 4.83-4.56 (m, 1H) 3.72 (d, J=8.4 Hz, 2H) 3.63-3.51 (m, 1H) 3.48-3.27 (m, 1H) 3.04-2.73 (m, 1H) 1.58 (d, J=4.9 Hz, 2H) 1.44 (s, 9H) 1.43, (s, 9H), 1.06 (s, 9H).

Step 5: (S)-di-tert-butyl (4-hydroxybutane-1,3-diyl)dicarbamate

To a solution of (S)-di-tert-butyl (4-((tert-butyldiphenylsilyl)oxy)butane-1,3-diyl)dicarbamate (6.25 g, 11.51 mmol) in MeOH (100 mL) was added sodium hydroxide (1.38 g, 34.5 mmol) in water (20.0 mL). The mixture was heated to 70° C.

for 18 h then cooled to room temperature and partially concentrated in vacuo. DCM was then added and the mixture was cooled to 0° C., whereupon acetic acid (2.31 mL, 40.3 mmol) was added. The organic layer was then separated, washed with saturated NaHCO₃ (aq) and brine. The combined aqueous portions were extracted with DCM and the combined organic layers were dried over Na₂SO₄ and concentrated in vacuo. The crude residue was purified via silica gel chromatography (EtOAc-Heptane) to afford the title compound (1.67 g, 48%). LCMS: $R_t$=0.67 min, m/z=305.1 (M+1) Method 2m_acidic. ¹H NMR (400 MHz, CDCl₃) δ ppm 5.06 (br s, 1H) 4.83 (br s, 1H) 3.82-3.64 (m, 2H) 3.61 (dd, J=10.3, 4.9 Hz, 1H) 3.43-3.25 (m, 1H) 3.11-2.93 (m, 1H) 2.18 (br s, 1H) 1.79-1.65 (m, 1H) 1.64-1.58 (m, 1H) 1.51-1.36 (m, 18H).

Step 6: (S)-di-tert-butyl (4-oxobutane-1,3-diyl)dicarbamate

To a solution of (S)-di-tert-butyl (4-oxobutane-1,3-diyl) dicarbamate (1.67 g, 5.49 mmol) and DIPEA (3.83 mL, 21.95 mmol) in DCM (20 mL) at 0° C. was added a slurry of DMSO (1.061 mL, 13.72 mmol) and sulfur trioxide pyridine complex (2.183 g, 13.72 mmol) in DCM (20 mL). After stirring at rt for 30 min, the mixture was diluted with saturated NaHCO₃ (aq) and the layers were separated. The aqueous layer was extracted with DCM and the combined organic layers were dried over Na₂SO₄ and concentrated in vacuo. The crude residue was purified via silica gel chromatography (EtOAc-Heptane) to afford the title compound (1.47 g, 89%). LCMS: $R_t$=0.70 min, m/z=325.0 (M+Na) Method 2m_acidic.

Step 7: (S)-di-tert-butyl pent-4-yne-1,3-diyldicarbamate

To a solution of (S)-di-tert-butyl (4-oxobutane-1,3-diyl) dicarbamate (1.47 g, 4.86 mmol) in MeOH (30 mL) was added potassium carbonate (1.680 g, 12.15 mmol) and dimethyl (1-diazo-2-oxopropyl)phosphonate (1.40 mL, 7.29 mmol), sequentially. After stirring for 15 h, the mixture was diluted with EtOAc, washed with water, brine, dried over Na₂SO₄ and concentrated in vacuo. The crude material was purified via silica gel chromatography (EtOAc-Heptane) to afford the title compound (0.943 g, 65%). LCMS: $R_t$=0.81 min, m/z=321.1 (M+Na) Method 2m_acidic.

Step 8: (S)-di-tert-butyl (1-(2H-1,2,3-triazol-4-yl) propane-1,3-diyl)dicarbamate To a solution of (S)-di-tert-butyl pent-4-yne-1,3-diyldicarbamate in DMF/MeOH (3.7 mL, 1.2:1) was added azidotrimethylsilane (330 μL, 2.38 mmol) and copper iodide (15 mg, 0.079 mmol). The mixture was heated at 100° C. for 16 h, cooled to rt then filtered through celite. The filtrate was concentrated in vacuo and the crude residue was purified via silica gel chromatography (EtOAc-Heptane) to afford the title compound. LCMS: $R_t$=0.68 min, m/z=342.1 (M+1) Method 2m_acidic.

Step 9

To a solution of (S)-di-tert-butyl (1-(2H-1,2,3-triazol-4-yl) propane-1,3-diyl)dicarbamate (852 mg, 2.50 mmol), benzyl ((2S,3S)-1-(2,4-dimethoxybenzyl)-2-(hydroxymethyl)-4-oxoazetidin-3-yl)carbamate (1.05 g, 2.62 mmol) and PPh₃ (785 mg, 2.99 mmol) in THF (13 mL) at 0° C. was added DIAD (0.582 ml, 2.99 mmol), dropwise. After stirring at rt for 7 h, it was concentrated in vacuo and purified via silica gel chromatography (EtOAc-Heptane) to afford the product (1.24 g, 68%). LCMS: $R_t$=1.01 min, m/z=724.5 (M+1) Method 2m_acidic.

Step 10

To the product of step 9 (1.240 g, 1.713 mmol) in acetonitrile (20 mL) was added K₂S₂O₈ (621 mg, 2.227 mmol) and a solution of K₂HPO₄ (477 mg, 2.74 mmol) in water (10 mL), sequentially. After heating at 90° C. with vigorous stirring for 1 h, additional K₂S₂O₈ (185 mg, 0.685 mmol) was added along with K₃PO₄ (363 mg, 1.71 mmol). The mixture was heated to 90° C. for 5 h then cooled to rt and diluted with EtOAc (120 mL). The layers were separated and the organic layer was washed with brine, dried over Na₂SO₄ and concentrated in vacuo. The crude material was purified via silica gel chromatography (EtOAc-Heptane) to afford the product (590 mg, 60%). LCMS: $R_t$=0.85 min, m/z=574.2 (M+1) Method 2m_acidic.

Step 11: Di-tert-butyl ((S)-1-(2-(((2R,3S)-3-amino-4-oxoazetidin-2-yl)methyl)-2H-1,2,3-triazol-4-yl) propane-1,3-diyl)dicarbamate Slurried the product of step 10 (590 mg, 1.03 mmol) and Pd—C (10% 200 mg) in EtOH/MeOH (21 mL, 2:1), whereupon the system was evacuated and recharged with H₂ (3×). After 4 h of vigorous stirring, the mixture was filtered through celite, washing with EtOH/DCM. The filtrate was concentrated in vacuo, affording the title compound (assumed quantitative) as a light yellow solid which was used as such without further purification. LCMS: $R_t$=0.61 min, m/z=440.2 (M+1) Method 2m_acidic.

Step 12: Benzhydryl 1-(((Z)-(1-(2-((tert-butoxycarbonyl)amino)thiazol-4-yl)-2-oxo-2-(((3S,4R)-2-oxo-4-((4-((S)-2,2,12,12-tetramethyl-4,10-dioxo-3,11-dioxa-5,9-diazatridecan-6-yl)-2H-1,2,3-triazol-2-yl) methyl)azetidin-3-yl)amino)ethylidene)amino)oxy) cyclopropanecarboxylate A mixture of (Z)-2-((1-((benzhydryloxy)carbonyl)cyclopropoxy)imino)-2-(2-((tert-butoxycarbonyl)amino)thiazol-4-yl)acetic acid (582 mg, 1.028 mmol), DIPEA (0.269 mL, 1.543 mmol) and HATU (430 mg, 1.131 mmol) in DCM/DMF (12 mL, 5:1) was stirred at 0° C. for 30 min. To this mixture was added di-tert-butyl ((S)-1-(2-(((2R,3S)-3-amino-4-oxoazetidin-2-yl)methyl)-2H-1,2,3-triazol-4-yl) propane-1,3-diyl)dicarbamate (1.03 mmol). After stirring for an additional 30 min at 0° C., it was diluted with EtOAc, washed with water, brine, dried over Na₂SO₄ and concentrated in vacuo. The crude material was purified via silica gel chromatography (EtOAc-Heptane) to afford the title compound (760 mg, 77%). LCMS: $R_t$=1.12 min, m/z=959.6 (M+1) Method 2m_acidic.

Step 13: (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((4-((S)-2,2,12,12-tetramethyl-4,10-dioxo-3,11-dioxa-5,9-diazatridecan-6-yl)-2H-1,2,3-triazol-2-yl)methyl) azetidine-1-sulfonic acid To benzhydryl 1-(((Z)-(1-(2-((tert-butoxycarbonyl)amino) thiazol-4-yl)-2-oxo-2-(((3S,4R)-2-oxo-4-((4-((S)-2,2,12,12-tetramethyl-4,10-dioxo-3,11-dioxa-5,9-diazatridecan-6-yl)-2H-1,2,3-triazol-2-yl)methyl)azetidin-3-yl)amino)

ethylidene)amino)oxy)cyclopropanecarboxylate (760 mg, 0.792 mmol) in DMF (4 mL) at 0° C. was added SO$_3$.DMF (850 mg, 5.55 mmol). After stirring for 2 h at rt, the solution was diluted with EtOAc, washed with LiCl (5% aq), brine, dried over Na$_2$SO$_4$ and concentrated in vacuo to afford the title compound (assumed quantitative) as an orange oil which was used directly without further purication. LCMS: R$_f$=1.01 min, m/z=1039.6 (M+1) Method 2m_acidic.

Step 14, Compound 1: 1-(((Z)-(1-(2-aminothiazol-4-yl)-2-(((2R,3S)-2-((4-((S)-1,3-diaminopropyl)-2H-1,2,3-triazol-2-yl)methyl)-4-oxo-1-sulfoazetidin-3-yl)amino)-2-oxoethylidene)amino)oxy)cyclopropanecarboxylic acid

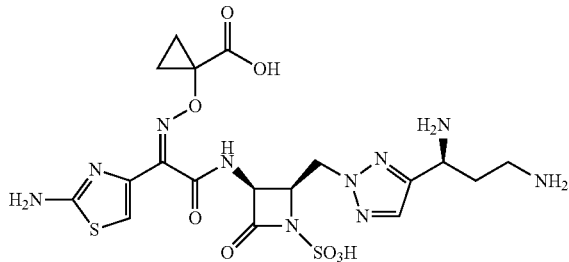 [SMILES: NCC[C@H](N)c1cnn(C[C@@H]2[C@H](NC(=O)/C(=N\OC3(C(=O)O)CC3)c3csc(N)n3)C(=O)N2S(=O)(=O)O)n1]

Step 14, Compound 2: 1-(((Z)-(1-(2-aminothiazol-4-yl)-2-(((2R,3S)-2-((4-((R)-1,3-diaminopropyl)-2H-1,2,3-triazol-2-yl)methyl)-4-oxo-1-sulfoazetidin-3-yl)amino)-2-oxoethylidene)amino)oxy)cyclopropanecarboxylic acid

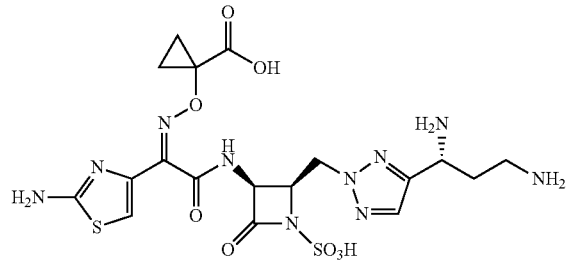 [SMILES: NCC[C@@H](N)c1cnn(C[C@@H]2[C@H](NC(=O)/C(=N\OC3(C(=O)O)CC3)c3csc(N)n3)C(=O)N2S(=O)(=O)O)n1]

To (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((4-((S)-2,2,12,12-tetramethyl-4,10-dioxo-3,11-dioxa-5,9-diazatridecan-6-yl)-2H-1,2,3-triazol-2-yl)methyl)azetidine-1-sulfonic acid (5.55 mmol) in formic acid (4 mL) at 0° C. was added anisole (173 µL, 1.58 mmol). The solution was heated at 40° C. for 2 h, whereupon it was cooled to rt and concentrated in vacuo. To the resulting residue was added DCM (15 mL) then ice-water (12 mL) and this was vigorously stirred for 1 h. The layers were separated and the aqueous layer was directly purified by reverse phase HPLC (XSELECT CSH, 30×100 mm, 5 µm, C18 column; ACN-water with 0.1% formic acid modifier, 60 mL/min), affording compound 1 (170 mg, 37%) and compound 2 (21 mg, 5%) as white solids. Compound 2 is thought to arise from slight epimerization of the stereocenter during step 7. 1-LCMS: R$_f$=0.31 min, m/z=573.3 (M+1) Method 2m_acidic_polar. $^1$H NMR (400 MHz, D$_2$O) δ ppm 7.86 (s, 1H) 7.07 (s, 1H) 5.60 (d, J=5.6 Hz, 1H) 5.03-4.82 (m, 4H assumed; partially obscured by solvent residual peak) 3.12-2.85 (m, 2H) 2.54-2.34 (m, 2H) 1.28-1.08 (m, 4H). 2-LCMS: R$_f$=0.30 min, m/z=573.3 (M+1) Method 2m_acidic_polar. $^1$H NMR (400 MHz, D$_2$O) δ ppm 7.86 (s, 1H) 7.07 (s, 1H) 5.58 (d, J=5.5 Hz, 1H) 5.07-4.85 (m, 4H assumed; partially obscured by solvent residual peak) 3.12-2.84 (m, 2H) 2.53-2.34 (m, 2H) 1.30-1.03 (m, 4H).

Bacterial Screens and Cultures

Bacterial isolates were cultivated from −70° C. frozen stocks by two consecutive overnight passages at 35° C. in ambient air on 5% blood agar (Remel, Lenexa, Kans.). Quality control and *P. aeruginosa* ATCC 27853) is from the American Type Culture Collection (ATCC; Rockville, Md.) and PAO1 was received from Dr. K. Poole.

Construction of *Escherichia coli* isogenic strains Strains NB27273-CDY0026 (parent), NB27273-CDY0033 (KPC2) and NB27273-CDY0030 (SHV12)

Strain NB27273 (BW25113 pspB::Km$^r$) was obtained from the Keio transposon insertion collection. The strain has the pspB gene replaced by a kanamycin resistance marker (BW25113 pspB::Km$^r$). This strain was cured of the transposon in pspB via FLP recombinase using published methodology. The resulting strain, BW25113 pspB, was used as a host for multicopy vectors expressing key β-lactamases. Multicopy plasmids directing constitutive expression of β-lactamases were established as follows: Synthetic, codon optimized genes encoding *E. coli* KPC2 and SHV12 β-lactamases were made by DNA2.0 (Palo Alto, Calif.). Each of the synthetic fragments were designed to contain NotI and NcoI restriction sites at their termini, allowing ligation into a NotI/NcoI digested pET28a(+) derivative for protein expression. The inserts in these vectors served as template DNA for PCR amplification of the gene encoding KPC2 and SHV12, using primer pairs E225 (tcgcCTCGAGgcgactgcgctgacgaatttgg) (SEQ ID NO:1) and E202 (aatcGAATTCttactgaccattaacgcccaagc) (SEQ ID NO:2) and E227 (tcgcCTCGAGgcgagcccgcaaccgctgga) (SEQ ID NO:3) and E204 (aatcGAATTCttaacgctgccagtgctcaatc) (SEQ ID NO:4), respectively. The codon optimized nucleotide sequences and relevant primer recognition information is shown below:

SHV12

(SEQ ID NO: 5)
ATGGGCCATCATCATCATCATCACAGCAGCGGCCTGGAAGTTCTGTTCCA

GGGGCCCGCGAGCCCGCAACCGCTGGAGCAGATCAAGCAGTCTGAGAGCC

AGCTGAGCGGCCGTGTGGGTATGATCGAGATGGATCTGGCTTCCGGCCGT

ACGCTGACGGCATGGCGTGCCGACGAACGTTTCCCGATGATGTCGACCTT

TAAAGTTGTTCTGTGTGGTGCGGTCTTGGCACGTGTAGACGCGGGTGACG

AACAACTGGAGCGCAAGATCCATTACCGCCAACAGGACTTGGTCGACTAC

AGCCCGGTTAGCGAAAAGCACCTGGCGGATGGCATGACCGTGGGTGAATT

GTGCGCCGCTGCGATTACCATGAGCGACAATAGCGCGGCTAATCTGCTGT

TGGCGACCGTTGGTGGCCCAGCGGGCTTGACCGCATTTCTGCGTCAAATC

GGCGATAATGTTACGCGTCTGGATCGCTGGGAAACGGAGCTGAACGAGGC

ACTGCCGGGTGATGCCCGTGATACCACGACTCCTGCTAGCATGGCAGCGA

CCCTGCGTAAACTGCTGACCAGCCAGCGTCTGAGCGCACGTAGCCAACGC

CAGCTGCTGCAATGGATGGTGGATGACCGCGTGGCGGGTCCGCTGATCCG

-continued

CTCCGTCCTGCCAGCAGGCTGGTTCATTGCGGACAAAACTGGTGCCTCTA

AGCGTGGTGCGCGTGGTATCGTCGCGCTGCTGGGTCCGAACAACAAAGCC

GAACGTATTGTGGTTATCTATCTGCGCGACACCCCGGCAAGCATGGCCGA

GCGCAACCAGCAAATTGCGGGCATTGGTGCGGCACTGATTGAGCACTGGC

AGCGTTAACGCCGGCG

E227
(SEQ ID NO: 6)
TCGCCTCGAGGCGAGCCCGCAACCGCTGGA

E204
(SEQ ID NO: 7)
AATCGAATTCTTAACGCTGCCAGTGCTCAATC

REV. COMP. E204
(SEQ ID NO: 8)
GATTGAGCACTGGCAGCGTTAAGAATTCGATT

KPC2
(SEQ ID NO: 9)
ATGGGCCATCATCATCATCATCACAGCAGCGGCCTGGAAGTTCTGTTCCA

GGGGCCCGCGACTGCGCTGACGAATTTGGTGGCCGAGCCGTTCGCGAAAT

TGGAGCAAGATTTTGGTGGTTCGATCGGTGTCTACGCGATGGACACCGGT

AGCGGTGCCACCGTGAGCTACCGTGCCGAAGAGCGTTTTCCGCTGTGTAG

CTCTTTCAAGGGTTTTCTGGCCGCAGCCGTGCTGGCACGCAGCCAACAGC

AAGCGGGCCTGCTGGACACCCCGATCCGTTACGGCAAAAATGCGCTGGTT

CCGTGGAGCCCGATTAGCGAAAAGTACCTGACCACCGGCATGACGGTGGC

GGAGTTGAGCGCTGCGGCGGTTCAGTATTCCGATAACGCTGCGGCAAATC

TGCTGCTGAAAGAACTGGGCGGTCCAGCGGGTCTGACGGCTTTCATGCGT

TCTATTGGCGACACCACCTTTCGCTTGGACCGCTGGGAGCTGGAGCTGAA

CAGCGCGATTCCGGGCGACGCACGTGATACGAGCAGCCCGCGTGCAGTGA

CCGAGAGCCTGCAGAAGCTGACCCTGGGCAGCGCACTGGCCGCACCGCAG

CGCCAACAGTTCGTCGATTGGCTGAAGGGTAACACCACCGGTAACCATCG

TATTCGCGCAGCGGTCCCGGCTGATTGGGCAGTTGGTGACAAGACTGGTA

CGTGCGGCGTTTATGGTACGGCGAATGACTACGCGGTTGTTTGGCCTACG

GGTCGTGCGCCGATCGTCCTGGCGGTGTATACCCGTGCTCCGAACAAAGA

CGATAAACACTCCGAAGCGGTCATCGCCGCAGCAGCGCGTCTGGCCCTGG

AAGGCTTGGGCGTTAATGGTCAGTAACGCCGGCG

E225
(SEQ ID NO: 10)
TCGCCTCGAGGCGACTGCGCTGACGAATTTGG

E202
(SEQ ID NO: 11)
AATCGAATTCTTACTGACCATTAACGCCCAAGC

REV. COMP. E202
(SEQ ID NO: 12)
GCTTGGGCGTTAATGGTCAGTAAGAATTCGATT
UNDERLINED = DNA ENCODING BL

The PCR products were then digested with XhoI and EcoRI and ligated into similarly digested plasmid pAH63-pstS(BlaP). Plasmid pAH63-pstS(BlaP) is a derivative of plasmid pAH63 (J Bacteriol: 183(21): 6384-6393) made by cloning the TEM-1 (b/a) promoter and signal peptide encoding region from plasmid pBAD (J Bacteriol. 1995 July 177 (14):4121-30) into plasmid pAH63. This fragment was PCR amplified from pBAD using primer pair E192 (ttcaCTG-CAGtgaacgttgcgaagcaacggC) (SEQ ID NO:13) and E194 (TCGAggatcctcgagagcaaaaacaggaaggcaaaatgccg) (SEQ ID NO:14), digested with PstI and BamHI and inserted into similarly digested plasmid pAH63. Therefore, expression of β-lactamases from pAH63-pstS(BlaP) based constructs is constitutive and the signal sequence is provided to direct these proteins to the periplasm. Plasmid pAH63 based vectors are used for insertion into the genome in single copy, however, to provide higher expression levels to allow more sensitive detection of the susceptibility of compounds to the β-lactamases, the expression inserts contained in these vectors were moved to the replicative multicopy vector pBAD-Kan (J Bacteriol. 1995 July 177(14):4121-30). To accomplish this, the inserts encompassing the β-lactamase genes, with the associated TEM promoter and signal sequences, were PCR amplified from their corresponding vectors using primer E269 (ccgTCTAGAcggatggccttttgcgtttc) (SEQ ID NO:15) and E202 (aatcGAATTCttactgaccattaacgcccaagc) (SEQ ID NO:16) for the KPC2 construct and E204 (aatcGAATTCt-taacgctgccagtgctcaatc) (SEQ ID NO:17) for the SHV12 construct. These fragments were then digested with XbaI and EcoRI, and each was inserted into pBAD18-kan that had been digested with the same enzymes to generate a pair of multicopy vectors expressing KPC2 and SHV12 respectively. These vectors were transformed into BW25113 pspB to generate strains NB27273-CDY0033 (expressing KPC2) and NB27273-CDY0030 (expressing SHV12). The pBAD18-kan vector also contains the TEM promoter region and signal sequence, (but lacks any intact β-lactamase genes) and was transformed into BW25113 pspB using standard protocols to generate the control strain NB27273-CDY0026. Expression of the β-lactamases was confirmed by verifying decreased susceptibility to example test antibiotics that are known substrates of KPC2 or SHV12.

Susceptibility Testing

Minimal Inhibitory Concentrations (MICs) were determined by the broth microdilution method in accordance with Clinical and Laboratories Institute (CLSI) guidelines. In brief, fresh overnight bacterial cultures were suspended in sterile saline, and adjusted to a 0.5 McFarland turbidity standard. Bacterial suspensions were then diluted in cation adjusted Mueller-Hinton Broth (MHB II; BBL) to yield a final inoculum of approximately $5 \times 10^5$ colony-forming units (CFU)/mL. A master plate of antibiotics was prepared at a concentration equivalent to hundred-fold the highest desired final concentration in 100% dimethyl sulfoxide (DMSO). The master antibiotic plate was then diluted by serial twofold dilution with a multichannel pipette. The resulting dilution series of compounds were diluted 1:10 with sterile water leading to a 10% DMSO final concentration. A volume of 10 μL of the drug dilution series was transferred to 96-well assay plates. Assay plates were inoculated with 90 μL of bacterial suspensions and incubated at 35-37° C. for 20 hrs. The assay plates were read using a microtiter plate reader (Molecular Devices) at 600 nm as well as by visual observation with a reading mirror. The lowest concentration of the compound that prevented visible growth was recorded as the MIC. Performance of the assay was monitored by testing aztreonam against laboratory quality control strains in accordance with guidelines of the CLSI.

Reference compounds: for comparison, the following known monobactam compounds are used herein:

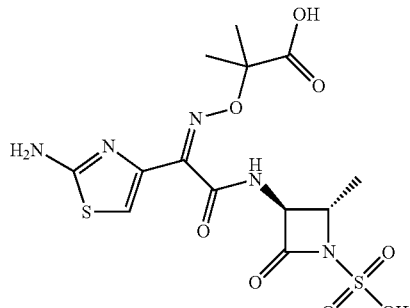

Reference compound 1: Aztreonam

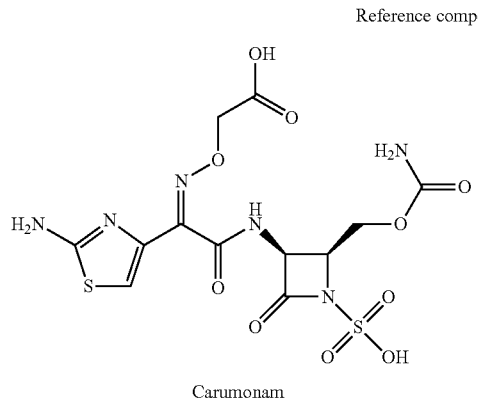

Carumonam

Reference compound 2

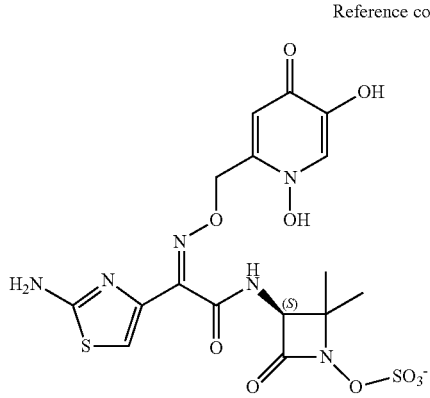

BAL30072

Reference compound 3

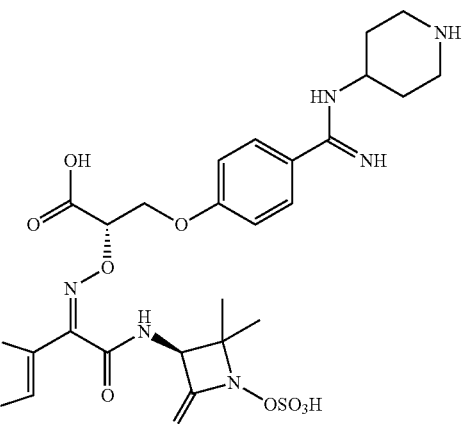

Reference compound 4: Aicuris WO2013110643

TABLE A

Minimum Inhibitory Concentrations (MIC) against isogenic strains of *E. coli*, carrying various resistance determinants.

| Example number | Strain 1 MIC (μg/mL) | Strain 2 MIC (μg/mL) | Strain 3 MIC (μg/mL) |
|---|---|---|---|
| Reference compound 1 | 0.125 | >32 | >32 |
| Reference compound 2 | 0.125 | 1 | >32 |
| Reference compound 3 | 0.25 | 0.5 | >32 |
| Reference compound 4 | 0.06 | 0.25 | 32 |
| Example 1 | 1 | 2 | 2 |
| Example 31 | 0.125 | 0.25 | 0.5 |
| Example 22 | 0.06 | 0.125 | 0.5 |
| Example 4 | 0.5 | 8 | 2 |
| Example 28 | 0.06 | 0.06 | 0.5 |

Strain 1: *E. coli* NB27273-CDY0026 (parent)
Strain 2: *E. coli* NB27273-CDY0033 (KPC2)
Strain 3: *E. coli* NB27273-CDY0030 (SHV12)

The data in Table A shows that compounds of the invention have good antibacterial potency against *E. coli*, including strains that show strong resistance to several known monobactam and sulfactam antibiotics.

Activity data for selected compounds of the invention is provided in the following table. Compounds were tested on *E. coli* strain 25922 and an *E. coli* containing KPC-2 (a known carbapenemase from *Klebsiella pneumoniae*), to determine Minimum Inhibitory Concentrations (MIC), in mg/L. Note that compounds identified as formate salts were subjected to lyophilization during isolation, which in some cases removed some formic acid, so the formate content of those salts may be less than stoichiometric.

TABLE B

Activity of Compounds in the Examples.

| Example No. | | Salt | Ec 25922 | Ec KPC2 Iso |
|---|---|---|---|---|
| 41 | [structure] | none | 1 | 2 |
| 43 | [structure] | none | 2 | 2 |
| 42 | [structure] | none | 1.4 | 2 |
| 46 | [structure] | none | | |

TABLE B-continued

Activity of Compounds in the Examples.

| Example No. | Structure | Salt | Ec 25922 | Ec KPC2 Iso |
|---|---|---|---|---|
| 48 | | none | | |
| 49 | | none | 2 | 16 |
| 47 | | none | 2 | 5 |
| 50 | | none | 2 | 2.8 |

TABLE B-continued
Activity of Compounds in the Examples.
| Example No. | | Salt | Ec 25922 | Ec KPC2 Iso |
|---|---|---|---|---|
| 44 | 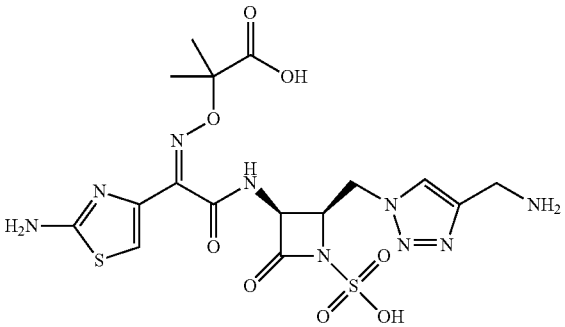 [SMILES: CC(C)(O/N=C(\C(=O)N[C@@H]1C(=O)N(S(=O)(=O)O)[C@@H]1Cn1cc(CN)nn1)c1csc(N)n1)C(=O)O] | none | 0.67 | 1.5 |
| 7 | 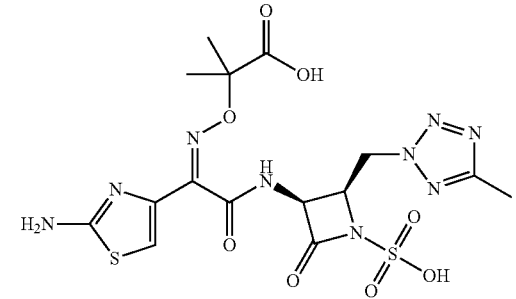 [SMILES: Cc1nnn(C[C@@H]2[C@H](NC(=O)/C(=N\OC(C)(C)C(=O)O)c3csc(N)n3)C(=O)N2S(=O)(=O)O)n1] | formate | 4 | 8 |
| 8 | 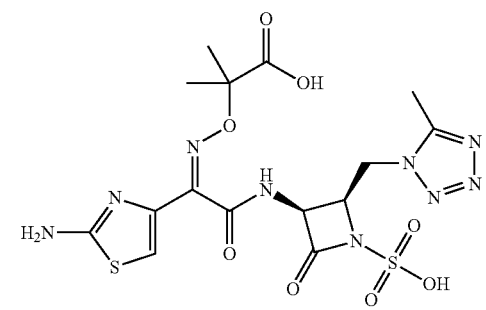 [SMILES: Cc1nnnn1C[C@@H]1[C@H](NC(=O)/C(=N\OC(C)(C)C(=O)O)c2csc(N)n2)C(=O)N1S(=O)(=O)O] | formate | 2 | 2 |
| 51 | 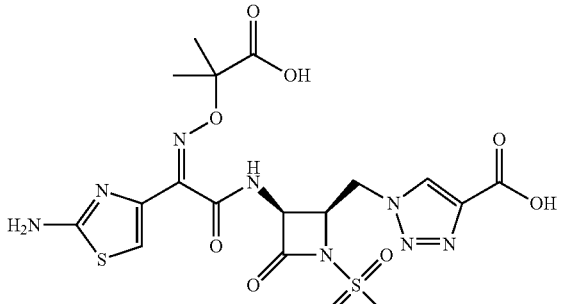 | none | >64 | 16 |

TABLE B-continued

Activity of Compounds in the Examples.

| Example No. | Structure | Salt | Ec 25922 | Ec KPC2 Iso |
|---|---|---|---|---|
| 4 | | formate | 1 | 8 |
| 1 | | none | 16 | 2 |
| 55 | | none | 16 | 4 |
| 5 | | formate | 1 | 4 |

TABLE B-continued

Activity of Compounds in the Examples.

| Example No. | Structure | Salt | Ec 25922 | Ec KPC2 Iso |
|---|---|---|---|---|
| 52 | | formate | 0.5 | 1 |
| 54 | | formate | 2 | 1 |
| 2 | | none | 1 | 0.5 |
| 12 | | formate | 4 | 4 |

TABLE B-continued

Activity of Compounds in the Examples.

| Example No. | Structure | Salt | Ec 25922 | Ec KPC2 Iso |
|---|---|---|---|---|
| 10 | | formate | 4 | 11 |
| 11 | | formate | 4 | 4 |
| 13 | | formate | 16 | 32 |
| 14 | | formate | 16 | 8 |

TABLE B-continued

Activity of Compounds in the Examples.

| Example No. | | Salt | Ec 25922 | Ec KPC2 Iso |
|---|---|---|---|---|
| 15 | | formate | 16 | 8 |
| 56 | | formate | 4 | 16 |
| 3 | | none | 2 | 1 |
| 16 | | formate | 4 | 2 |

TABLE B-continued

Activity of Compounds in the Examples.

| Example No. | Structure | Salt | Ec 25922 | Ec KPC2 Iso |
|---|---|---|---|---|
| 53 | | formate | 1 | 1 |
| 6 | | formate | 4 | 1 |
| 23 | | formate | 2 | 1 |
| 39 | | none | 64 | >64 |

TABLE B-continued

Activity of Compounds in the Examples.

| Example No. | Structure | Salt | Ec 25922 | Ec KPC2 Iso |
|---|---|---|---|---|
| 38 | | formate | 8 | 4 |
| 40 | | none | 2 | 2 |
| 18 | | formate | 0.5 | 0.25 |
| 62 | | formate | 0.5 | 2 |

TABLE B-continued

Activity of Compounds in the Examples.

| Example No. | Structure | Salt | Ec 25922 | Ec KPC2 Iso |
|---|---|---|---|---|
| 17 | | formate | 0.5 | 0.25 |
| 9 | | formate | 1 | 1 |
| 57 | | formate | 0.5 | 1 |
| 21 | | none | 0.25 | 0.5 |

TABLE B-continued

Activity of Compounds in the Examples.

| Example No. | Structure | Salt | Ec 25922 | Ec KPC2 Iso |
|---|---|---|---|---|
| 22 | | none | 0.25 | 0.125 |
| 37 | | formate | 2 | 2 |
| 36 | | formate | 2 | 1 |
| 35 | | formate | 2 | 1 |

TABLE B-continued

Activity of Compounds in the Examples.

| Example No. | | Salt | Ec 25922 | Ec KPC2 Iso |
|---|---|---|---|---|
| 24 | | formate | 0.25 | 1 |
| 63 | | none | 32 | 32 |
| 61 | | none | 8 | 2 |
| 34 | | formate | >64 | >64 |

TABLE B-continued

Activity of Compounds in the Examples.

| Example No. | | Salt | Ec 25922 | Ec KPC2 Iso |
|---|---|---|---|---|
| 33 | | formate | 2 | 2 |
| 45 | | formate | 0.5 | 0.5 |
| 30 | | none | 1 | 1 |
| 29 | | none | 0.25 | 1 |

TABLE B-continued
Activity of Compounds in the Examples.
| Example No. | Structure | Salt | Ec 25922 | Ec KPC2 Iso |
|---|---|---|---|---|
| 31 | 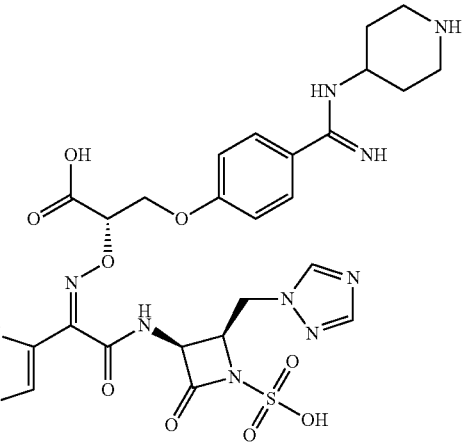 | formate | 0.25 | 0.25 |
| 28 | 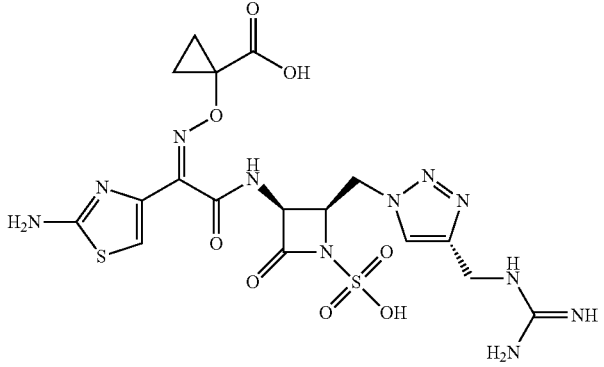 | formate | 0.25 | 0.125 |
| 60 | 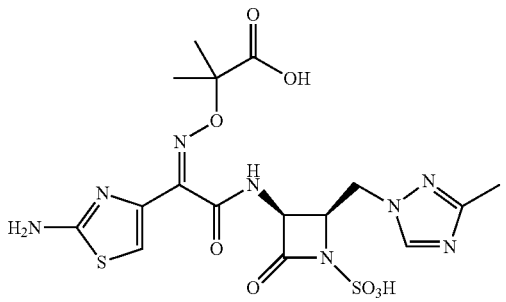 [SMILES: Cc1ncn(C[C@@H]2[C@H](NC(=O)/C(=N\OC(C)(C)C(=O)O)c3csc(N)n3)C(=O)N2S(=O)(=O)O)n1] | none | 8 | 8 |
| 32 | 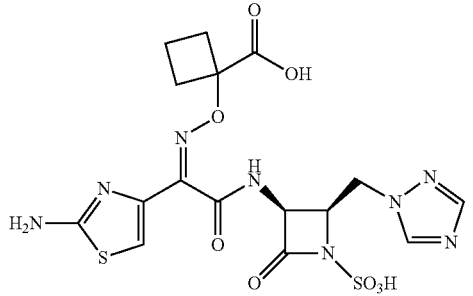 [SMILES: Nc1nc(/C(=N/OC2(C(=O)O)CCC2)C(=O)N[C@@H]2C(=O)N(S(=O)(=O)O)[C@@H]2Cn2cncn2)cs1] | none | 2 | 1 |

TABLE B-continued

Activity of Compounds in the Examples.

| Example No. | Structure | Salt | Ec 25922 | Ec KPC2 Iso |
|---|---|---|---|---|
| 59 | | none | 16 | 16 |
| 58 | | none | 2 | 1 |
| 27 | | None | ≤0.06 | 0.125 |
| 25 | | none | 0.125 | ≤0.06 |

TABLE B-continued

Activity of Compounds in the Examples.

| Example No. | Structure | Salt | Ec 25922 | Ec KPC2 Iso |
|---|---|---|---|---|
| 26 | | None | 0.125 | ≤0.06 |
| 19 | | None | 0.25 | 0.25 |
| 20 | | None | ≤0.06 | 0.125 |
| 64 | | none | 0.5 | 0.25 |

TABLE B-continued
Activity of Compounds in the Examples.
| Example No. | | Salt | Ec 25922 | Ec KPC2 Iso |
|---|---|---|---|---|
| 65 | 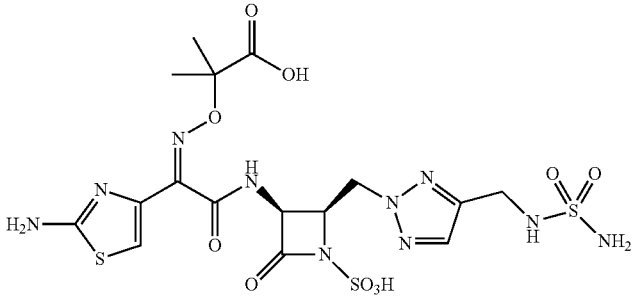 [SMILES: CC(C)(O/N=C(\C(=O)N[C@@H]1C(=O)N(S(=O)(=O)O)[C@@H]1Cn1ncc(CNS(N)(=O)=O)n1)c1csc(N)n1)C(=O)O] | none | 64 | 64 |
| 66 | 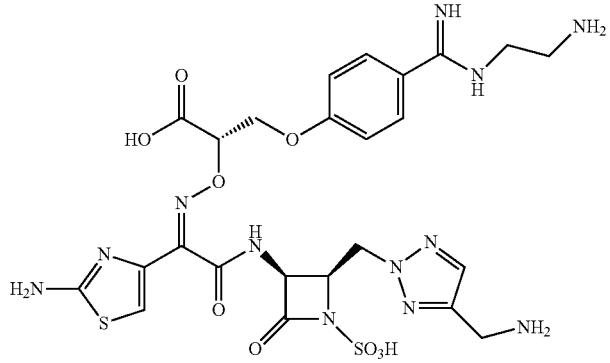 [SMILES: N=C(NCCN)c1ccc(OC[C@H](O/N=C(\C(=O)N[C@@H]2C(=O)N(S(=O)(=O)O)[C@@H]2Cn2ncc(CN)n2)c2csc(N)n2)C(=O)O)cc1] | none | 1 | 2 |
| 67 | 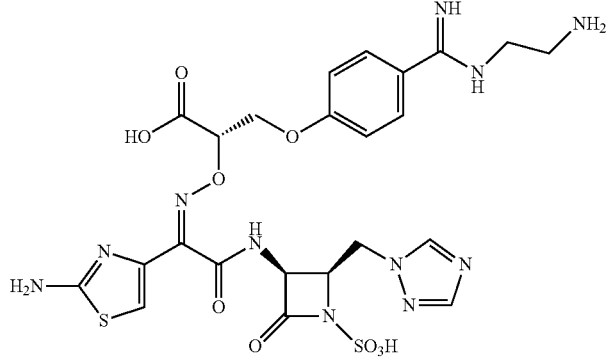 [SMILES: N=C(NCCN)c1ccc(OC[C@H](O/N=C(\C(=O)N[C@@H]2C(=O)N(S(=O)(=O)O)[C@@H]2Cn2cncn2)c2csc(N)n2)C(=O)O)cc1] | none | 0.25 | 0.125 |
| 68 | 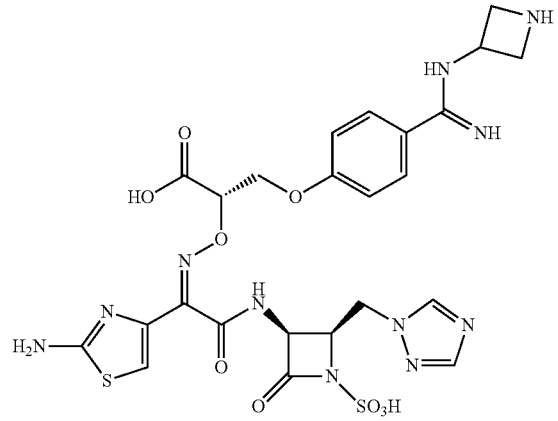 [SMILES: N=C(NC1CNC1)c1ccc(OC[C@H](O/N=C(\C(=O)N[C@@H]2C(=O)N(S(=O)(=O)O)[C@@H]2Cn2cncn2)c2csc(N)n2)C(=O)O)cc1] | none | 0.25 | 0.25 |

TABLE B-continued

Activity of Compounds in the Examples.

| Example No. | Structure | Salt | Ec 25922 | Ec KPC2 Iso |
|---|---|---|---|---|
| 69 | | formate | 0.25 | 0.125 |
| 70 | | formate | 8 | 8 |
| 71 | | none | 0.25 | 0.25 |
| 72 | | none | 4 | 4 |

TABLE B-continued

Activity of Compounds in the Examples.

| Example No. | | Salt | Ec 25922 | Ec KPC2 Iso |
|---|---|---|---|---|
| 73 | | none | 0.25 | 0.25 |
| 74 | | none | 8 | 32 |
| 75 | | formate | 0.5 | 0.5 |

TABLE B-continued

Activity of Compounds in the Examples.

| Example No. | | Salt | Ec 25922 | Ec KPC2 Iso |
|---|---|---|---|---|
| 76 | | none | 1 | 0.5 |
| 77 | | none | 0.25 | 0.125 |
| 78 | | none | ≤0.06 | 0.125 |

TABLE B-continued
Activity of Compounds in the Examples.
| Example No. | | Salt | Ec 25922 | Ec KPC2 Iso |
|---|---|---|---|---|
| 79 | 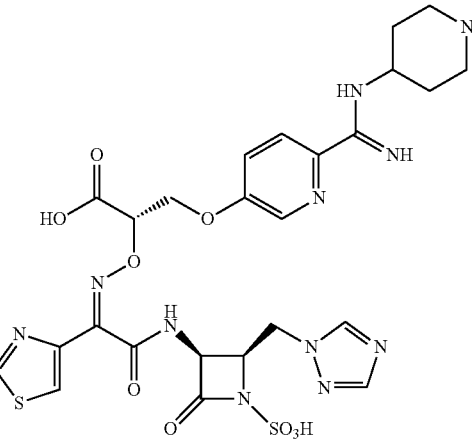 | formate | 0.25 | 0.25 |
| 80 | 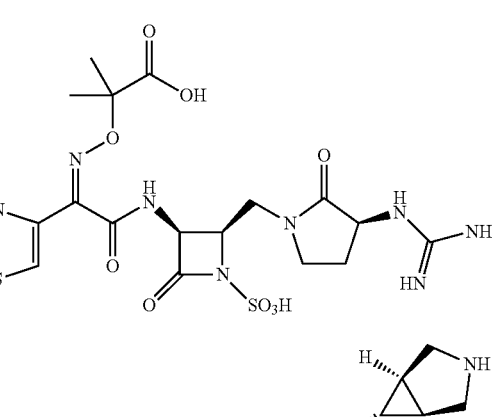 | none | 4 | 4 |
| 81 | 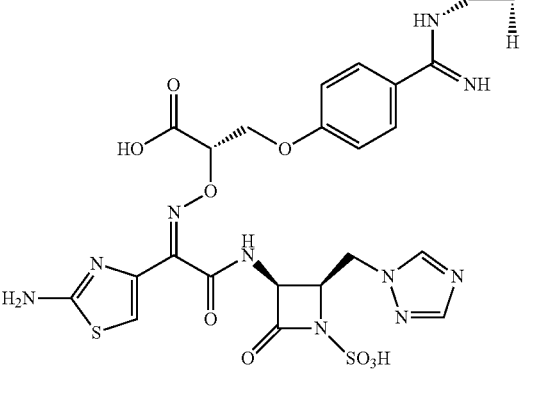 | none | 0.125 | 0.125 |
| 82 | 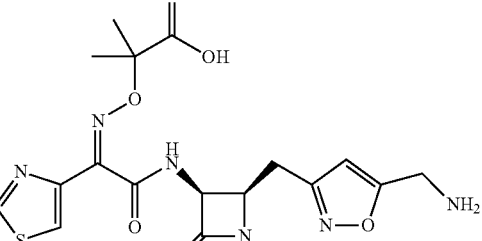 | none | 0.5 | 0.5 |

TABLE B-continued

Activity of Compounds in the Examples.

| Example No. | Structure | Salt | Ec 25922 | Ec KPC2 Iso |
|---|---|---|---|---|
| 83 | | none | 32 | 32 |
| 84 | | none | 0.5 | 0.5 |
| 85 | | none | 0.5 | 0.5 |
| 86 | | none | 1 | 1 |

TABLE B-continued

Activity of Compounds in the Examples.

| Example No. | | Salt | Ec 25922 | Ec KPC2 Iso |
|---|---|---|---|---|
| 87 | (structure) | none | 1 | 0.5 |
| 88 | (structure) | none | 2 | 4 |
| 89 | (structure) | none | 0.5 | 1 |
| 90 | (structure) | none | 0.25 | 0.25 |

TABLE B-continued
Activity of Compounds in the Examples.
| Example No. | | Salt | Ec 25922 | Ec KPC2 Iso |
|---|---|---|---|---|
| 91 | 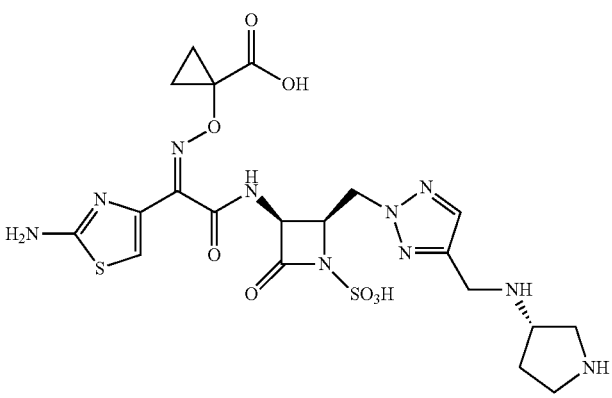 [SMILES: Nc1nc(/C(=N/OC2(C(=O)O)CC2)C(=O)N[C@@H]2C(=O)N(S(=O)(=O)O)[C@@H]2Cn2ncc(CN[C@H]3CCNC3)n2)cs1] | none | 0.125 | 0.25 |
| 92 | 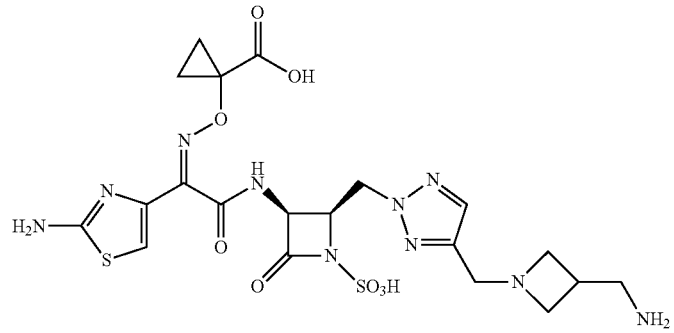 [SMILES: NCC1CN(Cc2cnn(C[C@@H]3[C@H](NC(=O)/C(=N\OC4(C(=O)O)CC4)c4csc(N)n4)C(=O)N3S(=O)(=O)O)n2)C1] | none | 0.25 | 0.5 |
| 93 | 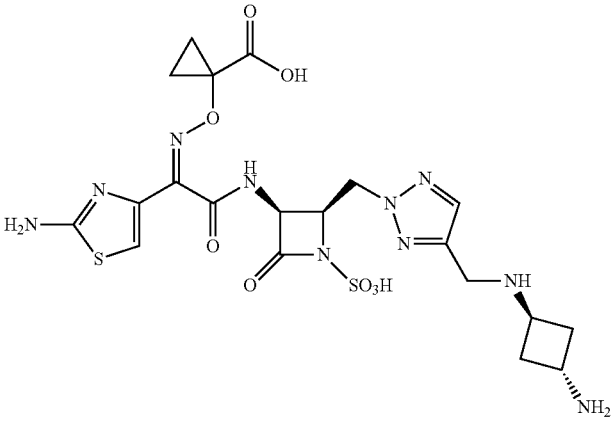 [SMILES: Nc1nc(/C(=N/OC2(C(=O)O)CC2)C(=O)N[C@@H]2C(=O)N(S(=O)(=O)O)[C@@H]2Cn2ncc(CN[C@H]3C[C@H](N)C3)n2)cs1] | none | 0.25 | 0.5 |

TABLE B-continued

Activity of Compounds in the Examples.

| Example No. | Salt | Ec 25922 | Ec KPC2 Iso |
|---|---|---|---|
| 94 | none | 0.5 | 1 |
| 95 | none | 0.25 | 0.125 |
| 96 | formate | 0.25 | 1 |
| 97 | none | 0.125 | 0.125 |

TABLE B-continued

Activity of Compounds in the Examples.

| Example No. | Structure | Salt | Ec 25922 | Ec KPC2 Iso |
|---|---|---|---|---|
| 98 | | none | 2 | 0.5 |
| 99 | | none | 2 | 4 |
| 100 | | none | 1 | 4 |
| 101 | | none | 1 | 1 |

TABLE B-continued

Activity of Compounds in the Examples.

| Example No. | | Salt | Ec 25922 | Ec KPC2 Iso |
|---|---|---|---|---|
| 102 | | none | 0.25 | 0.25 |
| 103 | | none | 0.25 | |
| 104 | | none | >64 | >64 |
| 105 | | none | 16 | 32 |

TABLE B-continued

Activity of Compounds in the Examples.

| Example No. | Salt | Ec 25922 | Ec KPC2 Iso |
|---|---|---|---|
| 106 | none | ≤0.06 | ≤0.06 |
| 107 | formate | 0.25 | 0.25 |
| 108 | formate | 0.125 | ≤0.06 |
| 109 | none | 0.125 | 0.25 |

TABLE B-continued
Activity of Compounds in the Examples.
| Example No. | Structure | Salt | Ec 25922 | Ec KPC2 Iso |
|---|---|---|---|---|
| 110 | 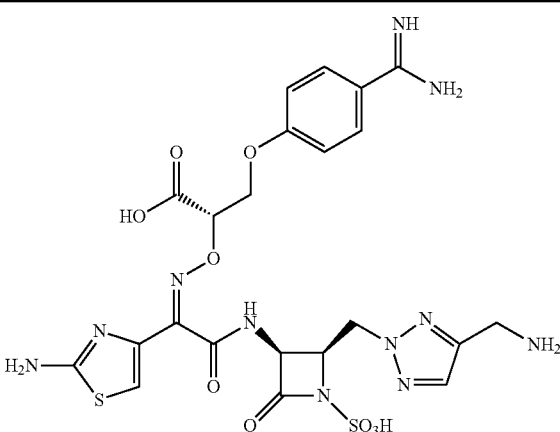 | none | 8 | 8 |
| 111 | 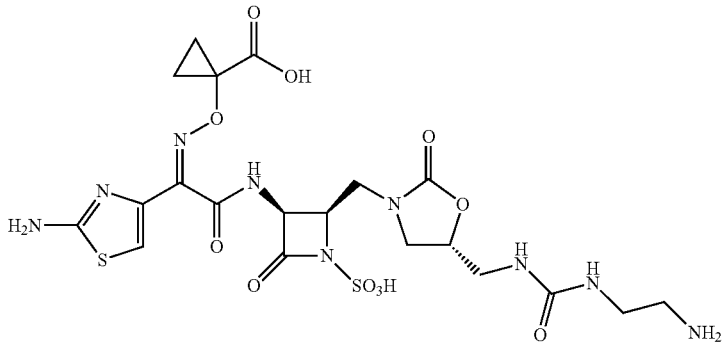 [SMILES: NCCNC(=O)NC[C@@H]1CN(C[C@@H]2[C@H](NC(=O)/C(=N\OC3(C(=O)O)CC3)c3csc(N)n3)C(=O)N2S(=O)(=O)O)C(=O)O1] | formate | ≤0.06 | ≤0.06 |
| 112 | 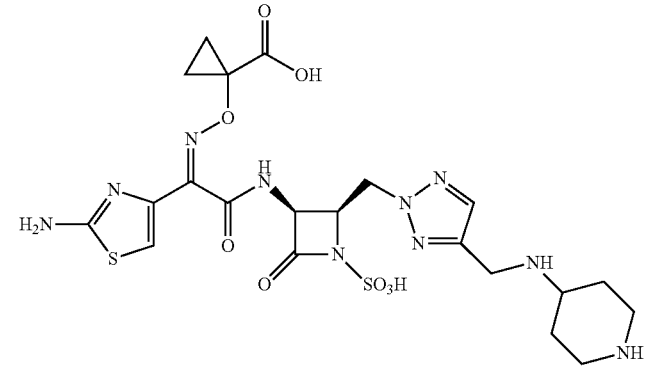 [SMILES: Nc1nc(/C(=N/OC2(C(=O)O)CC2)C(=O)N[C@@H]2C(=O)N(S(=O)(=O)O)[C@@H]2Cn2ncc(CNC3CCNCC3)n2)cs1] | formate | 0.5 | 0.5 |
| 20 | 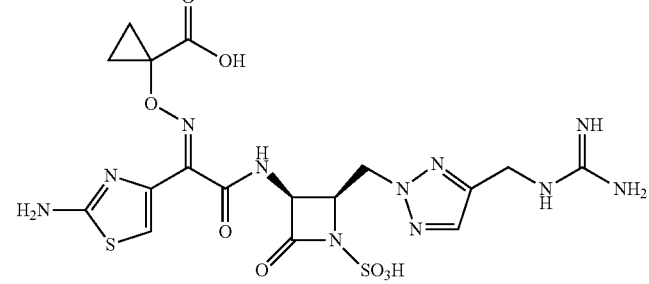 | none | 2 | 4 |

TABLE B-continued
Activity of Compounds in the Examples.
| Example No. | | Salt | Ec 25922 | Ec KPC2 Iso |
|---|---|---|---|---|
| 28 | 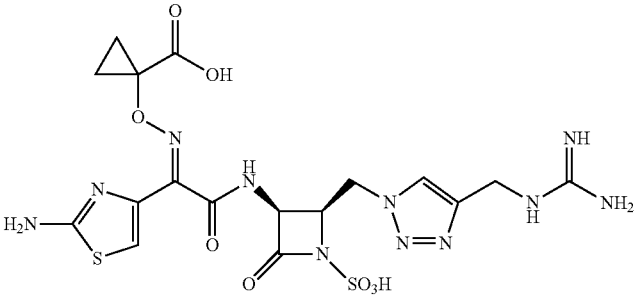 [SMILES: N=C(N)NCc1cn(C[C@@H]2[C@H](NC(=O)/C(=N/OC3(C(=O)O)CC3)c3csc(N)n3)C(=O)N2S(=O)(=O)O)nn1] | none | 4 | 8 |
| 113 | 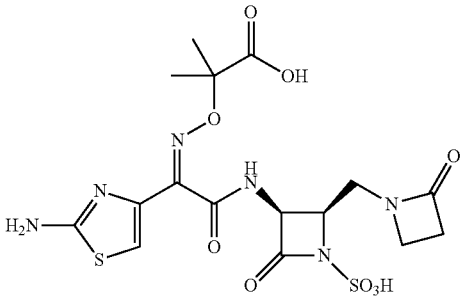 | none | 4 | 4 |
| 114 | 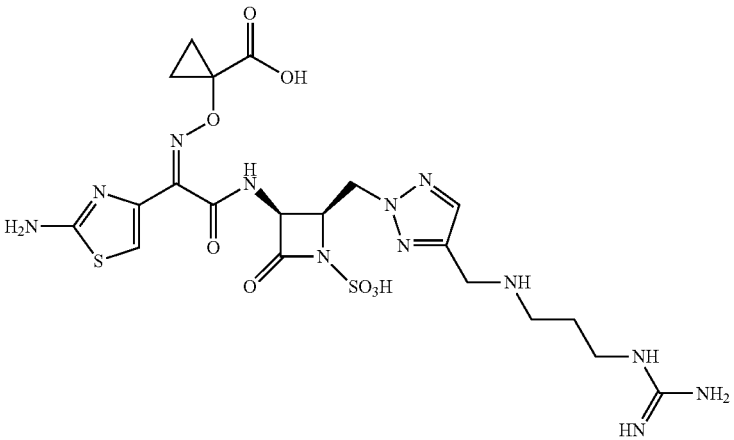 [SMILES: N=C(N)NCCCNCc1cnn(C[C@@H]2[C@H](NC(=O)/C(=N\OC3(C(=O)O)CC3)c3csc(N)n3)C(=O)N2S(=O)(=O)O)n1] | none | 0.25 | ≤0.06 |
| 115 | 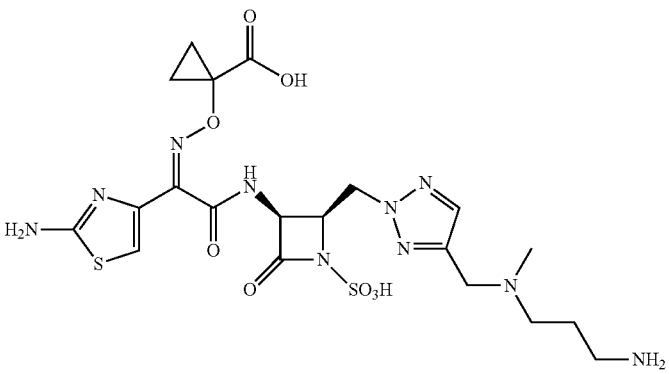 [SMILES: CN(CCCN)Cc1cnn(C[C@@H]2[C@H](NC(=O)/C(=N\OC3(C(=O)O)CC3)c3csc(N)n3)C(=O)N2S(=O)(=O)O)n1] | none | 0.125 | 0.25 |

TABLE B-continued

Activity of Compounds in the Examples.

| Example No. | Structure | Salt | Ec 25922 | Ec KPC2 Iso |
|---|---|---|---|---|
| 116 | | none | 0.25 | 0.125 |
| 117 | | none | 0.5 | 1 |
| 118 | | none | 0.5 | 0.25 |

TABLE B-continued

Activity of Compounds in the Examples.

| Example No. | Structure | Salt | Ec 25922 | Ec KPC2 Iso |
|---|---|---|---|---|
| 119 | | none | 0.25 | 0.25 |
| 120 | | none | 0.25 | 0.5 |
| 121 | | none | 0.25 | 0.25 |
| 122 | | formate | 0.125 | 0.125 |

TABLE B-continued

Activity of Compounds in the Examples.

| Example No. | | Salt | Ec 25922 | Ec KPC2 Iso |
|---|---|---|---|---|
| 122 | | formate | ≤0.06 | ≤0.06 |
| 123 | | none | 1 | 0.5 |
| 124 | | none | 1 | 1 |
| 125 | | none | 0.25 | 0.5 |

TABLE B-continued

Activity of Compounds in the Examples.

| Example No. | | Salt | Ec 25922 | Ec KPC2 Iso |
|---|---|---|---|---|
| 126 | (structure) | none | 0.5 | 0.5 |
| 127 | (structure) | none | 0.25 | 0.25 |
| 128 | (structure) | None | 0.5 | 1 |
| 129 | (structure) | None | 0.5 | 1 |

TABLE B-continued

Activity of Compounds in the Examples.

| Example No. | | Salt | Ec 25922 | Ec KPC2 Iso |
|---|---|---|---|---|
| 130 | [structure] | none | 1 | 2 |
| 131 | [structure] | none | 1 | 2 |
| 132 | [structure] | none | 1 | 1 |
| 133 | [structure] | none | 1 | 0.5 |

TABLE B-continued

Activity of Compounds in the Examples.

| Example No. | | Salt | Ec 25922 | Ec KPC2 Iso |
|---|---|---|---|---|
| 134 | | none | 0.5 | 0.25 |
| 135 | | none | 0.5 | 0.5 |
| 136 | | none | 0.5 | 0.5 |
| 137 | | none | 1 | 0.5 |

TABLE B-continued
Activity of Compounds in the Examples.
| Example No. | | Salt | Ec 25922 | Ec KPC2 Iso |
|---|---|---|---|---|
| 138 | 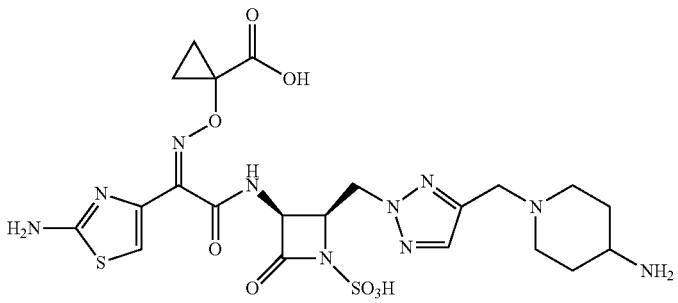 [SMILES: Nc1nc(/C(=N/OC2(C(=O)O)CC2)C(=O)N[C@@H]2C(=O)N(S(=O)(=O)O)[C@@H]2Cn2ncc(CN3CCC(N)CC3)n2)cs1] | none | 0.5 | 1 |
| 139 | 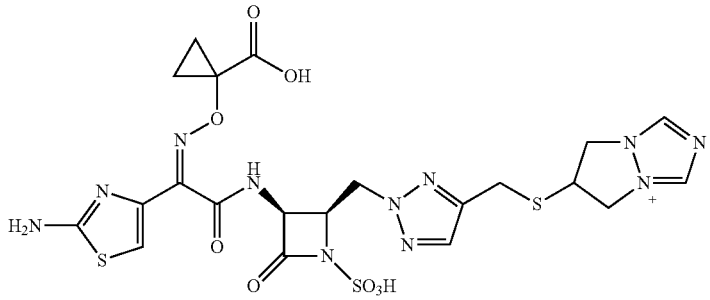 | none | 1 | 4 |
| 140 | 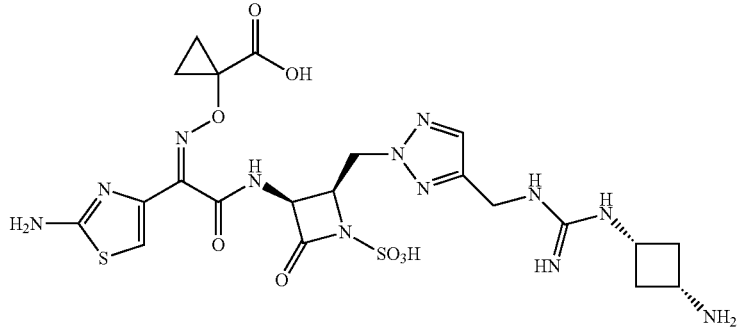 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N[C@H]1C[C@@H](N)C1] | none | 0.25 | 0.25 |
| 141 | 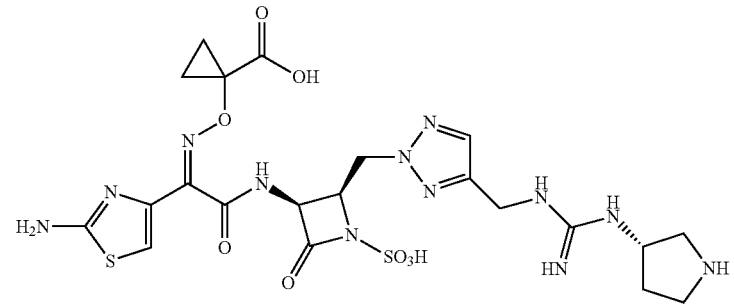 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N[C@H]1CCNC1] | none | 0.5 | 0.5 |

TABLE B-continued
Activity of Compounds in the Examples.
| Example No. | | Salt | Ec 25922 | Ec KPC2 Iso |
|---|---|---|---|---|
| 142 | 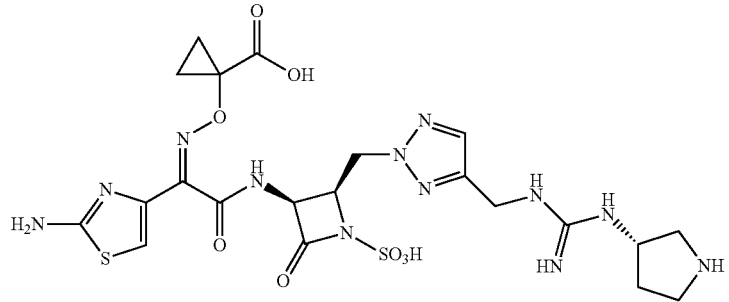 [SMILES: N=C(NCc1cnn(C[C@@H]2[C@H](NC(=O)/C(=N\OC3(C(=O)O)CC3)c3csc(N)n3)C(=O)N2S(=O)(=O)O)n1)N[C@H]1CCNC1] | none | 0.5 | 0.25 |
| 143 | 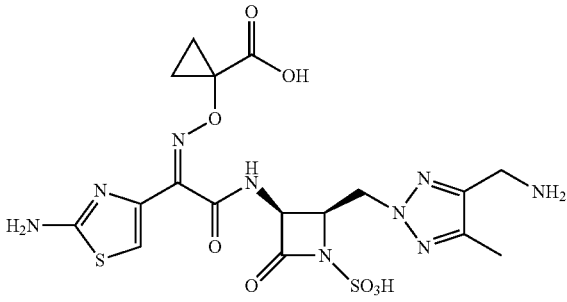 [SMILES: Cc1nn(C[C@@H]2[C@H](NC(=O)/C(=N\OC3(C(=O)O)CC3)c3csc(N)n3)C(=O)N2S(=O)(=O)O)nc1CN] | none | 0.5 | 0.25 |
| 144 | 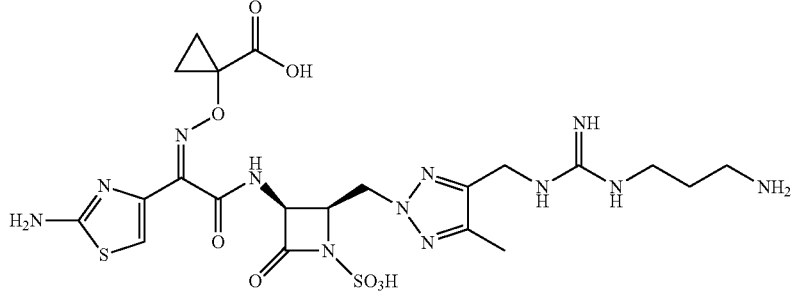 [SMILES: Cc1nn(C[C@@H]2[C@H](NC(=O)/C(=N\OC3(C(=O)O)CC3)c3csc(N)n3)C(=O)N2S(=O)(=O)O)nc1CNC(=N)NCCCN] | none | 1 | 1 |
| 145 | 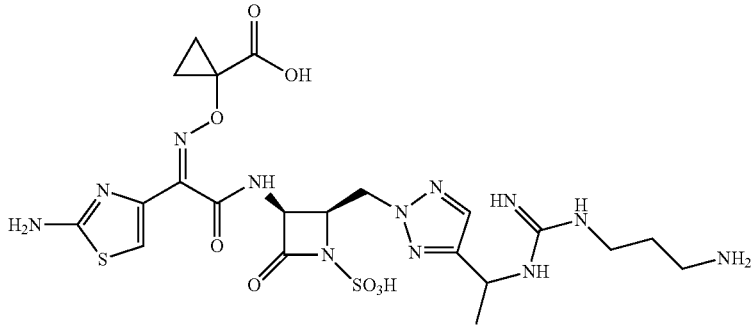 [SMILES: CC(NC(=N)NCCCN)c1cnn(C[C@@H]2[C@H](NC(=O)/C(=N\OC3(C(=O)O)CC3)c3csc(N)n3)C(=O)N2S(=O)(=O)O)n1] | none | 0.5 | 0.5 |

TABLE B-continued

Activity of Compounds in the Examples.

| Example No. | Salt | Ec 25922 | Ec KPC2 Iso |
|---|---|---|---|
| 146 | none | 0.5 | 0.5 |
| 147 | none | 0.5 | 0.5 |
| 148 | none | 1 | 1 |
| 149 | none | 0.5 | 0.5 |

TABLE B-continued
Activity of Compounds in the Examples.
| Example No. | | Salt | Ec 25922 | Ec KPC2 Iso |
|---|---|---|---|---|
| 150 | 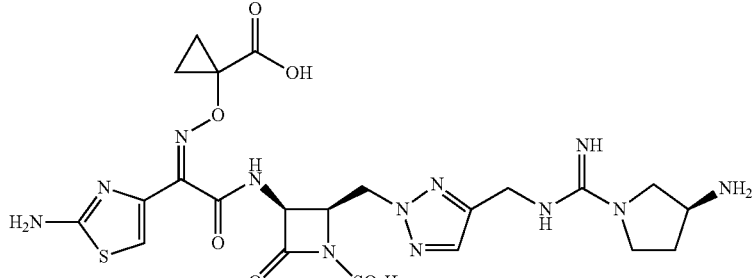 | none | 1 | 0.5 |
| 151 | 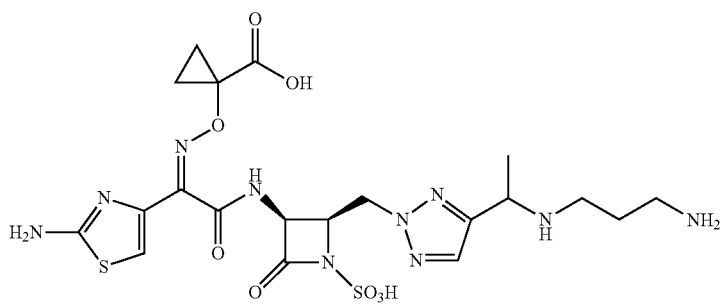 | none | 0.5 | 0.5 |
| 152 | 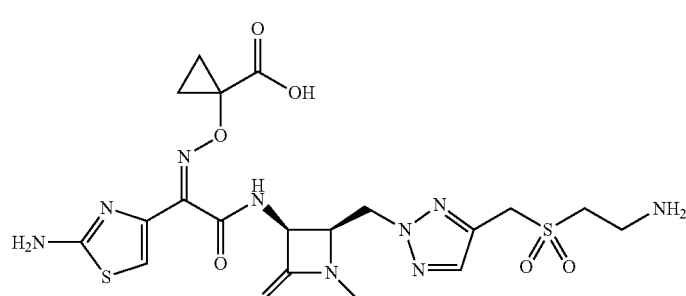 | none | 0.5 | 0.5 |
| 153 | 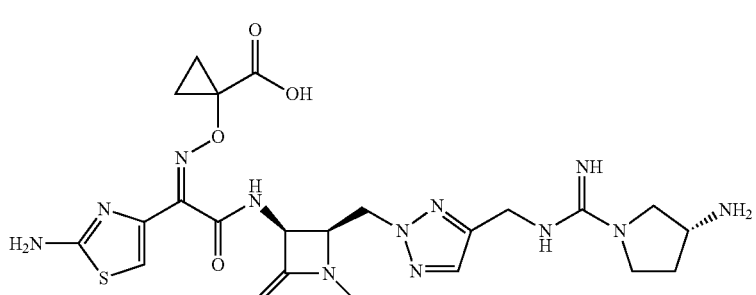 | None | | |

TABLE B-continued
Activity of Compounds in the Examples.
| Example No. | | Salt | Ec 25922 | Ec KPC2 Iso |
|---|---|---|---|---|
| 154 | | None | | |
| 155 | | None | | |
| 156 | | none | | |
By the same methods described herein, additional compounds can readily be prepared from known starting materials with use of ordinary skill. Examples of these compounds that are expected to have similar biological activity include:
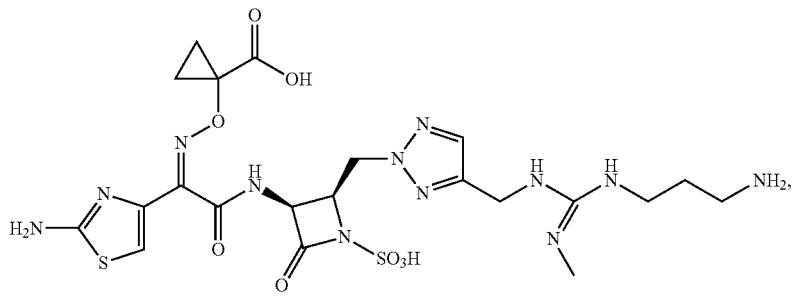

333
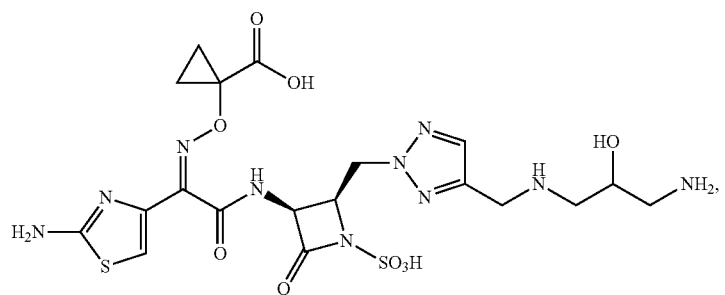
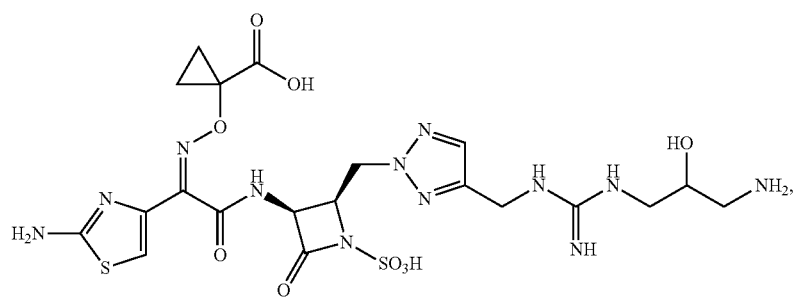 [SMILES: CN(Cc1cnn(C[C@@H]2[C@H](NC(=O)/C(=N\OC3(C(=O)O)CC3)c3csc(N)n3)C(=O)N2S(=O)(=O)O)n1)C(=N)NCCCN]
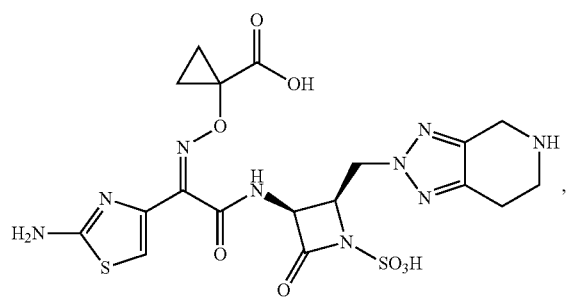
334
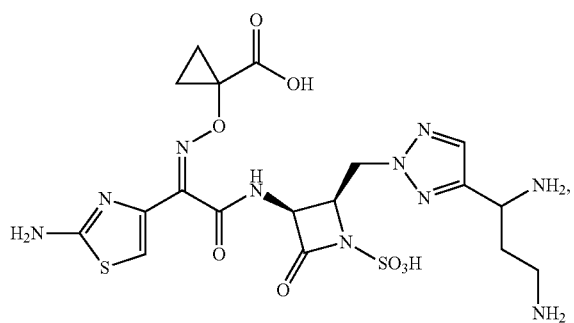
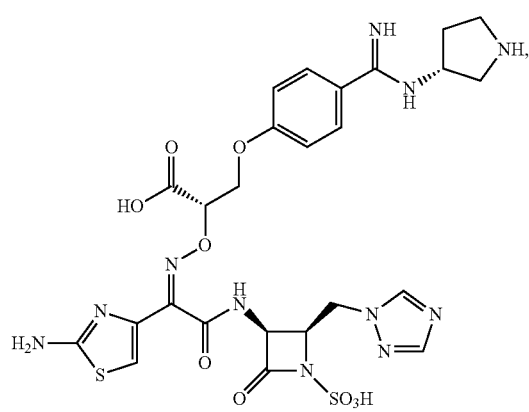
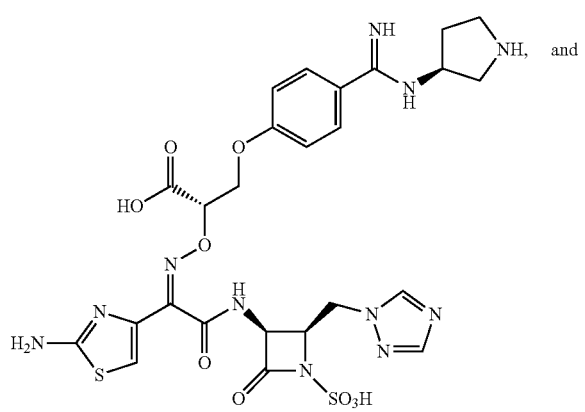
and -continued

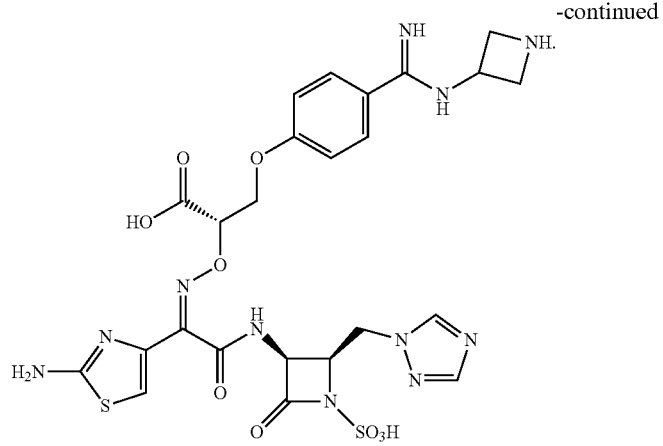

Those skilled in the art will recognize, or be able to ascertain using no more than routine experimentation, many equivalents to the specific embodiments and methods described herein. Such equivalents are intended to be encompassed by the scope of the following claims.

The invention claimed is:
1. A compound of Formula (IA):
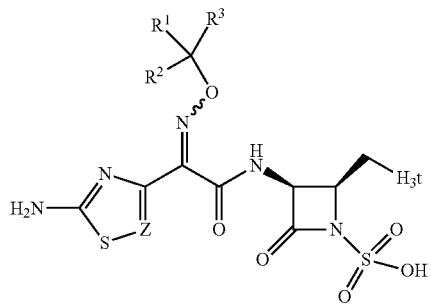
(IA)
or a pharmaceutically acceptable salt thereof, wherein:
Z is CH;
the group —O—CR¹R²R³ is selected from
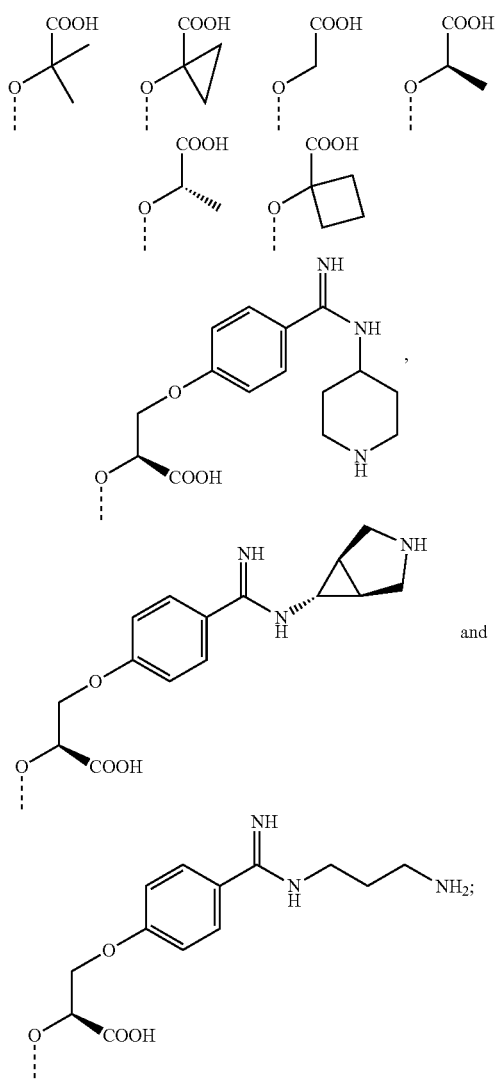
and
Het is selected from
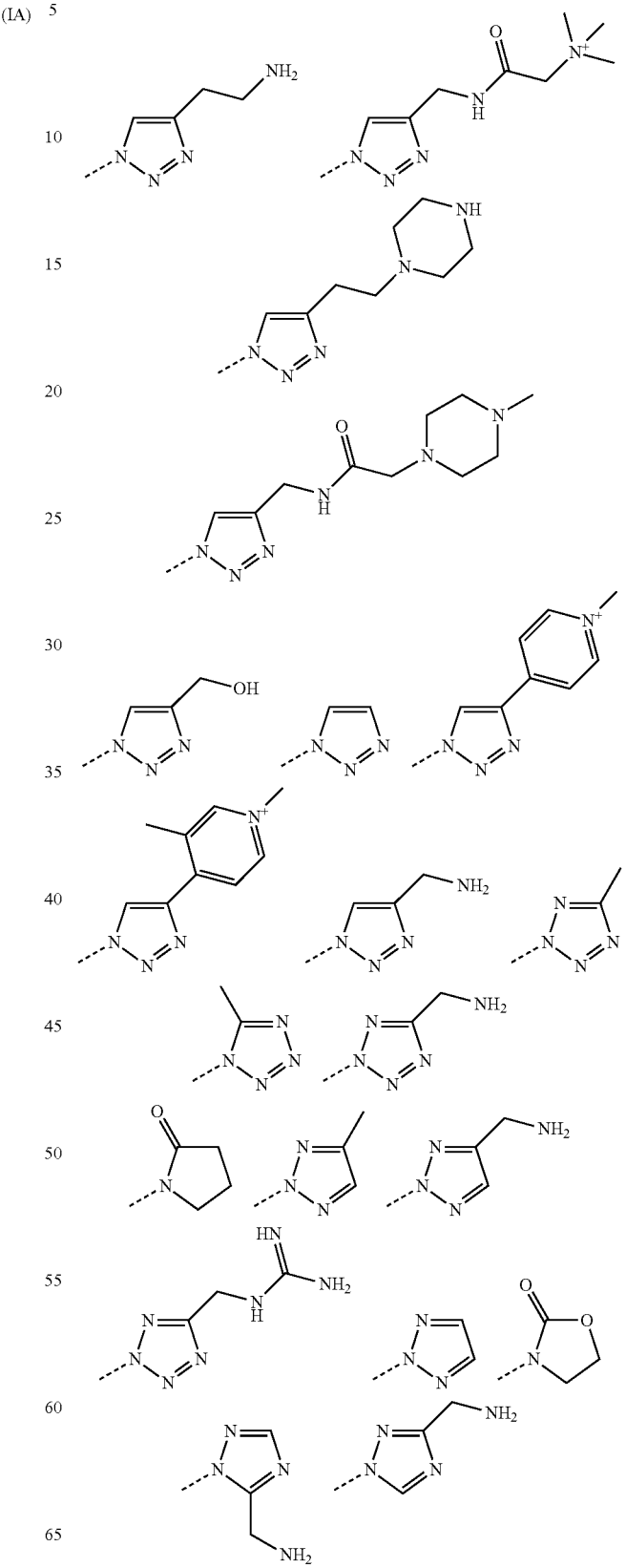

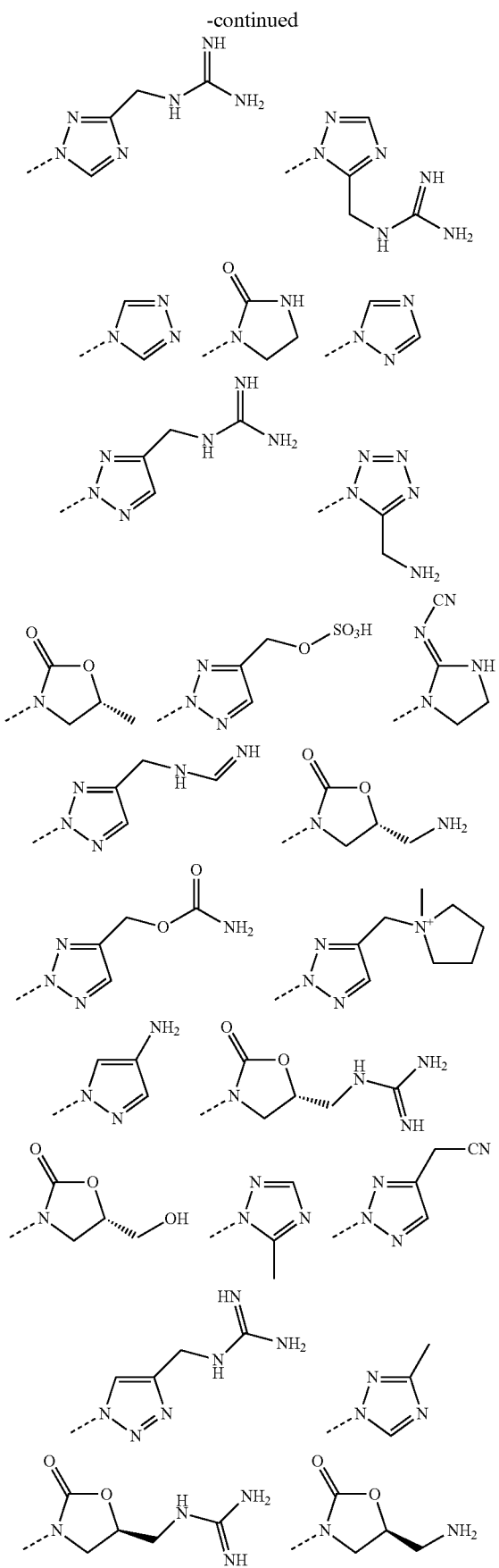
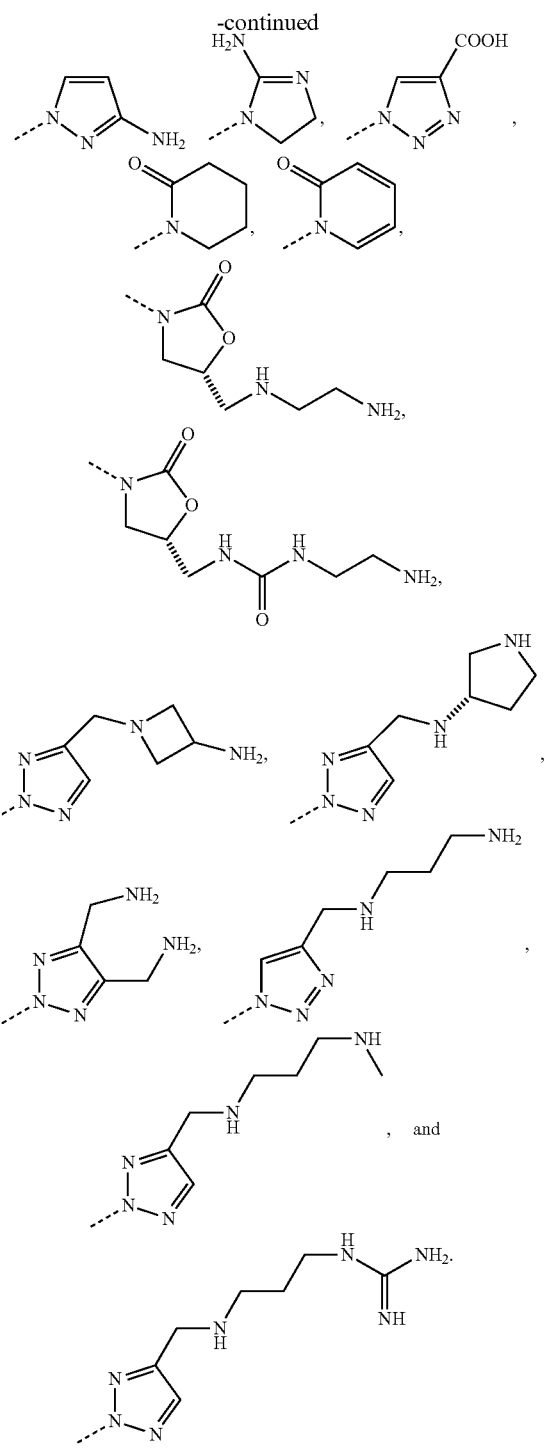
2. The compound of claim 1, wherein the group —OCR'R²R³ is selected from:
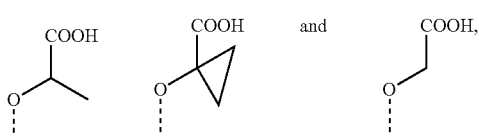
or a pharmaceutically acceptable salt thereof.

3. The compound of claim 1, wherein the group —O—CR'R²R³ is
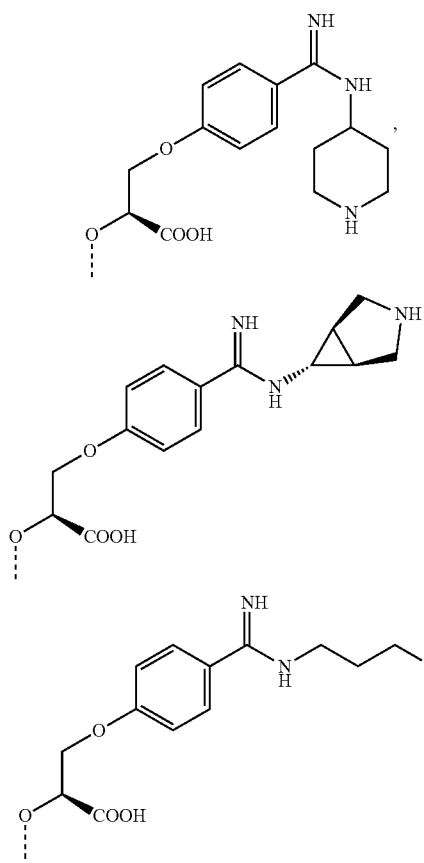
or a pharmaceutically acceptable salt thereof.
4. The compound of claim 1, wherein Het is selected from:
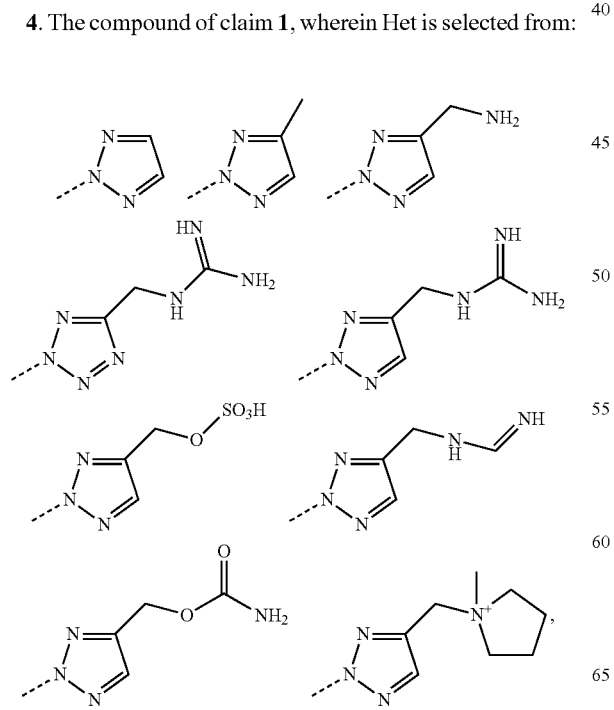
-continued
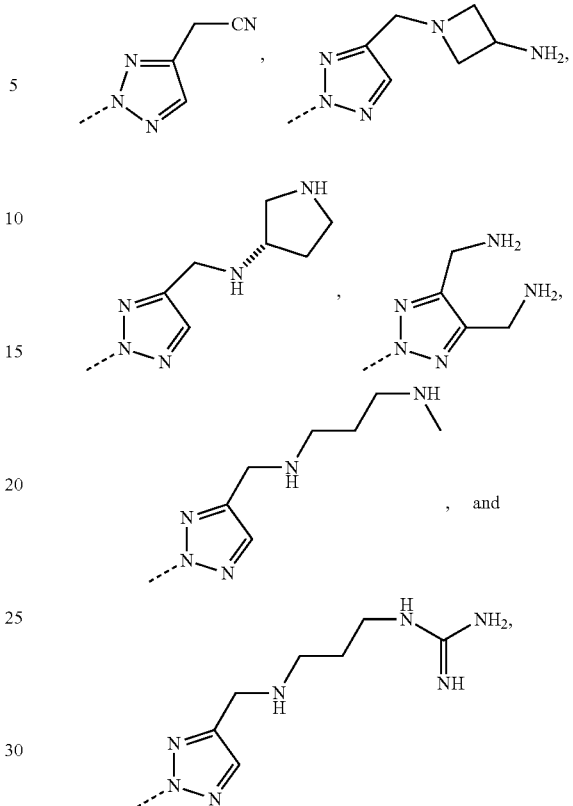
or a pharmaceutically acceptable salt thereof.
5. The compound of claim 1, wherein Het is selected from:
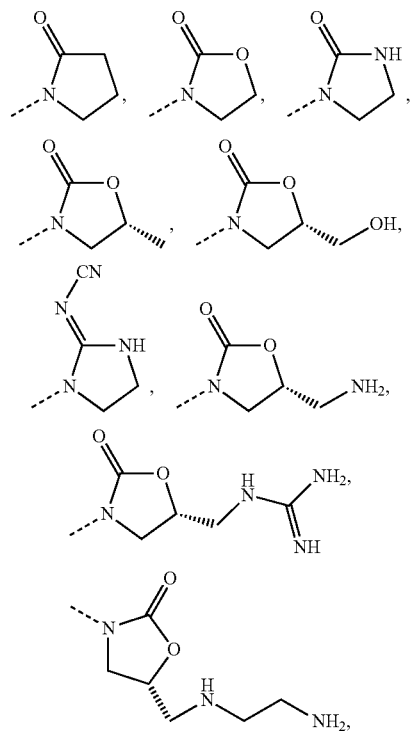

-continued

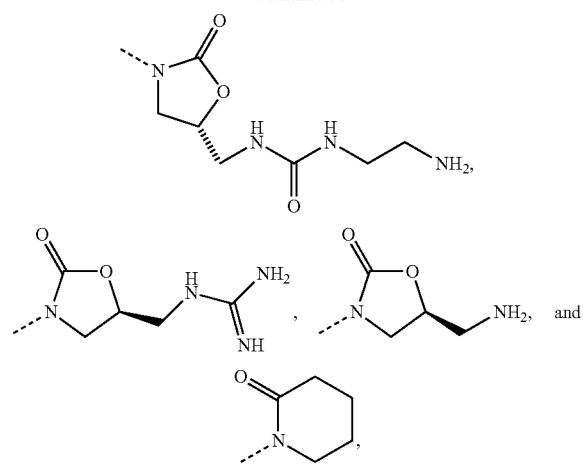

or a pharmaceutically acceptable salt thereof.

6. The compound of claim 1, wherein Het is selected from:

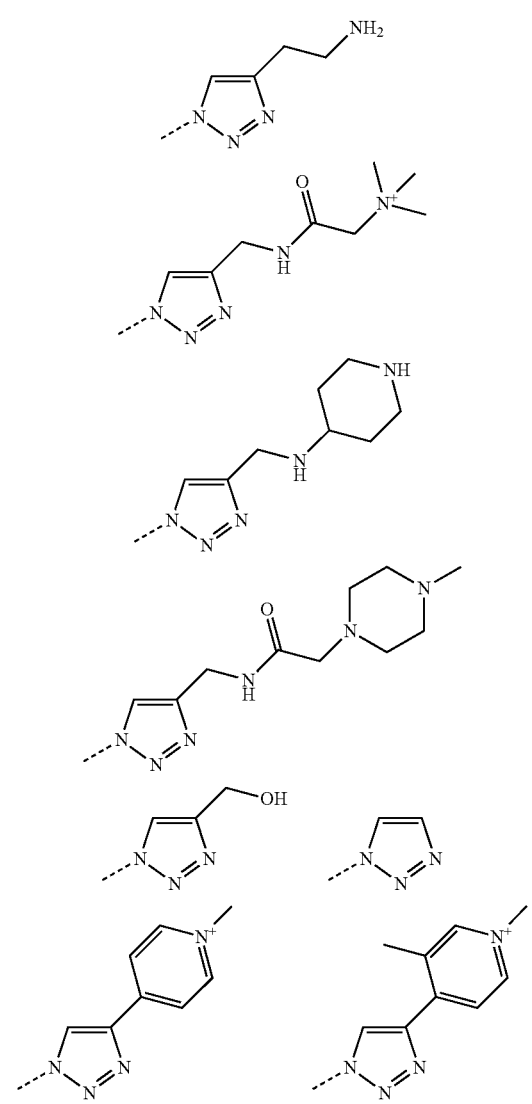

-continued

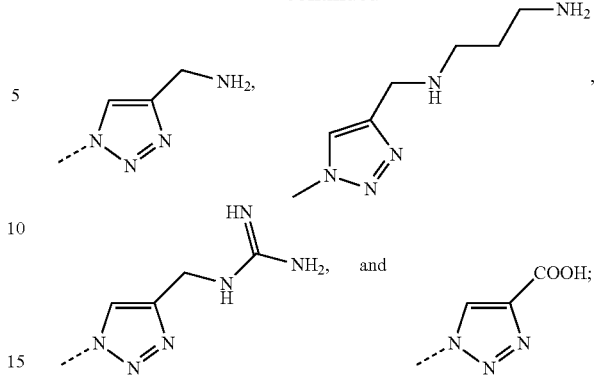

or a pharmaceutically acceptable salt thereof.

7. The compound of claim 1, wherein Het is selected from:

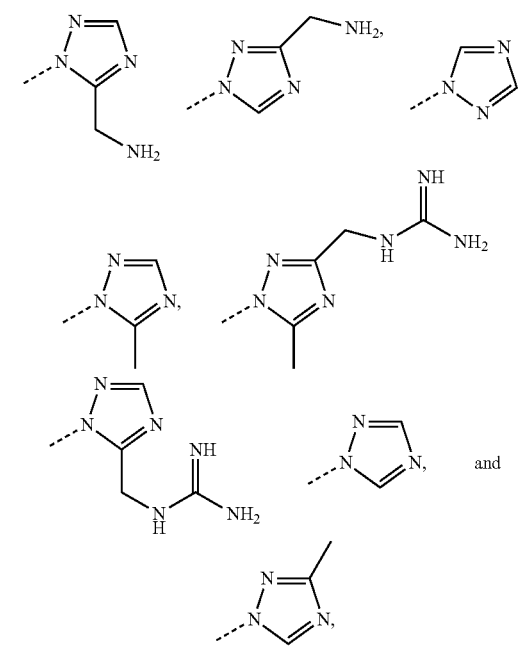

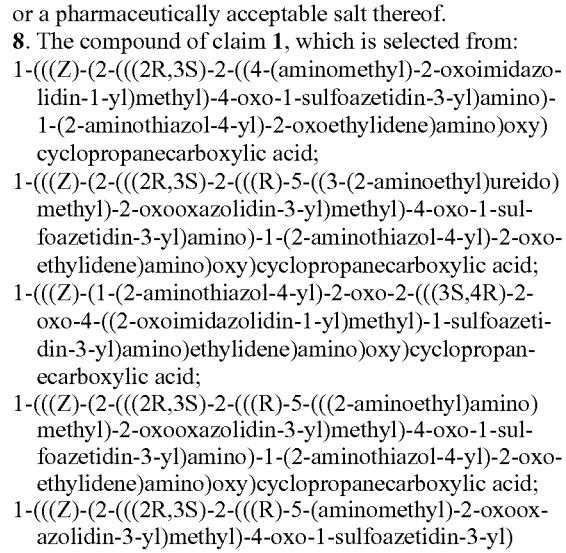

or a pharmaceutically acceptable salt thereof.

8. The compound of claim 1, which is selected from:
1-(((Z)-(2-(((2R,3S)-2-((4-(aminomethyl)-2-oxoimidazo-lidin-1-yl)methyl)-4-oxo-1-sulfoazetidin-3-yl)amino)-1-(2-aminothiazol-4-yl)-2-oxoethylidene)amino)oxy) cyclopropanecarboxylic acid;
1-(((Z)-(2-(((2R,3S)-2-(((R)-5-((3-(2-aminoethyl)ureido) methyl)-2-oxooxazolidin-3-yl)methyl)-4-oxo-1-sul-foazetidin-3-yl)amino)-1-(2-aminothiazol-4-yl)-2-oxo-ethylidene)amino)oxy)cyclopropanecarboxylic acid;
1-(((Z)-(1-(2-aminothiazol-4-yl)-2-oxo-2-(((3S,4R)-2-oxo-4-((2-oxoimidazolidin-1-yl)methyl)-1-sulfoazeti-din-3-yl)amino)ethylidene)amino)oxy)cyclopropan-ecarboxylic acid;
1-(((Z)-(2-(((2R,3S)-2-(((R)-5-(((2-aminoethyl)amino) methyl)-2-oxooxazolidin-3-yl)methyl)-4-oxo-1-sul-foazetidin-3-yl)amino)-1-(2-aminothiazol-4-yl)-2-oxo-ethylidene)amino)oxy)cyclopropanecarboxylic acid;
1-(((Z)-(2-(((2R,3S)-2-(((R)-5-(aminomethyl)-2-oxoox-azolidin-3-yl)methyl)-4-oxo-1-sulfoazetidin-3-yl)

amino)-1-(2-aminothiazol-4-yl)-2-oxoethylidene) amino)oxy)-cyclopropanecarboxylic acid;

1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid; and 1-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene) amino)oxy)-cyclopropanecarboxylic acid, or a pharmaceutically acceptable salt thereof.

9. The compound of claim 1, which is selected from:

1-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene) amino)oxy)-cyclopropanecarboxylic acid;

1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid;

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(2-aminoethyl)carbamimidoyl)phenoxy)propanoic acid;

1-(((Z)-(1-(2-aminothiazol-4-yl)-2-(((2R,3S)-2-((4-(((3-guanidinopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid;

1-(((Z)-(1-(2-aminothiazol-4-yl)-2-(((2R,3S)-2-((4,5-bis (aminomethyl)-2H-1,2,3-triazol-2-yl)methyl)-4-oxo-1-sulfoazetidin-3-yl)amino)-2-oxoethylidene)amino) oxy)cyclopropanecarboxylic acid;

1-(((Z)-(2-(((2R,3S)-2-((4-((3-aminoazetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid;

1-(((Z)-(1-(2-aminothiazol-4-yl)-2-oxo-2-(((3S,4R)-2-oxo-4-((4-(((S)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid;

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1R,5S,6s)-3-azabicyclo[3.1.0]hexan-6-yl) carbamimidoyl)phenoxy)propanoic acid; and (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(3-aminopropyl)carbamimidoyl)phenoxy)propanoic acid;

or a pharmaceutically acceptable salt thereof.

10. The compound of claim 1, which is selected from:

1-(((Z)-(2-(((2R,3S)-2-((4-(aminomethyl)-2-oxoimidazolidin-1-yl)methyl)-4-oxo-1-sulfoazetidin-3-yl)amino)-1-(2-aminothiazol-4-yl)-2-oxoethylidene)amino)oxy) cyclopropanecarboxylic acid;

1-(((Z)-(2-(((2R,3S)-2-(((R)-5-((3-(2-aminoethyl)ureido) methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid; and 1-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)cyclopropanecarboxylic acid;

or a pharmaceutically acceptable salt thereof.

11. The compound of claim 1, which is selected from:

1-(((Z)-(2-(((2R,3S)-2-(((R)-5-(((2-aminoethyl)amino) methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid;

1-(((Z)-(2-(((2R,3S)-2-(((R)-5-(aminomethyl)-2-oxooxazolidin-3-yl)methyl)-4-oxo-1-sulfoazetidin-3-yl) amino)-1-(2-aminothiazol-4-yl)-2-oxoethylidene) amino)oxy)-cyclopropanecarboxylic acid;

1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid; and 1-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene) amino)oxy)-cyclopropanecarboxylic acid, or a pharmaceutically acceptable salt thereof.

12. The compound of claim 1, which is selected from:

1-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene) amino)oxy)-cyclopropanecarboxylic acid;

1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid;

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(2-aminoethyl)carbamimidoyl)phenoxy)propanoic acid;

or a pharmaceutically acceptable salt thereof.

13. The compound of claim 1, which is selected from:

1-(((Z)-(1-(2-aminothiazol-4-yl)-2-(((2R,3S)-2-((4-(((3-guanidinopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid;

1-(((Z)-(1-(2-aminothiazol-4-yl)-2-(((2R,3S)-2-((4,5-bis (aminomethyl)-2H-1,2,3-triazol-2-yl)methyl)-4-oxo-1-sulfoazetidin-3-yl)amino)-2-oxoethylidene)amino) oxy)cyclopropanecarboxylic acid;

1-(((Z)-(2-(((2R,3S)-2-((4-((3-aminoazetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid;

or a pharmaceutically acceptable salt thereof.

14. The compound of claim 1, which is selected from:

1-(((Z)-(1-(2-aminothiazol-4-yl)-2-oxo-2-(((3S,4R)-2-oxo-4-((4-(((S)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid;

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1R,5S,6s)-3-azabicyclo[3.1.0]hexan-6-yl) carbamimidoyl)phenoxy)propanoic acid; and (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(3-aminopropyl)carbamimidoyl)phenoxy)propanoic acid;

or a pharmaceutically acceptable salt thereof.

15. A pharmaceutical composition comprising a compound of claim 1 and at least one pharmaceutically acceptable excipient.

16. The pharmaceutical composition of claim 15, wherein the compound is selected from:
- 1-(((Z)-(2-(((2R,3S)-2-((4-(aminomethyl)-2-oxoimidazolidin-1-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(2-(((2R,3S)-2-(((R)-5-((3-(2-aminoethyl)ureido)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)cyclopropanecarboxylic acid;
- 1-(((Z)-(2-(((2R,3S)-2-(((R)-5-(((2-aminoethyl)amino)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-cyclopropanecarboxylic acid;
- 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid; and
- 1-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene)amino)oxy)-cyclopropanecarboxylic acid,
- or a pharmaceutically acceptable salt thereof.

17. The pharmaceutical composition of claim 15, wherein the compound is selected from:
- 1-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene)amino)oxy)-cyclopropanecarboxylic acid;
- 1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid;
- (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(2-aminoethyl)carbamimidoyl)phenoxy)propanoic acid;
- 1-(((Z)-(1-(2-aminothiazol-4-yl)-2-(((2R,3S)-2-((4-(((3-guanidinopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid;
- 1-(((Z)-(1-(2-aminothiazol-4-yl)-2-(((2R,3S)-2-((4,5-bis(aminomethyl)-2H-1,2,3-triazol-2-yl)methyl)-4-oxo-1-sulfoazetidin-3-yl)amino)-2-oxoethylidene)amino)oxy)cyclopropanecarboxylic acid;
- 1-(((Z)-(2-(((2R,3S)-2-((4-((3-aminoazetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(1-(2-aminothiazol-4-yl)-2-oxo-2-(((3S,4R)-2-oxo-4-((4-(((S)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid;
- (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1R,5S,6s)-3-azabicyclo[3.1.0]hexan-6-yl)carbamimidoyl)phenoxy)propanoic acid; and
- (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(3-aminopropyl)carbamimidoyl)phenoxy)propanoic acid;
- or a pharmaceutically acceptable salt thereof.

18. A pharmaceutical combination, comprising a compound of claim 1 and a second therapeutic agent.

19. The pharmaceutical combination of claim 18, wherein the second therapeutic agent is a beta-lactamase inhibitor.

20. The pharmaceutical combination of claim 18, wherein the compound is selected from:
- 1-(((Z)-(2-(((2R,3S)-2-((4-(aminomethyl)-2-oxoimidazolidin-1-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(2-(((2R,3S)-2-(((R)-5-((3-(2-aminoethyl)ureido)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(1-(2-aminothiazol-4-yl)-2-oxo-2-(((3S,4R)-2-oxo-4-((2-oxoimidazolidin-1-yl)methyl)-1-sulfoazetidin-3-yl)amino)ethylidene)amino)oxy)cyclopropanecarboxylic acid;
- 1-(((Z)-(2-(((2R,3S)-2-(((R)-5-(((2-aminoethyl)amino)methyl)-2-oxooxazolidin-3-yl)methyl)-4-oxo-1-sulfoazetidin-3-yl)amino)-1-(2-aminothiazol-4-yl)-2-oxoethylidene)amino)oxy)cyclopropanecarboxylic acid;
- 1-(((Z)-(2-(((2R,3S)-2-(((R)-5-(aminomethyl)-2-oxooxazolidin-3-yl)methyl)-4-oxo-1-sulfoazetidin-3-yl)amino)-1-(2-aminothiazol-4-yl)-2-oxoethylidene)amino)oxy)-cyclopropanecarboxylic acid;
- 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid; and
- 1-(((Z)-(1-(2-aminothiazol-4-yl)-2-(((2R,3S)-2-(((R)-5-(guanidinomethyl)-2-oxooxazolidin-3-yl)methyl)-4-oxo-1-sulfoazetidin-3-yl)amino)-2-oxoethylidene)amino)oxy)-cyclopropanecarboxylic acid,
- or a pharmaceutically acceptable salt thereof.

21. The pharmaceutical combination of claim 18, wherein the compound is selected from:
- 1-(((Z)-(1-(2-aminothiazol-4-yl)-2-(((2R,3S)-2-((4-(guanidinomethyl)-2H-1,2,3-triazol-2-yl)methyl)-4-oxo-1-sulfoazetidin-3-yl)amino)-2-oxoethylidene)amino)oxy)-cyclopropanecarboxylic acid;
- 1-(((Z)-(2-(((2R,3S)-2-((4-(aminomethyl)-1H-1,2,3-triazol-1-yl)methyl)-4-oxo-1-sulfoazetidin-3-yl)amino)-1-(2-aminothiazol-4-yl)-2-oxoethylidene)amino)oxy)cyclopropanecarboxylic acid;
- (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(2-aminoethyl)carbamimidoyl)phenoxy)propanoic acid;
- 1-(((Z)-(1-(2-aminothiazol-4-yl)-2-(((2R,3S)-2-((4-(((3-guanidinopropyl)amino)methyl)-2H-1,2,3-triazol-2-yl)methyl)-4-oxo-1-sulfoazetidin-3-yl)amino)-2-oxoethylidene)amino)oxy)cyclopropanecarboxylic acid;
- 1-(((Z)-(1-(2-aminothiazol-4-yl)-2-(((2R,3S)-2-((4,5-bis(aminomethyl)-2H-1,2,3-triazol-2-yl)methyl)-4-oxo-1-sulfoazetidin-3-yl)amino)-2-oxoethylidene)amino)oxy)cyclopropanecarboxylic acid;
- 1-(((Z)-(2-(((2R,3S)-2-((4-((3-aminoazetidin-1-yl)methyl)-2H-1,2,3-triazol-2-yl)methyl)-4-oxo-1-sulfoazetidin-3-yl)amino)-1-(2-aminothiazol-4-yl)-2-oxoethylidene)amino)oxy)cyclopropanecarboxylic acid;

1-(((Z)-(1-(2-aminothiazol-4-yl)-2-oxo-2-(((3S,4R)-2-oxo-4-((4-(((S)-pyrrolidin-3-ylamino)methyl)-2H-1,2,3-triazol-2-yl)methyl)-1-sulfoazetidin-3-yl)amino)ethylidene)amino)oxy)cyclopropanecarboxylic acid;

(S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-((1R,5S,6s)-3-azabicyclo[3.1.0]hexan-6-yl)carbamimidoyl)phenoxy)propanoic acid; and (S)-2-(((Z)-(2-(((2R,3S)-2-((1H-1,2,4-triazol-1-yl)methyl)-4-oxo-1-sulfoazetidin-3-yl)amino)-1-(2-aminothiazol-4-yl)-2-oxoethylidene)amino)oxy)-3-(4-(N-(3-aminopropyl)carbamimidoyl)phenoxy)propanoic acid;

or a pharmaceutically acceptable salt thereof.

22. The compound of claim 1, which is 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid, or a pharmaceutically acceptable salt thereof.

23. The pharmaceutical composition of claim 16, wherein the compound is 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid, or a pharmaceutically acceptable salt thereof.

24. The pharmaceutical combination of claim 20, wherein the compound is 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid, or a pharmaceutically acceptable salt thereof.

* * * * *

SEQUENCE LISTING

<160> NUMBER OF SEQ ID NOS: 17

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 1
tcgcctcgag gcgactgcgc tgacgaattt gg                     32

<210> SEQ ID NO 2
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 2
aatcgaattc ttactgacca ttaacgccca agc                    33

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
tcgcctcgag gcgagcccgc aaccgctgga                        30

<210> SEQ ID NO 4
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 4
aatcgaattc ttaacgctgc cagtgctcaa tc        32

<210> SEQ ID NO 5
<211> LENGTH: 866
<212> TYPE: DNA
<213> ORGANISM: Artificial Sequence
<220> FEATURE:
<223> OTHER INFORMATION: Synthetic Polynucleotide

<400> SEQUENCE: 5
atgggccatc atcatcatca tcacagcagc ggcctggaag ttctgttcca ggggcccgcg        60
agcccgcaac cgctggagca gatcaagcag tctgagagcc agctgagcgg ccgtgtgggt       120
atgatcgaga tggatctggc ttccggccgt acgctgacgg catggcgtgc cgacgaacgt       180
ttcccgatga tgtcgacctt taaagttgtt ctgtgtggtg cggtcttggc acgtgtagac       240
gcgggtgacg aacaactgga gcgcaagatc cattaccgcc aacaggactt ggtcgactac       300
agcccggtta gcgaaaagca cctggcggat ggcatgaccg tgggtgaatt gtgcgccgct       360
gcgattacca tgagcgacaa tagcgcggct aatctgctgt tggcgaccgt tggtggccca       420
gcgggcttga ccgcatttct gcgtcaaatc ggcgataatg ttacgcgtct ggatcgctgg       480
gaaacggagc tgaacgaggc actgccgggt gatgcccgtg ataccacgac tcctgctagc       540
atggcagcga ccctgcgtaa actgctgacc agccagcgtc tgagcgcacg tagccaacgc       600
cagctgctgc aatggatggt ggatgaccgc gtggcgggtc cgctgatccg ctccgtcctg       660
ccagcaggct ggttcattgc ggacaaaact ggtgcctcta gcgtggtgc gcgtggtatc       720 gtcgcgctgc tgggtccgaa caacaaagcc gaacgtattg tggttatcta tctgcgcgac       780
accccggcaa gcatggccga gcgcaaccag caaattgcgg gcattggtgc ggcactgatt       840
gagcactggc agcgttaacg ccggcg        866

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 6
tcgcctcgag gcgagcccgc aaccgctgga        30

<210> SEQ ID NO 7
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 7
aatcgaattc ttaacgctgc cagtgctcaa tc        32

<210> SEQ ID NO 8
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 8
gattgagcac tggcagcgtt aagaattcga tt                                    32

<210> SEQ ID NO 9
<211> LENGTH: 884
<212> TYPE: DNA
<213> ORGANISM: Artificial Sequence
<220> FEATURE:
<223> OTHER INFORMATION: Synthetic Polynucleotide

<400> SEQUENCE: 9
atgggccatc atcatcatca tcacagcagc ggcctggaag ttctgttcca ggggcccgcg     60
actgcgctga cgaatttggt ggccgagccg ttcgcgaaat tggagcaaga ttttggtggt    120
tcgatcggtg tctacgcgat ggacaccggt agcggtgcca ccgtgagcta ccgtgccgaa    180
gagcgttttc cgctgtgtag ctctttcaag ggttttctgg ccgcagccgt gctggcacgc    240
agccaacagc aagcgggcct gctggacacc ccgatccgtt acggcaaaaa tgcgctggtt    300
ccgtggagcc cgattagcga aaagtacctg accaccggca tgacggtggc ggagttgagc    360
gctgcggcgg ttcagtattc cgataacgct gcggcaaatc tgctgctgaa agaactgggc    420
ggtccagcgg gtctgacggc tttcatgcgt tctattggcg acaccacctt tcgcttggac    480
cgctgggagc tggagctgaa cagcgcgatt ccgggcgacg cacgtgatac gagcagcccg    540
cgtgcagtga ccgagagcct gcagaagctg accctgggca gcgcactggc cgcaccgcag    600
cgccaacagt tcgtcgattg gctgaagggt aacaccaccg gtaaccatcg tattcgcgca    660
gcggtcccgg ctgattgggc agttggtgac aagactggta cgtgcggcgt ttatggtacg    720
gcgaatgact acgcggttgt ttggcctacg ggtcgtgcgc cgatcgtcct ggcggtgtat    780
acccgtgctc cgaacaaaga cgataaacac tccgaagcgg tcatcgccgc agcagcgcgt    840
ctggccctgg aaggcttggg cgttaatggt cagtaacgcc ggcg                     884

<210> SEQ ID NO 10
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 10
tcgcctcgag gcgactgcgc tgacgaattt gg                                    32

<210> SEQ ID NO 11
<211> LENGTH: 33
<212> TYPE: DNA
<213> ORGANISM: Artificial Sequence
<220> FEATURE:
<223> OTHER INFORMATION: Synthetic Oligonucleotide

```
<400> SEQUENCE: 11
aatcgaattc ttactgacca ttaacgccca agc                                    33

<210> SEQ ID NO 12
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 12
gcttgggcgt taatggtcag taagaattcg att                                    33

<210> SEQ ID NO 13
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 13
ttcactgcag tgaacgttgc gaagcaacgg c                                      31

<210> SEQ ID NO 14
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 14
tcgaggatcc tcgagagcaa aaacaggaag gcaaaatgcc g                           41

<210> SEQ ID NO 15
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 15
ccgtctagac ggatggcctt tttgcgtttc                                        30

<210> SEQ ID NO 16
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 16
aatcgaattc ttactgacca ttaacgccca agc                                    33

<210> SEQ ID NO 17
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 17
aatcgaattc ttaacgctgc cagtgctcaa tc                                     32
```